US009567580B2

(12) United States Patent
Rao et al.

(10) Patent No.: US 9,567,580 B2
(45) Date of Patent: Feb. 14, 2017

(54) REGULATORS OF NFAT AND/OR STORE-OPERATED CALCIUM ENTRY

(76) Inventors: Anjana Rao, La Jolla, CA (US); Patrick Hogan, La Jolla, CA (US); Sonia Sharma, La Jolla, CA (US)

( * ) Notice: Subject to any disclaimer, the term of this patent is extended or adjusted under 35 U.S.C. 154(b) by 269 days.

(21) Appl. No.: 13/877,472

(22) PCT Filed: Oct. 10, 2011

(86) PCT No.: PCT/US2011/055561
§ 371 (c)(1), (2), (4) Date: Nov. 21, 2013

(87) PCT Pub. No.: WO2012/048316
PCT Pub. Date: Apr. 12, 2012

(65) Prior Publication Data
US 2014/0093542 A1 Apr. 3, 2014

Related U.S. Application Data

(60) Provisional application No. 61/391,445, filed on Oct. 8, 2010.

(51) Int. Cl.
*C12N 15/113* (2010.01)
*A61K 48/00* (2006.01)

(52) U.S. Cl.
CPC ......... *C12N 15/113* (2013.01); *C12N 2310/14* (2013.01)

(58) Field of Classification Search
USPC ...... 424/9.1, 278; 435/6.1, 91.1, 91.31, 455, 435/375; 514/1, 2, 44; 536/23.1, 24.5
See application file for complete search history.

(56) References Cited

U.S. PATENT DOCUMENTS

| | | | |
|---|---|---|---|
| 6,875,581 B1 | 4/2005 | Voelkel | |
| 7,691,997 B2 * | 4/2010 | Khvorova ............ | A61K 31/713 536/24.5 |
| 2001/0018196 A1 | 8/2001 | Mendoza et al. | |
| 2004/0219521 A1 | 11/2004 | Tang et al. | |
| 2005/0107588 A1 | 5/2005 | Duggan et al. | |
| 2005/0255487 A1 | 11/2005 | Khvorova et al. | |
| 2006/0134663 A1 | 6/2006 | Harkin et al. | |
| 2006/0286605 A1 | 12/2006 | Liou et al. | |
| 2007/0031814 A1 | 2/2007 | Roos et al. | |
| 2007/0099251 A1 | 5/2007 | Zhang et al. | |
| 2008/0039392 A1 | 2/2008 | Cahalan et al. | |
| 2008/0096227 A1 | 4/2008 | Penner et al. | |
| 2008/0293092 A1 | 11/2008 | Stauderman et al. | |
| 2009/0143308 A1 | 6/2009 | Monk et al. | |
| 2009/0186422 A1 | 7/2009 | Hogan et al. | |
| 2010/0081129 A1 | 4/2010 | Belouchi et al. | |

FOREIGN PATENT DOCUMENTS

| | | | |
|---|---|---|---|
| CN | 1329064 A | | 1/2002 |
| EP | 1074617 A2 | | 2/2001 |
| EP | 1293569 A2 | | 3/2003 |
| WO | 02/30976 | | 4/2002 |
| WO | 02/070539 A2 | | 9/2002 |
| WO | 03/048305 A2 | | 6/2003 |
| WO | 03/052049 A2 | | 6/2003 |
| WO | 2005/016962 A2 | | 2/2005 |
| WO | 2005/019258 A2 | | 3/2005 |
| WO | 2007/081804 | | 7/2007 |

OTHER PUBLICATIONS

Peterson et al, Clin. Genet., vol. 77, pp. 511-524 (2010).*
Huang et al, Molecular Biology of the Cell, vol. 19, pp. 1717-1726 (2008).*
Huang et al., Molecular Biology of the Cell, 19(4):1717-1726 (2008). "Mammalian septins are requested for phagosome formation."
Mauri et al., Immunology Research, 15(2):126-140 (1996). "Involvement of CD80 in the generation of CD4+ cytotoxic T cells."
Peterson et al., Clinical Genetics, 77(6):511-524 (2010). "Conquering the complex world of human septins: implications for health and disease."
Abbas et al., 2005, computer printout pp. 2-6.
Chattopadhyay et al., Virus Research, 99:139-145 (2004). "Effect of single amino acid mutations in the conserved GDNQ motif of L protein of Rinderpest virus on RNA synthesis in vitro and in vivo."
Clapham, Cell, 136:814-816 (2009). "A STIMulus Package Puts Orai Calcium Channels to Work."
Coury et al., Am J Physiol, 274:F34-F42 (1998). "Reconstitution of water channel function of aquaporins 1 and 2 by expression in yeast secretory vesicles."
Coury et al., Methods in Enzymology, 306:169-186 (1999). "[10] Use of Yeast sec6 Mutant for Purification of Vesicles Containing Recombinant Membrane Proteins."
Derler et al., The Journal of Biological Chemistry, 284(23):15903-15915 (2009). "Increased Hydrophobicity at the N Terminus/Membrane Interface Impairs Gating of the Severe Combined Immunodeficiency-related ORAI1 Mutant."
Eid et al., BMC Developmental Biology, 8:104 (2008). "The *Drosophila* STIMI orthologue, dSTIM, has roles in cell fate specification and tissue patterning."
Gwack et al., Journal of Biological Chemistry, 282:16232-16243 (2007). "Biochemical and Functional Characterization of Orai Proteins."
Heyman et al., The Journal of Cell Biology, 127(5):1259-1273 (1994). "Role of the PAS1 Gene of Pichia pastoris in Peroxisome Biogenesis."

(Continued)

*Primary Examiner* — Jane Zara
(74) *Attorney, Agent, or Firm* — Nixon Peabody LLP; David S. Resnick; Tari W. Mills

(57) ABSTRACT

Embodiments of the inventions relate to modulating NFAT activity, modulating store-operated $Ca^{2+}$ entry into a cell and treating and/or preventing hyperactivity or inappropriate immune response by inhibiting the expression or activities of septin 4 (SEPT 4) and septin 5 (SEPT 5) proteins involved in the calcineurin/NFAT axis and T-cell activation.

11 Claims, 97 Drawing Sheets

(56) References Cited

OTHER PUBLICATIONS

Hogan et al., TRENDS in Biochemical Sciences, 32(5):235-245 (2007). "Dissecting ICRAC, a store-operated calcium current."
Huang et al., Nature Cell Biology, 8(9):1003-1010 (2006). "STIM1 carboxyl-terminus activates native SOC, Icrac and TRPC1 channels."
Ji et al., PNAS, 105(36):13668-13673 (2008). "Functional stoichiometry of the unitary calcium-release-activated calcium channel."
Kawasaki et al., Biochemical and Biophysical Research Communications, 385:49-54 (2009). "A minimal regulatory domain in the C terminus of STIM1 binds to and activates ORAI1 CRAC channels."
Koh et al., Developmental Biology, 330:368-376 (2009). "STIM1 regulates store-operated Ca2+ entry in oocytes."
Laize et al., FEBS Letters, 373:269-274 (1995). "Functional expression of the human CHIP28 water channel in a yeast secretory mutant."
Li et al., The Journal of Biological Chemistry, 282(40):29448-29456 (2007). "Mapping the Interacting Domains of STIM1 and Orai1 in Ca2+ Release-activated Ca2+ Channel Activation."
Liou et al., PNAS, 104(22):9301-9306 (2007). "Live-cell imaging reveals sequential oligomerization and local plasma membrane targeting of stromal interaction molecule 1 after Ca2+ store depletion."
Locke et al., Molecular and Cell Biology, 20(18):6686-6694 (2000). "A Homolog of Voltage-Gated Ca2+ Channels Stimulated by Depletion of Secretory Ca2+ in Yeast."
Lorin-Nebel et al., J Physiol, 580(1):67-85 (2007). "CRAC channel activity in C. elegans is mediated by Orai1 and STIM1 homologues and is essential for ovulation and fertility."
Luik et al., Nature, 454:538-542 (2008). "Oligomerization of STIM1 couples ER calcium depletion to CRAC channel activation."
Lyfenko et al., J Physiol, 586(20):4815-4824 (2008). "Differential dependence of store-operated and excitation-coupled Ca2+ entry in skeletal muscle on STIM1 and Orai1."
Muik et al., The Journal of Biological Chemistry, 283(12):8014-8022 (2008). "Dynamic Coupling of the Putative Coiled-coil Domain of ORAI1 with STIM1 Mediates ORAI1 Channel Activation."
Muik et al., The Journal of Biological Chemistry, 284(13):8421-8426 (2009). "A Cytosolic Homomerization and a Modulatory Domain within STIM1 C Terminus Determine Coupling to ORAI1 Channels."
Nakamoto et al., The Journal of Biological Chemistry, 266(12):7940-7949 (1991). "Expression of the Yeast PLasma Membrane [H+] ATPase in Secretory Vesicles."
Navarro-Borelly et al., J Physiol, 586(22):5383-5401 (2008). "STIM1-Orai1 interactions and Orai1 conformational changes revealed by live-cell FRET microscopy."
Ong et al., The Journal of Biological Chemistry, 282(16):12176-12185 (2007). "Relocalization of STIM1 for Activation of Store-operated Ca2+ Entry is Determined by the Depletion of Subplasma Membrane Endoplasmic Reticulum Ca2+ Store."
Penna et al., Nature, 456:116-120 (2008). "The CRAC channel consists of tetramer formed by Stim-induced dimerization of Orai dimers."
Prakriya et al., Nature, 443:230-231 (2006). "Orai1 is an essential pore subunit of the CRAC channel."
Putney, Cell Calcium, 42:103-110 (2007). "Recent breakthroughs in the molecular mechanism of capacitative calcium entry (with thoughts on how we got here)."
Ruetz et al., Cell, 77:1071-1081 (1994). "Phosphatidylcholine Translocase: A Physiological Role for the mdr2 Gene."
Silverman-Gavrila et al., Journal of Cell Science, 115:5013-5025 (2002). "An IP3-activated Ca2+ channel regulates fungal tip growth."
Skolnick et al., TIBTECH, 18:34-39 (2000). "From genes to protein structure and function: novel applications of computational approaches in the genomic era."
Smallwood et al., Virology, 304:135-145 (2002). "Different Substitutions at Conserved Amino Acids in Domains II and III in the Sendai L RNA Polymerase Protein Inactivate Viral RNA Synthesis."
Stathopulos et al., Cell, 135:110-122 (2008). "Structural and Mechanistic Insights into STIM1-Mediated Initiation of Store-Operated Calcium Entry."
Stiber et al., Nature Cell Biology, 10(6):688-697 (2008). "STIM1 signalling controls store-operated calcium entry required for development and contractile function in skeletal muscle."
Strausberg et al., GenEmbl Accession No. BC069270, computer printout, pp. 13-17, 2004.
Strayle et al., The EMBO Journal, 18(17):4733-4743 (1999). "Steady-state free Ca2+ in the yeast endoplasmic reticulum reaches only 10 μM and is mainly controlled by the secretory pathway pump Pmr1."
Terbush et al., The EMBO Journal, 15(23):6483-6494 (1996). "The Exocyst is a multiprotein complex required for exocytosis in *Saccharomyces cerevisiae*."
Tang et al., Viewing Sequences: 58, 182 of 412 for Document #20040219521, Publication Site for Issued and Published Sequences (PSIPS) online, Nov. 2004, United States Patent and Trademark Office, Alexandria, VA, USA (retrieved on Jun. 6, 2012). Retrieved from the Internet: <URL:http://seqdata.uspto.gov/?pageRequest=viewSequence&DocID=20040219521&seqID=58%2C182>, SEQ ID No. 58, 182.
Tomasinsig et al., Current Protein and Peptide Science, 6:23-34 (2005). "The Cathelicidins-Structure, Function and Evolution."
Varnai et al., J. Biol. Chem., 282:29678-29690 (2007). "Mechanisms of Signal Transduction: Visualization and Manipulation of Plasma Membrane-ENdoplasmic Reticulum Contact Sites Indicates the Presence of Additional Molecular Components within the STIM1-Orai1 Complex."
Vig et al., Current Biology, 16:2073-2079 (2006). "CRACM1 Multimers Form the Ion-Selective Pore of the CRAC Channel."
Wu et al., The Journal of Cell Biology, 174(6):803-813 (2006). "Ca2+ store depletion causes STIM1 to accumulate in ER regions closely associated with the plasma membrane."
Yeromin et al., Nature, 443:226-229 (2006). "Molecular identification of the CRAC channel by altered ion selectivity in a mutant of Orai."
Yuan et al., Nature Cell Biology, 11(3):337-343 (2009). "SOAR and the polybasic STIM1 domains gate and regulate Orai channels."
Zhang et al., The Journal of Biological Chemistry, 283(25):17662-17671 (2008). "Store-dependent and -independent Modes Regulating Ca2+ Release-activated Ca2+ Channel Activity of Human Orai1 and Orai3."
Parekh et al., Nature, 441(11):163-165 (2006). "Cell biology: Cracking the calcium entry code."
Parekh, A. B. and Penner, R., "Store Depletion and Calcium Influx." Physiological Reviews 77(4):901-930, 1997.
Parekh, A. B. and Putney, Jr., J. W., "Store-Operated Calcium Channels" Physiol Rev 85:757-810, 2005.
Park et al., Cell, 136:876-890 (2009). "STIM1 clusters and activates CRAC channels via direct binding of a cytosolic domain to Orai1."
Partiseti, M. et al., "The Calcium Current Activated by T Cell Receptor and Store Depletion in Human Lymphocytes Is Absent in a Primary Immunodeficiency." J Biol Chem 269(51):32327-32335, 1994.
Philipp, S. et al., "TRPC3 Mediates T-cell Receptor-dependent Calcium Entry in Human T-lymphocytes." J Biol Chem 278(29):26629-26638, 2003.
Prakriya, M. and Lewis, R. S., "CRAC channels: activation, permeation, and the search for a molecular identity." Cell Calcium 33:311-321, 2003.
Prakriya, M. and Lewis, R. S., "Separation and Characterization of Currents through Store-operated CRAC Channels and Mg2+-inhibited Cation (MIC) Channels." J Gen Physiol 119(5):487-508, 2002.
Puel, A. et al., "Inherited disorders of NF-kappa-B-mediated immunity in man." Current Opinion in Immunology 16:34-41, 2004.
Ranger, A.M. et al., Immunity, 9:627-635 (1998). "Inhibitory Function of Two NFAT Family Members in Lymphoid Homeostasis and Th2 Development."

(56) References Cited

OTHER PUBLICATIONS

Robinson et al., Current Biology, 16(14):R548-550 (2006). "Calcium influx: Beyond 'current' biology."
Roderick, H. L. and Bootman, M. D., "Calcium Influx: Is Homer the Missing Link?" Current Biology 13:R976-R978, 2003.
Roos, J. et al., "STIM1, an essential and conserved component of store-operated Ca2+ channel function." J Cell Biol 169(3):435-445, 2005.
Salazar, C. and Höfer, T., "Allosteric Regulation of the Transcription Factor NFAT1 by Multiple Phosphorylation Sites: A Mathematical Analysis." J. Mol. Biol. 327:31-45, 2003.
Salzar, C. et al., "Activation of the Transcription Factor NFATI: concerted or modular regulation?" FEBS Lett 579:621-626, 2005.
Schmidt-Ulrich, R. et al., "Requirement of NF-kappa-B/Rel for the development of hair follicles and other epidermal appendices." Development 128:3843-3853, 2001.
Smahi, A. et al., "The NF-kappa-B signalling pathway in human diseases: from incontinentia pigmenti to ectodermal dysplasias and immune-deficiency syndromes." Human Molecular Genetics 11(20):2371-2375, 2002.
Smyth et al., Biochimica Biophysica Acta (2006), doi:10, 1016/j.bbamer.2006.08.050. "Emerging perspective in store-operated Ca2+ entry: Roles of Orai, Stim and TRP."
Soboloff, J. et al., Current Biology, 16:1465-1470 (2006). "STIM2 Is an Inhibitor of STIM1-Mediated Store-Operated Ca2+ Entry."
Soboloff, J. et al., The Journal of Biological Chemistry, 281(30):20661-20665 (2006). "Orai1 and STIM Reconstitute Store-operated Calcium Channel Function."
The International HapMap Consortium, "The International HapMap Project." Nature 426:789-796, 2003.
Venkatachalam, K. et al., "The cellular and molecular basis of store-operated calcium entry." Nature Cell Biology 4:E263-E272, 2002.
Vig et al., Science, 312(5777):1220-1223 (2006). "CRACM1 is a plasma membrane protein essential for store-operated Ca2+ entry."
Voets, T. et al., "CaT1 and the Calcium Release-activated Calcium Channel Manifest Distinct Pore Properties." J Biol Chem 276(51):47767-47770, 2001.
Winslow, M. M. et al., "Calcium signalling in lymphocytes." Current Opinion in Immunology 16:299-307, 2003.
Yeromin, A. V. et al., "A Store-operated Calcium Channel in *Drosophila* S2 Cells." J Gen Physiol 123:167-182, 2004.
Yue, L. et al., "CaT1 manifests the pore properties of the calcium-release-activated calcium channel." Nature 410:705-709, 2001.
Zhang et al., PNAS USA, 103(4):9357-9362 (2006). "Genome wide RNAi screen of Ca2+ influx identifies genes that regulate Ca2+ channel activity."
Zhang, S. L. et al., "STIM1 is a Ca2+ sensor that activates CRAC channels and migrates from the Ca2+ store to the plasma membrane." Nature 437(7060):902-905, 2005.
Zweifach, A. and Lewis, R. S., "Calcium-dependent Potentiation of Store-operated Calcium Channels in T Lymphocytes." J Gen Physiol 107:597-610, 1996.
Zweifach, A. and Lewis, R. S., "Rapid Inactivation of Depletion-activated Calcium Current (Icrac) Due to Local Calcium Feedback." J Gen Physiol 105:209-226, 1995.
Carol et al., Frontiers in BioSciences, 2:12-26 (1997). "Cytokines in acute and chronic inflammation."
Ishikawa et al., J Immunol, 170:4441-4449 (2003). "A pyrazole derivative, YM-58483, potently inhibits store-operated sustained CA2+ influx and IL-2 production in T lymphocytes."
Ohga et al., International Immunopharmacology, 8:1787-1792 (2008). "Characterization of YM-58483/BTP2, a novel store-operated CA2+ entry blocker, on T cell-mediated immune responses in vivo."
Picard et al., N Engl J Med, 360(19):1971-1980 (2009). "Stim1 mutation associated with a syndrome of immunodeficiency and autoimmunity."
Swanson et al., Proc Natl Acad Sci, 89:3741-3745 (1992). "Cyclosporin-mediated inhibition of bovine calcineurin by cyclophilins A and B."
Trevillyan et al., The Journal of Biological Chemistry, 276(51):48118-48126 (2001). "Potent inhibition of NFAT activation and T cell cytokine production by novel low molecular weight pyrazole compounds."
Wittmann et al., Journal of Leukocyte Biology, 80:75-86 (2006). "Critical involvement of IL-12 in IFN-gamma induction by calcineurin antagonists in activated human lymphocytes."
Wulff et al., PNAS, 97(14):8151-8156 (2000). "Design of a potent and selective inhibitor of the intermediate-conductance CA2+-Activated K+ channel, IKCA1: a potential immunosuppressant."
Kloor et al., Biochimica et Biophysica Acta, 1579:219-224 (2002). Identification and characterization of UEV3, a human cDNA with similarities to inactive E2 ubiquitin-conjugating enzymes.
Abecasis, G. R. et al., "Merlin-rapid analysis of dense genetic maps using sparse gene flow trees." Nature Genetics 30:97-101, 2002.
Altshuler, D. et al., "A haplotype map of the human genome." Nature 437(7063):1299-1320, 2005.
Aramburu, J. et al., "Affinity-Driven Peptide Selection of an NFAT Inhibitor More Selective Than Cyclosporin A." Science 285:2129-2133, 1999.
Badou, A. et al., "Requirement of Voltage-Gated Calcium Channel β4 Subunit for T Lymphocyte Functions." Science 307:117-121, 2005.
Beals, C. R. et al., "Nuclear Export of NF-ATc Enhanced by Glycogen Synthase Kinase-3." Science 275:1930-1933, 1997.
Clipstone, N. A. et al., "Molecular Analysis of the Interaction of Calcineurin with Drug-Immunophilin Complexes." J Biol Chem 269(42):26431-26437, 1994.
Courtois, G. et al., "A hypermorphic I-kappa-B-beta mutation is associated with autosomal dominant anhidrotic ectodermal dysplasia and T cell immunodeficiency." J Clin Invest 112:1108-1115, 2003.
Crabtree, G. R. and Olson, E. N., "NFAT Signaling: Choreographing the Social Lives of Cells." Cell 109:S67-S79, 2002.
Cui, J. et al., "CaT1 Contributes to the Stores-operated Calcium Current in Jurkat T-lymphocytes." J Biol Chem 277 (49)47175-47183, 2002.
Döffinger, R. et al., "X-linked anhidrotic ectodermal dysplasia with immunodeficiency is caused by impaired NF-kappa-B signaling." Nature Genetics 27:277-285, 2001.
Eck et al., Goodman & Gilman's The Pharmacological Basis of Therapeutics, McGraw-Hill, New York, pp. 77-101 (1996).
Feske, S. et al., "A mutation in Orai1 causes immune deficiency by abrogating CRAC channel function." Nature 441:179-185, 2006.
Feske, S. et al., "A severe defect in CRAC Ca2+ channel activation and altered K+ channel gating in T cells from immunodeficient patients." JEM 202(5):651-662, 2005.
Feske, S. et al., "Ca2+/calcineurin signalling in cells of the immune system." Biochemical and Biophysical Research Communications 311:1117-1132, 2003.
Feske, S. et al., "Gene regulation mediated by calcium signals in T lymphocytes." Nature Immunology 2(4):316-324, 2001.
Feske, S. et al., "The Duration of Nuclear Residence of NFAT Determines the Pattern of Cytokine Expression in Human SCID T Cells." J Immunol 165:297-305, 2000.
Gabriel, S. B. et al., "The Structure of Haplotype Blocks in the Human Genome." Science 296:2225-2229, 2002.
Gorecki et al., Expert Opin Emerging Drugs, 6(2):187-198 (2001).
Gudbjartsson, D. F. et al., "Allegro, a new computer program for multipoint linkage analysis." Nature Genetics 25:12-13, 2000.
Gwack, Y. et al., "A genome-wide *Drosophila* RNAi screen identifies DYRK-family kinases as regulators of NFAT." Nature 441:646-650, 2006.
Hermosura, M. C. et al., "Dissociation of the store-operated calcium current Icrac and the Mg-nucleotide-regulated metal ion current MagNuM." J Physiol 539(2):445-458, 2002.
Hogan, P. G. et al., "Transcriptional regulation by calcium, calcineurin, and NFAT." Genes & Dev 17:2205-2232, 2003.
Horsley, V. and Pavlath, G. K., "NFAT: ubiquitous regulator of cell differentiation and adaptation." J Cell Biol 156 (5):771-774, 2002.

(56) References Cited

OTHER PUBLICATIONS

Im, S. and Rao, A., "Activation and Deactivation of Gene Expression by Ca2+/Calcineurin-NFAT-mediated Signaling." Mol Cells 18(1):1-9, 2004.
Käll, L. et al., "A Combined Transmembrane Topology and Signal Peptide Prediction Method." J Mol Biol338:1027-1036, 2004.
Kanno, T. and Siebenlist, U., "Activation of Nuclear Factor-kappa-B via T Cell Receptor Requires a Raf Kniase and Ca2+ Influx." J Immunol 157:5277-5283, 1996.
Kim, E. and Sheng, M., "PDZ Domain Proteins of Synapses." Nature Reviews Neuroscience 5:771-781, 2004.
Kodama, Current Medicinal Chemistry, 13:2155-2161 (2006).
Koonpaew, S. et al., The Journal of Experimental Medicine, 203(1):119-129 (2006). "LAT-mediated signaling in CD4+CD25+ regulatory T cell development."
Kotturi, M. F. et al., "Identification and Functional Characterization of Voltage-dependent Calcium Channels in T Lymphocytes." J Biol Chem 278(47):46949-46960, 2003.
Krogh, A. et al., "Predicting Transmembrane Protein Topology with a Hidden Markov Model: Application to Complete Genomes." J Mol Biol 305:567-580, 2001.
Le Deist, F. et al., "A primary T-cell immunodeficiency associated with defective transmembrane calcium influx." Blood 85:1053-1062, 1995.
Lepple-Wienhues, A. and Cahalan, M. D., "Conductance and Permeation of Monovalent Cations through Depletion-Activated Ca2+ Channels (Icrac) in Jurkat T Cells." Biophysical Journal 71:787-794, 1996.
Lewis, R. S., "Calcium Signaling Mechanisms in T Lymphocytes." Annu Rev Immunol 19:497-521, 2001.
Leykin, I. et al., "Comparative linkage analysis and visualization of high-density oligonucleotide SNP array data." BMC Genetics 6(7):1-16, 2005.
Liou, J. et al., Current Biology, 15:1235-1241 (2005). "STIM Is a Ca2+ Sensor Essential for Ca2+-Store-Depletion-Triggered Ca2+ Influx."
Liu, J., "FK506 and cyclosporin, molecular probes for studying intracellular signal transduction." Immunology Today 14 (6):290-295, 1993.
Macián, F., "NFAT Proteins: Key Regulators of T-Cell Development and Function." Nature 5:472-484, 2005.
Macián, F., "Partners in transcription: NFAT and AP-1." Oncogene 20:2476-2489, 2001.
Markianos, K. et al., "Efficient Multipoint Linkage Analysis through Reduction of Inheritance Space." Am J Hum Genet 68:963-977, 2001.
Mori, Y. et al., "Transient Receptor Potential 1 Regulates Capacitative Ca2+ Entry and Ca2+ Release from Endoplasmic Reticulum in B Lymphocytes." J Exp Med 195(6):673-681, 2002.
Myers, E. W. et al., "A Whole-Genome Assembly of *Drosophila*." Science 287:2196-2204, 2000.
Nishikawa et al., Human Gene Therapy, 12:861-870 (2001).
Oh-Hora, M. et al., Nature Immunology, 9(4):432-443 (2008). "Dual functions for the endoplasmic reticulum calcium sensors STIM1 and STIM2 in T cell activation and tolerance."
Ohora, M. et al., FASEB Summer Research Conferences, retrieved from the internet: https://secure.faseb.org/faseb/meetings/summrconf/programs/11643.pdf. Jun. 23, 2007.
Okamura, H. et al., "A Conserved Docking Motif for CK1 Binding Controls the Nuclear Localization of NFAT1." Molecular and Cellular Biology 24(10):4184-4195, 2004.
Okamura, H. et al., "Concerted Dephosphorylation of the Transcription Factor NFAT1 Induces a Conformational Switch that Regulates Transcriptional Activity." Molecular Cell 6:539-550, 2000.
Pan et al., Biochemical and Biophysical Research Communications, 240:314-323 (1997). "Molecular cloning and functional characterization of murine cDNA encoding transcription factor NFATc."

* cited by examiner

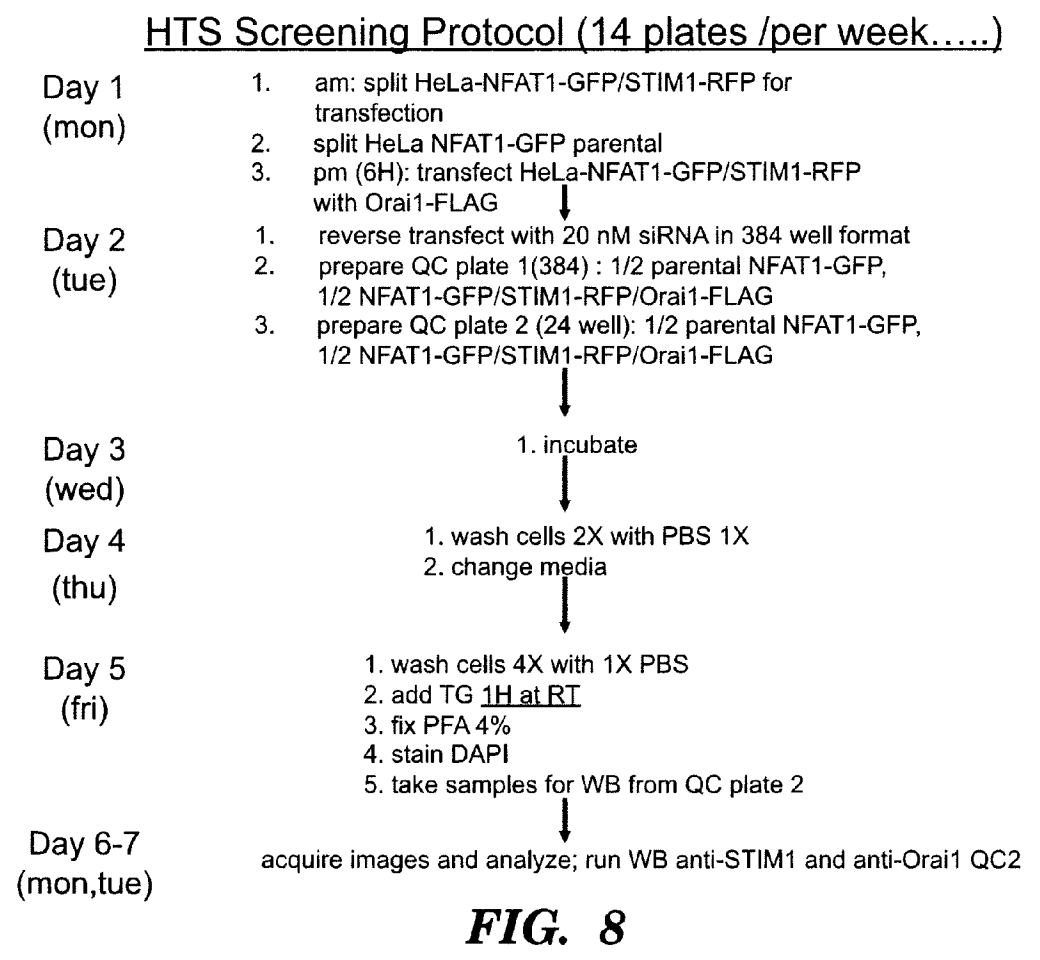

HTS Screening Protocol (14 plates /per week…..)

Day 1 (mon)

1. am: split HeLa-NFAT1-GFP/STIM1-RFP for transfection
2. split HeLa NFAT1-GFP parental
3. pm (6H): transfect HeLa-NFAT1-GFP/STIM1-RFP with Orai1-FLAG

↓

Day 2 (tue)

1. reverse transfect with 20 nM siRNA in 384 well format
2. prepare QC plate 1(384) : 1/2 parental NFAT1-GFP, 1/2 NFAT1-GFP/STIM1-RFP/Orai1-FLAG
3. prepare QC plate 2 (24 well): 1/2 parental NFAT1-GFP, 1/2 NFAT1-GFP/STIM1-RFP/Orai1-FLAG

↓

Day 3 (wed)

1. incubate

↓

Day 4 (thu)

1. wash cells 2X with PBS 1X
2. change media

↓

Day 5 (fri)

1. wash cells 4X with 1X PBS
2. add TG 1H at RT
3. fix PFA 4%
4. stain DAPI
5. take samples for WB from QC plate 2

↓

Day 6-7 (mon,tue)

acquire images and analyze; run WB anti-STIM1 and anti-Orai1 QC2

*FIG. 8*

Z' factor calculation for Hela clone 13.10 (STIM1-RFP + Orai1)
Clone 13.10.STIM1-RFP/Orai1

TG $Avg_{(-)} = 14.208$
$Avg_{(+)} = 81.320$
$SD_{(-)} = 2.183$
$SD_{(+)} = 2.006$

Z' factor = 0.81

Avg CC $_{(-)}$ = 0.2819
Avg CC $_{(+)}$ = 0.6142

<u>Platewise Analysis (+/- k SD ie Z score)</u>

1) Calculate Plate Average of <u>experimental wells</u>
(excludes buffer and empty wells)

2) Calculate Plate SD of <u>experimental wells</u>

3) Calculate Z score for each <u>experimental well</u>
$Z\ score = (X - Avg_{plate})/SD_{plate}$ 4) Filter data set to <u>omit data points with a Z score = +/-3 SD</u>
(extreme outliers)

5) Recalculate Plate Average (doesn't change much) and Plate SD (does change significantly)

6) Recalculate Z scores for each well
weak hits: k = 2-3
moderate hits: k = 3-5
strong hits: k = >5

*FIG. 10*

Candidates

- all expected candidates: calcineurin, nuclear transport proteins, Stim, Orai
- candidates involved in Golgi-to-plasma membrane trafficking
- candidates associated with mitochondria
- a handful of interesting scaffold proteins (with PDZ domains, etc)
- candidates involved in ubiquitin metabolism
- noncoding RNAs (containing microRNAs?)
- RNA-binding proteins

*FIG. 16*

Secondary Assay I: Cherry Picks for SmartPool Deconvolution

500 cherry picks: (496 S/M + 4 W)

SmartPool deconvolution to individual duplexes:
4 siRNA/gene x 500 genes = 2000 wells i) Primary Readout (NFAT-GFP translocation by TG)
4 color acquisition:
-DAPI (stain, nuclear)
-NFAT-GFP (stable living color, nuclear or cytoplasmic)
-STIM1-DSRed (stable living color, ER/punctae)
-Orai-Cy5 (transient FLAG ICC, surface)

ii) Second Readout (NFkB p65 translocation by TNF)
2 color acquisition:
-DAPI (stain, nuclear)
-p65-Cy5 (endogenous p65 ICC, nuclear or cytoplasmic)

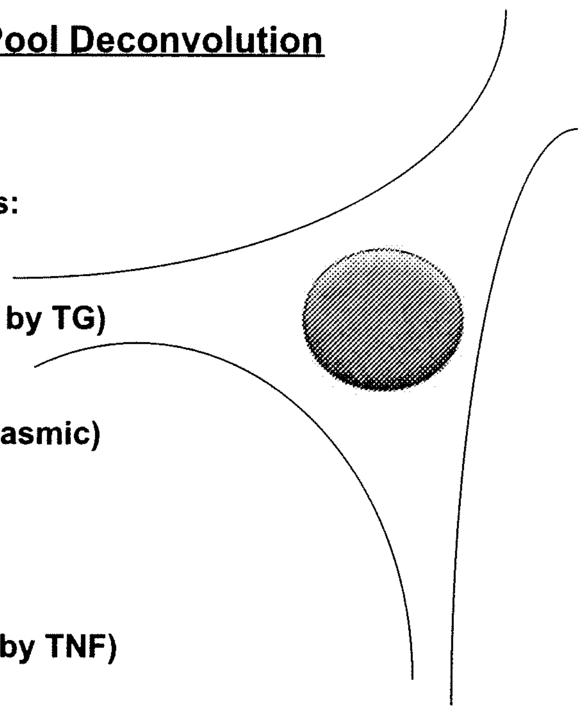

*FIG. 17*

Secondary Assay I: Cherry Picks for SmartPool Deconvolution

| | plate | genes tested | genes (+) | 1 oligo/4 (+) | 2 oligo/4 (+) | 3 oligo/4 (+) | 4 oligo/4 (+) |
|---|---|---|---|---|---|---|---|
| | 1 | 55 | 44 | 21 | 16 | 7 | 0 |
| | 2 | 57 | 52 | 31 | 15 | 2 | 4 |
| | 3 | 57 | 57 | 7 | 19 | 19 | 12 |
| | 4 | 53 | 48 | 23 | 17 | 6 | 2 |
| | 5 | 57 | 57 | 19 | 27 | 7 | 4 |
| | 6 | 57 | 51 | 31 | 14 | 6 | 0 |
| | 7 | 56 | 48 | 31 | 14 | 2 | 1 |
| | 8 | 56 | 51 | 17 | 18 | 15 | 1 |
| | 9 | 52 | 50 | 15 | 19 | 13 | 3 |
| **total** | **9** | **500** | **458** | **195** | **159** | **77** | **27** |
| **total %** | | **100%** | **92%** | **39%** | **31.8%** | **15.4%** | **5.40%** |

total>1/4 263 total %>1/4 52.6%

Tertiary Assay I: intracellular $Ca^{2+}$ measurements classify hits that affect calcium influx:

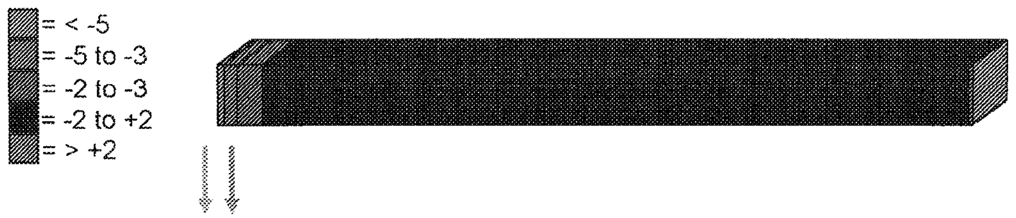

kinetic imaging in live cells of FURA2/AM fluorescence:

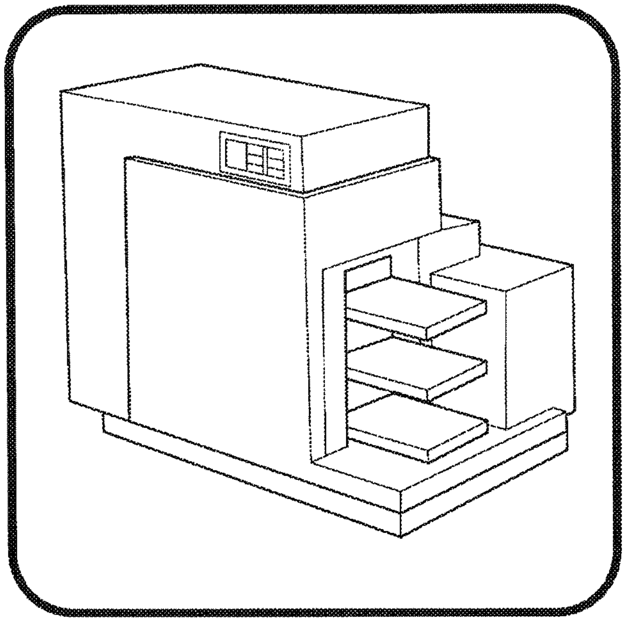

FlexStation III (Molecular Devices)

- -kinetic imaging with integrated fluid transfer and simultaneous read of 8 wells/ 10 minutes (ie one column/96 well plate)
- -integrated measurement of total fluorescence/well (no single cell measurements)

*FIG. 19*

| | Primary Z score | Secondary Z score | GO/function/rationale |
|---|---|---|---|
| FRMPD1 2/4 | -4.9 | -3.1<br>-11.4 | FERM and PDZ-containing |
| KCNN4 4/4 | -4.5 | -2.8<br>-7.6<br>-5.5<br>-4.8 | $Ca^{2+}$-activated K+ channel;<br>Maintains negative membrane potential as driving force for $Ca^{2+}$ entry;<br>Localized to IS during T cell activation |
| UEV3 2/4 | -5.8 | -18.1<br>- 6.6 | UEV and LD domains;<br>paralogue of TSG101;<br>may bind mono-ub proteins in the context of trafficking |
| SYT15 3/4 | -7.2 | -5.2<br>-6.9<br>-5.5 | Atypical $Ca^{2+}$-independent synaptogaminin membrane trafficking? |
| GPD1L 3/4 | -6.0 | -3.0<br>-7.0<br>-4.5 | Glycerol phosphate dehydrogenase 1-like;<br>mitochondrial localization?<br>4 mutations associated with SIDS and/or BS |

*FIG. 25*

THIS RESULT FOR KCNN4 VALIDATES OUR DECISION TO USE NFAT NUCLEAR TRANSLOCATION RATHER THAN AN INFLUX AS A READOUT

SEQUENCE LISTING

<160> NUMBER OF SEQ ID NOS: 106

<210> SEQ ID NO 1
<211> LENGTH: 4676
<212> TYPE: DNA
<213> ORGANISM: Homo sapiens

<400> SEQUENCE: 1
aggagcggcg cggggaggca gaggcgagcg cgggcgatcg cggcggcggg acgtctccgg 60
cggccgcggc accagcggcg gcgctctgtg tggagaagca ggggcagcgg cagcagcaac 120
agcggcagcg gcagcagcag cggcagcagc ggcggccgcc tctccgccgc cggggacgcc 180
aaggtgcggc tggtggcact gacatcggcg gccctgcctc tcctccctcg cccccggcct 240
tccccatgtg atcggtctta atcctggccg tgtgtgcgcg cgtggggctc cattccgcgg 300
tgctgggtct ccgtgccggg gtgggtgctc gtgtgtgcgc ttctcctccc catcccccctt 360 cccccaagaa taaaagaaga accgggaggc gtgctcagaa aataaataaa taaccaccac 420
acacgcgcag cccggagcga gtcggcgggg ctggcggcag cggcggagga ggagtgaagg 480
cggcggcggc ggaggaggga cgcgcggaaa aggcagcaac tttaaagcca gctcagagcc 540
tagacctcca gccgagcggt ttgcagcgcg gcggcggcgg cggcggcggc ggcgttgagt 600
gtctggcccg ccggtccggt cggggtgtgc agtcggacgg acgagcagcg cgtcgctgtc 660
ctccggcagc tggagatgtc cgagcccaag gcaattgatc ccaagttgtc gacgaccgac 720
agggtggtga aagctgttcc atttcctcca agtcaccggc ttacagcaaa agaagtgttt 780
gataatgatg gaaaacctcg tgtggatatc ttaaaggcgc atcttatgaa ggagggaagg 840
ctggaagaga gtgttgcatt gagaataata acagagggtg catcaattct tcgacaggaa 900
aaaaatttgc tggatattga tgcgccagtc actgtttgtg gggacattca tggacaattc 960

-continued

```
tttgatttga tgaagctctt tgaagtcggg ggatctcctg ccaacactcg ctacctcttc   1020
ttaggggact atgttgacag agggtacttc agtattgaat gtgtgctgta tttgtgggcc   1080
ttgaaaattc tctaccccaa aacactgttt ttacttcgtg gaaatcatga atgtagacat   1140
ctaacagagt atttcacatt taaacaagaa tgtaaaataa agtattcaga acgcgtatat   1200
gatgcctgta tggatgcctt tgactgcctt cccctggctg ccctgatgaa ccaacagttc   1260
ctgtgtgtgc atggtggttt gtctccagag attaacactt tagatgatat cagaaaatta   1320
gaccgattca aagaaccacc tgcatatgga cctatgtgtg atatcctgtg gtcagacccc   1380
ctggaagatt ttggaaatga gaagactcag gaacatttca ctcacaacac agtcaggggg   1440
tgttcatact tctacagtta cccggctgta tgtgaattct tacagcacaa taacttgtta   1500
tctatactcc gagcccacga agcccaagat gcagggtacc gcatgtacag gaaaagccaa   1560
acaacaggct tcccttctct aattacaatt ttttcagcac caaattactt agatgtatac   1620
aataacaaag ctgcagtatt gaagtatgag aacaatgtta tgaatatcag gcaattcaac   1680
tgttctcctc atccatactg gcttccaaat ttcatggatg tttttacttg gtcccttcca   1740
tttgttgggg aaaaagtgac tgagatgctg gtaaatgtcc tcaacatctg ctcagatgat   1800
gaactagggt cagaagaaga tggatttgat ggtgcaacag ctgcagcccg gaaagaggtg   1860
ataaggaaca agatccgagc aataggcaaa atggccagag tgttctcagt gctcagagaa   1920
gagagtgaga gtgtgctgac gctgaaaggc ttgaccccaa ctggcatgct ccccagcgga   1980
gtactttctg gagggaagca aaccctgcaa agcgctactg ttgaggctat tgaggctgat   2040
gaagctatca aaggattttc accacaacat aagatcacta gcttcgagga agccaagggc   2100
ttagaccgaa ttaatgagag gatgccgcct cgcagagatg ccatgccctc tgacgccaac   2160
cttaactcca tcaacaaggc tctcacctca gagactaacg gcacggacag caatggcagt   2220
aatagcagca atattcagtg accacttcct gttcactttt tttttttttt tttttttttt   2280
tttttgagct gcggggcatg atggggattg ctgcatatca gcagttggat gttcttgcct   2340
ctgacagtag cttatttgct ctgggggcca ggaattggat tcagtttaca ctatcattaa   2400
aaaagaggga gagagataat aaactatatt ttggtgggga tggtgattaa acacctcttt   2460
tgggtatgcc ttttaaaaat gcttatagag aaaaaaaatt ttaaaaagaa agctaatgct   2520
agtatatact gcaatgttag gggaatgaac atgttttcct actgcattgg ggacttctag   2580
ataggttaat gaaaggcctt ttattctgtt actggacatg aaaactttgt ctaatttctt   2640
actctattgt acgtttacag tcgcagcact aaaaatggat gacatcaaac atttttaaca   2700
aaatgatgta caaactaagg actatttatt gataatgttt tgctactctt gtcagacaat   2760
ggctataaac tgaattaggc agtcttaaaa aaaaaaaaaa acagaaaaag aaaaaaaaga   2820
acgttgcaaa tttgttaaaa tgccaaaaag gacagtttaa ttttgtacag attatgctta   2880
cctcaggttt ctttagtgtg cttgaatgcc cttctttcca tataacactt atcttcttct   2940
taattcggca atggaatatc ttttaagttt taaaaaaact ggaataatta tatctatctt   3000
ttttgccgtt tatatttagg ggtttttgtt gataaaatca agtcttggtt gtggcttgct   3060
gaattaaata tttatgagtg gtgcattttt aagtatagtg aacaagacac catattaagt   3120
acagtgataa agcatctata ttctgtaaaa aaaaaaaaaa tctgcctatg catgtttttt   3180
aagaaaaaaa aaatggctgt atcggcctgt atgggactgt aatgcgctta gtggtctgac   3240
atatactgga aatgtatgta tactggcgta ctttatattc tctaaaatgc ttaatgcctt   3300
```

-continued

```
tgaaattttg taatcaaaaa aaagctttga aaaaatctaa aggggagagt attctttaaa   3360

gtttttaaca taagcttgtc aatgcacatg tagatggtta gcatgtttag caaaccttgt   3420

gaaattataa taagtttgta gttacatgtg aaactctaaa tgcatggcaa ctgttaatgt   3480

cataacagtt tagttatttt gttctgttct gtcatgtgcc acaaaatatg tacttttttc   3540

acttttttcc ctttgtatat cagttacggg ttacaactgg ttcattctga aaacaacaac   3600

aacaaaagtc cattcatatt ttttaacaat tgtataagtg cccaagtaat tcactacagc   3660

ctaaagcctt gcctttgtaa tttgacttct gacatgttgg caatcaaagc atgcacttgt   3720

aacaatgaaa aagaaaaagc attttatatt actactcaat aaaatgtgca tgaacttaca   3780

gaattctcat ccttccactg agtccgctga agggatttat gtgcacaacc accatgtgtc   3840

ttctaggtgc tggcccacca ccacacatca caggctgatt tccacaggct tcttcctagg   3900

ggcctcgtga tctgaggggt ggtgcctact tccactgtaa gaaagaatct tggtggattt   3960

gtgtctcaaa tcagataaga gaagcctgtt taaagagcag atgccatctt ctggcttcct   4020

caaggagcca gttaaaaaac cagagcattc ctttttattg aaaaataaaa ttaatttgtt   4080

atcaggttgt ttcagttgta ttggatgccc tatctatctg ctaaagcaaa aagtactagg   4140

ctactaagtg cattttcatc acagaaaaga gttgcatttg tattaacaag aaatttgtat   4200

acccacgctt cagctactat ctaatcatca cccgaagatt taagatacac caaatttcag   4260

tttgtttgta acattgttca tctttagtgc actttgtttt atataataaa gtatgcctgt   4320

tatattaaat aataagaata tggcaattag cgatatagca tacccaaaca aagatgttct   4380

cgatacagtc tggcaaagac tatcccaagg ttattttaat gaattcagac atttttttcct   4440

gtggatattt ctccatccta aaaaaagtgg caaccaagga aaatatttag atgcaactta   4500

ctagagtgat gatgtgaaag aaatggtgat tctggtatca tggtgtttat tttctttctt   4560

ataactgcag agaaaatatc ctgactaaaa aaaattcatt tttttggatt cctttctttt   4620

acaaattgtg ctgaggcaac tatggcatag aaataaacat ttgacattaa aataag        4676
```

<210> SEQ ID NO 2
<211> LENGTH: 3079
<212> TYPE: DNA
<213> ORGANISM: Homo sapiens

<400> SEQUENCE: 2

```
gggccctaca gagggtccgc catgttcccc ggcggcgccg ccgcttggct ctggtagccg     60

ccgcccccgc ccccaacccc gcccggccca gagcctagcc gagccccggg cccagcatgg    120

ccgccccgga gccggcccgg gctgcaccgc ccccaccccc gcccccgccg ccccctcccg    180

gggctgaccg cgtcgtcaaa gctgtccctt tccccccaac acatcgcttg acatctgaag    240

aagtatttga tttggatggg atacccaggg ttgatgttct gaagaaccac ttggtgaaag    300

aaggtcgagt agatgaagaa attgcgctta gaattatcaa tgagggtgct gccatccttc    360

ggagagagaa aaccatgata gaagtagaag ctccaatcac agtgtgtggt gacatccatg    420

gccaattttt tgatctgatg aaactttttg aagtaggagg atcacctgct aatacacgat    480

acctttttct tggcgattat gtggacagag gttattttag tatagagtgt gtcttatatt    540

tatgggttct gaagattcta tacccaagca cattatttct tctgagaggc aaccatgaat    600

gcagacacct tactgaatat tttacccttta agcaggaatg taaaattaag tattcggaaa    660

gagtctatga agcttgtatg gaagcttttg atagtttgcc tcttgctgca cttttaaacc    720

aacagtttct ttgtgttcat ggtggacttt caccagaaat acacacactg gatgatatta    780
```

-continued

```
ggagattaga tagattcaaa gagccacctg catttggacc aatgtgtgac ttgttatggt    840
ccgatccttc tgaagatttt ggaaatgaaa aatcacagga acattttagt cacaatacag    900
ttcgaggatg ttcttatttt tataactatc cagcagtgtg tgaatttttg caaaacaata    960
atttgttatc gattattaga gctcatgaag ctcaagatgc aggctataga atgtacagaa   1020
aaagtcaaac tacagggttc ccttcattaa taacaatttt ttcggcacct aattacttag   1080
atgtctacaa taataaagct gctgtattaa agtatgaaaa taatgtgatg aatattcgac   1140
agtttaactg ttctccacat ccttactggt tgcctaattt tatggatgtc ttcacgtggt   1200
ctttaccgtt tgttggagaa aaagtgacag aaatgttggt aaatgttctg agtatttgct   1260
ctgatgatga actaatgact gaaggtgaag accagtttga tggttcagct gcagcccgga   1320
aagaaatcat aagaaacaaa attcgagcaa ttggcaagat ggcaagagtc ttctctgttc   1380
tcagggagga gagtgaaagt gtgctgacac tcaagggcct gactcccaca gggatgttgc   1440
ctagtggagt gttagctgga ggacggcaga ccctgcaaag tgccacagtt gaggctattg   1500
aggctgaaaa agcaatacga ggattctctc caccacatag aatctgcagt tttgaagagg   1560
caaagggttt ggataggatc aatgagagaa tgccacctcg gaaagatgct gtacagcaag   1620
atggtttcaa ttctctgaac accgcacatg ccactgagaa ccacgggacg ggcaaccata   1680
ctgcccagtg acccactact tcccagggac tctcacatct cgggccccaa atggacagat   1740
cacccgagga gctggagggg tcggccaagc tgactgtaaa tttcacagtc tctctgaaga   1800
aaccattgtg cttctgagac cctagccccc ttcctggatg gaggcttgag ggccctggga   1860
catgtgctat ctgataagat tgggtcatcg ctgccaaggt ggagagcagt gagcaagggg   1920
cttggggcaa tttccagtgg agggcatcca cacctccatt ttatgcttgt ggttcacaca   1980
tttaagttta caaatcagat ttcttttccc cttcagtaga attagatttt gtttttcaat   2040
catgatttca aatgcaatcc taagagctaa tgtggacttt tctttttcca tgaaatgtct   2100
ttaaaggatg aattagcatg gtcttaaaat acatttctga ggttactagc tgtattttga   2160
attgtgagca aaatgccgag aaacccagtt ggcatttata caaaatgttg acctcaggtc   2220
tatagttctt aaatgtggct aattctgtaa catagtcttg gtattttta attatgaatg    2280
catatcctat ttccaggcag gctctcttac ttgaacacaa atccaaaaac taatttagag   2340
tctttttgc ccagatcttt taagacttac accccagaga tttaagaaga aaacctctaa    2400
atttcaaaat tatgaagaat tacagaatta ctcatttaag gtactttaaa agaagtttgt   2460
acattgtcaa agtaaatttt aattcaaatc atgtctgtaa aacttgacgt attttgtgta   2520
tgcatgtttt cattttgcaa atatttaata tatagaccta tgatgtacag gtacgacatg   2580
tataggttac ctagatgtta tgagaaattt tagtttattg tgagtactca agttgcttag   2640
agagccacca gggtgatttg ctgctggctt tctatcattt ttatgtttta atgcaaagga   2700
aattttaaaa tgttctggaa gtgtttttga ttaagcaatg cagcctagaa gcaatggttc   2760
tgttcaatca ttcagatgtt agtggaagca taaaagtcaa gactgcatgt tgaaaccttt   2820
cttttgatag ttactgaact gcttggttaa actaaatgga accatgtgct aatttttcac   2880
aattattgac ctgtattgat tgccactgta gtttggtatt tccctttact ttggtggcct   2940
gcttccctca tgccctggaa tacaactcag agctccaggc agcggaacca tctattgttt   3000
tgtttgccag aaagtgcacc ctgtatggtc tcctgtctaa gttggaaata ttatgcatgt   3060
gcaggactat tcgagtatt                                                3079
```

<210> SEQ ID NO 3
<211> LENGTH: 1087
<212> TYPE: DNA
<213> ORGANISM: Homo sapiens

<400> SEQUENCE: 3

```
cgcttccgcc atctttccag cctcagtcgg acgggcgcgg agacgcttct ggaaggaacg     60

ccgcgatggc tgcgcaggga gagccccagg tccagttcaa acttgtattg gttggtgatg    120

gtggtactgg aaaaacgacc ttcgtgaaac gtcatttgac tggtgaattt gagaagaagt    180

atgtagccac cttgggtgtt gaggttcatc ccctagtgtt ccacaccaac agaggaccta    240

ttaagttcaa tgtatgggac acagccggcc aggagaaatt cggtggactg agagatggct    300

attatatcca agcccagtgt gccatcataa tgtttgatgt aacatcgaga gttacttaca    360

agaatgtgcc taactggcat agagatctgg tacgagtgtg tgaaaacatc cccattgtgt    420

tgtgtggcaa caaagtggat attaaggaca ggaaagtgaa ggcgaaatcc attgtcttcc    480

accgaaagaa gaatcttcag tactacgaca tttctgccaa aagtaactac aactttgaaa    540

agcccttcct ctggcttgct aggaagctca ttggagaccc taacttggaa tttgttgcca    600

tgcctgctct cgccccacca gaagttgtca tggacccagc tttggcagca cagtatgagc    660

acgacttaga ggttgctcag acaactgctc tcccggatga ggatgatgac ctgtgagaat    720

gaagctggag cccagcgtca gaagtctagt tttataggca gctgtcctgt gatgtcagcg    780

gtgcagcgtg tgtgccacct cattattatc tagctaagcg gaacatgtgc ttcatctgtg    840

ggatgctgaa ggagatgagt gggcttcgga gtgaatgtgg cagtttaaaa aataacttca    900

ttgtttggac ctgcatattt agctgttttg gaacgcagtt gattccttga gtttcatata    960

taagactgct gcagtcacat cacaatattc agtggtgaaa tcttgtttgt tactgtcatt   1020

cccattcctt ttcgtttaga atcagaataa agttgtattt caaatatcta aaaaaaaaaa   1080

aaaaaaa                                                             1087
```

<210> SEQ ID NO 4
<211> LENGTH: 11711
<212> TYPE: DNA
<213> ORGANISM: Homo sapiens

<400> SEQUENCE: 4

```
cacagtggtc ctccgccggc tacggcgctg cgtcactggt ttgcaggcgc tttcctcttg     60

gaagtggcga ctgctgcggg cctgagcgct ggtctcacgc gcctcgggag ccaggttggc    120

ggcgcgatga ggcgcagcaa ggctgacgtg gagcggtaca tcgcctcggt gcagggctcc    180

accccgtcgc ctcgacagaa gtcaatgaaa ggattctatt ttgcaaagct gtattatgaa    240

gctaaagaat atgatcttgc taaaaaatac atatgtactt acattaatgt gcaagagagg    300

gatcccaaag ctcacagatt tctgggtctt ctttatgaat tggaagaaaa cacagacaaa    360

gccgttgaat gttacaggcg ttcagtggaa ttaaacccaa cacaaaaaga tcttgtgttg    420

aagattgcag aattgctttg taaaaatgat gttactgatg gaagagcaaa atactggctt    480

gaaagagcag ccaaactttt cccaggaagt cctgcaattt ataaactaaa ggaacagctt    540

ctagattgtg aaggtgaaga tggatggaat aaactttttg acttgattca gtcagaactt    600

tatgtaagac ctgatgacgt ccatgtgaac atccggctag tggaggtgta tcgctcaact    660

aaaagattga aggatgctgt ggcccactgc catgaggcag agaggaacat agctttgcgt    720

tcaagtttag aatggaattc gtgtgttgta cagaccctta aggaatatct ggagtcttta    780
```

```
cagtgtttgg agtctgataa aagtgactgg cgagcaacca atacagactt actgctggcc     840
tatgctaatc ttatgcttct tacgctttcc actagagatg tgcaggaaag tagagaatta     900
ctgcaaagtt ttgatagtgc tcttcagtct gtgaaatctt tgggtggaaa tgatgaactg     960
tcagctactt tcttagaaat gaaaggacat ttctacatgc atgctggttc tctgcttttg    1020
aagatgggtc agcatagtag taatgttcaa tggcgagctc tttctgagct ggctgcattg    1080
tgctatctca tagcatttca ggttccaaga ccaaagatta aattaataaa aggtgaagct    1140
ggacaaaatc tgctggaaat gatggcctgt gaccgactga gccaatcagg gcacatgttg    1200
ctaaacttaa gtcgtggcaa gcaagatttt ttaaaagaga ttgttgaaac ttttgccaac    1260
aaaagcgggc agtctgcatt atatgatgct ctgttttcta gtcagtcacc taaggataca    1320
tcttttcttg gtagcgatga tattggaaac attgatgtac gagaaccaga gcttgaagat    1380
ttgactagat acgatgttgg tgctattcga gcacataatg gtagtcttca gcaccttact    1440
tggcttggct tacagtggaa ttcattgcct gctttacctg gaatccgaaa atggctaaaa    1500
cagcttttcc atcatttgcc ccatgaaacc tcaaggcttg aaacaaatgc acctgaatca    1560
atatgtattt tagatcttga agtatttctc cttggagtag tatataccag ccacttacaa    1620
ttaaaggaga aatgtaattc tcaccacagc tcctatcagc cgttatgcct gccccttcct    1680
gtgtgtaaac agctttgtac agaaagacaa aaatcttggt gggatgcggt ttgtactctg    1740
attcacagaa aagcagtacc tggaaacgta gcaaaattga gacttctagt tcagcatgaa    1800
ataaacactc taagagccca ggaaaaacat ggccttcaac ctgctctgct tgtacattgg    1860
gcagaatgcc ttcagaaaac gggcagcggt cttaattctt tttatgatca acgagaatac    1920
atagggagaa gtgttcatta ttggaagaaa gttttgccat tgttgaagat aataaaaaag    1980
aagaacagta ttcctgaacc tattgatcct ctgtttaaac attttcatag tgtagacatt    2040
caggcatcag aaattgttga atatgaagaa gacgcacaca taacttttgc tatattggat    2100
gcagtaaatg gaaatataga agatgctgtg actgcttttg aatctataaa aagtgttgtt    2160
tcttattgga atcttgcact gatttttcac aggaaggcag aagacattga aaatgatgcc    2220
ctttctcctg aagaacaaga agaatgcaaa aattatctga gaaagaccag ggactaccta    2280
ataaagatta tagatgacag tgattcaaat ctttcagtgg tcaagaaatt gcctgtgccc    2340
ctggagtctg taaaagagat gcttaattca gtcatgcagg aactcgaaga ctatagtgaa    2400
ggaggtcctc tctataaaaa tggttctttg cgaaatgcag attcagaaat aaaacattct    2460
acaccgtctc ctaccagata ttcactatca ccaagtaaaa gttacaagta ttctcccaaa    2520
acaccacctc gatgggcaga agatcagaat tctttactga aaatgatttg ccaacaagta    2580
gaggccatta agaaagaaat gcaggagttg aaactaaata gcagtaactc agcatcccct    2640
catcgttggc ccacagagaa ttatggacca gactcagtgc ctgatggata tcaggggtca    2700
cagacatttc atggggctcc actaacagtt gcaactactg gccctcagt atattatagt     2760
cagtcaccag catataattc ccagtatctt ctcagaccag cagctaatgt tactcccaca    2820
aagggcccag tctatggcat gaataggctt ccaccccaac agcatattta tgcctatccg    2880
caacagatgc acacaccgcc agtgcaaagc tcatctgctt gtatgttctc tcaggagatg    2940
tatggtcctc ctgcattgcg ttttgagtct cctgcaacgg gaattctatc gcccaggggt    3000
gatgattact ttaattacaa tgttcaacag acaagcacaa atccaccttt gccagaacca    3060
ggatatttca caaaacctcc gattgcagct catgcttcaa gatctgcaga atctaagact    3120
```

atagaatttg ggaaaactaa ttttgttcag cccatgccgg gtgaaggatt aaggccatct 3180
ttgccaacac aagcacacac aacacagcca actcctttta aatttaactc aaatttcaaa 3240
tcaaatgatg gtgacttcac gttttcctca ccacaggttg tgacacagcc ccctcctgca 3300
gcttacagta acagtgaaag ccttttaggt ctcctgactt cagataaacc cttgcaagga 3360
gatggctata gtggagccaa accaattcct ggtggtcaaa ccattgggcc tcgaaataca 3420
ttcaattttg gaagcaaaaa tgtgtctgga atttcattta cagaaaacat ggggtcgagt 3480
cagcaaaaga attctggttt tcggcgaagt gatgatatgt ttactttcca tggtccaggg 3540
aaatcagtat ttggaacacc cactttagag acagcaaaca agaatcatga gacagatgga 3600
ggaagtgccc atggggatga tgatgatgac ggtcctcact ttgagcctgt agtacctctt 3660
cctgataaga ttgaagtaaa aactggtgag gaagatgaag aagaattctt ttgcaaccgc 3720
gcgaaattgt ttcgtttcga tgtagaatcc aaagaatgga aagaacgtgg gattggcaat 3780
gtaaaaatac tgaggcataa aacatctggt aaaattcgcc ttctaatgag acgagagcaa 3840
gtattgaaaa tctgtgcaaa tcattacatc agtccagata tgaaattgac accaaatgct 3900
ggatcagaca gatcttttgt atggcatgcc cttgattatg cagatgagtt gccaaaacca 3960
gaacaacttg ctattaggtt caaaactcct gaggaagcag cactttttaa atgcaagttt 4020
gaagaagccc agagcatttt aaaagcccca ggaacaaatg tagccatggc gtcaaatcag 4080
gctgtcagaa ttgtaaaaga acccacaagt catgataaca aggatatttg caaatctgat 4140
gctggaaacc tgaattttga atttcaggtt gcaaagaaag aagggtcttg gtggcattgt 4200
aacagctgct cattaaagaa tgcttcaact gctaagaaat gtgtatcatg ccaaaatcta 4260
aacccaagca ataaagagct cgttggccca ccattagctg aaactgtttt tactcctaaa 4320
accagcccag agaatgttca agatcgattt gcattggtga ctccaaagaa agaaggtcac 4380
tgggattgta gtatttgttt agtaagaaat gaacctactg tatctaggtg cattgcgtgt 4440
cagaatacaa aatctgctaa caaaagtgga tcttcatttg ttcatcaagc ttcatttaaa 4500
tttggccagg gagatcttcc taaacctatt aacagtgatt tcagatctgt tttttctaca 4560
aaggaaggac agtgggattg cagtgcatgt ttggtacaaa atgaggggag ctctacaaaa 4620
tgtgctgctt gtcagaatcc gagaaaacag agtctacctg ctacttctat tccaacacct 4680
gcctctttta agtttggtac ttcagagaca agtaaaactc taaaaagtgg atttgaagac 4740
atgtttgcta agaaggaagg acagtgggat tgcagttcat gcttagtgcg aaatgaagca 4800
aatgctacaa gatgtgttgc ttgtcagaat ccggataaac caagtccatc tacttctgtt 4860
ccagctcctg cctcttttaa gtttggtact tcagagacaa gcaaggctcc aaagagcgga 4920
tttgagggaa tgttcactaa gaaggaggga cagtgggatt gcagtgtgtg cttagtaaga 4980
aatgaagcca gtgctaccaa atgtattgct tgtcagaatc caggtaaaca aaatcaaact 5040
acttctgcag tttcaacacc tgcctcttca gagacaagca aggctccaaa gagcggattt 5100
gagggaatgt tcactaagaa ggagggacag tgggattgca gtgtgtgctt agtaagaaat 5160
gaagccagtg ctaccaaatg tattgcttgt cagaatccag gtaaacaaaa tcaaactact 5220
tctgcagttt caacacctgc ctcttcagag acaagcaagg ctccaaagag cggatttgag 5280
ggaatgttca ctaagaagga aggacagtgg gattgcagtg tgtgcttagt aagaaatgaa 5340
gccagtgcta ccaaatgtat tgcttgtcag tgtccaagta aacaaaatca aacaactgca 5400
atttcaacac ctgcctcttc ggagataagc aaggctccaa agagtggatt tgaaggaatg 5460
ttcatcagga aaggacagtg ggattgtagt gtttgctgtg tacaaaatga gagttcttcc 5520

```
ttaaaatgtg tggcttgtga tgcctctaaa ccaactcata aacctattgc agaagctcct   5580
tcagctttca cactgggctc agaaatgaag ttgcatgact cttctggaag tcaggtggga   5640
acaggattta aaagtaattt ctcagaaaaa gcttctaagt ttggcaatac agagcaagga   5700
ttcaaatttg ggcatgtgga tcaagaaaat tcaccttcat ttatgtttca gggttcttct   5760
aatacagaat ttaagtcaac caaagaagga ttttccatcc ctgtgtctgc tgatggattt   5820
aaatttggca tttcggaacc aggaaatcaa gaaaagaaaa gtgaaaagcc tcttgaaaat   5880
ggtactggct tccaggctca ggatattagt ggccagaaga atggccgtgg tgtgattttt   5940
ggccaaacaa gtagcacttt tacatttgca gatcttgcaa aatcaacttc aggagaagga   6000
tttcagtttg gcaaaaaaga ccccaatttc aagggatttt caggtgctgg agaaaaatta   6060
ttctcatcac aatacggtaa aatggccaat aaagcaaaca cttccggtga ctttgagaaa   6120
gatgatgatg cctataagac tgaggacagc gatgacatcc attttgaacc agtagttcaa   6180
atgcccgaaa aagtagaact tgtaacagga gaagaagatg aaaaagttct gtattcacag   6240
cgggtaaaac tatttagatt tgatgctgag gtaagtcagt ggaaagaaag gggcttgggg   6300
aacttaaaaa ttctcaaaaa cgaggtcaat ggcaaactaa gaatgctgat gcgaagagaa   6360
caagtactaa aagtgtgtgc taatcattgg ataacgacta cgatgaacct gaagcctctc   6420
tctggatcag atagagcatg gatgtggtta gccagtgatt tctctgatgg tgatgccaaa   6480
ctagagcagt tggcagcaaa atttaaaaca ccagagctgg ctgaagaatt caagcagaaa   6540
tttgaggaat gccagcggct tctgttagac ataccacttc aaactcccca taaacttgta   6600
gatactggca gagctgccaa gttaatacag agagctgaag aaatgaagag tggactgaaa   6660
gatttcaaaa catttttgac aaatgatcaa acaaaagtca ctgaggaaga aaataagggt   6720
tcaggtacag gtgcggccgg tgcctcagac acaacaataa aacccaatcc tgaaaacact   6780
gggcccacat tagaatggga taactatgat ttaagggaag atgctttgga tgatagtgtc   6840
agtagtagct cagtacatgc ttctccattg gcaagtagcc ctgtgagaaa aaatcttttc   6900
cgttttggtg agtcaacaac aggatttaac ttcagtttta aatctgcttt gagtccatct   6960
aagtctcctg ccaagttgaa tcagagtggg acttcagttg gcactgatga agaatctgat   7020
gttactcaag aagaagagag agatggacag tactttgaac ctgttgttcc tttacctgat   7080
ctagttgaag tatccagtgg tgaggaaaat gaacaagttg tttttagtca cagggcaaaa   7140
ctctacagat atgataaaga tgttggtcaa tggaaagaaa ggggcattgg tgatataaag   7200
attttacaga attatgataa taagcaagtt cgtatagtga tgagaaggga ccaagtatta   7260
aaactttgtg ccaatcacag aataactcca gacatgactt tgcaaaatat gaaagggaca   7320
gaaagagtat ggttgtggac tgcatgtgat tttgcagatg gagaaagaaa agtagagcat   7380
ttagctgttc gttttaaact acaggatgtt gcagactcgt ttaagaaaat ttttgatgaa   7440
gcaaaaacag cccaggaaaa agattctttg ataacacctc atgtttctcg gtcaagcact   7500
cccagagagt caccatgtgg caaaattgct gtagctgtat tagaagaaac cacaagagag   7560
aggacagatg ttattcaggg tgatgatgta gcagatgcaa cttcagaagt tgaagtgtct   7620
agcacatctg aaacaacacc aaaagcagtg gtttctcctc caaagtttgt atttggttca   7680
gagtctgtta aaagcatttt tagtagtgaa aaatcaaaac catttgcatt cggcaacagt   7740
tcagccactg ggtctttgtt tggatttagt tttaatgcac ctttgaaaag taacaatagt   7800
gaaactagtt cagtagccca gagtggatct gaaagcaaag tggaacctaa aaaatgtgaa   7860
```

-continued

```
ctgtcaaaga actctgatat cgaacagtct tcagatagca aagtcaaaaa tctctttgct   7920
tcctttccaa cggaagaatc ttcaatcaac tacacattta aaacaccaga aaaggcaaaa   7980
gagaagaaaa aacctgaaga ttctccctca gatgatgatg ttctcattgt atatgaacta   8040
actccaaccg ctgagcagaa agcccttgca accaaactta aacttcctcc aactttcttc   8100
tgctacaaga atagaccaga ttatgttagt gaagaagagg aggatgatga agatttcgaa   8160
acagctgtca agaaacttaa tggaaaacta tatttggatg gctcagaaaa atgtagaccc   8220
ttggaagaaa atacagcaga taatgagaaa gaatgtatta ttgtttggga aaagaaacca   8280
acagttgaag agaaggcaaa agcagatacg ttaaaacttc cacctacatt tttttgtgga   8340
gtctgtagtg atactgatga agacaatgga aatggggaag actttcaatc agagcttcaa   8400
aaagttcagg aagctcaaaa atctcagaca gaagaaataa ctagcacaac tgacagtgta   8460
tatacaggtg ggactgaagt gatggtacct tctttctgta aatctgaaga acctgattct   8520
attaccaaat ccattagttc accatctgtt tcctctgaaa ctatggacaa acctgtagat   8580
ttgtcaacta gaaaggaaat tgatacagat tctacaagcc aaggggaaag caagatagtt   8640
tcatttggat ttggaagtag cacagggctc tcatttgcag acttggcttc cagtaattct   8700
ggagattttg cttttggttc taaagataaa aatttccaat gggcaaatac tggagcagct   8760
gtgtttggaa cacagtcagt cggaacccag tcagccggta aagttggtga agatgaagat   8820
ggtagtgatg aagaagtagt tcataatgaa gatatccatt ttgaaccaat agtgtcacta   8880
ccagaggtag aagtaaaatc tggagaagaa gatgaagaaa ttttgtttaa agagagagcc   8940
aaactttata gatgggatcg ggatgtcagt cagtggaagg agcgcggtgt tggagatata   9000
aagattcttt ggcatacaat gaagaattat taccggatcc taatgagaag agaccaggtt   9060
tttaaagtgt gtgcaaacca cgttattact aaaacaatgg aattaaagcc cttaaatgtt   9120
tcaaataatg ctttagtttg gactgcctca gattatgctg atggagaagc aaaagtagaa   9180
cagcttgcag tgagatttaa aactaaagaa gtagctgatt gtttcaagaa aacatttgaa   9240
gaatgtcagc agaatttaat gaaactccag aaaggacatg tatcactggc agcagaatta   9300
tcaaaggaga ccaatcctgt ggtgtttttt gatgtttgtg cggacggtga acctctaggg   9360
cggataacta tggaattatt ttcaaacatt gttcctcgga ctgctgagaa cttcagagca   9420
ctatgcactg gagagaaagg ctttggtttc aagaattcca tttttcacag agtaattcca   9480
gattttgttt gccaaggagg agatatcacc aaacatgatg gaacaggcgg acagtccatt   9540
tatggagaca aatttgaaga tgaaaatttt gatgtgaaac atactggtcc tggtttacta   9600
tccatggcca atcaaggcca gaataccaat aattctcaat ttgttataac actgaagaaa   9660
gcagaacatt tggactttaa gcatgtagta tttgggtttg ttaaggatgg catggatact   9720
gtgaaaaaga ttgaatcatt tggttctccc aaagggtctg tttgtcgaag aataactatc   9780
acagaatgtg gacagatata aaatcattgt tgttcataga aaatttcatc tgtataagca   9840
gttggattga agcttagcta ttacaatttg atagttatgt tcagcttttg aaaatggacg   9900
tttccgattt acaaatgtaa aattgcagct tatagctgtt gtcacttttt aatgtgttat   9960
aattgacctt gcatggtgtg aaataaaagt ttaaacactg gtgtatttca ggtgtacttg  10020
tgtttatgta ctcctgacgt attaaaatgg aataatacta atcttgttaa aagcaataga  10080
cctcaaacta ttgaaggaat atgatatatg caatttaatt ttaattcctt ttaagatatt  10140
tggacttcct gcatggatat acttaccatt tgaataaagg gaccacaact tggataattt  10200
aattttaggt ttgaaatata tttggtaatc ttaactattg gtgtactcat ttatgcatag  10260
```

```
agactcgttt atgaatgggt agagccacag aacgtataga gttaaccaaa gtgctcttct  10320
ctagaatctt tacacctcct gtgtggttac aagttaactt tgtaagtagc gtaccttcct  10380
tccttaaaat atctagcttc ctgtgccctt tcatagatat tcgattaatt tttacatttt  10440
aaacaagttg actatttcct ttaggggttt tgtttcaaac ttttctgtca tctgtctcta  10500
ctacctcaga aactgcagct tggttctgat gatagaaatt gaatttttcc ttgtagttat  10560
tgtgataaag tatgaatatt tttagaaagt ctataccatg ttctttcgtt aaagatttgc  10620
tttatacaag attgttgcag taccttttc tggtaaattt tgtagcagaa ataaaatgac  10680
aattcctaag agccactgac atccaaaaaa ttcattactt acgcttcggg ttcattctaa  10740
agtaaggaag acaatttaaa ggcagtaaat tcaaactgct gcataatttc cagagctcct  10800
agtttctcaa gtttgataca caccaaaaac gtatttggaa atggcttgta tcaaatgtta  10860
ggcaaattgc taaagaaaag aggatgttct tattggccta ctcaatatgg aactacaaag  10920
aatccaggta gaacacaaaa ttttgtatat tgcaattatg aatattgact gtcttccacc  10980
catctgtgtt ctttcgggtg aaattacctc attttattta gtgaggaaag acaggtttat  11040
tccctgttac atggggattt ggaaattggg tatcctaaag caagtaactg ttcaaccacc  11100
agtcaaaaga ggggagggat gttgtgcgag taatgagtga tggtatacca tcaccattcc  11160
actcggccac aaagccagat acttgaaata aacctactcc aaatgtatca gttcagtctt  11220
gaaccatgga ttacatatgt ttacactaaa tatttcaaat tggcttattt ggaaatctat  11280
gtaatataaa ctgatgtaaa gtgtgttgta acttttcagc tgagacagtt gatgccttcg  11340
tcatgatttt agaataaatt cttaagttaa tgcaagtgct ttttaagaga ctttttacag  11400
atttgtatgc tttcctaaag cactaaagtt acaaattaaa aagctttaaa aactttgacc  11460
aaaaatttga caaaatgaca tgtaaactga cttttcccgt attagtattc caaagatgct  11520
taaaagtggc ttgtggcatt tatgagaaag tctttgtgtc acatttcagg aaaggacttt  11580
gatttctctt tgttatttaa tcactgatgt ggtctaaacc cacgataata tgtatctttc  11640
cttttaaact ggattttatg ttgtctcatt aaaatctgct taaagataga ataaaattca  11700
ttatttgtac a                                                        11711
```

<210> SEQ ID NO 5
<211> LENGTH: 4205
<212> TYPE: DNA
<213> ORGANISM: Homo sapiens

<400> SEQUENCE: 5

```
ctccctcgct ccctccctgc gcgccgcctc tcactcacag cctcccttcc ttctttctcc     60
ctccgcctcc cgagcaccag cgcgctctga gctgccccca gggtccctcc cccgccgcca    120
gcagcccatt tggagggagg aagtaaggga agaggagagg aaggggagcc ggaccgacta    180
cccagacaga gccggtgaat gggtttgtgg tgacccccgc cccccacccc accctccctt    240
cccacccgac ccccaacccc catccccagt tcgagccgcc gcccgaaagg ccgggccgtc    300
gtcttaggag gagtcgccgc cgccgccacc tccgccatgg agctgatcac cattctcgag    360
aagaccgtgt ctcccgatcg gctggagctg gaagcggcgc agaagttcct ggagcgtgcg    420
gccgtggaga acctgcccac tttccttgtg gaactgtcca gagtgctggc aaatccagga    480
aacagtcagg ttgccagagt tgcagctggt ctacaaatca agaactcttt gacatctaaa    540
gatccagata tcaaggcaca atatcagcag aggtggcttg ctattgatgc taatgctcga    600
```

-continued

```
cgagaagtca agaactatgt tttgcagaca ttgggtacag aaacttaccg gcctagttct    660
gcctcacagt gtgtggctgg tattgcttgt gcagagatcc cagtaaacca gtggccagaa    720
ctcattcctc agctggtggc caatgtcaca aaccccaaca gcacagagca catgaaggag    780
tcgacattgg aagccatcgg ttatatttgc caagatatag acccagagca gctacaagat    840
aaatccaatg agattctgac tgccataatc caggggatga ggaaagaaga gcctagtaat    900
aatgtgaagc tagctgctac gaatgcactc ctgaactcat tggagttcac caaagcaaac    960
tttgataaag agtctgaaag gcactttatt atgcaggtgg tctgtgaagc cacacagtgt   1020
ccagatacga gggtacgagt ggctgcttta cagaatctgg tgaagataat gtccttatat   1080
tatcagtaca tggagacata tatgggtcct gctctttttg caatcacaat cgaagcaatg   1140
aaaagtgaca ttgatgaggt ggctttacaa gggatagaat tctggtccaa tgtctgtgat   1200
gaggaaatgg atttggccat tgaagcttca gaggcagcag aacaaggacg gccccctgag   1260
cacaccagca agttttatgc gaagggagca ctacagtatc tggttccaat cctcacacag   1320
acactaacta aacaggacga aaatgatgat gacgatgact ggaacccctg caaagcagca   1380
ggggtgtgcc tcatgcttct ggccacctgc tgtgaagatg acattgtccc acatgtcctc   1440
cccttcatta aagaacacat caagaaccca gattggcggt accgggatgc agcagtgatg   1500
gcttttggtt gtatcttgga aggaccagag cccagtcagc tcaaaccact agttatacag   1560
gctatgccca ccctaataga attaatgaaa gaccccagtg tagttgttcg agatacagct   1620
gcatggactg taggcagaat ttgtgagctg cttcctgaag ctgccatcaa tgatgtctac   1680
ttggctcccc tgctacagtg tctgattgag ggtctcagtg ctgaacccag agtggcttca   1740
aatgtgtgct gggctttctc cagtctggct gaagctgctt atgaagctgc agacgttgct   1800
gatgatcagg aagaaccagc tacttactgc ttatcttctt catttgaact catagttcag   1860
aagctcctag agactacaga cagacctgat ggacaccaga acaacctgag gagttctgca   1920
tatgaatctc tgatggaaat tgtgaaaaac agtgccaagg attgttatcc tgctgtccag   1980
aaaacgactt tggtcatcat ggaacgactg caacaggttc ttcagatgga gtcacatatc   2040
cagagcacat ccgatagaat ccagttcaat gaccttcagt ctttactctg tgcaactctt   2100
cagaatgttc ttcggaaagt gcaacatcaa gatgctttgc agatctctga tgtggttatg   2160
gcctccctgt taaggatgtt ccaaagcaca gctgggtctg gggggagtaca agaggatgcc   2220
ctgatggcag ttagcacact ggtggaagtg ttgggtggtg aattcctcaa gtacatggag   2280
gcctttaaac ccttcctggg cattggatta aaaaattatg ctgaatacca ggtttgtttg   2340
gcagctgtgg gcttagtggg agacttgtgc cgtgccctgc aatccaacat catacctttc   2400
tgtgacgagg tgatgcagct gcttctggaa aatttgggga atgagaacgt ccacaggtct   2460
gtgaagccgc agattctgtc agtgtttggt gatattgccc ttgctattgg aggagagttt   2520
aaaaaatact tagaggttgt attgaatact cttcagcagg cctcccaagc ccaggtggac   2580
aagtcagact atgacatggt ggattatctg aatgagctaa gggaaagctg cttggaagcc   2640
tatactggaa tcgtccaggg attaaagggg gatcaggaga acgtacaccc ggatgtgatg   2700
ctggtacaac ccagagtaga atttattctg tctttcattg accacattgc tggagatgag   2760
gatcacacag atggagtagt agcttgtgct gctggactaa taggggactt atgtacagca   2820
tttgggaagg atgtactgaa attagtagaa gctaggccaa tgatccatga attgttaact   2880
gaagggcgga gatcgaagac taacaaagca aaaacccttg ctacatgggc aacaaaagaa   2940
ctgaggaaac tgaagaacca agcttgatct gttaccattg ggatgataac ctgaggaccc   3000
```

ccactggaaa tctcccatct tttgaaaaac ctggaagtga ggagtgtgca cggatgctga 3060
atgtttggga atgagaggat gagtgagtga ggcttgaaaa cacaccacat tgaaaatcct 3120
gccacagcag cagccgcagc cgccaacagc agcgctgtta gtgagctaag taagcactga 3180
cttcgtagaa aaccataaca tcggccatct tggaaaagag aaaaacaatg gagttactta 3240
tttaaaaaaa aagaaagaaa gttatctctt cccaggagag gctagaagta gcttttctgt 3300
cttttggcca gtgccgagtg gaatgcctgg tttgggggag gaggagggac tgggttcagc 3360
tgtggtgctt tgttgtaaaa ggcagcctgg cctttgctac tgaggagaaa gatggagcct 3420
gggtctcaag cccaccttcg ctgtaccttt gccacatggt actgtatgct tgccagctag 3480
aaggagggtc agggattttt tacagtctga gaatgagtgt gtgtgagtga ggcggtatcc 3540
acattctcaa cttcaagtca ttgcagtttc tttttcccag aaaacaaggg gttagatgtt 3600
gcatttcata aaactaaccg aagttctgtc tactgatgca gcacaagaga tgtaaaaaaa 3660
aaaaaaaaaa aaaaaaaaaa aacacacaca cagaggaaag acgctcttta ggttttgttt 3720
tgtttttttt ttttggtttt gtttttgtt ttttttactc tagggaaaac actgacgaat 3780
ggtcagagct cctatcctga tcttttcatc aaggcgcctt tcctaataat atggttcaac 3840
tgtgaatgta gaagtggggg ggagggggga gaaaaagaaa actctggcgt tagaggatat 3900
agaaaaatat aagtacaatt gttacaaata acgcagactt caaaaacaaa aaaatcacaa 3960
cccaaacaaa ccaaaattta aatgatcaga attggcagca caaagaaaac gccctctcct 4020
gacttgtatt gtggcagtct gaacgccccc agaaaattgt gccaaagagt ttagaaaaat 4080
aaatatacaa taaaagtaaa cacatacaca caaaacagca aacttcaggt aactattttg 4140
gattgcaaac aggataaatt aaatgttcaa acaatctgat aaaataacca tttggaaact 4200
gaaaa 4205

<210> SEQ ID NO 6
<211> LENGTH: 3579
<212> TYPE: DNA
<213> ORGANISM: Homo sapiens

<400> SEQUENCE: 6
tcaggctcgc tgtcgcgcca ttttgccggg gtttgaatgt gaggcggagc ggcggcagga 60
gcgggtagtg ccagctacgg tccgcggctg gggttccctc ctccgtttct gtatccccac 120
gagatcctat agcaatggaa ctcagcgatg caaatctgca aacactaaca gaatatttaa 180
agaaaacact tgatcctgat cctgccatcc gacgtccagc tgagaaattt cttgaatctg 240
ttgaaggaaa tcagaattat ccactgttgc ttttgacatt actggagaag tcccaggata 300
atgttatcaa agtatgtgct tcagtaacat tcaaaaacta tattaaaagg aactggagaa 360
ttgttgaaga tgaaccaaac aaaatttgtg aagccgatcg agtggccatt aaagccaaca 420
tagtgcactt gatgcttagc agcccagagc aaattcagaa gcagttaagt gatgcaatta 480
gcattattgg cagagaagat tttccacaga aatggcctga cttgctgaca gaaatggtga 540
atcgctttca gagtggagat ttccatgtta ttaatggagt cctccgtaca gcacattcat 600
tatttaaaag ataccgtcat gaatttaagt caaacgagtt atggactgaa attaagcttg 660
ttctggatgc ctttgctttg cctttgacta atctttttaa ggccactatt gaactctgca 720
gtacccatgc aaatgatgcc tctgccctga ggattctgtt ttcttccctg atcctgatct 780
caaaattgtt ctatagttta aactttcagg atctccctga attttttgaa gataatatgg 840

-continued

```
aaacttggat gaataatttt catactctct taacattgga taataagctt ttacaaactg    900
atgatgaaga ggaagccggc ttattggagc tcttaaaatc ccagatttgt gataatgccg    960
cactctatgc acaaaagtac gatgaagaat tccagcgata cctgcctcgt tttgttacag   1020
ccatctggaa tttactagtt acaacgggtc aagaggttaa atatgatttg ttggtaagta   1080
atgcaattca atttctggct tcagtttgtg agagacctca ttataagaat ctatttgagg   1140
accagaacac gctgacaagt atctgtgaaa aggttattgt gcctaacatg gaatttagag   1200
ctgctgatga agaagcattt gaagataatt ctgaggagta cataaggaga gatttggaag   1260
gatctgatat tgatactaga cgcagggctg cttgtgatct ggtacgagga ttatgcaagt   1320
tttttgaggg acctgtgaca ggaatcttct ctggttatgt taattccatg ctgcaggaat   1380
acgcaaaaaa tccatctgtc aactggaaac acaaagatgc agccatctac ctagtgacat   1440
ctttggcatc aaaagcccaa acacagaagc atggaattac acaagcaaat gaacttgtaa   1500
acctaactga gttctttgtg aatcacatcc tccctgattt aaaatcagct aatgtgaatg   1560
aatttcctgt ccttaaagct gacggtatca aatatattat gatttttaga aatcaagtgc   1620
caaaagaaca tcttttagtc tcgattcctc tcttgattaa tcatcttcaa gctgaaagta   1680
ttgttgttca tacttacgca gctcatgctc ttgaacggct ctttactatg cgagggccta   1740
acaatgccac tctctttaca gctgcagaaa tcgcaccgtt tgttgagatt ctgctaacaa   1800
accttttcaa agctctcaca cttcctggct cttcagaaaa tgaatatatt atgaaagcta   1860
tcatgagaag tttttctctc ctacaagaag ccataatccc ctacatccct actctcatca   1920
ctcagcttac acagaagcta ttagctgtta gtaagaaccc aagcaaacct cactttaatc   1980
actacatgtt tgaagcaata tgtttatcca taagaataac ttgcaaagct aaccctgctg   2040
ctgttgtaaa ttttgaggag gctttgtttt tggtgtttac tgaaatctta caaaatgatg   2100
tgcaagaatt tattccatac gtctttcaag tgatgtcttt gcttctggaa acacacaaaa   2160
atgacatccc gtcttcctat atggccttat ttcctcatct ccttcagcca gtgctttggg   2220
aaagaacagg aaatattcct gctctagtga ggcttcttca agcattctta gaacgcggtt   2280
caaacacaat agcaagtgct gcagctgaca aaattcctgg gttactaggt gtctttcaga   2340
agctgattgc atccaaagca aatgaccacc aaggtttta tcttctaaac agtataatag    2400
agcacatgcc tcctgaatca gttgaccaat ataggaaaca aatcttcatt ctgctattcc   2460
agagacttca gaattccaaa acaaccaagt ttatcaagag ttttttagtc tttattaatt   2520
tgtattgcat aaaatatggg gcactagcac tacaagaaat atttgatggt atacaaccaa   2580
aaatgtttgg aatggttttg gaaaaaatta ttattcctga aattcagaag gtatctggaa   2640
atgtagagaa aaagatctgt gcggttggca taaccaaatt actaacagaa tgtcccccaa   2700
tgatggacac tgagtatacc aaactgtgga ctccattatt acagtctttg attggtcttt   2760
ttgagttacc cgaagatgat accattcctg atgaggaaca ttttattgac atagaagata   2820
caccaggata tcagactgcc ttctcacagt tggcatttgc tgggaaaaaa gagcatgatc   2880
ctgtaggtca aatggtgaat aaccccaaaa ttcacctggc acagtcactt cacaagttgt   2940
ctaccgcctg tccaggaagg gttccatcaa tggtgagcac cagcctgaat gcagaagcgc   3000
tccagtatct ccaagggtac cttcaggcag ccagtgtgac actgctttaa actgcatttt   3060
tctaatgggc taaacccaga tggtttccta ggaaatcaca ggcttctgag cacagctgca   3120
ttaaaacaaa ggaagttctc cttttgaact tgtcacgaat tccatcttgt aaaggatatt   3180
aaatgttgct ttaacctgaa ccttgagcaa attagttggt ttgtgtgatc atacagttat   3240
```

gtgggtggct tctagtttgc aacttcaagg gacaagtatt aatagttcag tgtatggcgt 3300
tggtttgtgt tgagcgtttg cacggtttgg ataatcttaa attttgacgg acactgtgga 3360
gactttctgt tactaaatcc ttttgttttg aagctgttgc tatttgtatt tctcttgtcc 3420
tttatatttt ttgtctgttt atttacgctt ttattggaaa tgtgaataag taaagaatta 3480
cttgtgttac ttgccaagca gtgcacattt catagtttca aatctgtaat cagcaataaa 3540
aatcctaaaa tatgtaccta aaaaaaaaaa aaaaaaaaa 3579

<210> SEQ ID NO 7
<211> LENGTH: 4830
<212> TYPE: DNA
<213> ORGANISM: Homo sapiens

<400> SEQUENCE: 7
caaccggttc cgagtttgag gcactaggag gagggggaga agcggctgca gcggccgcgg 60
caggagcagc gggagctaca gcatcagcaa gagcaacagt agctacagcc ccggcggcgg 120
tgcctgttcc agtctttgct gctgcagtcc gtgcaaccac ccagaggggg aggggggaac 180
caccagtcgc tgaggaacaa gagaaggggg gaaagtttag gcgagccttg gggggggggg 240
ggccagcgcc ggagccgcgt gagagaggga gccgtgtttt ggtagggggg agtcggactg 300
caactggcag cagagcgtct ccccggccgt gtggactcta cacccccctac tcctgccgct 360 tctgctgctg cctgtggctg gagggtcccc ctggggctga atctttggga cttgaccccg 420
ttccctcccc cttccctcac tccccagccg ggcgggagca tttattcccc agattaattc 480
cccttttggg ggggggcggg tgtgtgtgtg tgtgtgtgtg tgtgtgtgtg ttgggggaag 540
cgtccctgaa atagtaaata ttattgagct ctttttgccc ttttcctgtc cgttttttta 600
atttcctttt ttgaggtggg aaaactgaaa cccaccttga ttcgtcccct ctcccccctc 660
cccaccttcc ctcgccctaa tcccccaacg aggaaggaag gagcagttgg ttcaatctct 720
ggtaatctat gccagcaatt atgacaatgt tagcagacca tgcagctcgt cagctgcttg 780
atttcagcca aaaactggat atcaacttat tagataatgt ggtgaattgc ttataccatg 840
gagaaggagc ccagcaaaga atggctcaag aagtactgac acatttaaag gagcatcctg 900
atgcttggac aagagtcgac acaattttgg aattttctca gaatatgaat acgaaatact 960
atggactaca aattttggaa aatgtgataa aaacaaggtg gaagattctt ccaaggaacc 1020
agtgcgaagg aataaaaaaa tacgttgttg gcctcattat caagacgtca tctgacccaa 1080
cttgtgtaga gaaagaaaag gtgtatatcg gaaaattaaa tatgatcctt gttcagatac 1140
tgaaacaaga atggcccaaa cattggccaa cttttatcag tgatattgtt ggagcaagta 1200
ggaccagcga aagtctctgt caaaataata tggtgattct taaactcttg agtgaagaag 1260
tatttgattt ctctagtgga cagataaccc aagtcaaatc taagcattta aaagacagca 1320
tgtgcaatga attctcacag atatttcaac tgtgtcagtt tgtaatggaa aattctcaaa 1380
atgctccact tgtacatgca accttggaaa cattgctcag atttctgaac tggattcccc 1440
tgggatatat ttttgagacc aaattaatca gcacattgat ttataagttc ctgaatgttc 1500
caatgtttcg aaatgtctct ctgaagtgcc tcactgagat tgctggtgtg agtgtaagcc 1560
aatatgaaga acaatttgta aactatttta ctctgacaat gatgcaacta aagcagatgc 1620
ttcctttaaa taccaatatt cgacttgcgt actcaaatgg aaaagatgat gaacagaact 1680
tcattcaaaa tctcagtttg tttctctgca cctttcttaa ggaacatgat caacttatag 1740

-continued

```
aaaaaagatt aaatctcagg gaaactctta tggaggccct tcattatatg ttgttggtat   1800
ctgaagtaga agaaactgaa atctttaaaa tttgtcttga atactggaat catttggctg   1860
ctgaactcta tagagagagt ccattctcta catctgcctc tccgttgctt tctggaagtc   1920
aacattttga tgttcctccc aggagacagc tatatttgcc catgttattc aaggtccgtt   1980
tattaatggt tagtcgaatg gctaaaccag aggaagtatt ggttgtagag aatgatcaag   2040
gagaagttgt gagagaattc atgaaggata cagattccat aaatttgtat aagaatatga   2100
gggaaacatt ggtttatctt actcatctgg attatgtaga tacagaaaga ataatgacag   2160
agaagcttca caatcaagtg aatggtacag agtggtcatg gaaaaatttg aatacattgt   2220
gttgggcaat aggctccatt agtggagcaa tgcatgaaga ggacgaaaaa cgatttcttg   2280
ttactgttat aaaggatcta ttaggattat gtgaacagaa aagaggcaaa gataataaag   2340
ctattattgc atcaaatatc atgtacatag taggtcaata cccacgtttt ttgagagctc   2400
actggaaatt tctgaagact gtagttaaca agctgttcga attcatgcat gagacccatg   2460
atggagtcca ggatatggct tgtgatactt tcattaaaat agcccaaaaa tgccgcaggc   2520
atttcgttca ggttcaggtt ggagaagtga tgccatttat tgatgaaatt ttgaacaaca   2580
ttaacactat tatttgtgat cttcagcctc aacaggttca tacgttttat gaagctgtgg   2640
ggtacatgat tggtgcacaa acagatcaaa cagtacaaga acacttgata gaaaagtaca   2700
tgttactccc taatcaagtg tgggatagta taatccagca ggcaaccaaa aatgtggata   2760
tactgaaaga tcctgaaaca gtcaagcagc ttggtagcat tttgaaaaca aatgtgagag   2820
cctgcaaagc tgttggacac ccctttgtaa ttcagcttgg aagaatttat ttagatatgc   2880
ttaatgtata caagtgcctc agtgaaaata tttctgcagc tatccaagct aatggtgaaa   2940
tggttacaaa gcaaccattg attagaagta tgcgaactgt aaaaagggaa actttaaagt   3000
taatatctgg ttgggtgagc cgatccaatg atccacagat ggtcgctgaa aattttgttc   3060
cccctctgtt ggatgcagtt ctcattgatt atcagagaaa tgtcccagct gctagagaac   3120
cagaagtgct tagtactatg gccataattg tcaacaagtt agggggacat ataacagctg   3180
aaatacctca aatatttgat gctgtttttg aatgcacatt gaatatgata aataaggact   3240
ttgaagaata tcctgaacat agaacgaact tttcttact acttcaggct gtcaattctc    3300
attgtttccc agcattcctt gctattccac ctacacagtt taaacttgtt ttggattcca   3360
tcatttgggc tttcaaacat actatgagga atgtcgcaga tacgggctta cagatacttt   3420
ttacactctt acaaaatgtt gcacaagaag aagctgcagc tcagagtttt tatcaaactt   3480
atttttgtga tattctccag catatctttt ctgttgtgac agacacttca catactgctg   3540
gtttaacaat gcatgcatca attcttgcat atatgtttaa tttggttgaa gaaggaaaaa   3600
taagtacatc attaaatcct ggaaatccag ttaacaacca aatctttctt caggaatatg   3660
tggctaatct ccttaagtcg gccttccctc acctacaaga tgctcaagta aagctctttg   3720
tgacagggct tttcagctta aatcaagata ttcctgcttt caaggaacat ttaagagatt   3780
tcctagttca aataaaggaa tttgcaggtg aagacacttc tgatttgttt ttggaagaga   3840
gagaaatagc cctacggcag gctgatgaag agaaacataa acgtcaaatg tctgtccctg   3900
gcatctttaa tccacatgag attccagaag aaatgtgtga ttaaaatcca aattcatgct   3960
gtttttttc tctgcaactc gttagcagag gaaaacagca tgtgggtatt tgtcgaccaa    4020
aatgatgcca atttgtaaat taaaatgtca cctagtggcc ctttttctta tgtgtttttt   4080
tgtataagaa attttctgtg aaatatcctt ccattgttta agcttttgtt ttggtcatct   4140
```

ttatttagtt tgcatgaagt tgaaaattaa ggcattttta aaaattttac ttcatgccca 4200
tttttgtggc tgggctgggg ggaggaggca aattcgattt gaacatatac ttgtaattct 4260
aatgcaaaat tatacaattt ttcctgtaaa caataccaat ttttaattag ggagcatttt 4320
ccttctagtc tatttcagcc tagaagaaaa gataatgagt aaaacaaatt gcgttgttta 4380
aaggattata gtgctgcatt gtctgaagtt agcacctctt ggactgaatc gtttgtctag 4440
actacatgta ttacaaagtc tctttggcaa gattgcagca agatcatgtg catatcatcc 4500
cattgtaaag cgacttcaaa aatatgggaa cacagttagt tatttttaca cagttctttt 4560
tgtttttgtg tgtgtgtgct gtcgcttgtc gacaacagct tttgttttc ctcaatgagg 4620 agtgttgctc atttgtgagc cttcattaac tcgaagtgaa atggttaaaa atatttatcc 4680
tgttagaata ggctgcatct ttttaacaac tcattaaaaa acaaaacaac tctggctttt 4740
gagatgactt atactaattt acattgttta ccaagctgta gtgctttaag aacactactt 4800
aaaaagcaaa ataaacttgg tttacattta 4830

<210> SEQ ID NO 8
<211> LENGTH: 4039
<212> TYPE: DNA
<213> ORGANISM: Homo sapiens

<400> SEQUENCE: 8
ctggacctgg gcaccgccag ccgcctgggc acgggactgg gcgggggcgc tgacctcggc 60
ctaggaggcc caggatcccg gagacgcccg cgccctcagg accctgcggg tcgcacgccc 120
tccccagctt ctgctgctcg ccgctcttcg gcagggcgag gtcaggtgcc cccttctcgc 180
ctctcttctc ttctcttcct cctccacttc tgtgcccgcg gagactccgg ccgccccctt 240
ccgcaggggt gtagtaatct gcggagctga cagcagcccc gcagccaccc tgcccgaagt 300
ctccggaagc ggcacgagct caggccgccg cagccccggc gaacccactg ttggacctga 360
ggagccagcc ctcctcccgc acccaaactt ggagcacttg acctttggct gttggagggg 420
gcaggctcgc gggtggctgg acagctgcgg agccgcgagg gcatcttgcc tggagaccgt 480
cggctgcact cccgggctcc tggctttgcc tctgggatcc cgaggtgtcc acatcagacg 540
catgttgact gagacctaga gtcatggatg tatgcgtccg tcttgccctg tggctcctct 600
ggggactcct cctgcaccag ggccagagcc tcagccatag tcacagtgag aaggcgacag 660
gaaccagctc gggggccaac tctgaggagt ccactgcagc agagttttgc cgaattgaca 720
agcccctgtg tcacagtgag gatgagaaac tcagcttcga ggcagtccgt aacatccaca 780
aactgatgga cgatgatgcc aatggtgatg tggatgtgga agaaagtgat gagttcctga 840
gggaagacct caattaccat gacccaacag tgaaacacag caccttccat ggtgaggata 900
agctcatcag cgtggaggac ctgtggaagg catggaagtc atcagaagta tacaattgga 960
ccgtggatga ggtggtacag tggctgatca catatgtgga gctgcctcag tatgaggaga 1020
ccttccggaa gctgcagctc agtggccatg ccatgccaag gctggctgtc accaacacca 1080
ccatgacagg gactgtgctg aagatgacag accggagtca tcggcagaag ctgcagctga 1140
aggctctgga tacagtgctc tttgggcctc ctctcttgac tcgccataat cacctcaagg 1200
acttcatgct ggtggtgtct atcgttattg gtgtgggcgg ctgctggttt gcctatatcc 1260
agaaccgtta ctccaaggag cacatgaaga agatgatgaa ggacttggag gggttacacc 1320
gagctgagca gagtctgcat gaccttcagg aaaggctgca caaggcccag gaggagcacc 1380
gcacagtgga ggtggagaag gtccatctgg aaaagaagct gcgcgatgag atcaaccttg 1440
ctaagcagga agcccagcgg ctgaaggagc tgcgggaggg tactgagaat gagcggagcc 1500
gccaaaaata tgctgaggag gagttggagc aggttcggga ggccttgagg aaagcagaga 1560
aggagctaga atctcacagc tcatggtatg ctccagaggc ccttcagaag tggctgcagc 1620
tgacacatga ggtggaggtg caatattaca acatcaagaa gcaaaatgct gagaagcagc 1680
tgctggtggc caaggagggg gctgagaaga taaaaaagaa gagaaacaca ctctttggca 1740
ccttccacgt ggcccacagc tcttccctgg atgatgtaga tcataaaatt ctaacagcta 1800
agcaagcact gagcgaggtg acagcagcat tgcgggagcg cctgcaccgc tggcaacaga 1860
tcgagatcct ctgtggcttc cagattgtca acaaccctgg catccactca ctggtggctg 1920
ccctcaacat agaccccagc tggatgggca gtacacgccc caaccctgct cacttcatca 1980
tgactgacga cgtggatgac atggatgagg agattgtgtc tcccttgtcc atgcagtccc 2040
ctagcctgca gagcagtgtt cggcagcgcc tgacggagcc acagcatggc ctgggatctc 2100
agagggattt gacccattcc gattcggagt cctccctcca catgagtgac cgccagcgtg 2160
tggcccccaa acctcctcag atgagccgtg ctgcagacga ggctctcaat gccatgactt 2220
ccaatggcag ccaccggctg atcgaggggg tccacccagg gtctctggtg gagaaactgc 2280
ctgacagccc tgccctggcc aagaaggcat tactggcgct gaaccatggg ctggacaagg 2340
cccacagcct gatggagctg agcccctcag ccccacctgg tggctctcca catttggatt 2400
cttcccgttc tcacagcccc agctccccag acccagacac accatctcca gttggggaca 2460
gccgagccct gcaagccagc cgaaacacac gcattcccca cctggctggc aagaaggctg 2520
tggctgagga ggataatggc tctattggcg aggaaacaga ctccagccca ggccggaaga 2580
agtttcctct caaaatcttt aagaagcctc ttaagaagta ggcaggatgg ggtggcagta 2640
aagggacagc ttgtccttcc ctgggtgttc tgtctctcct tccctccctt ccttcaagat 2700
aactggcccc aagagtgggg catgggaagg gctggtccag ggtctgggc actgtacata 2760
cctgcccct catccttggg tccttcatta ttatttatta actgaccacc atggcctgcc 2820
tgccctgcct ccgtcccaac catgggctgc tgctgtcact ccctctccac ttcagtgcat 2880
gtcttagttg ctgttccctc agctcccagc tccacctctg gggttcagct tctgtctctg 2940
ctgtcccagt tttgaggttt ggtttcttgt ttctgtctct tgctttcagg ctcctccctc 3000
ccaccactcc ccaacttccc ctagcagttg cagggaagat aggacgagta gcttctgaca 3060
tgtgtgcctc agatctgttc caccccactc acagtggttc tgtttgctcc agactggggc 3120
tagggcctaa tctttgaagt ttgttctttg gtattgatgt gggtcagaag gagcctcatc 3180
ctaatctcac tcaggcctcc agggatccat gggggagtga aaccaattct cagagaacaa 3240
cccaccagag acttttaaag agaggccagg cttgggaatg ggttgggaga ggcatctgtt 3300
cattggagca tgagtggatg ccagaactgt aggttataag gcagtcactt tttctctcta 3360
ctcccaccca cacctgcctc cctcttaccc ctgctccccc acactgcagg aggatttgtc 3420
tctaagaggt gctgccccaa agctccccaa gcatcaatac tcctagggct caggacaagt 3480
ggctcccctg gccaggagag ccacagccat gatacagggc tcttatggag ccctggagtt 3540
gttgggcaag gatgctgtca ttttttgaac caaaagacaa acaggttaaa aggaaaaaaa 3600
gtaatctgaa tttcccaagt gcctacgctg catattcccc ttgttagatc ccattttcat 3660
gttactttgt agccttggcc agaggctcaa aaaggacaca accagtttgg ggaaggggtg 3720
gctaaggaag atggtatagg tgaaggcggc tgtgtgacca ctttccccca cccttcccac 3780

```
cctctagaca actctctccc ttacctgttt ttgctatggc tgtaaaggta tttttcctct   3840

gccccactcc ctgccatacc tttatcctgg gatcctattt tgggcctggg gtgggtatac   3900

ctggggctgg tcttaggagg gtgctaggct gcagactgcc ttgtactccc tggacaccct   3960

caaatggggt tttctgtgtt atttcataaa attctttgaa gtccaataaa gcatgtagga   4020

gattttaacc acaaaaaaa                                                4039
```

<210> SEQ ID NO 9
<211> LENGTH: 3924
<212> TYPE: DNA
<213> ORGANISM: Homo sapiens

<400> SEQUENCE: 9

```
ggcggagcgt ggtactacga ccagcgcggg ccggaggggg cggggggatg cgccgcggcg     60

gcggcggcgc gggagctggg gttggtgttt ggcggcgcca gagcagcgga tcccggtctc    120

gccgcagcag cagcgcgggt gtcgtgcacc gcctgaagac gccgtacctt tctacccccc    180

accttttttt tttttttttt taaataaccg gaaccaatga acgcagccgg gatcagagct    240

ccggaggccg ccggtgccga tgggaccagg ctggcgcccg gcgggagccc gtgtctgagg    300

cggcgggggc ggccggagga gtcgccggcg gcggtggtgg cgcctcgcgg agccggcgag    360

ctgcaggcgg ccggggcgcc gctgcgcttt cacccggctt ctcctcggcg ccttcatccc    420

gcctcgactc ctggcccagc gtggggctgg ctgctgcggc ggcggcgctg ggctgcgttg    480

ctggtgctcg ggctgctggt agccggagcg gcggacggat gcgagcttgt gccccggcac    540

ctccgcgggc ggcgggcgac tggctctgcc gcaactgccg cctcctctcc cgccgcggcg    600

gccggcgata gcccggcgct catgacagat ccctgcatgt cactgagtcc accatgcttt    660

acagaagaag acagatttag tctggaagct cttcaaacaa tacataaaca aatggatgat    720

gacaaagatg gtggaattga agtagaggaa agtgatgaat tcatcagaga agatatgaaa    780

tataaagatg ctactaataa acacagccat ctgcacagag aagataaaca tataacgatt    840

gaggatttat ggaaacgatg gaaaacatca gaagttcata attggaccct tgaagacact    900

cttcagtggt tgatagagtt tgttgaacta ccccaatatg agaagaattt tagagacaac    960

aatgtcaaag gaacgacact tcccaggata gcagtgcacg aaccttcatt tatgatctcc   1020

cagttgaaaa tcagtgaccg gagtcacaga caaaaacttc agctcaaggc attggatgtg   1080

gttttgtttg gacctctaac acgcccacct cataactgga tgaaagattt tatcctcaca   1140

gtttctatag taattggtgt tggaggctgc tggtttgctt atacgcagaa taagacatca   1200

aaagaacatg ttgcaaaaat gatgaaagat ttagagagct tacaaactgc agagcaaagt   1260

ctaatggact tacaagagag gcttgaaaag gcacaggaag aaaacagaaa tgttgctgta   1320

gaaaagcaaa atttagagcg caaaatgatg gatgaaatca attatgcaaa ggaggaggct   1380

tgtcggctga gagagctaag ggagggagct gaatgtgaat tgagtagacg tcagtatgca   1440

gaacaggaat tggaacaggt tcgcatggct ctgaaaaagg ccgaaaaaga atttgaactg   1500

agaagcagtt ggtctgttcc agatgcactt cagaaatggc ttcagttaac acatgaagta   1560

gaagtgcaat actacaatat taaaagacaa aacgctgaaa tgcagctagc tattgctaaa   1620

gatgaggcag aaaaaattaa aaagaagaga agcacagtct ttgggactct gcacgttgca   1680

cacagctcct ccctagatga ggtagaccac aaaattctgg aagcaaagaa agctctctct   1740

gagttgacaa cttgtttacg agaacgactt tttcgctggc aacaaattga gaagatctgt   1800
```

```
ggctttcaga tagcccataa ctcaggactc cccagcctga cctcttccct ttattctgat   1860

cacagctggg tggtgatgcc cagagtctcc attccaccct atccaattgc tggaggagtt   1920

gatgacttag atgaagacac acccccaata gtgtcacaat ttcccgggac catggctaaa   1980

cctcctggat cattagccag aagcagcagc ctgtgccgtt cacgccgcag cattgtgccg   2040

tcctcgcctc agcctcagcg agctcagctt gctccacacg ccccccaccc gtcacaccct   2100

cggcaccctc accacccgca acacacacca cactccttgc cttcccctga tccagatatc   2160

ctctcagtgt caagttgccc tgcgctttat cgaaatgaag aggaggaaga ggccatttac   2220

ttctctgctg aaaagcaatg ggaagtgcca gacacagctt cagaatgtga ctccttaaat   2280

tcttccattg gaaggaaaca gtctcctcct ttaagcctcg agatatacca aacattatct   2340

ccgcgaaaga tatcaagaga tgaggtgtcc ctagaggatt cctcccgagg ggattcgcct   2400

gtaactgtgg atgtgtcttg ggttctcccc gactgtgtag gtctgacaga aactaagagt   2460

atgatcttca gtcctgcaag caaagtgtac aatggcattt tggagaaatc ctgtagcatg   2520

aaccagcttt ccagtggcat cccggtgcct aaacctcgcc acacatcatg ttcctcagct   2580

ggcaacgaca gtaaaccagt tcaggaagcc ccaagtgttg ccagaataag cagcatccca   2640

catgaccttt gtcataatgg agagaaaagc aaaaagccat caaaaatcaa aagccttttt   2700

aagaagaaat ctaagtgaac tggctgactt gatggaatca tgttcaagtg gcatctgtaa   2760

actattatcc cccaccctcc actccccacc tttttttgg tttaatttta ggaatgtaac   2820

tccattgggg ctttccaggc cggatgccat agtggaacat ccagaagggc aactgtctac   2880

tgtctgctta tttaagtgac tatatataat caattcatca agccagttat tactgaaaaa   2940

tcattgaaat gagacagttt acagtcattt ctgcctattt atttctgctt tgttctcagt   3000

gatgtatatg caacattttg ttgaaagcca cgatggactt acaagcttta atggactcgt   3060

aagccagcat gggcttgcaa aaatttcttg tttaccagag catcttctta tctttccaca   3120

gagctattta catcctggac tatataactt aaaagaagta aaacgtaatt gcactactgt   3180

tttccagact ggaaaaaaaa aaaatctctg caagtgaaac tgtatagagt ttataaaatg   3240

actatggata ggggactgtt ttcactttta gatcaaaatg ggtttttaag tagaacctag   3300

ggtttctaat tgacttgatt tctggaaatg aaaacccgcg cttttattat gggaagcttc   3360

ttgaactgca tttactattg tgaagtttca agtcccgctg taaagatcat gttgttttgt   3420

tttccccagg gctttcactg tgatttactg cattgcaggc tgtatgataa aacacacata   3480

atttaaagag agaaggctct tgattcctta tgcaagtgga agagttgaaa cttgattgaa   3540

ggacttaaaa cattcacaac cttaagccga ggtgggggga tatggggatt caggcaattg   3600

tttacacact ttgaataact gcaaaggatt tacggtttgt gaaaaatgtg tactgtggaa   3660

aagataataa attgaagaca ttattgtgtg ggattgtgct gatttttgtt gataacacaa   3720

aaaacactat gttttctgga gagctgtgta agctgtcttg ttgcttagtt gcaatataag   3780

aaatagtgat gttttggacg taagttgtca acaaatttct attttatatt gttatatttt   3840

tatgtagttt gaaatgtaaa aatgttctaa tatcaagatt aacaaatata aatttatggt   3900

gcatttagaa aaaaaaaaaa aaaa                                          3924
```

<210> SEQ ID NO 10
<211> LENGTH: 1496
<212> TYPE: DNA
<213> ORGANISM: Homo sapiens

<400> SEQUENCE: 10
gccgcccggg ggcttttgcc agcggcgccg cgggcctgcg tgctggggca gcgggcactt 60
cttcgacctc gtcctcctcg tcctgtgcgg ccggccgggt gaggccgggc ccgcgtaggg 120
ggcagtcggc ggctgcctcc ggcggaggtg cctcgcggcg cccgggccgg cccgcgcctc 180
ggcggcgtgc tccatgcatc cggagcccgc cccgccccg agccgcagca gtcccgagct 240
tcccccaagc ggcggcagca ccaccagcgg cagccgccgg agccgccgcc gcagcgggga 300
cggggagccc ccgggggccc cgccaccgcc gccgtccgcc gtcacctacc cggactggat 360
cggccagagt tactccgagg tgatgagcct caacgagcac tccatgcagg cgctgtcctg 420
gcgcaagctc tacttgagcc gcgccaagct taaagcctcc agccggacct cggctctgct 480
ctccggcttc gccatggtgg caatggtgga ggtgcagctg gacgctgacc acgactaccc 540
accggggctg ctcatcgcct tcagtgcctg caccacagtg ctggtggctg tgcacctgtt 600
tgcgctcatg atcagcacct gcatcctgcc caacatcgag gcggtgagca acgtgcacaa 660
tctcaactcg gtcaaggagt ccccccatga gcgcatgcac cgccacatcg agctggcctg 720
ggccttctcc accgtcatcg gcacgctgct cttcctagct gaggtggtgc tgctctgctg 780
ggtcaagttc ttgcccctca agaagcagcc aggccagcca aggcccacca gcaagccccc 840
cgccagtggc gcagcagcca acgtcagcac cagcggcatc accccgggcc aggcagctgc 900
catcgcctcg accaccatca tggtgccctt cggcctgatc tttatcgtct tcgccgtcca 960
cttctaccgc tcactggtta gccataagac tgaccgacag ttccaggagc tcaacgagct 1020
ggcggagttt gcccgcttac aggaccagct ggaccacaga ggggaccacc ccctgacgcc 1080
cggcagccac tatgcctagg cccatgtggt ctgggccctt ccagtgcttt ggccttacgc 1140
ccttcccctt gaccttgtcc tgccccagcc tcacggacag cctgcgcagg gggctgggct 1200
tcagcaaggg gcagagcatg gagggaagag gatttttata agagaaattt ctgcactttg 1260
aaactgtcct ctaagagaat aagcatttcc tgttcttcca gctccaggtc cacctcctgt 1320
tgggaggcgg tgggggccca aagtggggcc acacactcgc tgtgtcccct ctcctcccct 1380
gtgccagtgc cacctgggtg cctcctcctg tcctgtccgt ctcaacctcc ctcccgtcca 1440
gcattgagtg tgtacatgtg tgtgtgacac ataaatatac tcataaggac acctcc 1496

<210> SEQ ID NO 11
<211> LENGTH: 2240
<212> TYPE: DNA
<213> ORGANISM: Homo sapiens

<400> SEQUENCE: 11
gtccttcggt gtctgggtgt ggtgagtaga ggtgtgtgtc acaaagtaca gaccattgtg 60
tgtgacaaag cccatcgtgt gtctgtgtgt gtctttatcc acgtggatgg acgtctcttt 120
cttgctctgc cccaagacac accctagccc ctccttattc tcaaaagggg gagctgggga 180
gcctccccct accctggggc ctcccctgcc cctccccgcc ctgcctggcc gtcaccactc 240
cccagagggc acagggctct gctgtgcctc agagcaaaag tcccagagcc agcagagcag 300
gctgacgacc tgcaagccac agtggctgcc ctgtgcgtgc tgcgaggtgg gggaccctgg 360
gcaggaagct ggctgagccc caagaccccg ggggccatgg gcggggatct ggtgcttggc 420
ctgggggcct tgagacgccg aaagcgcttg ctggagcagg agaagtctct ggccggctgg 480
gcactggtgc tggcaggaac tggcattgga ctcatggtgc tgcatgcaga gatgctgtgg 540 ttcgggggggt gctcgtgggc gctctacctg ttcctggtta aatgcacgat cagcatttcc 600

```
accttcttac tcctctgcct catcgtggcc tttcatgcca aagaggtcca gctgttcatg    660

accgacaacg ggctgcggga ctggcgcgtg gcgctgaccg ggcggcaggc ggcgcagatc    720

gtgctggagc tggtggtgtg tgggctgcac ccggcgcccg tgcggggccc gccgtgcgtg    780

caggatttag gggcgccgct gacctccccg cagccctggc cgggattcct gggccaaggg    840

gaagcgctgc tgtccctggc catgctgctg cgtctctacc tggtgccccg cgccgtgctc    900

ctgcgcagcg gcgtcctgct caacgcttcc taccgcagca tcggcgctct caatcaagtc    960

cgcttccgcc actggttcgt ggccaagctt tacatgaaca cgcaccctgg ccgcctgctg   1020

ctcggcctca cgcttggcct ctggctgacc accgcctggg tgctgtccgt ggccgagagg   1080

caggctgtta atgccactgg gcacctttca gacacacttt ggctgatccc catcacattc   1140

ctgaccatcg gctatggtga cgtggtgccg ggcaccatgt ggggcaagat cgtctgcctg   1200

tgcactggag tcatgggtgt ctgctgcaca gccctgctgg tggccgtggt ggcccggaag   1260

ctggagttta acaaggcaga gaagcacgtg cacaacttca tgatggatat ccagtatacc   1320

aaagagatga aggagtccgc tgcccgagtg ctacaagaag cctggatgtt ctacaaacat   1380

actcgcagga aggagtctca tgctgcccgc aggcatcagc gcaagctgct ggccgccatc   1440

aacgcgttcc gccaggtgcg gctgaaacac cggaagctcc gggaacaagt gaactccatg   1500

gtggacatct ccaagatgca catgatcctg tatgacctgc agcagaatct gagcagctca   1560

caccgggccc tggagaaaca gattgacacg ctggcgggga agctggatgc cctgactgag   1620

ctgcttagca ctgccctggg gccgaggcag cttccagaac ccagccagca gtccaagtag   1680

ctggacccac gaggaggaac caggctactt tccccagtac tgaggtggtg gacatcgtct   1740

ctgccactcc tgacccagcc ctgaacaaag cacctcaagt gcaaggacca aaggggggccc   1800

tggcttggag tgggttggct tgctgatggc tgctggaggg gacgctggct aaagtgggta   1860

ggccttggcc cacctgaggc cccaggtggg aacatggtca cccccactct gcataccctc   1920

atcaaaaaca ctctcactat gctgctatgg acgacctcca gctctcagtt acaagtgcag   1980

gcgactggag gcaggactcc tgggtccctg ggaaagaggg tactaggggc ccggatccag   2040

gattctggga ggcttcagtt accgctggcc gagctgaaga actgggtatg aggctggggc   2100

ggggctggag gtggcgcccc ctggtgggac aacaaagagg acaccatttt tccagagctg   2160

cagagagcac ctggtgggga ggaagaagtg taactcacca gcctctgctc ttatctttgt   2220

aataaatgtt aaagccagaa                                                2240
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 12

```
aannnnnnnn nnnnnnnnnn ntt                                              23
```

<210> SEQ ID NO 13
<211> LENGTH: 1708
<212> TYPE: DNA
<213> ORGANISM: Homo sapiens -continued

<400> SEQUENCE: 13

```
acttgcacta ggaagggatt gggccaggtt tgcccaagtc cactgggcat ctttagtaaa      60
tttctctttt tctcctccta ttggcactct ctgaattcca tttgctgccc cctgggaatg     120
cctggcttct actctgttat gacagatgag gagatcaagc gtttcctgga ggacaccacg     180
gatgatggag aactgagcaa gttcgtgaag gatttctcag gaaatgcgag ctgccaccca     240
ccagaggcta agacctgggc atccaggccc caagtcccgg agccaaggcc ccaggccccg     300
gacctctatg atgatgacct ggagttcaga ccccccctcgc ggccccagtc ctctgacaac     360
cagcagtact tctgtgcccc agcccctctc agcccatctg ccaggccccg cagcccatgg     420
ggcaagcttg atccctatga ttcctctgag gatgacaagg agtatgtggg ctttgcaacc     480
ctccccaacc aagtccaccg aaagtccgtg aagaaaggct ttgactttac cctcatggtg     540
gcaggagagt ctggcctggg caaatccaca cttgtcaata gcctcttcct cactgatctg     600
taccgggacc ggaaacttct tggtgctgaa gagaggatca tgcaaactgt ggagatcact     660
aagcatgcag tggacataga agagaagggt gtgaggctgc ggctcaccat tgtggacaca     720
ccaggttttg gggatgcagt caacaacaca gagtgctgga agcctgtggc agaatacatt     780
gatcagcagt ttgagcagta tttccgagac gagagtggcc tgaaccgaaa gaacatccaa     840
gacaacaggg tgcactgctg cctgtacttc atctcaccct tcggccatgg gctccggcca     900
ttggatgttg aattcatgaa ggccctgcat cagcgggtca acatcgtgcc tatcctggct     960
aaggcagaca cactgacacc tcccgaagtg gaccacaaga aacgcaaaat ccgggaggag    1020
attgagcatt ttggaatcaa gatctatcaa ttcccagact gtgactctga tgaggatgag    1080
gacttcaaat tgcaggacca agccctaaag gaaagcatcc catttgcagt aattggcagc    1140
aacactgtag tagaggccag agggcggcga gttcggggtc gactctaccc ctggggcatc    1200
gtggaagtgg aaaacccagg gcactgcgac tttgtgaagc tgaggacaat gctggtacgt    1260
acccacatgc aggacctgaa ggatgtgaca cgggagacac attatgagaa ctaccgggca    1320
cagtgcatcc agagcatgac ccgcctggtg gtgaaggaac ggaatcgcaa caaactgact    1380
cgggaaagtg gtaccgactt ccccatccct gctgtcccac cagggacaga tccagaaact    1440
gagaagctta tccgagagaa agatgaggag ctgcggcgga tgcaggagat gctacacaaa    1500
atacaaaaac agatgaagga gaactattaa ctggctttca gccctggata tttaaatctc    1560
ctcctcttct tcctgtccat gccggcccct cccagcacca gctctgctca ggccccttca    1620
gctactgcca cttcgcctta catccctgct gactgcccag agactcagag gaaataaagt    1680
ttaataaatc tgtaggtggc ttctggaa                                       1708
```

<210> SEQ ID NO 14
<211> LENGTH: 2284
<212> TYPE: DNA
<213> ORGANISM: Homo sapiens

<400> SEQUENCE: 14

```
gggcgcctgc gacgccccgc ctctggctcg ggtgcgggag cggggcctgc ccggactgcg      60
acgccgccac agcttggggc cagttcgccc agtcaggggg atggctcggt cggcctcggg     120
ggtcgacgat cccccgggta ggcgacgtgc cctgtccagg cctcacttcc cgcgtccgca     180
aaacggggtg gacaacgcag cctaaggcag agccgcgcca aggtccctcg ctgtcgccgg     240
gctctggcgg cctgaccggg cctggggtcc gagcgtgccc ccgggcctgg gggggtcgcc     300
gcgatggact cgctggcagc gccccaggac cgcctggtgg agcagctgct gtcgccgcgg     360
```

acccaggccc agaggcggct caaggacatt gacaagcagt acgtgggctt cgccacactg 420
cccaaccagg tgcaccgcaa gtcggtgaag aaaggctttg acttcacact catggtggct 480
ggtgagtcag gcctggggaa gtccacactg gtccacagcc tcttcctgac agacttgtac 540
aaggaccgga agctgctcag tgctgaggag cgcatcagcc agacggtaga gattctaaaa 600
cacacggtgg acattgagga gaagggagtc aagctgaagc tcaccatcgt ggacacgccg 660
ggattcgggg acgctgtcaa caacaccgag tgctggaagc ccatcaccga ctatgtggac 720
cagcagtttg agcagtactt ccgtgatgag agcggcctca accgaaagaa catccaagac 780
aaccgagtgc actgctgcct atacttcatc tccccccttcg ggcatgggct gcggccagtg 840
gatgtgggtt tcatgaaggc attgcatgag aaggtcaaca tcgtgcctct catcgccaaa 900
gctgactgtc ttgtccccag tgagatccgg aagctgaagg agcggatccg ggaggagatt 960
gacaagtttg ggatccatgt ataccagttc cctgagtgtg actcggacga ggatgaggac 1020
ttcaagcagc aggaccggga actgaaggag agcgcgccct tcgccgttat aggcagcaac 1080
acggtggtgg aggccaaggg gcagcgggtc cggggccgac tgtacccctg gggatcgtg 1140 gagggcgcat tgcgacttcg tgaagctgcg caacatgctc atccgcacgc atatgcacga 1200
cctcaaggac gtgacgtgcg acgtgcacta cgagaactac cgcgcgcact gcatccagca 1260
gatgaccagc aaactgaccc aggacagccg catggagagc ccccatcccga tcctgccgct 1320 gcccaccccg gacgccgaga ctgagaagct tatcaggatg aaggatgagg aactgaggcg 1380
catgcaggag atgctgcaga ggatgaagca gcagatgcag gaccagtgac gctcgccgcg 1440
gacacaccgt ccgtctccgg gacgccctcg cacccctgga caccagaccg gactgttccc 1500
gacccggaga cgcggggcca cagcccccag ctgaccctaa tttattctca gcaccacccc 1560
ctcccaggtc attgtgtctg tttccgaggg gcctggaccg tagcccccgc ccagctggcc 1620
ctctctgacc ttgggggatc aggagcgaag ttgggcggga cttcagagat ccgcctccct 1680
tgcccttccc ccgcccccgg acggtcacag cacccaaacc gcaggccctg ctctggcagg 1740
caggcaaagc taggcagaag aggattccca ggatcctggg tctgttccct gccccagtgc 1800
tgcagaacgg acttgggagc cctcctttgc ctgctcccgc gggtcaccca gcgagtgctg 1860
agaccccatt ttctgtcgag gcgggccgag tcttccctta tccccagacg cctagcgggc 1920
agggttgggc tgaatcaaat gggagccctc cagacataag gaggccagag gctgcaagga 1980
gcggggtcgt gaccgcttac acccccttctc cacagcccgg cccgacctgg agggccccccg 2040 gggcactggg cggtgagcca cctcctggca actctcggtg ccgtcccctg ccctcgctcg 2100
aggcctcttc tccccagcac cgctgtggtg tgccgggatc ctgagcctag gcctcccgat 2160
gttcccaccc gcatgatccc ttcccgccac acgatgctcc gttttcttcc gttgtgaatg 2220
ccgcgtcctg tcctggtgac aggagaacaa tgttggtgaa cgtcgcaaaa aaaaaaaaaa 2280
aaaa 2284

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
gcuauugcau gucgaaaua 19

```
<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

gguggugucu aucguuauu                                                  19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17

ggacaaugcu gguacguac                                                  19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18

ggagacacau uaugagaac                                                  19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19

gggucaacau cgugccuau                                                  19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20

gaacauccaa gacaaccga                                                  19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

ggagaacagu ggcuuugaa                                                  19
```

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
guggagggaa ugacaauaa 19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
ugccaugcau uaagagcua 19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24
ggacacaggg cuucagcuu 19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25
gggcaugggu cagaaggau 19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 26
caacaagauu ccuggccua 19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27
ggccugaucu uuaucgucu 19

-continued

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 28
ucacacagau ggaguagua 19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 29
auagugcacu ugaugcuua 19

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
agcgtagaat atgtacctgg ta 22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
taccaggtac atattctacg cg 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
aggcaaggat gttatatttg aa 22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ttcaaatata acatccttgc cc 22

<210> SEQ ID NO 34

-continued

<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
aacggttgca atcggcgatg ta 22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
tacatcgccg attgcaaccg tg 22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
aggtgactcc ctccaggaat at 22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
atattcctgg agggagtcac cc 22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
accctttgac tctgtaagga aa 22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
tttccttaca gagtcaaagg gc 22

<210> SEQ ID NO 40
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
accctattaa caggatagct ta 22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
taagctatcc tgttaatagg gc 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
cgctaagttt gctgacattt at 22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
ataaatgtca gcaaacttag ct 22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
acctaagcaa acttggttgt aa 22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
ttacaaccaa gtttgcttag gg 22

<210> SEQ ID NO 46
<211> LENGTH: 22
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 46
cgccgagact cggagagtga ta 22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
tatcactctc cgagtctcgg ct 22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
cgggactcaa catgtcaaca ta 22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
tagttgacat gttgagtccc at 22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
agcacctttc cttaagagcc ta 22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
taggctctta aggaaaggtg cc 22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
cggtgtctct tgcctcaata ta 22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
tatattgagg caagagacac ca 22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
acgccaggac agttaatatt aa 22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
ttaatattaa ctgtcctggc gc 22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
tctcctctga cttcaacagc 20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ctgttgctgt agccaaattc g 21

<210> SEQ ID NO 58
<211> LENGTH: 24
<212> TYPE: DNA
<213> ORGANISM: Artificial Sequence
<220> FEATURE:

<223> OTHER INFORMATION: Description of Artificial Sequence: Synthetic
primer

<400> SEQUENCE: 58
aaagtgaagc tgacccttgt ggac 24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
agtcctggat gttcttccgg ttca 24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
ttgagaggta cctgcatgac gaga 24

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
ccttcataaa cgccacatct aagggc 26

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
atttctcagg aaatgcgagc tgcc 24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
aagtactgct ggttgtcaga ggac 24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tgtcaacaac accgagtgct ggaa 24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
gccttcatga aacccacatc cact 24

<210> SEQ ID NO 66
<211> LENGTH: 1609
<212> TYPE: DNA
<213> ORGANISM: Homo sapiens

<400> SEQUENCE: 66
ccctgctaac aaagggagcc acttccttcc tctctgcaca taccccatgt ctcaccacga 60
tgatggagct acagtgggac ttggaatcca gatgtgtgaa ggatggaggg ttgaagccgc 120
actcagcttc ctgccccacc agaggaagtg gggagagacg gcaggtgcag tgatggctgg 180
cggagtcatg gacaaggagt acgtgggttt tgctgccctc cccaaccagc tgcaccgcaa 240
gtctgtcaag aaggggtttg acttcacgct aatggtggca ggggagtcag gcctagggaa 300
atccaccctc atcaacagcc tcttcctcac caacctctat gaggatcgcc aggtgccaga 360
ggccagtgct cgcttgacac agaccctggc cattgagcgc cggggcgtag agattgagga 420
agggggtgtg aaagtgaagc tgacccttgt ggacacacct ggctttgggg actcagtgga 480
ctgctctgac tgctggcttc cggtggtgaa attcatcgag gagcaatttg agcagtacct 540
tagggatgag agtggcctga accggaagaa catccaggac tcccgagtcc actgctgcct 600
ctacttcatc tcacccttcg gccgggggct ccggccccta gatgtggcct tcctccgggc 660
agtacacgag aaagtcaaca tcatcccagt cattggcaaa gcggatgctc tgatgcccca 720
ggaaacccag gccctcaagc agaagatccg ggatcagttg aaggaagagg agatccacat 780
ctaccagttc cccgaatgtg actctgatga agatgaagac ttcaagaggc aggatgcaga 840
gatgaaggaa agcatccctt ttgcagtcgt gggatcatgc gaggtggtga gggatggcgg 900
gaaccggccg gtgaggggac gccgctactc ctgggggacc gtggaggtgg agaacccaca 960
tcactgcgat ttcctgaacc tgcgacggat gctggtgcag acacacctgc aggacctgaa 1020
agaggtgacg cacgatctgc tctacgaggg ctaccgggcc cgctgcctac agagcctggc 1080
ccggcctggg gctcgcgatc gagccagccg cagtaagctt tcccgccaga gcgccacaga 1140
gatcccgctg cccatgctgc ctctggcgga caccgagaag ctgatccgcg agaaagacga 1200
agagctgcgc cgcatgcaag agatgctgga gaagatgcag gcccaaatgc agcagagcca 1260
ggcccagggc gagcagtcag acgccctctg aggccacgcc ccgcccggcc ttacctcggc 1320
tccgccttca gtcggcctct tgtccaatcc ccgcgcccca cactgcccag cgcccccgg 1380 gacctccgcg ggtgccgccc tcgcgcgggc taggggggagg ttctcccagc ctgagtccgt 1440
agccccgccc cggcgctggt cccgcccacc cagacaccgc ccacttcccg gcccggggcc 1500
tgcacaatct ccgaccgcat cactgtcttc cggagtcccc cttcttctcc cagactctgt 1560

-continued

```
cttcaataaa aactgagctt cccgcggcca cgaaaaaaaa aaaaaaaaa           1609


<210> SEQ ID NO 67
<211> LENGTH: 3598
<212> TYPE: DNA
<213> ORGANISM: Homo sapiens

<400> SEQUENCE: 67

gtggtgggct agaccagttt cgcgcggccg ctcgccgtcc cccgcccagt cgtactcggc     60

gccccagctc ggtgctgccg ccatcttctt ggaggacagg aggagaggcg aaggctcccc    120

ctccccgtga tcgctccgca ctcccgccac cacctgccct cccgcgaccg cctctctcct    180

cctcagtggg cacttgtctc cttctaacaa acggccttcc ccccactcca gttacccacc    240

gcaaggcgaa gattctcatt acctgttcca ctcttataag cataagaaaa ccgagctcat    300

aagcatacag aaactgctgt aaaagaagaa gttgtgggta tttttttttt tttttttgtc    360

tggaggaatg gggacaccaa aactcatttg gcagcagagg tgagacgaag cttcacaaaa    420

gatgtctaag caacagccaa ctcagtttat aaatccagaa acacctggct atgttggatt    480

tgcaaacctc cccaatcaag ttcaccgaaa atcagtgaaa aaaggttttg agttcacact    540

gatggtggtc ggtgaatcag gtctaggaaa atcgactctc ataaacagcc tattcctaac    600

tgatctgtac ccagaaagag tcatacctgg agcagcagaa aaaattgaaa gaactgtcca    660

gattgaggct tcaactgttg aaattgaaga gcgaggggtc aagctacgcc tgacagtggt    720

agatacccct ggctatggtg acgctatcaa ctgcagagat tgttttaaga caattatctc    780

ctatattgat gagcaatttg agaggtacct gcatgacgag agcggcttga acaggcggca    840

catcattgat aatagggtgc attgttgctt ttactttatt tcaccttttg gacatggact    900

taagccctta gatgtggcgt ttatgaaggc aatacacaac aaggtgaata ttgtgcctgt    960

cattgcaaaa gctgacactc tcaccctgaa ggaacgggag cggctgaaga aaaggattct   1020

ggatgaaatt gaagaacata acatcaaaat ctatcactta cctgatgcag aatcagatga   1080

agatgaagat tttaaagagc agactagact tctcaaggct agcatcccat tctctgtggt   1140

tggatccaat cagttgattg aagccaaagg aaagaaggtc agaggccgcc tctacccctg   1200

ggtgttgtg gaagtggaga acccagagca caatgacttt ctgaagctga gaaccatgct   1260

catcacccac atgcaggatc tccaggaggt gacccaggac cttcattatg aaaacttccg   1320

ttctgagaga ctcaagagag gcggcaggaa agtggagaat gaggacatga ataaagacca   1380

gatcttgctg gaaaaagaag ctgagctccg ccgcatgcaa gagatgattg caaggatgca   1440

ggcgcagatg cagatgcaga tgcagggcgg ggatggcgat ggcggggctc tcgggcacca   1500

cgtgtaaggt gatgtgcaca tatcaagaag tcagagaaaa cactttcctg gataaaaaag   1560

aaaacattcc agatgcatga tccagctgtg tgttttcaat ccttgggagg gtgccatcca   1620

cattttaaca gtacctgtgc ctgagaattt aatttttaaa agactttgat gtgtttttgt   1680

atgaagtact tttaacgtat gtatttcatt gctgtgtcac actctgtgtt ttgtgaggtg   1740

aatgtcttcc ttttctttct ccctaaccac taatgttaga attgatttcc aagaatcggc   1800

atgtatactt aatactgaat ttctttgatt taactgactt aacaactgac taaccattga   1860

tgagcactcc tgatttttat ctagaacatt cagatttacc ataatgttcc ttagtggtag   1920

aggtgtgtgc ctagtgatgt agaaagatac actgacttgg tgcaaggcca tctgcttacc   1980

acatcacacc acttggagat ctttgcttcc ttgcttttat gtttgtacac aacacctaaa   2040

accagttttg ctgctataat tctatactgt tgattcgtct gcgattttat ctgttaacca   2100
```

```
aataaaacat aatagaattt cctaatgaga tatatcttta tacttaaaca gctttttag   2160

aggtgagttt taaagaagtc tcttaattct gatgctaggt tgtttttaaa accactatgc   2220

aaagaactca ccacaagcca ccttttgtag tgttctccac taatactggt tatcctgtgc   2280

tacagagaaa atcaaagcag tcataagctc cagttttcgt attgcaaata agactcttac   2340

ctacaaaatg agattcagtg aactaatttg gtttttactc aaccaaatta aaaatttttt   2400

taaggaaaat tagcagttgg tctattcaga atcaaacctt tttatatttt atactgcact   2460

ttagtgtatt ttctgtcact gtaggtatag aagatctgcc tcccctgtgg aaattggggt   2520

ctgttggtgg gcgtgcccct gaagcctggc ttgggttgaa aagtgttccc gccctaaggc   2580

cttggtgccc tgaacctctg atgcctaccg ggttctcctg atttgagttt cctttaaata   2640

ctcccttttt gagtaatttt ctgatgggag gaaagtagca gtcatcatct ttttgtgtgc   2700

aggctgtctc atttattttt agccattgtc gtttcattca ttttgtgtaa tataaaccgt   2760

gtgtcatgtc aaagtgaaag acatttcaaa tctgtagcat aggctagtgg gcaggtccgc   2820

acagtcgaag ccacacctgg tctgttttct gtgcactgta gccttagtgt cacctttctt   2880

cttgtgtctc cttatggtac actccagcgg ttgccttttt tatcatttct actgaagttg   2940

ggaaattcaa ccccagaaat tgacagatga aaggagacaa tggttgtgta gggagatgga   3000

gaaaatgctt aatctgagga tgagacaggg ttttttcatt tttgtggggg ctagaaaaaa   3060

cataaaatga ggcagttaaa taataatagt taatgaaggt gtgctacaga aaataatctg   3120

gtgttcttgc taactttgcc cttcactgtt gcttaattgt gaacagccaa aagctatatg   3180

ttatggctta ttgtgtgaag gtaactaaga agtggtgttc catgacttca gagtacatcc   3240

atgcggagtc cattatttga gtttgacatt taataacttt gctggaaaat ctgtaaaaaa   3300

gaaaaacaag tttgctagtg actaagcccc gcatatgtga gtgaaagtac ttcaggcacg   3360

ctgcctcctg gtaacagcta tgcagggagg gaggacccac actgctacac ttctgatccc   3420

ctttggtttt actacccaaa tctaaataga tacttttgat aatagataac tgctctttta   3480

ctaagacata gtctctacct atagaaatgt attttgaaaa cacttatttt acacagcaat   3540

tttgtatcca tttaaactaa ccttttatca ataaagcact attgtttaga tattaaaa     3598


<210> SEQ ID NO 68
<211> LENGTH: 3396
<212> TYPE: DNA
<213> ORGANISM: Homo sapiens

<400> SEQUENCE: 68

aatccgcctg cgcgctgggc ggggcggggc gggctggggc gggctgtgag cggaccgcga     60

gcgctgggcg ggtccgcggc gcggtcggtc ggcgcctgtt ctcgggctgt ttggcggagg    120

cttggaatag ttaaatgact ttggtcttgt ccaaggttag atggagttca actctaacgt    180

caagtcttgg tccttttcat tgacgaagct tcacaaaaga tgtctaagca acagccaact    240

cagtttataa atccagaaac acctggctat gttggatttg caaacctccc caatcaagtt    300

caccgaaaat cagtgaaaaa aggttttgag ttcacactga tggtggtcgg tgaatcaggt    360

ctaggaaaat cgactctcat aaacagccta ttcctaactg atctgtaccc agaaagagtc    420

atacctggag cagcagaaaa aattgaaaga actgtccaga ttgaggcttc aactgttgaa    480

attgaagagc gaggggtcaa gctacgcctg acagtggtag atacccctgg ctatggtgac    540

gctatcaact gcagagattg ttttaagaca attatctcct atattgatga gcaatttgag    600
```

-continued

```
aggtacctgc atgacgagag cggcttgaac aggcggcaca tcattgataa tagggtgcat    660
tgttgctttt actttatttc accttttgga catggactta agcccttaga tgtggcgttt    720
atgaaggcaa tacacaacaa ggtgaatatt gtgcctgtca ttgcaaaagc tgacactctc    780
accctgaagg aacgggagcg gctgaagaaa aggattctgg atgaaattga agaacataac    840
atcaaaatct atcacttacc tgatgcagaa tcagatgaag atgaagattt taaagagcag    900
actagacttc tcaaggctag catcccattc tctgtggttg gatccaatca gttgattgaa    960
gccaaaggaa agaaggtcag aggccgcctc taccccctggg gtgttgtgga agtggagaac   1020
ccagagcaca atgactttct gaagctgaga accatgctca tcacccacat gcaggatctc   1080
caggaggtga cccaggacct tcattatgaa aacttccgtt ctgagagact caagagaggc   1140
ggcaggaaag tggagaatga ggacatgaat aaagaccaga tcttgctgga aaaagaagct   1200
gagctccgcc gcatgcaaga gatgattgca aggatgcagg cgcagatgca gatgcagatg   1260
cagggcgggg atggcgatgg cggggctctc gggcaccacg tgtaaggtga tgtgcacata   1320
tcaagaagtc agagaaaaca ctttcctgga taaaaaagaa aacattccag atgcatgatc   1380
cagctgtgtg ttttcaatcc ttgggagggt gccatccaca ttttaacagt acctgtgcct   1440
gagaatttaa tttttaaaag actttgatgt gtttttgtat gaagtacttt taacgtatgt   1500
atttcattgc tgtgtcacac tctgtgtttt gtgaggtgaa tgtcttcctt ttctttctcc   1560
ctaaccacta atgttagaat tgatttccaa gaatcggcat gtatacttaa tactgaattt   1620
ctttgattta actgacttaa caactgacta accattgatg agcactcctg atttttatct   1680
agaacattca gatttaccat aatgttcctt agtggtagag gtgtgtgcct agtgatgtag   1740
aaagatacac tgacttggtg caaggccatc tgcttaccac atcacaccac ttggagatct   1800
ttgcttcctt gcttttatgt ttgtacacaa cacctaaaac cagttttgct gctataattc   1860
tatactgttg attcgtctgc gattttatct gttaaccaaa taaaacataa tagaatttcc   1920
taatgagata tatctttata cttaaacagc tttttttagag gtgagtttta aagaagtctc   1980
ttaattctga tgctaggttg tttttaaaac cactatgcaa agaactcacc acaagccacc   2040
ttttgtagtg ttctccacta atactggtta tcctgtgcta cagagaaaat caaagcagtc   2100
ataagctcca gttttcgtat tgcaaataag actcttacct acaaaatgag attcagtgaa   2160
ctaatttggt ttttactcaa ccaaattaaa aattttttta aggaaaatta gcagttggtc   2220
tattcagaat caaacctttt tatattttat actgcacttt agtgtatttt ctgtcactgt   2280
aggtatagaa gatctgcctc ccctgtggaa attggggtct gttggtgggc gtgcccctga   2340
agcctggctt gggttgaaaa gtgttcccgc cctaaggcct tggtgccctg aacctctgat   2400
gcctaccggg ttctcctgat ttgagtttcc tttaaatact cccttttttga gtaattttct   2460
gatgggagga aagtagcagt catcatcttt ttgtgtgcag gctgtctcat ttatttttag   2520
ccattgtcgt ttcattcatt ttgtgtaata taaaccgtgt gtcatgtcaa agtgaaagac   2580
atttcaaatc tgtagcatag gctagtgggc aggtccgcac agtcgaagcc acacctggtc   2640
tgttttctgt gcactgtagc cttagtgtca cctttcttct tgtgtctcct tatggtacac   2700
tccagcggtt gcctttttta tcatttctac tgaagttggg aaattcaacc ccagaaattg   2760
acagatgaaa ggagacaatg gttgtgtagg gagatggaga aaatgcttaa tctgaggatg   2820
agacagggtt ttttcatttt tgtgggggct agaaaaaaca taaaatgagg cagttaaata   2880
ataatagtta atgaaggtgt gctacagaaa ataatctggt gttcttgcta actttgccct   2940
tcactgttgc ttaattgtga acagccaaaa gctatatgtt atggcttatt gtgtgaaggt   3000
```

```
aactaagaag tggtgttcca tgacttcaga gtacatccat gcggagtcca ttatttgagt   3060

ttgacattta ataactttgc tggaaaatct gtaaaaaaga aaaacaagtt tgctagtgac   3120

taagccccgc atatgtgagt gaaagtactt caggcacgct gcctcctggt aacagctatg   3180

cagggaggga ggacccacac tgctacactt ctgatcccct ttggttttac tacccaaatc   3240

taaatagata cttttgataa tagataactg ctcttttact aagacatagt ctctacctat   3300

agaaatgtat tttgaaaaca cttattttac acagcaattt tgtatccatt taaactaacc   3360

ttttatcaat aaagcactat tgtttagata ttaaaa                             3396


<210> SEQ ID NO 69
<211> LENGTH: 3311
<212> TYPE: DNA
<213> ORGANISM: Homo sapiens

<400> SEQUENCE: 69

aatccgcctg cgcgctgggc ggggcggggc gggctggggc gggctgtgag cggaccgcga     60

gcgctgggcg ggtccgcggc gcggtcggtc ggcgcctgtt ctcgggctgt ttggcggacg    120

aagcttcaca aaagatgtct aagcaacagc caactcagtt tataaatcca gaaacacctg    180

gctatgttgg atttgcaaac ctccccaatc aagttcaccg aaaatcagtg aaaaaaggtt    240

ttgagttcac actgatggtg gtcggtgaat caggtctagg aaaatcgact ctcataaaca    300

gcctattcct aactgatctg tacccagaaa gagtcatacc tggagcagca gaaaaaattg    360

aaagaactgt ccagattgag gcttcaactg ttgaaattga agagcgaggg gtcaagctac    420

gcctgacagt ggtagatacc cctggctatg gtgacgctat caactgcaga gattgtttta    480

agacaattat ctcctatatt gatgagcaat ttgagaggta cctgcatgac gagagcggct    540

tgaacaggcg gcacatcatt gataataggg tgcattgttg cttttacttt atttcacctt    600

ttggacatgg acttaagccc ttagatgtgg cgtttatgaa ggcaatacac aacaaggtga    660

atattgtgcc tgtcattgca aaagctgaca ctctcaccct gaaggaacgg gagcggctga    720

agaaaaggat tctggatgaa attgaagaac ataacatcaa aatctatcac ttacctgatg    780

cagaatcaga tgaagatgaa gattttaaag agcagactag acttctcaag gctagcatcc    840

cattctctgt ggttggatcc aatcagttga ttgaagccaa aggaaagaag gtcagaggcc    900

gcctctaccc ctggggtgtt gtggaagtgg agaacccaga gcacaatgac tttctgaagc    960

tgagaaccat gctcatcacc cacatgcagg atctccagga ggtgacccag gaccttcatt   1020

atgaaaactt ccgttctgag agactcaaga gaggcggcag gaaagtggag aatgaggaca   1080

tgaataaaga ccagatcttg ctggaaaaag aagctgagct ccgccgcatg caagagatga   1140

ttgcaaggat gcaggcgcag atgcagatgc agatgcaggg cggggatggc gatggcgggg   1200

ctctcgggca ccacgtgtaa ggtgatgtgc acatatcaag aagtcagaga aaacactttc   1260

ctggataaaa aagaaaacat tccagatgca tgatccagct gtgtgttttc aatccttggg   1320

agggtgccat ccacatttta acagtacctg tgcctgagaa tttaattttt aaaagacttt   1380

gatgtgtttt tgtatgaagt acttttaacg tatgtatttc attgctgtgt cacactctgt   1440

gttttgtgag gtgaatgtct tccttttctt tctccctaac cactaatgtt agaattgatt   1500

tccaagaatc ggcatgtata cttaatactg aatttctttg atttaactga cttaacaact   1560

gactaaccat tgatgagcac tcctgatttt tatctagaac attcagattt accataatgt   1620

tccttagtgg tagaggtgtg tgcctagtga tgtagaaaga tacactgact tggtgcaagg   1680
```

```
ccatctgctt accacatcac accacttgga gatctttgct tccttgcttt tatgtttgta   1740
cacaacacct aaaaccagtt ttgctgctat aattctatac tgttgattcg tctgcgattt   1800
tatctgttaa ccaaataaaa cataatagaa tttcctaatg agatatatct ttatacttaa   1860
acagcttttt tagaggtgag ttttaaagaa gtctcttaat tctgatgcta ggttgttttt   1920
aaaaccacta tgcaaagaac tcaccacaag ccaccttttg tagtgttctc cactaatact   1980
ggttatcctg tgctacagag aaaatcaaag cagtcataag ctccagtttt cgtattgcaa   2040
ataagactct tacctacaaa atgagattca gtgaactaat ttggttttta ctcaaccaaa   2100
ttaaaaattt ttttaaggaa aattagcagt tggtctattc agaatcaaac ctttttatat   2160
tttatactgc actttagtgt attttctgtc actgtaggta tagaagatct gcctcccctg   2220
tggaaattgg ggtctgttgg tgggcgtgcc cctgaagcct ggcttgggtt gaaaagtgtt   2280
cccgccctaa ggccttggtg ccctgaacct ctgatgccta ccgggttctc ctgatttgag   2340
tttcctttaa atactccctt tttgagtaat tttctgatgg gaggaaagta gcagtcatca   2400
tctttttgtg tgcaggctgt ctcatttatt tttagccatt gtcgtttcat tcattttgtg   2460
taatataaac cgtgtgtcat gtcaaagtga aagacatttc aaatctgtag cataggctag   2520
tgggcaggtc cgcacagtcg aagccacacc tggtctgttt tctgtgcact gtagccttag   2580
tgtcaccttt cttcttgtgt ctccttatgg tacactccag cggttgcctt ttttatcatt   2640
tctactgaag ttgggaaatt caaccccaga aattgacaga tgaaaggaga caatggttgt   2700
gtagggagat ggagaaaatg cttaatctga ggatgagaca gggttttttc atttttgtgg   2760
gggctagaaa aaacataaaa tgaggcagtt aaataataat agttaatgaa ggtgtgctac   2820
agaaaataat ctggtgttct tgctaacttt gcccttcact gttgcttaat tgtgaacagc   2880
caaaagctat atgttatggc ttattgtgtg aaggtaacta agaagtggtg ttccatgact   2940
tcagagtaca tccatgcgga gtccattatt tgagtttgac atttaataac tttgctggaa   3000
aatctgtaaa aaagaaaaac aagtttgcta gtgactaagc cccgcatatg tgagtgaaag   3060
tacttcaggc acgctgcctc ctggtaacag ctatgcaggg agggaggacc cacactgcta   3120
cacttctgat cccctttggt tttactaccc aaatctaaat agatactttt gataatagat   3180
aactgctctt ttactaagac atagtctcta cctatagaaa tgtattttga aaacacttat   3240
tttacacagc aatttttgtat ccatttaaac taacctttta tcaataaagc actattgttt   3300
agatattaaa a                                                          3311
```

<210> SEQ ID NO 70
<211> LENGTH: 3497
<212> TYPE: DNA
<213> ORGANISM: Homo sapiens

<400> SEQUENCE: 70

```
gtggtgggct agaccagttt cgcgcggccg ctcgccgtcc cccgcccagt cgtactcggc     60
gccccagctc ggtgctgccg ccatcttctt ggaggacagg aggagaggcg aaggctcccc    120
ctccccgtga tcgctccgca ctcccgccac cacctgccct cccgcgaccg cctctctcct    180
cctcagtggg cacttgtctc cttctaacaa acggccttcc ccccactcca gttacccacc    240
gcaaggcgaa gattctcatt acctgttcca ctcttataag cataagaaaa ccgagctcat    300
aagacgaagc ttcacaaaag atgtctaagc aacagccaac tcagtttata aatccagaaa    360
cacctggcta tgttggattt gcaaacctcc ccaatcaagt tcaccgaaaa tcagtgaaaa    420
aaggttttga gttcacactg atggtggtcg gtgaatcagg tctaggaaaa tcgactctca    480
```

```
taaacagcct attcctaact gatctgtacc cagaaagagt catacctgga gcagcagaaa    540
aaattgaaag aactgtccag attgaggctt caactgttga aattgaagag cgaggggtca    600
agctacgcct gacagtggta gataccccctg gctatggtga cgctatcaac tgcagagatt    660
gttttaagac aattatctcc tatattgatg agcaatttga gaggtacctg catgacgaga    720
gcggcttgaa caggcggcac atcattgata atagggtgca ttgttgcttt tactttattt    780
caccttttgg acatggactt aagcccttag atgtggcgtt tatgaaggca atacacaaca    840
aggtgaatat tgtgcctgtc attgcaaaag ctgacactct caccctgaag gaacgggagc    900
ggctgaagaa aaggattctg gatgaaattg aagaacataa catcaaaatc tatcacttac    960
ctgatgcaga atcagatgaa gatgaagatt ttaaagagca gactagactt ctcaaggcta   1020
gcatcccatt ctctgtggtt ggatccaatc agttgattga agccaaagga aagaaggtca   1080
gaggccgcct ctacccctgg ggtgttgtgg aagtggagaa cccagagcac aatgactttc   1140
tgaagctgag aaccatgctc atcacccaca tgcaggatct ccaggaggtg acccaggacc   1200
ttcattatga aaacttccgt tctgagagac tcaagagagg cggcaggaaa gtggagaatg   1260
aggacatgaa taaagaccag atcttgctgg aaaaagaagc tgagctccgc cgcatgcaag   1320
agatgattgc aaggatgcag gcgcagatgc agatgcagat gcagggcggg gatggcgatg   1380
gcggggctct cgggcaccac gtgtaaggtg atgtgcacat atcaagaagt cagagaaaac   1440
actttcctgg ataaaaaaga aaacattcca gatgcatgat ccagctgtgt gttttcaatc   1500
cttgggaggg tgccatccac attttaacag tacctgtgcc tgagaattta atttttaaaa   1560
gactttgatg tgtttttgta tgaagtactt ttaacgtatg tatttcattg ctgtgtcaca   1620
ctctgtgttt tgtgaggtga atgtcttcct tttctttctc cctaaccact aatgttagaa   1680
ttgatttcca agaatcggca tgtatactta atactgaatt tctttgattt aactgactta   1740
acaactgact aaccattgat gagcactcct gatttttatc tagaacattc agatttacca   1800
taatgttcct tagtggtaga ggtgtgtgcc tagtgatgta gaaagataca ctgacttggt   1860
gcaaggccat ctgcttacca catcacacca cttggagatc tttgcttcct tgcttttatg   1920
tttgtacaca acacctaaaa ccagttttgc tgctataatt ctatactgtt gattcgtctg   1980
cgattttatc tgttaaccaa ataaaacata atagaatttc ctaatgagat atatctttat   2040
acttaaacag ctttttttaga ggtgagtttt aaagaagtct cttaattctg atgctaggtt   2100
gtttttaaaa ccactatgca aagaactcac cacaagccac cttttgtagt gttctccact   2160
aatactggtt atcctgtgct acagagaaaa tcaaagcagt cataagctcc agttttcgta   2220
ttgcaaataa gactcttacc tacaaaatga gattcagtga actaatttgg tttttactca   2280
accaaattaa aaattttttt aaggaaaatt agcagttggt ctattcagaa tcaaaccttt   2340
ttatatttta tactgcactt tagtgtattt tctgtcactg taggtataga agatctgcct   2400
cccctgtgga aattggggtc tgttggtggg cgtgcccctg aagcctggct tgggttgaaa   2460
agtgttcccg ccctaaggcc ttggtgccct gaacctctga tgcctaccgg gttctcctga   2520
tttgagtttc ctttaaatac tcccttttttg agtaattttc tgatgggagg aaagtagcag   2580
tcatcatctt tttgtgtgca ggctgtctca tttattttta gccattgtcg tttcattcat   2640
tttgtgtaat ataaaccgtg tgtcatgtca aagtgaaaga catttcaaat ctgtagcata   2700
ggctagtggg caggtccgca cagtcgaagc cacacctggt ctgttttctg tgcactgtag   2760
ccttagtgtc acctttcttc ttgtgtctcc ttatggtaca ctccagcggt tgcctttttt   2820
```

-continued

```
atcatttcta ctgaagttgg gaaattcaac cccagaaatt gacagatgaa aggagacaat   2880
ggttgtgtag ggagatggag aaaatgctta atctgaggat gagacagggt tttttcattt   2940
ttgtggggc tagaaaaaac ataaaatgag gcagttaaat aataatagtt aatgaaggtg   3000
tgctacagaa aataatctgg tgttcttgct aactttgccc ttcactgttg cttaattgtg   3060
aacagccaaa agctatatgt tatggcttat tgtgtgaagg taactaagaa gtggtgttcc   3120
atgacttcag agtacatcca tgcggagtcc attatttgag tttgacattt aataactttg   3180
ctggaaaatc tgtaaaaaag aaaaacaagt ttgctagtga ctaagccccg catatgtgag   3240
tgaaagtact tcaggcacgc tgcctcctgg taacagctat gcagggaggg aggacccaca   3300
ctgctacact tctgatcccc tttggtttta ctacccaaat ctaaatagat acttttgata   3360
atagataact gctcttttac taagacatag tctctaccta tagaaatgta ttttgaaaac   3420
acttatttta cacagcaatt ttgtatccat ttaaactaac cttttatcaa taaagcacta   3480
ttgtttagat attaaaa                                                  3497
```

<210> SEQ ID NO 71
<211> LENGTH: 4656
<212> TYPE: DNA
<213> ORGANISM: Homo sapiens

<400> SEQUENCE: 71

```
gggcgggtgg gaggagagcg cgaaggggcg aggcccgttt gcaggggccg ctcggcccgg     60
ggaagcccgc gccccgctca gccttgcagc cccgcgcccg gagcatctcc ctggaggaac    120
ggagacaaag gaggattcat gtccaaaggg ctcccagaga ccaggacgga cgcagccatg    180
tcagagctgg tgcctgagcc caggcctaag ccagcggtgc ccatgaagcc catgagcatc    240
aactccaacc tgctgggcta catcggcatc gacaccatca tcgagcagat gcgcaagaag    300
accatgaaga ccggtttcga cttcaacatc atggtcgttg gccagagtgg actgggcaaa    360
tcaacgctgg tcaacacgct cttcaaatcc caagtgagcc gcaaggcctc cagctggaac    420
cgggaggaga agatccccaa gacagtggag atcaaagcta tcgggcatgt gatagaggaa    480
ggcggtgtca aaatgaagct gaccgtcatc gacaccccag gctttggaga ccaaatcaac    540
aatgaaaact gctgggagcc cattgagaag tacatcaatg agcagtacga gaagttcctg    600
aaggaggagg tcaacatcgc caggaagaaa cgcatccctg acactcgtgt ccactgctgc    660
ctttacttca tctctcccac aggacactcc ttgcgacctc tggatcttga gttcatgaaa    720
cacctcagca aggttgtgaa catcatccct gtcattgcta aggctgacac catgaccctg    780
gaggagaagt ctgaattcaa gcaaagggtt cgcaaggagc ttgaagtaaa tggcattgaa    840
ttctaccccc agaaggaatt tgatgaggat ttggaggata agacggagaa tgacaaaatc    900
aggcaggaga gcatgccttt tgctgtggtg ggaagtgaca aggagtacca agtgaatggc    960
aagagggtcc tcggccgaaa aactccatgg gggatcatcg aagtggaaaa cctcaaccac   1020
tgtgagtttg ccctgcttcg agactttgtc atcaggaccc acctccagga cctcaaggaa   1080
gtgacacaca acatccacta tgagacttac agggccaagc ggctcaatga caatggaggc   1140
ctccctccgg tgagcgtgga cacagaggaa agccacgaca gtaacccatg acgaccactt   1200
ctctgtgtca tcacacatac ccacttcaca cacacacatc ccaaatacca ccaccaacca   1260
ccttcttcct ctcaactctg tcccacaggc ctgtctggta tttgtggagc atcttgtctg   1320
tgtgtgtgtg tgtgtgtgtg tgtgtgtgtg tgtgtgtgac agagagagag cgagagagcc   1380
tgtgtgtgtg catgcagggg tgaggtattt tcactgccct ccctggagag tcccttgtaa   1440
```

-continued

```
gtttggctcc tccatgcctg tccattatct gtctcctttc cttgtgtccc aaaacaaagc   1500
tgtttgcctc actcaggaga tctgggggag gtttcattta aaagtgctgg gagcaggtga   1560
gccacaggca actcttctct cggaacctgc acacaaactg gggctataga gattctccaa   1620
ggacagatgg cagtggagct agacctgagt agggggcagg gagttcagga caaccctcct   1680
gtaagttggg ggtggtctgg gggtaaggct ggggcttcct gggaaaagga aggccatgag   1740
aaggcagaga agtaggccag agctgggttc ttgcagaaag catcagtgcc tacaaatgga   1800
gctccaccct tcagtctgtg tcgtgttcag tgtcacaaag ctaccacctg tcaccagagc   1860
ctactgctgc tctccactca actggcctct gctgccaggc cactgcctgt ctctgcttcc   1920
gactttgtct tctttctccc tttccctcct tccctcatac attgctttct ctccctctcc   1980
tgcgtgtctc tgacatctct cacttccttt tagatgaatc tactttaggt tcattcctat   2040
atttagcatt tatgcccagt ctacttccag aaatgacttt agactgcctt tcacataaaa   2100
tcacaaaact acaggacagt acaaacagat tgccagagaa atctgggtca aagaaaggaa   2160
taggaaagaa agtttctgta gtcaagcacc tgaacaggcc ctgagctcac aggcagccaa   2220
tgtaaagagg gaaacacagt gagttatgca gttcccagtg tccagttaaa ggaagcacac   2280
atgctagtca tgtgagacaa ccttttattg ggacatcagg ttctagaact aattctaaag   2340
aagtatcaga aacaatatac ataatttgtc tttcttagta atttggcttc aaagacaaat   2400
ttttgaccac acctccgttt tctccgtcag acttctctcc cttctaagca ggcttctctg   2460
ttgctccatt tgcttcatac atacttgacc tctcttttct attccccatc acttttgtgc   2520
tgaagctaat catatttatg tctgtctttc tctacttttc cctaattccc tctcctcctg   2580
actcctgtag acattcccaa tgatacccac cgtcatacat ttaggctttt cttgcctttc   2640
cctgaagccc tgtatttatt aatgcatata tttcccctgc ttgttgtaca agtaagttac   2700
tcttttcctt taatctgtaa gattcatgaa attcggggcc agggaaacag tttagcctta   2760
gggaagggaa aacactaagt gaaactgttt acaataacct catacaacct tctgtcccat   2820
ctcctggttc agcctaggtg tttcactggt cctctatgaa tcccagcact tataatccca   2880
gtcttttatc actcaggtgc taggaaaaaa aacatagact caagacccaa gattcaatgg   2940
accaggagaa agggggggcgg tgatcaggtc accagtgacc ccaacctatg ctctcggtct   3000
ttcctggagg ctgccaaccc agccctcatc ctcccttgct cacaaagtta cagggtaggc   3060
acctgtcagg acagaacagc agcagcgcta cagcccagag gttatacatt tcaacagaac   3120
agggatcctt ggctactgta gaagcagtcc tgtatggaga ccttggacca gcaggggaag   3180
atctatgggc atgggaggtg ggcgttggaa aggctgagta ggaatggtgc ctggcacccc   3240
tgaaccatga tctgagcctc cctggagaag gtattttata tgtctgctgc cagctgctgg   3300
tctccacacc ctcaaccgtt ctcaaccccc ctgcagggag aaggcctcct gggcactgtc   3360
cttccacctg tgccagccac cccctgcccc actgctgaat gaaggccatt tcaagcgctg   3420
cttctcactc cattcctctc agctgttatt gctgcagggc caagcccttt ttagtgctgt   3480
gctcgtccag ctcaccacca cagcccctct cagccctcag taggtgggag gggccagctg   3540
cctctttagg ccagttgcat cctccattta tccaaaccac tcctctcctc ccagtggagt   3600
ggggttctgc cagtacagcc ctactgcatc atctgcgtca gccggtccta gcccatctgc   3660
agggtgaaag aactcatcaa gagctccttc tgcccttgta agcccatccc agctacttgt   3720
aaccatctct aagggcaatg gcattgctcc ctacccattc atctgcatga gctactcttg   3780
```

```
gcttccttaa agggtcaaga aagcaatttt tctgcttact agattcattg agatcagctg   3840

tgtgagcccc aaagtgggac aagggtgtct ccttcattac ttaaagatat tcatgagggt   3900

gggtcactac agatgttggg gagcaagggc taggatcact ttttaaaaaa tcaccacttg   3960

tggctgtccc agagtgcggt tgtacatcct ccccacctca taacgcagcc actgaggaag   4020

agtggttttc ctaagaagac attgctggag ttgacttttct tctgtccaaa caaacaaaca   4080

aaaactaaac acacacacaa acccccagaa acccacaata tgtacacgct aaggaaaaac   4140

tagcaccctt ctgtccactc agcaataaga gggatctctt cccacctacc ctacctactc   4200

ctacccccaa cccccttccc cattaatgtg agtaatgaat tagcctgacc acaggtggtc   4260

actgtaggct aatggaaaat acccaaggga gggcaaagcc ccccatcaga tgcatgaatg   4320

tttgcgaatg ttgactgcca ctgccccaca cactgtgtct ttatagaatt cccctttgcc   4380

caccctcttc ctgtctccac ctggacacaa cttgctcaaa ggctggtgac ttgtgggcca   4440

ttcatctaca accaagtcct gatggagcaa gaggcccacg cctaggggat gcaagaacaa   4500

cccgtttctt aaatgttacc agtcccagcc aatcttacgg tgacattaca gttaaatttc   4560

ccaattgaaa acaagcaaac agacactcaa actggtcctg taattgttgc tagactttat   4620

gtgttgtaca actaaacatt gctgtttgaa cagtaa                             4656
```

<210> SEQ ID NO 72
<211> LENGTH: 2469
<212> TYPE: DNA
<213> ORGANISM: Homo sapiens

<400> SEQUENCE: 72

```
gggcgggtgg gaggagagcg cgaaggggcg aggcccgttt gcaggggccg ctcggcccgg     60

ggaagcccgc gccccgctca gccttgcagc cccgcgcccg gagcatctcc ctggaggaac    120

ggagacaaag gaggattcat gtccaaaggg ctcccagaga ccaggacgga cgcagccatg    180

tcagagctgg tgcctgagcc caggcctaag ccagcggtgc ccatgaagcc catgagcatc    240

aactccaacc tgctgggcta catcggcatc gacaccatca tcgagcagat gcgcaagaag    300

accatgaaga ccggtttcga cttcaacatc atggtcgttg gccagagtgg actgggcaaa    360

tcaacgctgg tcaacacgct cttcaaatcc caagtgagcc gcaaggcctc cagctggaac    420

cgggaggaga agatccccaa gacagtggag atcaaagcta tcgggcatgt gatagaggaa    480

ggcggtgtca aaatgaagct gaccgtcatc gacaccccag gctttggaga ccaaatcaac    540

aatgaaaact gctgggagcc cattgagaag tacatcaatg agcagtacga gaagttcctg    600

aaggaggagg tcaacatcgc caggaagaaa cgcatccctg acactcgtgt ccactgctgc    660

ctttacttca tctctcccac aggacactcc ttgcgacctc tggatcttga gttcatgaaa    720

cacctcagca aggttgtgaa catcatccct gtcattgcta aggctgacac catgaccctg    780

gaggagaagt ctgaattcaa gcaaagggtt cgcaaggagc ttgaagtaaa tggcattgaa    840

ttctaccccc agaaggaatt tgatgaggat ttggaggata agacggagaa tgacaaaatc    900

aggcaggaga gcatgccttt tgctgtggtg ggaagtgaca aggagtacca agtgaatggc    960

aagagggtcc tcggccgaaa aactccatgg gggatcatcg aagtggaaaa cctcaaccac   1020

tgtgagtttg ccctgcttcg agactttgtc atcaggaccc acctccagga cctcaaggaa   1080

gtgacacaca acatccacta tgagacttac agggccaagc ggctcaatga caatggaggc   1140

ctccctccgg gagaaggcct cctgggcact gtccttccac ctgtgccagc caccccctgc   1200

cccactgctg aatgaaggcc atttcaagcg ctgcttctca ctccattcct ctcagctgtt   1260
```

attgctgcag ggccaagccc tttttagtgc tgtgctcgtc cagctcacca ccacagcccc 1320
tctcagccct cagtaggtgg gaggggccag ctgcctcttt aggccagttg catcctccat 1380
ttatccaaac cactcctctc ctcccagtgg agtggggttc tgccagtaca gccctactgc 1440
atcatctgcg tcagccggtc ctagcccatc tgcagggtga aagaactcat caagagctcc 1500
ttctgccctt gtaagcccat cccagctact tgtaaccatc tctaagggca atggcattgc 1560
tccctaccca ttcatctgca tgagctactc ttggcttcct taaagggtca agaaagcaat 1620
ttttctgctt actagattca ttgagatcag ctgtgtgagc cccaaagtgg gacaagggtg 1680
tctccttcat tacttaaaga tattcatgag ggtgggtcac tacagatgtt ggggagcaag 1740
ggctaggatc actttttaaa aaatcaccac ttgtggctgt cccagagtgc ggttgtacat 1800
cctccccacc tcataacgca gccactgagg aagagtggtt ttcctaagaa gacattgctg 1860
gagttgactt tcttctgtcc aaacaaacaa acaaaaacta aacacacaca caaacccccca 1920 gaaacccaca atatgtacac gctaaggaaa aactagcacc cttctgtcca ctcagcaata 1980
agagggatct cttcccacct accctaccta ctcctacccc caaccccctt ccccattaat 2040
gtgagtaatg aattagcctg accacaggtg gtcactgtag gctaatggaa aatacccaag 2100
ggagggcaaa gccccccatc agatgcatga atgtttgcga atgttgactg ccactgcccc 2160
acacactgtg tctttataga attccccttt gcccaccctc ttcctgtctc cacctggaca 2220
caacttgctc aaaggctggt gacttgtggg ccattcatct acaaccaagt cctgatggag 2280
caagaggccc acgcctaggg gatgcaagaa caacccgttt cttaaatgtt accagtccca 2340
gccaatctta cggtgacatt acagttaaat ttcccaattg aaaacaagca aacagacact 2400
caaactggtc ctgtaattgt tgctagactt tatgtgttgt acaactaaac attgctgttt 2460
gaacagtaa 2469

<210> SEQ ID NO 73
<211> LENGTH: 1858
<212> TYPE: DNA
<213> ORGANISM: Homo sapiens

<400> SEQUENCE: 73
gagctgtcct tggagggtgg gagccaaggg aaggggagga gaagaggggt ggggaaggac 60
attccacagg ctttttggc ccctgccaga gacagaaggg ggtcaaagag aaagggaaag 120
gagcaagcca ggaagccaga caacaacagc atcaaaacaa ggctgtttct gtgtgtgagg 180
aactttgcct gggagataaa attagaccta gagctttctg acagggagtc tgaagcgtgg 240
gacatggacc gttcactggg atggcaaggg aattctgtcc ctgaggacag gactgaagct 300
gggatcaagc gtttcctgga ggacaccacg gatgatggag aactgagcaa gttcgtgaag 360
gatttctcag gaaatgcgag ctgccaccca ccagaggcta agacctgggc atccaggccc 420
caagtcccgg agccaaggcc ccaggccccg gacctctatg atgatgacct ggagttcaga 480
cccccctcgc ggccccagtc ctctgacaac cagcagtact tctgtgcccc agcccctctc 540
agcccatctg ccaggccccg cagcccatgg ggcaagcttg atccctatga ttcctctgag 600
gatgacaagg agtatgtggg ctttgcaacc ctccccaacc aagtccaccg aaagtccgtg 660
aagaaaggct ttgactttac cctcatggtg gcaggagagt ctggcctggg caaatccaca 720
cttgtcaata gcctcttcct cactgatctg taccgggacc ggaaacttct tggtgctgaa 780
gagaggatca tgcaaactgt ggagatcact aagcatgcag tggacataga agagaagggt 840

```
gtgaggctgc ggctcaccat tgtggacaca ccaggttttg gggatgcagt caacaacaca    900
gagtgctgga agcctgtggc agaatacatt gatcagcagt ttgagcagta tttccgagac    960
gagagtggcc tgaaccgaaa gaacatccaa gacaacaggg tgcactgctg cctgtacttc   1020
atctcaccct tcggccatgg gctccggcca ttggatgttg aattcatgaa ggccctgcat   1080
cagcgggtca acatcgtgcc tatcctggct aaggcagaca cactgacacc tcccgaagtg   1140
gaccacaaga aacgcaaaat ccgggaggag attgagcatt ttggaatcaa gatctatcaa   1200
ttcccagact gtgactctga tgaggatgag gacttcaaat tgcaggacca agccctaaag   1260
gaaagcatcc catttgcagt aattggcagc aacactgtag tagaggccag agggcggcga   1320
gttcggggtc gactctaccc ctggggcatc gtggaagtgg aaaacccagg gcactgcgac   1380
tttgtgaagc tgaggacaat gctggtacgt acccacatgc aggacctgaa ggatgtgaca   1440
cgggagacac attatgagaa ctaccgggca cagtgcatcc agagcatgac ccgcctggtg   1500
gtgaaggaac ggaatcgcaa caaactgact cgggaaagtg gtaccgactt ccccatccct   1560
gctgtcccac cagggacaga tccagaaact gagaagctta tccgagagaa agatgaggag   1620
ctgcggcgga tgcaggagat gctacacaaa atacaaaaac agatgaagga gaactattaa   1680
ctggctttca gccctggata tttaaatctc ctcctcttct tcctgtccat gccggcccct   1740
cccagcacca gctctgctca ggccccttca gctactgcca cttcgcctta catccctgct   1800
gactgcccag agactcagag gaaataaagt ttaataaatc tgtaggtggc ttctggaa     1858
```

```
<210> SEQ ID NO 74
<211> LENGTH: 1945
<212> TYPE: DNA
<213> ORGANISM: Homo sapiens

<400> SEQUENCE: 74

agcggtccgc actcggggag gcgggagggt gacggcggtg ctgcgaggtc ggcgcgcagc     60
tccgccgcgg gtcgctcggg cgctgtccag gcggagccgg ccccgcccgg gctgcagcca    120
tgatcaagcg tttcctggag gacaccacgg atgatggaga actgagcaag ttcgtgaagg    180
atttctcagg aaatgcgagc tgccacccac cagaggctaa gacctgggca tccaggcccc    240
aagtcccgga gccaaggccc caggccccgg acctctatga tgatgacctg gagttcagac    300
ccccctcgcg gccccagtcc tctgacaacc agcagtactt ctgtgcccca gcccctctca    360
gcccatctgc caggccccgc agcccatggg gcaagcttga tccctatgat tcctctgagg    420
atgacaagga gtatgtgggc tttgcaaccc tccccaacca agtccaccga aagtccgtga    480
agaaaggctt tgactttacc ctcatggtgg caggagagtc tggcctgggc aaatccacac    540
ttgtcaatag cctcttcctc actgatctgt accgggaccg gaaacttctt ggtgctgaag    600
agaggatcat gcaaactgtg gagatcacta agcatgcagt ggacatagaa gagaagggtg    660
tgaggctgcg gctcaccatt gtggacacac caggttttgg ggatgcagtc aacaacacag    720
agtgctggaa gcctgtggca gaatacattg atcagcagtt tgagcagtat ttccgagacg    780
agagtggcct gaaccgaaag aacatccaag acaacagggt gcactgctgc ctgtacttca    840
tctcaccctt cggccatggg tatggtccaa gcctgaggct cctggcacca ccgggtgctg    900
tcaagggaac aggccaagag caccaggggc agggctgcca ctagcaggtg gtcacaggtt    960
cctgttcccc aggctccggc cattggatgt tgaattcatg aaggccctgc atcagcgggt   1020
caacatcgtg cctatcctgg ctaaggcaga cacactgaca cctcccgaag tggaccacaa   1080
gaaacgcaaa atccgggagg agattgagca ttttggaatc aagatctatc aattcccaga   1140
```

ctgtgactct gatgaggatg aggacttcaa attgcaggac caagccctaa aggaaagcat 1200
cccatttgca gtaattggca gcaacactgt agtagaggcc agagggcggc gagttcgggg 1260
tcgactctac ccctggggca tcgtggaagt ggaaaaccca gggcactgcg actttgtgaa 1320
gctgaggaca atgctggtac gtacccacat gcaggacctg aaggatgtga cacgggagac 1380
acattatgag aactaccggg cacagtgcat ccagagcatg acccgcctgg tggtgaagga 1440
acggaatcgc aagtatgacc agaagccagg acaaagctgg caggggggaga tcccaagcct 1500 agccttgggt gagaccaagc cctacttttg ttcttctata ggccctgggc tcaatctaag 1560
cgggtgctgg ggtcctcctc gccttatcaa cccttttctc cctttagcaa actgactcgg 1620
gaaagtggta ccgacttccc catccctgct gtcccaccag ggacagatcc agaaactgag 1680
aagcttatcc gagagaaaga tgaggagctg cggcggatgc aggagatgct acacaaaata 1740
caaaaacaga tgaaggagaa ctattaactg gctttcagcc ctggatattt aaatctcctc 1800
ctcttcttcc tgtccatgcc ggcccctccc agcaccagct ctgctcaggc cccttcagct 1860
actgccactt cgccttacat ccctgctgac tgcccagaga ctcagaggaa ataaagttta 1920
ataaatctgt aggtggcttc tggaa 1945

<210> SEQ ID NO 75
<211> LENGTH: 1677
<212> TYPE: DNA
<213> ORGANISM: Homo sapiens

<400> SEQUENCE: 75
agcggtccgc actcggggag gcgggagggt gacggcggtg ctgcgaggtc ggcgcgcagc 60
tccgccgcgg gtcgctcggg cgctgtccag gcggagccgg ccccgcccgg gctgcagcca 120
tgatcaagcg tttcctggag gacaccacgg atgatggaga actgagcaag ttcgtgaagg 180
atttctcagg aaatgcgagc tgccacccac cagaggctaa gacctgggca tccaggcccc 240
aagtcccgga gccaaggccc caggccccgg acctctatga tgatgacctg gagttcagac 300
ccccctcgcg gccccagtcc tctgacaacc agcagtactt ctgtgcccca gcccctctca 360
gcccatctgc caggccccgc agcccatggg gcaagcttga tccctatgat tcctctgagg 420
atgacaagga gtatgtgggc tttgcaaccc tccccaacca agtccaccga aagtccgtga 480
agaaaggctt tgactttacc ctcatggtgg caggagagtc tggcctgggc aaatccacac 540
ttgtcaatag cctcttcctc actgatctgt accgggaccg gaaacttctt ggtgctgaag 600
agaggatcat gcaaactgtg gagatcacta agcatgcagt ggacatagaa gagaagggtg 660
tgaggctgcg gctcaccatt gtggacacac caggttttgg ggatgcagtc aacaacacag 720
agtgctggaa gcctgtggca gaatacattg atcagcagtt tgagcagtat ttccgagacg 780
agagtggcct gaaccgaaag aacatccaag acaacagggt gcactgctgc ctgtacttca 840
tctcaccctt cggccatggg ctccggccat tggatgttga attcatgaag gccctgcatc 900
agcgggtcaa catcgtgcct atcctggcta aggcagacac actgacacct cccgaagtgg 960
accacaagaa acgcaaaatc cgggaggaga ttgagcattt tggaatcaag atctatcaat 1020
tcccagactg tgactctgat gaggatgagg acttcaaatt gcaggaccaa gccctaaagg 1080
aaagcatccc atttgcagta attggcagca acactgtagt agaggccaga gggcggcgag 1140
ttcggggtcg actctacccc tggggcatcg tggaagtgga aaacccaggg cactgcgact 1200
ttgtgaagct gaggacaatg ctggtacgta cccacatgca ggacctgaag gatgtgacac 1260

-continued

```
gggagacaca ttatgagaac taccgggcac agtgcatcca gagcatgacc cgcctggtgg   1320

tgaaggaacg gaatcgcaac aaactgactc gggaaagtgg taccgacttc cccatccctg   1380

ctgtcccacc agggacagat ccagaaactg agaagcttat ccgagagaaa gatgaggagc   1440

tgcggcggat gcaggagatg ctacacaaaa tacaaaaaca gatgaaggag aactattaac   1500

tggctttcag ccctggatat ttaaatctcc tcctcttctt cctgtccatg ccggcccctc   1560

ccagcaccag ctctgctcag gccccttcag ctactgccac ttcgccttac atccctgctg   1620

actgcccaga gactcagagg aaataaagtt taataaatct gtaggtggct tctggaa      1677
```

<210> SEQ ID NO 76
<211> LENGTH: 2090
<212> TYPE: DNA
<213> ORGANISM: Homo sapiens

<400> SEQUENCE: 76

```
ggagcgggcg gcggcggcgg cggcgcggag gggccgctca ccccgcagcc cggcctcggc     60

ctccgccgct tgtcgtcgcg ccccgcccgc gagcccgccc cgcacgtccc ccgccggcgg    120

ccaccatgag cacaggcctg cggtacaaga gcaagctggc gaccccagag gacaagcagg    180

acattgacaa gcagtacgtg ggcttcgcca cactgcccaa ccaggtgcac cgcaagtcgg    240

tgaagaaagg ctttgacttc acactcatgg tggctggtga gtcaggcctg ggaagtcca     300

cactggtcca cagcctcttc ctgacagact tgtacaagga ccggaagctg ctcagtgctg    360

aggagcgcat cagccagacg gtagagattc taaaacacac ggtggacatt gaggagaagg    420

gagtcaagct gaagctcacc atcgtggaca cgccgggatt cggggacgct gtcaacaaca    480

ccgagtgctg gaagcccatc accgactatg tggaccagca gtttgagcag tacttccgtg    540

atgagagcgg cctcaaccga aagaacatcc aagacaaccg agtgcactgc tgcctatact    600

tcatctcccc cttcgggcat gggctgcggc cagtggatgt gggtttcatg aaggcattgc    660

atgagaaggt caacatcgtg cctctcatcg ccaaagctga ctgtcttgtc cccagtgaga    720

tccggaagct gaaggagcgg atccgggagg agattgacaa gtttgggatc catgtatacc    780

agttccctga gtgtgactcg gacgaggatg aggacttcaa gcagcaggac cgggaactga    840

aggagagcgc gccccttcgcc gttataggca gcaacacggt ggtggaggcc aaggggcagc   900

gggtccgggg ccgactgtac ccctggggga tcgtggaggt ggagaaccag gcgcattgcg    960

acttcgtgaa gctgcgcaac atgctcatcc gcacgcatat gcacgacctc aaggacgtga   1020

cgtgcgacgt gcactacgag aactaccgcg cgcactgcat ccagcagatg accagcaaac   1080

tgacccagga cagccgcatg gagagcccca tcccgatcct gccgctgccc accccggacg   1140

ccgagactga gaagcttatc aggatgaagg atgaggaact gaggcgcatg caggagatgc   1200

tgcagaggat gaagcagcag atgcaggacc agtgacgctc gccgcggaca caccgtccgt   1260

ctccgggacg ccctcgcacc cctggacacc agaccggact gttcccgacc cggagacgcg   1320

gggccacagc ccccagctga ccctaattta ttctcagcac cacccccctcc caggtcattg  1380

tgtctgtttc cgaggggcct ggaccgtagc ccccgcccag ctggccctct ctgaccttgg   1440

gggatcagga gcgaagttgg gcgggacttc agagatccgc ctcccttgcc cttcccccgc   1500

ccccggacgg tcacagcacc caaaccgcag gccctgctct ggcaggcagg caaagctagg   1560

cagaagagga ttcccaggat cctgggtctg ttccctgccc cagtgctgca gaacggactt   1620

gggagccctc ctttgcctgc tcccgcgggt cacccagcga gtgctgagac cccattttct   1680

gtcgaggcgg gccgagtctt cccttatccc cagacgccta gcgggcaggg ttgggctgaa   1740
```

tcaaatggga gccctccaga cataaggagg ccagaggctg caaggagcgg ggtcgtgacc 1800
gcttacaccc cttctccaca gcccggcccg acctggaggg cccccggggc actgggcggt 1860
gagccacctc ctggcaactc tcggtgccgt cccctgccct cgctcgaggc ctcttctccc 1920
cagcaccgct gtggtgtgcc gggatcctga gcctaggcct cccgatgttc ccacccgcat 1980
gatcccttcc cgccacacga tgctccgttt tcttccgttg tgaatgccgc gtcctgtcct 2040
ggtgacagga gaacaatgtt ggtgaacgtc gcaaaaaaaa aaaaaaaaaa 2090

<210> SEQ ID NO 77
<211> LENGTH: 3387
<212> TYPE: DNA
<213> ORGANISM: Homo sapiens

<400> SEQUENCE: 77
gaagaactgg aactggtctg gccatagggg gaagcggcgc gttaaatccg ccccctctcc 60
ataccctact ttcaaggggt gggcggtaga ggggaggttg gggttggagc agcggcgagg 120
gggcccctcc cttgcacctc cccccaccgg acttggtcgc gcccgaagtg taacactttc 180
tctttgtcgg aggagctcct ctgtttcctg tgcagtagct cccgttgcgg cggcacccgt 240
ggcagccctg gcggacgcag gagcgatggc agcgaccgat atagctcgcc aggtgggtga 300
aggttgccga actgtccccc tggctggaca tgtggggttt gacagcttgc ctgaccagct 360
ggtgaataag tccgtcagcc agggcttctg cttcaacatc ctgtgcgtgg gagagacagg 420
tttgggcaag tccaccctca tggacaccct gttcaacacc aaattcgaag gggagccagc 480
cacccacaca cagccgggtg tccagctcca gtctaatacc tatgacctcc aagagagcaa 540
cgtgaggcta aagctcacga tcgttagcac agttggcttt ggggaccaga tcaacaaaga 600
ggacagctac aagcctatcg tggaattcat cgatgcacaa ttcgaggcct acctgcagga 660
agagctaaag atccgaagag tgctacacac ctaccatgac tcccgaatcc atgtctgctt 720
gtatttcatt gcccccacgg gtcattccct gaagtctctg gacctagtga ctatgaagaa 780
gctggacagt aaggtgaaca tcatccccat cattgccaaa gcagatgcca tttcgaagag 840
tgagctaaca aagttcaaaa tcaaaatcac cagcgagctt gtcagcaacg gagtccagat 900
ctatcagttt cctacagatg atgagtcggt ggcagagatc aatggaacca tgaacgccca 960
cctgccgttt gctgtcattg gcagcacaga agaactgaag ataggcaaca agatgatgag 1020
ggcgcggcag tatccttggg gcactgtgca ggttgaaaac gaggcccact gcgactttgt 1080
gaagctgcgg gagatgctga ttcgggtcaa catggaggat ctgcgggagc agacccacac 1140
ccggcactat gagctgtatc gccgctgtaa gctggaggag atgggcttca aggacaccga 1200
ccctgacagc aaacccttca gtttacagga gacatatgag gccaaaagga acgagttcct 1260
aggggaactc cagaaaaaag aagaggagat gagacagatg ttcgtccagc gagtcaaaga 1320
gaaagaagcg gagctcaaag aggcagagaa agagctgcac gagaagtttg accgtctgaa 1380
gaaactgcac caggacgaga agaagaaact ggaggataag aagaaatccc tggatgatga 1440
agtgaatgct ttcaagcaaa gaaagacggc ggctgagctg ctccagtccc agggctccca 1500
ggctggaggc tcacagactc tgaagagaga caaagagaag aaaaataatc catggctgtg 1560
tactgaatag tattccccgc tacagctgga ctggactcca tttagccttt taagccgagg 1620
ttcctatttt aactgacagc tttcctttgg ggtgccaggc agcgaggccc cccaccccta 1680
tcctgccatg tacttcaagc tcacttcttc tttttgagtt ccgcaacttg ctcctgcctc 1740

```
ccagccccac tggcactgac catgaccacc tacttctatt tttttttag agtttctttt   1800

tttgatcact tactttcaaa gcacacagtc aaacaaggtt atgccaaatt tccaggcctt   1860

tttgaagtat tgagaagggg aaggggattt ctcacttcaa ttatagatca taataggaag   1920

caaaaagaaa aaaatgaaaa gcaaacatat gcacgcactt ttcttgttga caaagcaaga   1980

atataggttt gctgtgtagg tttggtgctc tattgattgg tgagtgacca gagcaagtat   2040

gaaggtgatg ctgccaaagc acaagccagt ttcttgggaa aattcaagtt acagtggagt   2100

attttttga agaccatatg cttggaggta gaaacaaacc aacgaccaaa aaaaaaaaaa   2160

aaaaaatctg ctcagatact cagccagtag ctcagagaga tgctgagtta ggcctgtcag   2220

gtctccttgg gaaaggcttc atatttgcaa ctttgatgat tctatgtcca gcttcagagc   2280

tgctttccca gaaattcacg cttaaacaac caaccggtaa ccaccacttc cccacaccgc   2340

cgcccggtaa ttatttgcat tacaaaccgg aggcgccctc atttgcattt gtgtacagat   2400

taactagtta aggcttgaga agctctgaat aattcaaaag tattagaccc acacagcctt   2460

ggagagacct tcagaaacta aggaggagtt ttatattaag ggagacattt tagtcagtaa   2520

gacgatataa cctacttact ccgtaagggg aaatgaaggc ccagagaagg gaagggactt   2580

gaccgaggtc ccacttctgt ttcgaggcag aagccagact aattttcatg cctcctgact   2640

cccaatcagt ttcacaaagg gattcaatct gtttatatac gttacattcc tggatacgag   2700

gtcttttgat gttcagagta actgactagt tagtattaga agaccctcga ggttttttc   2760

cacagaaaaa catctgaaga tggattgggt gagggctggc aaaacgaagg catgccgggc   2820

cagctcctta acccaatgac ccagtgatgc tgcaaggctg gaacggggtc caggagactg   2880

tgtgtaacag gtgccctagg tgacccttat aatcagggaa gtttggtgaa caaaaatcga   2940

acccatgagt gaacataaat taaaaagttg atcaacctat taaaatgtgt atttcattgg   3000

gtagcttttc tcactgtaga cagatttttt ccttcttcaa tgaaaaggct tttaaattag   3060

tacaactgtt actatttaaa aaaaaaatac cctaagtact ctgtttactt ctggtgaaac   3120

aaaaccagtc attagaaatg gtctgtgctt ttattttccc agactggagt ggcttttctg   3180

aaacacacac acacacacac acacacacac acacacacac acacacacac acgtacacac   3240

atccctcact tctcttaagc caagaagttt gctttcccta gctgcagtgt agatggctct   3300

tgtttttgtt tttttgtttt aatcatttgg cattcacatg tggctgttaa tatgtgcttg   3360

tttttaatta aaacaagaag ctttaaa                                       3387
```

<210> SEQ ID NO 78
<211> LENGTH: 4716
<212> TYPE: DNA
<213> ORGANISM: Homo sapiens

<400> SEQUENCE: 78

```
gaagaactgg aactggtctg gccatagggg gaagcggcgc gttaaatccg ccccctctcc     60

ataccctact ttcaaggggt gggcggtaga ggggaggttg gggttggagc agcggcgagg    120

gggcccctcc cttgcacctc cccccaccgg acttggtcgc gcccgaagtg taacactttc    180

tctttgtcgg aggagctcct ctgtttcctg tgcagtagct cccgttgcgg cggcacccgt    240

ggcagccctg gcggacgcag gagcgatggc agcgaccgat atagctcgcc aggtgggtga    300

aggttgccga actgtccccc tggctggaca tgtggggttt gacagcttgc ctgaccagct    360

ggtgaataag tccgtcagcc agggcttctg cttcaacatc ctgtgcgtgg gagagacagg    420

tttgggcaag tccaccctca tggacaccct gttcaacacc aaattcgaag gggagccagc    480
```

```
cacccacaca cagccgggtg tccagctcca gtctaatacc tatgacctcc aagagagcaa    540
cgtgaggcta aagctcacga tcgttagcac agttggcttt ggggaccaga tcaacaaaga    600
ggacagctac aagcctatcg tggaattcat cgatgcacaa ttcgaggcct acctgcagga    660
agagctaaag atccgaagag tgctacacac ctaccatgac tcccgaatcc atgtctgctt    720
gtatttcatt gcccccacgg gtcattccct gaagtctctg gacctagtga ctatgaagaa    780
gctggacagt aaggtgaaca tcatccccat cattgccaaa gcagatgcca tttcgaagag    840
tgagctaaca aagttcaaaa tcaaaatcac cagcgagctt gtcagcaacg gagtccagat    900
ctatcagttt cctacagatg atgagtcggt ggcagagatc aatggaacca tgaacgccca    960
cctgccgttt gctgtcattg gcagcacaga agaactgaag ataggcaaca agatgatgag   1020
ggcgcggcag tatccttggg gcactgtgca ggttgaaaac gaggcccact gcgactttgt   1080
gaagctgcgg gagatgctga ttcgggtcaa catggaggat ctgcgggagc agacccacac   1140
ccggcactat gagctgtatc gccgctgtaa gctggaggag atgggcttca aggacaccga   1200
ccctgacagc aaacccttca gtttacagga gacatatgag gccaaaagga acgagttcct   1260
aggggaactc cagaaaaaag aagaggagat gagacagatg ttcgtccagc gagtcaaaga   1320
gaaagaagcg gagctcaaag aggcagagaa agagctgcac gagaagtttg accgtctgaa   1380
gaaactgcac caggacgaga agaagaaact ggaggataag aagaaatccc tggatgatga   1440
agtgaatgct ttcaagcaaa gaaagacggc ggctgagctg ctccagtccc agggctccca   1500
ggctggaggc tcacagactc tgaagagaga caaagagaag aaaaattaac tctgctgttt   1560
gctgcatgct gcatgagacc cagggtcctg tttgggcttc ctgtagacac ccttttcctg   1620
cgcaacagag ctgggcctcc ctttctctaa tttcccctt aacatgcctg gggggcatac    1680
aatccaaccc gcgccctctc ctctcttcct gccaaggttt atagaaacct gagaatctga   1740
gggtgatgtc tggccgctgg tcaagaagcc aacagtcatg tggctcgcag atgcatcctg   1800
catcccagtc cccctcccag cacccccagc catccccccct gtcttccccc acatctttgc  1860
cagaggtgtg acatggtcag gggcccatc tgctactctt tcccaccagc tcccctgttc    1920
cagttctggt tgctgttagt ttccctgagg tatttgcaac caccatggct gggtaaccac   1980
cgatcagcac agctgtcccc ttggtctcct gtatcccagt cactagtcct ccctggtcca   2040
ccccaccctc atcctcagga gccacagcca tttcttagag ggtttcaaaa ggacagcctt   2100
tggcgccttt tccttctaac ctttgagtcc agccctttcc agttttcatt cactcgaagt   2160
aactgcactc aagctgtgct caaaatcggc aacgcattta tttacaccaa gcccttccca   2220
taaaacacaa ctgctgaaga aaatagcaga cgtttcccct ctctctaact ctgggtatcc   2280
cacagatgca aaagggagaa taaacctgaa tattattacc agcctagagt cttgaatgat   2340
agccttaccg aattcttctt gtgaggtatt tcagcatctc ggggggtaat ttccggaagg   2400
gctccatact gtcccaataa ggtgaggcca gtagcaggaa taataaatcc cactttgtag   2460
gctggaaaac tgagctgtca aaagaatcaa gtgtttgggg gtttgctctg atgagtcttc   2520
tagttcattt ggtgaatgtc atgatgattt ttaacatgca ttttgcatgc atcccccaat   2580
aagaagagat gagactcggc cggagagaag aaaaggccct taactttctt tccaatttaa   2640
ggagttgaga gtttaaaaat attccagccc taagttttta tcatgggtcc catctgatag   2700
tggctttggg aacctctgtg aagtagagag ccctcccttg tcagggttat gaggcacagt   2760
ggcctttggt gtttggccag tgacagtgtg agagatggag ttgacctggc aatgatctgt   2820
```

-continued

```
ggctaacatg ccgtctctct gcccttcctt tgcagtaatc catggctgtg tactgaatag   2880
tattccccgc tacagctgga ctggactcca tttagccttt taagccgagg ttcctatttt   2940
aactgacagc tttcctttgg ggtgccaggc agcgaggccc cccaccccta tcctgccatg   3000
tacttcaagc tcacttcttc tttttgagtt ccgcaacttg ctcctgcctc ccagccccac   3060
tggcactgac catgaccacc tacttctatt tttttttag agtttctttt tttgatcact   3120
tactttcaaa gcacacagtc aaacaaggtt atgccaaatt tccaggcctt tttgaagtat   3180
tgagaagggg aaggggattt ctcacttcaa ttatagatca taataggaag caaaaagaaa   3240
aaaatgaaaa gcaaacatat gcacgcactt ttcttgttga caaagcaaga atataggttt   3300
gctgtgtagg tttggtgctc tattgattgg tgagtgacca gagcaagtat gaaggtgatg   3360
ctgccaaagc acaagccagt ttcttgggaa aattcaagtt acagtggagt atttttttga   3420
agaccatatg cttggaggta gaaacaaacc aacgaccaaa aaaaaaaaaa aaaaaatctg   3480
ctcagatact cagccagtag ctcagagaga tgctgagtta ggcctgtcag gtctccttgg   3540
gaaaggcttc atatttgcaa ctttgatgat tctatgtcca gcttcagagc tgctttccca   3600
gaaattcacg cttaaacaac caaccggtaa ccaccacttc cccacaccgc cgcccggtaa   3660
ttatttgcat tacaaaccgg aggcgccctc atttgcattt gtgtacagat taactagtta   3720
aggcttgaga agctctgaat aattcaaaag tattagaccc acacagcctt ggagagacct   3780
tcagaaacta aggaggagtt ttatattaag ggagacattt tagtcagtaa gacgatataa   3840
cctacttact ccgtaagggg aaatgaaggc ccagagaagg gaagggactt gaccgaggtc   3900
ccacttctgt ttcgaggcag aagccagact aattttcatg cctcctgact cccaatcagt   3960
ttcacaaagg gattcaatct gtttatatac gttacattcc tggatacgag gtcttttgat   4020
gttcagagta actgactagt tagtattaga agaccctcga ggtttttttc cacagaaaaa   4080
catctgaaga tggattgggt gagggctggc aaaacgaagg catgccgggc cagctcctta   4140
acccaatgac ccagtgatgc tgcaaggctg gaacggggtc caggagactg tgtgtaacag   4200
gtgccctagg tgacccttat aatcagggaa gtttggtgaa caaaaatcga acccatgagt   4260
gaacataaat taaaaagttg atcaacctat taaaatgtgt atttcattgg gtagcttttc   4320
tcactgtaga cagatttttt ccttcttcaa tgaaaaggct tttaaattag tacaactgtt   4380
actatttaaa aaaaaaatac cctaagtact ctgtttactt ctggtgaaac aaaaccagtc   4440
attagaaatg gtctgtgctt ttattttccc agactggagt ggcttttctg aaacacacac   4500
acacacacac acacacacac acacacacac acacacacac acgtacacac atccctcact   4560
tctcttaagc caagaagttt gctttcccta gctgcagtgt agatggctct tgtttttgtt   4620
tttttgtttt aatcatttgg cattcacatg tggctgttaa tatgtgcttg tttttaatta   4680
aaacaagaag ctttaaaaaa aaaaaaaaaa aaaaaa                             4716
```

<210> SEQ ID NO 79
<211> LENGTH: 2609
<212> TYPE: DNA
<213> ORGANISM: Homo sapiens

<400> SEQUENCE: 79

```
gaagaactgg aactggtctg gccatagggg gaagcggcgc gttaaatccg ccccctctcc     60
ataccctact ttcaaggggt gggcggtaga ggggaggttg gggttggagc agcggcgagg    120
gggcccctcc cttgcacctc cccccaccgg acttggtcgc gcccgaagtg taacactttc    180
tctttgtcgg aggagctcct ctgtttcctg tgcagtagct cccgttgcgg cggcacccgt    240
```

-continued

```
ggcagccctg gcggacgcag gagcgatggc agcgaccgat atagctcgcc aggtgggtga    300
aggttgccga actgtccccc tggctggaca tgtggggttt gacagcttgc ctgaccagct    360
ggtgaataag tccgtcagcc agggcttctg cttcaacatc ctgtgcgtgg gagagacagg    420
tttgggcaag tccaccctca tggacaccct gttcaacacc aaattcgaag gggagccagc    480
cacccacaca cagccgggtg tccagctcca gtctaatacc tatgacctcc aagagagcaa    540
cgtgaggcta aagctcacga tcgttagcac agttggcttt ggggaccaga tcaacaaaga    600
ggacagctac aagcctatcg tggaattcat cgatgcacaa ttcgaggcct acctgcagga    660
agagctaaag atccgaagag tgctacacac ctaccatgac tcccgaatcc atgtctgctt    720
gtatttcatt gcccccacgg gtcattccct gaagtctctg gacctagtga ctatgaagaa    780
gctggacagt aaggtgaaca tcatccccat cattgccaaa gcagatgcca tttcgaagag    840
tgagctaaca aagttcaaaa tcaaaatcac cagcgagctt gtcagcaacg gagtccagat    900
ctatcagttt cctacagatg atgagtcggt ggcagagatc aatggaacca tgaacgccca    960
cctgccgttt gctgtcattg gcagcacaga agaactgaag ataggcaaca agatgatgag   1020
ggcgcggcag tatccttggg gcactgtgca ggttgaaaac gaggcccact gcgactttgt   1080
gaagctgcgg gagatgctga ttcgggtcaa catggaggat ctgcgggagc agacccacac   1140
ccggcactat gagctgtatc gccgctgtaa gctggaggag atgggcttca aggacaccga   1200
ccctgacagc aaacccttca gtttacagga gacatatgag gccaaaagga acgagttcct   1260
aggggaactc cagaaaaaag aagaggagat gagacagatg ttcgtccagc gagtcaaaga   1320
gaaagaagcg gagctcaaag aggcagagaa agagctgcac gagaagtttg accgtctgaa   1380
gaaactgcac caggacgaga agaagaaact ggaggataag aagaaatccc tggatgatga   1440
agtgaatgct ttcaagcaaa gaaagacggc ggctgagctg ctccagtccc agggctccca   1500
ggctggaggc tcacagactc tgaagagaga caaagagaag aaaaattaac tctgctgttt   1560
gctgcatgct gcatgagacc cagggtcctg ctttttttaa tcttgtcttc agcagctgca   1620
ctaagtctaa aggagaagac tgccattata gaagagttag ggttccatat tgtctcaaat   1680
cagaaatcaa ccaatttcct ctcccctcaa actgcaagca cacacacata caccacacca   1740
ctcaacaagt gttcatgtgt ccctgtgtcc aggcaagaag ctctcttcct gactcacatg   1800
gtattttaaa tggaagtgtc ttgtcctaac taacaaggca ggaaaagaac catcagagct   1860
ggaaaatgga cgaaatgtaa cctcagagaa acaactacag gaccactcac ccaagtgtaa   1920
gtgactgggg caggacacct cagctgtggg tatgaaagta ctgttctgtt cacaaggttt   1980
tgtttgagtt ttatgttttt cttttaaaca tttctctggt tcgatgggtt gactgtctac   2040
agccactgtt aaacatttct gaatatgcaa gagaaagtca agtgacattt gtatcttctt   2100
cagcattcgc agaccttcta tagattccag caaaggggga aaatgtatcc actatctaac   2160
acttaggtag agaagggagg gggtttaagc ttagtgaggg caaaattact ccattccacc   2220
ttccgagacc agttagggtt ttgagagagg tttctgctca acctgggatc tggagggaga   2280
gctttgatgt tggtaaatct gccttgaatt cattggttta acttgcatca aaataccatg   2340
tgagtgtgct cattctcata tatcccctac caccatcacc accattctgc tgttcagtgt   2400
ctcttgagag agcctctttg catgttttcc agaatctgtg tgtgtttttc ctttcttctc   2460
ctttgttctt tttgctcaaa ggtgtgacca gtcattgccc ctctggggct ttcattctcc   2520
aggagaaaca tcccagaacc agcactgttt agcctgatac ctttctaatg tccatgtcaa   2580
```

ttttcaataa aattcaaaga aatgctaaa 2609

<210> SEQ ID NO 80
<211> LENGTH: 2564
<212> TYPE: DNA
<213> ORGANISM: Homo sapiens

<400> SEQUENCE: 80
gaagaactgg aactggtctg gccatagggg gaagcggcgc gttaaatccg ccccctctcc 60
ataccctact ttcaaggggt gggcggtaga ggggaggttg gggttggagc agcggcgagg 120
gggcccctcc cttgcacctc cccccaccgg acttggtcgc gcccgaagtg taacactttc 180
tctttgtcgg aggagctcct ctgtttcctg tgcagtagct cccgttgcgg cggcacccgt 240
ggcagccctg gcggacgcag gagcgatggc agcgaccgat atagctcgcc aggtgggtga 300
aggttgccga actgtccccc tggctggaca tgtggggttt gacagcttgc ctgaccagct 360
ggtgaataag tccgtcagcc agggcttctg cttcaacatc ctgtgcgtgg gagagacagg 420
tttgggcaag tccaccctca tggacaccct gttcaacacc aaattcgaag gggagccagc 480
cacccacaca cagccgggtg tccagctcca gtctaatacc tatgacctcc aagagagcaa 540
cgtgaggcta aagctcacga tcgttagcac agttggcttt ggggaccaga tcaacaaaga 600
ggacagctac aagcctatcg tggaattcat cgatgcacaa ttcgaggcct acctgcagga 660
agagctaaag atccgaagag tgctacacac ctaccatgac tcccgaatcc atgtctgctt 720
gtatttcatt gcccccacgg gtcattccct gaagtctctg gacctagtga ctatgaagaa 780
gctggacagt aaggtgaaca tcatccccat cattgccaaa gcagatgcca tttcgaagag 840
tgagctaaca aagttcaaaa tcaaaatcac cagcgagctt gtcagcaacg gagtccagat 900
ctatcagttt cctacagatg atgagtcggt ggcagagatc aatggaacca tgaacgccca 960
cctgccgttt gctgtcattg gcagcacaga agaactgaag ataggcaaca agatgatgag 1020
ggcgcggcag tatccttggg gcactgtgca ggttgaaaac gaggcccact gcgactttgt 1080
gaagctgcgg gagatgctga ttcgggtcaa catggaggat ctgcgggagc agacccacac 1140
ccggcactat gagctgtatc gccgctgtaa gctggaggag atgggcttca aggacaccga 1200
ccctgacagc aaacccttca gtttacagga gacatatgag gccaaaagga acgagttcct 1260
aggggaactc cagaaaaaag aagaggagat gagacagatg ttcgtccagc gagtcaaaga 1320
gaaagaagcg gagctcaaag aggcagagaa agagctgcac gagaagtttg accgtctgaa 1380
gaaactgcac caggacgaga agaagaaact ggaggataag aagaaatccc tggatgatga 1440
agtgaatgct ttcaagcaaa gaaagacggc ggctgagctg ctccagtccc agggctccca 1500
ggctggaggc tcacagactc tgaagagaga caaagagaag aaaaactttt tttaatcttg 1560
tcttcagcag ctgcactaag tctaaaggag aagactgcca ttatagaaga gttagggttc 1620
catattgtct caaatcagaa atcaaccaat ttcctctccc ctcaaactgc aagcacacac 1680
acatacacca caccactcaa caagtgttca tgtgtccctg tgtccaggca agaagctctc 1740
ttcctgactc acatggtatt ttaaatggaa gtgtcttgtc ctaactaaca aggcaggaaa 1800
agaaccatca gagctggaaa atggacgaaa tgtaacctca gagaaacaac tacaggacca 1860
ctcacccaag tgtaagtgac tggggcagga cacctcagct gtgggtatga aagtactgtt 1920
ctgttcacaa ggttttgttt gagttttatg tttttctttt aaacatttct ctggttcgat 1980
gggttgactg tctacagcca ctgttaaaca tttctgaata tgcaagagaa agtcaagtga 2040
catttgtatc ttcttcagca ttcgcagacc ttctatagat tccagcaaag ggggaaaatg 2100

```
tatccactat ctaacactta ggtagagaag ggagggggtt taagcttagt gagggcaaaa   2160
ttactccatt ccaccttccg agaccagtta gggttttgag agaggtttct gctcaacctg   2220
ggatctggag ggagagcttt gatgttggta aatctgcctt gaattcattg gtttaacttg   2280
catcaaaata ccatgtgagt gtgctcattc tcatatatcc cctaccacca tcaccaccat   2340
tctgctgttc agtgtctctt gagagagcct ctttgcatgt tttccagaat ctgtgtgtgt   2400
ttttcctttc ttctcctttg ttctttttgc tcaaaggtgt gaccagtcat tgcccctctg   2460
gggctttcat tctccaggag aaacatccca gaaccagcac tgtttagcct gataccttc    2520
taatgtccat gtcaattttc aataaaattc aaagaaatgc taaa                    2564
```

<210> SEQ ID NO 81
<211> LENGTH: 2531
<212> TYPE: DNA
<213> ORGANISM: Homo sapiens

<400> SEQUENCE: 81

```
agcctcgtct gagggggcgg gggacggagg agggagcggg agtcgagcga gagcctgtgg     60
aggagtccgc ctgctgtagc gtgcgtaagc aaggcagcta cgccgggcgg ctacgctgcg    120
gaatcggcgt aggcgccttt ggagaatcgg cgggctgcgc tccgctgggg ctggtcgcgg    180
agggggggag gggatgtcgg tcagtgcgag atccgctgct gctgaggaga ggagcgtcaa    240
cagcagcacc atggctcaac agaagaacct tgaaggctat gtgggatttg ccaatctccc    300
aaatcaagta tacagaaaat cggtgaagag aggttttgaa ttcacgctta tggtagtggg    360
tgaatctgga ttgggaaagt cgacattaat caactcatta ttcctcacag atttgtattc    420
tccagagtat ccaggtcctt ctcatagaat taaaaagact gtacaggtgg aacaatccaa    480
agttttaatc aaagaaggtg gtgttcagtt gctgctcaca atagttgata ccccaggatt    540
tggagatgca gtggataata gtaattgctg gcagcctgtt atcgactaca ttgatagtaa    600
atttgaggac tacctaaatg cagaatcacg agtgaacaga cgtcagatgc ctgataacag    660
ggtgcagtgt tgtttatact tcattgctcc ttcaggacat ggacttaaac cattggatat    720
tgagtttatg aagcgtttgc atgaaaaagt gaatatcatc ccacttattg ccaaagcaga    780
cacactcaca ccagaggaat gccaacagtt taaaaaacag ataatgaaag aaatccaaga    840
acataaaatt aaaatatacg aatttccaga aacagatgat gaagaagaaa ataaacttgt    900
taaaaagata aaggaccgtt tacctcttgc tgtggtaggt agtaatacta tcattgaagt    960
taatggcaaa agggtcagag gaaggcagta tccttggggt gttgctgaag ttgaaaatgg   1020
tgaacattgt gattttacaa tcctaagaaa tatgttgata agaacacaca tgcaggactt   1080
gaaagatgtt actaataatg tccactatga gaactacaga agcagaaaac ttgcagctgt   1140
gacttataat ggagttgata acaacaagaa taaagggcag ctgactaaga gccctctggc   1200
acaaatggaa gaagaaagaa gggagcatgt agctaaaatg aagaagatgg agatggagat   1260
ggagcaggtg tttgagatga aggtcaaaga aaaagttcaa aaactgaagg actctgaagc   1320
tgagctccag cggcgccatg agcaaatgaa aaagaatttg gaagcacagc acaaagaatt   1380
ggaggaaaaa cgtcgtcagt tcgaggatga gaaagcaaac tgggaagctc aacaacgtat   1440
tttagaacaa cagaactctt caagaacctt ggaaaagaac aagaagaaag ggaagatctt   1500
ttaaactctc tattgaccac cagttaacgt attagttgcc aatatgccag cttggacatc   1560
agtgtttgtt ggatccgttt gaccaatttg caccagtttt atccataatg atggatttaa   1620
```

```
cagcatgaca aaaattattt ttttttttgt tcttgatgga gattaagatg ccttgaattg   1680
tctagggtgt tctgtactta gaaagtaaga gctctaagta cctttcctac attttctttt   1740
tttattaaac agatatcttc agtttaatgc aagagaacat tttactgttg tacaatcatg   1800
ttctggtggt ttgattgttt acaggatatt ccaaaataaa aggactctgg aagattttca   1860
ttgaggataa attgccataa tatgatgcaa actgtgcttc tctatgataa ttacaataca   1920
aaggttccat tcagtgcagc atatacaata atgtaattta gtctaacaca gttgacccta   1980
tttttgaca cttccattgt ttaaaaatac acatggaaaa aaaaaaaacc ctatatgctt   2040
actgtgcacc tagagctttt ttataacaac gtctttttgt ttgtttgttt tggattcttt   2100
aaatatatat tattctcatt tagtgccctc tttagccaga atctcattac tgcttcattt   2160
ttgtaataac atttaattta gatattttcc atatattggc actgctaaaa tagaatatag   2220
catctttcat atggtaggaa ccaacaagga aactttcctt taactccctt tttacacttt   2280
atggtaagta gcaggggggg aaatgcattt atagatcatt tctaggcaaa attgtgaagc   2340
taatgaccaa cctgtttcta cctatatgca gtctctttat tttactagaa atgggaatca   2400
tggcctcttg aagagaaaaa agtcaccatt ctgcatttag ctgtattcat atattgcatt   2460
tctgtatttt ttgtttgtat tgtaaaaaat tcacataata aacgatgttg tgatgtaaaa   2520
aaaaaaaaaa a                                                        2531
```

<210> SEQ ID NO 82
<211> LENGTH: 4380
<212> TYPE: DNA
<213> ORGANISM: Homo sapiens

<400> SEQUENCE: 82

```
gagatggaag ccagcctccg ctaggcccgg aagcctcgtc tgagggggcg gggggacggag    60
gagggagcgg gagtcgagcg agagcctgtg gaggagtccg cctgctgtag cgtgcgtaag   120
caaggcagct acgccgggcg gctacgctgc ggaatcggcg taggcgcctt tggagaatcg   180
gcgggctgcg ctccgctggg gctggtcgcg gagggggggga ggggatgtcg gtcagtgcga   240
gatccgctgc tgctgaggag aggagcgtca acagcagcac catggtagct caacagaaga   300
accttgaagg ctatgtggga tttgccaatc tcccaaatca agtatacaga aaatcggtga   360
agagaggttt tgaattcacg cttatggtag tgggtgaatc tggattggga aagtcgacat   420
taatcaactc attattcctc acagatttgt attctccaga gtatccaggt ccttctcata   480
gaattaaaaa gactgtacag gtggaacaat ccaaagtttt aatcaaagaa ggtggtgttc   540
agttgctgct cacaatagtt gataccccag gatttggaga tgcagtggat aatagtaatt   600
gctggcagcc tgttatcgac tacattgata gtaaatttga ggactaccta aatgcagaat   660
cacgagtgaa cagacgtcag atgcctgata acagggtgca gtgttgttta tacttcattg   720
ctccttcagg acatggactt aaaccattgg atattgagtt tatgaagcgt ttgcatgaaa   780
aagtgaatat catcccactt attgccaaag cagacacact cacaccagag gaatgccaac   840
agtttaaaaa acagataatg aaagaaatcc aagaacataa aattaaaata tacgaatttc   900
cagaaacaga tgatgaagaa gaaaataaac ttgttaaaaa gataaaggac cgtttacctc   960
ttgctgtggt aggtagtaat actatcattg aagttaatgg caaaagggtc agaggaaggc  1020
agtatccttg ggtgttgct gaagttgaaa atggtgaaca ttgtgatttt acaatcctaa  1080
gaaatatgtt gataagaaca cacatgcagg acttgaaaga tgttactaat aatgtccact  1140
atgagaacta cagaagcaga aaacttgcag ctgtgactta taatggagtt gataacaaca  1200
```

agaataaagg gcagctgact aagagccctc tggcacaaat ggaagaagaa agaagggagc 1260
atgtagctaa aatgaagaag atggagatgg agatggagca ggtgtttgag atgaaggtca 1320
aagaaaaagt tcaaaaactg aaggactctg aagctgagct ccagcggcgc catgagcaaa 1380
tgaaaaagaa tttggaagca cagcacaaag aattggagga aaaacgtcgt cagttcgagg 1440
atgagaaagc aaactgggaa gctcaacaac gtattttaga acaacagaac tcttcaagaa 1500
ccttggaaaa gaacaagaag aaagggaaga tcttttaaac tctctattga ccaccagtta 1560
acgtattagt tgccaatatg ccagcttgga catcagtgtt tgttggatcc gtttgaccaa 1620
tttgcaccag ttttatccat aatgatggat ttaacagcat gacaaaaatt attttttttt 1680
ttgttcttga tggagattaa gatgccttga attgtctagg gtgttctgta cttagaaagt 1740
aagagctcta agtacctttc ctacattttc ttttttttatt aaacagatat cttcagttta 1800
atgcaagaga acattttact gttgtacaat catgttctgg tggtttgatt gtttacagga 1860
tattccaaaa taaaaggact ctggaagatt ttcattgagg ataaattgcc ataatatgat 1920
gcaaactgtg cttctctatg ataattacaa tacaaaggtt ccattcagtg cagcatatac 1980
aataatgtaa tttagtctaa cacagttgac cctatttttt gacacttcca ttgtttaaaa 2040
atacacatgg aaaaaaaaaa aaccctatat gcttactgtg cacctagagc tttttttataa 2100
caacgtcttt ttgtttgttt gttttggatt ctttaaatat atattattct catttagtgc 2160
cctctttagc cagaatctca ttactgcttc atttttgtaa taacatttaa tttagatatt 2220
ttccatatat tggcactgct aaaatagaat atagcatctt tcatatggta ggaaccaaca 2280
aggaaacttt cctttaactc cctttttaca ctttatggta agtagcaggg ggggaaatgc 2340
atttatagat catttctagg caaaattgtg aagctaatga ccaacctgtt tctacctata 2400
tgcagtctct ttattttact agaaatggga atcatggcct cttgaagaga aaaaagtcac 2460
cattctgcat ttagctgtat tcatatattg catttctgta tttttttgttt gtattgtaaa 2520
aaattcacat aataaacgat gttgtgatgt aatattgtgt gaggtcttaa atatcctaca 2580
gtcgatgtac aagagtagag tatgtttggg aagaaacttt tcagcttaag tttgcctcct 2640
ctacaatgac atcttttata tgcttgtctc atttagaatg catatgtgct gattttctaa 2700
tttaagagat accatatctc tctattcatt tctatctctc atttgtatgc ttatttttct 2760
gagaacattt tttttttccc ccagacaggg tcttgcttca ttgcccaggc tggagtgcgg 2820
tggcacaaac acgacttgac tgcagcctca accctctggg ctcaagcagt cctcctgcct 2880
cagccccctg agtatctggg attgcaggcg tgcaccacca cgcctggcta atttttgtat 2940
tttttgcagc ctcccaaagt tctgggatta caggcatgag ccgtcatgcc tggcctctga 3000
gaacagtttc tgactcattc agattaggta tactctcaag tccctggaaa ctgaaatttt 3060
ttttaactgt aaagagggta gtgtcatttc ttttcttaag gtcaagtgac atagatttta 3120
atgtaatgca taatttaggt aagaaattaa ttaatgtagc ctagtttatt atcttgaaat 3180
gttttaccct atttactttt taaaattaat gacctaagcg gagggaataa ttataagtca 3240
atagcagaga gattgttgtt tgggtgttta tttttttcag tttttgtttt gagagattgg 3300
gttaacacct ctagccaaaa ttgtttggtt ttagggaggc taacaataac ctactgaatt 3360
tggaaaatgc aaaggtaaaa aatgtatata gactgcctgc tgaactggtt aagtactact 3420
gcttctggga aatactattt caaaattcta tgtattataa taataaattt gtaagacatt 3480
cattattcta ccatcctaat gaaaactttc agaagtcttt ctttatccat ggcatgccca 3540
gggttttacc tgaatctgat acaggatcta tataacttta ctaggacttt tgattgttga 3600
ctccaggctt aggtatatca gaaggttctt tttgccattt ggcctgtgga tgtctgagaa 3660
gatcattcac aatacatgta aaattcaggt aggcctaagg aaaggccagc ctgtagaaag 3720
caaaatggca gtgtctgttc tccactgttg gaggcattat gtaatttaag tatcctgtta 3780
gccactgtct ttctgctaat taagtggggc tgaacaagta agcactaata ataccagtga 3840
accacttggg caccttgtgg gtagagtttt gctgccacct agtggaatgg gatatcattg 3900
cttccatatc aggttcacaa gcaagttaag tgggcacagt ttatttctgt gtagctcagg 3960
ctgtaatctt gaaagctgag gagataccca tgcctctcag actcattagc tgggtgtcac 4020
attaccacct gcacattctg acccaccgca tcttaatatg ttttgtcctc ttggagaaac 4080
taggagtaga agtcaggata tggtaggtaa gggggaaaaa ggaaagacgg cttgatagct 4140
atgaatgcat gaggagcgaa atgttgactc agttatctag atcatggtct ccaaacctga 4200
tgctatttcc ttacaaaaat atttgttgag catgtgtcca taattatatg tattgaacaa 4260
tgaaaatatg tgtcaacaaa tgtactgcta cactaatgtg aacattatgg aacaaaattt 4320
gaaagagtga aataaaaggt ttacactttc aaaaaaaaaa aaaaaaaaaa aaaaaaaaaa 4380

<210> SEQ ID NO 83
<211> LENGTH: 2889
<212> TYPE: DNA
<213> ORGANISM: Homo sapiens

<400> SEQUENCE: 83
gcggcggggc tccggctgcg ctcgtggccg ggccgggcgg ggaggccggt cccgcgggcg 60
ggggcagggg cggctccgcg gcttctcccg ccgccgccgc caaggggagt ttccaggaag 120
tggccatatt ggatccattc agccgcagcc gcccgggcgg agcgcgtccc gcagccggct 180
ggtccctgtc gctgcccctg cgctcgtccc agcccacccg cccggtgcgg agctcgccat 240
ggcggccacc gacctggagc gcttctcgaa tgcagagcca gagccccgga gcctctccct 300
gggcggccat gtgggtttcg acagcctccc cgaccagctg gtcagcaagt cggtcactca 360
gggcttcagc ttcaacatcc tctgtgtggg ggagaccggc attggcaaat ccacactgat 420
gaacacactc ttcaacacga ccttcgagac tgaggaagcc agtcaccatg aggcatgcgt 480
gcgcctgcgg ccccagacct atgacctcca ggagagcaac gtgcagctca agctgaccat 540
tgtggatgcc gtgggctttg gggatcagat caataaggat gagagttaca ggcccatagt 600
tgactacatc gatgcgcagt ttgaaaatta tctgcaggag gagctgaaga tccgccgctc 660
gctcttcgac taccatgaca caaggatcca cgtttgcctc tacttcatca cgcccacagg 720
gcactccctg aagtctctag atctagtgac catgaagaaa ctagacagca aggtgaacat 780
tattcccatc atcgccaagg ctgacaccat ctccaagagc gagctccaca agttcaagat 840
caagatcatg ggcgagttgg tcagcaacgg ggtccagatc taccagttcc ccacggatga 900
tgaggctgtt gcagagatta acgcagtcat gaatgcacat ctgccctttg ccgtggtggg 960
cagcaccgag gaggtgaagg tggggaacaa gctggtccga gcacggcagt accccctgggg 1020 agtggtgcag gtggagaatg agaatcactg cgacttcgtg aagctgcggg agatgttgat 1080
ccgggtgaac atggaagacc tccgcgagca gacccacagc cggcactacg agctctaccg 1140
gcgctgcaag ttggaggaga tgggctttca ggacagcgat ggtgacagcc agcccttcag 1200
cctacaagag acatacgagg ccaagaggaa ggagttccta agtgagctgc agaggaagga 1260
ggaagagatg aggcagatgt ttgtcaacaa agtgaaggag acagagctgg agctgaagga 1320

```
gaaggaaagg gagctccatg agaagtttga gcacctgaag cgggtccacc aggaggagaa   1380
gcgcaaggtg gaggaaaagc gccgggaact ggaggaggag accaacgcct tcaatcgccg   1440
gaaggctgcg gtggaggccc tgcagtcgca ggccttgcac gccacctcgc agcagcccct   1500
gaggaaggac aaggacaaga agaacagatc agatatagga gcacaccagc cgggcatgag   1560
cctctccagc tctaaggtga tgatgaccaa ggccagtgtg gagcccttga actgcagcag   1620
ctggtggccc gccatacagt gctgcagctg cctggtcagg gatgcgacgt ggagggaagg   1680
attcctctga ggcagcagct ccaacacatg gggccagctc aggaccacca gggcatggaa   1740
ctggagacca tggtttttaa tgttagaaca gaaaacgcca tacttttcct atatcaatga   1800
tcaaaagtgc aaacaattta aatttccatc agggaacatc aaatgttgcc caacccttt   1860
cattcctatc catggctccg taaggggctt gaggcttaat gcccatcctg tggccaagct   1920
gagcttccac tccgggacca aaaaaaaaaa aaagtctgct ttgtgacatc atcgttatga   1980
gcggaaagta cctagatgac aatgtttcca ttctgaaaaa tagaaacata ctattcaaga   2040
ccaaggtagc agaaaagtta cttgtatctg cttatcataa gacgaaactc tgcaacttgg   2100
caacggtggc cagttttcgt aatgaaacag tctttagtaa tttaatcttc atgcttcata   2160
acaaaccaaa accccatgag atttccacat tgcataattt tgccttacta acagaatcat   2220
atccttaagg atgaccatca ttccccccaac taaaacaaat acaaactaat gtatgatatt   2280
tttttaagtg ccagatcaat atggtctaaa gcttcaataa ggattgtgtg taggtgaata   2340
aagacagcta agtgaatgtg tgtaaagtgt agcaaaagca gacagatatt tatgtacagt   2400
attcatagaa tggaaagtta aatatttttg cagtgtgtat ttaaaagaga aactcaccat   2460
aatagtgccg tctaaaaatc tttgtaaagt taatttaatg tcctttagaa gtgggagtct   2520
ggtggaactg tgttggattt aagatacctt ttcactcttc cgtatgtcat gagccttgtg   2580
cgtcacctca ctgtggtgca tgtgcaaggg cgtgtgcacg cctgtgcttt gccatcccat   2640
gttgtaaaca gctgttccaa aggcacaaac gagtttaggg tagactctgt aaacacctcc   2700
ttactcacta tagtcaagaa gtccagcggc gtcccaatat agaggtccca gtgcagtctg   2760
tccagaatag ccagctccat cctcagcagc tcattcgggg aatagtcaga gccatagtgc   2820
tttgtgaagt cttttacttg tggaataaac tgtaaaaaga aaataaagag gccaaagccc   2880
tacatcatg                                                           2889

<210> SEQ ID NO 84
<211> LENGTH: 4076
<212> TYPE: DNA
<213> ORGANISM: Homo sapiens

<400> SEQUENCE: 84

gcggcggggc tccggctgcg ctcgtggccg ggccgggcgg ggaggccggt cccgcgggcg     60
ggggcagggg cggctccgcg gcttctcccg ccgccgccgc caaggggagt ttccaggaag    120
tggccatatt ggatccattc agccgcagcc gcccgggcgg agcgcgtccc gcagccggct    180
ggtccctgtc gctgcccctg cgctcgtccc agcccacccg cccggtgcgg agctcgccat    240
ggcggccacc gacctggagc gcttctcgaa tgcagagcca gagccccgga gcctctccct    300
gggcggccat gtgggtttcg acagcctccc cgaccagctg gtcagcaagt cggtcactca    360
gggcttcagc ttcaacatcc tctgtgtggg ggagaccggc attggcaaat ccacactgat    420
gaacacactc ttcaacacga ccttcgagac tgaggaagcc agtcaccatg aggcatgcgt    480
```

-continued

```
gcgcctgcgg ccccagacct atgacctcca ggagagcaac gtgcagctca agctgaccat    540
tgtggatgcc gtgggctttg gggatcagat caataaggat gagagttaca ggcccatagt    600
tgactacatc gatgcgcagt ttgaaaatta tctgcaggag gagctgaaga tccgccgctc    660
gctcttcgac taccatgaca caaggatcca cgtttgcctc tacttcatca cgcccacagg    720
gcactccctg aagtctctag atctagtgac catgaagaaa ctagacagca aggtgaacat    780
tattcccatc atcgccaagg ctgacaccat ctccaagagc gagctccaca agttcaagat    840
caagatcatg ggcgagttgg tcagcaacgg ggtccagatc taccagttcc ccacggatga    900
tgaggctgtt gcagagatta acgcagtcat gaatgcacat ctgccctttg ccgtggtggg    960
cagcaccgag gaggtgaagg tggggaacaa gctggtccga gcacggcagt acccctgggg   1020
agtggtgcag gtggagaatg agaatcactg cgacttcgtg aagctgcggg agatgttgat   1080
ccgggtgaac atggaagacc tccgcgagca gacccacagc cggcactacg agctctaccg   1140
gcgctgcaag ttggaggaga tgggctttca ggacagcgat ggtgacagcc agcccttcag   1200
cctacaagag acatacgagg ccaagaggaa ggagttccta agtgagctgc agaggaagga   1260
ggaagagatg aggcagatgt ttgtcaacaa agtgaaggag acagagctgg agctgaagga   1320
gaaggaaagg gagctccatg agaagtttga gcacctgaag cgggtccacc aggaggagaa   1380
gcgcaaggtg gaggaaaagc gccgggaact ggaggaggag accaacgcct tcaatcgccg   1440
gaaggctgcg gtggaggccc tgcagtcgca ggccttgcac gccacctcgc agcagcccct   1500
gaggaaggac aaggacaaga agaaagccag tggctggtct tccatttaca gtgtcactat   1560
tccctgacgg agctgttatg tgccgctcta gcgaaggccc cagccgggat gctaggccta   1620
attgttcagc gtggagatgg caactcacgt ggtgccctag gtgcagctgc gtggtctggt   1680
atacatgctg caaaattcac ccagttcccc tcattttaat ttttctaacc tacagcttaa   1740
ttttaataac tttaaaacac ttctaaatat ttattttggc accagcgtca agacaaataa   1800
tatcctctcc cattattttc ataagtaaca cagattccct gatttttaaa aactaaaaat   1860
acagctaaac ctttcttatg tataaagtat gcctatcata tacagggaga ggtgggtaat   1920
aaacttcctg taatgacagt gtttggcatt tctttatgga tggaattgga acatgaacaa   1980
gaccatgtcc agcgttttta ctgtgaatgt aaatggaaca gcagcccaaa gctgttgtct   2040
gtgccccaga ggtgctacct gtagacaggg accaactcca tgtgtgtgtg ttaagtgttt   2100
gactccaatt aagactccca agcaaatcct gcatattcca aatgtaaaga gtactcagtg   2160
ggaaaaaggt tgttacctca aagtcattgc ttctttcctg gctgggtcac agggtgaaga   2220
gatgaaggtg tctgatgtat atagacaatt agggaaaaat gagcggcaaa ggagctttcc   2280
ccttcagctg cactctaaag gggaacattt taaggaagta ctagcagctt tgactcttct   2340
atgctcctgt tggtttacaa gccaccaaga atgtcagtgt tgagaatacg gcctggtaaa   2400
atgggagatg taaaatgact aaatgaaagg aagggtagtt ttaatgttga agcaccgtgc   2460
tgggcactgg agctacccag aggaatgcac aacgctcccc tcaaggagct cacagtctag   2520
cctactccct ggctggaagc ctcaggaaga cgtgctaatt tattgtggaa ttggtagttt   2580
gcttttcatg cccctgtctt ccttctcatg accatttccc cctttctgtc tggcttgcat   2640
tattgatttc caggaccaag tcctggcttc ctcctgcctt cctgagatga tgttctgctc   2700
agggagaagt ggaggggtga gctgtgtgtg tccaccgagg cacggccagg aagaggcagc   2760
ctttacctgt gaggggctcc atgctccagc agcagagcag gttctagtga caattcaact   2820
ttttatgcta tgaccagggg tggatctaaa ttttatgggg ctgaaagctt gaattattta   2880
```

gaaagacttc tttaagaaaa acaatgttaa tataaaatta ggtacagggt cttggaaggg 2940
gccctgaaga ttaagcttcc ttagcgtcac aataagtccg tatctggttg caattgaaaa 3000
ctgatgcttc agtgagggta tctaaaaagg taaactggca tatccagggc aaatgtgggc 3060
tgccaatggc tcatctctag ggtaatttta tgtctgaaag tgtatgcagt tgggtcagag 3120
catgaccttt aagatagcct ctctcagcta acatatttat gaagatgagg cctggtgacc 3180
cagcaggttc attggataca taagaaatga gaattcctgg ttcatgggcc aacctaggac 3240
tctggagtat gcagacttgg ccattcgtcc attgtggcct gcgggtcgca ccccaggcat 3300
actgaaaggc catactcgtg gctggctgcc tgcgggccta agccttccca ggatcttcag 3360
gacacttgac agacttgtgt ttctggtct gagctgcctc cacaggtccc tccagcaagc 3420
ctcactgcac ctctcccctg ctgtttgtgt ttggaatttt gtcttcttta gctgagacca 3480
aattaaacct tggtgcataa agtgagctta aaacttgcca ctgtttagta agttagcccc 3540
catagaatgt gaccctgtct gcagagtctc atttacccct ctttttctca ttgtcatttg 3600
ttggctttat tagggctgtc ttacaggatc atgttggcat ttactatcat gtctttatca 3660
taaaccatgt ttgtttgagg tagaagaatc accatataat tcgttgccca aattgggact 3720
attgagagag aaaggggatg ctattaatta caccagatca aaaggcataa accagacctg 3780
tcccaggccg atgtggaaat atgttctttc tagttgtggg taccctgatc taggtggttt 3840
gtaattgtgc attactgact gcatatgttt gtgtatgtgt aaatgtgggc tccctgttaa 3900
gtggggctca tggatacgag gcctgaggaa gtgtggcttg ctagtctgtt acgttaacat 3960
gcttttctaa aattgcttca cgtgttaatt catttactcc tgcattcatt gactgttttt 4020
gttcttttcc attcactttg tacttatttt tttcattaaa ttttgcattt attttg 4076

<210> SEQ ID NO 85
<211> LENGTH: 4270
<212> TYPE: DNA
<213> ORGANISM: Homo sapiens

<400> SEQUENCE: 85
tgctcgttgg ttgcacaagg agccgaaggc tggtcccttg cccgggaagg ccgcctggcc 60
ggacgcgcgg gtcccgccgg ggttcccgcc ttagctccgg ccggagcatc aggtggggcc 120
caagacaccc gcagactagg ctgccgcggc ctctcccgga tccgacgggt ctcccgcagc 180
ttgtccacac tctgaatgca gagccagagc cccggagcct ctccctgggc ggccatgtgg 240
gtttcgacag cctccccgac cagctggtca gcaagtcggt cactcagggc ttcagcttca 300
acatcctctg tgtgggggag accggcattg gcaaatccac actgatgaac acactcttca 360
acacgacctt cgagactgag gaagccagtc accatgaggc atgcgtgcgc ctgcggcccc 420
agacctatga cctccaggag agcaacgtgc agctcaagct gaccattgtg gatgccgtgg 480
gctttgggga tcagatcaat aaggatgaga gttacaggcc catagttgac tacatcgatg 540
cgcagtttga aaattatctg caggaggagc tgaagatccg ccgctcgctc ttcgactacc 600
atgacacaag gatccacgtt tgcctctact tcatcacgcc cacagggcac tccctgaagt 660
ctctagatct agtgaccatg aagaaactag acagcaaggt gaacattatt cccatcatcg 720
ccaaggctga caccatctcc aagagcgagc tccacaagtt caagatcaag atcatgggcg 780
agttggtcag caacggggtc cagatctacc agttccccac ggatgatgag gctgttgcag 840
agattaacgc agtcatgaat gcacatctgc cctttgccgt ggtgggcagc accgaggagg 900

-continued

```
tgaaggtggg gaacaagctg gtccgagcac ggcagtaccc ctggggagtg gtgcaggtgg    960
agaatgagaa tcactgcgac ttcgtgaagc tgcgggagat gttgatccgg gtgaacatgg   1020
aagacctccg cgagcagacc cacagccggc actacgagct ctaccggcgc tgcaagttgg   1080
aggagatggg ctttcaggac agcgatggtg acagccagcc cttcagccta caagagacat   1140
acgaggccaa gaggaaggag ttcctaagtg agctgcagag gaaggaggaa gagatgaggc   1200
agatgtttgt caacaaagtg aaggagacag agctggagct gaaggagaag gaaagggagc   1260
tccatgagaa gtttgagcac ctgaagcggg tccaccagga ggagaagcgc aaggtggagg   1320
aaaagcgccg ggaactggag gaggagacca acgccttcaa tcgccggaag gctgcggtgg   1380
aggccctgca gtcgcaggcc ttgcacgcca cctcgcagca gcccctgagg aaggacaagg   1440
acaagaagaa ttaacgcacg cacagactta catgtcaaga gtggacttta gactttcatg   1500
tgttaagttg cttgagttac accttgtgac ccttctccca taacatggtg tgaggacgga   1560
ctgggagccg gtacagactc cagtgtttac agccttgctt tcctcccacc gaccctggcc   1620
ccaggctgcc ccgggcctgg cgggccaccc ctctctatgc aaacacgtaa aagccatgaa   1680
tgctggaatc caaaactgac gaggtttatt tttttcagag ccagtggctg gtcttccatt   1740
tacagtgtca ctattccctg acggagctgt tatgtgccgc tctagcgaag gccccagccg   1800
ggatgctagg cctaattgtt cagcgtggag atggcaactc acgtggtgcc ctaggtgcag   1860
ctgcgtggtc tggtatacat gctgcaaaat tcacccagtt cccctcattt taatttttct   1920
aacctacagc ttaattttaa taactttaaa acacttctaa atatttattt tggcaccagc   1980
gtcaagacaa ataatatcct ctcccattat tttcataagt aacacagatt ccctgatttt   2040
taaaaactaa aaatacagct aaacctttct tatgtataaa gtatgcctat catatacagg   2100
gagaggtggg taataaactt cctgtaatga cagtgtttgg catttcttta tggatggaat   2160
tggaacatga acaagaccat gtccagcgtt tttactgtga atgtaaatgg aacagcagcc   2220
caaagctgtt gtctgtgccc cagaggtgct acctgtagac agggaccaac tccatgtgtg   2280
tgtgttaagt gtttgactcc aattaagact cccaagcaaa tcctgcatat tccaaatgta   2340
aagagtactc agtgggaaaa aggttgttac ctcaaagtca ttgcttcttt cctggctggg   2400
tcacagggtg aagagatgaa ggtgtctgat gtatatagac aattagggaa aaatgagcgg   2460
caaaggagct ttccccttca gctgcactct aaaggggaac attttaagga agtactagca   2520
gctttgactc ttctatgctc ctgttggttt acaagccacc aagaatgtca gtgttgagaa   2580
tacggcctgg taaaatggga gatgtaaaat gactaaatga aaggaagggt agttttaatg   2640
ttgaagcacc gtgctgggca ctggagctac ccagaggaat gcacaacgct cccctcaagg   2700
agctcacagt ctagcctact ccctggctgg aagcctcagg aagacgtgct aatttattgt   2760
ggaattggta gtttgctttt catgcccctg tcttccttct catgaccatt tccccctttc   2820
tgtctggctt gcattattga tttccaggac caagtcctgg cttcctcctg ccttcctgag   2880
atgatgttct gctcagggag aagtggaggg gtgagctgtg tgtgtccacc gaggcacggc   2940
caggaagagg cagcctttac ctgtgagggg ctccatgctc cagcagcaga gcaggttcta   3000
gtgacaattc aactttttat gctatgacca ggggtggatc taaattttat ggggctgaaa   3060
gcttgaatta tttagaaaga cttctttaag aaaaacaatg ttaatataaa attaggtaca   3120
gggtcttgga aggggccctg aagattaagc ttccttagcg tcacaataag tccgtatctg   3180
gttgcaattg aaaactgatg cttcagtgag ggtatctaaa aaggtaaact ggcatatcca   3240
gggcaaatgt gggctgccaa tggctcatct ctagggtaat tttatgtctg aaagtgtatg   3300
```

```
cagttgggtc agagcatgac ctttaagata gcctctctca gctaacatat ttatgaagat   3360
gaggcctggt gacccagcag gttcattgga tacataagaa atgagaattc ctggttcatg   3420
ggccaaccta ggactctgga gtatgcagac ttggccattc gtccattgtg gcctgcgggt   3480
cgcaccccag gcatactgaa aggccatact cgtggctggc tgcctgcggg cctaagcctt   3540
cccaggatct tcaggacact tgacagactt gtgttttctg gtctgagctg cctccacagg   3600
tccctccagc aagcctcact gcacctctcc cctgctgttt gtgtttggaa ttttgtcttc   3660
tttagctgag accaaattaa accttggtgc ataaagtgag cttaaaactt gccactgttt   3720
agtaagttag cccccataga atgtgaccct gtctgcagag tctcatttac ccctcttttt   3780
ctcattgtca tttgttggct ttattagggc tgtcttacag gatcatgttg gcatttacta   3840
tcatgtcttt atcataaacc atgtttgttt gaggtagaag aatcaccata taattcgttg   3900
cccaaattgg gactattgag agagaaaggg gatgctatta attacaccag atcaaaaggc   3960
ataaaccaga cctgtcccag gccgatgtgg aaatatgttc tttctagttg tgggtaccct   4020
gatctaggtg gtttgtaatt gtgcattact gactgcatat gtttgtgtat gtgtaaatgt   4080
gggctccctg ttaagtgggg ctcatggata cgaggcctga ggaagtgtgg cttgctagtc   4140
tgttacgtta acatgctttt ctaaaattgc ttcacgtgtt aattcattta ctcctgcatt   4200
cattgactgt ttttgttctt ttccattcac tttgtactta tttttttcat taaattttgc   4260
atttattttg                                                          4270
```

<210> SEQ ID NO 86
<211> LENGTH: 4344
<212> TYPE: DNA
<213> ORGANISM: Homo sapiens

<400> SEQUENCE: 86

```
gcggcggggc tccggctgcg ctcgtggccg ggccgggcgg ggaggccggt cccgcgggcg     60
ggggcagggg cggctccgcg gcttctcccg ccgccgccgc caaggggagt ttccaggaag    120
tggccatatt ggatccattc agccgcagcc gcccgggcgg agcgcgtccc gcagccggct    180
ggtccctgtc gctgcccctg cgctcgtccc agcccacccg cccggtgcgg agctcgccat    240
ggcggccacc gacctggagc gcttctcgaa tgcagagcca gagccccgga gcctctccct    300
gggcggccat gtgggtttcg acagcctccc cgaccagctg gtcagcaagt cggtcactca    360
gggcttcagc ttcaacatcc tctgtgtggg ggagaccggc attggcaaat ccacactgat    420
gaacacactc ttcaacacga ccttcgagac tgaggaagcc agtcaccatg aggcatgcgt    480
gcgcctgcgg ccccagacct atgacctcca ggagagcaac gtgcagctca agctgaccat    540
tgtggatgcc gtgggctttg gggatcagat caataaggat gagagttaca ggcccatagt    600
tgactacatc gatgcgcagt ttgaaaatta tctgcaggag gagctgaaga tccgccgctc    660
gctcttcgac taccatgaca caaggatcca cgtttgcctc tacttcatca cgcccacagg    720
gcactccctg aagtctctag atctagtgac catgaagaaa ctagacagca aggtgaacat    780
tattcccatc atcgccaagg ctgacaccat ctccaagagc gagctccaca agttcaagat    840
caagatcatg ggcgagttgg tcagcaacgg ggtccagatc taccagttcc ccacggatga    900
tgaggctgtt gcagagatta acgcagtcat gaatgcacat ctgccctttg ccgtggtggg    960
cagcaccgag gaggtgaagg tggggaacaa gctggtccga gcacggcagt acccctgggg   1020
agtggtgcag gtggagaatg agaatcactg cgacttcgtg aagctgcggg agatgttgat   1080
```

ccgggtgaac atggaagacc tccgcgagca gacccacagc cggcactacg agctctaccg 1140
gcgctgcaag ttggaggaga tgggctttca ggacagcgat ggtgacagcc agcccttcag 1200
cctacaagag acatacgagg ccaagaggaa ggagttccta agtgagctgc agaggaagga 1260
ggaagagatg aggcagatgt ttgtcaacaa agtgaaggag acagagctgg agctgaagga 1320
gaaggaaagg gagctccatg agaagtttga gcacctgaag cgggtccacc aggaggagaa 1380
gcgcaaggtg gaggaaaagc gccgggaact ggaggaggag accaacgcct tcaatcgccg 1440
gaaggctgcg gtggaggccc tgcagtcgca ggccttgcac gccacctcgc agcagcccct 1500
gaggaaggac aaggacaaga agaattaacg cacgcacaga cttacatgtc aagagtggac 1560
tttagacttt catgtgttaa gttgcttgag ttacaccttg tgacccttct cccataacat 1620
ggtgtgagga cggactggga gccggtacag actccagtgt ttacagcctt gctttcctcc 1680
caccgaccct ggccccaggc tgccccgggc ctggcgggcc acccctctct atgcaaacac 1740
gtaaaagcca tgaatgctgg aatccaaaac tgacgaggtt tatttttttc agagccagtg 1800
gctggtcttc catttacagt gtcactattc cctgacggag ctgttatgtg ccgctctagc 1860
gaaggcccca gccgggatgc taggcctaat tgttcagcgt ggagatggca actcacgtgg 1920
tgccctaggt gcagctgcgt ggtctggtat acatgctgca aaattcaccc agttcccctc 1980
attttaattt ttctaaccta cagcttaatt ttaataactt taaaacactt ctaaatattt 2040
attttggcac cagcgtcaag acaaataata tcctctccca ttattttcat aagtaacaca 2100
gattccctga tttttaaaaa ctaaaaatac agctaaacct ttcttatgta taaagtatgc 2160
ctatcatata cagggagagg tgggtaataa acttcctgta atgacagtgt ttggcatttc 2220
tttatggatg gaattggaac atgaacaaga ccatgtccag cgtttttact gtgaatgtaa 2280
atggaacagc agcccaaagc tgttgtctgt gccccagagg tgctacctgt agacagggac 2340
caactccatg tgtgtgtgtt aagtgtttga ctccaattaa gactcccaag caaatcctgc 2400
atattccaaa tgtaaagagt actcagtggg aaaaaggttg ttacctcaaa gtcattgctt 2460
ctttcctggc tgggtcacag ggtgaagaga tgaaggtgtc tgatgtatat agacaattag 2520
ggaaaaatga gcggcaaagg agctttcccc ttcagctgca ctctaaaggg gaacatttta 2580
aggaagtact agcagctttg actcttctat gctcctgttg gtttacaagc caccaagaat 2640
gtcagtgttg agaatacggc ctggtaaaat gggagatgta aaatgactaa atgaaaggaa 2700
gggtagtttt aatgttgaag caccgtgctg ggcactggag ctacccagag gaatgcacaa 2760
cgctcccctc aaggagctca cagtctagcc tactccctgg ctggaagcct caggaagacg 2820
tgctaattta ttgtggaatt ggtagtttgc ttttcatgcc cctgtcttcc ttctcatgac 2880
catttccccc tttctgtctg gcttgcatta ttgatttcca ggaccaagtc ctggcttcct 2940
cctgccttcc tgagatgatg ttctgctcag ggagaagtgg aggggtgagc tgtgtgtgtc 3000
caccgaggca cggccaggaa gaggcagcct ttacctgtga ggggctccat gctccagcag 3060
cagagcaggt tctagtgaca attcaacttt ttatgctatg accaggggtg gatctaaatt 3120
ttatggggct gaaagcttga attatttaga aagacttctt taagaaaaac aatgttaata 3180
taaaattagg tacagggtct tggaaggggc cctgaagatt aagcttcctt agcgtcacaa 3240
taagtccgta tctggttgca attgaaaact gatgcttcag tgagggtatc taaaaaggta 3300
aactggcata tccagggcaa atgtgggctg ccaatggctc atctctaggg taattttatg 3360
tctgaaagtg tatgcagttg ggtcagagca tgacctttaa gatagcctct ctcagctaac 3420
atatttatga agatgaggcc tggtgaccca gcaggttcat tggatacata agaaatgaga 3480
attcctggtt catgggccaa cctaggactc tggagtatgc agacttggcc attcgtccat 3540
tgtggcctgc gggtcgcacc ccaggcatac tgaaaggcca tactcgtggc tggctgcctg 3600
cgggcctaag ccttcccagg atcttcagga cacttgacag acttgtgttt tctggtctga 3660
gctgcctcca caggtccctc cagcaagcct cactgcacct ctcccctgct gtttgtgttt 3720
ggaattttgt cttctttagc tgagaccaaa ttaaaccttg gtgcataaag tgagcttaaa 3780
acttgccact gtttagtaag ttagccccca tagaatgtga ccctgtctgc agagtctcat 3840
ttacccctct ttttctcatt gtcatttgtt ggctttatta gggctgtctt acaggatcat 3900
gttggcattt actatcatgt ctttatcata aaccatgttt gtttgaggta gaagaatcac 3960
catataattc gttgcccaaa ttgggactat tgagagagaa aggggatgct attaattaca 4020
ccagatcaaa aggcataaac cagacctgtc ccaggccgat gtggaaatat gttctttcta 4080
gttgtgggta ccctgatcta ggtggtttgt aattgtgcat tactgactgc atatgtttgt 4140
gtatgtgtaa atgtgggctc cctgttaagt ggggctcatg gatacgaggc ctgaggaagt 4200
gtggcttgct agtctgttac gttaacatgc ttttctaaaa ttgcttcacg tgttaattca 4260
tttactcctg cattcattga ctgtttttgt tcttttccat tcactttgta cttatttttt 4320
tcattaaatt ttgcatttat tttg 4344

<210> SEQ ID NO 87
<211> LENGTH: 3837
<212> TYPE: DNA
<213> ORGANISM: Homo sapiens

<400> SEQUENCE: 87
actccagacg gcgggccgcc ccctcttccc gccttcctac taccggccca ggattagcgc 60
cctgggagcg cgcgccccgc tgcctcgccg ccacactttc ctgggagcgg cggccacgga 120
ggcaccatga agaagtctta ctcaggaggc acgcggacct ccagtggccg gctccggagg 180
cttggtgact ccagtggccc agccttgaaa agatcttttg aggtcgagga ggtcgagaca 240
cccaactcca ccccaccccg gagggtccag actcccctac tccgagccac tgtggccagc 300
tccacccaga aattccagga cctgggcgtg aagaactcag aaccctcggc ccgccatgtg 360
gactccctaa gccaacgctc cccccaaggcg tccctgcgga gggtggagct ctcgggcccc 420
aaggcggccg agccggtgtc ccggcgcact gagctgtcca ttgacatctc gtccaagcag 480
gtggagaacg ccggggccat cggcccgtcc cggttcgggc tcaagagggc cgaggtgttg 540
ggccacaaga cgccagaacc ggcccctcgg aggacggaga tcaccatcgt caaaccccag 600
gagtcagccc accggaggat ggagcccccct gcctccaagg tccccgaggt gcccactgcc 660
cctgccaccg acgcagcccc caagagggtg gagatccaga tgcccaagcc tgctgaggcg 720
cccaccgccc ccagcccagc ccagaccttg gagaattcag agcctgcccc tgtgtctcag 780
ctgcagagca ggctggagcc caagccccag cccccctgtgg ctgaggctac accccggagc 840
caggaggcca ctgaggcggc tcccagctgc gttggcgaca tggccgacac ccccagagat 900
gccgggctca agcaggcgcc tgcatcacgg aacgagaagg ccccggtgga cttcggctac 960
gtggggattg actccatcct ggagcagatg cgccggaagg ccatgaagca gggcttcgag 1020
ttcaacatca tggtggtcgg gcagagcggc ttgggtaaat ccaccttaat caacaccctc 1080
ttcaaatcca aaatcagccg gaagtcggtg cagcccacct cagaggagcg catccccaag 1140
accatcgaga tcaagtccat cacgcacgat attgaggaga aaggcgtccg gatgaagctg 1200

-continued acagtgattg acacaccagg gttcggggac cacatcaaca acgagaactg ctggcagccc 1260
atcatgaagt tcatcaatga ccagtacgag aaatacctgc aggaggaggt caacatcaac 1320
cgcaagaagc gcatcccgga cacccgcgtc cactgctgcc tctacttcat ccccgccacc 1380
ggccactccc tcaggcccct ggacatcgag tttatgaaac gcctgagcaa ggtggtcaac 1440
atcgtccctg tcatcgccaa ggcggacaca ctcaccctgg aggagagggt ccacttcaaa 1500
cagcggatca ccgcagacct gctgtccaac ggcatcgacg tgtacccccca gaaggaattt 1560
gatgaggact cggaggaccg gctggtgaac gagaagttcc gggagatgat cccatttgct 1620
gtggtgggca gtgaccacga gtaccaggtc aacggcaaga ggatccttgg gaggaagacc 1680
aagtggggta ccatcgaagt tgaaaacacc acacactgtg agtttgccta cctgcgggac 1740
cttctcatca ggacgcacat gcagaacatc aaggacatca ccagcagcat ccacttcgag 1800
gcgtaccgtg tgaagcgcct caacgagggc agcagcgcca tggccaacgg catggaggag 1860
aaggagccag aagccccgga gatgtagacg ccaccctgcc cacccccggg atcctgcccc 1920
caagtcattt ccgtcccccc ccaggccctc ccaccacccc attttatttt atatgatttt 1980
ctccatttgt catcgttccc cacccccttcg acatgctgcc aggaaacaag ggaaggggcc 2040
tccctccgag tgagtcagtg atgaggccgc ggcctccccg aggttgtggg gaggctgcac 2100
tggagccaca ggcaggggtg agagcaccca ctgaattgac atgaccctct gtccccaggc 2160
ctggctcccc gagggctcag aagagcagct tcggtgtgca gatcatccgt ctgtgtgggg 2220
ttctcagtgc cggaggcctt ggggtggggg ccaggcctcg cacttgcaga ggagcccagt 2280
gggctgcacg ctcccctcca tccccatcgg ccctgtcccc tggagtgtgt cagagcccag 2340
gggagaatgc agcccaccag gagcacctgg accccctgcc cgccacatgg tgtggccatc 2400
actcagcccc taccccctgcc ctgctcctaa gggtagaaaa ctccagggtc ccctgccacc 2460
gactgcccag ccactccaag ccccctggca gctgcccctc ctggagcaga aagtgccttt 2520
atctcagcca tccgcagact gcttggccag atgcggggac aggctggaat gagggaggcg 2580
tcttcatctc cctgccatcc ccctctcacg ccaccccccgc ccccaccggg ctgcaggtgc 2640
tgctgatgcg ctgggatctg attgaggata aaaaggaagg agagatgacc cctacccccct 2700
catcccccag ttttgaaaag gtctaagcaa gtgagtctgg tggaggagct gagggaggga 2760
gccatggaag gtgccagaag gaaggttggc gggggcacgt gtgggccgtg gcttgggctg 2820
gtcagagtgg cgtgagctgc ccggcgcctg ccctgcccaa gtgaccaggg aagtgtgtgt 2880
gtgtccatgt gtatgcgtgt ccgtctgtct gtctagtgtc tgggtttggc ccaagactgg 2940
gctgtagtta cattaatgcc cagccagcca cccctgccac tcacccctcc tggcccaggc 3000
cttgctgact ctctgagctg gggaggtggg aggccaggcg agcctgactc tgttgatcta 3060
cccgtgcctg ggcccctccc ctcagagccc atggtaacga accccctagaa aggagagaac 3120
gggcgtcagg ggtgcacagt ccacagctga agagcaaggt ttcgtggcag cacggcccgg 3180
cccctcaccc tctgtcccca cgaggggacc catgggggct gtctttgcag ggcacagatg 3240
accaaagtcc cttcctgctt cctgttacct gtcttgctcc tggggagaaa gaggggcctg 3300
atgagactcc actcaggtgc acacatcacc aggtgcatct gcaggcaccg ggctggctgc 3360
ttgcagccag gagaaggtca gcgagaagga gtgtatgagt gtgagtgtgt gtgcatggaa 3420
gttggggcac tgggcgtctg actccctccc cacccaagag aggaaggacc cctcaccacc 3480
cccactggcg agacagttta ctttgccgac ttgccatgtt tttgccaaaa ccaagatttt 3540
gaaggaaatg agtggccagc gccagggccc aggccatgtg gcctgcccag cctcaatgtc 3600

-continued

```
acttggtggc ggggtggggt gggggtgggc agcagcatcc cagccttgag atgcttcact   3660

ttccttctct gtaaccagac tttgaaaaat tgttcgtttc atcaggctct gttcctcaat   3720

ggccttttgc tacgtgcctc ccgagaaatt tgtctttttg tataaatgac aaagtgttga   3780

aaatgtattt cctgaaataa atgtttcaaa tgcagaaacc cagaaaaaaa aaaaaaa      3837
```

<210> SEQ ID NO 88
<211> LENGTH: 4012
<212> TYPE: DNA
<213> ORGANISM: Homo sapiens

<400> SEQUENCE: 88

```
actgggcggc ccttagaccc aggctgcctg ctgtctctgg caggaactca agtcgctggt     60

catcctcaga gcggtgttgg cccggggcct tcagtggcct ttgtgtctgg gtgagaggaa    120

ccctggatgg ccactctgcc ctgagtgtgt gggtccccag aagtgctggg ttagggggca    180

cggagggcca gaaagtcccc tttggagcgc tggactctct cgctgactcc taccccaccc    240

cggcctgggg tttcagagaa ggggtccagg caggagtgtc atcttttctc aatggggatg    300

tggcttcagt ctctgtccag gaggcacgcg gacctccagt ggccggctcc ggaggcttgg    360

tgactccagt ggcccagcct tgaaaagatc ttttgaggtc gaggaggtcg agacacccaa    420

ctccacccca ccccggaggg tccagactcc cctactccga gccactgtgg ccagctccac    480

ccagaaattc caggacctgg gcgtgaagaa ctcagaaccc tcggcccgcc atgtggactc    540

cctaagccaa cgctccccca aggcgtccct gcggagggtg gagctctcgg gccccaaggc    600

ggccgagccg gtgtcccggc gcactgagct gtccattgac atctcgtcca agcaggtgga    660

gaacgccggg gccatcggcc cgtcccggtt cgggctcaag agggccgagg tgttgggcca    720

caagacgcca gaaccggccc ctcggaggac ggagatcacc atcgtcaaac cccaggagtc    780

agcccaccgg aggatggagc cccctgcctc caaggtcccc gaggtgccca ctgcccctgc    840

caccgacgca gcccccaaga gggtggagat ccagatgccc aagcctgctg aggcgcccac    900

cgcccccagc ccagcccaga ccttggagaa ttcagagcct gcccctgtgt ctcagctgca    960

gagcaggctg gagcccaagc cccagccccc tgtggctgag gctacacccc ggagccagga   1020

ggccactgag gcggctccca gctgcgttgg cgacatggcc gacaccccca gagatgccgg   1080

gctcaagcag gcgcctgcat cacggaacga gaaggccccg gtggacttcg gctacgtggg   1140

gattgactcc atcctggagc agatgcgccg gaaggccatg aagcagggct tcgagttcaa   1200

catcatggtg gtcgggcaga gcggcttggg taaatccacc ttaatcaaca ccctcttcaa   1260

atccaaaatc agccggaagt cggtgcagcc cacctcagag gagcgcatcc ccaagaccat   1320

cgagatcaag tccatcacgc acgatattga ggagaaaggc gtccggatga agctgacagt   1380

gattgacaca ccagggttcg gggaccacat caacaacgag aactgctggc agcccatcat   1440

gaagttcatc aatgaccagt acgagaaata cctgcaggag gaggtcaaca tcaaccgcaa   1500

gaagcgcatc ccggacaccc gcgtccactg ctgcctctac ttcatccccg ccaccggcca   1560

ctccctcagg cccctggaca tcgagtttat gaaacgcctg agcaaggtgg tcaacatcgt   1620

ccctgtcatc gccaaggcgg acacactcac cctggaggag agggtccact tcaaacagcg   1680

gatcaccgca gacctgctgt ccaacggcat cgacgtgtac ccccagaagg aatttgatga   1740

ggactcggag gaccggctgg tgaacgagaa gttccgggag atgatcccat ttgctgtggt   1800

gggcagtgac cacgagtacc aggtcaacgg caagaggatc cttgggagga agaccaagtg   1860
```

gggtaccatc gaagttgaaa acaccacaca ctgtgagttt gcctacctgc gggaccttct 1920
catcaggacg cacatgcaga acatcaagga catcaccagc agcatccact tcgaggcgta 1980
ccgtgtgaag cgcctcaacg agggcagcag cgccatggcc aacggcatgg aggagaagga 2040
gccagaagcc ccggagatgt agacgccacc ctgcccaccc ccgggatcct gcccccaagt 2100
catttccgtc cccccccagg ccctcccacc accccatttt attttatatg attttctcca 2160
tttgtcatcg ttccccaccc cttcgacatg ctgccaggaa acaagggaag ggcctccct 2220 ccgagtgagt cagtgatgag gccgcggcct ccccgaggtt gtggggaggc tgcactggag 2280
ccacaggcag gggtgagagc acccactgaa ttgacatgac cctctgtccc caggcctggc 2340
tccccgaggg ctcagaagag cagcttcggt gtgcagatca tccgtctgtg tggggttctc 2400
agtgccggag gccttggggt gggggccagg cctcgcactt gcagaggagc ccagtgggct 2460
gcacgctccc ctccatcccc atcggccctg tcccctggag tgtgtcagag cccaggggag 2520
aatgcagccc accaggagca cctggacccc ctgcccgcca catggtgtgg ccatcactca 2580
gcccctaccc ctgccctgct cctaagggta gaaaactcca gggtcccctg ccaccgactg 2640
cccagccact ccaagccccc tggcagctgc ccctcctgga gcagaaagtg cctttatctc 2700
agccatccgc agactgcttg gccagatgcg gggacaggct ggaatgaggg aggcgtcttc 2760
atctccctgc catccccctc tcacgccacc cccgccccca ccgggctgca ggtgctgctg 2820
atgcgctggg atctgattga ggataaaaag gaaggagaga tgacccctac cccctcatcc 2880
cccagttttg aaaaggtcta agcaagtgag tctggtggag gagctgaggg agggagccat 2940
ggaaggtgcc agaaggaagg ttggcggggg cacgtgtggg ccgtggcttg ggctggtcag 3000
agtggcgtga gctgcccggc gcctgccctg cccaagtgac cagggaagtg tgtgtgtgtc 3060
catgtgtatg cgtgtccgtc tgtctgtcta gtgtctgggt ttggcccaag actgggctgt 3120
agttacatta atgcccagcc agccacccct gccactcacc cctcctggcc caggccttgc 3180
tgactctctg agctggggag gtgggaggcc aggcgagcct gactctgttg atctacccgt 3240
gcctgggccc ctcccctcag agcccatggt aacgaacccc tagaaaggag agaacgggcg 3300
tcaggggtgc acagtccaca gctgaagagc aaggtttcgt ggcagcacgg cccggcccct 3360
caccctctgt ccccacgagg ggacccatgg gggctgtctt tgcagggcac agatgaccaa 3420
agtcccttcc tgcttcctgt tacctgtctt gctcctgggg agaaagaggg gcctgatgag 3480
actccactca ggtgcacaca tcaccaggtg catctgcagg caccgggctg gctgcttgca 3540
gccaggagaa ggtcagcgag aaggagtgta tgagtgtgag tgtgtgtgca tggaagttgg 3600
ggcactgggc gtctgactcc ctccccaccc aagagaggaa ggacccctca ccaccccac 3660 tggcgagaca gtttactttg ccgacttgcc atgtttttgc caaaaccaag attttgaagg 3720
aaatgagtgg ccagcgccag ggcccaggcc atgtggcctg cccagcctca atgtcacttg 3780
gtggcggggt ggggtggggg tgggcagcag catcccagcc ttgagatgct tcactttcct 3840
tctctgtaac cagactttga aaaattgttc gtttcatcag gctctgttcc tcaatggcct 3900
tttgctacgt gcctcccgag aaatttgtct ttttgtataa atgacaaagt gttgaaaatg 3960
tatttcctga aataaatgtt tcaaatgcag aaacccagaa aaaaaaaaaa aa 4012

<210> SEQ ID NO 89
<211> LENGTH: 3998
<212> TYPE: DNA
<213> ORGANISM: Homo sapiens

<400> SEQUENCE: 89

-continued

```
ccccaggcct ggccttgaca ggcgggcgga gcagccagtg cgagacaggg aggccggtgc     60
gggtgcggga acctgatccg cccgggaggc gggggcgggg cgggggcgca gcgcgcgggg    120
aggggccggc gcccgccttc ctcccccatt cattcagctg agccaggggg cctaggggct    180
cctccggcgg ctagctctgc actgcaggag cgcgggcgcg gcgccccagc cagcgcgcag    240
ggcccgggcc ccgccggggg cgcttcctcg ccgctgccct ccgcgcgacc cgctgcccac    300
cagccatcat gtcggacccc gcggtcaacg cgcagctgga tgggatcatt tcggacttcg    360
aagccttgaa aagatctttt gaggtcgagg aggtcgagac acccaactcc accccacccc    420
ggagggtcca gactccccta ctccgagcca ctgtggccag ctccacccag aaattccagg    480
acctgggcgt gaagaactca gaaccctcgg cccgccatgt ggactcccta agccaacgct    540
cccccaaggc gtccctgcgg agggtggagc tctcgggccc caaggcggcc gagccggtgt    600
cccggcgcac tgagctgtcc attgacatct cgtccaagca ggtggagaac gccggggcca    660
tcggcccgtc ccggttcggg ctcaagaggg ccgaggtgtt gggccacaag acgccagaac    720
cggcccctcg gaggacggag atcaccatcg tcaaacccca ggagtcagcc caccggagga    780
tggagccccc tgcctccaag gtccccgagg tgcccactgc ccctgccacc gacgcagccc    840
ccaagagggt ggagatccag atgcccaagc ctgctgaggc gcccaccgcc cccagcccag    900
cccagacctt ggagaattca gagcctgccc ctgtgtctca gctgcagagc aggctggagc    960
ccaagcccca gccccctgtg gctgaggcta caccccggag ccaggaggcc actgaggcgg   1020
ctcccagctg cgttggcgac atggccgaca cccccagaga tgccgggctc aagcaggcgc   1080
ctgcatcacg gaacgagaag gccccggtgg acttcggcta cgtggggatt gactccatcc   1140
tggagcagat gcgccggaag gccatgaagc agggcttcga gttcaacatc atggtggtcg   1200
ggcagagcgg cttgggtaaa tccaccttaa tcaacaccct cttcaaatcc aaaatcagcc   1260
ggaagtcggt gcagcccacc tcagaggagc gcatccccaa gaccatcgag atcaagtcca   1320
tcacgcacga tattgaggag aaaggcgtcc ggatgaagct gacagtgatt gacacaccag   1380
ggttcgggga ccacatcaac aacgagaact gctggcagcc catcatgaag ttcatcaatg   1440
accagtacga gaaatacctg caggaggagg tcaacatcaa ccgcaagaag cgcatcccgg   1500
acacccgcgt ccactgctgc ctctacttca tccccgccac cggccactcc ctcaggcccc   1560
tggacatcga gtttatgaaa cgcctgagca aggtggtcaa catcgtccct gtcatcgcca   1620
aggcggacac actcaccctg gaggagaggg tccacttcaa acagcggatc accgcagacc   1680
tgctgtccaa cggcatcgac gtgtaccccc agaaggaatt tgatgaggac tcggaggacc   1740
ggctggtgaa cgagaagttc cgggagatga tcccatttgc tgtggtgggc agtgaccacg   1800
agtaccaggt caacggcaag aggatccttg ggaggaagac caagtggggt accatcgaag   1860
ttgaaaacac cacacactgt gagtttgcct acctgcggga ccttctcatc aggacgcaca   1920
tgcagaacat caaggacatc accagcagca tccacttcga ggcgtaccgt gtgaagcgcc   1980
tcaacgaggg cagcagcgcc atggccaacg gcatggagga gaaggagcca gaagccccgg   2040
agatgtagac gccaccctgc ccacccccgg gatcctgccc ccaagtcatt tccgtccccc   2100
cccaggccct cccaccaccc cattttattt tatatgattt tctccatttg tcatcgttcc   2160
ccacccccttc gacatgctgc caggaaacaa gggaaggggc ctccctccga gtgagtcagt   2220
gatgaggccg cggcctcccc gaggttgtgg ggaggctgca ctggagccac aggcaggggt   2280
gagagcaccc actgaattga catgaccctc tgtccccagg cctggctccc cgagggctca   2340
```

```
gaagagcagc ttcggtgtgc agatcatccg tctgtgtggg gttctcagtg ccggaggcct   2400
tggggtgggg gccaggcctc gcacttgcag aggagcccag tgggctgcac gctcccctcc   2460
atccccatcg gccctgtccc ctggagtgtg tcagagccca ggggagaatg cagcccacca   2520
ggagcacctg gacccccctgc ccgccacatg gtgtggccat cactcagccc ctacccctgc   2580
cctgctccta agggtagaaa actccagggt cccctgccac cgactgccca gccactccaa   2640
gccccctggc agctgcccct cctggagcag aaagtgcctt tatctcagcc atccgcagac   2700
tgcttggcca gatgcgggga caggctggaa tgagggaggc gtcttcatct ccctgccatc   2760
cccctctcac gccacccccg cccccaccgg gctgcaggtg ctgctgatgc gctgggatct   2820
gattgaggat aaaaaggaag gagagatgac ccctacccc tcatccccca gttttgaaaa   2880
ggtctaagca agtgagtctg gtggaggagc tgagggaggg agccatggaa ggtgccagaa   2940
ggaaggttgg cgggggcacg tgtgggccgt ggcttgggct ggtcagagtg gcgtgagctg   3000
cccggcgcct gccctgccca agtgaccagg gaagtgtgtg tgtgtccatg tgtatgcgtg   3060
tccgtctgtc tgtctagtgt ctgggtttgg cccaagactg ggctgtagtt acattaatgc   3120
ccagccagcc acccctgcca ctcacccctc ctggcccagg ccttgctgac tctctgagct   3180
ggggaggtgg gaggccaggc gagcctgact ctgttgatct acccgtgcct gggcccctcc   3240
cctcagagcc catggtaacg aacccctaga aaggagagaa cgggcgtcag gggtgcacag   3300
tccacagctg aagagcaagg tttcgtggca gcacggcccg gcccctcacc ctctgtcccc   3360
acgaggggac ccatgggggc tgtctttgca gggcacagat gaccaaagtc ccttcctgct   3420
tcctgttacc tgtcttgctc ctggggagaa agaggggcct gatgagactc cactcaggtg   3480
cacacatcac caggtgcatc tgcaggcacc gggctggctg cttgcagcca ggagaaggtc   3540
agcgagaagg agtgtatgag tgtgagtgtg tgtgcatgga agttggggca ctgggcgtct   3600
gactccctcc ccacccaaga gaggaaggac ccctcaccac ccccactggc gagacagttt   3660
actttgccga cttgccatgt ttttgccaaa accaagattt tgaaggaaat gagtggccag   3720
cgccagggcc caggccatgt ggcctgccca gcctcaatgt cacttggtgg cggggtgggg   3780
tgggggtggg cagcagcatc ccagccttga gatgcttcac tttccttctc tgtaaccaga   3840
ctttgaaaaa ttgttcgttt catcaggctc tgttcctcaa tggcctttttg ctacgtgcct   3900
cccgagaaat ttgtcttttt gtataaatga caaagtgttg aaaatgtatt tcctgaaata   3960
aatgtttcaa atgcagaaac ccagaaaaaa aaaaaaaa                            3998
```

```
<210> SEQ ID NO 90
<211> LENGTH: 3951
<212> TYPE: DNA
<213> ORGANISM: Homo sapiens

<400> SEQUENCE: 90

gtcagtatgg aggaggcgga ccttgaggga gagtaggaat tggattgcaa gaggaaggag     60
agccttctgg ccagcagcag ccagcagcag tgggggaggc tggaatgagc tggctggaga    120
gggggctggg gcataaggag gggcctgcct gtgaagatca tatgggccag gctgcggagg    180
gccaggcatg cccgccggga gtgcagctgg tccacgggaa gcatctggag tggctgggaa    240
tgggcgcagg agcagcgccg tgggagcaca ggtctctttc ccggggcggc tcacctggtg    300
tcttggttcc tgcaagcctt gaaaagatct tttgaggtcg aggaggtcga gacacccaac    360
tccaccccac cccggagggt ccagactccc ctactccgag ccactgtggc cagctccacc    420
cagaaattcc aggacctggg cgtgaagaac tcagaaccct cggcccgcca tgtggactcc    480
```

```
ctaagccaac gctcccccaa ggcgtccctg cggagggtgg agctctcggg ccccaaggcg    540
gccgagccgg tgtcccggcg cactgagctg tccattgaca tctcgtccaa gcaggtggag    600
aacgccgggg ccatcggccc gtcccggttc gggctcaaga gggccgaggt gttgggccac    660
aagacgccag aaccggcccc tcggaggacg gagatcacca tcgtcaaacc ccaggagtca    720
gcccaccgga ggatggagcc ccctgcctcc aaggtccccg aggtgcccac tgcccctgcc    780
accgacgcag cccccaagag ggtggagatc cagatgccca agcctgctga ggcgcccacc    840
gcccccagcc cagcccagac cttggagaat tcagagcctg cccctgtgtc tcagctgcag    900
agcaggctgg agcccaagcc ccagcccccct gtggctgagg ctacaccccg gagccaggag    960
gccactgagg cggctcccag ctgcgttggc gacatggccg acacccccag agatgccggg   1020
ctcaagcagg cgcctgcatc acggaacgag aaggccccgg tggacttcgg ctacgtgggg   1080
attgactcca tcctggagca gatgcgccgg aaggccatga agcagggctt cgagttcaac   1140
atcatggtgg tcgggcagag cggcttgggt aaatccacct taatcaacac cctcttcaaa   1200
tccaaaatca gccggaagtc ggtgcagccc acctcagagg agcgcatccc caagaccatc   1260
gagatcaagt ccatcacgca cgatattgag gagaaaggcg tccggatgaa gctgacagtg   1320
attgacacac cagggttcgg ggaccacatc aacaacgaga actgctggca gcccatcatg   1380
aagttcatca atgaccagta cgagaaatac ctgcaggagg aggtcaacat caaccgcaag   1440
aagcgcatcc cggacacccg cgtccactgc tgcctctact tcatccccgc caccggccac   1500
tccctcaggc ccctggacat cgagtttatg aaacgcctga gcaaggtggt caacatcgtc   1560
cctgtcatcg ccaaggcgga cacactcacc ctggaggaga gggtccactt caaacagcgg   1620
atcaccgcag acctgctgtc caacggcatc gacgtgtacc cccagaagga atttgatgag   1680
gactcggagg accggctggt gaacgagaag ttccgggaga tgatcccatt tgctgtggtg   1740
ggcagtgacc acgagtacca ggtcaacggc aagaggatcc ttgggaggaa gaccaagtgg   1800
ggtaccatcg aagttgaaaa caccacacac tgtgagtttg cctacctgcg ggaccttctc   1860
atcaggacgc acatgcagaa catcaaggac atcaccagca gcatccactt cgaggcgtac   1920
cgtgtgaagc gcctcaacga gggcagcagc gccatggcca acggcatgga ggagaaggag   1980
ccagaagccc cggagatgta gacgccaccc tgcccacccc cgggatcctg cccccaagtc   2040
atttccgtcc ccccccaggc cctcccacca ccccatttta ttttatatga ttttctccat   2100
ttgtcatcgt tccccacccc ttcgacatgc tgccaggaaa caagggaagg ggcctccctc   2160
cgagtgagtc agtgatgagg ccgcggcctc cccgaggttg tggggaggct gcactggagc   2220
cacaggcagg ggtgagagca cccactgaat tgacatgacc ctctgtcccc aggcctggct   2280
ccccgagggc tcagaagagc agcttcggtg tgcagatcat ccgtctgtgt ggggttctca   2340
gtgccggagg ccttggggtg ggggccaggc ctcgcacttg cagaggagcc cagtgggctg   2400
cacgctcccc tccatcccca tcggccctgt cccctggagt gtgtcagagc ccaggggaga   2460
atgcagccca ccaggagcac ctggaccccc tgcccgccac atggtgtggc catcactcag   2520
cccctacccc tgccctgctc ctaagggtag aaaactccag ggtcccctgc caccgactgc   2580
ccagccactc caagccccct ggcagctgcc cctcctggag cagaaagtgc ctttatctca   2640
gccatccgca gactgcttgg ccagatgcgg ggacaggctg gaatgaggga ggcgtcttca   2700
tctccctgcc atccccctct cacgccaccc ccgcccccac cgggctgcag gtgctgctga   2760
tgcgctggga tctgattgag gataaaaagg aaggagagat gacccctacc ccctcatccc   2820
```

-continued

```
ccagttttga aaaggtctaa gcaagtgagt ctggtggagg agctgaggga gggagccatg   2880
gaaggtgcca gaaggaaggt tggcgggggc acgtgtgggc cgtggcttgg gctggtcaga   2940
gtggcgtgag ctgcccggcg cctgccctgc ccaagtgacc agggaagtgt gtgtgtgtcc   3000
atgtgtatgc gtgtccgtct gtctgtctag tgtctgggtt tggcccaaga ctgggctgta   3060
gttacattaa tgcccagcca gccacccctg ccactcaccc ctcctggccc aggccttgct   3120
gactctctga gctggggagg tgggaggcca ggcgagcctg actctgttga tctacccgtg   3180
cctgggcccc tcccctcaga gcccatggta acgaacccct agaaaggaga gaacgggcgt   3240
caggggtgca cagtccacag ctgaagagca aggtttcgtg gcagcacggc ccggcccctc   3300
accctctgtc cccacgaggg gacccatggg ggctgtcttt gcagggcaca gatgaccaaa   3360
gtcccttcct gcttcctgtt acctgtcttg ctcctgggga gaaagagggg cctgatgaga   3420
ctccactcag gtgcacacat caccaggtgc atctgcaggc accgggctgg ctgcttgcag   3480
ccaggagaag gtcagcgaga aggagtgtat gagtgtgagt gtgtgtgcat ggaagttggg   3540
gcactgggcg tctgactccc tccccaccca agagaggaag gacccctcac cacccccact   3600
ggcgagacag tttactttgc cgacttgcca tgtttttgcc aaaaccaaga ttttgaagga   3660
aatgagtggc cagcgccagg gcccaggcca tgtggcctgc ccagcctcaa tgtcacttgg   3720
tggcggggtg gggtgggggt gggcagcagc atcccagcct tgagatgctt cactttcctt   3780
ctctgtaacc agactttgaa aaattgttcg tttcatcagg ctctgttcct caatggcctt   3840
ttgctacgtg cctcccgaga aatttgtctt tttgtataaa tgacaaagtg ttgaaaatgt   3900
atttcctgaa ataaatgttt caaatgcaga aacccagaaa aaaaaaaaaa a            3951
```

<210> SEQ ID NO 91
<211> LENGTH: 3651
<212> TYPE: DNA
<213> ORGANISM: Homo sapiens

<400> SEQUENCE: 91

```
agttaccatc gtggggagac tgtctggacg cagagagcag gctctgtgtg ggagcgggga     60
gggcaagccc tggttgcgag gcagggcttc cccaggattc agcagggatc tgaaggactt    120
tgcaggcacc cagggagata ggagaggagg agggagcagc cctggccgga cactgtcctc    180
ctagcattgc ctgcatcagg gactcactca gctttaagaa gccccttttgt gggggacagg   240
gagcatctgt tagtttatag gacctgaagt gcccccatgg gctcaagttt ctgggaaggc    300
ctgcaggtgg ccgtagggct gccgcagggg tgctggcccc agggtctgga ttcaggggag    360
cctgcagagg gagggcagct ggaggctgct ccagtgtgca ttgttacgag gcaaagtaag    420
gagactgctg ggcccacgct gggccggggt ggatggaggc aaggaagtct tcgccggggc    480
aagggcacca gctgtagatg ccggcagctt tctcctggac acgggcctgg aaggctgaca    540
gggtgtggtg agtgccaccg gctcccctgc cgtggcctgg tcagtggctt cacaggcctc    600
cgtgggcagg aggaggatga ccttgcattc tgcttggcca ccattggcag tgacagacaa    660
gccactgagg cggctcccag ctgcgttggc gacatggccg acacccccag agatgccggg    720
ctcaagcagg cgcctgcatc acggaacgag aaggccccgg tggacttcgg ctacgtgggg    780
attgactcca tcctggagca gatgcgccgg aaggccatga agcagggctt cgagttcaac    840
atcatggtgg tcgggcagag cggcttgggt aaatccacct taatcaacac cctcttcaaa    900
tccaaaatca gccggaagtc ggtgcagccc acctcagagg agcgcatccc caagaccatc    960
gagatcaagt ccatcacgca cgatattgag gagaaaggcg tccggatgaa gctgacagtg   1020
```

-continued

```
attgacacac cagggttcgg ggaccacatc aacaacgaga actgctggca gcccatcatg   1080
aagttcatca atgaccagta cgagaaatac ctgcaggagg aggtcaacat caaccgcaag   1140
aagcgcatcc cggacacccg cgtccactgc tgcctctact tcatccccgc caccggccac   1200
tccctcaggc ccctggacat cgagtttatg aaacgcctga gcaaggtggt caacatcgtc   1260
cctgtcatcg ccaaggcgga cacactcacc ctggaggaga gggtccactt caaacagcgg   1320
atcaccgcag acctgctgtc caacggcatc gacgtgtacc cccagaagga atttgatgag   1380
gactcggagg accggctggt gaacgagaag ttccgggaga tgatcccatt tgctgtggtg   1440
ggcagtgacc acgagtacca ggtcaacggc aagaggatcc ttgggaggaa gaccaagtgg   1500
ggtaccatcg aagttgaaaa caccacacac tgtgagtttg cctacctgcg ggaccttctc   1560
atcaggacgc acatgcagaa catcaaggac atcaccagca gcatccactt cgaggcgtac   1620
cgtgtgaagc gcctcaacga gggcagcagc gccatggcca acggcatgga ggagaaggag   1680
ccagaagccc cggagatgta gacgccaccc tgcccacccc cgggatcctg cccccaagtc   1740
atttccgtcc ccccccaggc cctcccacca ccccatttta ttttatatga ttttctccat   1800
ttgtcatcgt tccccacccc ttcgacatgc tgccaggaaa caagggaagg ggcctccctc   1860
cgagtgagtc agtgatgagg ccgcggcctc cccgaggttg tggggaggct gcactggagc   1920
cacaggcagg ggtgagagca cccactgaat tgacatgacc ctctgtcccc aggcctggct   1980
ccccgagggc tcagaagagc agcttcggtg tgcagatcat ccgtctgtgt ggggttctca   2040
gtgccggagg ccttggggtg ggggccaggc ctcgcacttg cagaggagcc cagtgggctg   2100
cacgctcccc tccatcccca tcggccctgt cccctggagt gtgtcagagc ccaggggaga   2160
atgcagccca ccaggagcac ctggaccccc tgcccgccac atggtgtggc catcactcag   2220
cccctacccc tgccctgctc ctaagggtag aaaactccag ggtcccctgc caccgactgc   2280
ccagccactc caagcccccct ggcagctgcc cctcctggag cagaaagtgc ctttatctca   2340
gccatccgca gactgcttgg ccagatgcgg ggacaggctg gaatgaggga ggcgtcttca   2400
tctccctgcc atccccctct cacgccaccc ccgcccccac cgggctgcag gtgctgctga   2460
tgcgctggga tctgattgag gataaaaagg aaggagagat gacccctacc ccctcatccc   2520
ccagttttga aaaggtctaa gcaagtgagt ctggtggagg agctgaggga gggagccatg   2580
gaaggtgcca gaaggaaggt tggcgggggc acgtgtgggc cgtggcttgg gctggtcaga   2640
gtggcgtgag ctgcccggcg cctgccctgc ccaagtgacc agggaagtgt gtgtgtgtcc   2700
atgtgtatgc gtgtccgtct gtctgtctag tgtctgggtt tggcccaaga ctgggctgta   2760
gttacattaa tgcccagcca gccacccctg ccactcaccc ctcctggccc aggccttgct   2820
gactctctga gctggggagg tgggaggcca ggcgagcctg actctgttga tctacccgtg   2880
cctgggcccc tcccctcaga gcccatggta acgaacccct agaaaggaga gaacgggcgt   2940
caggggtgca cagtccacag ctgaagagca aggtttcgtg gcagcacggc ccggcccctc   3000
accctctgtc cccacgaggg gacccatggg ggctgtcttt gcagggcaca gatgaccaaa   3060
gtcccttcct gcttcctgtt acctgtcttg ctcctgggga gaaagagggg cctgatgaga   3120
ctccactcag gtgcacacat caccaggtgc atctgcaggc accgggctgg ctgcttgcag   3180
ccaggagaag gtcagcgaga aggagtgtat gagtgtgagt gtgtgtgcat ggaagttggg   3240
gcactgggcg tctgactccc tccccaccca agagaggaag gacccctcac cacccccact   3300
ggcgagacag tttactttgc cgacttgcca tgtttttgcc aaaaccaaga ttttgaagga   3360
```

-continued

```
aatgagtggc cagcgccagg gcccaggcca tgtggcctgc ccagcctcaa tgtcacttgg   3420
tggcggggtg gggtgggggt gggcagcagc atcccagcct tgagatgctt cactttcctt   3480
ctctgtaacc agactttgaa aaattgttcg tttcatcagg ctctgttcct caatggcctt   3540
ttgctacgtg cctcccgaga aatttgtctt tttgtataaa tgacaaagtg ttgaaaatgt   3600
atttcctgaa ataaatgttt caaatgcaga aacccagaaa aaaaaaaaaa a            3651
```

<210> SEQ ID NO 92
<211> LENGTH: 3246
<212> TYPE: DNA
<213> ORGANISM: Homo sapiens

<400> SEQUENCE: 92

```
acttgggttc agaggtcgtg gcactgagat gggtctggca gatcccagcg tccaggccca     60
gcccctatag tgtcagctcc ctcctctggg gaccccccttg cttgtgcccc tctgggtccc   120
agcacatccc aggcctgcag ggagggggag aggaagagac tgactcactg gccaggtccc    180
ccaggggctg gagaggctgg agaggcagga gctggatcag atctgaatcc agaggctctc    240
ggaggaagag ctcaggccac tgaggcggct cccagctgcg ttggcgacat ggccgacacc    300
cccagagatg ccgggctcaa gcaggcgcct gcatcacgga acgagaaggc cccggtggac    360
ttcggctacg tggggattga ctccatcctg gagcagatgc gccggaaggc catgaagcag    420
ggcttcgagt tcaacatcat ggtggtcggg cagagcggct tgggtaaatc caccttaatc    480
aacaccctct tcaaatccaa aatcagccgg aagtcggtgc agcccacctc agaggagcgc    540
atccccaaga ccatcgagat caagtccatc acgcacgata ttgaggagaa aggcgtccgg    600
atgaagctga cagtgattga cacaccaggg ttcggggacc acatcaacaa cgagaactgc    660
tggcagccca tcatgaagtt catcaatgac cagtacgaga aatacctgca ggaggaggtc    720
aacatcaacc gcaagaagcg catcccggac acccgcgtcc actgctgcct ctacttcatc    780
cccgccaccg gccactccct caggcccctg gacatcgagt ttatgaaacg cctgagcaag    840
gtggtcaaca tcgtccctgt catcgccaag gcggacacac tcaccctgga ggagagggtc    900
cacttcaaac agcggatcac cgcagacctg ctgtccaacg gcatcgacgt gtacccccag    960
aaggaatttg atgaggactc ggaggaccgg ctggtgaacg agaagttccg ggagatgatc   1020
ccatttgctg tggtgggcag tgaccacgag taccaggtca acggcaagag gatccttggg   1080
aggaagacca agtggggtac catcgaagtt gaaaacacca cacactgtga gtttgcctac   1140
ctgcgggacc ttctcatcag gacgcacatg cagaacatca aggacatcac cagcagcatc   1200
cacttcgagg cgtaccgtgt gaagcgcctc aacgagggca gcagcgccat ggccaacggc   1260
atggaggaga aggagccaga agccccggag atgtagacgc caccctgccc acccccggga   1320
tcctgccccc aagtcatttc cgtccccccc caggccctcc caccacccca ttttatttta   1380
tatgattttc tccatttgtc atcgttcccc accccttcga catgctgcca ggaaacaagg   1440
gaaggggcct ccctccgagt gagtcagtga tgaggccgcg gcctccccga ggttgtgggg   1500
aggctgcact ggagccacag gcaggggtga gagcacccac tgaattgaca tgaccctctg   1560
tccccaggcc tggctccccg agggctcaga agagcagctt cggtgtgcag atcatccgtc   1620
tgtgtggggt tctcagtgcc ggaggccttg gggtgggggc caggcctcgc acttgcagag   1680
gagcccagtg ggctgcacgc tcccctccat ccccatcggc cctgtcccct ggagtgtgtc   1740
agagcccagg ggagaatgca gcccaccagg agcacctgga ccccctgccc gccacatggt   1800
gtggccatca ctcagcccct acccctgccc tgctcctaag ggtagaaaac tccagggtcc   1860
```

```
cctgccaccg actgcccagc cactccaagc cccctggcag ctgcccctcc tggagcagaa   1920
agtgccttta tctcagccat ccgcagactg cttggccaga tgcggggaca ggctggaatg   1980
agggaggcgt cttcatctcc ctgccatccc cctctcacgc cacccccgcc cccaccgggc   2040
tgcaggtgct gctgatgcgc tgggatctga ttgaggataa aaaggaagga gagatgaccc   2100
ctacccccctc atcccccagt tttgaaaagg tctaagcaag tgagtctggt ggaggagctg   2160
agggagggag ccatggaagg tgccagaagg aaggttggcg ggggcacgtg tgggccgtgg   2220
cttgggctgg tcagagtggc gtgagctgcc cggcgcctgc cctgcccaag tgaccaggga   2280
agtgtgtgtg tgtccatgtg tatgcgtgtc cgtctgtctg tctagtgtct gggtttggcc   2340
caagactggg ctgtagttac attaatgccc agccagccac ccctgccact cacccctcct   2400
ggcccaggcc ttgctgactc tctgagctgg ggaggtggga ggccaggcga gcctgactct   2460
gttgatctac ccgtgcctgg gcccctcccc tcagagccca tggtaacgaa cccctagaaa   2520
ggagagaacg ggcgtcaggg gtgcacagtc cacagctgaa gagcaaggtt tcgtggcagc   2580
acggcccggc ccctcaccct ctgtccccac gaggggaccc atgggggctg tctttgcagg   2640
gcacagatga ccaaagtccc ttcctgcttc ctgttacctg tcttgctcct ggggagaaag   2700
aggggcctga tgagactcca ctcaggtgca cacatcacca ggtgcatctg caggcaccgg   2760
gctggctgct tgcagccagg agaaggtcag cgagaaggag tgtatgagtg tgagtgtgtg   2820
tgcatggaag ttggggcact gggcgtctga ctccctcccc acccaagaga ggaaggaccc   2880
ctcaccaccc ccactggcga gacagtttac tttgccgact tgccatgttt ttgccaaaac   2940
caagattttg aaggaaatga gtggccagcg ccagggccca ggccatgtgg cctgcccagc   3000
ctcaatgtca cttggtggcg gggtggggtg ggggtgggca gcagcatccc agccttgaga   3060
tgcttcactt tccttctctg taaccagact ttgaaaaatt gttcgtttca tcaggctctg   3120
ttcctcaatg gccttttgct acgtgcctcc cgagaaattt gtctttttgt ataaatgaca   3180
aagtgttgaa aatgtatttc ctgaaataaa tgtttcaaat gcagaaaccc agaaaaaaaa   3240
aaaaaa                                                              3246
```

<210> SEQ ID NO 93
<211> LENGTH: 4469
<212> TYPE: DNA
<213> ORGANISM: Homo sapiens

<400> SEQUENCE: 93

```
tgcctctgtc actgcagact aatgggacgg aggggggtga cttctcaggg ttcctcctgg     60
gcaggtgctc cggaaccttt tctcagcacg ctggcctggg gcacggccgt tcctcctgcc    120
cagccacgtt ggggtacagg gtgaagaagg gctggggcca gcccaggaca gaggaaggcg    180
aggcaggcac gcaggaactg ggctttttaa acccttaagc ccaaggaaat cgtagcatcg    240
cgggacaggg aaaatgaaag actttggaag tcgtcaggaa tttgactctg tgagttggtt    300
tccaagagtc taagttaagc atctccaagt ggatattaaa aaggagcagc aagcctcggg    360
gcggcggggg ctggaggagg tggagagagg aggctgccgg aagccgcact cgggacctct    420
gcagccaccg accagaccgg gcggccggga ctctgggact ctcgcaggca gacccggtgg    480
tctgccggac tcctcggggc ccacttcggg ccctctctcc tgcctcctat ttttggattt    540
ctctcctttg ctcccttttt cctcccgttt tgaagagaca atgctacttc agtttggagc    600
acaaacatat gatcagcaca tggaaatgtg gtaattcgga tgcattcgtg attgcaacag    660
```

-continued

```
attgaagaaa ttagaccaga caaagagtgt ttttagagga ggaggaggag gaggaggagg    720
ctgagagagg gagggcgacg ggggtgagaa aggggaggcc gcctctgagc gggacgccgg    780
gactcccgcc gctgctaaat atatccgtag gaatggagag ggaccggatc tcagccttga    840
aaagatcttt tgaggtcgag gaggtcgaga cacccaactc caccccaccc cggagggtcc    900
agactcccct actccgagcc actgtggcca gctccaccca gaaattccag gacctgggcg    960
tgaagaactc agaaccctcg gcccgccatg tggactccct aagccaacgc tcccccaagg   1020
cgtccctgcg gagggtggag ctctcgggcc ccaaggcggc cgagccggtg tcccggcgca   1080
ctgagctgtc cattgacatc tcgtccaagc aggtggagaa cgccggggcc atcggcccgt   1140
cccggttcgg gctcaagagg gccgaggtgt tgggccacaa gacgccagaa ccggcccctc   1200
ggaggacgga gatcaccatc gtcaaacccc aggagtcagc ccaccggagg atggagcccc   1260
ctgcctccaa ggtccccgag gtgcccactg cccctgccac cgacgcagcc cccaagaggg   1320
tggagatcca gatgcccaag cctgctgagg cgcccaccgc ccccagccca gcccagacct   1380
tggagaattc agagcctgcc cctgtgtctc agctgcagag caggctggag cccaagcccc   1440
agccccctgt ggctgaggct acaccccgga gccaggaggc cactgaggcg gctcccagct   1500
gcgttggcga catggccgac acccccagag atgccgggct caagcaggcg cctgcatcac   1560
ggaacgagaa ggcccccggtg gacttcggct acgtggggat tgactccatc ctggagcaga   1620
tgcgccggaa ggccatgaag cagggcttcg agttcaacat catggtggtc gggcagagcg   1680
gcttgggtaa atccacctta atcaacaccc tcttcaaatc caaaatcagc cggaagtcgg   1740
tgcagcccac ctcagaggag cgcatcccca agaccatcga gatcaagtcc atcacgcacg   1800
atattgagga gaaaggcgtc cggatgaagc tgacagtgat tgacacacca gggttcgggg   1860
accacatcaa caacgagaac tgctggcagc ccatcatgaa gttcatcaat gaccagtacg   1920
agaaatacct gcaggaggag gtcaacatca accgcaagaa gcgcatcccg gacacccgcg   1980
tccactgctg cctctacttc atccccgcca ccggccactc cctcaggccc ctggacatcg   2040
agtttatgaa acgcctgagc aaggtggtca acatcgtccc tgtcatcgcc aaggcggaca   2100
cactcaccct ggaggagagg gtccacttca aacagcggat caccgcagac ctgctgtcca   2160
acggcatcga cgtgtacccc cagaaggaat ttgatgagga ctcggaggac cggctggtga   2220
acgagaagtt ccgggagatg atcccatttg ctgtggtggg cagtgaccac gagtaccagg   2280
tcaacggcaa gaggatcctt gggaggaaga ccaagtgggg taccatcgaa gttgaaaaca   2340
ccacacactg tgagtttgcc tacctgcggg accttctcat caggacgcac atgcagaaca   2400
tcaaggacat caccagcagc atccacttcg aggcgtaccg tgtgaagcgc ctcaacgagg   2460
gcagcagcgc catggccaac ggcatggagg agaaggagcc agaagccccg gagatgtaga   2520
cgccaccctg cccacccccg ggatcctgcc cccaagtcat ttccgtcccc ccccaggccc   2580
tcccaccacc ccattttatt ttatatgatt ttctccattt gtcatcgttc cccacccctt   2640
cgacatgctg ccaggaaaca agggaagggg cctccctccg agtgagtcag tgatgaggcc   2700
gcggcctccc cgaggttgtg gggaggctgc actggagcca caggcagggg tgagagcacc   2760
cactgaattg acatgaccct ctgtccccag gcctggctcc ccgagggctc agaagagcag   2820
cttcggtgtg cagatcatcc gtctgtgtgg ggttctcagt gccggaggcc ttggggtggg   2880
ggccaggcct cgcacttgca gaggagccca gtgggctgca cgctcccctc catccccatc   2940
ggccctgtcc cctggagtgt gtcagagccc aggggagaat gcagcccacc aggagcacct   3000
ggaccccctg cccgccacat ggtgtggcca tcactcagcc cctacccctg ccctgctcct   3060
```

aagggtagaa aactccaggg tcccctgcca ccgactgccc agccactcca agccccctgg 3120
cagctgcccc tcctggagca gaaagtgcct ttatctcagc catccgcaga ctgcttggcc 3180
agatgcgggg acaggctgga atgagggagg cgtcttcatc tccctgccat ccccctctca 3240
cgccaccccc gcccccaccg ggctgcaggt gctgctgatg cgctgggatc tgattgagga 3300
taaaaaggaa ggagagatga cccctacccc ctcatccccc agttttgaaa aggtctaagc 3360
aagtgagtct ggtggaggag ctgagggagg gagccatgga aggtgccaga aggaaggttg 3420
gcgggggcac gtgtgggccg tggcttgggc tggtcagagt ggcgtgagct gcccggcgcc 3480
tgccctgccc aagtgaccag ggaagtgtgt gtgtgtccat gtgtatgcgt gtccgtctgt 3540
ctgtctagtg tctgggtttg gcccaagact gggctgtagt tacattaatg cccagccagc 3600
cacccctgcc actcacccct cctggcccag gccttgctga ctctctgagc tggggaggtg 3660
ggaggccagg cgagcctgac tctgttgatc tacccgtgcc tgggcccctc ccctcagagc 3720
ccatggtaac gaacccctag aaaggagaga acgggcgtca ggggtgcaca gtccacagct 3780
gaagagcaag gtttcgtggc agcacggccc ggcccctcac cctctgtccc cacgagggga 3840
cccatggggg ctgtctttgc agggcacaga tgaccaaagt cccttcctgc ttcctgttac 3900
ctgtcttgct cctggggaga aagaggggcc tgatgagact ccactcaggt gcacacatca 3960
ccaggtgcat ctgcaggcac cgggctggct gcttgcagcc aggagaaggt cagcgagaag 4020
gagtgtatga gtgtgagtgt gtgtgcatgg aagttggggc actgggcgtc tgactccctc 4080
cccacccaag agaggaagga cccctcacca cccccactgg cgagacagtt tactttgccg 4140
acttgccatg tttttgccaa aaccaagatt ttgaaggaaa tgagtggcca gcgccagggc 4200
ccaggccatg tggcctgccc agcctcaatg tcacttggtg gcggggtggg gtgggggtgg 4260
gcagcagcat cccagccttg agatgcttca ctttccttct ctgtaaccag actttgaaaa 4320
attgttcgtt tcatcaggct ctgttcctca atggcctttt gctacgtgcc tcccgagaaa 4380
tttgtctttt tgtataaatg acaaagtgtt gaaaatgtat ttcctgaaat aaatgtttca 4440
aatgcagaaa cccagaaaaa aaaaaaaaa 4469

<210> SEQ ID NO 94
<211> LENGTH: 3269
<212> TYPE: DNA
<213> ORGANISM: Homo sapiens

<400> SEQUENCE: 94
cacttccggc ctcgcgaggg ccgcaatcac tgctccgcag ttcccgcctg cattcctcgc 60
gccgtcttcc tggagtccca gctctccttc agcccgcccc aacgctgacg ctcagtcctc 120
aggcgtcgag ggtagctcct gtgaggggct cgcttggcgc acgcaaaacg ctcagcgcgc 180
accacagggc gtccgcccca accccgcccc cggaggcctc cagctcggcc ccgcccctgt 240
cccttccccg tcgcggaggc agcctagcct cgcgccccgc ccgttgcttc tgccctccgg 300
ccttcccgcc gccgtcgccg ggaccagccg ctcggggccg ggctgataca gccgcttcac 360
cgtgcccctg cccgcgacca tggcctcctc cgaggtggcg cggcacctgc tctttcagtc 420
tcacatggca acgaaaacaa cttgtatgtc ttcacaagga tcagatgatg aacagataaa 480
aagagaaaac attcgttcgt tgactatgtc tggccatgtt ggttttgaga gtttgcctga 540
tcagctggtg aacagatcca ttcagcaagg tttctgcttt aatattctct gtgtgggga 600 aactggaatt ggaaaatcaa cactgattga cacattgttt aatactaatt ttgaagacta 660

-continued

```
tgaatcctca catttttgcc caaatgttaa acttaaagct cagacatatg aactccagga    720
aagtaatgtt caattgaaat tgaccattgt gaatacagtg ggatttggtg accaaataaa    780
taaagaagag agctaccaac caatagttga ctacatagat gctcagtttg aggcctatct    840
ccaagaagaa ctgaagatta agcgttctct ctttacctac catgattctc gcatccatgt    900
gtgtctctac ttcatttcac cgacaggcca ctctctgaag acacttgatc tcttaaccat    960
gaagaacctt gacagcaagg taaacattat accagtgatt gccaaagcag atacggtttc   1020
taaaactgaa ttacagaagt ttaagatcaa gctcatgagt gaattggtca gcaatggcgt   1080
ccagatatac cagttcccaa cggatgatga cactattgct aaggtcaacg ctgcaatgaa   1140
tggacagttg ccgtttgctg ttgtgggaag tatggatgag gtaaaagtcg gaaacaagat   1200
ggtcaaagct cgccagtacc cttggggtgt tgtacaagtg gaaaatgaaa accactgtga   1260
ctttgtaaag ctgcgggaaa tgctcatttg tacaaatatg gaggacctgc gagagcagac   1320
ccataccagg cactatgagc tttacaggcg ctgcaaactg gaggaaatgg gctttacaga   1380
tgtgggccca gaaaacaagc cagtcagtgt tcaagagacc tatgaagcca aaagacatga   1440
gttccatggt gaacgtcaga ggaaggaaga agaaatgaaa cagatgtttg tgcagcgagt   1500
aaaggagaaa gaagccatat tgaaagaagc tgagagagag ctacaggcca aatttgagca   1560
ccttaagaga cttcaccaag aagagagaat gaagcttgaa gaaaagagaa gacttttgga   1620
agaagaaata attgctttct ctaaaaagaa agctacctcc gagatatttc acagccagtc   1680
ctttctggca acaggcagca acctgaggaa ggacaaggac cgtaagaact ccaatttttt   1740
gtaaaacaga agttccagag cacagaaggt catcatcaca agcaaacttt attaaaaaaa   1800
aactagaagt gtgctttgat tttgctgtta tttgttttat cacttctata tttggtgaac   1860
agccacagtt actgatattt atggaaaagt actttcaagt acaaggtcaa tacataagcc   1920
agagtgaatg atactacaag ttgagcatct ctaattcaaa aatctgaaat ccagaagctt   1980
caaaatctga atctttttga gcactgactt gaccccacaa gtggaaaatt ccccacccga   2040
cacctttgct ttctgatggt tcagtttaaa cagattttgt ttcttgcaca aaatttttgt   2100
ataaattact ttcaggctat atgtataagg tggatgtgaa acatgaatta tgtaattaga   2160
gtcgggtccc gttgtgtata tgcagatatt ccaaacctga aatccaaaac acttctggtc   2220
cctagcattt tggataaggg atactcagct tgtacctata tattcatata tattcactgt   2280
tgttagaaat gtttaagttg ctgttctgtg atgaatctaa atcttttctc ttgctaccaa   2340
gctattgtca ctgcagtgca ttataccaaa gagcgaagtc agtgccactg aaaatacaga   2400
acccattaat atcgtggcta tctgattaca tttatattcc aagatgaacc tttttttatat   2460
atgctaaaaa ttttggggaa tatgttttgg gatgtattat ggagctaaaa ctctaacctc   2520
ttaatagttt tatagaactt aaaaattttt tatacaatta cccaattggt gatatgatct   2580
taagcttttg tgtcagatta tttaatatga tgacttcatg ctttattatg ccttattatg   2640
gctgacgtat tactgtggtg aaacaaaata tctttaaaag ttaaaacatc cagatatata   2700
agctattttt tcctaaggat aaagtacctt tgagcatgag tgtatcacag ctttcattag   2760
gaaaactttt cattacatac ttgtttaaac tctgtcttcc agggtaaaaa taataaggtt   2820
gaatcatttt attaaaaata ctttttaaga aaataactat gaacatctga atattaaaga   2880
tataaaaatg cacataattc atatttcagg tggtatttgc attcagtgcc ttactggtat   2940
tctcagaaca ttttaatgat ttctaacatt tcttaacagt catagatata tacattttca   3000
ttttttgtac ttgaatattc taaataaaac tgacatttac tcttgacaaa taaaacatat   3060
```

atttactaaa atgtgtttaa ttttcctttc tgaaaactct cattttaaaa acgttcattt 3120
aattatgtat ttgaattatt ttggagatga ggtattttat gagtattttc agacaatgaa 3180
acttattagt ctgtgtcaga ttctgagcaa tcatagagtc atctaagttg taaataaaac 3240
cttgcatagc acaaaaaaaa aaaaaaaaa 3269

<210> SEQ ID NO 95
<211> LENGTH: 3200
<212> TYPE: DNA
<213> ORGANISM: Homo sapiens

<400> SEQUENCE: 95
cacttccggc ctcgcgaggg ccgcaatcac tgctccgcag ttcccgcctg cattcctcgc 60
gccgtcttcc tggagtccca gctctccttc agcccgcccc aacgctgacg ctcagtcctc 120
aggcgtcgag ggtagctcct gtgaggggct cgcttggcgc acgcaaaacg ctcagcgcgc 180
accacagggc gtccgcccca accccgcccc cggaggcctc cagctcggcc ccgcccctgt 240
cccttccccg tcgcggaggc agcctagcct cgcgccccgc ccgttgcttc tgccctccgg 300
ccttcccgcc gccgtcgccg ggaccagccg ctcggggccg ggctgataca gccgcttcac 360
cgtgcccctg cccgcgacca tggcctcctc cgaggtggcg cggcacctga aaagagaaaa 420
cattcgttcg ttgactatgt ctggccatgt tggttttgag agtttgcctg atcagctggt 480
gaacagatcc attcagcaag gtttctgctt taatattctc tgtgtggggg aaactggaat 540
tggaaaatca acactgattg acacattgtt taatactaat tttgaagact atgaatcctc 600
acatttttgc ccaaatgtta aacttaaagc tcagacatat gaactccagg aaagtaatgt 660
tcaattgaaa ttgaccattg tgaatacagt gggatttggt gaccaaataa ataaagaaga 720
gagctaccaa ccaatagttg actacataga tgctcagttt gaggcctatc tccaagaaga 780
actgaagatt aagcgttctc tctttaccta ccatgattct cgcatccatg tgtgtctcta 840
cttcatttca ccgacaggcc actctctgaa gacacttgat ctcttaacca tgaagaacct 900
tgacagcaag gtaaacatta taccagtgat tgccaaagca gatacggttt ctaaaactga 960
attacagaag tttaagatca agctcatgag tgaattggtc agcaatggcg tccagatata 1020
ccagttccca acggatgatg acactattgc taaggtcaac gctgcaatga atggacagtt 1080
gccgtttgct gttgtgggaa gtatggatga ggtaaaagtc ggaaacaaga tggtcaaagc 1140
tcgccagtac ccttggggtg ttgtacaagt ggaaaatgaa aaccactgtg actttgtaaa 1200
gctgcgggaa atgctcattt gtacaaatat ggaggacctg cgagagcaga cccataccag 1260
gcactatgag ctttacaggc gctgcaaact ggaggaaatg ggctttacag atgtgggccc 1320
agaaaacaag ccagtcagtg ttcaagagac ctatgaagcc aaaagacatg agttccatgg 1380
tgaacgtcag aggaaggaag aagaaatgaa acagatgttt gtgcagcgag taaaggagaa 1440
agaagccata ttgaaagaag ctgagagaga gctacaggcc aaatttgagc accttaagag 1500
acttcaccaa gaagagagaa tgaagcttga agaaaagaga agacttttgg aagaagaaat 1560
aattgctttc tctaaaaaga aagctacctc cgagatattt cacagccagt cctttctggc 1620
aacaggcagc aacctgagga aggacaagga ccgtaagaac tccaattttt tgtaaaacag 1680
aagttccaga gcacagaagg tcatcatcac aagcaaactt tattaaaaaa aaactagaag 1740
tgtgctttga ttttgctgtt atttgtttta tcacttctat atttggtgaa cagccacagt 1800
tactgatatt tatggaaaag tactttcaag tacaaggtca atacataagc cagagtgaat 1860

-continued

```
gatactacaa gttgagcatc tctaattcaa aaatctgaaa tccagaagct tcaaaatctg   1920
aatctttttg agcactgact tgaccccaca agtggaaaat tccccacccg acacctttgc   1980
tttctgatgg ttcagtttaa acagattttg tttcttgcac aaaatttttg tataaattac   2040
tttcaggcta tatgtataag gtggatgtga aacatgaatt atgtaattag agtcgggtcc   2100
cgttgtgtat atgcagatat tccaaacctg aaatccaaaa cacttctggt ccctagcatt   2160
ttggataagg gatactcagc ttgtacctat atattcatat atattcactg ttgttagaaa   2220
tgtttaagtt gctgttctgt gatgaatcta aatcttttct cttgctacca agctattgtc   2280
actgcagtgc attataccaa agagcgaagt cagtgccact gaaaatacag aacccattaa   2340
tatcgtggct atctgattac atttatattc caagatgaac cttttttata tatgctaaaa   2400
attttgggga atatgttttg ggatgtatta tggagctaaa actctaacct cttaatagtt   2460
ttatagaact taaaaatttt ttatacaatt acccaattgg tgatatgatc ttaagctttt   2520
gtgtcagatt atttaatatg atgacttcat gctttattat gccttattat ggctgacgta   2580
ttactgtggt gaaacaaaat atctttaaaa gttaaaacat ccagatatat aagctatttt   2640
ttcctaagga taaagtacct ttgagcatga gtgtatcaca gctttcatta ggaaaacttt   2700
tcattacata cttgtttaaa ctctgtcttc cagggtaaaa ataataaggt tgaatcattt   2760
tattaaaaat actttttaag aaaataacta tgaacatctg aatattaaag atataaaaat   2820
gcacataatt catatttcag gtggtatttg cattcagtgc cttactggta ttctcagaac   2880
attttaatga tttctaacat ttcttaacag tcatagatat atacattttc atttttttgta   2940
cttgaatatt ctaaataaaa ctgacattta ctcttgacaa ataaaacata tatttactaa   3000
aatgtgttta attttccttt ctgaaaactc tcattttaaa aacgttcatt taattatgta   3060
tttgaattat tttggagatg aggtatttta tgagtatttt cagacaatga aacttattag   3120
tctgtgtcag attctgagca atcatagagt catctaagtt gtaaataaaa ccttgcatag   3180
cacaaaaaaa aaaaaaaaaa                                               3200
```

<210> SEQ ID NO 96
<211> LENGTH: 5582
<212> TYPE: DNA
<213> ORGANISM: Homo sapiens

<400> SEQUENCE: 96

```
ggcgtggggg gagcagatgc cgctggctgc cagcgggacg ccggcgagca gagcgcagcc     60
gcgagggagg cgcgagggag gcgagccgga gcccgagcac tagcagcagc cggagtcggc    120
gtaaagcacc cgggcgcagc cggagccggt gccgcagctg cgatggccgt ggccgtgggg    180
agaccgtcta atgaagagct tcgaaacttg tctttgtctg gccatgtggg atttgacagc    240
ctccctgacc agctggtcaa caagtctact tctcaaggat tctgtttcaa catcctttgt    300
gttggtgaga caggcattgg caaatccacg ttaatggaca ctttgttcaa caccaaattt    360
gaaagtgacc cagctactca caatgaacca ggtgttcggt taaaagccag aagttatgag    420
cttcaggaaa gcaatgtacg gctgaagtta accattgttg acaccgtggg atttggagac    480
cagataaata aagatgacag ctataagccg atagtagaat atattgatgc ccagttcgag    540
gcctacctgc aagaggaatt gaagattaaa cgttctctct tcaactacca tgacacgagg    600
atccatgcct gcctctactt tattgcccct actggacatt cactaaagtc cctggatctg    660
gtcaccatga aaaagctgga cagtaaggtg aacatcattc caataattgc aaaagctgac    720
accattgcca agaatgaact gcacaaattc aagagtaaga tcatgagtga actggtcagc    780
```

-continued

```
aatggggtcc agatatatca gtttcccact gatgaagaaa cggtggcaga gattaacgca    840
acaatgagtg tccatctccc atttgcagtg gttggcagca ccgaagaggt gaagattggc    900
aacaagatgg caaaggccag gcagtacccc tggggtgtgg tgcaggttga gaatgaaaat    960
cattgcgatt ttgtgaaact tcgagagatg ctgatccgcg tgaacatgga ggacttgcga   1020
gagcagactc acacccgcca ctatgaattg taccgacgct gtaagcttga agagatgggg   1080
ttcaaggaca ctgaccctga cagcaaaccc ttcagtcttc aggagacata tgaagcaaaa   1140
aggaatgaat tcctgggaga actgcagaag aaagaagaag aaatgagaca aatgtttgtt   1200
atgagagtga aggagaaaga agctgaactt aaggaggcag agaaagagct tcacgagaag   1260
tttgaccttc taaagcggac acaccaagaa gaaaagaaga aagtggaaga caagaagaag   1320
gagcttgagg aggaggtgaa caacttccag aagaagaaag cagcggctca gttactacag   1380
tcccaggccc agcaatctgg ggcccagcaa accaagaaag acaaggataa gaaaaaatgca   1440
agcttcacat aaagcctggc aagccaagga tgttcccgca ttcacctgct tttgcagtaa   1500
tatcgtatct ctgccatgtg tgttctttag ttttatttta ttttatttta ttttttttacc   1560
cttcctcaaa caccagtaac tattattaac tcgttttgct gaatgttgtt gggtggtaga   1620
aaatgataga acaagggaat aaccgcgaat gctctgtgca gctggactct gtttccggaa   1680
agtaaatgat ttgcttttta tgcctgttct gaatggcagc acgaagcagg cctgttactt   1740
gtatgtcgct ttggacagag gaaagtgggg taaaatgcta cctgtacgtc tgacatgaaa   1800
acttctcacc gcctcagcag ctgaactaaa aacctgaata gccatgacaa gagtttgcat   1860
tttcttgatg attcatctcc atgagtgcac aatccctgaa ctcactgtct tttctccaca   1920
cttgtcctaa gccaaggtag atttgtacgt agacagactg gtgagcaagc attatatttt   1980
atttttaccc ttgcatgaca ttttcatttt aatcaataac attatttggc ctgagcttgt   2040
gggtctgttc agactgtctc ctctcatggt ttgaaactgc atctgaatgc ctgccttcaa   2100
tcctggccaa gttggagtag actggtatga gaaaactatg attagttcac atttactggt   2160
gcatccttga tcctctcaca gatagaggtc ttaaaggttg gatcatgtaa cattgcttag   2220
tagaagaatc ttcttctaag gatgatgggc tttctacagc ctgcttacca ctaacagtaa   2280
ggaatctttc ataaacacac ctcagtttgt tcccagtggg cttagaggga ggacctgatg   2340
actgattcca ggatacttgt acttctaata acatttttca tgaatcatga gaaaatttcc   2400
acagatactt cccttagaaa atttgctata aactctgtat cattggtagc acaaatttga   2460
gcgaggcctt gtcaatttta aggtggaaat aggaaggacc acaacatgac ccgtaagtca   2520
agaaggtaga catttcatat ccagcttcct tgcttagtct cctttcagta tttggcaata   2580
aaagaaagaa gaaatagaac agctgaagtc tcaaatcatt gtctggaatt ttcctcacct   2640
tggctagctc cacctgctct ttgtctaagg ccccttgcctc atcagggatt agaactggcc   2700
catatgccag aacctgtact aaatgcctaa tttgtatgga agagtgcata tttaatctct   2760
tttctatact gctcctttct gatgcttatc ctttcatctg tgtgattgtt ttttcccctc   2820
tactaacaag atcctcccag ctttctctct acatgtagaa aggataacat ttctcatgaa   2880
cccactgccc ctctgcattt tcctcactgg ttagagatta agtaaatagg atagaatatg   2940
ctgcgtctcc cctgacacac actttctttt ttgaatgagc aagtctccat tttgatttca   3000
gcaaagattt tttctccttt tctttgtcct caaccatact tagaggaaag aaggaatggt   3060
cttccatgaa ctgattatgc ttaattaagc aaagtaagga aattagtttc atggaagcct   3120
```

-continued

```
aaacaaagct ggaatagaaa ctacacacta gacacagcag tagtcatagt cttcacaggt   3180
ttaggagcta ctggaccaac attcttgttt ttgcttttgt ttttttaaat aattctagtc   3240
tggagctaac tgtggagcag ccaaatagta gctggcatgt tgattcaaac catgggctga   3300
atttgctcat aggctgtgca tcagacaaaa gcttgaatat ttgtgttgta tgcttgttcc   3360
aaccaccgct tgtgtgagca tttttgtggc ttgtacagaa agtacacttt taaattgtct   3420
cttgcatcac taaaattttt ttaaaatgag cataacaacg aaaggcatcc agctgacttt   3480
ttgattccaa gattattgat tggattgact tttttgcatt aaatttttcc cagcaaaata   3540
aatcatatgg cgagtcaggg aataaaaagt caaaagaaac aaatagaagc tttttttttt   3600
aaaaaatgta ttgcttctga actttttttct gccactgctc cctagccctg tttagtttgt   3660
tattgctgct tttcttttttt ctttctgtat ctatgccttt ttttcacagt agtccttggc   3720
tctgcacgga ataaatgata ccctcaaatc taattggatg tgctttcgcc tttgcatgta   3780
agtacggtag taagaaacct ttgagatctt tctgactttt caaaattaga gaaagcaaat   3840
gggatggata gatttttttt ttcttttcaa ggggggcagg aaggtaatgg tttgagtagc   3900
ctttgtttaa aaaaaagact aaatatattt aaaaggccac atttatattt ttttcacaag   3960
aaccacataa taaattccac ttcttgacct gaatttggaa atccgaaatt actaatccag   4020
gccaggtgtg gtggctcatg cctgtaatcc cagcactttg agaggccgag gtgggcagat   4080
cacttgaggc ctggagttca agaccacctt ggcgaacacg gtgaaacccc gtctctacaa   4140
aaaatacaaa aattagccag gcgtggtggc acgtgcctgt agtcccagct acttgggagg   4200
ctaagtcagg agaattgctt gaacttggga gatggaggtt gcagtgagcc aagattgcac   4260
cactgcattc caacctgggt gatgaagtga gactctccaa aaaaaaaaaa gaaattatta   4320
atccctgcct gtgctctaca tagcctcatg ggcatcattg gatagctcag agggcccttg   4380
attctggcaa ggcaaataaa gccagaatga gaaattacca tcttctacta gagaaaacca   4440
agagaaaaat ttttatgcta ggatgccttt atgaccactt aattttttaa tcttagttta   4500
atggtctctc cctggtgcta actgctgaca gtggccacct cttttttggg gattgagggg   4560
cctacataac tagctggcct taccccatat cttttgttca aacataatac catctttttg   4620
cttcttctga actttagatc tccataacac atgtactgta gaatgtgatg gaaaagcatt   4680
gatgagaatt tattggcagt tcagattgtg ttttcccaac ttaggctctt tattaattgg   4740
ttaaggtttt ctccaaaaag ggcatttcaa caatgggaat tatttaatgt aacagtgggc   4800
acagattact tatcttcctt ctctgctttg tgactcacca gcagtaacac acacaatcca   4860
catcttgtgc acctcaaatg aacagacttg gtttccttgc tttcttgaca tttccatgac   4920
tgtttcacat acaaactatt gggtgaggtt tttcagctgt taccgaccca cgtcctgctg   4980
tctctgtgtg gtcctacaaa aactgtccat tcccacccct ttgctttgcc atttgcaaga   5040
gtctggaatt gtcaggtctc agcttcgaaa agtcctggtt ccactgacag gacacattct   5100
ttagtgggaa ttaagaccta caaagtctag tttgtatgta ggtatgaagg gaatttttta   5160
aataaattga aaagctgtga acagcattag aactttgtct atttcttaat tttaaaatat   5220
gctgatatgc cttaaactgt agttgtagat ccttgtcatt ttgctgtttg aaaataacca   5280
atgtgttttc taaaactgtc gtgtaatcta ctttcattgt taatgcagaa ttgtcatata   5340
tgtaagctgc atgttagaca tttgtctttt ttaaactaaa gtaattgtat tgatgtgaag   5400
catatcattt tttcaaatat gaaagtgatc acttagcaac atgcttggta atttggcatc   5460
tgttaaggta ggagagtggt gaacagataa tctatgcata tatcactagt gccaagacat   5520
```

-continued

```
aaagcggggg aaaatatatt tttacccaaa cattaaaaaa aaaaaaaaaa aaaaaaaaaa   5580

aa                                                                  5582


<210> SEQ ID NO 97
<211> LENGTH: 1223
<212> TYPE: DNA
<213> ORGANISM: Homo sapiens

<400> SEQUENCE: 97

gcagatggag ctcagattct tcggttaact gtcaccctct cccctccccc atcacacaca     60

ccaggccctg ccaggacaag gcagctcctg gaagctccac caggacccac gtccaccagg    120

catctcgaac ccttggcccc catggacccc ctgaggcgct ccccctctcc ctgcctgtcc    180

tcgcagccct ccagccccag caccccaccc tgcgagatgc ttggtcctgt gggcattgag    240

gctgtgctgg accagctgaa gatcaaggct atgaagatgg ggtttgagtt caacatcatg    300

gtggtggggc aaagcgggct gggcaagtcc acgatggtga acacgctgtt caagtccaaa    360

gtgtggaagt caaacccacc gggcttgggg gtgcccacac cccagacgct gcagctgcat    420

tcactgaccc atgtcataga ggagaagggt gtgaagctga agctgacggt gacggacacg    480

cccggcttcg gggaccagat caacaatgac aactgcctgc ggcccctgga cattgagttc    540

ctgcagcggc tgtgccggac tgtgaatgtg gtgcccgtga ttgccagggc cgacagcctg    600

accatggagg agcgagaggc cttcaggcgc aggatccagc agaacctgag gacccactgc    660

atcgacgtct acccccagat gtgctttgac gaggacatca atgacaaaat cctcaacagc    720

aagttacggg accgaatccc ttttgccgtg gtaggggctg accaagagca cctggtgaac    780

gggaggtgtg tcctgggccg gaagaccaag tggggcatca ttgaagtgga gaacatggcg    840

cactgtgaat ttcctctcct gagagacctg cttatccgct cccacctcca agacctgaag    900

gacataaccc acaacatcca ctatgagaac taccgcgtca tcagactcaa tgaaagccac    960

ctgctgcccc gcgggcccgg ctgggtgaac ctggccccgg cctccccagg acagctgacc   1020

acccccccgga ccttcaaggt ctgcaggggg gcccatgacg attctgatga tgagttctga  1080

ccaccggcgg atcccggggc tgctgggctt cctgagtccc cagcggctct caacacacac   1140

ctatgtacca gagcatctat taaatgtgag ccttgctttt tatgaaaagc tgtgctttga   1200

aaacaaaaaa aaaaaaaaaa aaa                                           1223


<210> SEQ ID NO 98
<211> LENGTH: 1524
<212> TYPE: DNA
<213> ORGANISM: Homo sapiens

<400> SEQUENCE: 98

cttgggcccc tggttctact tggggattat tgtattatta ggctggggtc attgtgggga     60

ttagaagggt aacagctcct gctcctgctg cagagaagcc tccaggtggg ggtcacagca    120

agtgcagatg gagctcagat tcttcggtta actgtcaccc tctcccctcc cccatcacac    180

acaccaggcc ctgccaggac aaggcagctc ctggaagctc caccaggacc cacgtccacc    240

aggcatctcg aacccttggc cccatggac cccctgaggc gctccccctc tccctgcctg     300

tcctcgcagc cctccagccc cagcacccca ccctgcgaga tgcttggtcc tgtgggcatt    360

gaggctgtgc tggaccagct gaagatcaag gctatgaaga tggggtttga gttcaacatc    420

atggtggtgg ggcaaagcgg gctgggcaag tccacgatgg tgaacacgct gttcaagtcc    480
```

-continued

```
aaagtgtgga agtcaaaccc accgggcttg ggggtgccca caccccagac gctgcagctg    540

cattcactga cccatgtcat agaggagaag ggtgtgaagc tgaagctgac ggtgacggac    600

acgcccggct tcggggacca gatcaacaat gacaactgct gggaccccat cctgggctac    660

atcaacgagc aatacgagca gtacctgcag gaggagatcc tcatcacccg ccagcgccac    720

atcccagaca cccgggtgca ctgctgcgtg tactttgtac cacccactgg gcactgcctg    780

cggcccctgg acattgagtt cctgcagcgg ctgtgccgga ctgtgaatgt ggtgcccgtg    840

attgccaggg ccgacagcct gaccatggag gagcgagagg ccttcaggcg caggatccag    900

cagaacctga ggacccactg catcgacgtc taccccccaga tgtgctttga cgaggacatc    960

aatgacaaaa tcctcaacag caagttacgg gaccgaatcc cttttgccgt ggtaggggct   1020

gaccaagagc acctggtgaa cgggaggtgt gtcctgggcc ggaagaccaa gtggggcatc   1080

attgaagtgg agaacatggc gcactgtgaa tttcctctcc tgagagacct gcttatccgc   1140

tcccacctcc aagacctgaa ggacataacc cacaacatcc actatgagaa ctaccgcgtc   1200

atcagactca atgaaagcca cctgctgccc cgcgggcccg gctgggtgaa cctggccccg   1260

gcctccccag gacagctgac cacccccccgg accttcaagg tctgcagggg ggcccatgac   1320

gattctgatg atgagttctg accaccggcg gatcccgggg ctgctgggct tcctgagtcc   1380

ccagcggctc tcaacacaca cctatgtacc agagcatcta ttaaatgtga gccttgcttt   1440

ttatgaaaag ctgtgctttg aaaacaaaag gcattttgta aatgacttct ttgagctatc   1500

cacaaataaa aaggctgggt gtca                                          1524


<210> SEQ ID NO 99
<211> LENGTH: 2731
<212> TYPE: DNA
<213> ORGANISM: Homo sapiens

<400> SEQUENCE: 99

ctagccagac ccaccccttt atttcaggcc atcccttcat ttcccataag ggatactttt     60

agttaattga atatctatag aaacaatgct aatgactggt ttgctgttaa taaataagtg    120

ggtaaatctc tgttcggggc tctcagctct gaaggctgtg agacccctga tttcccactt    180

tacacctcta tatttctgtg tgtgtgtctt taattcctct agcaccactg ggttagggtc    240

tccccaactg agctggtctc ggcacttctc tttgccttaa aaacaggtac agcggacctt    300

cctggcatca gaaaaaggcc tccagaaaaa gagacacagg tactagcaat tccaaattat    360

ccagagccct tctaagttgt aagatctgaa agaaatgtct gccatctata ttctcagcca    420

cacttagttt cttaatctgc aagatggaat taataatagt acttacttta tgatgctgtt    480

gcagaaattc actgagttgc tacacgccaa acactgagaa cccagctggg catataataa    540

gcattctatt gcatggcatt attgccatca tttttacttc tattactgct actgcttgta    600

actgcttgta actgtttgtg ctttttttgat atgaaagtcc accatcaggg agcactgtag    660

tggaaaaggt attaggccag gcatagcctt tagttctctg gccttgggtc cttcatctgt    720

gatattcagt taacaatacc tagccagtag ggtgttaaa gattaaataa atgtgagaat    780

gtgcctgttg cttaatcttc ctcaaagggt tatggactct cagagccaga agaaggtcat    840

ctctcctttg ctcctcgtat gctgggatct gccacatcaa tggcaacagc tgggcctcca    900

gaatttgctc cagggtgttt ggaagtcctg acaccctcct gatcttctct gtaacatgca    960

cactttggcc tgtgtcagtt tgctggaacc acatcaggcc ggccctcttc ctgggacaaa   1020

attctttctt tttctttctt tctttttctt tctctttctt tctttttctt tctctttctt   1080
```

tctcttttcc cttccttcct tccttccttc cttccttcct tccttccttc ccttttcttt 1140
tcttttcttt ctactgtgac ataatcttgg ctcactgcaa tctctctctc ctgggttcaa 1200
gtgattctac tgcctcagcc tccaaagtag ctgggattac aggtttgcac caccatgccc 1260
ggctaatttt ttgtattttt agtagagaca gtgtttcacc atgttggcca ggctggtctc 1320
catcacctga tctcaggtga tccacccacc tcagcctccc aaagtgctgg gactacaggc 1380
atgagccacc acgcctggcc gagagacagt taagttatac tttaaatgat aataggcctc 1440
ccccaaaact cagctgcttt tgtaaagcta atgggaggcc atcaggctgg gggcaaggag 1500
gagagcccgg atcctgctaa ggtgcagaca taaacgagta tcagccatta ttctggaggt 1560
tataagatat gcaccttccc caattacccc tgcaatcaca ccattattgt agattggccc 1620
ttagagtatc ttttcaggtt ttttggcatg tctgacactc atggctctac ttggacccac 1680
caaccctgct cctatggctc cacccagaag ccattcagcc tagaggacag ctctgacccc 1740
ccctgtgatt tcatacaatc agcagcaagt aactgttacc tcaccatccc cacccccttct 1800 gccagactgc ctttgaaaaa cctctaacct gtgagcacga gatgattcca gaacaaactc 1860
tgtctcccat gtggcatgac cagccttggg tctcttaaac tttttctcca ctataatgcc 1920
atggtcttta tgcagcaggc aggaagaatt caggtggtta taattccgta tgtgcttttt 1980
gaacattttt ctactgggct attgctctct tcataatgat ttttttaact tctctctata 2040
aggaactgat ttcatctgaa attgaagaga caatcagaga aaaactatag accactcatg 2100
atggttgtta tatgtgcttg gctgggccat gggtcccagt gtttggtgaa acacagcagc 2160
agatgtccct gtgagtagat gttgctttga aggtatcttt tagatgtgat gaacatttgt 2220
catcagtaga ctttgagtaa ggcagatagc ccgtcacaat gtggatgggc cttatccaat 2280
tagttgaagg cctttgaaaa aagactgaga tcccaaacga agaaggaatt ctgcctccag 2340
acagccttcc aactcaagta gcaacattac ctcctccctg cggctctagc ctgctggcct 2400
ttcctataga cttcagactt gccagcccca caatcatgta agccaattcc ttaaaataaa 2460
ttctctgtcc tgtttttgcc ccctctctct ttctgacagc acacacatgc cctcttggtt 2520
ctgtttcttt gaagaacccc aggaaaacac acaaaggaaa aacaactcga tagacagaag 2580
attcttcaat gacaacaatg gaagccatct tcaccattca actaaacttg aatgggatat 2640
tatcaaactt aaaaaaaaat tatcaactga tcgtgtaatc agtttcatct tttaagacag 2700
gaaatgaaat aaagtattta cagatgaatg t 2731

<210> SEQ ID NO 100
<211> LENGTH: 3634
<212> TYPE: DNA
<213> ORGANISM: Homo sapiens

<400> SEQUENCE: 100
gatatctgag aatagtagga aaaaaattgg gtaatcccaa aataaatcag tgatttcagt 60
atgaagtttt ctcaacataa atctgctata attaaaaatt acaggccttc aggaagtgtc 120
gagtctggga cgcccagcgc gggcccgagc agggggaagg gaagcgcagc tcggtccgcg 180
tgggtggagg ggacgtgaag ccgccctgag atgatggttg aggaagggct ctacggctcc 240
caagccaggc caaatgcctc cggcggccgc gcccgggcgc cccttcccct gtggggcaac 300
cctagcttgg gacgcgtgaa ccacctccgt agctgcccca ccagcacccc cagccgtgcg 360
cccctgcacc atgcagctgc cctgcgcatg gagccgcgag ggacagcagg cccagccctc 420

-continued

```
agcaccacct gcctgccagg aggttcggga aactggcgcc gcagcggaga gggcatctgt    480
ccaacgcctc ccccggggct cagctgcggg cccccaggca taggcaccca tgacccttct    540
gtgttgtttg tctttgtata gtctgcagat gtggatcctg actcctgaga gaagtagctc    600
accgtgacga agctgcgttt gcttttatcg atttgcaaat caaagaaggg ggacatattg    660
ggagaaggcc ccccaaaatc tggccataaa ctggccacaa aactggccat aaaatctctg    720
cagcactgtg acatgctcat gatggccata acgcccacgc tggaaggttt tgggtttacc    780
ggaatgaaag caaggaacac ctggcctgcc cagggcagaa aaccacttaa aggcattctt    840
aaaccacaaa cagtagcatg agcgatctgt gccttaaggg catgttcctg ctgcagataa    900
ctagccagac ccaccccttt atttcaggcc atcccttcat ttcccataag ggatactttt    960
agttaattga atatctatag aaacaatgct aatgactggt ttgctgttaa taaataagtg   1020
ggtaaatctc tgttcggggc tctcagctct gaaggctgtg agacccctga tttcccactt   1080
tacacctcta tatttctgtg tgtgtgtctt taattcctct agcaccactg ggttagggtc   1140
tccccaactg agctggcctc ggcacttctc tttgccttaa aaacaggtac agcggacctt   1200
cctggcatca gaaaaaggcc tccagaaaaa gagacacagg tactagcaat tccaaattat   1260
ccagagccct tctaagttgt aagatctgaa agaaatgtct gccatctata ttctcagcca   1320
cacttagttt cttaatctgc aagatggaat taataatagt acttacttta tgatgctgtt   1380
gcagaaattc actgagttgc tacacgccaa acactgagaa cccagctggg catataataa   1440
gcattctatt gcatggcatt attgccatca tttttacttc tattactgct actgcttgta   1500
actgcttgta actgtttgtg ctttttttgat atgaaagtcc accatcaggg agcactgtag   1560
tggaaaaggt attaggccag gcatagcctt tagttctctg gccttgggtc cttcatctgt   1620
gatattcagt taacaatacc tagccagtag ggtgttaaa gattaaataa atgtgagaat   1680
gtgcctgttg cttaatcttc ctcaaagggt tatggactct cagagccaga agaaggtcat   1740
ctctcctttg ctcctcgtat gctgggatct gccacatcaa tggcaaccgc tgggcctcca   1800
gaatttgctc cagggtgttt ggaagtcctg acaccctcct gatcttctct gtaacatgca   1860
cactttggcc tgtgtcagtt tgctggaacc acatcaggcc ggccctcttc ctgggacaaa   1920
attctttctt tttctttctt tctttttctt tctctttctt tctttttctt tctctttctt   1980
tctcttttcc cttccttcct tccttccttc cttccttcct tccttccttc cttccttccc   2040
ttttcttttc ttttctttct actgtgacat gatcttggct cactgcaatc tctctctcct   2100
gggttcaagt gattctactg cctcagcctc caaagtagct gggattacag gtttgcacca   2160
ccatgcccgg ctaatttttt gtatttttag tagagacagt gtttcaccat gttggccagg   2220
ctggtctcca tcacctgatc tcaggtgatc cacccacctc agcctcccaa agtgctggga   2280
ctacaggcat gagccaccac gcctggccga gagacagtta agttatactt taaatgataa   2340
taggcctccc ccaaaactca gctgcttttg taaagctaat gggaggccat caggctgggg   2400
gcaaggagga gagcccggat cctgctaagg tgcagacata aacgagtatc agccattatt   2460
ctggaggtta taagatatgc accttcccca attacccctg caatcacacc attattgtag   2520
attggccctt agagtatctt ttcaggtttt ttggcatgtc tgacactcat ggctctactt   2580
ggacccacca accctgctcc tatggctcca cccagaagcc attcagccta gaggacagct   2640
ctgacccccc ctgtgatttc atacaatcag cagcaagtaa ctgttacctc accatcccca   2700
ccccttctgc cagactgcct ttgaaaaacc tctaacctgt gagcacgaga tgattccaga   2760
acaaactctg tctcccatgt ggcatgacca gccttgggtc tcttaaactt tttctccact   2820
```

```
ataatgccat ggtctttatg cagcaggcag gaagaattca ggtggttata attccgtatg   2880
tgctttttga acatttttct actgggctat tgctctcttc ataatgattt ctttaacttc   2940
tctctataag gaactgattt catctgaaat tgaagagaca atcagagaaa aactatagac   3000
cactcatgat ggtcgttata tgtgcttggc tgggccatgg gtcccagtgt ttggtgaaac   3060
acagcagcag atgtccctgt gagtagatgt tgctttgaag gtatctttta gatgtgatga   3120
acatttgtca tcagtagact ttgagtaagg cagatagccc gtcacaatgt ggatgggcct   3180
tatccaatta gttgaaggcc tttgaaaaaa gactgagatc ccaaacgaag aaggaattct   3240
gcctccagac agccttccaa ctcaagtagc aacataacct cctccctgcg gctctagcct   3300
gctggccttt cctatagact tcagacttgc cagccccaca atcatgtaag ccaattcctt   3360
aaaataaatt ctctgtcctg tttttgcccc ctctctcttt ctgacagcac acacatgccc   3420
tcttggttct gtttctttga agaaccccag gaaaacacac aaaggaaaaa caactcgata   3480
gacagaagat tcttcaatga caacaatgga agccatcttc accattcaac taaacttgaa   3540
tgggatatta tcaaacttaa aaaaaaatta tcaactgatc gtgtaatcag tttcatcttt   3600
taagacagga aatgaaataa agtatttaca gatg                                3634
```

<210> SEQ ID NO 101
<211> LENGTH: 3035
<212> TYPE: DNA
<213> ORGANISM: Homo sapiens

<400> SEQUENCE: 101

```
ggacgctggc tacgggtggc cgggcgggat gtaaccggct gctgagctgg cagttctgtg     60
tccccaggct tcggcccggc cgccgccgca cataaactgc gaggaggagc tttacgactt    120
cccggtcttc ggggccgggc gcagcaaggg ccagactctg cgctagcagg cgctgcgcgc    180
caaccggccg gcccctgtcg cagaaggtgc aaccgatcgc actgtcgcgc agaagctcct    240
caatggccag cgccagctgc agccccggct gcccactcgc ctcacctgag cctgggtgga    300
acaatccaaa gttttaatca aagaaggtgg tattcagttg ctgcttacaa tagttgatac    360
cccaggattt ggagatgcag tggataatag taattgctgg cagcctgtta tcaattacat    420
tgatagtaaa tttgaggact acctaaatgc agaatcgcaa gtgaacagat gtcagatgcc    480
tggtaacagg gtgcactgtt gtttatactt cattgctcct tcaggacatg gaccgttaca    540
taactgaaga ctcccacctt caggcaggat tgggtagtac atgtttgtaa ctacctggca    600
ttgccttttg ttgagactta aaccattgga tattgagttt acaaagcatt tgcatgaaaa    660
agtgaatatc atcccactta ttgccaaagc agacacactc atgccagagg aatgccaaca    720
gtttaaaaaa cagataaaga aatccaagaa cataaagtta aaatatatga atttccagaa    780
acagatgatg aagaagaaaa aaaacttgtt aaaaagataa aggaccattt acctcttgct    840
gtggtgggta gtaatactat cattgaagtt aatggcaaaa gggtcatagg aaggcagtat    900
ccttggagtg ttgctgaaga tggagtctcg ctctgccacc caggctggaa tgcagtggca    960
tgatcttggc tcactgcaac ctccgcctcc cgagttcaag agattcttct gcctcagcct   1020
cccaagtagc tgggactaaa gttgaaaatg gtgaacattg tgattttaca gttttaagaa   1080
atatgttgat aagaacacac gcaggacttg aaagatgtta ctaataatgt ccactacgag   1140
aactatggaa tcagaaaact ggcggctgtg acttatcatg gagttgataa caagaagaat   1200
aaagggcagc tcactaagag ccctctggca caaatggaag aagaaagaag ggagcaagta   1260
```

gctaaaatta agaagatgga gatggagatg gagcaggtgt ttgagatgaa ggtcaaagaa 1320
aaagttcaaa aactgaagga ctctgaagct gaggtacagc ggaccttcct ggcatcagaa 1380
aaaggcctcc agaaaaagag acacagggtt atggactctc agagccagaa gaaggtcatc 1440
tctcctttgc tcctcgtatg ctgggatctg ccacatcaat ggcaaccgct gggcctccag 1500
aatttgctcc agggtgtttg gaagtcctga caccctcctg atcttctctg taacatgcac 1560
actttggcct gtgtcagttt gctggaacca catcaggccg gccctcttcc tgggacaaaa 1620
ttctttcttt ttctttcttt ctttttcttt ctctttcttt ctttttcttt ctctttcttt 1680
ctcttttccc ttccttcctt ccttccttcc ttccttcctt ccttccttcc cttttctttt 1740
cttttctttc tactgtgaca tgatcttggc tcactgcaat ctctctctcc tgggttcaag 1800
tgattctact gcctcagcct ccaaagtagc tgggattaca ggtttgcacc accatgcccg 1860
gctaattttt tgtattttta gtagagacag tgtttcacca tgttggccag gctggtctcc 1920
atcacctgat ctcaggtgat ccacccacct cagcctccca aagtgctggg actacaggca 1980
tgagccacca cgcctggccg agagacagtt aagttatact ttaaatgata ataggcctcc 2040
cccaaaactc agctgctttt gtaaagctaa tgggaggcca tcaggctggg ggcaaggagg 2100
agagcccgga tcctgctaag gtgcagacat aaacgagtat cagccattat tctggaggtt 2160
ataagatatg caccttcccc aattacccct gcaatcacac cattattgta gattggccct 2220
tagagtatct tttcaggttt tttggcatgt ctgacactca tggctctact tggacccacc 2280
aaccctgctc ctatggctcc acccagaagc cattcagcct agaggacagc tctgaccccc 2340
cctgtgattt catacaatca gcagcaagta actgttacct caccatcccc accccttctg 2400
ccagactgcc tttgaaaaac ctctaacctg tgagcacgag atgattccag aacaaactct 2460
gtctcccatg tggcatgacc agccttgggt ctcttaaact ttttctccac tataatgcca 2520
tggtctttat gcagcaggca ggaagaattc aggtggttat aattccgtat gtgctttttg 2580
aacatttttc tactgggcta ttgctctctt cataatgatt tttttaactt ctctctataa 2640
ggaactgatt tcatctgaaa ttgaagtgac aatcagagaa aaactataga ccactcatga 2700
tggttgttat atgtgcttgg ctgggccatg ggtcccagtg tttggtgaaa cacagcagca 2760
gatgtccctc acacacatgc cctcttggtt ctgtttcttt gaagaacccc aggaaaacac 2820
acaaaggaaa aacaactcga tagacagaag attcttcaat gacaacaatg gaagccatct 2880
tcaccattca actaaacttg aatgggatat tatcaaactt aaaaaaaaat tatcaactga 2940
tcgtgtaatc agtttcatct tttaagacag gaaatgaaat aaagtattta cagatgaatg 3000
taaaataaaa aaaaaaaaaa aaaaaaaaaa aaaaa 3035

<210> SEQ ID NO 102
<211> LENGTH: 932
<212> TYPE: DNA
<213> ORGANISM: Homo sapiens

<400> SEQUENCE: 102
gtgaagccgc cctgagatga tggttgagga agggctctac ggctcccaag ctaggccaaa 60
tgcctccggc ggccgcgccc gggcgcccct tcccctgtgg ggcaacccta gcttgggacg 120
cgtgaaccac ctccgtagct gccccaccag cacccccagc cgtgcgcccc tgcaccatgc 180
agctgccctg cgcatggagc cgcgagggac agcaggccca gccctcagca ccacctgcct 240
gccaggaggt tcgggaaact ggcgccgcag cggagagggc atctgtccaa cgcctccccc 300
ggggctcagc tgcgggcccc caggcatagg cacccatgac ccttctgtgt tgtttgtctt 360
tgtatagtct gcagatgtgg atcctgactc ctgagagaag tagctcaccg tgacgaagct 420
gcgtttgctt ttatcgattt gcaaatcaaa gaagggggac atattgggag aaggcccccc 480
aaaatctggc cataaactgg ccacaaaact ggccataaaa tctctgcagc actgtgacat 540
gctcatgatg gccataacgc ccacgctgga aggttttggg tttaccggaa tgaaggcaag 600
gaacacctgg cctgcccagg gcagaaaacc acttaaaggc attcttaaac cacaaacagt 660
agcatgagcg atctgtgcct taagggcatg ttcctgctgc agataactag ccagacccac 720
ccctttattt caggccatcc cttcatttcc cataagggat acttttagtt aattgaatat 780
ctatagaaac aatgctaatg actggtttgc tgttaataaa taagtgggta aatctctgtt 840
cggggctctc agctctgaag gctgtgagac ccctgatttc cccctttaca cctctaaaaa 900
aaaaaaaaaa aaaaaaaaaa aaaaaaaaaa aa 932

<210> SEQ ID NO 103
<211> LENGTH: 1935
<212> TYPE: DNA
<213> ORGANISM: Homo sapiens

<400> SEQUENCE: 103
gcgcattagc ggacgctggc tacgggtggc cgggcgggat gtaaccggct gctgagcggc 60
agttctgtgt ccccaggctt cggcccggcc gccgccgcac ataaactgcg aggaggagct 120
ttacgacttc ccggtcttcg gggccgggcg cagcaagggc cagactctgc gctagcaggc 180
gctgcgcgcc aaccggccgg cccctgtcgc agaaggtgca accgatcgca ctgtcgcgca 240
gaagctcctc aatggccagc gccagctgca gccccggctg cccactcgcc tcacctgagc 300
ctgggtggaa caatccaaag ttttaatcaa agaaggtggt attcagttgc tgcttacaat 360
agttgatacc ccaggatttg gagatgcagt ggataatagt aattgctggc agcctgttat 420
caattacatt gatagtaaat ttgaggacta cctaaatgca gaatcgcaag tgaacagatg 480
tcagatgcct ggtaacaggg tgcactgttg tttatacttc attgctcctt caggacatgg 540
accgttacat aactgaggac tcccaccttc aggcaggatt gggtagtaca tgtttgtaac 600
tacctggcat tgccttttgt tgagacttaa accattggat attgagttta caaagcattt 660
gcatgaaaaa gtgaatatca tcccacttat tgccaaagca gacacactca tgccagagga 720
atgccaacag tttaaaaaac agataaagaa atccaagaac ataaagttaa aatatatgaa 780
tttccagaaa cagatgatga agaagaaaaa aaacttgtta aaaagataaa ggaccattta 840
cctcttgctg tggtgggtag taatactatc attgaagtta atggcaaaag ggtcatagga 900
aggcagtatc cttggagtgt tgctgaagtt gaaaatggtg aacattgtga ttttacagtt 960
ttaagaaata tgttgataag aacacacgca ggacttgaaa gatgttacta ataatatcca 1020
ctacgagaac tatggaatca gaaaactggc agctgtgact tatcatggag ttgataacaa 1080
gaagaataaa gggcagctca ctaatagaga cggtatttca ccatgttagc caggatggtc 1140
ttgatctcct gacctcgtga tccacccgcc tcggcctccc aaagtgctgg gattacaggc 1200
atgagccacc acgcccggcc aagtggaatg aattttcaag agcattgaag ttaccataag 1260
gggcctagaa atactctgta tacctatata gtgctctagg agccctctgg cacaaatgga 1320
agaagaaaga agggagcaag tagctaaaat taagaagatg gagatggaga tggagcaggt 1380
gtttgagatg aaggtcaaag aaaaagttca aaaactgaag gactctgaag ctgaggtaca 1440
gcggaccttc ctggcatcag aaaaaggcct ccagaaaaag agacacagga actgatttca 1500

-continued

```
tctgaaattg aagagacaat cagagaaaaa ctatagacca ctcatgatgg ttgttatatg   1560

tgcttggctg ggccatgggt cccagtgttt ggtgaaacac agcagcagat gtccctgtga   1620

gtagatgttg ctttgaaggt atcttttaga tgcgatgaac atttgtcatc agtagacttt   1680

gagtaaggca gacagcccgt cacaatgtgg atgggcctta tccaattagt tgaaggcctt   1740

tgaaaaaaga ctgagatccc aaacgaagaa ggaattctgc ctccagacag ccttccaact   1800

caagtagcaa cataacctcc tccctgcggc tctagcctgc tggcctttcc tatagacttc   1860

agacttgcca gccccacaat catgtaagcc aattccttaa aataaattct ctgtcctgta   1920

aaaaaaaaaa aaaaa                                                    1935


<210> SEQ ID NO 104
<211> LENGTH: 3785
<212> TYPE: DNA
<213> ORGANISM: Homo sapiens

<400> SEQUENCE: 104

acagtgaata tttatttggt ccacaactgg ggacagtaga aaggacacca gcttggaatc     60

agttcggacc tgtgtctgct gcacagctga atccctggga aactctttta gtgtagcatg    120

gcagaaagaa caatggctat gcccacacaa atacctgctg atggagatac acaaaaagaa    180

aataatattc gttgtttaac tacgattgga cattttggtt ttgaatgttt gcccaatcag    240

ttggtgagca gatctatccg acaaggattc acttttaata ttctctgtgt gggggagact    300

ggaattggaa aatcgacact gatagacaca ttgtttaata ctaacttgaa agataacaaa    360

tcctcacatt tttactcaaa tgttggactt caaattcaga catatgaact tcaggaaagc    420

aatgttcagt tgaaattgac tgttgtggag acagtagggt atggtgatca aatagacaaa    480

gaagccagct accaaccaat agttgactac atagatgccc aatttgaggc ctatcttcaa    540

gaagaactga agattaaacg ttccttgttt gagtaccatg attctcgcgt ccacgtgtgt    600

ctttacttca tttcacctac aggacattcc ctgaagtctc ttgatctatt aacaatgaag    660

aaccttgaca gtaaggtgaa tattatacca ctgattgcca aagcagacac tatttctaaa    720

aatgatttac agacgtttaa gaataagata atgagtgaat tgattagcaa tggcatccag    780

atatatcagc tcccaacaga tgaagaaact gctgctcaag cgaactcctc agttagtggg    840

ctgttaccct ttgctgtggt agggagtaca gatgaagtga aagttggaaa aaggatggtc    900

agaggccgtc actacccttg ggggagtttg caagtggaaa atgaaaatca ctgtgacttc    960

gttaagctcc gagatatgct tctttgtacc aatatggaaa atctaaaaga aaaaacccac   1020

actcagcact atgaatgtta taggtaccaa aaactgcaga aaatgggctt tacagatgtg   1080

ggtccaaaca accagccagt tagttttcaa gaaatctttg aagccaaaag acaagagttc   1140

tatgatcaat gtcagaggga agaagaagag ttgaaacaga gatttatgca gcgagtcaag   1200

gagaaagaag caacatttaa agaagctgaa aaagagctgc aggacaagtt cgagcatctt   1260

aaaatgattc aacaggagga gataaggaag ctcgaggaag agaaaaaaca actggaagga   1320

gaaatcatag atttttataa aatgaaagct gcctccgaag cactgcagac tcagctgagc   1380

accgatacaa agaaagacaa acatcgtaag aaataatagt ttctcttact attctgagag   1440

ccctatcatt ctacatcgca acttcctgtg agattgtctt tgtagcattt aactctgaag   1500

ttctcatttt aaaaattggc ttgcttattg tatattttcc ccaactaaag tgtgaactcc   1560

tagcggggtg tggtggctca tgcctgtaat cccagcactt tgggaggctg aggcgggtgg   1620

accacctgag gtcaggagtt caaaaccagc ctgaccaaaa tgatgaaacc ctgcctctac   1680
```

taaaaataca aaaattagct gggtttggtg gccggtacct gtaatcccag ccacttggga 1740
ggctgaggca ggagaatcac ttgaaccccg gaggtggagg ttgcagtgag ccaagatctc 1800
accattgtac tccagcctgg gtgacaagag caaaactccg cctcaaaaaa aaaaaaaaaa 1860
aaaaaagtat gaactcccag aaggcagatc ctgtgtccct cttttcagat tctgtatctt 1920
ggcacttagg acgtacacta acacaaatat gactttcaat caatatttgc caaaatgaaa 1980
aaacaaaaga aacacgtagc atcatgtaaa aggagctggt taggtggaga aatttattta 2040
ccatagtcct gcttttggat ccagtagtga cttttaactt ttatatccaa atagaagctg 2100
gaggctttgt tggggactca taggcataaa atgttaagtt atacaaatct aattaatagg 2160 cctatttcc tttttaagtt ctactactga taatttcttg acagttttta tgataaaagg 2220
ttggaatttg ataagaactc ccatgctttt gtgtcagact taaaactgat attagaataa 2280
agaattcaaa agctagagaa agagttgcat ttgaatgata atattatgtg ttacagattt 2340
ggggtatatg ccaaagttat caaagttgta gaaaataagg ccaggtgtgg tggctcacac 2400
ctgtaatccc agcactttgg gaggccgagg tgggcggatc acttgcggtc aggagcttga 2460
gaacagcccg gccaacatga cgaaacccca tctctactaa taatacaaaa gttagccggg 2520
tgtggtgttg tgcacctgta gtccctgcta ctcggaaagc tgaggcagga gaatcgcttg 2580
tagccaggag gcagaggttg tagtgagcag agattgcgcc actgcactcc agcctgggtg 2640
acagagcgct gagtcaccac acctggtata agccactgtg cctgacccac aatgactttt 2700
atacatattg ttaaatcatc ttacagattt tataatttgg gggaagaaaa attttactaa 2760
atgatctttt aatggaaact ctacaagaac cagaatcttt gctttgttca cttatgtatc 2820
cattcctagg cctagaaaaa tgtctgacgc atagcagcaa ttattcattg aataaatgga 2880
cccagcaata gtacattagc tatgccatat gcatacatta aaaatgtaga ttattgactt 2940
tcaaaagata attaatgtaa cttcttactg cttctgaaca tgtttgtgag ttatattgct 3000
gagggacctt tatcttctca ttctttcatc ttaatccaat gttattaaaa ctgaaactga 3060
aatcaccaat attattccat atttaaaaat aacatctacc ttataaaaat tatcattgtg 3120
ctgcatttga gaatagactt tttaggtaat aatggtataa tccatagggt ttttgagggc 3180
acagaaggat tcatgctaac agaacatttt attttctatt ttccaagagc tataaaacat 3240
gatattatat gatactataa ggcatatttt tattttccat aattttttct aaaaaaaatt 3300
agtgttggtt ttccatataa cttttaactt tataagtaaa tatttgtctc tttcagctcc 3360
agtttcatgt gaaatagagt ttccagattt atgtagcatg gaaagtttta atacgtcagt 3420
tactgatttt tgccagtcat tttctcaatt atttacttct tttatcttta gttgattttt 3480
tttgtagtga caagttttgt ttctattctc atttcctttt gtgtatattc tatgtagatt 3540
tcgtttttgg ttactatgaa aattacatat aacatcctgg agttataaca ttctgatttg 3600
aatttatttc aacttaactt caatcacata ccaaaattct actgctatat aggtctactc 3660
tttttaggtt attgatgtaa caaattgtat ctttattcat tgtacaccac ctaacagatt 3720
tataattaca ttttatgcat ttgtctttta aatcctgtag aaaataaaaa gcggagttac 3780
aaacc 3785

<210> SEQ ID NO 105
<211> LENGTH: 2136
<212> TYPE: DNA
<213> ORGANISM: Homo sapiens

<400> SEQUENCE: 105
agcggcttcc gtcctgcagc aagtccggaa gaaggtccgg gggctggagt cctgggacct 60
agctcgggac cggcctggag atggagttcg actgcgaggg cctgagacgg ctgcttggca 120
agtacaagtt cagggaccta actgtggaag aactaaggaa tgtaaatgta tttttcccac 180
atttcaaata ttccatggac acctatgttt ttaaagatag ttctcagaaa gacctgctga 240
attttactgg cacaattcct gtgatgtatc agggtaatac atataacata ccaattcgtt 300
tctggatttt ggattctcac cctttcgctc cccctatttg cttcttgaag ccaactgcaa 360
atatgggaat cttagtcgga aaacatgtgg atgctcaagg cagaatatat ttgccctatc 420
tccaaaactg gagccatcct aaatctgtca ttgttggatt aattaaagaa atgattgcca 480
agtttcaaga ggaacttccc atgtattctc tatcatcatc tgatgaggca cggcaggtag 540
acttgctagc ctatattgca aaaatcactg aaggtgtttc agatacaaat tcaaagagct 600
gggcaaatca tgagaataaa acagtcaata aaattactgt ggttggaggt ggagaactcg 660
gtattgcctg cacattagca atttcagcaa agggtattgc agacaggctt gtcctcttag 720
acctctcaga agggactaaa ggagccacga tggaccttga aatcttcaac cttcctaatg 780
tggagatcag caaagatttg tctgcctctg ctcattccaa ggtggtgatc ttcacagtca 840
actctttggg tagttctcag tcgtaccttg atgtggtaca gagcaatgtg gatatgttca 900
gagcccttgt cccagctctg ggacattata gtcaacacag tgtcctgctc gttgcatctc 960
aaccagtgga aatcatgacc tatgtaacat ggaaactgag tacatttcct gcaaatcgag 1020
tgatcggaat tggatgtaat ctggattcac agagattaca gtatattatt acaaatgttt 1080
tgaaggcaca gacttcaggc aaagaagtat gggttattgg cgagcaagga gaagacaaag 1140
tgctcacatg gagtggccaa gaagaagtag tgagtcatac ctctcaagtg cagctgtcca 1200
acagagccat ggaactgcta agagtaaaag gtcaaagatc ctggtctgtt ggactatcag 1260
tagctgacat ggttgacagt attgtaaaca ataagaagaa agtgcattct gtatcagctt 1320
tagcaaaggg atattatgat ataaatagtg aagtgttttt aagtttgcct tgcatccttg 1380
gaaccaatgg agtatctgaa gttatcaaaa ccacactgaa agaagataca gttactgaga 1440
aactccaaag cagtgcatcc tcaatccaca gtctccaaca acagttaaaa ctttgattct 1500
caaatgcaat ttgagaggct ggacttctac ctaaagggaa aagtcattta attttaccta 1560
tatataggtt tgaggatttc tgtatcctgc tacttacttt tacaaactgc ttggttaaag 1620
tagagggttt cttgattagc tttgtgatgt aaatccttaa ggagttatac aaggagggga 1680
aaaattaatt ttatttgggg ttcttgagat atctatgctg ttctttaaat ctacagcagg 1740
ggtaaacatt catctgcagt gtgcatcaat ttaaatcata tatcctaaac taaaagcaca 1800
attcatactt cgggaatatt ttataagtaa tatatcttta aaagaaaatt accctttgac 1860
ttttataatc aacataagtt ccaggcccag tatggattta caaaatctgt gtcagttgta 1920
cattcacagg atccacagct taagttacta atgtttcttg tgtaaaatcc tgttggtagt 1980
aatagtaaag cattgtattt cccttcttca aattaattac ctaccaaaaa atggaaaaga 2040
attttacatg cactttaaaa tagtaaaatg gaaagtgaat ttttaaaata tatgcattaa 2100
aagtttactt taatttccaa aaaaaaaaaa aaaaaa 2136

<210> SEQ ID NO 106
<211> LENGTH: 2012
<212> TYPE: DNA
<213> ORGANISM: Homo sapiens -continued

<400> SEQUENCE: 106

```
agcggcttcc gtcctgcagc aagtccggaa gaaggtccgg gggctggagt cctgggacct     60
agctcgggac cggcctggag atggagttcg actgcgaggg cctgagacgg ctgcttggca    120
agtacaagtt cagggaccta actgtggaag aactaaggaa tgtaaatgta tttttcccac    180
atttcaaata ttccatggac acctatgttt ttaaagatag ttctcagaaa gacctgctga    240
attttactgg cacaattcct gtgatgtatc agggtaatac atataacata ccaattcgtt    300
tctggatttt ggattctcac cctttcgctc cccctatttg cttcttgaag ccaactgcaa    360
atatgggaat cttagtcgga aaacatgtgg atgctcaagg cagaatatat ttgccctatc    420
tccaaaactg gagccatcct aaatctgtca ttgttggatt aattaaagaa atgattgcca    480
agtttcaaga ggaacttccc atgtattctc tatcatcatc tgatgaggca cggcaggtag    540
acttgctagc ctatattgca aaaatcactg aaggtgtttc agatacaaat tcaaagagct    600
gggcaaatca tgagaataaa acagtcaata aaattactgt ggttggaggt ggagaactcg    660
gtattgcctg cacattagca atttcagcaa agggtattgc agacaggctt gtcctcttag    720
acctctcaga agggactaaa ggagccacga tggaccttga aatcttcaac cttcctaatg    780
tggagatcag caaagatttg tctgcctctg ctcattccaa ggtggtgatc ttcacagtca    840
actctttggg tagttctcag tcgtaccttg atgtggtaca gagcaatgtg gatatgttca    900
gagcccttgt cccagctctg ggacattata gtcaacacag tgtcctgctc gttgcatctc    960
aaccagtgga aatcatgacc tatgtaacat ggaaactgag tacatttcct gcaaatcgag   1020
tgatcggaat tggatgtaat ctggattcac agagattaca gtatattatt acaaatgttt   1080
tgaaggcaca gacttcaggc aaagaagtat gggttattgg cgagcaagga gaagacaaag   1140
tgctcacatg gagtggccaa gaagaagtag tgagtcatac ctctcaagtg cagctgtcca   1200
acagggatat tatgatataa atagtgaagt gtttttaagt ttgccttgca tccttggaac   1260
caatggagta tctgaagtta tcaaaaccac actgaaagaa gatacagtta ctgagaaact   1320
ccaaagcagt gcatcctcaa tccacagtct ccaacaacag ttaaaacttt gattctcaaa   1380
tgcaatttga gaggctggac ttctacctaa agggaaaagt catttaattt tacctatata   1440
taggtttgag gatttctgta tcctgctact tacttttaca aactgcttgg ttaaagtaga   1500
gggtttcttg attagctttg tgatgtaaat ccttaaggag ttatacaagg aggggaaaaa   1560
ttaattttat ttggggttct tgagatatct atgctgttct ttaaatctac agcaggggta   1620
aacattcatc tgcagtgtgc atcaatttaa atcatatatc ctaaactaaa agcacaattc   1680
atacttcggg aatattttat aagtaatata tctttaaaag aaaattaccc tttgactttt   1740
ataatcaaca taagttccag gcccagtatg gatttacaaa atctgtgtca gttgtacatt   1800
cacaggatcc acagcttaag ttactaatgt ttcttgtgta aaatcctgtt ggtagtaata   1860
gtaaagcatt gtatttccct tcttcaaatt aattacctac caaaaaatgg aaaagaattt   1920
tacatgcact ttaaaatagt aaaatggaaa gtgaattttt aaaatatatg cattaaaagt   1980
ttactttaat ttccaaaaaa aaaaaaaaaa aa                                 2012
```

REGULATORS OF NFAT AND/OR STORE-OPERATED CALCIUM ENTRY

CROSS REFERENCE TO RELATED APPLICATIONS

This application is a 35 U.S.C. §371 National Phase Entry Application of International Application No. PCT/US2011/055561 filed Oct. 10, 2011, which designates the U.S., and which claims benefit under 35 U.S.C. §119(e) of the U.S. Provisional Application No. 61/391,445 filed on Oct. 8, 2010, the contents of which are incorporated herein by reference in their entireties.

GOVERNMENT SUPPORT

This invention was made with Government support under contract Nos. AI40127 and GM075256, awarded by the National Institutes of Health. The Government has certain rights in the invention.

REFERENCE TO SEQUENCE LISTING

This application contains a Sequence Listing which has been submitted in ASCII format via EFS-Web and is hereby incorporated by reference in its entirety. The ASCII copy, created on Apr. 1, 2013, is 033393-062757-US_Sequence-Listing.txt and is 248,192 bytes in size.

FIELD OF THE INVENTION

The invention relates to modulating nuclear factors of activated T-cell (NFAT) and/or store operated $Ca^{2+}$ entry (SOCE) in cells, in particular T cells. The invention relates to the regulation of the activation of T cells and the modulation of immune responses.

BACKGROUND OF INVENTION

The calcium/calcineurin-dependent NFAT family is thought to have arisen following the recombination of an ancient precursor with a Rel domain about 500 million years ago, producing a new group of signaling and transcription factors (the NFAT genes) found only in the genomes of vertebrates. The family of NFAT transcription factor consists of five members NFAT1, NFAT2, NFAT3, NFAT4 and NFAT5. The NFAT proteins are activated by an increase in intracellular calcium levels, e.g., by means of store-operated calcium entry (SOCE) into a cell (see FIG. 1).

SUMMARY OF THE INVENTION

Embodiments of the invention are based on the discovery that several hundred genes in the human and mouse genomes whose gene products directly and/or indirectly modulate nuclear factors of activated T cell (NFAT) activation and/or modulate the store-operated $Ca^{2+}$ entry (SOCE) into a cell. For example, the SEPT 4, SEPT 5 and UEV3 gene product modulate SOCE into a cell, modulate NFAT nuclear translocation and the consequential T cell activation.

NFAT is a family of transcription factors that normally reside in the cytoplasm when inactive. When activated by dephosphorylation by calcineurin, the NFATs can translocate into the nucleus and "turn on" specific gene transcription. The inventors developed a cell-based reporter system for screening for modulators of NFAT and/or SOCE into a cell, with NFAT nuclear translocation as the readout for scoring a modulator. The cell-based reporter system comprises a mammalian cell co-expressing a NFAT-GFP, a STIM1-RFP, and an Orai1-FLAG. The markers: GFP, RFP and FLAG-tag facilitate the visual localization of the respectively expressed proteins within the cell compartments. Thapsigargin (TG), a tight-binding inhibitor of sarco/endoplasmic reticulum $Ca^{2+}$ ATPase, was used to deplete the $Ca^{2+}$ in the endoplasmic reticulum and initiate SOCE, which in turn leads to NFAT dephosphorylation and NFAT nuclear translocation. The inventors used the cytoplasm-to-nuclear translocation of NFAT-GFP as their assay readout.

The inventors performed a large scale high-throughput siRNA screening of the human and mouse genome for genes that modulate NFAT nuclear translocation and/or SOCE. Genes that modulate the NFAT nuclear translocation and/or SOCE can either up-regulate (i.e. promote) or down-regulate (i.e., inhibit) NFAT nuclear translocation and/or SOCE. NFAT nuclear translocation and/or SOCE are necessary for the activation of T cells, the proliferation of activated T cells, and for maintaining the immune response involving T- and B-cells in the body. In addition, the NFAT translocation is associated with multiple signaling pathways such as the MAP kinase, WNT, and NOTCH signaling pathways. As such, NFATs directly and/or indirectly play important roles in cell proliferation and regeneration, cancer, angiogenesis, cardiovascular diseases, diabetes, neural regeneration, bone diseases and T cell adaptation to name a few. Therefore, identification of the modulator genes of NFAT nuclear translocation and/or SOCE allows therapeutic regulation of the immune system, immune responses and other disease conditions associated with NFATs.

The inventors found that the inhibition of the SEPT 4 and SEPT 5 gene expressions by RNA interference methods greatly reduced NFAT nuclear translocation in their assay system (see FIGS. 75B, 78) and also SOCE in the affected cell (see FIGS. 53, 58, 70, 73, 75C, 77B). Septin proteins have functions in cytokinesis, membrane remodeling and compartmentalization in a cell.

The inventors also found that the inhibition of the UEV3 gene expression by RNA interference methods greatly reduced NFAT nuclear translocation in their assay system (see FIGS. 25, 35, 36) and also SOCE in the affected cell (see FIGS. 24-26, 31).

Inhibition of genes that up-regulate NFAT nuclear translocation and/or SOCE can help inhibit T-cell activation and immune response associated with hyperactivity or inappropriate activity of the immune system. Conversely, inhibition of genes that down-regulate NFAT nuclear translocation and/or SOCE can help increase T cells activation and immune responses associated with immune deficiency disease or conditions.

Secondary and tertiary screens of the hits from primary screens were conducted. Secondary and tertiary screens comprise $Ca^{2+}$ influx as readout for scoring.

Accordingly, provided herein is a pharmaceutical composition comprising an agent that inhibits the function of a septin protein and/or the expression of a septin gene, and a pharmaceutically acceptable carrier. In one embodiment of the pharmaceutical composition, the septin is a septin 4. Other not limiting examples of septins include septin 2, 4, 5, 6, 7, and 9. In another embodiment, the pharmaceutical composition further comprises an agent that inhibits the function of a UEV3 protein and/or the expression of a UEV3 gene.

In one embodiment of the pharmaceutical composition, the agent inhibits the function of at least two septin proteins and/or the expression of at least two septin genes. In one embodiment, the at least two septins are septin 4 and 5. In another embodiment, the at least two septins are septin 3 and 4. In another embodiment, the pharmaceutical composition further comprises an agent that inhibits the function of a UEV3 protein and/or the expression of a UEV3 gene.

In another embodiment, the pharmaceutical composition comprises a first agent that inhibits the function of a first septin protein and/or the expression of a first septin gene, a second agent that inhibits the function of a second septin protein and/or the expression of a second septin gene, and a pharmaceutically acceptable carrier. In one embodiment of the pharmaceutical composition, the first septin is a septin 4 and the second septin is a septin 5. In another embodiment, the pharmaceutical composition further comprises an agent that inhibits the function of a UEV3 protein and/or the expression of a UEV3 gene.

In one embodiment, provided herein is a pharmaceutical composition comprising an agent that inhibits the function of a septin 4 protein and/or the expression of a septin 4 gene, and a pharmaceutically acceptable carrier. In one embodiment, the pharmaceutical composition further comprises an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a pharmaceutical composition comprising an agent that inhibits the function of a septin 4 protein and/or the expression of a septin 4 gene, an agent that inhibits the function of a septin 5 protein and/or the expression of a septin 5 gene and a pharmaceutically acceptable carrier. In another embodiment, the pharmaceutical composition further comprises an agent that inhibits the function of a UEV3 protein and/or the expression of a UEV3 gene.

In one embodiment, provided herein is a pharmaceutical composition comprising an agent that inhibits the function of a UEV3 protein and/or the expression of a UEV3 gene, and a pharmaceutically acceptable carrier.

In one embodiment, provided herein is a pharmaceutical composition comprising an agent that inhibits the function of a UEV3 protein and/or the expression of a UEV3 gene, an agent that inhibits the function of a septin protein and/or the expression of a septin gene, and a pharmaceutically acceptable carrier. In one embodiment of the pharmaceutical composition, the septin is a septin 4. In another embodiment of the pharmaceutical composition, the agent inhibits the function of at least two septin proteins and/or the expression of at least two septin genes. In one embodiment, the at least two septins are septin 4 and 5.

In one embodiment, provided herein is a pharmaceutical composition comprising an agent that inhibits the function of a UEV3 protein and/or the expression of a UEV3 gene, a first agent that inhibits the function of a first septin protein and/or the expression of a first septin gene, a second agent that inhibits the function of a second septin protein and/or the expression of the second septin gene, and a pharmaceutically acceptable carrier. In one embodiment of the pharmaceutical composition, the first septin is a septin 4 and the second septin is a septin 5.

In one embodiment, provided herein is a composition for use of modulating NFAT activity in a subject in need thereof, the composition comprising an agent that inhibits the function of a septin protein and/or the expression of a septin gene. In one embodiment, the septin is a septin 4. Other not limiting examples of septins include septin 2, 4, 5, 6, 7, and 9. In another embodiment, the composition further comprises an agent that inhibits the function of a UEV3 protein and/or the expression of a UEV3 gene.

In one embodiment, provided herein is a composition for use of modulating NFAT activity in a subject in need thereof, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use of modulating NFAT activity in a subject in need thereof, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use of modulating NFAT activity in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use of modulating NFAT activity in a subject in need thereof, the composition comprising an agent that inhibits the function of a UEV3 protein and/or the expression of a UEV3 gene.

In one embodiment, provided herein is a composition for use of modulating NFAT activity in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5. In one embodiment, the septins inhibited are septin 3, 4 and 5.

In one embodiment, provided herein is a composition for use of modulating NFAT activity in a subject in need thereof, the composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of a second septin gene. In one embodiment of the composition, the first septin is a septin 4 and the second septin is a septin 5.

In one embodiment, provided herein is a composition for use of modulating store-operated $Ca^{2+}$ entry into a cell, the composition comprising an agent that inhibits the function of a septin protein and/or the expression of a septin gene. In one embodiment, the septin is a septin 4. Other not limiting examples of septins include septin 2, 3, 4, 5, 6, 7, and 9. In another embodiment, the composition further comprises an agent that inhibits the function of a UEV3 protein and/or the expression of a UEV3 gene.

In one embodiment, provided herein is a composition for use of modulating store-operated $Ca^{2+}$ entry into a cell, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use of modulating store-operated $Ca^{2+}$ entry into a cell, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use of modulating store-operated $Ca^{2+}$ entry into a cell, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use of modulating store-operated $Ca^{2+}$ entry into a cell, the composition comprising an agent that inhibits the function of a septin 4 protein and/or the expression of a septin 4 gene, and an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use of modulating store-operated $Ca^{2+}$ entry into a cell, the composition comprising an agent that inhibits the function of a UEV3 protein and/or the expression of a UEV3 gene.

In one embodiment, provided herein is a composition for use of modulating store-operated $Ca^{2+}$ entry into a cell, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use of modulating store-operated $Ca^{2+}$ entry into a cell, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the composition, the first septin is a septin 4 and the second septin is a septin 5.

In one embodiment, provided herein is a composition for use treating and/or preventing hyperactivity or inappropriate immune response in a subject in need thereof, the composition comprising an agent that inhibits the function of a septin protein and/or the expression of a septin gene. In one embodiment, the septin is a septin 4. Other not limiting examples of septins include septin 2, 3, 4, 5, 6, 7, and 9. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a septin 4 protein and/or the expression of a septin 4 gene, and an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the composition, the first septin is a septin 4 and the second septin is a septin 5.

In one embodiment, provided herein is a composition for of modulating NFAT activity in a subject in need thereof, for use of modulating store-operated $Ca^{2+}$ entry into a cell or for use treating and/or preventing hyperactivity or inappropriate immune response in a subject in need thereof, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, the composition for use of modulating NFAT activity in a subject in need thereof, for use of modulating store-operated $Ca^{2+}$ entry into a cell, or for use treating and/or preventing hyperactivity or inappropriate immune response in a subject in need thereof, further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition described herein.

In one embodiment, provided herein is a method of modulating store-operated Ca2+ entry into a cell, the method comprising administering a therapeutically effective amount of a pharmaceutical composition described herein.

In one embodiment, provided herein is a method of treating and/or preventing hyperactivity or inappropriate immune response in a subject in need thereof, the method comprising administering a therapeutically effective amount of a pharmaceutical composition described herein.

In one embodiment, provided herein is a method of modulating NFAT activity in a subject in need thereof, the method comprising administering a therapeutically effective amount of a pharmaceutical composition comprising an agent that inhibits the function of a septin protein and/or the expression of a septin gene. In one embodiment, the septin is a septin 4. In other embodiments, the septins are septin 2, 3, 5, 6, 7, and 9. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent inhibits the function of at least two septin proteins and/or the expression of at least two septin genes. In one embodiment, the at least two septins are septin 4 and 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising a first agent that inhibits the function of a first septin protein and/or the expression of the first septin gene, and a second agent that inhibits the function of a second septin protein and/or the expression of the second septin gene. In one embodiment, the first septin is a septin 4 and the second septin is a septin 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent that inhibits the function of a septin 4 protein and/or the expression of a septin 4 gene. In one embodiment, the method further administering a therapeutically effective amount of a pharmaceutical composition comprising an agent that inhibits the function of a septin 5 protein and/or the expression of a septin 5 gene or the pharmaceutical composition further comprises an agent that inhibits the function of a septin 5 protein and/or the expression of a septin 5 gene. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of a second septin gene. In one embodiment of the method, the first septin is a septin 4 and the second septin is a septin 5.

In one embodiment, provided herein is a method of modulating store-operated $Ca^{2+}$ entry into a cell, the method comprising administering a therapeutically effective amount of a pharmaceutical composition comprising an agent that inhibits the function of a septin protein and/or the expression of a septin gene. In one embodiment, the septin is a septin 4. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating store-operated $Ca^{2+}$ entry into a cell, the method comprising administering a therapeutically effective amount of a pharmaceutical composition comprising an agent inhibits the function of at least two septin proteins and/or the expression of at least two septin genes. In one embodiment, the at least two septins are septin 4 and 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating store-operated $Ca^{2+}$ entry into a cell, the method comprising administering a therapeutically effective amount of a pharmaceutical composition comprising a first agent that inhibits the function of a first septin protein and/or the expression of the first septin gene, and a second agent that inhibits the function of a second septin protein and/or the expression of the second septin gene. In one embodiment, the first septin is a septin 4 and the second septin is a septin 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent that inhibits the function of a septin 4 protein and/or the expression of a septin 4 gene. In one embodiment, the method further administering a therapeutically effective amount of a pharmaceutical composition comprising an agent that inhibits the function of a septin 5 protein and/or the expression of a septin 5 gene or the pharmaceutical composition further comprises an agent that inhibits the function of a septin 5 protein and/or the expression of a septin 5 gene. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of the second septin gene. In one embodiment of the composition, the first septin is a septin 4 and the second septin is a septin 5.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a septin protein and/or the expression of a septin gene. In one embodiment, the septin is a septin 4. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent inhibits the function of at least two septin proteins and/or the expression of at least two septin genes. In one embodiment, the at least two septins are septin 4 and 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a septin 4 protein and/or the expression of a septin 4 gene. In one embodiment, the method further administering a therapeutically effective amount of a pharmaceutical composition comprising an agent that inhibits the function of a septin 5 protein and/or the expression of a septin 5 gene or the pharmaceutical composition further comprises an agent that inhibits the function of a septin 5 protein and/or the expression of a septin 5 gene. In another embodiment, the method further comprises administering a therapeutically effective amount of a pharmaceutical composition comprising an agent that inhibits the function of a UEV3 protein and/or the expression of a UEV3 gene or the pharmaceutical composition further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of a second septin gene. In one embodiment of the composition, the first septin is a septin 4 and the second septin is a septin 5.

In one embodiment, provided herein is a method of modulating NFAT activity in a subject in need thereof, of modulating store-operated $Ca^{2+}$ entry into a cell, or for treating and/or preventing hyperactivity or inappropriate immune response in a subject in need thereof, the method comprising administering a therapeutically effective amount of a pharmaceutical composition comprising an agent that inhibits the function of a septin 4 protein and/or the expression of a septin 4 gene, an agent that inhibits the function of a septin 5 protein and/or the expression of a septin 5 gene and a pharmaceutically acceptable carrier.

In one embodiment of the methods of modulating NFAT activity in a subject in need thereof, of modulating store-operated $Ca^{2+}$ entry into a cell, or for treating and/or preventing hyperactivity or inappropriate immune response in a subject in need thereof, the method further administering a therapeutically effective amount of an agent that inhibits the function of a UEV3 protein and/or the expression of a UEV3 gene.

In one embodiment of all aspects of the methods described, the modulation of NFAT activity comprises inhibiting NFAT translocation into the nucleus and decreasing the immune response in a subject.

In another embodiment of all aspects of the methods described, the modulation of NFAT activity comprises enhancing, promoting and/or increasing NFAT translocation into the nucleus and enhancing the immune response in a subject.

In one embodiment of all aspects of the methods described, the modulation of NFAT activity comprises decreasing the immune response in a subject in need thereof.

In another embodiment of all aspects of the methods described, the modulation of NFAT activity comprises enhancing the immune response in a subject in need thereof.

A decrease or enhancement of an immune response in a subject can be determined by any methods known in the art, e.g., measuring the titer of cytokines in circulation or assessment of symptoms of immune condition.

In one embodiment of all aspects of the methods described, the modulation of SOCE comprises decreasing or inhibiting $Ca^{2+}$ influx in a cell.

In another embodiment of all aspects of the methods described, the modulation of SOCE comprises increasing or promoting $Ca^{2+}$ influx in a cell.

In one embodiment, all decreasing, inhibiting, increasing, promoting or enhancing are scored by comparing with the condition in the absence of the agent described. For example, comparing $Ca^{2+}$ influx in a cell in the presence and in the absence of an agent that that inhibits the function of a septin 4 protein and/or the expression of a septin 4 gene.

In one aspect, the agent is a nucleic acid inhibitor. In some aspects, the nucleic acid is DNA, RNA, nucleic acid analogue, peptide nucleic acid (PNA), pseudo-complementary PNA (pcPNA), locked nucleic acid (LNA) or analogue thereof. In other aspects, the RNA is a small inhibitory RNA, siRNA, microRNA, shRNA, miRNA and analogues and homologues and variants thereof effective in gene silencing.

In one embodiment of all aspects of the compositions and methods described, the agent is a nucleic acid inhibitor which inhibits gene expression.

In one embodiment of all aspects of the compositions and methods described, the agent inhibits gene expression of at least two genes or the expression of two messenger transcripts, e.g., the expressions of SEPT 4 mRNA and SEPT 5 mRNA.

In one embodiment of all aspects of the compositions and methods described, the nucleic acid inhibitor is an siRNA or shRNA.

In one embodiment of all aspects of the compositions and methods described the siRNA or shRNA comprises the sequence of GGGUCAACAUCGUGCCUAU (SEQ ID NO: 19).

In one embodiment of all aspects of the methods described the hyperactivity or inappropriate immune response in a subject is associated with acute and chronic immune diseases selected from a group consisting of asthma, allergic rhinitis, allergic conjunctivitis, atopic dermatitis, rheumatoid arthritis, insulin-dependent diabetes, inflammatory bowel disease, autoimmune thyroiditis, hemolytic anemia, multiple sclerosis, transplant graft rejections and graft-versus-host disease.

BRIEF DESCRIPTION OF THE DRAWINGS

FIG. 8 shows another exemplary high-throughput screening (HTS) protocol in the form of a flow diagram.

FIG. 10 summarizes the steps for calculating Z scores.

FIG. 16 shows the summary of the identified genes/proteins categorized into groups.

FIG. 17 shows the summary of the secondary screening protocol of the hits from the primary HTS screen.

FIG. 19 shows the instrumentation used in the tertiary screen.

FIG. 25 shows the summary of Z scores obtained during the primary and secondary screen for a few select hits.

FIG. 73A shows the genes that encode validated structural molecules among the 486 identified primary screen hits. Venn diagram represents the intersection of strong and moderate screen hits with GO:0005198. Out of the 11 intersecting scaffold candidates, 4/11 deconvolute to ¼ positive siRNA (grey), and 7/11 deconvolute to >²⁄₄ siRNA (black) using the NFAT1-GFP translocation assay, measured after TG stimulation (1 μM) in HeLa cells expressing NFAT1-GFP.

FIG. 73B shows the absolute NFAT1-GFP translocation values, measured after TG stimulation (1 μM) of HeLa cells expressing NFAT1-GFP, after siRNA-mediated depletion of the 7 candidate scaffold hits using the strongest gene-specific siRNA.

FIG. 73C shows the $[Ca^{2+}]_i$ measurements for the 7 candidate scaffolds hits after gene depletion in HeLa cells expressing NFAT1-GFP. Time-lapse fura-2 fluorescence (5 sec intervals) was recorded from cell populations (>30,000 cells/well) before and after (time=20 s) stimulation with 1 μM TG in the presence of 10 mM $[Ca^{2+}]_o$.

FIG. 73D shows the quantification of integrated fura-2 fluorescence from FIG. 73C.

FIG. 73E shows the single-cell $[Ca^{2+}]_i$ measurements in siControl and siSEPT4/5-treated HeLa cells, exposed to 1 μM TG in the presence of 1 mM $[Ca^{2+}]_o$. Each grey trace represents a single cell; the black traces represent the averages of all cells examined.

FIG. 73F shows the reduced store-operated $Ca^{2+}$ influx in cells treated with siSTIM1, siSeptin 4#3 or siSeptin 4#4. Top, averaged measurements over >75 cells. Bottom, Peak $[Ca^{2+}]_i$ due to release from stores and $Ca^{2+}$ add-back, $[Ca^{2+}]_i$ levels at 900 sec, and initial rates of $[Ca^{2+}]_i$ (inset).

FIG. 74A shows histograms of mCherry-ORAI1 pixel intensity in resting cells treated with control siRNA (siControl, solid lines) or siSept4 (dotted line).

FIG. 74B shows the tracing of averaged kinetics of GFP-STIM1 translocation to the plasma membrane in siControl and siSEPT4/5-treated HeLa cells, as measured by TIRFM before and after TG stimulation. Note the visible delay in STIM1 membrane accumulation in siSEPT4/5-treated cells compared to siControl.

FIG. 74C shows histograms of the statistical analysis of GFP-STIM1 and mCherry-ORAI1 co-localization in siControl and siSEPT4/5-treated cells, at indicated time points (0, 6 and 10 min).

FIG. 75A shows a soluble STIM1 C-terminal fragment localizes to the plasma membrane in unstimulated ORAI1-expressing HeLa cells. Confocal images of HeLa cells transfected with GFP-ORAI1 and a soluble STIM1 C-terminal fragment (mCherry-STIM1-CT473, amino acid 233-473); single fluorescence channel images and overlay are indicated.

FIG. 75B shows the expression of mCherry-STIM1-CT473 rescues NFAT1-GFP nuclear localisation in unstimulated SEPT4/5-depleted HeLa cells. siControl or siSEPT4/5-treated HeLa cells expressing NFAT1-GFP were transfected with plasmids encoding mCherry or mCherry-STIM1-CT473. NFAT1-GFP nuclear localisation was measured in mCherry positive cells after incubation with 1 μM TG and 2.0 mM CaCl2 (black bars), 2.0 mM CaCl2 (grey bars), without or with pre-treatment with cyclosporine A (CsA) (white bars).

FIG. 75C shows the tracings of a single-cell $[Ca^{2+}]_i$ measurements in siSEPT4/5-treated HeLa cells, transfected with plasmids encoding mCherry or mCherry-STIM1 CT, and exposed to different concentrations of $[Ca^{2+}]_o$ before and after treatment with 1 μM TG. Each trace represents measurements averaged over >75 cells.

FIG. 76A shows the Z scores for total cell number are represented. The Venn diagram shows overlap between the viability genes and the NFAT regulators.

FIG. 76B shows the gene ontology analysis was performed for the strong viability hits (Z<−4).

FIG. 77A shows the percent of HeLa cells having nuclear NFAT1-GFP or p65. The HeLa cells were transfected with the indicated siRNAs for 72H, then analyzed for nuclear translocation by fluorescent imaging and automated analysis.

FIG. 77B shows the integrated $[Ca^{2+}]_i$ measurements in siControl, siSTIM1 and siSEPT4-treated HeLa cells expressing NFAT1-GFP, STIM1-mDSRed and FLAG-ORAI1. Time-lapse Fura-2 fluorescence (5 s intervals) was recorded from cell populations (>30,000 cells/well) before and after (time=20 s) stimulation with TG (1 μM) in the presence of 2.0 mM $[Ca^{2+}]_o$. Bottom panel shows quantification of fura-2 fluorescence.

FIG. 78A shows the percent of HeLa cells having nuclear NFAT1-GFP after transfected with indicated siRNAs for 72H. Each of the 4 siRNA duplexes in the original Smart-Pool was assayed individually using the NFAT1-GFP nuclear translocation assay.

FIG. 78B shows a schematic representation of Septin 4 and Septin 5 proteins, where the polybasic region (PBR), GTP binding (GTPase) and coiled coiled (CC) domains are indicated. Binding of siRNA duplexes to the corresponding nucleotide sequence is shown.

FIG. 78C shows histograms of mRNA expression of the group III septins as analyzed by qRT-PCR. Results (average of three independent experiments) are normalized to β-actin and depicted relative to siControl.

FIG. 78D shows histograms of mRNA expression of SEPT4 and SEPT5 as analyzed by qRT-PCR. Results (average of three independent experiments) are normalized to β-actin and depicted relative to siControl.

FIG. 78E shows the percent of HeLa cells having nuclear NFAT1-GFP after transfected with siRNAs to SEPT4 (oligo#3) and SEPT5 (oligo#4).

FIG. 79A shows the pipeline for quantification of STIM1-ORAI1 puncta formation and co-localization from confocal images of HeLa cells stably expressing GFP-STIM1 and mCherry-ORAI1 imported and analyzed using CellProfiler Cell Image Analysis Software.

FIG. 79B shows the Pearson's correlation for STIM1-ORAI1 co-localization plotted from timecourse of stimulation with 1 μM TG in the presence 3.0 mM EGTA (black) or 1.5 mM CaCl2 (grey).

DETAILED DESCRIPTION OF THE INVENTION

Figure 1:
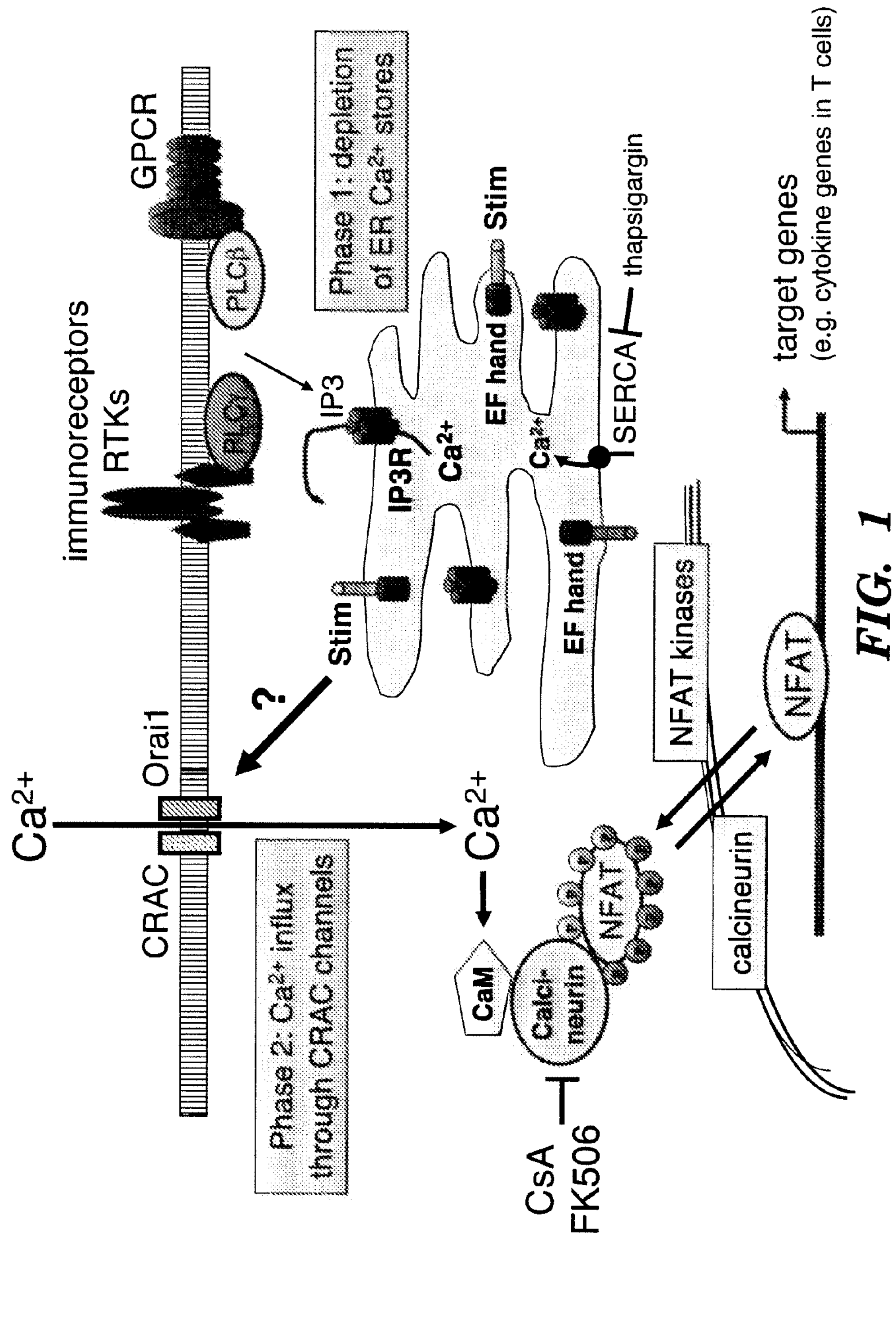
FIG. 1 shows schematic diagram of NFAT translocation and activation.
Figure 2:
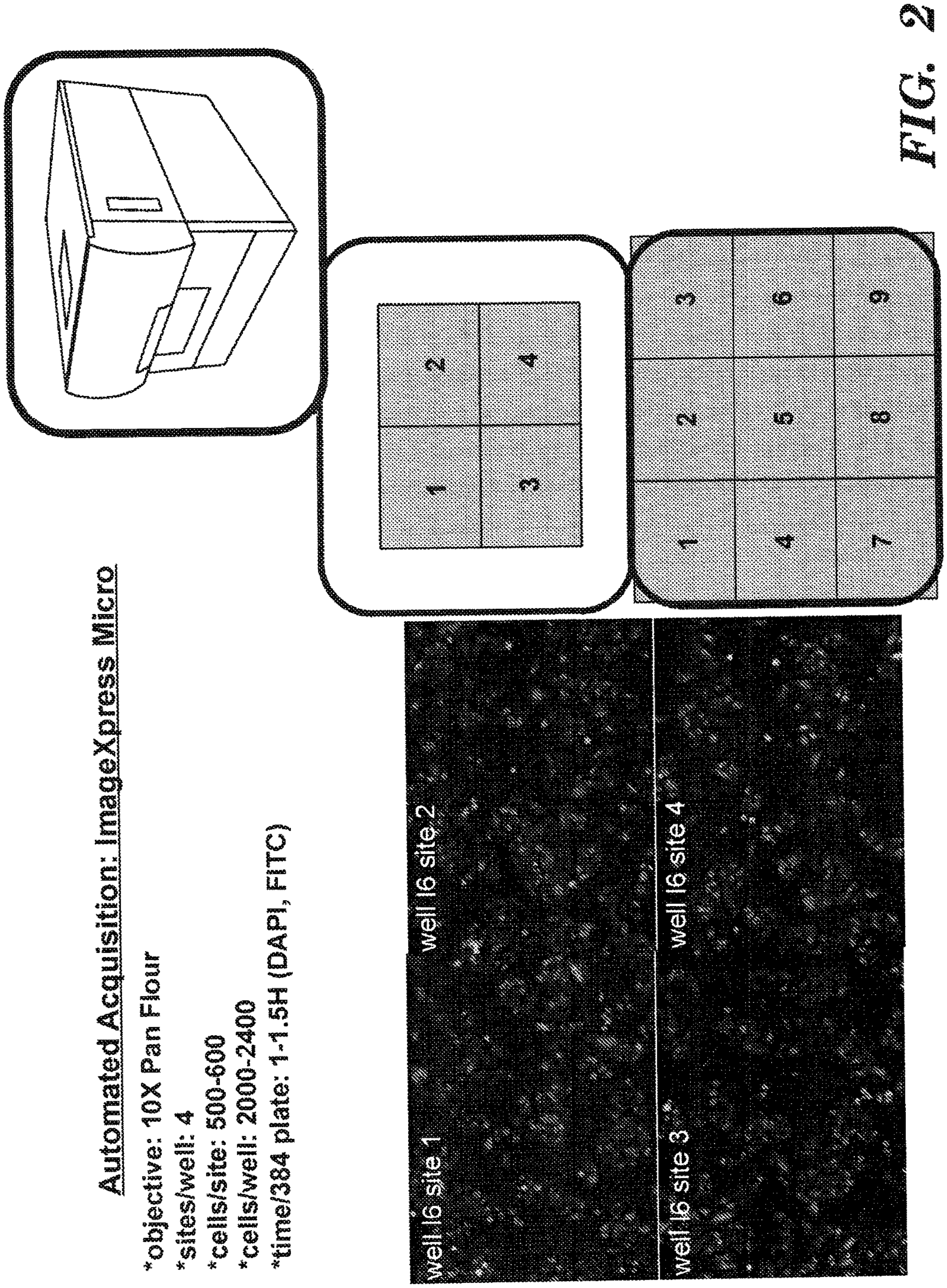
FIG. 2 shows the automated data acquisition by ImageXpress Micro.

Unless otherwise explained, all technical and scientific terms used herein have the same meaning as commonly understood by one of ordinary skill in the art to which this disclosure belongs. Definitions of common terms in immunology, and molecular biology can be found in The Merck Manual of Diagnosis and Therapy, 18th Edition, published by Merck Research Laboratories, 2006 (ISBN 0-911910-18-

2); Robert S. Porter et al. (eds.); The Encyclopedia of Molecular Biology, published by Blackwell Science Ltd., 1994 (ISBN 0-632-02182-9); Robert A. Meyers (ed.), Molecular Biology and Biotechnology: a Comprehensive Desk Reference, published by VCH Publishers, Inc., 1995 (ISBN 1-56081-569-8); and Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications cited throughout this application are expressly incorporated herein by reference for the purpose of describing and disclosing, for example, the methodologies described in such publications that can be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DEFINITIONS OF TERMS

The term "NFAT activation" refers to the nuclear translocation of NFAT from the cytoplasm to the nucleus. Nuclear factor of activated T-cells (NFAT) is a general name applied to a family of transcription factors shown to be important in immune response. Cytoplasmic NFAT proteins are phosphorylated. To enter the nucleus, NFAT has to be dephosphorylated. Activated serine/threonine phosphatase calcineurin rapidly dephosphorylates the serine rich region (SRR) and SP-repeats in the amino termini of NFAT proteins resulting in a conformational change that exposes a nuclear localization signal resulting in NFAT nuclear import. In one embodiment, the term "NFAT activity" means the nuclear translocation of NFAT from the cytoplasm to the nucleus.

As used herein, the term "pharmaceutical composition" refers to an active agent in combination with a pharmaceutically acceptable carrier of chemicals and compounds commonly used in the pharmaceutical industry. The term "pharmaceutically acceptable carriers" excludes tissue culture medium.

As used herein, the term "therapeutically effective amount" refers to that amount of active agent that reduces the function of a protein by at least 5% or the expression of a gene identified in Tables 1-5 by at least 5%, e.g., 5% reduction of the expression of Sept 4 and/or Sept 5 protein in the presence of the agent compared to in the absence of the agent. In one embodiment, the term means a reduction of at least 5% in NFAT-GFP nuclear localization and/or SOCE and/or cytokine production in the cell-based assay as described herein or other methods that are known to one skilled in the art. In another embodiment, the term means providing "effective" treatment as that term is defined herein. An effective amount as used herein would also include an amount sufficient to prevent or delay the development of a symptom of the disease, alter the course of a symptom disease (for example but not limited to, slow the progression of a symptom of the disease), or reverse a symptom of the disease.

The term "function" refers to any activity or cellular process a protein involved in. For example, septins are a family of GTP-binding proteins that play a role in cytokinesis. Thus, the function of septins may refer to their role in cytokinesis and an agent that inhibits the function of a septin protein could refer to an agent that inhibits cytokinesis. Septins are scaffold proteins that bind to, interact with, and recruit additional cellular factors and/or proteins. Therefore, the term "function" may also refer to the binding, the interaction or the recruitment of cellular factors and/or proteins. Thus, an agent that inhibits the function of a septin protein could refer to an agent that inhibits its binding to, interaction with, or recruitment of additional cellular factors and/or proteins. The term "function" may also refer to cellular processes including, but not limited to, transcription, translation, post-translational modifications (e.g., phosphorylation, methylation, acetylation, ubiquitination, or sumoylation), and cellular pathways (e.g., MAP kinase, WNT, Notch, or calcineurin/NFAT).

As used herein, the term "treat" or "treatment" refers to reducing or alleviating at least one adverse effect or symptom associated with medical conditions that are associated with hyperactive or inappropriately active immune system, a cell proliferation disease or disorder, a cardiovascular disorder, a nervous system disease or disorder, a bone disease, diabetes and an angiogenic disease or disorder. These include reducing the amount of cytokine production, suppression of T cell activation and proliferation, suppression of the immune system, and reducing inflammation.

As used herein, the terms "administering," and "introducing" are used interchangeably and refer to the placement of the agents that inhibit a gene identified in Tables 1-5 as disclosed herein into a subject by a method or route which results in at least partial localization of the agents at a desired site. The pharmaceutical compositions of the present invention can be administered by any appropriate route which results in an effective treatment in the subject.

The term "agent" refers to any entity which is normally not present or not present at the levels being administered, in the cell. Agents for use in the invention include, but are not limited to chemicals, small molecules, nucleic acid sequences, nucleic acid analogues, proteins, peptides, aptamers, and antibodies or fragments thereof. A nucleic acid sequence can be RNA or DNA, and can be single or double stranded, and can be selected from a group comprising nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins, therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of a gene identified in Tables 1-5 within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "inhibiting" as used herein as it pertains to the expression, activity or function of the protein or polypeptide of genes identified in Tables 1-5. The term does not necessarily mean complete inhibition of expression and/or activity. Rather, expression or activity of the protein, polypeptide or polynucleotide is inhibited to an extent, and/or for a time, sufficient to produce the desired effect, for example, reduced nuclear translocation of NFAT. In particular, inhibition of expression or function of a gene from Tables 1-5 can be determined using an assay such as the bioassay for the protein encoded by the gene, for example, western blot analysis for the detection and quantification of expressed protein. Agents that inhibit the genes of Tables 1-5 are agents that inhibit the protein function and/or genes expression by at least 5%.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e., although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the invention, are used interchangeably herein.

As used herein an "siRNA" refers to a nucleic acid that forms a double stranded RNA which has the ability to reduce or inhibit expression of a gene or target gene when the siRNA is present or expressed in the same cell as the target gene, for example SEPT 4 and SEPT 5. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g., about 19 to about 25 nucleotide comprising an antisense strand, followed by a nucleotide loop of about 5 to about 9 nucleotides, and an analogous sense strand. Alternatively, the sense strand can precede the nucleotide loop structure and the antisense strand can follow.

The terms "microRNA" or "miRNA" are used interchangeably herein and they refer to endogenous RNAs, some of which are known to regulate the expression of protein-coding genes at the posttranscriptional level. Endogenous microRNAs are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al., Science 299, 1540

(2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference in their entirety. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. The two strands are held together by complementary base pairing. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "complementary base pair" refers to A:T and G:C in DNA and A:U and G:C in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

As used herein, the term "nucleic acid sequence" or "nucleic acid" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid is a DNA. In another aspect, the nucleic acid is an RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it can be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-β-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292, and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

The term "vector", as used herein, refers to a nucleic acid construct designed for delivery to a host cell or transfer between different host cells. As used herein, a vector can be viral or non-viral.

As used herein, the term "expression vector" refers to a vector that has the ability to incorporate and express heterologous nucleic acid fragments in a cell. An expression vector can comprise additional elements, for example, the expression vector can have two replication systems, thus allowing it to be maintained in two organisms, for example in human cells for expression and in a prokaryotic host for cloning and amplification.

As used herein, the term "heterologous nucleic acid fragments" refers to nucleic acid sequences that are not naturally occurring in that cell. For example, when a human SEPT 4 gene is inserted into the genome of a bacteria or virus, that human SEPT 4 gene is heterologous to that recipient bacteria or virus because the bacteria and viral genome do not naturally have the human SEPT 4 gene.

As used herein, the term "viral vector" refers to a nucleic acid vector construct that includes at least one element of viral origin and has the capacity to be packaged into a viral vector particle. The viral vector can contain the shRNA for the human SEPT 4 in place of non-essential viral genes. The vector and/or particle can be utilized for the purpose of transferring any nucleic acids into cells either in vitro or in vivo. Numerous forms of viral vectors are known in the art.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins from packaging the virus) and viral particles cannot be formed in the patient's cells.

The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments. In one embodiment, the term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. In another embodiment, the gene can be an mRNA or cDNA corresponding to the coding regions (e.g., exons and miRNA) optionally comprising 5'- or 3' untranslated sequences linked thereto. In another embodiment, the gene can be an amplified nucleic acid molecule produced in vitro comprising all or a part of the coding region and/or 5'- or 3'-untranslated sequences linked thereto.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human.

As used herein, the term "comprising" means that other elements can also be present in addition to the defined elements presented. The use of "comprising" indicates inclusion rather than limitation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

As used herein, the term "modulate" means the regulation of the cellular function of a protein. In one embodiment, modulation means up regulation of the cellular function of the protein, whereby its function is enhances, increased and/or promoted. In another embodiment, modulation means up regulation or increase in the expression of the gene of interest. In one embodiment, modulation can mean down regulation of the cellular function of the protein, whereby its function is reduced, decreased, blocked, and/or prevented. In another embodiment, modulation means down regulation or decrease in the expression of the gene of interest. In some embodiments, the up regulation or down regulation is at least 5% deviation from the protein activity or expression level in the absence of the agent that modulates the protein function or expression level respectively.

As used herein, the term "a neoplastic cell proliferation disorder" refers to any disorder that is characterized by deregulated or unregulated cell proliferation that arises from a stem cell. A normal stem cell may be transformed into a cancer stem cell through disregulation of the proliferation and differentiation pathways controlling it. Examples include but are not limited to cancer and tumors formation.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant (i.e., non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "therapy resistant cancer" as used herein refers to a cancer present in a subject who is resistant to, or refractory to at least two different anti-cancer agents such as chemotherapy agents, which means, typically a subject has been treated with at least two different anti-cancer agents that did not provide effective treatment as that term is defined herein.

NFAT Activation

The calcium/calcineurin-dependent NFAT family is thought to have arisen following the recombination of an ancient precursor with a Rel domain about 500 million years ago, producing a new group of signaling and transcription factors (the NFAT genes) found only in the genomes of vertebrates. The family of NFAT transcription factor consists of five members NFAT1, NFAT2, NFAT3, NFAT4 and NFAT5. The NFAT proteins are activated by an increase in intracellular calcium levels, e.g., by means of store-operated calcium entry (SOCE) into a cell.

Calcium signaling is critical to NFAT activation because calmodulin, a well known calcium sensor protein, activates the serine/threonine phosphatase calcineurin. Activated calcineurin rapidly dephosphorylates the serine rich region (SRR) and SP-repeats in the amino termini of NFAT proteins resulting in a conformational change that exposes a nuclear localization signal resulting in NFAT nuclear import. The activated NFAT proteins, in turn, induce transcription of cytokine genes which are required for an immune response (see FIG. 1).

Nuclear import of NFAT proteins is opposed by maintenance kinases in the cytoplasm and export kinases in the nucleus. Export kinases, such as PKA and GSK-3β, must be inactivated for NFAT nuclear retention. NFAT proteins have weak DNA binding capacity. Therefore, to effectively bind DNA NFAT proteins must cooperate with other nuclear resident transcription factors. This important feature of NFAT transcription factors enables integration and coincidence detection of calcium signals with other signaling pathways such as ras-MAPK or PKC. In fact, cell biological, genetic and biochemical evidence indicates that the circuitry of this pathway is well suited for intercalation with older pathways, such as MAP kinase, WNT and NOTCH. This recombination enabled Ca2+ signals to be redirected to a new transcriptional program, which provides part of the groundwork for vertebrate morphogenesis and organogenesis. Indeed, the calcineurin/NFAT axis is involved in numerous aspects of vertebrate morphogenesis: cell cycle regulation, cell differentiation, cell survival, angiogenesis, tumor cell invasion and metastasis, myogenesis, chondrocytes differentiation and the development of the cardiovascular system, the complex nervous system and the recombinational immune system. Consequently, deregulation of calcineurin/NFAT signaling and/or abnormal expression of its components have been associated with cell proliferation diseases such as cancer, autoimmune diseases, cardiovascular diseases, diabetes, and bone diseases to name a few. Discovery of modulators of Ca2+ influxes and/or the calcineurin/NFAT axis can provide alternative therapeutic avenues for these diseases that are related to T-activation.

Screens for NFAT Modulators

Embodiments of the invention are based on the discovery of several hundred genes in the human and mouse genomes whose gene products directly and/or indirectly modulate NFAT activation and/or modulate the store-operated $Ca^{2+}$ entry (SOCE) into the cell. The inventors developed a cell-based reporter system for screening for modulators of nuclear factors of activated T cells (NFAT) and/or store-operated $Ca^{2+}$ entry into a cell. The cell-based reporter system comprises a mammalian cell co-expressing a NFAT-GFP, a STIM1-RFP, and an Orai1-FLAG. The markers: GFP, RFP and FLAG-tag facilitate the visual localization of the respectively expressed proteins within the cell compartments. For example, whether NFAT is localized to the cytoplasm under non-$Ca^{2+}$ depletion conditions (in the absence of thapsigargin (TG)) or has translocated to the nucleus upon treatment with TG, and whether STIM1/Orai1 are expressed and properly localized to the membranes. TG is a tight-binding inhibitor of a class of enzymes known by the acronym SERCA, which stands for sarco/endoplasrnic reticulum $Ca^{2+}$ ATPase. TG raises cytosolic calcium concentration by blocking the ability of the cell to pump calcium into the sarcoplasmic and endoplasmic reticula which causes these stores to become depleted. Store-depletion can secondarily activate plasma membrane calcium channels, triggering store-operated $Ca^{2+}$ entry into a cell via plasma membrane channels. It was found that the co-expression of STIM1-RFP, and Orai1-FLAG in HeLa cells enhanced SOCE in these cells upon TG treatment. The inventors used the cytoplasm-to-nuclear translocation of NFAT-GFP as their assay readout, counting the number of cells that have nuclear GFP fluorescence after TG treatment. For a population of these cells treated with TG, a mean number of cells will have NFAT-GFP nuclear localization after TG treatment for a fixed period of time, e.g., 10 minutes. This is the control population for the high-throughput screen. Within this population data, a standard deviation is also obtained. The data (number of cells having NFAT-GFP nuclear localization after TG treatment) is assumed to have a normal distribution. This data of this control population of cells are normalized to a standard normal distribution, which has a mean of 0 (the mean number of cell with nuclear NFAT-GAT) and standard deviation of 1.

To screen for modulators of NFAT and/or store-operated $Ca^{2+}$ entry into a cell, the inventors performed a high-throughput siRNA screen of 23-mer siRNAs that target all human or mouse genes. For each gene, at least four different siRNAs were used. In such a cell-based assay, the inventors seek to discover genes that can modulate the cytoplasm-to-nuclear translocation of NFAT-GFP and/or store-operated $Ca^{2+}$ entry into a cell. The siRNAs to such a gene result in either a decrease or an increase in the nuclear GFP fluorescence after TG treatment. The decrease or increase is at least two fold of the standard deviation for the control population of cells treated with TG but conducted in the absence of any siRNA, i.e. at least an average Z score of −2.0 or +2.0. The number of standard deviations from the mean is called the Z-score and can be found by the formula:

$$z = \frac{x-\mu}{\sigma}$$

where x is the mean number of cells having NFAT-GFP localization for the population of cells treated with siRNA, μ is mean number of cells having NFAT-GFP localization for the control population, and σ is the standard deviation for the control population of cells. The control population of cells is assayed in parallel with the siRNAs.

From this screen, the inventors uncovered ~500 genes that strongly modulate NFAT and/or store-operated $Ca^{2+}$ entry into a cell, having an average Z-score of ≥141 and ~650 genes that moderately/weakly at modulate NFAT and/or store-operated $Ca^{2+}$ entry into a cell, having an average z-score of $-4<Z<-2$ or $2<Z<4$. The designation 141 refers to the mathematical symbol for four absolute.

The screen identified known modulator of NFAT: calcineurin (CanB1 and CanAα) which are involved in the dephosphorylating NFAT which is necessary for nuclear translocation; known store-operated $Ca^{2+}$ entry sensor proteins: Stim1 and Orai1; and KCNN4 (IKCa1, potassium intermediate/small conductance calcium-activated channel, subfamily N, member 4). Calcineurin (CN) is a protein phosphatase also known as protein phosphatase 2B (PP2B). Protein phosphatase 3 (formerly 2B), catalytic subunit, alpha isoform, also known as PPP3CA. The identification of known modulators of NFAT activity or store-operated $Ca^{2+}$ entry validates the accuracy and utility of the cell-based assay used by the inventors.

In addition to calcineurin, the siRNA screen identified KCNN4 (IKCa1, potassium intermediate/small conductance calcium-activated channel, subfamily N, member 4) that is known to be indirectly involved in NFAT nuclear localization via SOCE. Several reports have demonstrated that Kv1.3 and IKCa1 $K^+$ channels play crucial roles in T-cell activation, inflammation, progression of autoimmune diseases, and of other immunological disorders (Cahalan et al., 2001, Clin Immunol 21:235-252; Wulff et al., 2003, Curr. Opin. Drug Discov. Devel. 6:640-647; Chandy et al., 2004, Trends Pharmacolog Sci 25:280-289; Vicente et al., 2004, FEBS Lett 572:189-194). The use of Kv1.3 and IKCa1 K+ channel-blockers have been shown to ameliorate several types of disorders.

The high-throughput siRNA screen also identified several nuclear transport proteins: RAN (ras-related nuclear protein), RANBP2 (RAN binding protein 2), KPNB1 (karyopherin (importin) beta 1), CSE1L (chromosome segregation 1-like), and CRM1 (exportin 1, XPO1).

The entry and exit of large molecules from the cell nucleus is tightly controlled by the nuclear pore complexes (NPCs). Although small molecules can enter the nucleus without regulation, macromolecules such as RNA and proteins require association with karyopherins called importins to enter the nucleus and exportins to exit. The ability of both importins (KPNB1 and CSE1L) and exportins (CRM1) to transport their cargo is regulated by the small Ras related GTPase, RAN.

In some embodiments, the identified genes are SEQ. ID. NOS:1-11 (Genbank Accession No. NM_000944; NM_021132.1; NM_006325; NM_006267.4; NM_002265.4, NM_001316; NM_003400.3; NM_003156.2, NM_020860.2, NM_032790.3, NM_002250.2).

Other examples of modulate genes identified in the cell-base assay as described herein include those that are involved in (1) Golgi-to-plasma membrane trafficking, (2) associated with mitochondria, (3) scaffold proteins (with PDZ domains, etc), (4) ubiquitin metabolism, (5) noncoding RNAs (possibility containing microRNAs), (6) RNA-binding proteins, and (7) potassium channels: KCNN4 (see Tables 1-5).

Figure 35:
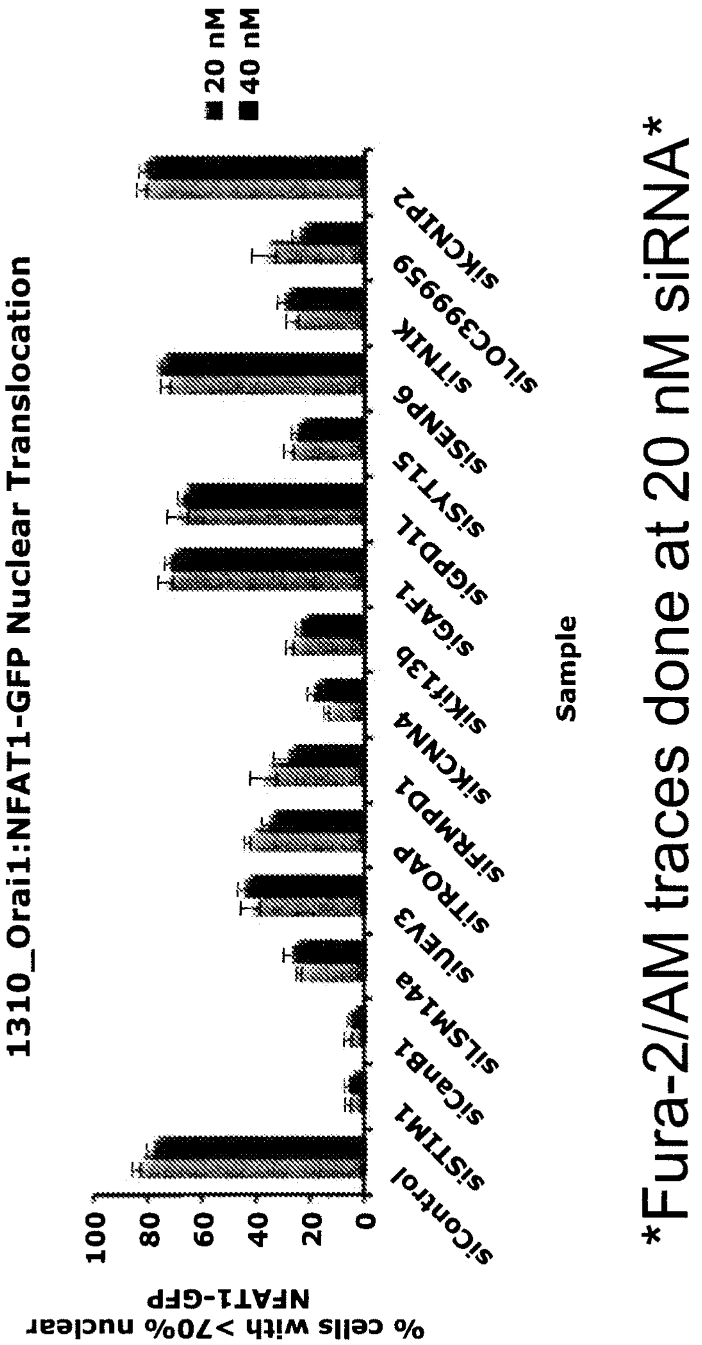
FIG. 35 shows genes that enhances NFAT-GFP nuclear localization.
Figure 36:
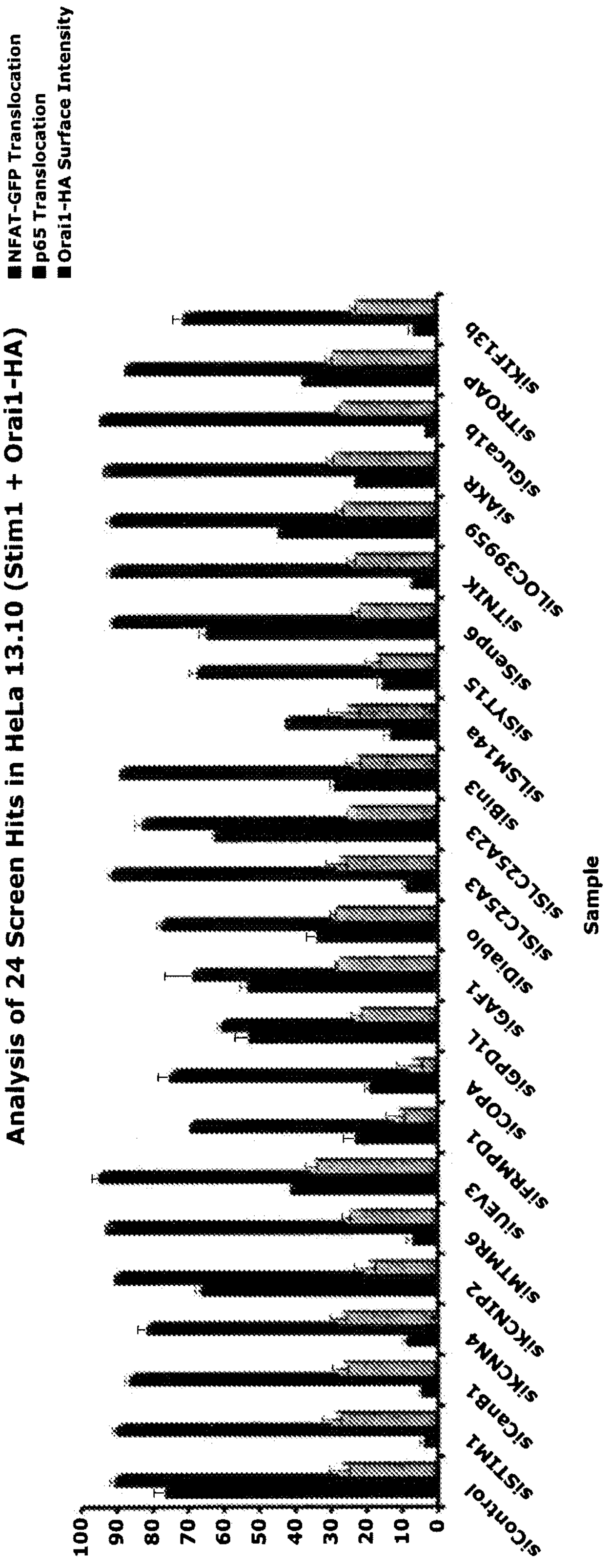
FIG. 36 is a summary of genes that affects NFAT-GFP nuclear localization, p65 translocation and Orai 1 cell surface localization.
Figure 37:
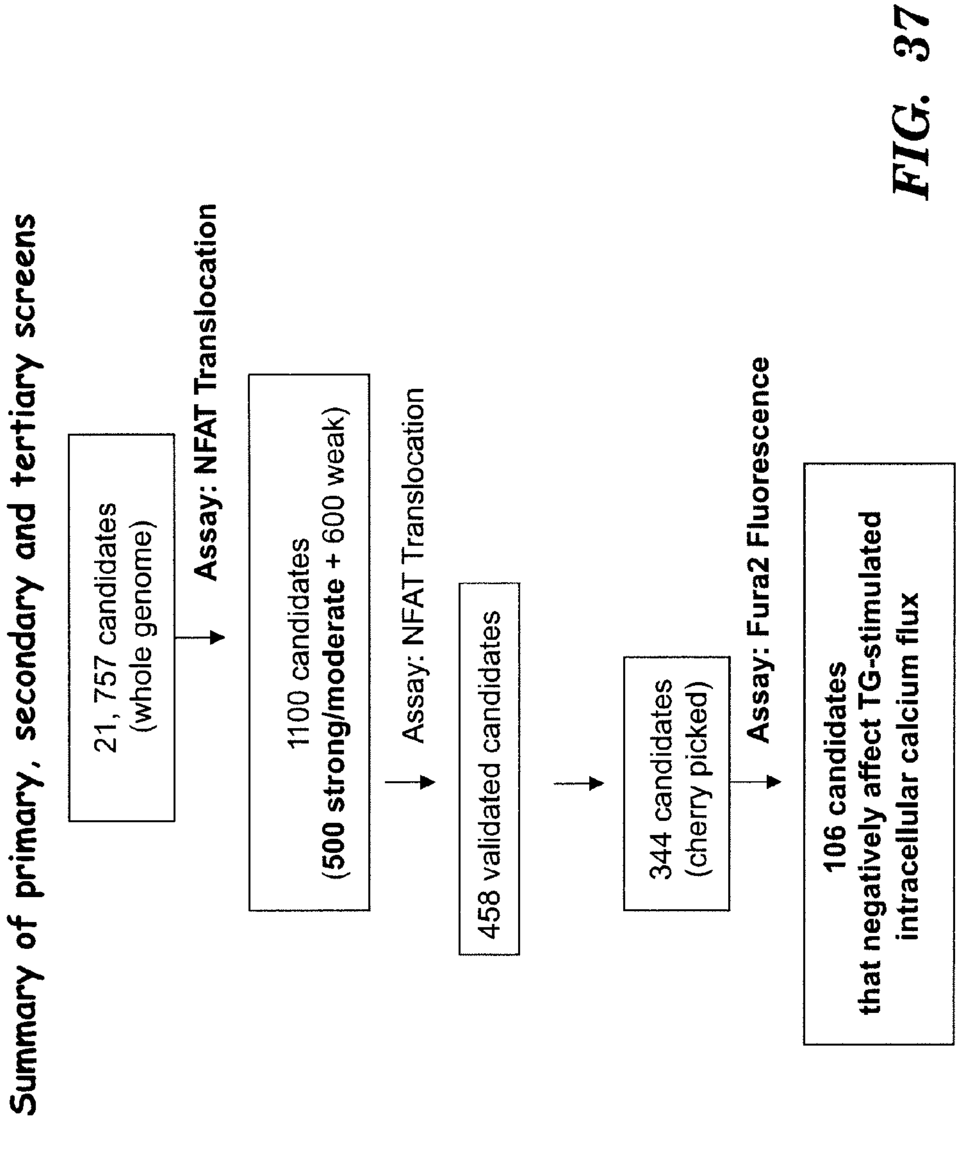
FIG. 37 shows the summary of primary, secondary and tertiary screens.
Figure 38:
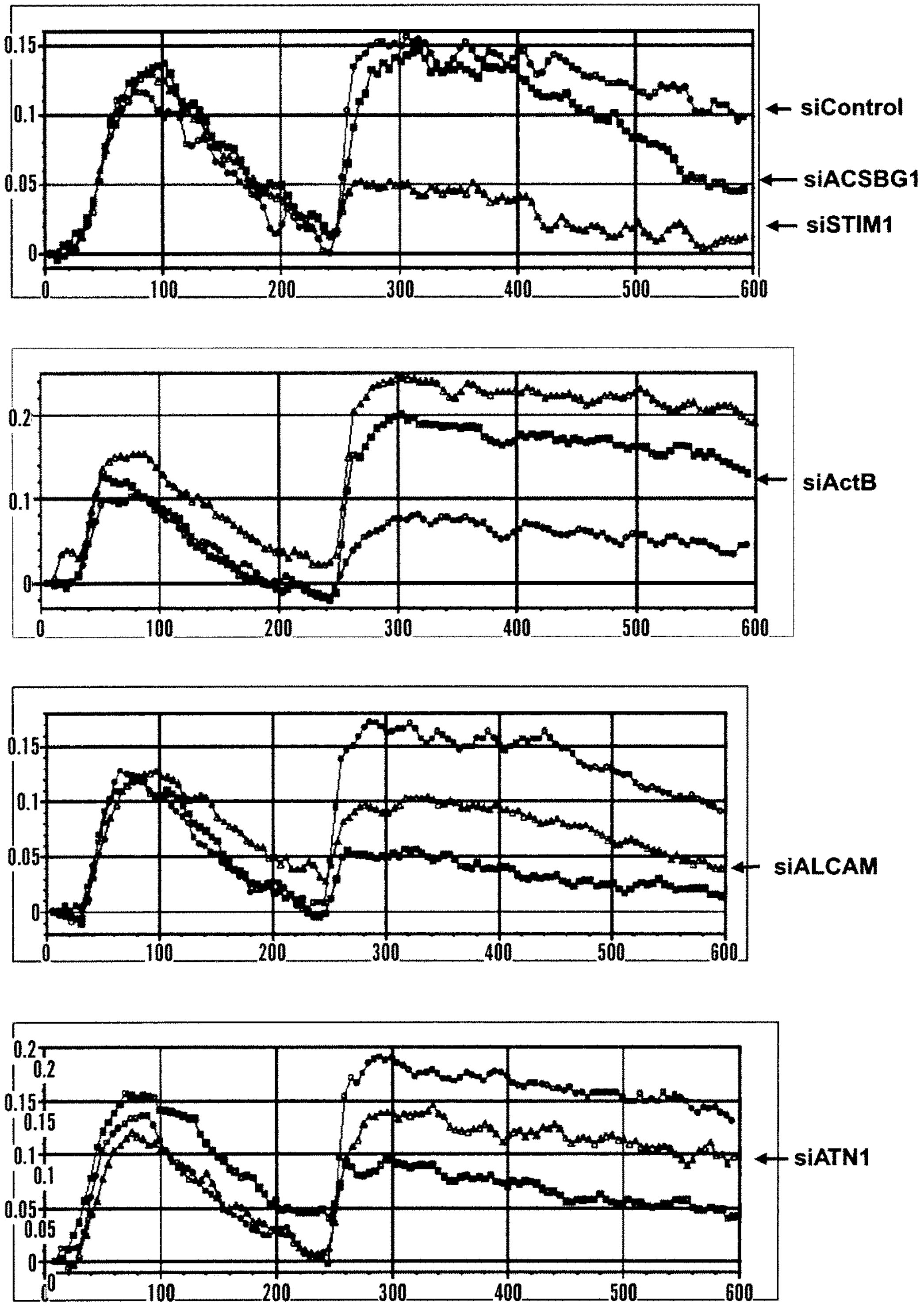
FIG. 38 shows the traces of calcium fluxes in cells treated with siRNA to the respective genes: ACSBG1, ActB, ALCAM and ATN1.
Figure 39:
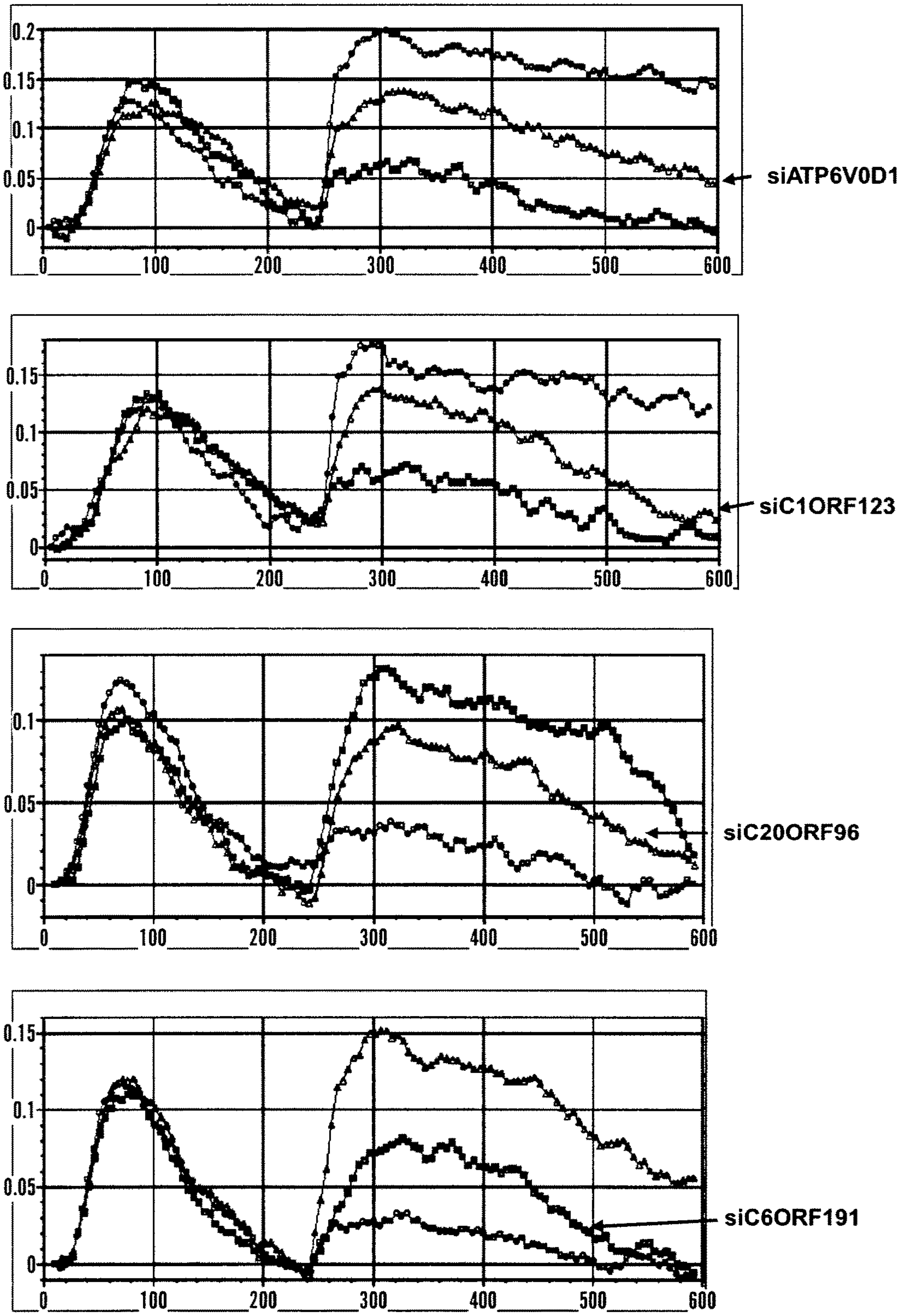
FIG. 39 shows the traces of calcium fluxes in cells treated with siRNA to the respective genes: ATP6V0D1, C1ORF123, C20ORF96 and C6ORF191.
Figure 40:
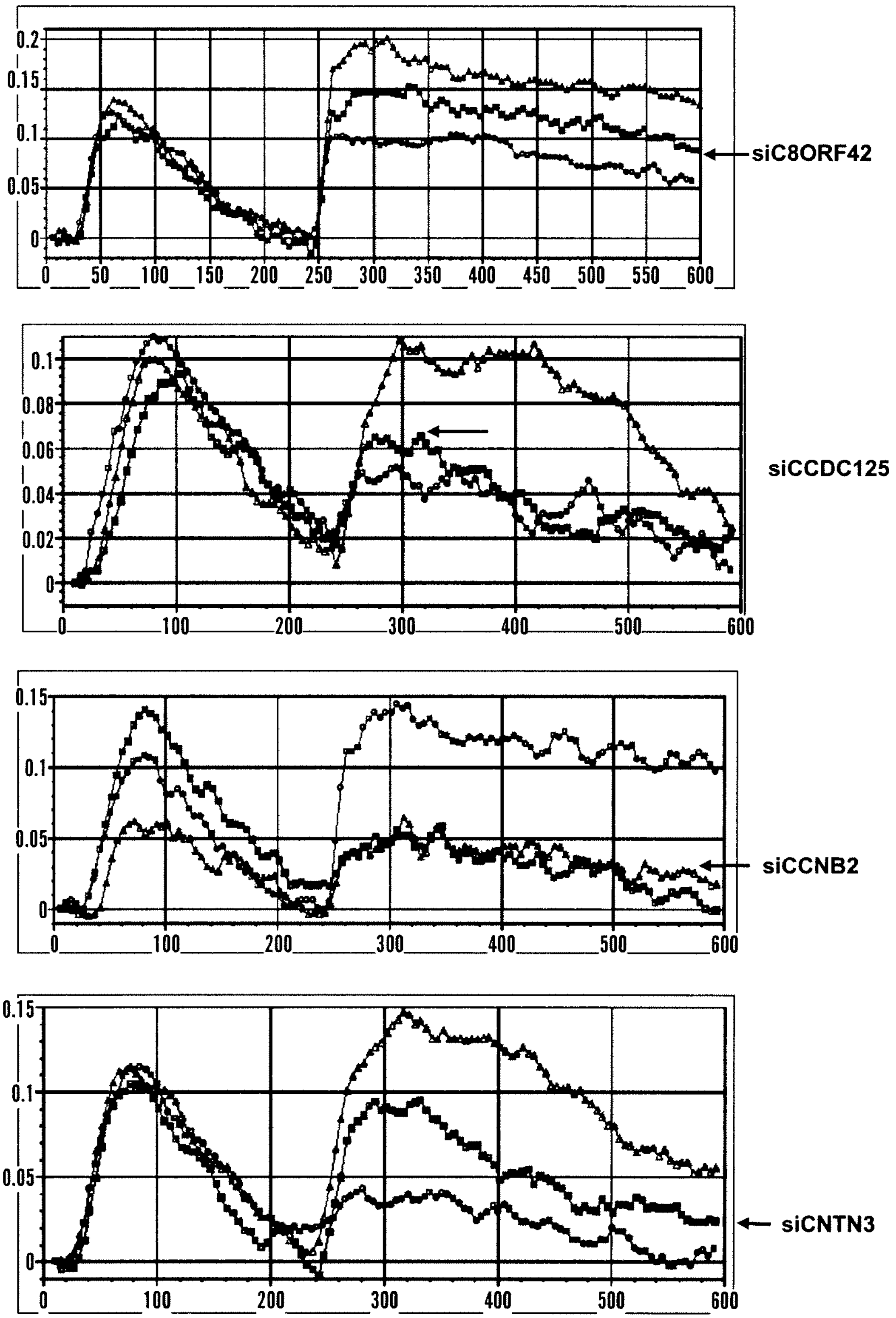
FIG. 40 shows the traces of calcium fluxes in cells treated with siRNA to the respective genes: C8ORF42, CCDC125, CCNB2 and CNTN3.
Figure 41:
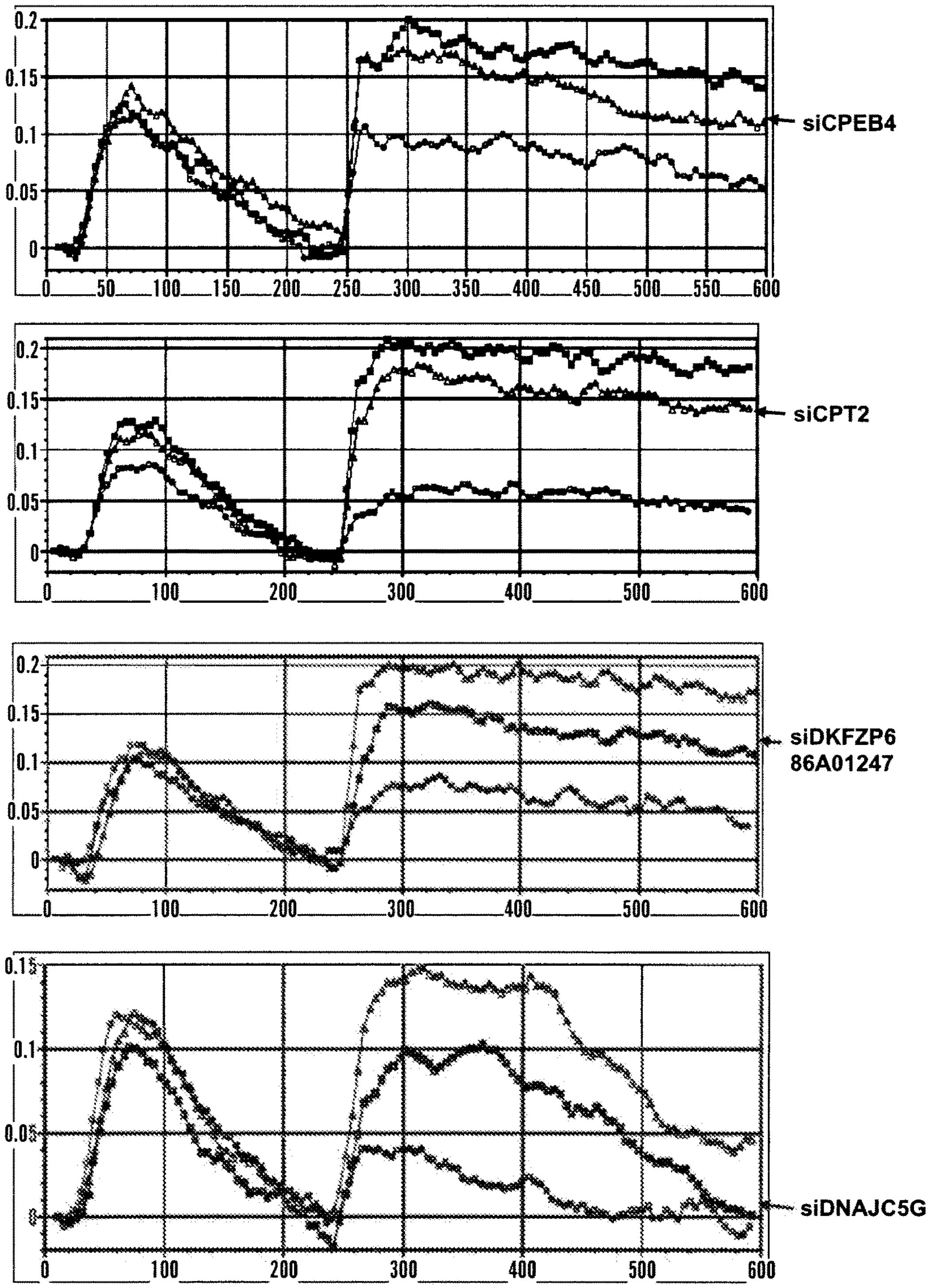
FIG. 41 show the traces of calcium fluxes in cells treated with siRNA to the respective genes: CPEB4, CPT2, DKFZP686A01247 and DNAJC5G.
Figure 42:
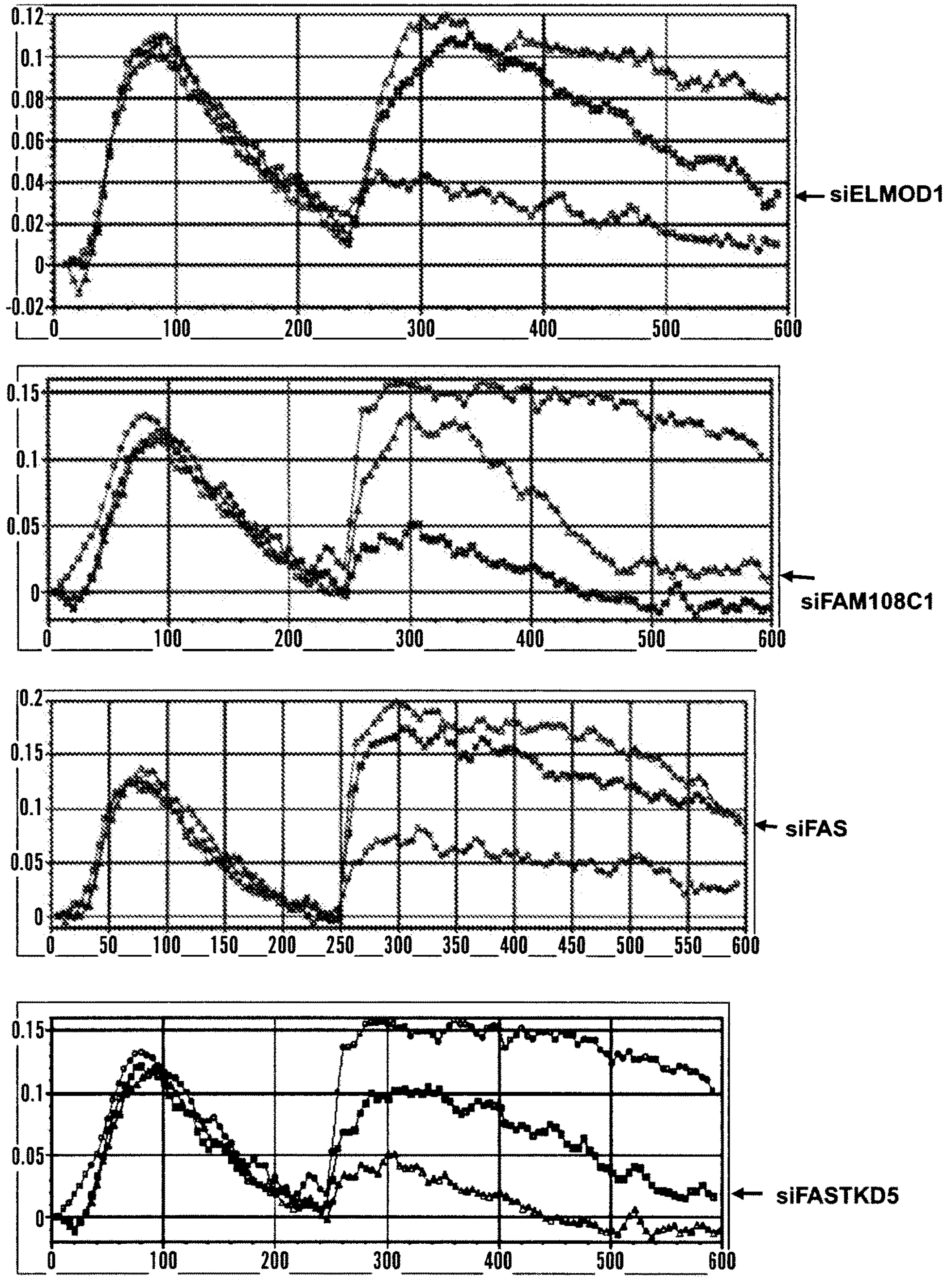
FIG. 42 shows the traces of calcium fluxes in cells treated with siRNA to the respective genes: ELMOD1, FAM108C1, FAS and FASTKD5.
Figure 43:
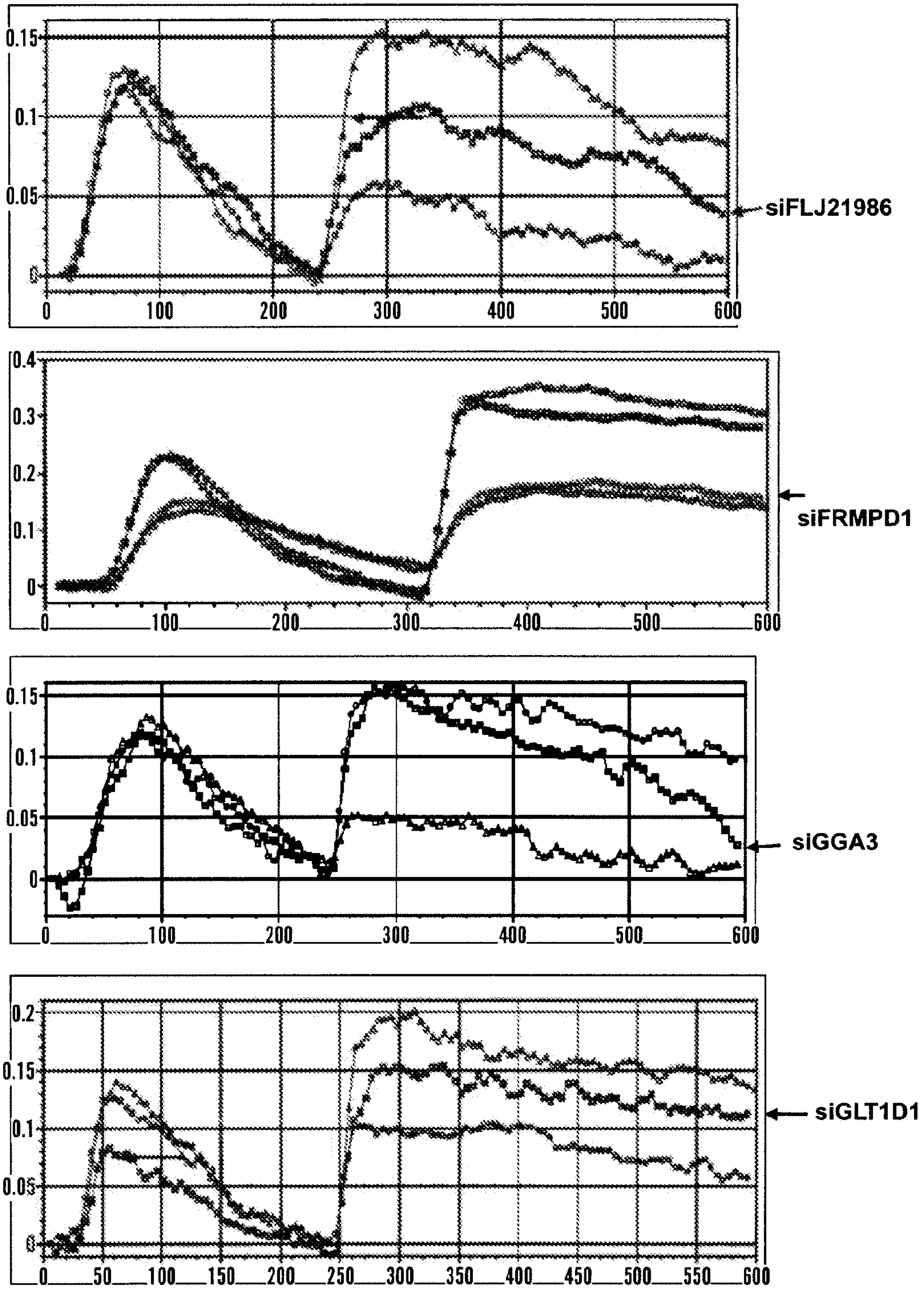
FIG. 43 shows the traces of calcium fluxes in cells treated with siRNA to the respective genes: FLJ21986, FRMPD1, GGA3 and GLTID1.
Figure 44:
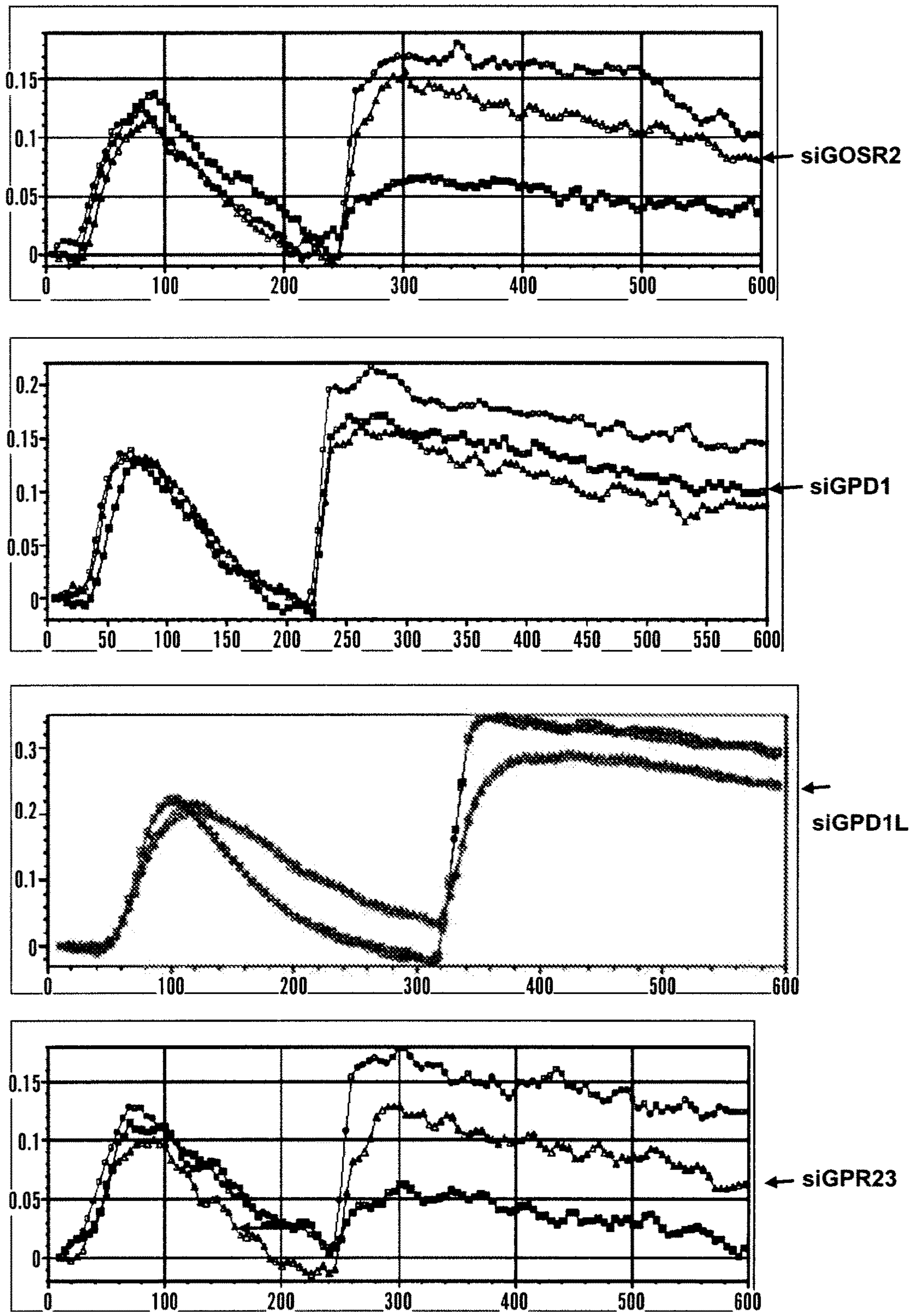
FIG. 44 shows the traces of calcium fluxes in cells treated with siRNA to the respective genes: GOSR2, GPD1, GPD1L and GPR23.
Figure 45:
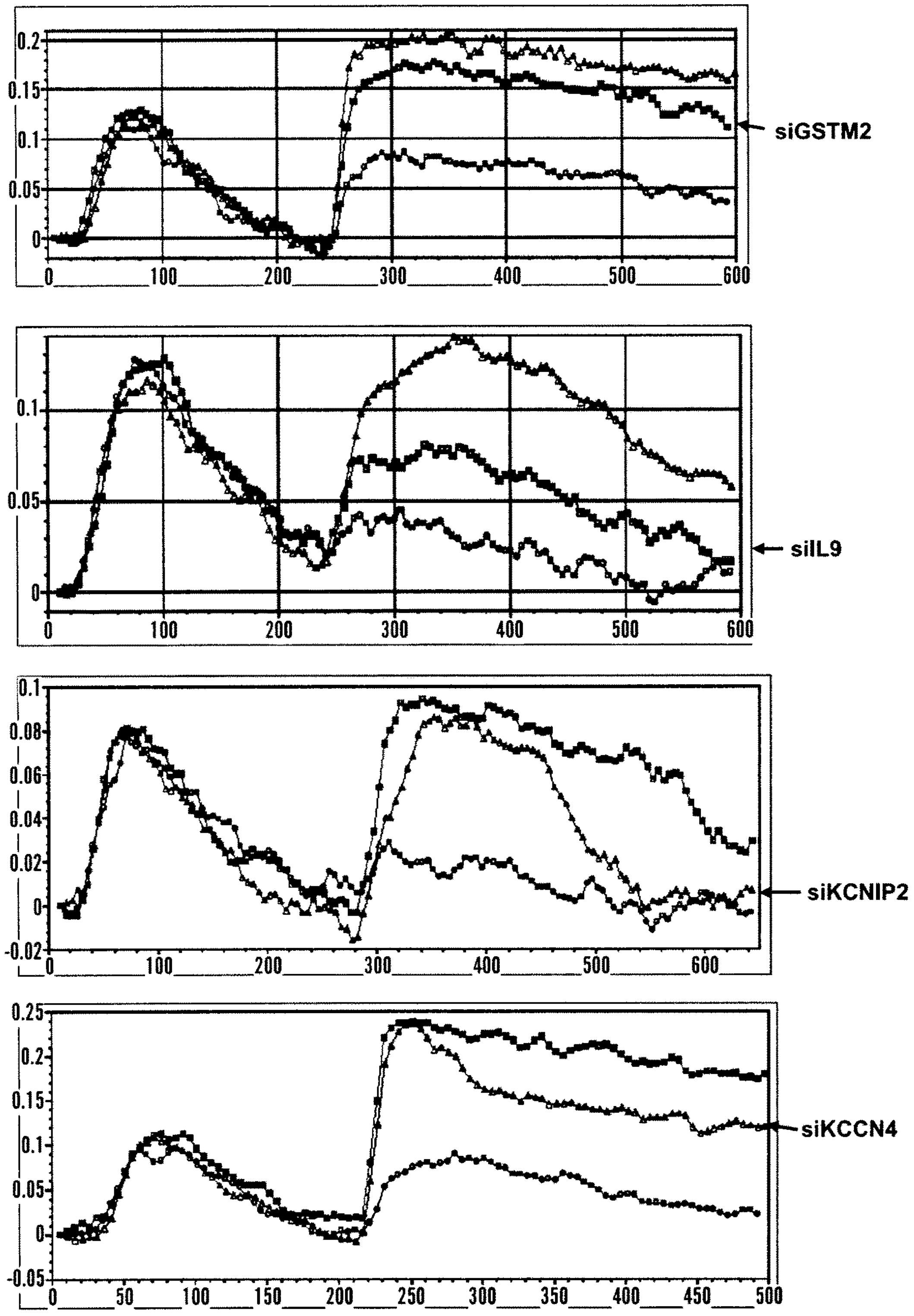
FIG. 45 shows the traces of calcium fluxes in cells treated with siRNA to the respective genes: GSTM2, IL9, KCNIP2 and KCCN4.
Figure 46:
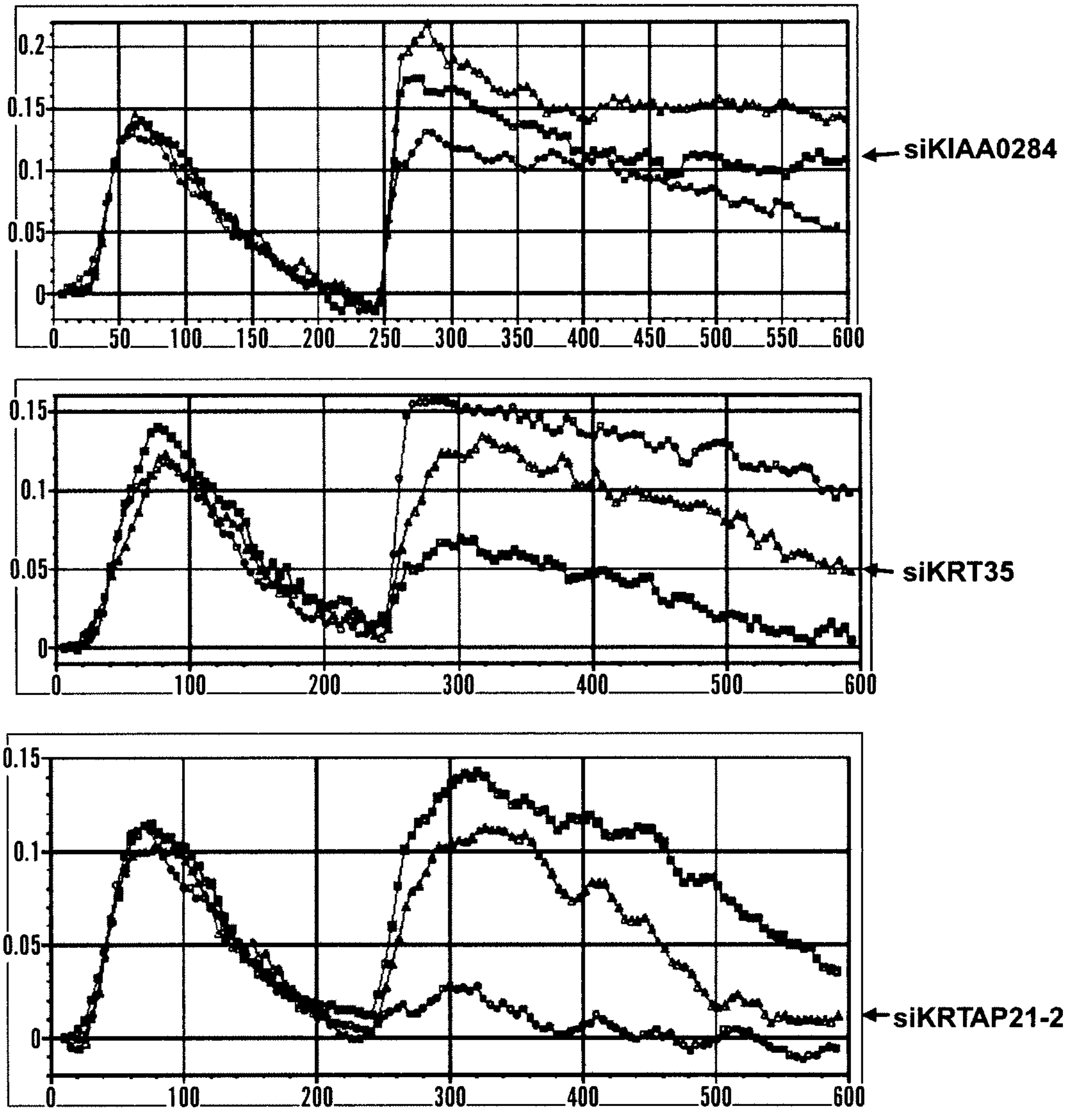
FIG. 46 shows the traces of calcium fluxes in cells treated with siRNA to the respective genes: KIAA0284, KRT35 and KRTAP21-2.
Figure 47:
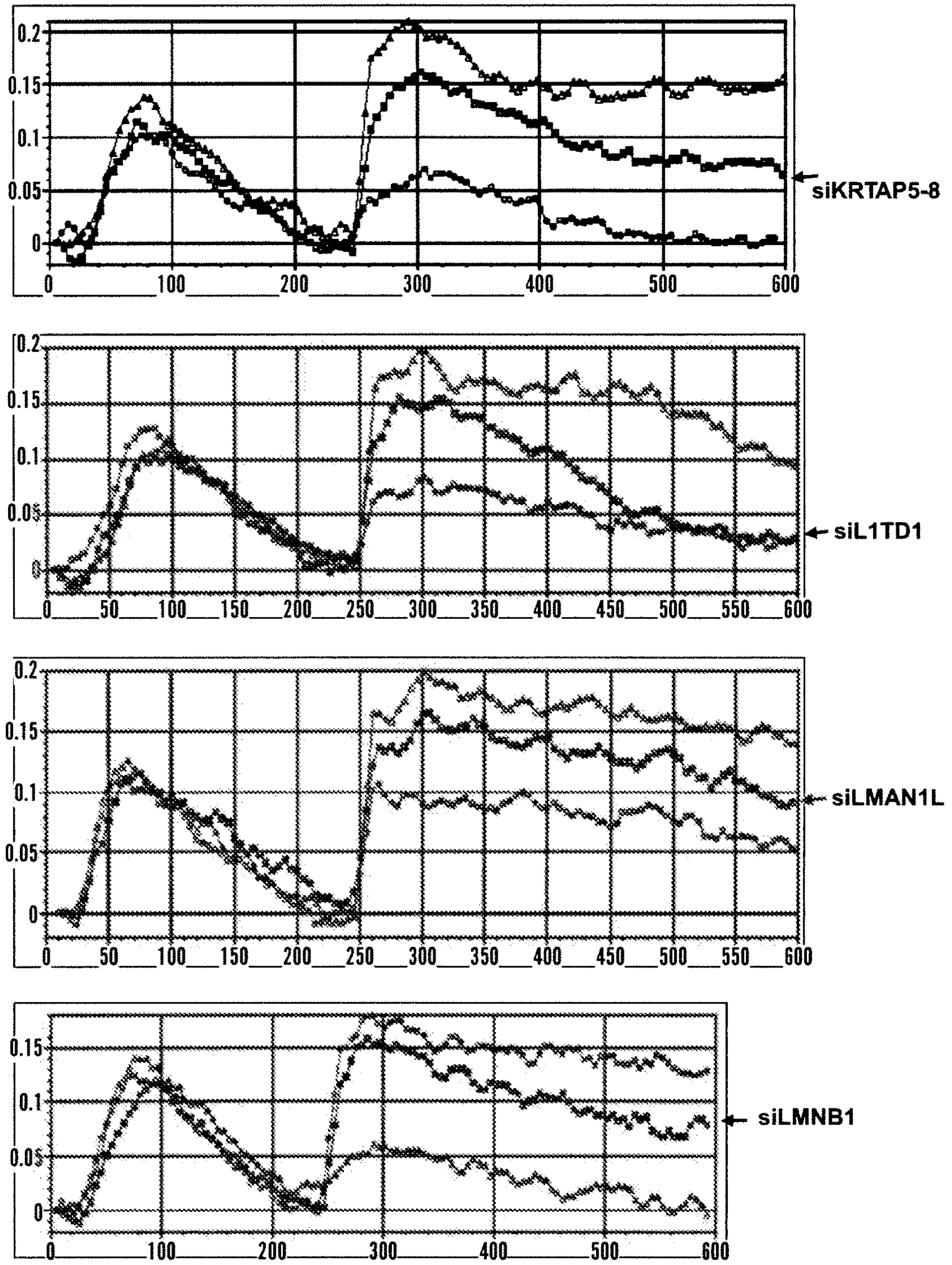
FIG. 47 shows the traces of calcium fluxes in cells treated with siRNA to the respective genes: KPTAP5-8, L1TD1, LMAN1L and LMNB1.
Figure 48:
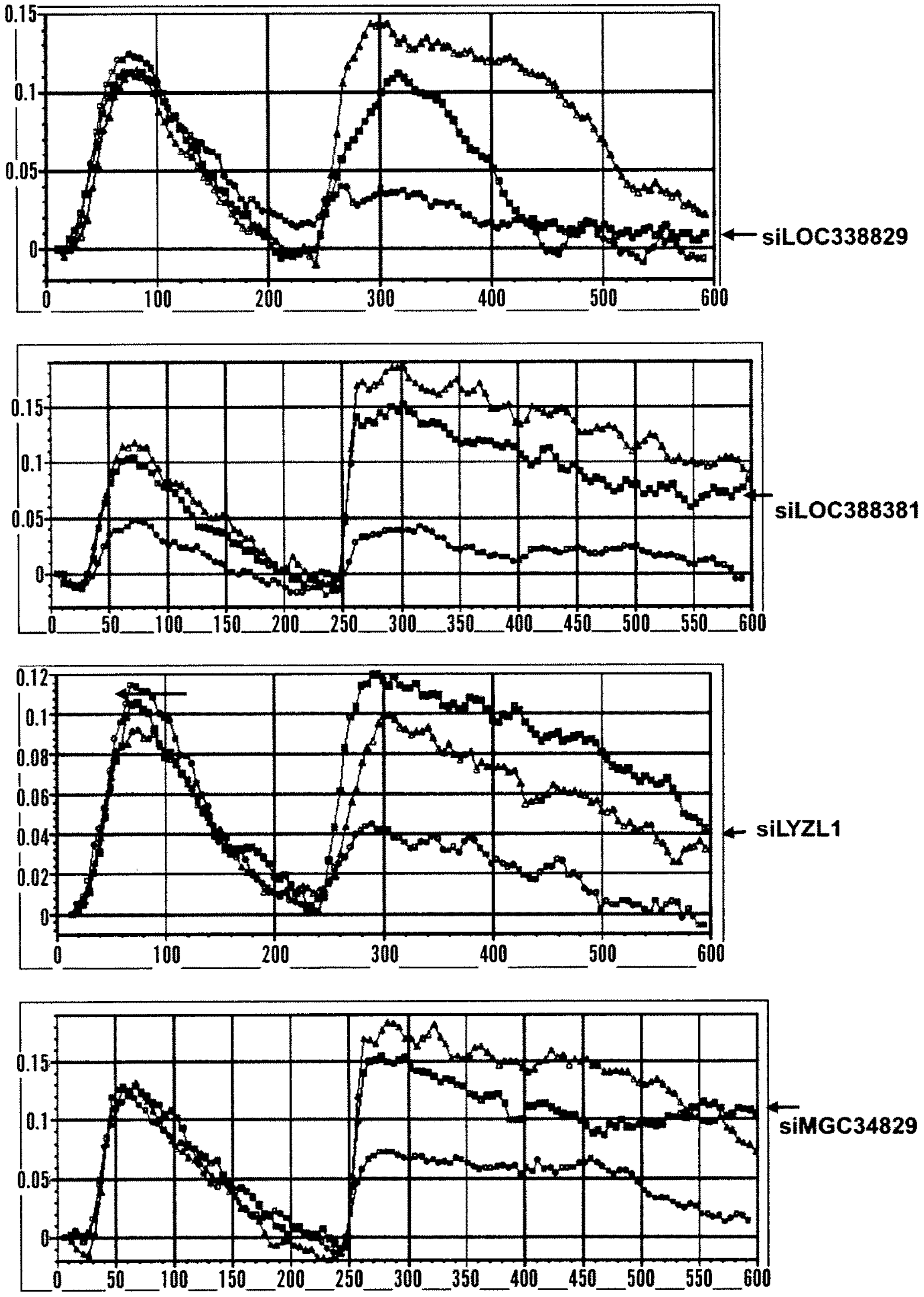
FIG. 48 shows the traces of calcium fluxes in cells treated with siRNA to the respective genes: LOC338829, LOC388381, LYZL and MGC34829.
Figure 49:
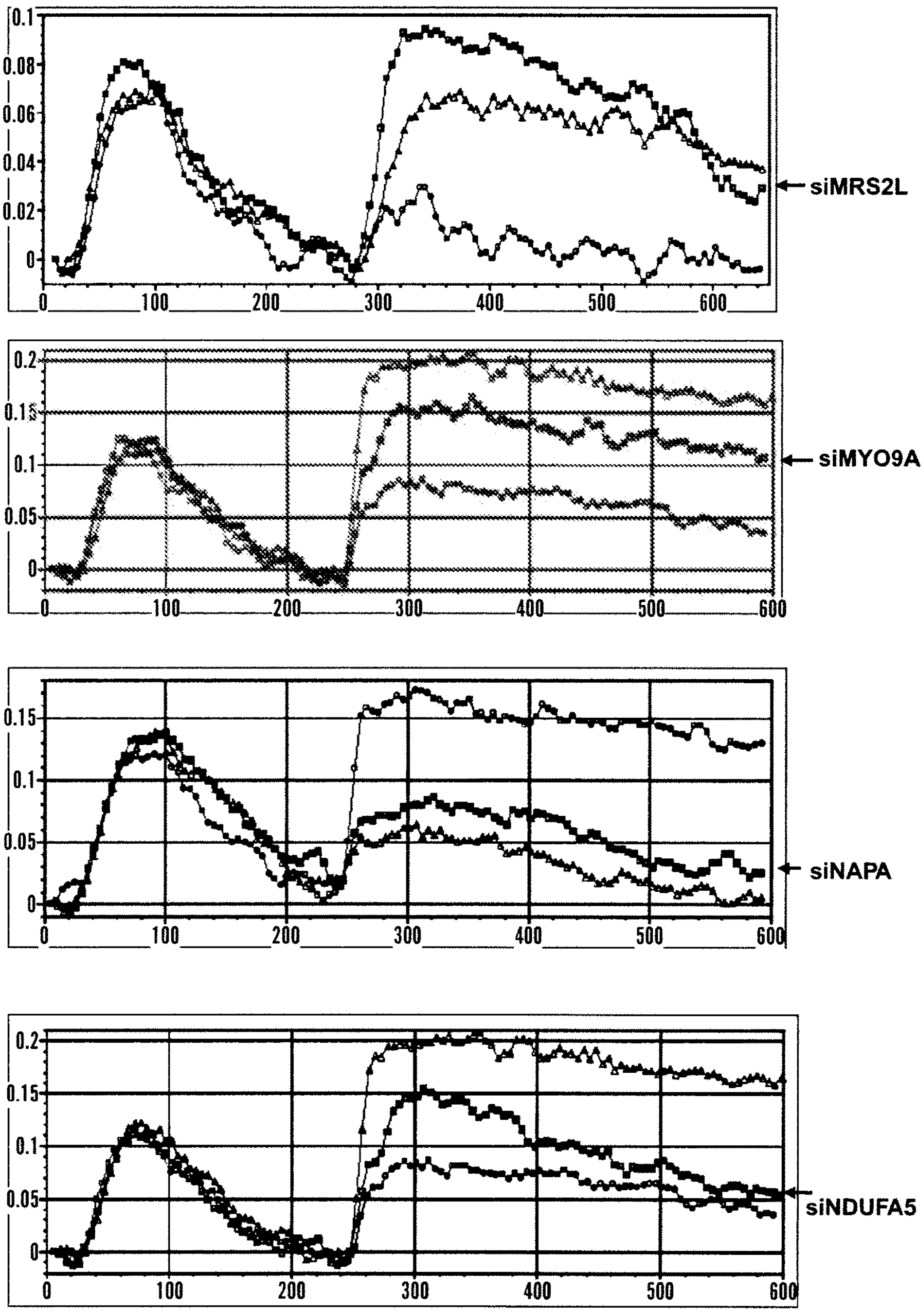
FIG. 49 shows the traces of calcium fluxes in cells treated with siRNA to the respective genes: MRS2L, MYO9A, NAPA and NDUFA5.
Figure 50:
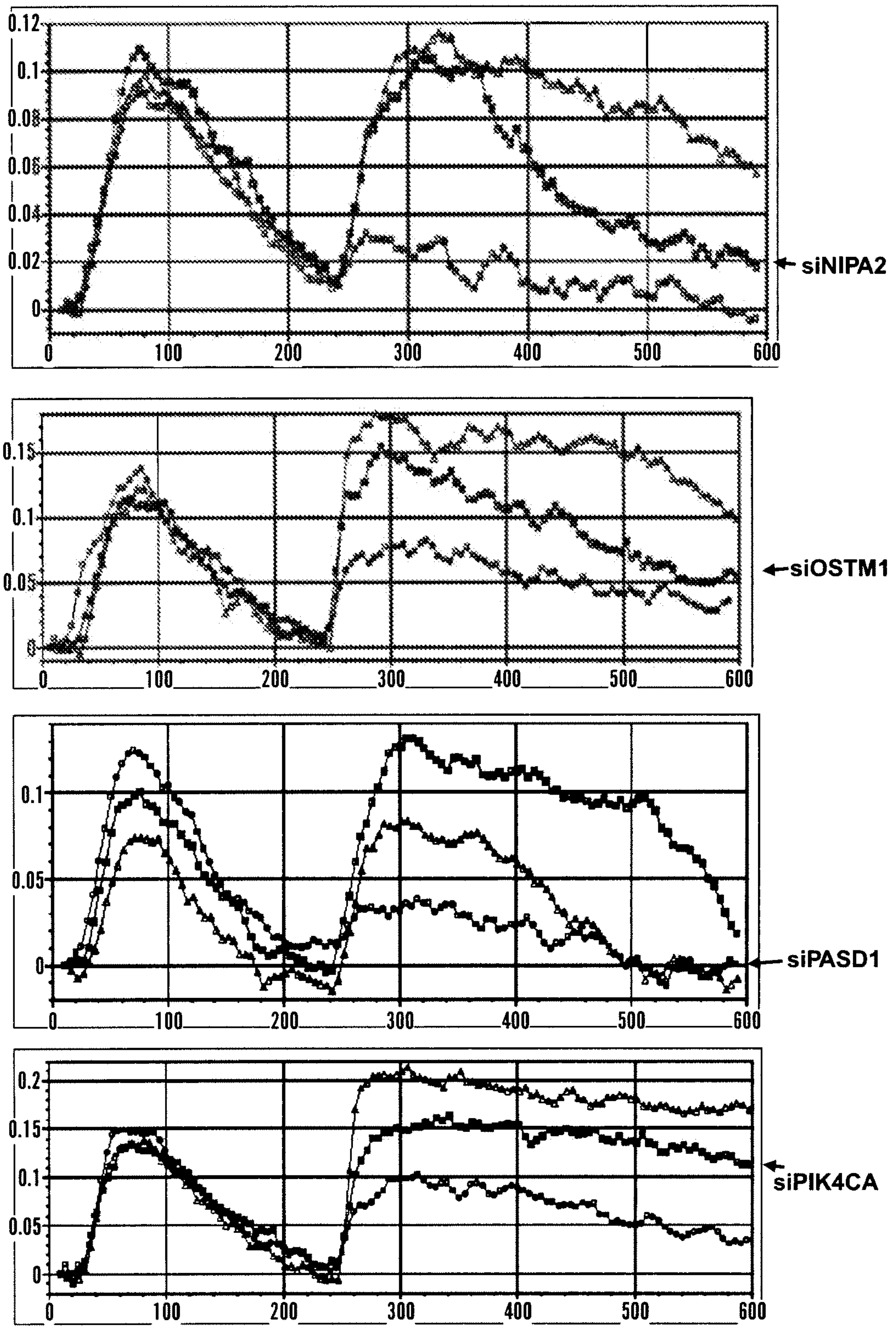
FIG. 50 shows the traces of calcium fluxes in cells treated with siRNA to the respective genes: NIPA2, OSTM1, PASD and PIK4CA.
Figure 51:
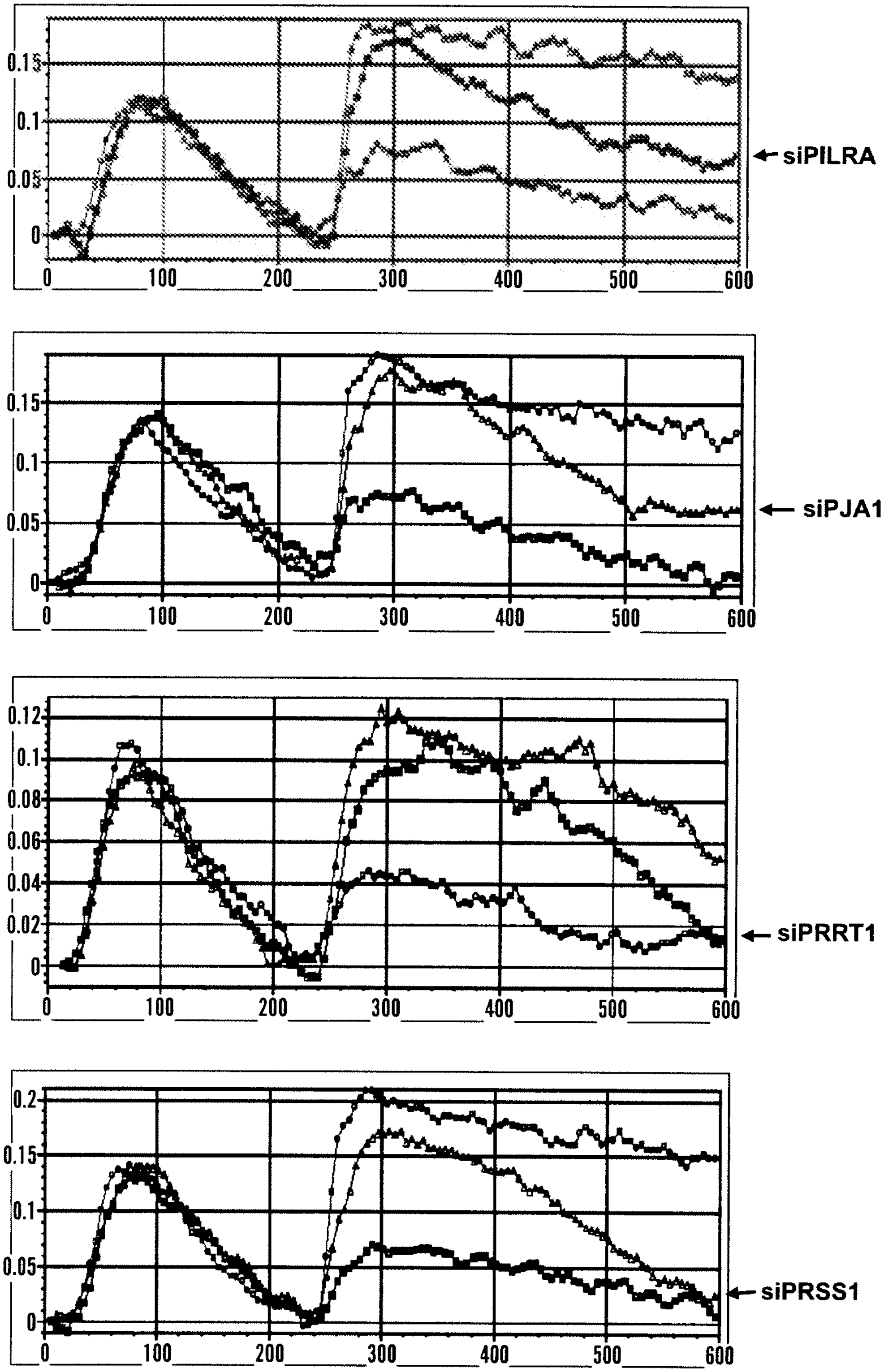
FIG. 51 shows the traces of calcium fluxes in cells treated with siRNA to the respective genes: PILRA, PJA1, PRRT1 and PRSS1.
Figure 52:
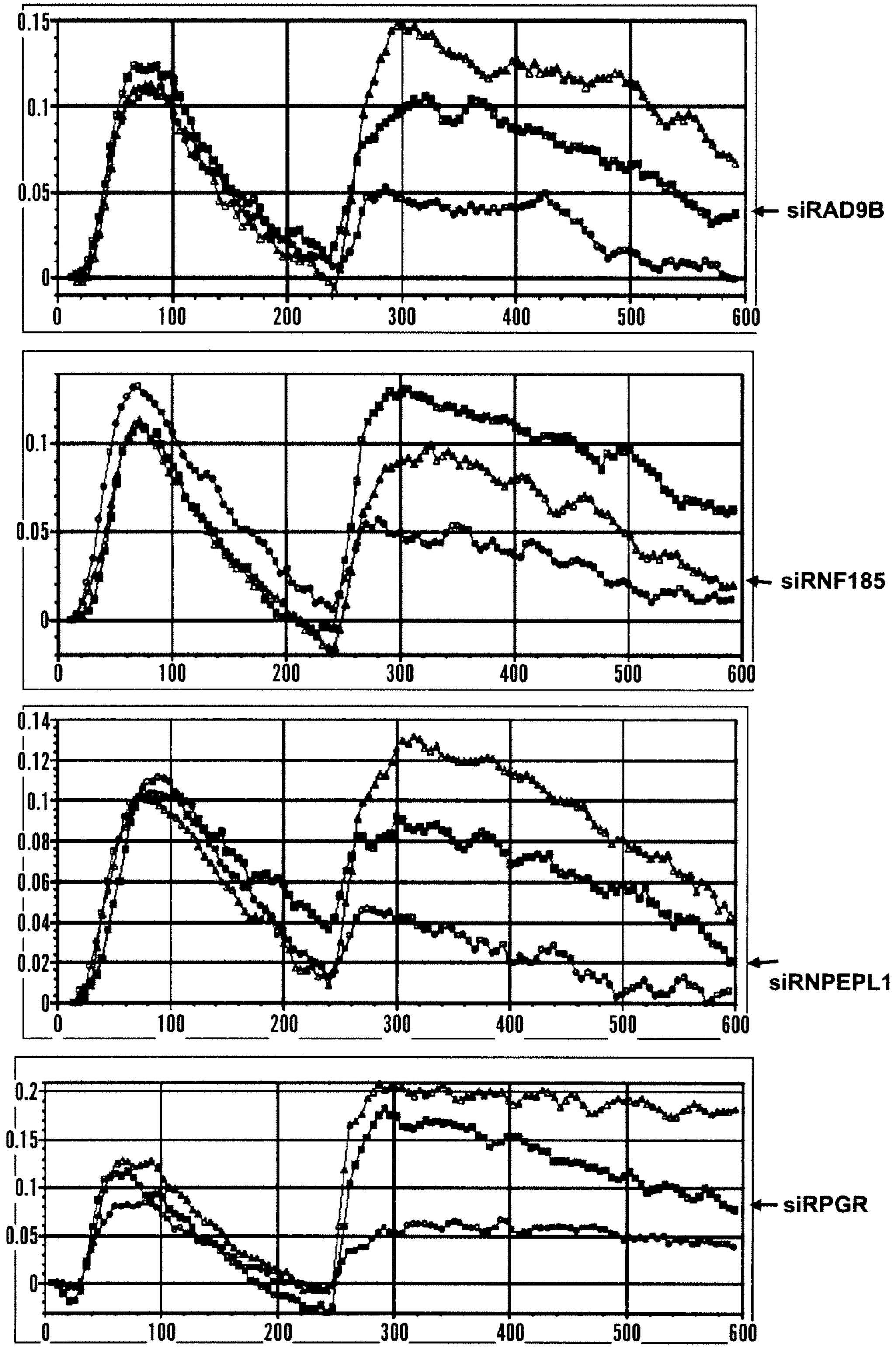
FIG. 52 shows the traces of calcium fluxes in cells treated with siRNA to the respective genes: RAD9B, RNF185, RNPEPL1 and RPGR.
Figure 53:
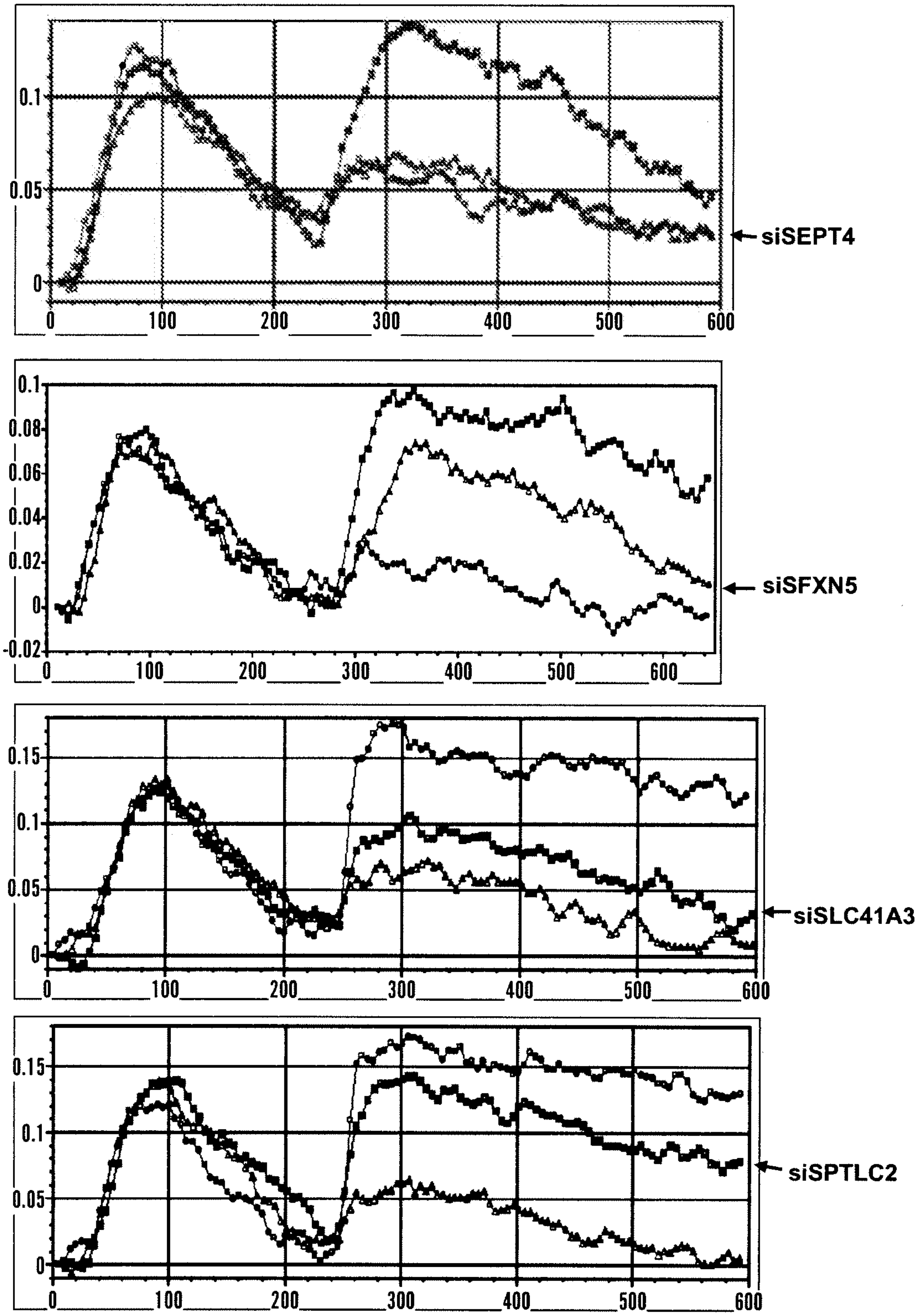
FIG. 53 show the traces of calcium fluxes in cells treated with siRNA to the respective genes: SEPT4/PNUTL2, SFXN5, SLC41A3 and SPTLC2.
Figure 54:
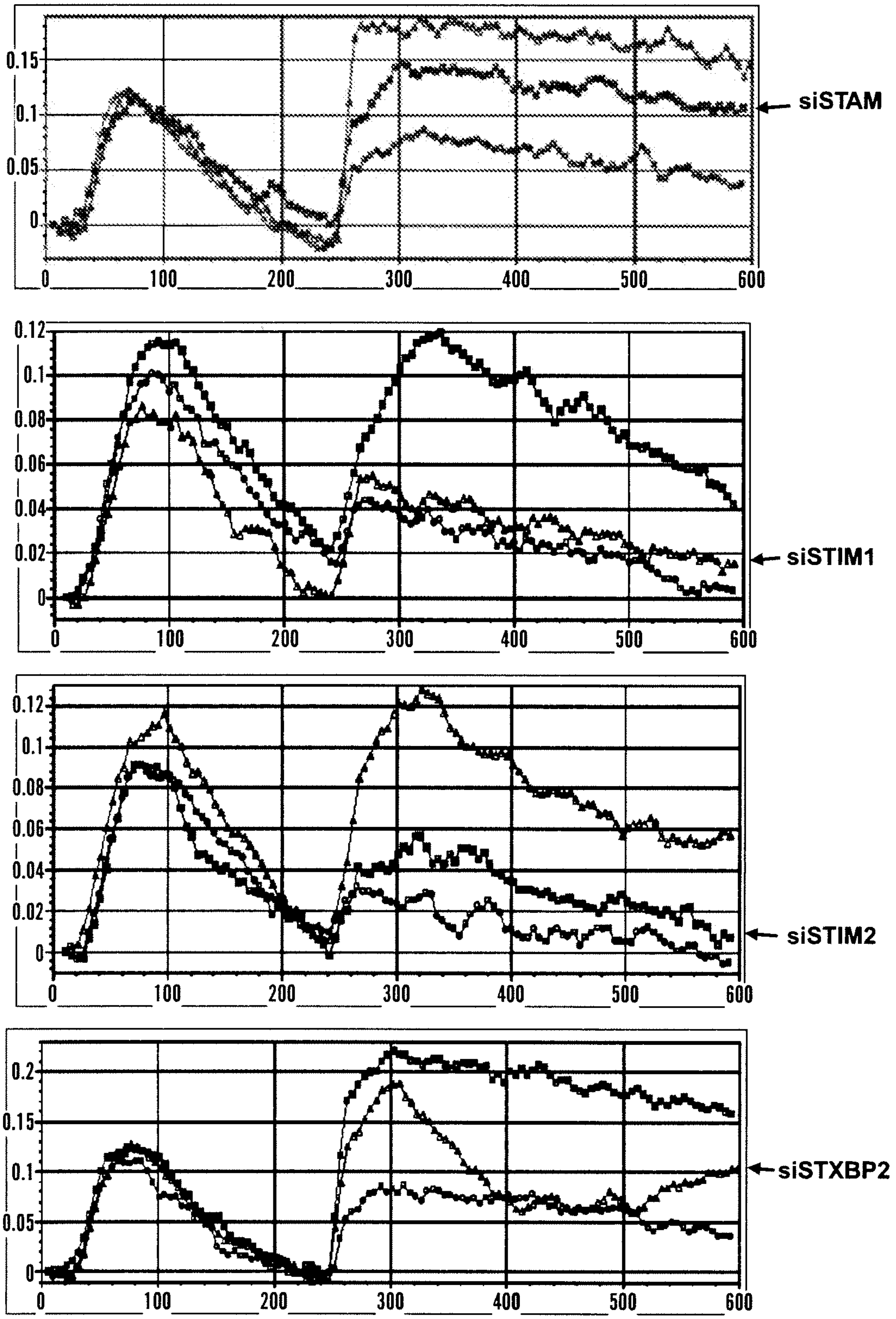
FIG. 54 shows the traces of calcium fluxes in cells treated with siRNA to the respective genes: STAM, STIM2, STIM1 and STXBP2.
Figure 55:
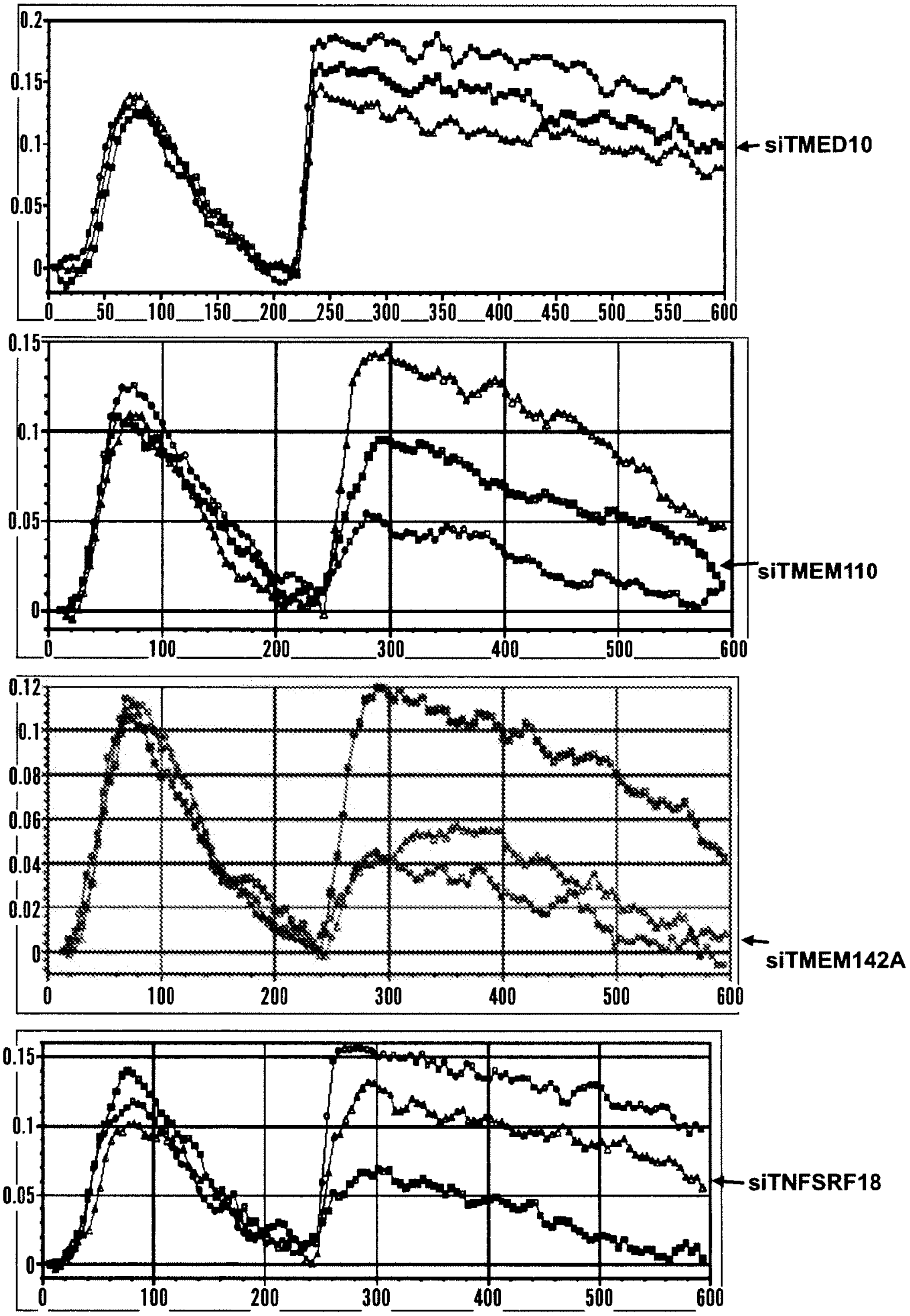
FIG. 55 shows the traces of calcium fluxes in cells treated with siRNA to the respective genes: TMED10, TMEM110, TMEM142A and TNFSRF18.
Figure 56:
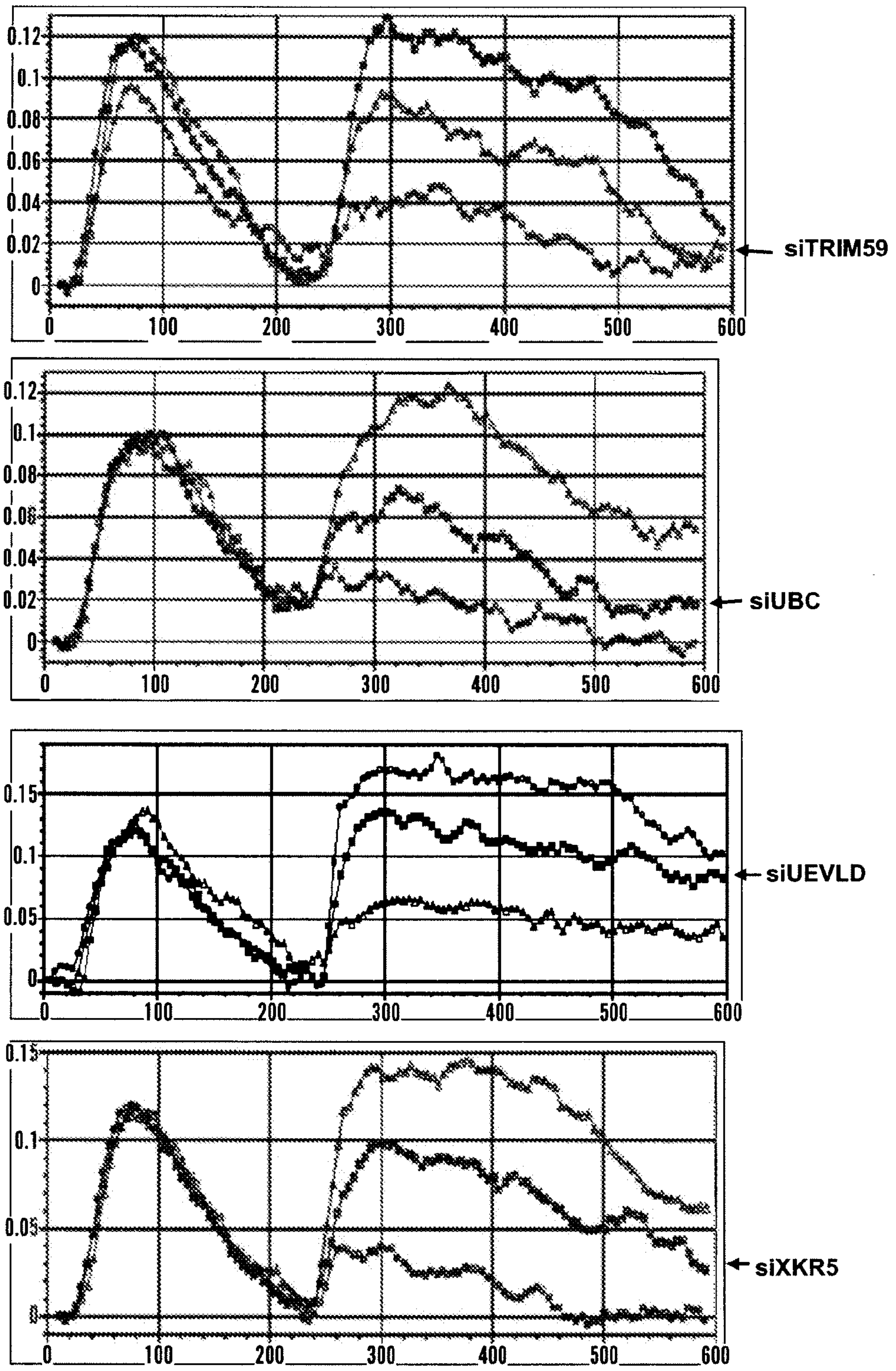
FIG. 56 shows the traces of calcium fluxes in cells treated with siRNA to the respective genes: TRIM59, UBC, UEVLD and XKR5.
Figure 57:
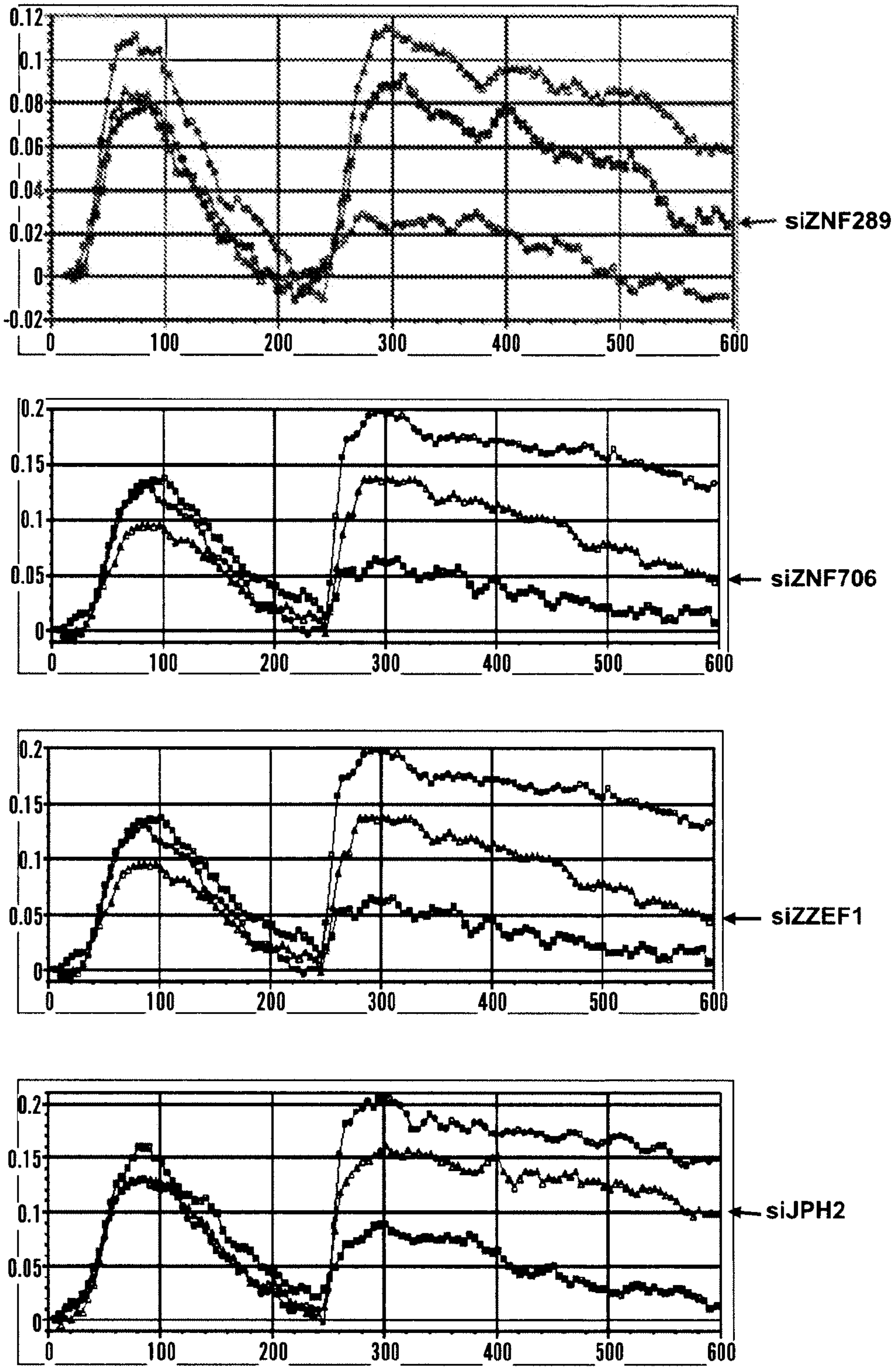
FIG. 57 shows the traces of calcium fluxes in cells treated with siRNA to the respective genes: ZNF289, ZNF706, ZZEF1 and JPH2.
Figure 58:
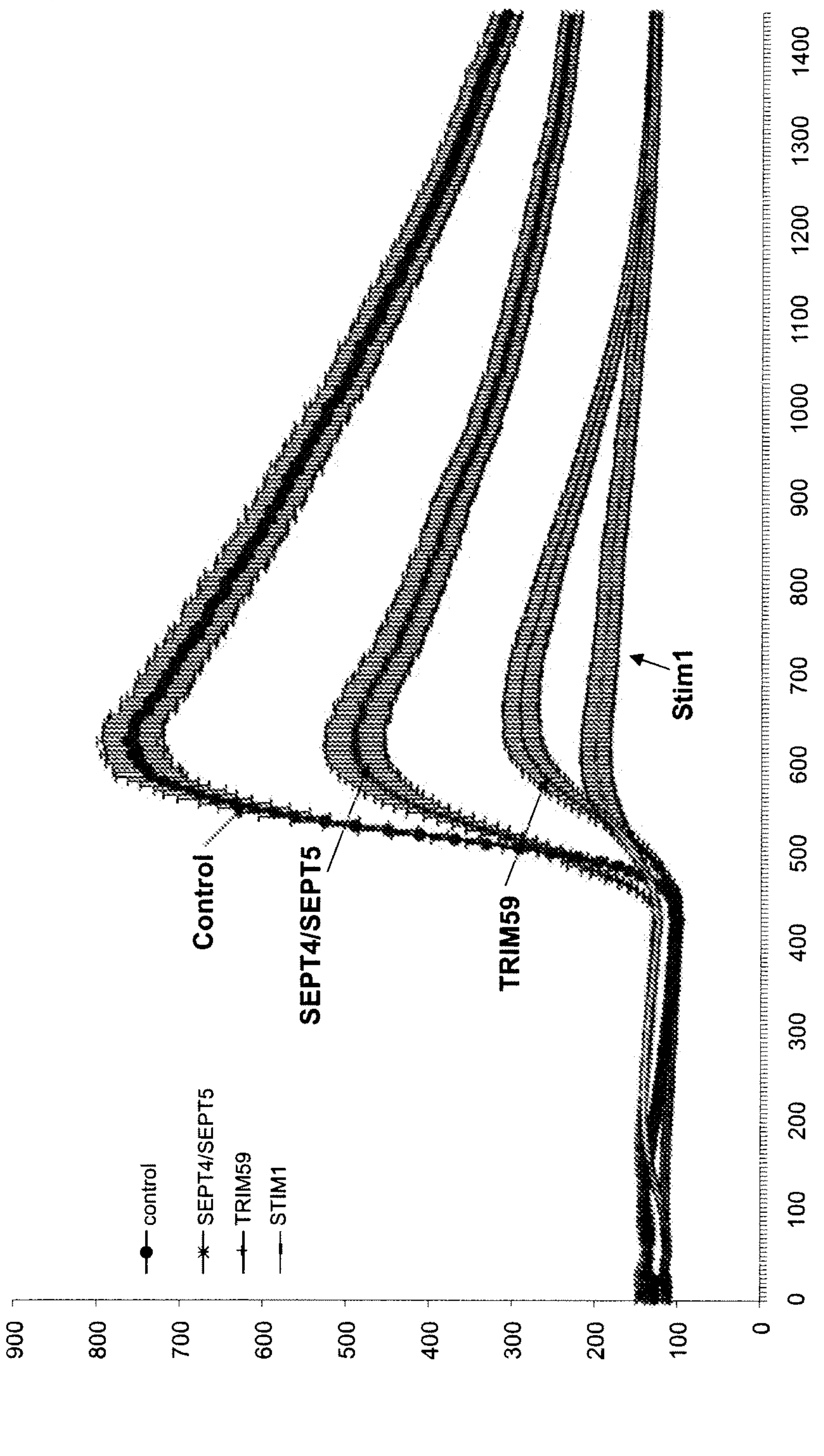
FIG. 58 shows the calcium fluxes traces of single cells treated with siRNA to the respective genes: SEPT4/PNUTL2, TRIM59 and STIM1 compared to a control siRNA.
Figure 59:
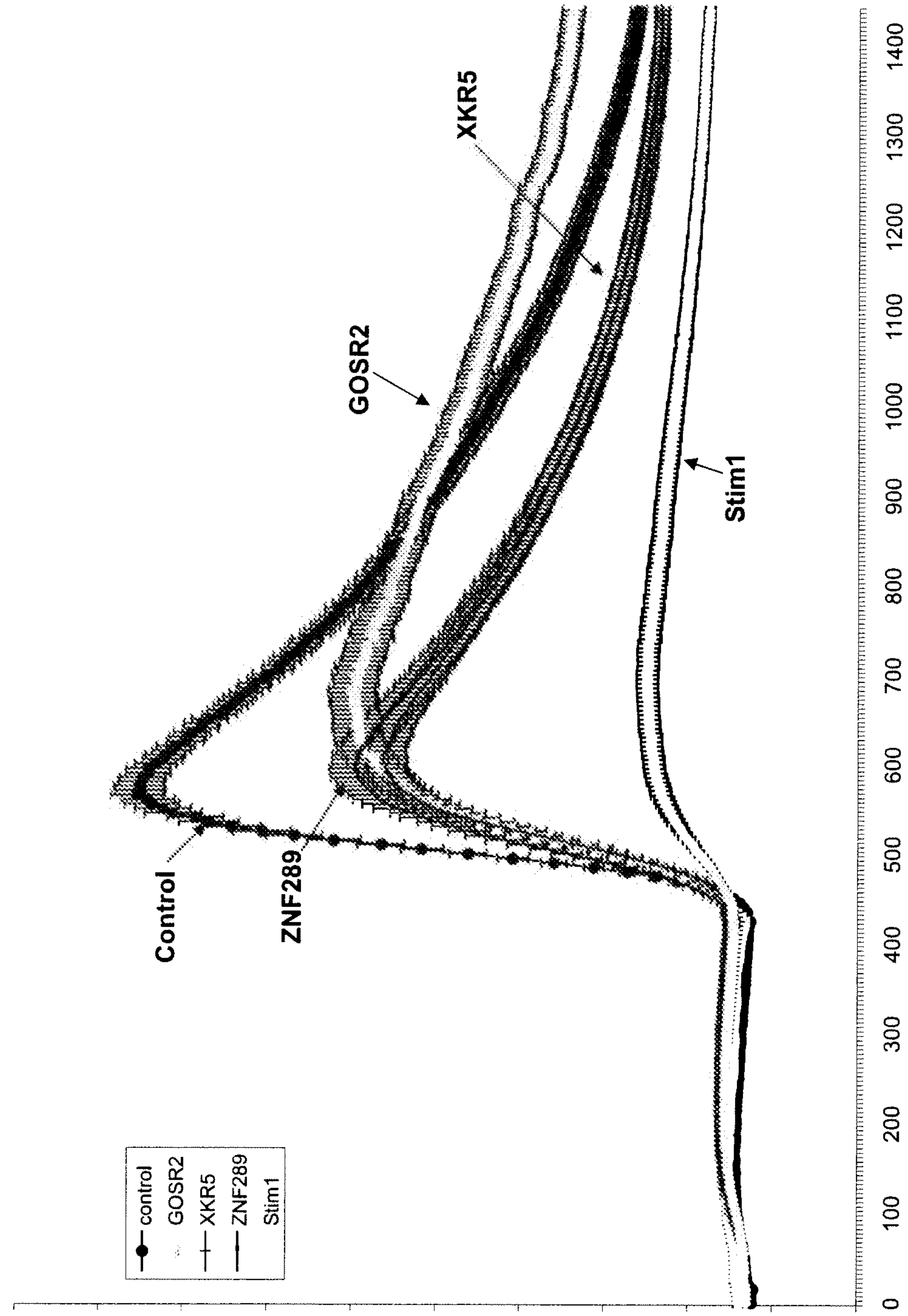
FIG. 59 shows the calcium fluxes traces of single cells treated with siRNA to the respective genes: ZNF289, XKR5, GOSR2 and STIM1 compared to a control siRNA.
Figure 60:
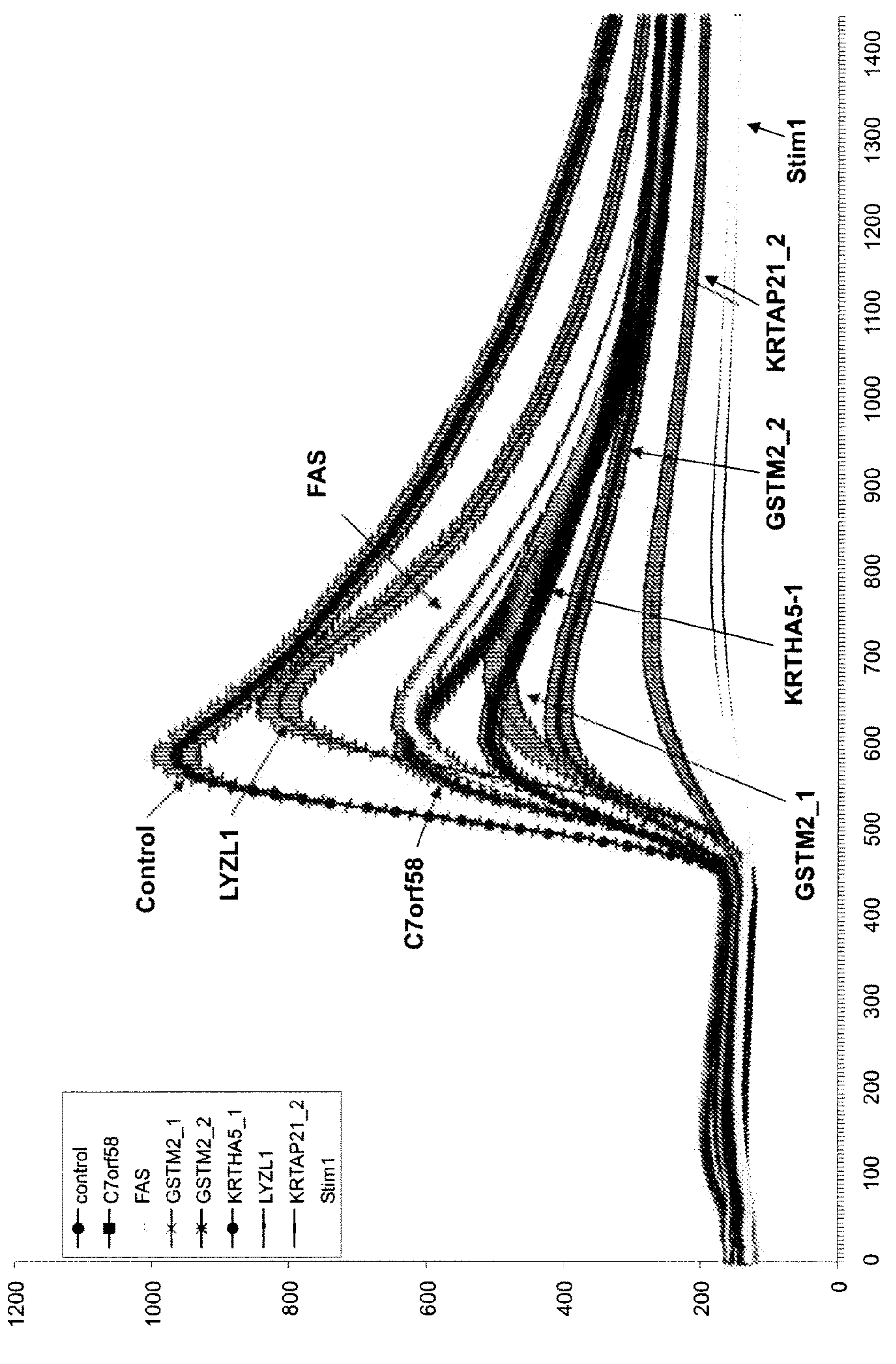
FIG. 60 shows the calcium fluxes traces of single cells treated with siRNA to the respective genes: C7ORF58, FAS, GSTM2-1, GSTM2-2, KRTHA5_1, LYZL1, KRTAP21-2 and STIM1 compared to a control siRNA.
Figure 61:
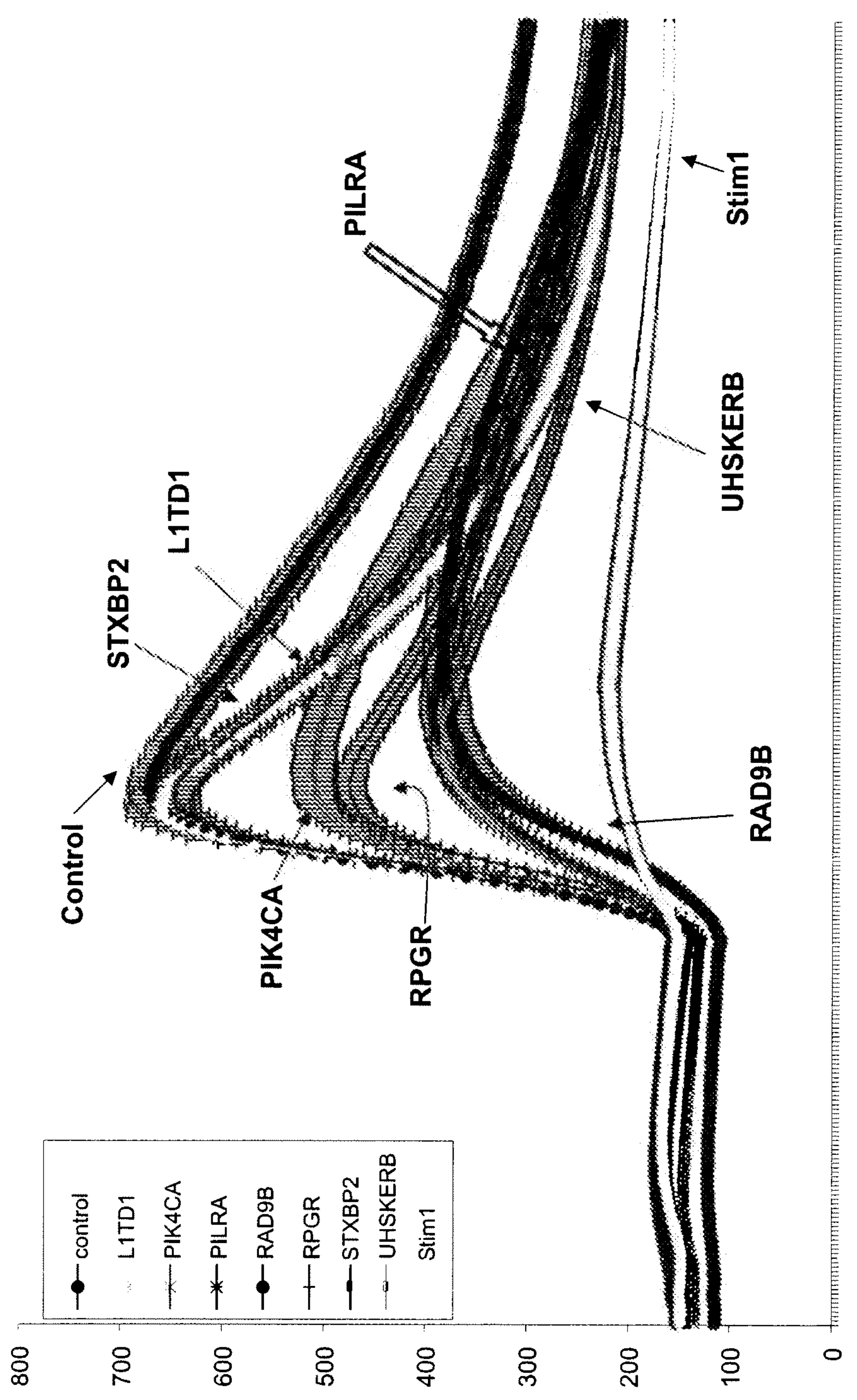
FIG. 61 shows the calcium fluxes traces of single cells treated with siRNA to the respective genes: L1TD1, PIK4CA. PILRA, RAD9B, RPGR, STXBP2, UHSKERB and STIM1 compared to a control siRNA.
Figure 62:
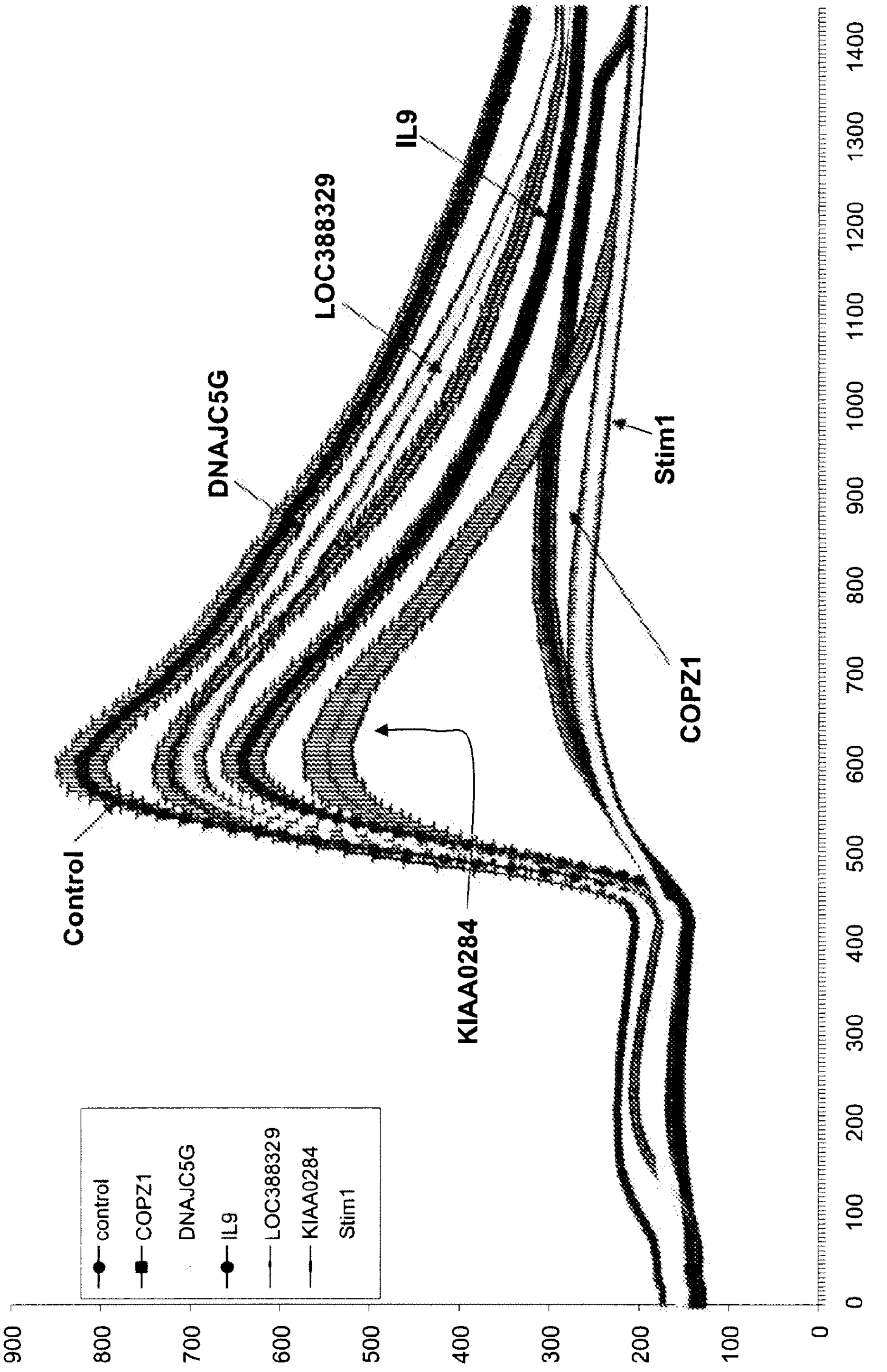
FIG. 62 shows the calcium fluxes traces of single cells treated with siRNA to the respective genes: COPZ1, DNAJC5G, IL9, LOC388329, KIAA0284 and STIM1 compared to a control siRNA.
Figure 63:
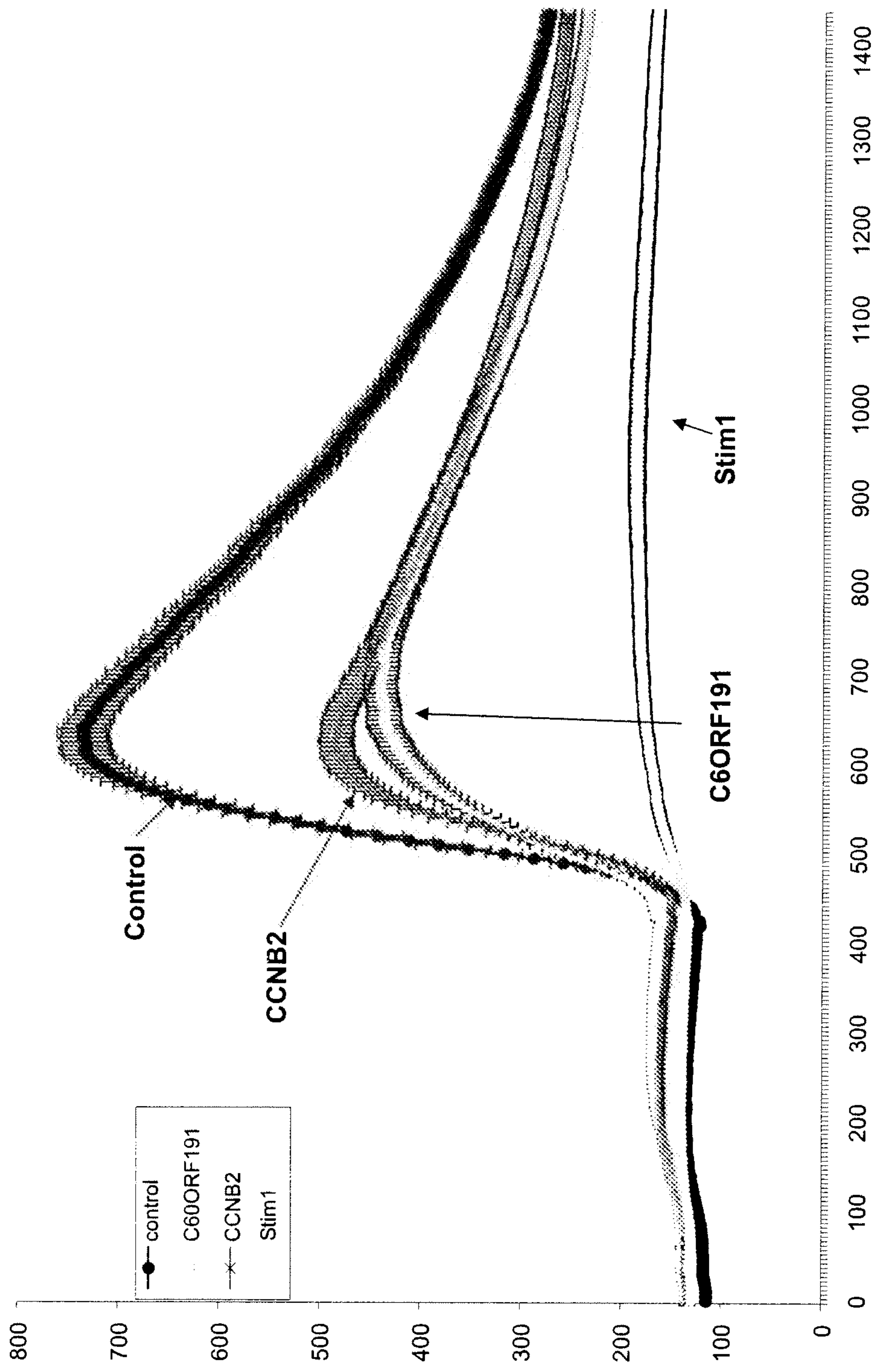
FIG. 63 shows the calcium fluxes traces of single cells treated with siRNA to the respective genes: C6ORF191, CCNB2, and STIM1 compared to a control siRNA.
Figure 64:
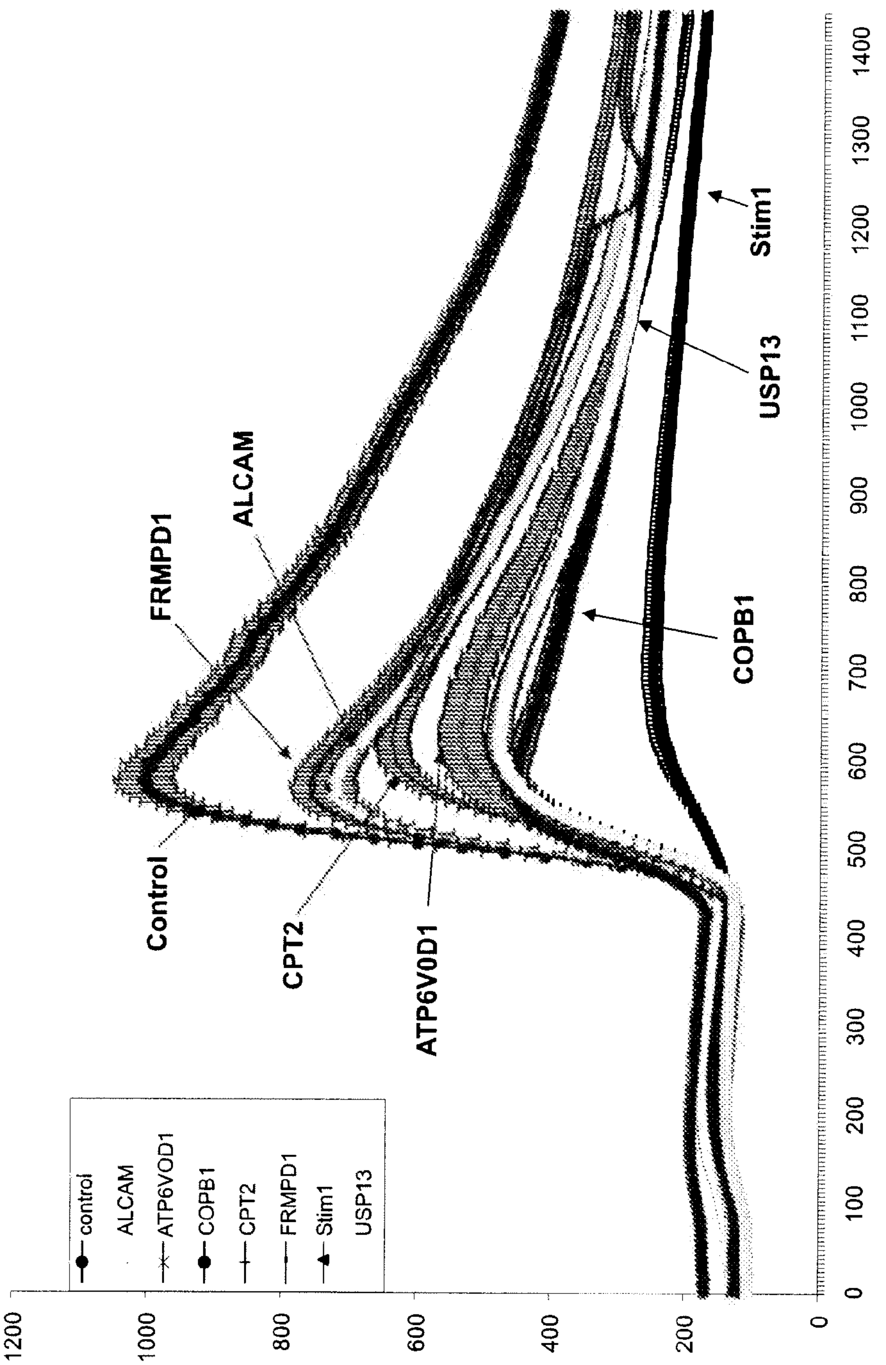
FIG. 64 shows the calcium fluxes traces of single cells treated with siRNA to the respective genes: ALCAM, ATP6V0D1, COPB1, CPT2, FRMPD1, USP13 and STIM1 compared to a control siRNA.
Figure 65:
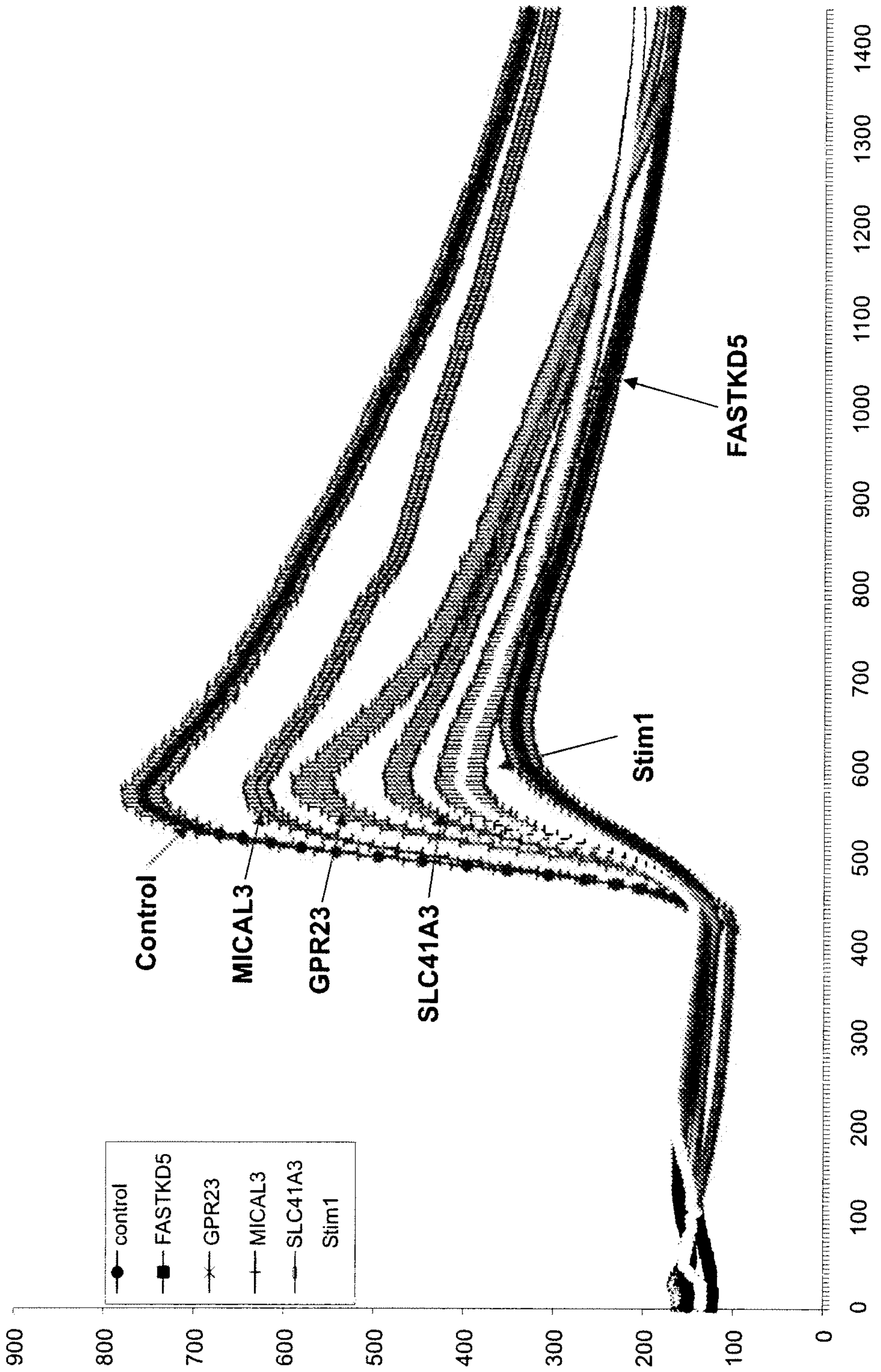
FIG. 65 shows the calcium fluxes traces of single cells treated with siRNA to the respective genes: FASTKD5, GPR23, MICAL3, SLC41A3 and STIM1 compared to a control siRNA.
Figure 66:
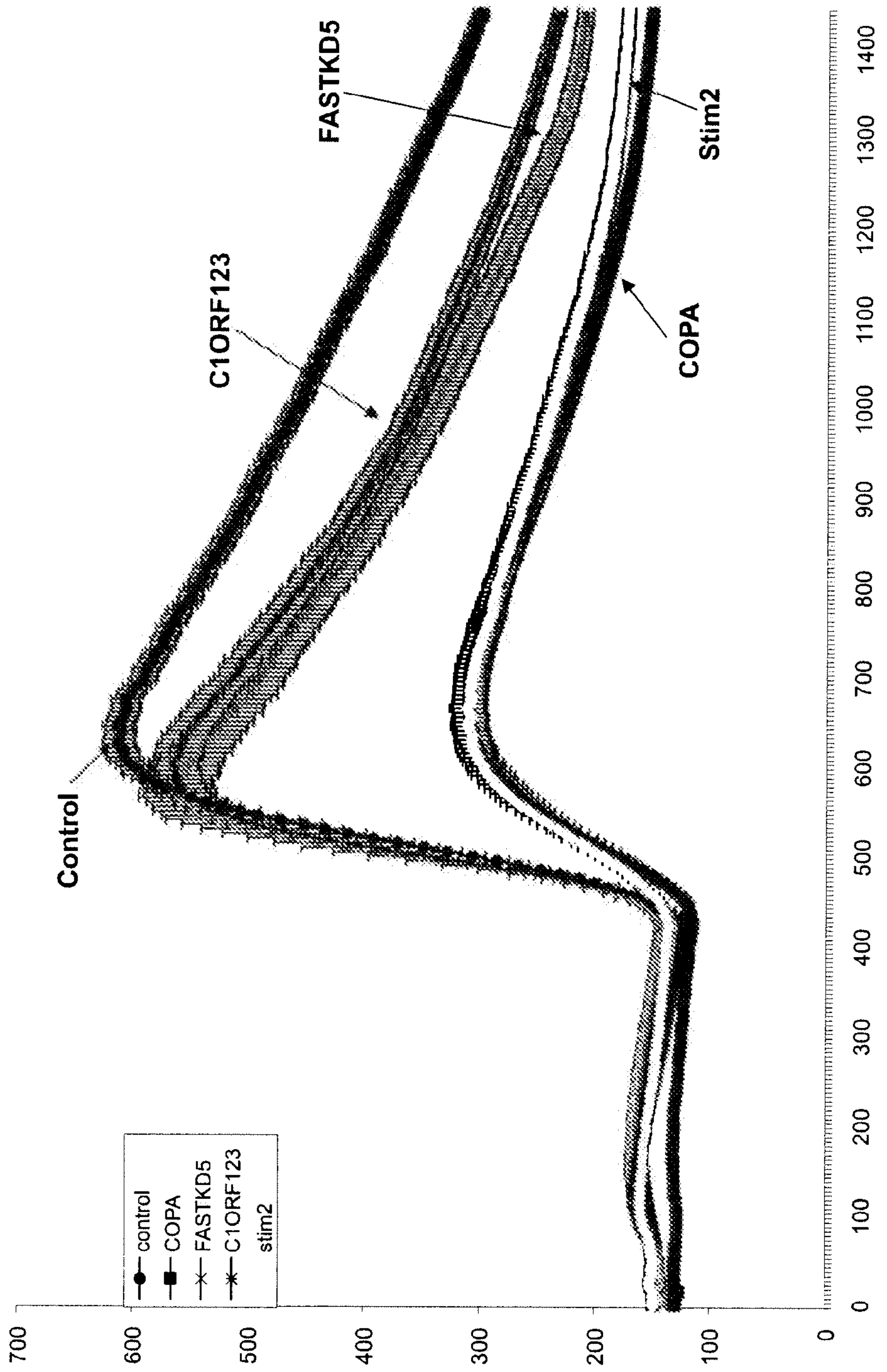
FIG. 66 shows the calcium fluxes traces of single cells treated with siRNA to the respective genes: COPA, FASTKD5, C1ORF123 and STIM2 compared to a control siRNA.
Figure 67:
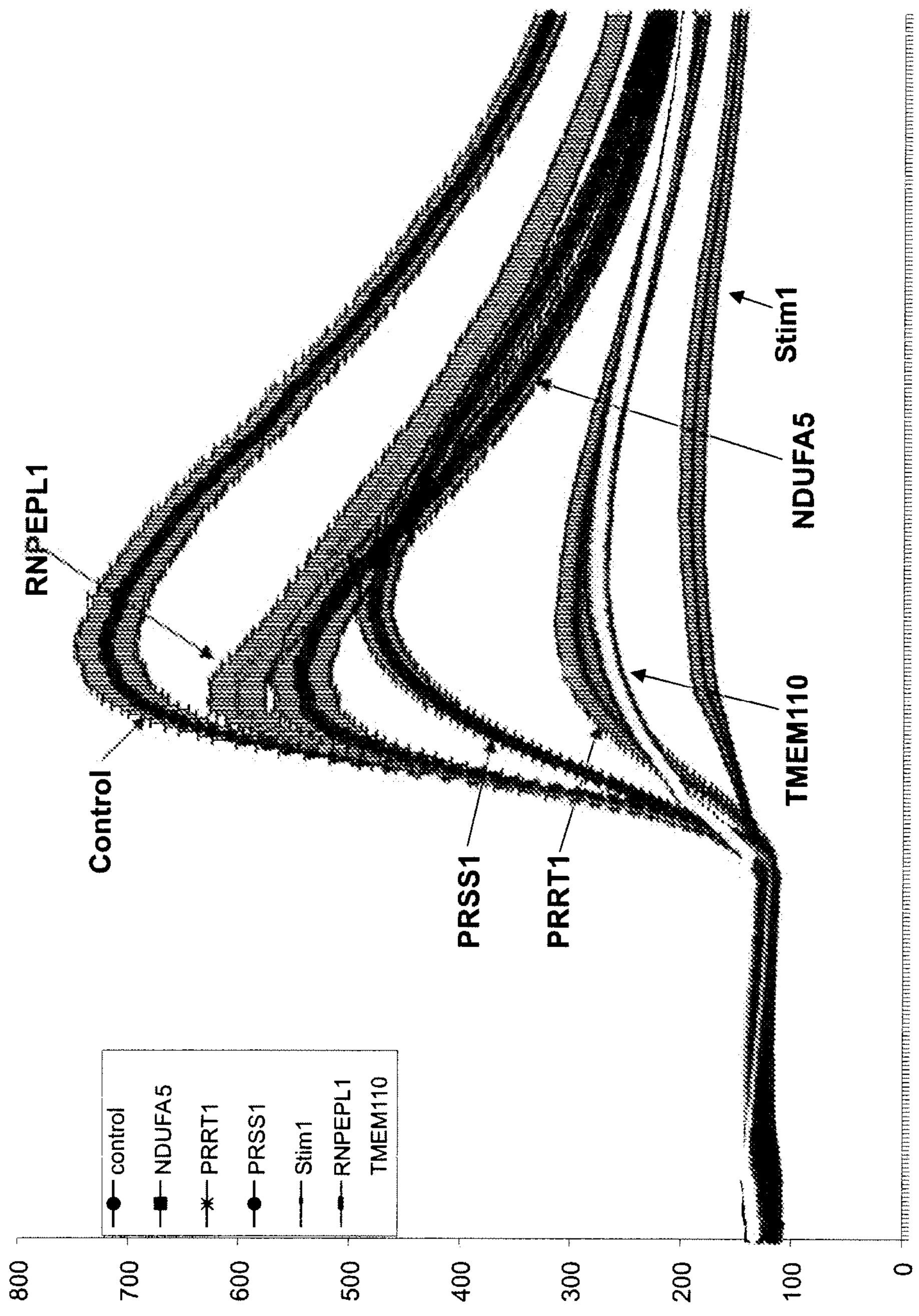
FIG. 67 shows the calcium fluxes traces of single cells treated with siRNA to the respective genes: NDUFA5, PRRT1, PRSS1, RNPEPL1, TMEM110 and STIM1 compared to a control siRNA.
Figure 68:
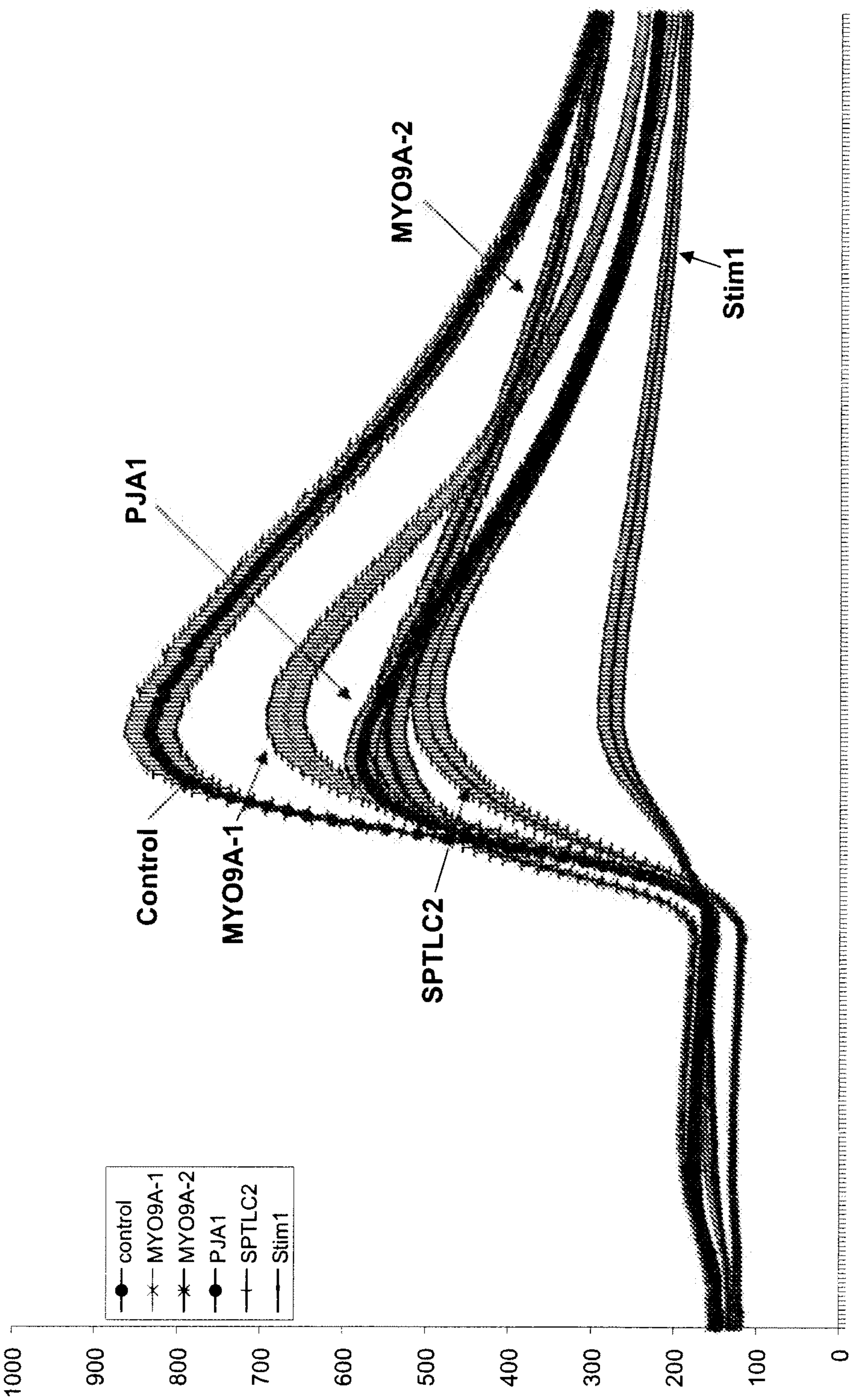
FIG. 68 shows the calcium fluxes traces of single cells treated with siRNA to the respective genes: MYO9A-1, MYO9A-2, PJA1, SPTLC2 and STIM1 compared to a control siRNA.
Figure 69:
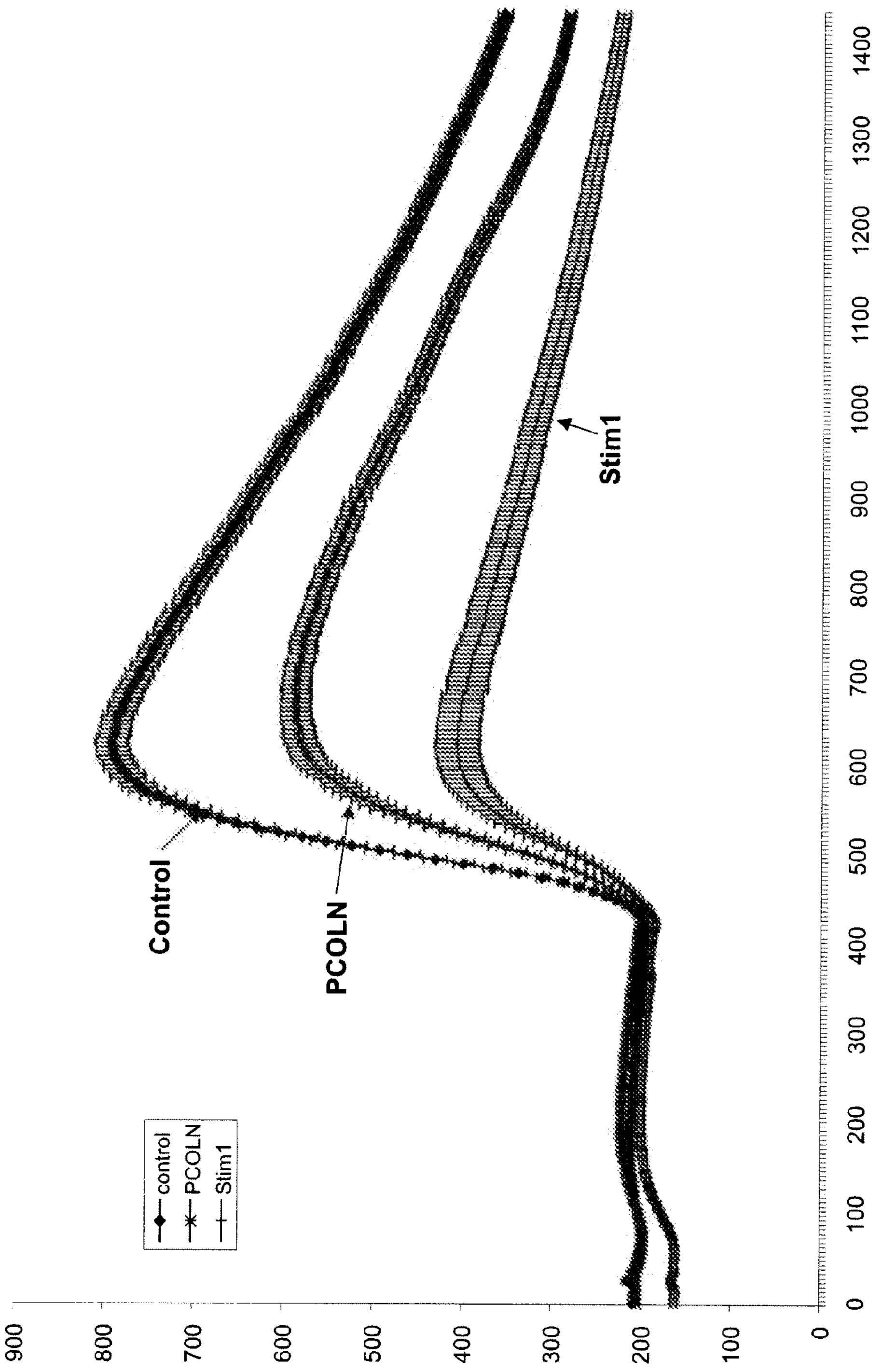
FIG. 69 shows the calcium fluxes traces of single cells treated with siRNA to the respective genes: PCOLN and STIM1 compared to a control siRNA.
Figure 70:
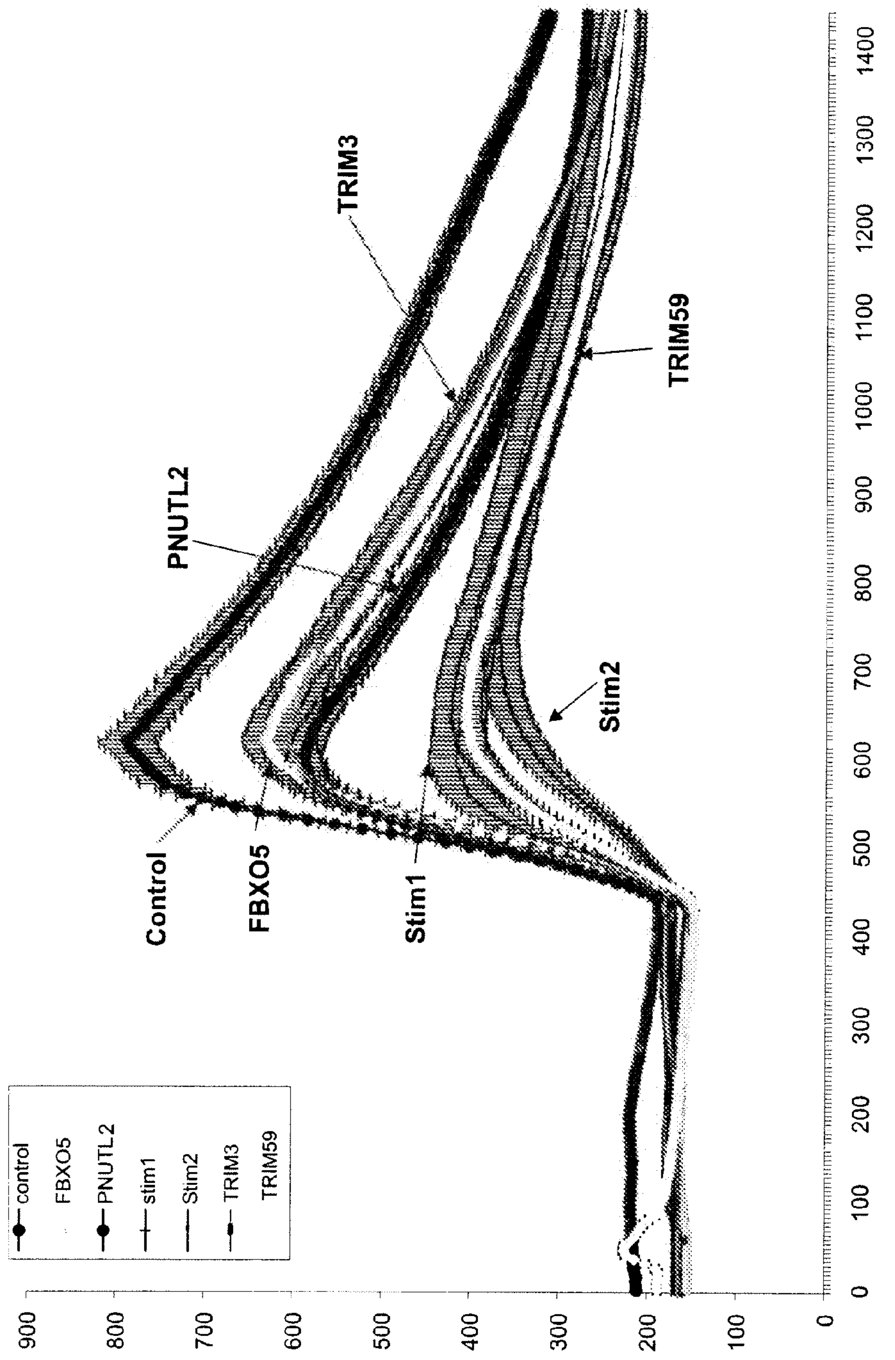
FIG. 70 shows the calcium fluxes traces of single cells treated with siRNA to the respective genes: FBXO5, PNUTL2/SEPT4, TRIM3, TRIM59, STIM1 and STIM2 compared to a control siRNA.

From the sceen, the inventors discovered that the Sept 4 and Sept 5 gene product modulated SOCE into a cell, and modulated NFAT nuclear translocation and subsequent activation. The inventors found that the inhibition of Sept 4 and Sept 5 gene expressions by RNA interference methods greatly reduced NFAT nuclear translocation in their assay system (FIGS. 75B, 78) and also the SOCE in the affected cell (FIGS. 53, 58, 73, 75C, 77B). In addition, the inventors found that the inhibition of the UEV3 gene expression by RNA interference methods greatly reduced NFAT nuclear translocation in their assay system (see FIGS. 25, 35, 36) and also SOCE in the affected cell (see FIGS. 24-26, 31). Therefore, the inhibition of septin function(s), UEV3 function(s), the inhibition of the expressions of septins and UEV3 can be used to modulate NFAT nuclear translocation, SOCE in the cell, and the activation of T-cells. A As a corollary, an immune response can be modulated, i.e., enhanced or suppressed, by the inhibition of septin function(s), UEV3 function(s), the inhibition of the expressions of septins and UEV3.

Accordingly, in one embodiment, provided herein is a pharmaceutical composition comprising an agent that inhibits the function of a septin protein and/or the expression of a septin gene, and a pharmaceutically acceptable carrier. In another embodiment, the pharmaceutical composition further comprises an agent that inhibits the function of a UEV3 protein and/or the expression of a UEV3 gene.

Any member of the septin family can be targeted by the agent. More than one member of the septin family can be simultaneously targeted by the agent. By "targeted" means that the agent would inhibit the function of the "targeted" septin protein and/or the expression of the "targeted" septin gene.

In one embodiment of the pharmaceutical composition, the septin is a septin 4. Other not limiting examples of septins include septin 2, 3, 4, 5, 6, 7, and 9.

In one embodiment of the pharmaceutical composition, the agent inhibits the functions of at least two septin proteins and/or the expression of at least two septin genes. For example, a single agent can inhibit the expressions of both septin 4 and septin 5 genes simultaneously.

In another embodiment, the pharmaceutical composition comprises a first agent that inhibits the function of a first septin protein and/or the expression of a first septin gene, a second agent that inhibits the function of a second septin protein and/or the expression of a second septin gene, and a pharmaceutically acceptable carrier. In other words, two septin genes are targeted by the pharmaceutical composition having two separate and distinct agents. In one embodiment of the pharmaceutical composition, the first septin is a septin 4 and the second septin is a septin 5. In another embodiment, the pharmaceutical composition further comprises an agent that inhibits the function of a UEV3 protein and/or the expression of a UEV3 gene.

In one embodiment, provided herein is a pharmaceutical composition comprising at least one agent that inhibits the function of a septin protein and/or the expression of a septin gene. In other words, the pharmaceutical composition can have more than one agent that targets septins. The plurality of agents can all be targeting the same septin or a different septin. For example, the pharmaceutical composition comprises three agents all targeting septin 4 and another pharmaceutical composition comprises a combination of two agents targeting septin 4 and another two agents targeting septin 5.

In one embodiment, provided herein is a pharmaceutical composition comprising at least one agent that inhibits the function of a septin protein and/or the expression of a septin gene and at least an agent that inhibits the function of a UEV3 protein and/or the expression of a UEV3 gene. In other words, the pharmaceutical composition can be a combination of a plurality of agents targeting a septin and a plurality of agents targeting UEV3.

In one embodiment, provided herein is a pharmaceutical composition comprising an agent that inhibits the function of a septin 4 protein and/or the expression of a septin 4 gene, and a pharmaceutically acceptable carrier. In one embodiment, the pharmaceutical composition further comprises an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a pharmaceutical composition comprising an agent that inhibits the function of a septin 4 protein and/or the expression of a septin 4 gene, an agent that inhibits the function of a septin 5 protein and/or the expression of a septin 5 gene and a pharmaceutically acceptable carrier. In other words, the pharmaceutical composition comprises one agent targeting septin 4 and another agent targeting septin 5. In another embodiment, the pharmaceutical composition further comprises an agent that inhibits the function of a UEV3 protein and/or the expression of a UEV3 gene. In this embodiment, the pharmaceutical composition comprises one agent targeting septin 4, another agent targeting septin 5 and a third agent targeting UEV3.

In one embodiment, provided herein is a pharmaceutical composition comprising an agent that inhibits the function of a UEV3 protein and/or the expression of a UEV3 gene, and a pharmaceutically acceptable carrier.

In one embodiment, provided herein is a pharmaceutical composition comprising an agent that inhibits the function of a UEV3 protein and/or the expression of a UEV3 gene, an agent that inhibits the function of a septin protein and/or the expression of a septin gene, and a pharmaceutically acceptable carrier. In one embodiment of the pharmaceutical composition, the septin is a septin 4. In another embodiment of the pharmaceutical composition, the agent inhibits the function of at least two septin proteins and/or the expression of at least two septin genes. In one embodiment, the at least two septins are septin 4 and 5. For example, a single agent can inhibit the expressions of both septin 4 and septin 5 genes simultaneously.

In one embodiment, provided herein is a pharmaceutical composition comprising an agent that inhibits the function of a UEV3 protein and/or the expression of a UEV3 gene, a first agent that inhibits the function of a first septin protein and/or the expression of a first septin gene, a second agent that inhibits the function of a second septin protein and/or the expression of the second septin gene, and a pharmaceutically acceptable carrier. In one embodiment of the pharmaceutical composition, the first septin is a septin 4 and the second septin is a septin 5.

In one embodiment, provided herein is a composition for use of modulating NFAT activity in a subject in need thereof, the composition comprising an agent that inhibits the function of a septin protein and/or the expression of a septin gene. In another embodiment, the composition further comprises an agent that inhibits the function of a UEV3 protein and/or the expression of a UEV3 gene. In one embodiment, the septin is a septin 4.

The NFAT activity can be monitored or assessed by any method known to one skilled in the art or by the methods described herein, the titers are assessed before and after use of the composition. For example, the level of cytokine circulating in the subject can be titered by known blood component titering methods, e.g., enzyme-linked immunoassay (ELISA).

In one embodiment, provided herein is a composition for use of modulating NFAT activity in a subject in need thereof, the composition comprising an agent inhibits the function of at least two septin proteins and/or the expression of at least two septin genes. In another embodiment, the composition further comprises an agent that inhibits the function of a UEV3 protein and/or the expression of a UEV3 gene. In one embodiment, the at least two septins are septin 4 and 5. For example, a single agent can inhibit the expressions of both septin 4 and septin 5 genes simultaneously.

In one embodiment, provided herein is a composition for use of modulating NFAT activity in a subject in need thereof, comprising at least one agent that inhibits the function of a septin protein and/or the expression of a septin gene.

In one embodiment, provided herein is a composition for use of modulating NFAT activity in a subject in need thereof, comprising at least one agent that inhibits the function of a septin protein and/or the expression of a septin gene and at least an agent that inhibits the function of a UEV3 protein and/or the expression of a UEV3 gene.

In one embodiment, provided herein is a composition for use of modulating NFAT activity in a subject in need thereof, the composition comprising a first agent that inhibits the function of a first septin protein and/or the expression of a first septin gene, and a second agent that inhibits the function of a second septin protein and/or the expression of a second septin gene. In another embodiment, the composition further comprises an agent that inhibits the function of a UEV3 protein and/or the expression of a UEV3 gene. In one embodiment, the first septin is a septin 4 and the second septin is a septin 5.

In one embodiment, provided herein is a composition for use of modulating NFAT activity in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use in modulating NFAT activity in a subject in need thereof, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use of modulating NFAT activity in a subject in need thereof, the composition comprising an agent that inhibits the function of a UEV3 protein and/or the expression of a UEV3 gene.

In one embodiment, provided herein is a composition for use of modulating NFAT activity in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use of modulating NFAT activity in a subject in need thereof, the composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of a second septin gene. In one embodiment of the composition, the first septin is a septin 4 and the second septin is a septin 5.

In one embodiment, provided herein is a composition for use in the manufacture of medicament for modulating NFAT activity in a subject in need thereof, the composition comprising an agent that inhibits the function of a septin protein and/or the expression of a septin gene. In another embodiment, the composition further comprises an agent that inhibits the function of a UEV3 protein and/or the expression of a UEV3 gene. In one embodiment, the septin is a septin 4. Example of an embodiment of the composition is one comprising an agent targeting septin 4 and an agent targeting UEV3.

In one embodiment, provided herein is a composition for use in the manufacture of medicament for modulating NFAT activity in a subject in need thereof, the composition comprising an agent inhibits the function of at least two septin proteins and/or the expression of at least two septin genes. Example of an embodiment of the composition is one comprising an agent targeting septin 4 and targeting septin 5. In another embodiment, the composition further comprises an agent that inhibits the function of a UEV3 protein and/or the expression of a UEV3 gene. In one embodiment, the at least two septins are septin 4 and 5. Example of an embodiment of the composition is one comprising an agent targeting both septin 4 and Septin 5, and an agent targeting UEV3.

In one embodiment, provided herein is a composition for use in the manufacture of medicament for modulating NFAT activity in a subject in need thereof, the composition comprising at least one agent that inhibits the function of a septin protein and/or the expression of a septin gene.

In one embodiment, provided herein is a composition for use in the manufacture of medicament for modulating NFAT activity in a subject in need thereof, the composition comprising at least one agent that inhibits the function of a septin protein and/or the expression of a septin gene and at least an agent that inhibits the function of a UEV3 protein and/or the expression of a UEV3 gene.

In one embodiment, provided herein is a composition for use in the manufacture of medicament for modulating NFAT activity in a subject in need thereof, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. Example of an embodiment of the composition is one comprising an agent targeting septin 4 and an agent targeting Septin 5. In another embodiment, the composition further comprises an agent that inhibits the function of a UEV3 protein and/or the expression of a UEV3 gene.

In one embodiment, provided herein is a composition for use in the manufacture of medicament for modulating NFAT activity in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use in the manufacture of medicament for modulating NFAT activity in a subject in need thereof, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use in the manufacture of medicament for modulating NFAT activity in a subject in need thereof, the composition comprising an agent that inhibits the function of a UEV3 protein and/or the expression of a UEV3 gene.

In one embodiment, provided herein is a composition for use in the manufacture of medicament for modulating NFAT activity in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. Example of an embodiment of the composition is one comprising an agent targeting septin 4 and an agent targeting UEV3. In another embodiment of the composition, the agent inhibits the function of at least two septin proteins and/or the expression of at least two septin genes. In one embodiment, the at least two septins are septin 4 and 5. Example of an embodiment of the composition is one comprising an agent targeting septin 4, an agent targeting Septin 5 and an agent targeting UEV3.

In one embodiment, provided herein is a composition for use in the manufacture of medicament for modulating NFAT activity in a subject in need thereof, the composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of a second septin gene. In one embodiment of the composition, the first septin is a septin 4 and the second septin is a septin 5. Example of an embodiment of the composition is one comprising an agent targeting septin 4, an agent targeting Septin 5 and an agent targeting UEV3.

In one embodiment, provided herein is a composition for use of modulating store-operated Ca2+ entry into a cell, the composition comprising an agent that inhibits the function of a septin protein and/or the expression of a septin gene. An embodiment of such a composition is one comprising an agent targeting septin 4. In another embodiment, the composition further comprises an agent that inhibits the function of a UEV3 protein and/or the expression of a UEV3 gene. In one embodiment, the septin is a septin 4. An embodiment of such a composition is one comprising an agent targeting septin 4 and an agent targeting UEV3.

In one embodiment, provided herein is a composition for use of modulating store-operated Ca2+ entry into a cell, the composition comprising an agent inhibits the function of at least two septin proteins and/or the expression of at least two septin genes. In another embodiment, the composition further comprises an agent that inhibits the function of a UEV3 protein and/or the expression of a UEV3 gene. In one embodiment, the at least two septins are septin 4 and 5. An embodiment of such a composition is one comprising an agent targeting septin 4 and targeting septin 5.

In one embodiment, provided herein is a composition for use of modulating store-operated Ca2+ entry into a cell, the composition comprising at least one agent that inhibits the function of a septin protein and/or the expression of a septin gene.

In one embodiment, provided herein is a composition for use of modulating store-operated Ca2+ entry into a cell, the composition comprising at least one agent that inhibits the function of a septin protein and/or the expression of a septin gene and at least an agent that inhibits the function of a UEV3 protein and/or the expression of a UEV3 gene.

In one embodiment, provided herein is a composition for use of modulating store-operated Ca2+ entry into a cell, the composition comprising a first agent that inhibits the function of a first septin protein and/or the expression of a first septin gene, and a second agent that inhibits the function of a second septin protein and/or the expression of a second septin gene. An embodiment of such a composition is one comprising an agent targeting septin 4 and an agent targeting septin 5. In another embodiment, the composition further comprises an agent that inhibits the function of a UEV3 protein and/or the expression of a UEV3 gene. In one embodiment, the first septin is a septin 4 and the second septin is a septin 5. An embodiment of such a composition is one comprising an agent targeting septin 4, an agent targeting septin 5 and an agent targeting UEV3.

In one embodiment, provided herein is a composition for use of modulating store-operated Ca2+ entry into a cell, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use of modulating store-operated Ca2+ entry into a cell, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use of modulating store-operated Ca2+ entry into a cell, the composition comprising an agent that inhibits the function of a UEV3 protein and/or the expression of a UEV3 gene.

In one embodiment, provided herein is a composition for use of modulating store-operated Ca2+ entry into a cell, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use of modulating store-operated Ca2+ entry into a cell, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene.

In one embodiment of the composition, the first septin is a septin 4 and the second septin is a septin 5.

In one embodiment, provided herein is a composition for use in the manufacture of medicament for modulating store-operated $Ca^{2+}$ entry into a cell, the composition comprising an agent that inhibits the function of a septin protein and/or the expression of a septin gene. In one embodiment, the septin is a septin 4. In another embodiment, the composition further comprises an agent that inhibits the function of a UEV3 protein and/or the expression of a UEV3 gene.

In one embodiment, provided herein is a composition for use in the manufacture of medicament for modulating store-operated $Ca^{2+}$ entry into a cell, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use in the manufacture of medicament for modulating store-operated Ca2+ entry into a cell, the composition comprising at least one agent that inhibits the function of a septin protein and/or the expression of a septin gene. In another embodiment, the composition further comprises an agent that inhibits the function of a UEV3 protein and/or the expression of a UEV3 gene.

In one embodiment, provided herein is a composition for use in the manufacture of medicament for modulating store-operated Ca2+ entry into a cell, the composition comprising at least one agent that inhibits the function of a septin protein and/or the expression of a septin gene and at least an agent that inhibits the function of a UEV3 protein and/or the expression of a UEV3 gene.

In one embodiment, provided herein is a composition for use in the manufacture of medicament for modulating store-operated $Ca^{2+}$ entry into a cell, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use in the manufacture of medicament for modulating store-operated $Ca^{2+}$ entry into a cell, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use in the manufacture of medicament for modulating store-operated Ca2+ entry into a cell, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use in the manufacture of medicament for modulating store-operated $Ca^{2+}$ entry into a cell, the composition comprising an agent that inhibits the function of a UEV3 protein and/or the expression of a UEV3 gene.

In one embodiment, provided herein is a composition for use in the manufacture of medicament for modulating store-operated $Ca^{2+}$ entry into a cell, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use in the manufacture of medicament for modulating store-operated $Ca^{2+}$ entry into a cell, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the composition, the first septin is a septin 4 and the second septin is a septin 5.

In one embodiment, provided herein is a composition for use treating and/or preventing hyperactivity or inappropriate immune response in a subject in need thereof, the composition comprising an agent that inhibits the function of a septin protein and/or the expression of a septin gene. In one embodiment, the septin is a septin 4. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising at least one agent that inhibits the function of a septin protein and/or the expression of a septin gene. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising at least one agent that inhibits the function of a septin protein and/or the expression of a septin gene and at least an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use treating and/or preventing hyperactivity or inappropriate immune response in a subject in need thereof, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the composition, the first septin is a septin 4 and the second septin is a septin 5.

In one embodiment, provided herein is a composition for use in the manufacture of medicament for treating and/or preventing hyperactivity or inappropriate immune response in a subject in need thereof, the composition comprising an agent that inhibits the function of a septin protein and/or the expression of a septin gene. In another embodiment, the composition further comprises an agent that inhibits the function of a UEV3 protein and/or the expression of a UEV3 gene. In one embodiment, the septin is a septin 4.

In one embodiment, provided herein is a composition for use in the manufacture of medicament for treating and/or preventing hyperactivity or inappropriate immune response in a subject in need thereof, the composition comprising an agent inhibits the function of at least two septin proteins and/or the expression of at least two septin genes. In one embodiment, the at least two septins are septin 4 and 5. In another embodiment, the composition further comprises an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising at least one agent that inhibits the function of a septin protein and/or the expression of a septin gene. In another embodiment, the composition further comprises an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising at least one agent that inhibits the function of a septin protein and/or the expression of a septin gene and at least an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the composition further comprises an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising an agent that inhibits the function of a septin 4 protein and/or the expression of a septin 4 gene. In one embodiment, the composition further comprises an agent that inhibits the function of a septin 5 protein and/or the expression of a septin 5 gene. In another embodiment, the composition further comprises an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprises an agent that inhibits the function of a septin 4 protein and/or the expression of a septin 4 gene, and an agent that inhibits the function of a septin 5 protein and/or the expression of a septin 5 gene. In one embodiment of the compositions described, the composition further comprises a pharmaceutically acceptable carrier. In another embodiment, the composition further comprises an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising an agent that inhibits the function of a UEV3 protein and/or the expression of a UEV3 gene.

In one embodiment, provided herein is a composition for use in the manufacture of medicament for treating and/or preventing hyperactivity or inappropriate immune response in a subject in need thereof, the composition comprising an agent that inhibits the function of a UEV3 protein and/or the expression of a UEV3 gene, and an agent that inhibits the function of a septin protein and/or the expression of a septin gene. In one embodiment of the composition, the septin is a septin 4. In another embodiment of the composition, the agent inhibits the function of at least two septin proteins and/or the expression of at least two septin genes. In one embodiment, the at least two septins are septin 4 and 5.

In one embodiment, provided herein is a composition for use in the manufacture of medicament for treating and/or preventing hyperactivity or inappropriate immune response in a subject in need thereof, the composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the composition, the first septin is a septin 4 and the second septin is a septin 5.

In one embodiment, provided herein is a method of modulating NFAT activity in a subject in need thereof, the method comprising administering a therapeutically effective amount of a pharmaceutical composition described herein.

In one embodiment, provided herein is a method of modulating store-operated Ca2+ entry into a cell, the method comprising administering a therapeutically effective amount of a pharmaceutical composition described herein.

In one embodiment, provided herein is a method of treating and/or preventing hyperactivity or inappropriate immune response in a subject in need thereof, the method comprising administering a therapeutically effective amount of a pharmaceutical composition described herein.

In one embodiment, provided herein is a method of modulating NFAT activity, the method comprises administering a therapeutically effective amount of a pharmaceutical composition comprising at least agent that inhibits the activity or function of at least a protein and/or the expression of at least a gene identified in Tables 1-5.

In one embodiment, provided herein is a method of modulating NFAT activity in a subject in need thereof, the method comprising administering a therapeutically effective amount of a pharmaceutical composition comprising an agent that inhibits the function of a septin protein and/or the expression of a septin gene. In one embodiment, the septin is a septin 4. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent inhibits the function of at least two septin proteins and/or the expression of at least two septin genes. In one embodiment, the at least two septins are septin 4 and 5. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising at least one agent that inhibits the function of a septin protein and/or the expression of a septin gene. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising at least one agent that inhibits the function of a septin protein and/or the expression of a septin gene and at least an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprises administering a therapeutically effective amount of a pharmaceutical composition comprising an agent that inhibits the function of a septin 4 protein and/or the expression of a septin 4 gene. In one embodiment of this method, the method further comprises administering a therapeutically effective amount of a pharmaceutical composition comprising an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprises administering a therapeutically effective amount of a pharmaceutical composition comprising an agent that inhibits the function of a septin 4 protein and/or the expression of a septin 4 gene, and an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of modulating NFAT activity in a subject in need thereof, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of the first septin gene, and a second agent that inhibits the function of a second septin protein and/or the expression of the second septin gene. In one embodiment of the method, the first septin is a septin 4 and the second septin is a septin 5.

In one embodiment, provided herein is a method modulating store-operated $Ca^{2+}$ entry into a cell, the method comprising administering a therapeutically effective amount of a pharmaceutical composition comprising an agent that inhibits the function of a protein expressed from a gene identified in Tables 1-5 and/or the expression of a gene identified in Tables 1-5.

In one embodiment, provided herein is a method of modulating store-operated Ca2+ entry into a cell, the method comprising administering a therapeutically effective amount of a pharmaceutical composition comprising an agent that inhibits the function of a septin protein and/or the expression of a septin gene. In one embodiment, the septin is a septin 4. In another embodiment, the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent inhibits the function of at least two septin proteins and/or the expression of at least two septin genes. In one embodiment, the at least two septins are septin 4 and 5. In another embodiment, the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising at least one agent that inhibits the function of a septin protein and/or the expression of a septin gene. In another embodiment, the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising at least one agent that inhibits the function of a septin protein and/or the expression of a septin gene and at least an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5.

In another embodiment, the pharmaceutical composition further comprises an agent that inhibits the function of a UEV3 protein and/or the expression of a UEV3 gene.

In one embodiment, provided herein is a method of modulating store-operated $Ca^{2+}$ entry (SOCE) into a cell, the method comprises administering a therapeutically effective amount of a pharmaceutical composition comprising an agent that inhibits the function of a septin 4 protein and/or the expression of a septin 4 gene. In one embodiment of this method, the method further comprises administering a therapeutically effective amount of a pharmaceutical composition comprising an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a method of modulating store-operated $Ca^{2+}$ entry (SOCE) into a cell, the method comprises administering a therapeutically effective amount of a pharmaceutical composition comprising an agent that inhibits the function of a septin 4 protein and/or the expression of a septin 4 gene, and an agent that inhibits the function of a septin 5 protein and/or the expression of a septin 5 gene. In another embodiment, the pharmaceutical composition further comprises an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of modulating store-operated Ca2+ entry into a cell, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of the second septin gene. In one embodiment of the composition, the first septin is a septin 4 and the second septin is a septin 5.

In some embodiments of all aspects of method of modulating store-operated Ca2+ entry into a cell, the method comprises contacting the cell with a therapeutically effective amount of a pharmaceutical composition comprising an agent that inhibits the function of a septin protein and/or the expression of a septin gene. In another embodiment, the pharmaceutical composition further comprises an agent that inhibits the function of a UEV3 protein and/or the expression of a UEV3 gene. In another embodiment, the method further comprises contacting the cell with a therapeutically effective amount of a pharmaceutical composition comprising an agent that inhibits the function of UEV3 protein and/or the expression of a UEV3 gene.

The inventors also discovered that the expression of septin 4 and 5 from RNAi-resistant cDNAs after knockdown of endogenous septin 4 and 5 partially restores signalling. In other words, at least in a cell where septin 4/5 levels are relatively low, calcium signalling via increased Ca2+ influx into the cell can be increased by adding more septin.

Accordingly, provided herein is a pharmaceutical composition comprising an agent that enhances the function of a septin protein and/or the expression of a septin gene, and a pharmaceutically acceptable carrier. In one embodiment of this pharmaceutical composition, the septin is a septin 4. In another embodiment of this pharmaceutical composition, the septin is a septin 5. In one embodiment of the pharmaceutical composition, the agent enhances the function of at least two septin proteins and/or the expression of at least two septin genes.

In one embodiment, provided herein is a pharmaceutical composition comprising at least one agent that enhances the function of a septin protein and/or the expression of a septin gene.

In another embodiment, the pharmaceutical composition comprises a first agent that enhances the function of a first septin protein and/or the expression of a first septin gene, a second agent that enhances the function of a second septin protein and/or the expression of a second septin gene, and a pharmaceutically acceptable carrier. In one embodiment of the pharmaceutical composition, the first septin is a septin 4 and the second septin is a septin 5.

In one embodiment, provided herein is a pharmaceutical composition comprising an agent that enhances the function of a septin 4 protein and/or the expression of a septin 4 gene, and a pharmaceutically acceptable carrier. In one embodiment, the pharmaceutical composition further comprises an agent that enhances the function of a septin 5 protein and/or the expression of a septin 5 gene.

In one embodiment, provided herein is a pharmaceutical composition comprising an agent that inhibits the function of a septin 4 protein and/or the expression of a septin 4 gene, an agent that inhibits the function of a septin 5 protein and/or the expression of a septin 5 gene and a pharmaceutically acceptable carrier.

In one embodiment, provided herein is a composition for use of modulating NFAT activity in a subject in need thereof, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use of modulating NFAT activity in a subject in need thereof, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use of modulating NFAT activity in a subject in need thereof, the composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a composition for use of modulating NFAT activity in a subject in need thereof, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use of modulating NFAT activity in a subject in need thereof, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for modulating NFAT activity in a subject in need thereof, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use in the manufacture of medicament for modulating NFAT activity in a subject in need thereof, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use in the manufacture of medicament for modulating NFAT activity in a subject in need thereof, the composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a composition for use in the manufacture of medicament for modulating NFAT activity in a subject in need thereof, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for modulating NFAT activity in a subject in need thereof, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a composition for use of modulating store-operated Ca2+ entry into a cell, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use of modulating store-operated Ca2+ entry into a cell, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use of modulating store-operated Ca2+ entry into a cell, the composition comprising a first agent that enhances the function of a first septin protein and/or the expression of the first septin gene, and a second agent that enhances the function of a second septin protein and/or the expression of the second septin gene. In one embodiment, the first septin is a septin 4 and the second septin is a septin 5. In one embodiment, the composition further comprises a pharmaceutically acceptable carrier.

In one embodiment, provided herein is a composition for use of modulating store-operated Ca2+ entry into a cell, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use of modulating store-operated Ca2+ entry into a cell, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for modulating store-operated Ca2+ entry into a cell, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use in the manufacture of medicament for modulating store-operated Ca2+ entry into a cell, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use in the manufacture of medicament for modulating store-operated Ca2+ entry into a cell, the composition comprising a first agent that enhances the function of a first septin protein and/or the expression of the first septin gene, and a second agent that enhances the function of a second septin protein and/or the expression of the second septin gene. In one embodiment, the first septin is a septin 4 and the second septin is a septin 5. In one embodiment, the composition further comprises a pharmaceutically acceptable carrier.

In one embodiment, provided herein is a composition for use in the manufacture of medicament for modulating store-operated Ca2+ entry into a cell, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for modulating store-operated Ca2+ entry into a cell, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a method of modulating NFAT activity in a subject in need thereof, the method comprising administering a therapeutically effective amount of a pharmaceutical composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a method of modulating NFAT activity in a subject in need thereof, the method comprising administering a therapeutically effective amount of a pharmaceutical composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a method of modulating NFAT activity in a subject in need thereof, the method comprising administering a therapeutically effective amount of a pharmaceutical composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a method of modulating NFAT activity in a subject in need thereof, the method comprising administering a therapeutically effective amount of a pharmaceutical composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a method of modulating NFAT activity in a subject in need thereof, the method comprising administering a therapeutically effective amount of a pharmaceutical composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a method of modulating store-operated Ca2+ entry into a cell, the method comprising administering a therapeutically effective amount of a pharmaceutical composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a method of modulating store-operated Ca2+ entry into a cell, the method comprising administering a therapeutically effective amount of a pharmaceutical composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a method of modulating store-operated Ca2+ entry into a cell, the method comprising administering a therapeutically effective amount of a pharmaceutical composition comprising a first agent that enhances the function of a first septin protein and/or the expression of the first septin gene, and a second agent that enhances the function of a second septin protein and/or the expression of the second septin gene. In one embodiment, the first septin is a septin 4 and the second septin is a septin 5. In one embodiment, the composition further comprises a pharmaceutically acceptable carrier.

In one embodiment, provided herein is a method of modulating store-operated Ca2+ entry into a cell, the method comprising administering a therapeutically effective amount of a pharmaceutical composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a method of modulating store-operated Ca2+ entry into a cell, the method comprising administering a therapeutically effective amount of a pharmaceutical composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment of all aspects of the methods described, the modulation of NFAT activity comprises decreasing the immune response in a subject in need thereof. In another embodiment of all aspects of the methods described, the modulation of NFAT activity comprises increasing or enhancing the immune response in a subject in need thereof. A decrease or increase in the immune response in a subject can be determined by any methods known in the art, e.g., measuring the titer of cytokines in circulation.

In one embodiment of all aspects of the methods described, the modulation of SOCE comprises decreasing $Ca^{2+}$ influx in a cell. In another embodiment of all aspects of the methods described, the modulation of SOCE comprises increasing $Ca^{2+}$ influx in a cell. The decrease or increase herein is in reference to the $Ca^{2+}$ influx in a cell in the absence of any agent added.

Assaying for any modulation of SOCE and/or NFAT activity can be performed by any method known in the art, including those described herein. Samples of circulating cells can be harvested from the subject for analysis prior to and after administration of the pharmaceutical compositions described.

In one embodiment, provided herein is a method of treating and/or preventing hyperactivity or inappropriate immune responses in a subject in need thereof, the method comprising administering a therapeutically effective amount of a pharmaceutical composition comprising at least agent that inhibits the activity or function of a protein expressed from at least a gene identified in Tables 1-5 and/or the expression of a gene identified in Tables 1-5, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing hyperactivity or inappropriate immune response, for example, an organ transplant recipient.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a septin protein and/or the expression of a septin gene. In one embodiment, the septin is a septin 4. In another embodiment, the method further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent inhibits the function of at least two septin proteins and/or the expression of at least two septin genes. In one embodiment, the at least two septins are septin 4 and 5. In one embodiment, the pharmaceutical composition further comprises a pharmaceutically acceptable carrier. In another embodiment, the method further comprises administering a therapeutically effective amount of an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising at least one agent that inhibits the function of a septin protein and/or the expression of a septin gene. In another embodiment, the pharmaceutical composition further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising at least one agent that inhibits the function of a septin protein and/or the expression of a septin gene and at least an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising a first agent that inhibits the function of a first septin protein and/or the expression of a first septin gene, and a second agent that inhibits the function of a second septin protein and/or the expression of a second septin gene. In one embodiment, the first septin is a septin 4 and the second septin is a septin 5. In another embodiment, the method further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a septin 4 protein and/or the expression of a septin 4 gene. In one embodiment, the method further comprises an agent that inhibits the function of a septin 5 protein and/or the expression of a septin 5 gene. In another embodiment, the method further comprises an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene, and an agent that inhibits the function of a septin protein and/or the expression of a septin gene. In one embodiment of the method, the septin is a septin 4. In another embodiment of the method, the agent inhibits the function of at least two septin proteins and/or the expression of at least two septin genes. In one embodiment, the at least two septins are septin 4 and 5.

In one embodiment, provided herein is a method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of a UEV3 gene, a first agent that inhibits the function of a first septin protein and/or the expression of a first septin gene, and a second agent that inhibits the function of a second septin protein and/or the expression of a second septin gene. In one embodiment of the composition, the first septin is a septin 4 and the second septin is a septin 5.

In one embodiment, provided herein is a method of treating and/or preventing hyperactivity or inappropriate immune responses in a subject in need thereof, the method comprises administering a therapeutically effective amount of a pharmaceutical composition comprising an agent that inhibits the function of a septin 4 protein and/or the expression of a septin 4 gene. In one embodiment of this method, the method further comprises administering a therapeutically effective amount of a pharmaceutical composition comprising, and an agent that inhibits the function of a septin 5 protein and/or the expression of a septin 5 gene. In one embodiment, the pharmaceutical composition further comprises a pharmaceutically acceptable carrier. In another embodiment, the method further comprises an agent that inhibits the function of a UEV3 protein and/or the expression of a UEV3 gene.

In some aspects, the hyperactivity or inappropriate immune response in a subject is associated with acute and chronic immune diseases, e.g., allergic and atopic diseases, e.g., asthma, allergic rhinitis, allergic conjunctivitis and atopic dermatitis, and to autoimmune diseases, e.g., rheumatoid arthritis, insulin-dependent diabetes, inflammatory bowel disease, autoimmune thyroiditis, hemolytic anemia and multiple sclerosis. Hyperactivity or inappropriate activity of the immune system is also involved in transplant graft rejections and graft-versus-host disease. Administering an agent that inhibits a gene identified in Tables 1-5 can down-regulate NFAT activity and/or store-operated $Ca^{2+}$ entry and thereby reduce chronic T cell activation.

In some embodiments, the genes identified in Tables 1-5 are involved in down-regulating NFAT activity and/or store-operated $Ca^{2+}$ entry. Agents that inhibit such genes can enhance NFAT activity and/or store-operated $Ca^{2+}$ entry and thereby increase immune response. Accordingly, provided herein is method of increasing immune response in a subject in need thereof, the method comprising administering a therapeutically effective amount of a pharmaceutical composition comprising at least agent that inhibits the function of a protein expressed from at least one gene identified in Tables 1-5 and/or the expression of a gene identified in Tables 1-5.

In some embodiment of some aspects of the compositions described, the composition further comprises an agent that inhibits the function of a septin 5 protein and/or the expression of a septin 5 gene.

In one embodiment of the all aspects of the methods described herein, the method further comprises selecting a subject, e.g., a subject having hyperactivity or inappropriate immune response or having a suppressed immune system. After selecting the subject, the pharmaceutical composition is administered to that subject. A skilled physician will be able to diagnose the condition diseases or disorders of the subject based on symptoms and/or biomarkers of the various conditions, diseases or disorders.

In some aspects, the subject is a mammal, for example, a human, mouse, rat, guinea pig, dog, cat, horse, cow, pig, monkey, chimpanzee, baboon, or rhesus. The methods provided herein are applicable to any subject that comprises an immune system which comprises NFAT transcription activation factors and the need for sustained $Ca^{2+}$ influx for NFAT activation.

In one embodiment, provided herein is a composition for use in increasing the immune response in a subject in need thereof, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use in increasing the immune response in a subject in need thereof, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use in increasing the immune response in a subject in need thereof, the composition comprising at least one agent that enhances the function of a septin protein and/or the expression of a septin gene. In one embodiment, the composition further comprises a pharmaceutically acceptable carrier.

In one embodiment, provided herein is a composition for use in increasing the immune response in a subject in need thereof, the composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a composition for use in increasing the immune response in a subject in need thereof, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use in increasing the immune response in a subject in need thereof, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for increasing the immune response in a subject in need thereof, the composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a composition for use in the manufacture of medicament for increasing the immune response in a subject in need thereof, the composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a composition for use in the manufacture of medicament for increasing the immune response in a subject in need thereof, the composition comprising at least one agent that enhances the function of a septin protein and/or the expression of a septin gene. In one embodiment, the composition further comprises a pharmaceutically acceptable carrier.

In one embodiment, provided herein is a composition for use in the manufacture of medicament for increasing the immune response in a subject in need thereof, the composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a composition for use in the manufacture of medicament for increasing the immune response in a subject in need thereof, the composition comprising an agent that enhances the function of a septin 4 protein and/or the expression of a septin 4 gene. In one embodiment, the composition further comprises an agent that enhances the function of a septin 5 protein and/or the expression of a septin 5 gene. In one embodiment, the composition further comprises a pharmaceutically acceptable carrier.

In one embodiment, provided herein is a composition for use in the manufacture of medicament for increasing the immune response in a subject in need thereof, the composition comprising an agent that enhances the function of a septin 4 protein and/or the expression of a septin 4 gene, and an agent that enhances the function of a septin 5 protein and/or the expression of a septin 5 gene. In one embodiment, the composition further comprises a pharmaceutically acceptable carrier.

In one embodiment, provided herein is a method for increasing the immune response in a subject in need thereof, the method comprising administering a therapeutically effective amount of a pharmaceutical composition described.

In one embodiment, provided herein is a method for increasing the immune response in a subject in need thereof, the method comprising administering a therapeutically effective amount of a pharmaceutical composition comprising an agent that enhances the function of a septin protein and/or the expression of a septin gene. In one embodiment, the septin is a septin 4. In one embodiment, the septin is a septin 5. In one embodiment, the composition further comprises a pharmaceutically acceptable carrier.

In one embodiment, provided herein is a method for increasing the immune response in a subject in need thereof, the method comprising administering a therapeutically effective amount of a pharmaceutical composition comprising an agent enhances the function of at least two septin proteins and/or the expression of at least two septin genes. In one embodiment, the at least two septins are septin 4 and 5. In one embodiment, the composition further comprises a pharmaceutically acceptable carrier.

In one embodiment, provided herein is a method for increasing the immune response in a subject in need thereof, the method comprising administering a therapeutically effective amount of a pharmaceutical composition comprising at least one agent that enhances the function of a septin protein and/or the expression of a septin gene. In one embodiment, the composition further comprises a pharmaceutically acceptable carrier.

In one embodiment, provided herein is a method for increasing the immune response in a subject in need thereof, the method comprising administering a therapeutically effective amount of a pharmaceutical composition comprising a first agent that enhances the function of a first septin protein and/or the expression of a first septin gene, and a second agent that enhances the function of a second septin protein and/or the expression of a second septin gene. In one embodiment, the first septin is a septin 4 and the second septin is a septin 5.

In one embodiment, provided herein is a method for increasing the immune response in a subject in need thereof, the method comprising administering a therapeutically effective amount of a pharmaceutical composition comprising an agent that enhances the function of a septin 4 protein and/or the expression of a septin 4 gene. In one embodiment, the composition further comprises an agent that enhances the function of a septin 5 protein and/or the expression of a septin 5 gene.

In one embodiment, provided herein is a method for increasing the immune response in a subject in need thereof, the method comprising administering a therapeutically effective amount of a pharmaceutical composition comprising an agent that enhances the function of a septin 4 protein and/or the expression of a septin 4 gene, and an agent that enhances the function of a septin 5 protein and/or the expression of a septin 5 gene.

Subjects having immunodeficiency disorders can benefit from the method described herein of increasing immune response. Immunodeficiency disorders can include or result from but not limited to common variable immunodeficiency, selective antibody deficiency (such as IgA deficiency), transient hypogammaglobulinemia of infancy, X-linked agammaglobulinemia, chronic mucocutaneous candidiasis, DiGeorge anomaly, ataxia-telangiectasia, severe combined immunodeficiency disease, Wiskott-Aldrich syndrome, X-linked lymphoproliferative syndrome, Chédiak-Higashi syndrome, chronic granulomatous disease, hyperimmunoglobulinemia E syndrome, leukocyte adhesion defects, leukocyte glucose-6-phosphate dehydrogenase deficiency, myeloperoxidase deficiency, complement component 1 (C1) inhibitor deficiency (hereditary angioedema), C3 deficiency, C6 deficiency, C7 deficiency, C8 deficiency, chemotherapy and radiation therapy, human immunodeficiency virus (HIV) infection, cancer, blood disorders (such as aplastic anemia, leukemia, and myelofibrosis), kidney failure, diabetes, liver disorders, and spleen disorders.

In some embodiments, the subject requiring enhancing of the immune response suffers from a T-cell immunodeficiency disease. In some embodiments, the T-cell immunodeficiency disease include but are limited to the following: adenosine deaminase deficiency, ataxia telangiectasia, Chronic mucocutaneous candidiasis, DiGeorge syndrome, Purine nucleoside phosphorylase deficiency, severe combined immunodeficiencies (SCID), and Wiskott-Aldrich syndrome (WAS).

In one embodiment, the subject who requires increased or enhanced the immune response is one who is suffering from an immunodeficiency disorder selected from a group consisting of HIV (human immunodeficiency virus) and AIDS (acquired immunodeficiency syndrome), X-linked agammaglobulinemia, selective IgA deficiency, Wiskott-Aldrich syndrome, chronic granulomatous disease, leukocyte adhesion defects, Bruton disease, kidney failure, and combined immunodeficiency disease.

In one embodiment, the subject who requires increased or enhanced the immune response or requires the modulation of NFAT activity is one who is suffering from a cell proliferation disease or disorder.

In one embodiment, the cell proliferation disease or disorder is a neoplastic cell proliferation disorder.

In one embodiment, the neoplastic cell proliferation disorder is a therapy resistant cancer, a metastasis or malignant cancer.

In one embodiment, the subject who requires the modulation of NFAT activity is one who is suffering from a cardiovascular disorder.

In one embodiment, the subject who requires increased or enhanced the immune response is one who the cardiovascular disorders is cardiac hypertrophy, restenosis, atherosclerosis, or angiogenesis.

In one embodiment, the subject who requires the modulation of NFATactivity is one who is suffering from a bone disease associated with excessive osteoclast formation and the excessive activity needs to be suppressed.

In one embodiment, the subject who requires the modulation of NFATactivity is one who is suffering from an angiogenic disease or disorder.

In one embodiment, the angiogenesis disorder is associated with VEGF-induced and IL-1 induced gene expression.

In one embodiment, the angiogenesis disorder is selected from a group consisting of cancer, age-related macular degeneration, diabetic retinopathy; rheumatoid arthritis; Alzheimer's disease; obesity and endometriosis.

In one embodiment, provided herein is a method of treating a cell proliferation disease or disorder in a subject in need thereof, the method comprising administering a therapeutically effective amount of a pharmaceutical composition comprising at least one agent that inhibits the activity or function of a protein expressed from at least one gene identified in Tables 1-5 and/or the expression of a gene identified in Tables 1-5, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing a cell proliferation disease or disorder. In some embodiment, the cell proliferation disease or disorder is a neoplastic cell proliferation disorder and the neoplastic cell proliferation disorder is a therapy resistant cancer, a metastasis or malignant cancer.

In one embodiment, provided herein is a method of treating a cell proliferation disease or disorder in a subject in need thereof, the method comprising administering a therapeutically effective amount of a pharmaceutical composition comprising at least one agent that enhances the activity or function of a protein expressed from at least one gene identified in Tables 1-5 and/or increases the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). For example, septin 4 and/or septin 5.

As used herein, cell proliferation disease or disorder is a neoplastic cell proliferation disorder, such as a therapy resistant cancer, a metastasis or malignant cancer. In one embodiment, the methods described herein are applied to subject who has or is at risk of having a metastasis or malignant cancer. The metastasis or malignant cancer can also be a recurring or relapsed cancer, after the subject has been treated with conventional cancer therapy such as radiation and/or chemotherapy. Accordingly, the neoplastic cell proliferation disorder is a therapy resistant cancer. Other cancers include but are not limited to solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma;

osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In another embodiment, provided herein is a method of treating a cardiovascular disorder in a subject in need thereof, the method comprising administering a therapeutically effective amount of a pharmaceutical composition comprising an agent that inhibits the activity or function of a protein expressed from a gene identified in Tables 1-5 and/or the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). The cardiovascular disorders are cardiac hypertrophy, restenosis, atherosclerosis, or angiogenesis.

In another embodiment, provided herein is a method of treating a cardiovascular disorder in a subject in need thereof, the method comprising administering a therapeutically effective amount of a pharmaceutical composition comprising at least agent that enhances the activity or function of a protein expressed from at least one gene identified in Tables 1-5 and/or increases the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). For example, septin 4 and/or septin 5.

Cardiovascular disease is the major cause of death in industrialized nations. Targeted intervention in calcineurin, a calmodulin-dependent, calcium-activated phosphatase and its substrate, nuclear factor of activated T cells (NFAT), was demonstrated to be effective in the treatment of cardiovascular diseases. In one embodiment, provided herein is a method of treating a cardiovascular disorder in a subject in need thereof, the method comprising administering a therapeutically effective amount of a pharmaceutical composition comprising an agent that inhibits the activity or function of a protein expressed from a gene identified in Tables 1-5 and/or the expression of a gene identified in Tables 1-5, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing a cardiovascular disorder. Cardiovascular disorders including cardiac hypertrophy, restenosis, atherosclerosis, and angiogenesis.

Since there is a potential role for NFAT in axon re-growth and regeneration following axonal injury, modulating NFAT activity after such injury can promote axonal re-growth and regeneration. Accordingly, in one embodiment, provided herein is a method of treating an injury to the nervous system in a subject in need thereof, the method comprising administering a therapeutically effective amount of a pharmaceutical composition comprising an agent that inhibits the activity or function of a protein expressed from a gene identified in Tables 1-5 and/or the expression of a gene identified in Tables 1-5, wherein the gene is not calcineurin, calmodulin, Stim1, Stim2, Orai1 or dual-specificity tyrosine-(Y)-phosphorylation regulated kinase 2 (DYRK2).

In another embodiment, provided herein is a method of treating an injury to the nervous system in a subject in need thereof, the method comprising administering a therapeutically effective amount of a pharmaceutical composition comprising at least one agent that enhances the activity or function of a protein expressed from at least one gene identified in Tables 1-5 and/or increases the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). For example, the agent enhances the activity or function of a protein expressed from the septin 4 and/or septin 5 genes.

Excessive osteoclast formation is characteristic of a variety of bone diseases such as rheumatoid arthritis. Hence a strategy for suppressing the excessive osteoclast formation can be novel therapeutic approach for the treatment of bone disease. Accordingly, in one embodiment, provided herein is a method of treating a bone disease in a subject in need thereof, the method comprising administering a therapeutically effective amount of a pharmaceutical composition comprising at least an agent that inhibits the activity or function of a protein expressed from at least one gene identified in Tables 1-5 and/or inhibits the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). The method comprises suppressing the excessive osteoclast formation and activity.

In one embodiment, provided herein is a method of treating diabetes in a subject in need thereof, the method comprising administering a therapeutically effective amount of a pharmaceutical composition comprising at least one agent that inhibits the activity or function of a protein expressed from at least one gene identified in Tables 1-5 and/or inhibits the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing diabetes.

In one embodiment, provided herein is a method of treating an angiogenic disease or disorder in a subject in need thereof, the method comprising administering a therapeutically effective amount of a pharmaceutical composition comprising at least one agent that inhibits the activity or function of a protein expressed from at least one gene identified in Tables 1-5 and/or inhibits the expression of at least one gene identified in Tables 1-5, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing an angiogenesis. In some embodiments, the angiogenic disease or disorder is related to VEGF-induced and IL-1 induced gene expression.

In some aspects, the angiogenesis disorder is selected from a group consisting of cancer, age-related macular degeneration, diabetic retinopathy, rheumatoid arthritis, Alzheimer's disease, obesity and endometriosis.

In one embodiment, provided herein is a method of promoting or inhibiting T cell energy in a subject in need thereof, the method comprising administering a therapeutically effective amount of a pharmaceutical composition comprising an agent that inhibits the activity or function of a protein expressed from a gene identified in Tables 1-5 and/or the expression of a gene identified in Tables 1-5, wherein the gene is not calcineurin, calmodulin, Stim1, Stim2, Orai1 or dual-specificity tyrosine-(Y)-phosphorylation regulated kinase 2 (DYRK2).

In one embodiment, the agent that inhibits the activity or function of a protein expressed from a gene identified in Tables 1-5 and/or the expression of the gene identified in Tables 1-5 can be administered to the subject together with additional therapeutic agents, cancer therapy, immunosuppressant therapy, immunodeficiency therapy, steroid therapy, and psychotherapy.

In one embodiment, the agent that inhibits the activity or function of a protein expressed from a gene identified in Tables 1-5 and/or the expression of the gene identified in Tables 1-5 is a small molecule, nucleic acid, nucleic acid analogue, protein, antibody, peptide, aptamer or variants or fragments thereof. Such an agent can take the form of any entity which is normally not present or not present at the levels being administered to the cell or organism.

Other forms of inhibitors include a nucleic acid agent which is an RNAi agent such as a siRNA, shRNA, miRNA, dsRNA or ribozyme or variants thereof.

In one embodiment of all aspects of the pharmaceutical composition or method described herein, the agent is a nucleic acid inhibitor which inhibits gene expression.

In one embodiment of all aspects of the pharmaceutical composition or method described herein, the nucleic acid inhibitor is an siRNA or shRNA.

In one embodiment of all aspects of the pharmaceutical composition or method described herein, the siRNA or shRNA comprises the sequence of GGGUCAACAUCGUGCCUAU (SEQ ID NO: 19).

In one embodiment, the effects of the inhibitory agent such as an RNAi agent can be determined by measuring the $Ca^{2+}$ fluxes in a treated cell using any method known in the art, e.g., Feske et al., (2006) Nature 441, 179-815 or a high-throughput assay as described below.

HTS $Ca^{2+}$ Assay—HeLa cells are transfected with 20 nM siRNA (siGenome SmartPools obtained from DHARMACON/ThermoFischer) in 96-well plates. The siRNA tested are against the gene expression of ACSBG1, ActB, ALCAM, ATN1, ATP6V0D1, C1ORF123, C20ORF96, C6ORF191, C8ORF42, CCDC125, CCNB2, CNTN3, CPEB4, CPT2, DKFZP686A01247, DNAJC5G, ELMOD1, FAM108C1, FAS, FASTKD5, FLJ21986, FRMPD1, GGA3, GLT1D1, GOSR2, GPD1, GPD1L, GPR23, GSTM2, IL9, KCNIP2, KCCN4, KIAA0284, KRT35, KRTAP21-2, KPTAP5-8, L1TD1, LMAN1L, LMNB1, LOC338829, LOC388381, LYZL1, MGC34829, MRS2L, MYO9A, NAPA, NDUFA5, NIPA2, OSTM1, PASD1, PIK4CA, PILRA, PJA1, PRRT1, PRSS1, RAD9B, RNF185, RNPEPL1, RPGR, SEPT4/PNUTL2, SFXN5, SLC41A3, SPTLC2, STAM, STIM2, STIM1, ORA1, STXBP2, TMED10, TMEM110, TMEM142A, TNFSRF18, TRIM59, UBC, UEVLD, XKR5, ZNF289, ZNF706, ZZEF1 and JPH2. The names of these genes are shown in Table 5.

After 72 hours, the cells are loaded with FURA2/AM and intra-cellular $Ca^{2+}$ traces are measured on a Flexstation III kinetic fluorescent imager (Molecular Devices). Cells are then stimulated with 1 uM thapsigargin (TG) and 3 mM EGTA for 4 minutes, then 2 mM $CaCl_2$ for an additional 6 minutes. Each gene-specific siRNA is analysed using 4 biological replicates, and positive hits are identified if at least 2 replicates showed a decrease in the second peak of Fura2 fluorescence greater or equal to 20% of the control. For each hit, one representative Fura2 trace is represented along with the corresponding trace from siControl or siSTIM1-treated cells. Exemplary $Ca^{2+}$ traces are shown in FIG. 38-70.

For single cell imaging of the calcium fluxes due to the treatment of the respective siRNA, the method of Feske et al., (2006) supra can be used and the method is briefly described below.

After the indicated siRNA treatment, i.e., treatment with siRNA against the gene expression of ACSBG1, ActB, ALCAM, ATN1, ATP6V0D1, C1ORF123, C20ORF96, C6ORF191, C8ORF42, CCDC125, CCNB2, CNTN3, CPEB4, CPT2, DKFZP686A01247, DNAJC5G, ELMOD1, FAM108C1, FAS, FASTKD5, FLJ21986, FRMPD1, GGA3, GLTID1, GOSR2, GPD1, GPD1L, GPR23, GSTM2, IL9, KCNIP2, KCCN4, KIAA0284, KRT35, KRTAP21-2, KPTAP5-8, L1TD1, LMAN1L, LMNB1, LOC338829, LOC388381, LYZL1, MGC34829, MRS2L, MYO9A, NAPA, NDUFA5, NIPA2, OSTM1, PASD1, PIK4CA, PILRA, PJA1, PRRT1, PRSS1, RAD9B, RNF185, RNPEPL1, RPGR, SEPT4/PNUTL2, SFXN5, SLC41A3, SPTLC2, STAM, STIM2, STIM1, ORA1, STXBP2, TMED10, TMEM110, TMEM142A, TNFSRF18, TRIM59, UBC, UEVLD, XKR5, ZNF289, ZNF706, ZZEF1 and JPH2, the HeLa cells were loaded with the calcium indicator FURA-2, using the cell-permeant precursor FURA-2-AM. Coverslips are mounted in a flow chamber on the stage of a microscope for fluorescence imaging. Fluorescence emission is monitored at 510 nm, with alternating excitation at 340 nm and 380 nm. Initial perfusion is with calcium-free Ringer solution, then with calcium-free Ringer solution containing 1 micromolar thapsigargin to release calcium from ER stores (the first low peak in the graphs), and finally with ordinary Ringer solution that contains calcium and therefore supports calcium influx through store-operated channels (the second higher peak in the graphs). Fura-2 fluorescence data are then converted to cytoplasmic calcium concentrations as described in Feske et al (2006) Nature 441, 179-185. Cytoplasmic calcium concentration (nM) is plotted on the vertical axis, and time (s) on the horizontal axis.

Cells treated with control siRNA are also included in each experiment. The siRNAs that are effective in this assay produced differences in one or more of the following parameters: rate of rise of the signal due to store-operated calcium entry, its peak height, or its plateau. Exemplary of single cell $Ca^{2+}$ traces are shown in FIG. 58-70.

In some embodiments, it is possible that a siRNA, by itself, can target more than one gene, especially when the genes are highly related in sequence. For example, the siRNA targeting SEPT4/PNUTL2 also targets SEPT5 gene expression, leading to reduced SEPT5 protein (see in FIG. 58).

In one embodiment, the agent that enhances the activity or function of a protein expressed from a gene identified in Tables 1-5 and/or the expression of the gene identified in Tables 1-5 is a small molecule, nucleic acid, nucleic acid analogue, protein, antibody, peptide, aptamer or variants or fragments thereof. Such an agent can take the form of any entity which is normally not present or not present at the levels being administered to the cell or organism.

In one embodiment, the agent that enhances the expression of a septin gene is an expression vector. In one embodiment, the expression vector is a viral expression vector. In one embodiment, the expression vector comprises the coding sequence of a septin gene, e.g., the messenger RNA of a septin gene, mRNA of SEPT 4 or mRNA of SEPT 5. Methods of constructing an expression vector comprising the coding sequence of a septin gene is known in the art.

Calcineurin/NFAT Axis in Vertebrates

Calcineurin is a calmodulin-dependent, calcium-activated protein phosphatase composed of catalytic and regulatory subunits. The serine/threonine-specific phosphatase functions within signal transduction pathways that regulate gene expression and biological responses in many developmentally important cell types. Calcineurin signaling was first defined in T lymphocytes as a regulator of nuclear factor of activated T cells (NFAT) transcription factor nuclear translocation and activation.

The NFAT transcription factor family consists of five members NFAT1, NFAT2, NFAT3, NFAT4 and NFAT5. NFAT1-4 are regulated by calcium signaling. All family members contain the rel DNA binding domain, however only NFAT1-4 contains the $Ca^{2+}$ sensor/translocation domain. The activation process of the NFAT transcription factor family is tightly regulated by calcium-dependent phosphatase calcineurin. NFAT activation is dependent upon a rise in intracellular $Ca^{2+}$, which activates the serine/threonine phosphatase, calcineurin. The increase in intracellular calcium levels can occur, e.g., by means of store-operated calcium entry (SOCE). Activated calcineurin rapidly dephosphorylates the serine rich region (SRR) and SP-repeats in the amino termini of NFAT proteins resulting in a conformational change that exposes a nuclear localization signal resulting in NFAT nuclear import.

Opposing this, the nuclear export of NFAT requires the sequential re-phosphorylation of this domain by several kinases including GSK-3β. Other post-translational modifications such as acetylation and sumoylation, as well as phosphorylation events distinct from those in the $Ca^{2+}$/translocation domain, also modulate NFAT transcriptional activity.

As the sole $Ca^{2+}$ entry mechanism in a variety of non-excitable cells, store-operated calcium (SOC) influx is important in $Ca^{2+}$ signaling and many other cellular processes, in particular, for the calcium-release-activated calcium (CRAC) channels in T lymphocytes. The CRAC channels are essential to the immune response, sustained activity of CRAC channels being required for gene expression and proliferation of the activated T cell. STIM1 and Orai 1 function as $Ca^{2+}$ sensors of changes in the intracellular $Ca^{2+}$ stores to activate CRAC channels.

NFAT functions as an integrator of multiple signaling pathways and achieves this through a combinatorial mechanism of transcriptional regulation. Other cellular signaling pathways including MAP kinase, WNT or NOTCH. NFAT, along with other transcription factors and co-activators, integrates signaling pathways by binding to chromatin in a highly specific and concerted fashion only upon receiving the appropriate signaling cues. The composition of the NFAT transcription complexes assembled at the promoter and enhancer elements of target genes is thus dependent upon both signaling and chromatin context, which determines when and where NFAT complexes activate or repress transcription. The NFAT family of transcription factors functions in combination with other transcription factors and co-activators to regulate genes central for many developmental systems. NFAT proteins have been found to be involved in numerous cellular processes, for example, cell cycle regulation, cell differentiation, cell survival, angiogenesis, tumor cell invasion and metastasis, myogenesis, chondrocyte differentiation and the development of the cardiovascular system, the complex nervous system, the recombinational immune system, and the cardiovascular system in a vertebrate (Graef I A et. al., Curr Opin Genet Dev. 2001, 11:505-12; Macian F., Nat Rev Immunol. 2005; 5:472-84; Schulz and Yutzey, Dev Biol. 2004, 266:1-16; Crabtree and Olson, Cell. 2002; 109(Suppl):567-79).

The development, activation, and maintenance of the immune system is dependent on several factors, of which $Ca^{2+}$ influx and the activation of transcription factors are two of the most important factors. NFAT proteins are expressed in immune cells and play a key role in eliciting immune responses. $Ca^{2+}$/calcineurin/NFAT signaling pathway is essential for lymphocyte activation, for short-term as well as long-term responses by immune-system cells, which include T and B cell proliferation and differentiation.

The activated NFAT proteins, in turn, induce transcription of cytokine genes which are required for an immune response. For example, NFAT1 and NFAT2 are much higher in memory and effector T cells than in naïve T cells, suggesting that they play an important function in memory T cells activation by way of IL-2 cytokine production in the memory T cells.

Calcineurin is indirectly responsible for activating the transcription of interleukin 2 (IL-2) that stimulates the growth and differentiation of T cell response. When an antigen presenting cell interacts with a T cell receptor on T cells, there is an increase in the cytoplasmic level of calcium, (Yamashita M., et. al., J Exp Med. 2000, 191: 1869-1880) which activates calcineurin, by binding a regulatory subunit and activating calmodulin binding. Calcineurin induces different transcription factors such as NFATs that are important in the transcription of IL-2 genes. Calcineurin dephosphorylates the cytoplasmic component of NFATs, transcription factors that can then go into the nucleus and turn on genes involved in IL-2 synthesis. IL-2 activates T-helper lymphocytes and induces the production of other cytokines. In this way, it governs the action of cytotoxic lymphocytes and NK cells. The amount of IL-2 being produced by the T-helper cells is believed to influence the extent of the immune response significantly. In immunosuppressive therapy, calcineurin is inhibited by cyclosporin, pimecrolimus (Elidel) and tacrolimus (FK506)—these drugs are known as calcineurin inhibitors.

Interleukin-21 (IL-21), a potent immunomodulatory four-alpha-helical-bundle type I cytokine, is produced by NKT and CD4(+) T cells and has pleiotropic effects on both innate and adaptive immune responses. These actions include positive effects such as enhanced proliferation of lymphoid cells, increased cytotoxicity of CD8(+) T cells and natural killer (NK) cells, and differentiation of B cells into plasma cells. Conversely, IL-21 also has direct inhibitory effects on the antigen-presenting function of dendritic cells and can be proapoptotic for B cells and NK cells. IL-21 is also produced by Th17 cells and is a critical regulator of Th17 development. The regulatory activity of IL-21 is modulated by the differentiation state of its target cells as well as by other cytokines or costimulatory molecules. IL-21 has potent antitumor activity but is also associated with the development of autoimmune disease. IL-21 transcription is dependent on a calcium signal and NFAT sites, and IL-21 requires Stat3 for its signaling. The key to harnessing the power of IL-21 will depend on better understanding its range of biological actions, its mechanism of action, and the molecular basis of regulation of expression of IL-21 and its receptor (Spolski and Leonard, Annu Rev Immunol. 2008, 26:57-79).

NFAT has also been shown to the crucial sensor of T cell receptor signaling in the interleukin (IL)-17 promoter and expression. IL-17 is a pro-inflammatory cytokine produced by T helper type 17 (Th17) cells, which have critical role in immunity to extracellular bacteria and the pathogenesis of several autoimmune disorders and asthma. There are two NFAT binding sites in the minimal promoter of IL-17. (Liu et. al., J Biol. Chem. 2004, 279:52762-71, Sundrud and Rao, Curr Opin Immunol. 2007, 9(3):287-93).

Central tolerance in the thymus is the primary mechanism for deleting autoreactive T cells. Despite this, escape of self-reactive T lymphocytes into the periphery reveals the threat of autoimmunity. To compensate for its imperfection, the thymus also produces a naturally occurring subset of Foxp3+CD4+CD25+ regulatory T cells with suppressive function, capable of controlling autoreactive cells. Foxp3 (forkhead box P3), the lineage-specific marker for this subset of cells, is crucial to their thymic development and peripheral function. NFAT, in cooperation with Foxp 3, are crucial for the phenotype, development, maintenance, and function of these regulatory T cells, and the ultimately for maintaining immunological tolerance in an organism (Wu et. al, Cell. 2006, 126:375-87; Rudensky A Y, et. al., Cell. 2006, 126:253-6; Mays and Chen, Cell Res. 2007, 17:904-18; Oh-Hora M, et. al., 2008, Nat. Immunol. 2008, 9:432-43).

Inhibitory modulation of NFAT function can be a strategy for immunosuppressive therapy, a bottleneck of T cell receptor-dependent activation of T cells and for promoting T-cell energy.

Recently report show that NFAT is involved in axonal growth and guidance during vertebrate development (Nguyen and Di Giovanni, Int J Dev Neurosci. 2008, 26: 141-145). The extension and organization of sensory axon projection and commissural axon growth are both dependent upon NFAT activity. Triple NFAT2/3/4 mutant mice demonstrate that the extension and organization of sensory axon projection and commissural axon growth are both dependent upon NFAT activity. Neurotrophin and L-type calcium channel signaling modulate intracellular calcium levels to regulate the nuclear import and transcriptional activity of NFAT by activating the phosphatase calcineurin. The rephosphorylation and subsequent export of NFAT from the nucleus is mediated by several kinases, including GSK-3 beta, which contribute to the fine tuning of NFAT transcriptional activity in neurons. Thus there is a potential role for NFAT in axon re-growth and regeneration following axonal injury.

The calcium/calcineurin/NFAT signaling is also involved in cardiovascular and skeletal muscle development in vertebrates. Inhibition, mutation, or forced expression of calcineurin pathway genes result in defects or alterations in cardiomyocyte maturation, heart valve formation, vascular development, skeletal muscle differentiation and fiber-type switching, and cardiac and skeletal muscle hypertrophy (Schulz and Yutzey, Dev Biol. 2004, 266:1-16). Inhibition of calcineurin-NFAT is a negative regulator of cardiac myocyte (CM) hypertrophy (Fiedler et. al., Proc Natl Acad Sci USA. 2002, 99:11363-8). Since cardiovascular disease is the major cause of death in industrialized nations. Targeted intervention in calcineurin, a calmodulin-dependent, calcium-activated phosphatase and its substrate, nuclear factor of activated T cells (NFAT), can be effective in the treatment of cardiovascular diseases. Calcineurin/NFAT signaling pathway inhibition can be a therapeutic strategy in cardiovascular disorders including cardiac hypertrophy, restenosis, atherosclerosis, and angiogenesis.

Osteoclasts are multinucleated cells of monocyte/macrophage origin that degrade bone matrix. The differentiation of osteoclasts is dependent on a tumor necrosis factor (TNF) family cytokine, receptor activator of nuclear factor (NF)-kappaB ligand (RANKL), as well as macrophage colony-stimulating factor (M-CSF). Congenital lack of osteoclasts causes osteopetrosis. Among the essential molecules for osteoclastogenesis, including TNF receptor-associated factor (TRAF) 6, NF-kappaB, c-Fos and NFAT2. NFAT2 is activated by calcium signaling and binds to its own promoter, thus switching on an autoregulatory loop. C-Fos, as an activator protein (AP)-1 complex, is required for the autoamplification of NFAT2, enabling the robust induction of NFAT2. NFAT2 cooperates with other transcriptional partners to activate osteoclast-specific genes. Thus, NFAT2, the master transcription factor for osteoclast differentiation (Takayanagi, Ann. N.Y. Acad. Sci. 2007, 1116: 227-237). Excessive osteoclast formation characteristic of a variety of bone diseases. In rheumatoid arthritis, bone destruction is caused by the enhanced activity of osteoclasts. Suppressing the excessive osteoclast formation and/or the enhanced activity of osteoclasts by way of modulating the calcineurin/NFAT axis can be a strategy for the treatment and/or prevention of a variety of bone diseases.

Calcineurin/NFAT signaling axis is also important in the renal regulation of water homeostasis. A new member of the nuclear factor of activated T cells (NFAT) family has recently been discovered, NFAT 5, or Ton EBP. Ton EBP is the only known mammalian transcription factor that regulates gene expression in response to hypertonicity (Tyagi and Nandhakumar, Indian J Exp Biol. 2008, 46:89-93).

Deregulations of calcineurin/NFAT signaling and/or abnormal expression of its components have recently been reported in solid tumors of epithelial origin, lymphoma and lymphoid leukemia. Mouse models of human T-ALL/lymphoma shows that persistent activation of calcineurin/NFAT signaling is pro-oncogenic in vivo (Medyouf and Ghysdael, Cell Cycle. 2008, 7:297-303). Experimental evidence indicate the critical role of NFAT3 in some carcinogen-induced cell transformation and tumorigenicity (Lu and Huan, Curr Cancer Drug Targets. 2007, 7:343-53). There is an emerging role for $Ca^{2+}$/calcineurin/NFAT signaling in cancerogenesis (Buchholz and Ellenrieder, Cell Cycle. 2007, 6(1):16-9). Modulation of NFAT can be suitable for the treatment of neoplastic cell proliferation diseases such as cancers.

Deregulation of calcineurin/NFAT signaling is also reported to be associated with defects in vertebrate development, since NFAT family of transcription factors are major regulators of vertebrate development. In human trisomy 21 or Down's syndrome, there is a human chromosome 21. Anon J R, et al. (Nature. 2006, 441:595-600) and Gwack Y, et al., (Nature, 2006, 441:646-50) report of two genes, DSCR1 and DYRK1A, that lie within the critical region of human chromosome 21 and the gene products act synergistically to inhibit the activation of NFATc transcription factors. The increase in expression of DSCR1 and DYRK1A can lead to a decrease in NFAT activation. In the mouse models of Down's syndrome, which are actually Dscr1- and Dyrk1a-overexpressing mice, these mice are found to be calcineurin- and NFAT-deficient. The reduced amount of NFAT can be associated with many of the features of Down's syndrome and also in many human diseases such as autoimmune disease and cancer as described herein.

Pancreatic beta-cells in the islet of Langerhans produce the hormone insulin, which maintains blood glucose homeostasis. Perturbations in beta-cell function may lead to impairment of insulin production and secretion and the onset of diabetes mellitus. Several essential beta-cell factors have been identified that are required for normal beta-cell function, including six genes that when mutated give rise to inherited forms of diabetes known as Maturity Onset Diabetes of the Young (MODY) (Heit, Bioessays. 2007, 29(10): 1011-21). Mice with a beta-cell-specific deletion of the calcineurin phosphatase regulatory subunit, calcineurin b1

(Cnb1), develop age-dependent diabetes characterized by decreased beta-cell proliferation and mass, reduced pancreatic insulin content and hypoinsulinaemia. Moreover, beta-cells lacking Cnb1 have a reduced expression of established regulators of beta-cell proliferation. Conditional expression of active NFAT1 in Cnb1-deficient beta-cells rescues these defects and prevents diabetes. In normal adult beta-cells, conditional NFAT activation promotes the expression of cell-cycle regulators and increases beta-cell proliferation and mass, resulting in hyperinsulinaemia. Calcineurin/NFAT signaling regulates pancreatic beta-cell growth and function. Conditional NFAT activation also induces the expression of genes critical for beta-cell endocrine function, including all six genes mutated in hereditary forms of monogenic type 2 diabetes (Heit, Nature. 2006, 443(7109):345-9). Modulation of NFAT provides novel therapeutic approaches for the treatment of diabetes and for the prevention of diabetes for those at risk of developing diabetes.

There are evidences that the activation of calcineurin and NFAT and subsequently the PKC and the MEK/ERK MAPK pathways are induced by VEGF-A and IL-1 in endothelial cells. Gene activation via PLC-gamma provides VEGF with the potency to induce a wide spectrum of genes including many also upregulated by IL-1 (Schweighofer, Clin Hemorheol Microcirc. 2007, 37:57-62). Modulate calcineurin/NFAT can reduce VEGF-induced gene expression and reduced sprouting in undesired angiogenesis, such as in cancer, age-related macular degeneration, diabetic retinopathy; rheumatoid arthritis; Alzheimer's disease; obesity and endometriosis.

Septins and their Functions

Septins are a highly conserved superfamily of GTP-binding proteins. They consist of a central conserved GTP-binding domain flanked by N- and C-terminal extensions of varying length and divergent sequence. Many septin family members undergo complex alternative splicing, making the number of unique septin polypeptides even greater. These proteins associate with each other to form ordered oligomeric complexes and filaments, which are thought to regulate a vast array of cellular processes, including membrane traffic, phagocytosis, spermatogenesis, and dendrite branching.

In eukaryotic cells, septins regulate the organization, dynamics and architecture of the cytoskeleton, by forming highly structured homo- and heteromeric protein complexes at or near membranes. The crystal structures of septin 2 and a septin 7-6-2-2-6-7 oligomer show that septins interact through two types of interfaces—one involving the guanine nucleotide binding region (G dimer interface) and the second involving apposed N and C-terminal regions (N-C interface). Septins are classified into groups based on evolutionary relatedness, and septin oligomers contain septins from different groups. Within a septin filament (such as 7-6-2-2-6-7), it is thought that a given septin might be replaced by another septin from that same group, for example, septin 2 might be replaced by the group III septins 1, 4 or 5.

SEPT1 is believed to be involved in filament-forming cytoskeletal GTPase and may play a role in cytokinesis.

SEPT2 has been found to be involved in filament-forming cytoskeletal GTPase and is required for normal organization of the actin cytoskeleton. SEPT2 also plays a role in the biogenesis of polarized columnar-shaped epithelium by maintaining polyglutamylated microtubules and by impeding MAP4 binding to tubulin. Data also supports a role for SEPT2 in the progression through mitosis. SEPT2 forms a scaffold at the midplane of the mitotic spindle required to maintain CENPE localization at kinetochores and consequently chromosome congression. During anaphase, it may be required for chromosome segregation and spindle elongation. It also plays a role in ciliogenesis and collective cell movements and may play a role in the internalization of two intracellular microbial pathogens, *Listeria monocytogenes* and *Shigella flexneri*.

SEPT3 is believed to be involved in filament-forming cytoskeletal GTPase and may also play a role in cytokinesis.

SEPT4 is hypothesized to be involved in filament-forming cytoskeletal GTPase. In addition, SEPT4 may play a role in cytokinesis and in platelet secretion. Isoform ARTS of SEPT4 is required for the induction of cell death mediated by TGF-beta and by other apoptotic stimuli.

SEPT5 is believed to be involved in filament-forming cytoskeletal GTPase and may play a role in cytokinesis and in platelet secretion.

SEPT6 is involved in filament-forming cytoskeletal GTPase and is required for normal organization of the actin cytoskeleton. SEPT6 is also involved in cytokinesis and may play a role in HCV RNA replication.

SEPT7 is involved in filament-forming cytoskeletal GTPase and is required for normal organization of the actin cytoskeleton and for normal progress through mitosis. SEPT7 is also involved in cytokinesis and is required for normal association of CENPE with the kinetochore. It also plays a role in ciliogenesis and collective cell movements.

SEPT8 is believed to be involved in filament-forming cytoskeletal GTPase and may play a role in cytokinesis and in platelet secretion.

SEPT9 is believed to be involved in filament-forming cytoskeletal GTPase and may play a role in cytokinesis.

SEPT10 is involved in filament-forming cytoskeletal GTPase and may play a role in cytokinesis.

SEPT11 is involved in filament-forming cytoskeletal GTPase. It may also play a role in cytokinesis and in the cytoarchitecture of neurons, including dendritic arborization and dendritic spines, and in GABAergic synaptic connectivity.

SEPT12 is believed to be involved in filament-forming cytoskeletal GTPase and may also play a role in cytokinesis.

SEPT13 is a conserved GTP-binding protein that is believed to function as a dynamic, regulatable scaffold for the recruitment of other proteins. It is thought to be involved in membrane dynamics, vesicle trafficking, apoptosis, and cytoskeleton remodeling, as well as infection, neurodegeneration, and neoplasia.

SEPT14 is believed to be involved in filament-forming cytoskeletal GTPase and may also play a role in cytokinesis.

Some lipids and proteins that may participate in these membrane domains are known. Septins bind phosphoinositides, at least in part through a conserved polybasic region (Bertin et al., 2010; Casamayor and Snyder, 2003; Zhang et al., 1999), which in mammalian SEPT4 preferentially binds phosphatidylinositol 4,5-bisphosphate (PIP2) and to a lesser extent to phosphatidylinositol 3,4,5-trisphosphate (PIP3) (Zhang et al., 1999). The presence of target phosphoinositides promotes the formation of organized yeast septin filaments on lipid monolayers (Bertin et al., 2010) and mammalian septin 7-6-2-2-6-7 filamentson giant liposomes (Tanaka-Takiguchi et al., 2009). Septin binding may promote formation of lipid domains in the membrane, by a mechanism described for other peripheral membrane proteins (Gambhir et al., 2004; Mbamala et al., 2005; McLaughlin and Murray, 2005; Rauch et al., 2002), and this lateral segregation of lipids and proteins might be further accentuated by the protein-lipid interactions of STIM and ORAI. The polybasic region at the C-terminus of STIM1 is targeted to the plasma membrane by interactions with PIP2 and PIP3 (Carrasco and Meyer, 2011; Ercan et al., 2010; Liou et al., 2007; Park et al., 2009; Walsh et al., 2010). Productive interaction of STIM1 and ORAI1 is preferentially enhanced by PIP2 in ordered lipid regions, derived from PIP5KIβ, and inhibited by PIP2 in disordered regions, derived from PIP5KIγ (Calloway et al., 2011). Because diffusion of free PIP2 in the plasma membrane is rapid, its confinement to separate definable domains implies diffusion barriers or binding interactions that reduce the concentration of freely diffusing PIP2 (Hilgemann, 2007; McLaughlin et al., 2002). Septin filaments could therefore influence STIM-ORAI localization and productive interaction by binding phosphoinositides directly, or by regulating their distribution in membrane microdomains, or by restricting the localization the PIP5K isoforms in conjunction with other mechanisms to limit diffusion of PIP2. Since STIM1 recruitment to puncta depends both on interactions of its polybasic tail with PIP2/PIP3 and on protein-protein interactions with ORAI1 (Hogan et al., 2010; Park et al., 2009), an important question for the future is whether septins modulate STIM1 recruitment in a manner that requires PIP2 binding and the STIM1 polybasic domain.

While wishing not to be held in theory, structural proteins such as septins have various roles is organizing other cellular proteins. First, septins contribute to the spatial organization of microtubules and facilitate the delivery of newly synthesized apical and basal membrane proteins along microtubule tracks in polarized epithelial cells (Spiliotis and Gladfelter, 2011; Spiliotis et al., 2008). Whether septins are similarly involved in ER remodelling has not been examined, but ER is known to extend toward the cell periphery along microtubules (Waterman-Storer and Salmon, 1998). ER-resident STIM1 can further this process by interacting with the plus end of microtubules (Grigoriev et al., 2008; Honnappa et al., 2009), overexpression of STIM1 or a C-terminal fragment of the yeast ER protein Ist2p in mammalian cells increases the extent of ER-plasma membrane contacts (Lavieu et al., 2010; Orci et al., 2009), and microtubules are implicated in formation of the Ist2p-dependent contacts (Lavieu et al., 2010). Second, septin 5 limits the population of vesicles within 20 nm of the plasma membrane active zone at immature mouse calyx of Held synapses (Yang et al., 2010). Third, the effects of plasma membrane-associated septins are not restricted to the plasma membrane, since the septin collar in budding yeast, acting through other proteins, is responsible for a diffusion barrier that restricts movement of ER integral membrane proteins through the bud neck (Luedeke et al., 2005). Fourth, a functional connection between septins and ER-plasma membrane contacts is suggested by the finding that interfering with inheritance of cortical ER in yeast leads to defects in the organization of septins at the bud neck (Loewen et al., 2007).

Nucleic Acid Inhibitors

In some embodiments, agents that inhibit the expression of a Dicer are nucleic acids. Nucleic acid inhibitors of a Dicer gene include, but not are limited to, RNA interference-inducing molecules (RNAi), for example, but not limited to, siRNA, dsRNA, stRNA, shRNA, an anti-sense oligonucleotide and modified versions thereof, where the RNA interference molecule silences the gene expression of the Dicer gene. In some embodiments, the nucleic acid inhibitor of a Dicer gene is an anti-sense oligonucleic acid, or a nucleic acid analogue, for example, but not limited to DNA, RNA, peptide-nucleic acid (PNA), pseudo-complementary PNA (pc-PNA), or locked nucleic acid (LNA) and the like. In alternative embodiments, the nucleic acid is DNA or RNA, or nucleic acid analogues, for example, PNA, pcPNA and LNA. A nucleic acid can be single or double stranded, and can be selected from a group comprising nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. Additional sequences can also be present.

RNA interference (RNAi) is a phenomenon in which double-stranded RNA (dsRNA) specifically suppresses the expression of a gene with its complementary sequence. Small interfering dsRNAs (siRNA) mediate post-transcriptional gene-silencing, and can be used to induce RNAi in mammalian cells. The dsRNA is processed intracellularly to release a short single stranded nucleic acid that can complementary base pair with the gene's primary transcript or mRNA. The resultant a double stranded RNA is susceptible to RNA degradation. Protein translation is thus prevented.

In some embodiments, single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Protein expression from the genes identified in Tables 1-5 can be reduced by inhibition of the expression of polypeptide (e.g., transcription, translation, post-translational processing) or by "gene silencing" methods commonly known by persons of ordinary skill in the art.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionary conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76:9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 5%, 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

Double-stranded RNA (dsRNA) has been shown to trigger one of these posttranscriptional surveillance processes, in which gene silencing involves the degradation of single-stranded RNA (ssRNA) targets complementary to the dsRNA trigger (Fire A, 1999, Trends Genet. 15:358-363). RNA interference (RNAi) effects triggered by dsRNA have been demonstrated in a number of organisms including plants, protozoa, nematodes, and insects (Cogoni C. and Macino G, 2000, Curr Opin Genet Dev 10:638-643).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. that of calcineurin, Ran-GTPase, or Stim1 sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence includes RNA derivatives and analogs. Preferably, the siRNA is identical to its target.

In one embodiment of the compositions and methods described, the target gene or sequence of the RNA interfering agent in the mRNA of a septin and/or a UEV3, e.g., those disclosed in Table 10.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2% O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The more preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

Locked nucleic acids (LNAs), also known as bridged nucleic acids (BNAs), developed by Wengel and co-workers (Koshkin A. A., 1998, Tetrahedron, 54:3607-3630) and Imanishi and co-workers (Obika S., 1998, Tetrahedron Lett., 39:5401-5404). LNA bases are ribonucleotide analogs containing a methylene linkage between the 2' oxygen and the 4' carbon of the ribose ring. The constraint on the sugar moiety results in a locked 3'-endo conformation that preorganizes the base for hybridization and increases melting temperature (Tm) values as much as 10° C. per base (Wengel J., 1999, Acc. Chem. Res., 32:301-310; Braasch D. A. and Corey, D. R., 2001, Chem. Biol., 8:1-7). LNA bases can be incorporated into oligonucleotides using standard protocols for DNA synthesis. This commonality facilitates the rapid synthesis of chimeric oligonucleotides that contain both DNA and LNA bases and allows chimeric oligomers to be tailored for their binding affinity and ability to activate RNase H. Because oligomers that contain LNA bases have a native phosphate backbone they are readily soluble in water. Introduction of LNA bases also confers resistance to nucleases when incorporated at the 5' and 3' ends of oligomers (Crinelli R., et. al., 2002, Nucleic Acids Res., 30:2435-2443). The ability to use LNAs for in vivo applications is also favored by the finding that LNAs have demonstrated low toxicity when delivered intravenously to animals (Wahlestedt C., et. al., 2000, Proc. Natl. Acad. Sci. USA, 97: 5633-5638).

LNAs and LNA-DNA chimeras have been shown to be potent inhibitors of human telomerase and that a relatively short eight base LNA is a 1000-fold more potent agent than an analogous peptide nucleic acid (PNA) oligomer (Elayadi A. N., et. al., 2002, Biochemistry, 41: 9973-9981). LNAs and LNA-DNA chimeras have also been shown to be useful agents for antisense gene inhibition. Wengel and co-workers have used LNAs to inhibit gene expression in mice (Wahlestedt C., et. al., 2000, Proc. Natl. Acad. Sci. USA, 97:5633-5638), while Erdmann and colleagues have described the design of LNA-containing oligomers that recruit RNase H and have described the rules governing RNase H activation by LNA-DNA chimeras in cell-free systems (Kurreck J., et. al., 2002, Nucleic Acids Res., 30:1911-1918).

The syntheses of LNA-containing oligomers are known in the art, for examples, those described in U.S. Pat. Nos. 6,316,198, 6,670,461, 6,794,499, 6,977,295, 6,998,484, 7,053,195, and U.S Patent Publication No. US 2004/0014959, and all of which are hereby incorporated by reference in their entirety.

Another nucleic acid derivative envisioned in the methods described herein is phosphorodiamidate morpholino oligomer (PMO). PMOs are DNA mimics that inhibit expression of specific mRNA in eukaryotic cells (Arora, V., et. al., 2000, J. Pharmacol. Exp. Ther. 292:921-928; Qin, G., et. al., 2000, Antisense Nucleic Acid Drug Dev. 10:11-16; Summerton, J., et. al., 1997, Antisense Nucleic Acid Drug Dev. 7:63-70). They are synthesized by using the four natural bases, with a base sequence that is complementary (antisense) to a region of a specific mRNA. They are different than DNA in the chemical structure that links the bases together. Ribose has been replaced with a morpholine group, and the phosphodiester is replaced with a phosphorodiamidate. These alterations make the antisense molecule resistant to nucleases (Hudziak, R., et. al., 1996 Antisense Nucleic Acid Drug Dev. 6:267-272) and free of charges at physiological pH, yet it retains the molecular architecture required for binding specifically to a complementary strand of nucleic acid (Stein, D., et. al, 1997, Antisense Nucleic Acid Drug Dev. 7:151-157; Summerton, J., et. al., 1997, Antisense Nucleic Acid Drug Dev. 7:63-70; Summerton, J., and D. Weller., 1997, Antisense Nucleic Acid Drug Dev. 7:187-195).

The synthesis, structures, and binding characteristics of morpholine oligomers are detailed in U.S. Pat. Nos. 5,698,685, 5,127,866, 5,142,047, 5,166,315, 5,521,063, and 5,506,337, and all of which are hereby hereby incorporated by reference in their entirety. PMOs can be synthesized at AVI BioPharma (Corvallis, Oreg.) in accordance with known methods, as described, for example, in Summerton, J., and D. Weller U.S. Pat. No. 5,185,444; and Summerton, J., and D. Weller. 1997, Antisense Nucleic Acid Drug Dev. 7:187-195. For example, PMO against calcineurin or KCNN4 transcripts should containing between 12-40 nucleotide bases, and having a targeting sequence of at least 12 subunits complementary to the respective transcript. Methods of making and using PMO for the inhibition of gene expression in vivo are described in U.S. Patent Publication No. US 2003/0171335; US 2003/0224055; US 2005/0261249; US 2006/0148747; US 2007/0274957; US 2007/003776; and US 2007/0129323; and these are hereby incorporated by reference in their entirety.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting the genes identified in Tables 1-5 can be readily designed and tested. Accordingly, siRNAs useful for the methods described herein include siRNA molecules of about 15 to about 40 or about 15 to about 28 nucleotides in length, which are homologous to an gene identified in Tables 1-5. Preferably, the siRNA molecules targeting the gene identified in Tables 1-5 have a length of about 19 to about 25 nucleotides. More preferably, the siRNA molecules have a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment, the RNA molecule that targets the gene identified in Tables 1-5 is double stranded—one strand has a 3' overhang and the other strand can be blunt-ended or have an overhang. In the embodiment in which the gene identified in Tables 1-5 targeting RNA molecule is double stranded and both strands comprise an overhang, the length of the overhangs can be the same or different for each strand. In a embodiment, the RNA comprises at least 6, 7, 8, 9, 10, 11, 12, 13, 14, 15, 16, 17, 18, 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

In some embodiments, assessment of the expression and/or knock down of gene identified in Tables 1-5 using gene specific siRNAs can be determined by methods that are well known in the art, such as western blot analysis or enzyme activity assays. Other methods can be readily prepared by those of skill in the art based on the known sequence of the target mRNA.

siRNA sequences are chosen to maximize the uptake of the antisense (guide) strand of the siRNA into RISC and thereby maximize the ability of RISC to target the mRNA of the gene identified in Tables 1-5 for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the mRNA of the human gene identified in Tables 1-5.

In a preferred embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into a siRNA capable of targeting a specific gene identified in Tables 1-5. In one embodiment, the vector can be a plasmid, a cosmid, a phagmid, a hybrid thereof, or a virus. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN® Inc., Valencia, Calif. and AMBION® Inc., Austin, Tex.)

In some embodiments, an agent is protein or polypeptide or RNAi agent that inhibits the expression of genes identified in Tables 1-5 and/or activity of proteins encoded by gene identified in Tables 1-5. In such embodiments, cells can be modified (e.g., by homologous recombination) to provide increased expression of such an agent, for example, by replacing, in whole or in part, the naturally occurring promoter with all or part of a heterologous promoter so that the cells express the natural inhibitor agent. For example, a protein or miRNA inhibitor of a gene identified in Tables 1-5 become expressed at higher levels. The heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of a peptide or nucleic acid agent inhibitor of the gene identified in Tables 1-5 can also include an affinity column containing agents which will bind to the protein; one or more column steps over such affinity resins as concanavalin A-agarose, heparin-Toyopearl™ or Cibacrom blue 3GA Sepharose; one or more steps involving hydrophobic interaction chromatography using such resins as phenyl ether, butyl ether, or propyl ether; immunoaffnity chromatography, or complementary cDNA affinity chromatography.

In one embodiment, the nucleic acid inhibitors of the genes identified in Tables 1-5 can be obtained synthetically, for example, by chemically synthesizing a nucleic acid by any method of synthesis known to the skilled artisan. The synthesized nucleic acid inhibitors of the gene identified in Tables 1-5 can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro'phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. No. 5,672,697 and U.S. Pat. No. 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

The siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) Proc. Natl. Acad. Sci. USA 99:6047-52). The siRNA molecules can also be chemically synthesized (Elbashir et al. (2001) Nature 411:494-98)

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), DHARMACON Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi.

siRNA can also be produced by in vitro transcription using single-stranded DNA templates (Yu et al., supra). Alternatively, the siRNA molecules can be produced biologically, either transiently (Yu et al., supra; Sui et al. (2002) Proc. Natl. Acad. Sci. USA 99:5515-20) or stably (Paddison et al. (2002) Proc. Natl. Acad. Sci. USA 99:1443-48), using an expression vector(s) containing the sense and antisense siRNA sequences. siRNA can be designed into short hairpin RNA (shRNA) for plasmid- or vector-based approaches for supplying siRNAs to cells to produce stable gene identified in Tables 1-5 silencing. Examples of vectors for shRNA are #AM5779: —pSILENCER™ 4.1-CMV neo; #AM5777: —pSILENCER™ 4.1-CMV hygro; #AM5775: —pSILENCER™ 4.1-CMV puro; #AM7209: —pSILENCER™ 2.0-U6; #AM7210: —pSILENCER™ 3.0-H1; #AM5768: —pSILENCER™ 3.1-H1 puro; #AM5762: —pSILENCER™ 2.1-U6 puro; #AM5770: —pSILENCER™ 3.1-H1 neo; #AM5764: —pSILENCER™ 2.1-U6 neo; #AM5766: —pSILENCER™ 3.1-H1 hygro; #AM5760: —pSILENCER™ 2.1-U6 hygro; #AM7207: —pSILENCER™ 1.0-U6 (circular) from Ambion®.

Recently, reduction of levels of target mRNA in primary human cells, in an efficient and sequence-specific manner, was demonstrated using adenoviral vectors that express hairpin RNAs, which are further processed into siRNAs (Arts et al. (2003) Genome Res. 13:2325-32). In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., the coding sequence of a gene identified in Tables 1-5, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (SEQ. ID. NO: 12) (where N can be any nucleotide), and selecting hits with at least 25%, 30%, 35%, 40%, 45%, 50%, 55%, 60%, 65%, 70% or 75% G/C content. The “TT” portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as Oligoengine®, can also be used to select siRNA sequences against EST libraries to ensure that only one gene is targeted.

Methods of predicting and selecting antisense oligonucleotides and siRNA are known in the art and are also found at the Website for GENSCRIPT, AMBION, DHARMACON, OLIGOENGINE, WADSWORTH, Whitehead Institute at the Massachusetts Institute of Technology and described in U.S. Pat. No. 6,060,248 which is incorporated here by reference in its entirety. In one embodiment, the target sequences use for f predicting and selecting antisense oligonucleotides, shRNA and siRNA are those of Septins and/or UEV3, e.g., those disclosed in Table 10.

In some aspects, antisense nucleic acid technology can be used to inhibit the expression of gene identified in Tables 1-5. It is possible to synthesize a strand of nucleic acid (DNA, RNA or a chemical analogue) that will bind to the messenger RNA (mRNA) produced by that gene and inactivate it, effectively turning that gene "off". This is because mRNA has to be single stranded for it to be translated. This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

Delivery of RNA Interfering Agents: Methods of delivering RNA interfering agents, e.g., an siRNA, or vectors containing an RNA interfering agent, to the target cells (e.g., cells of the brain or other desired target cells, for cells in the central and peripheral nervous systems), can include, for example (i) injection of a composition containing the RNA interfering agent, e.g., an siRNA, or (ii) directly contacting the cell, e.g., a cell of the brain, with a composition comprising an RNA interfering agent, e.g., an siRNA. In one embodiment, the RNA interfering agent can be targeted to the bone marrow where the lymphocytes expressing the genes identified in Tables 1-5 are made. In another embodiment, RNA interfering agents, e.g., an siRNA can be injected directly into any blood vessel, such as vein, artery, venule or arteriole, via, e.g., hydrodynamic injection or catheterization. In yet another embodiment, the RNA interfering agent can be injected or applied topically directly to the site of the skin ulcers.

Administration can be by a single injection or by two or more injections. The RNA interfering agent is delivered in a pharmaceutically acceptable carrier. One or more RNA interfering agents can be used simultaneously. The RNA interfering agents, e.g., the siRNAs targeting the mRNA of genes identified in Tables 1-5, can be delivered singly, or in combination with other RNA interfering agents, e.g., siRNAs, such as, for example siRNAs directed to other cellular genes. siRNAs targeting gene identified in Tables 1-5 can also be administered in combination with other pharmaceutical agents which are used to treat or prevent immunological diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) Nat Biotechnol 20(10): 1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501).

RNA interfering agents, for e.g., an siRNA, can also be introduced into cells via the vascular or extravascular circulation, the blood or lymph system, and the cerebrospinal fluid.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi molecules do not have to match perfectly to their target sequence. Preferably, however, the 5' and middle part of the antisense (guide) strand of the siRNA is perfectly complementary to the target nucleic acid sequence.

Accordingly, the RNAi molecules functioning as nucleic acid inhibitors of the genes identified in Tables 1-5 disclosed herein are, for example, but not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g., Baulcombe, Science 297:2002-2003, 2002). The dsRNA molecules, e.g., siRNA, also can contain 3' overhangs, preferably 3'UU or 3TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of a gene identified in Tables 1-5 is any agent which binds to and inhibits the expression of mRNA of that gene identified in Tables 1-5, where the mRNA or a product of transcription of nucleic acid is encoded by SEQ. ID NOS: 1-11 (GENBANK™ Accession Nos. NM_000944; NM_021132.1; NM_006325; NM_006267.4; NM_002265.4, NM_001316; NM_003400.3; NM_003156.2, NM_020860.2, NM_032790.3, NM_002250.2).

In some embodiments of all aspects of the composition or method described herein, the nucleic acid inhibitor inhibits the expression of mRNA (transcript variant 4) of the SEPT 4 gene (SEQ. ID. NO: 13, GENBANK™ Accession No. NM_001198713) and/or the expression of mRNA (transcript variant 2) of the SEPT 5 gene (SEQ. ID. NO: 14, GENBANK™ Accession No. NM_001009939). The mRNA variant transcripts of the members of the Septin family (Septins 1, 2, 3, 4, 5, 6, 7, 8, 9, 10, 11, 12, 13 and 14) are found in Table 10.

In some embodiments of all aspects of the composition or method described herein, the nucleic acid inhibitor inhibits the expression of mRNA (transcript variant) of the UEV3 gene (SEQ. ID. NO: 105, GENBANK™ Accession No. NM_001040697; SEQ. ID. NO:106, GENBANK™ Accession No. NM_018314) found in Table 10.

In some embodiments of all aspects of the composition or method described herein, the nucleic acid inhibitor is selected from the group consisting of GGACAAUGCUGGUACGUAC (SEQ. ID. NO: 17), GGAGACACAUUAUGAGAAC (SEQ. ID. NO: 18), GGGUCAACAUCGUGCCUAU (SEQ. ID. NO: 19) and GAACAUCCAAGACAACCGA (SEQ. ID. NO: 20).

In another embodiment, agents inhibiting the genes identified in Tables 1-5 are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example, for the cleavage of the genes identified in Tables 1-5 or homologues or variants thereof can be achieved by techniques well known to those skilled in the art (for example Lleber and Strauss, (1995) Mol Cell Biol 15:540.551, the disclosure of which is incorporated herein by reference).

Pharmaceutical Compositions and Administration

In one embodiment, the invention provides a pharmaceutical composition comprising an agent that inhibits the activity or function of a protein encoded by a gene identified in Tables 1-5 and/or the expression of a gene identified in Tables 1-5 and a pharmaceutically acceptable carrier. The agent can be a small molecule, nucleic acid, nucleic acid analogue, protein, antibody, peptide, aptamer or variants or fragments thereof. Other forms of inhibitors include a nucleic acid agent which is an RNAi agent such as a siRNA, shRNA, miRNA, dsRNA or ribozyme or variants thereof.

In one embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). In one embodiment, other ingredients can be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; cHeLating agents such as EDTA; and sugar alcohols such as mannitol or sorbitol.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, to name a few.

Various delivery systems are known in the art and can be used to administer agent that inhibits the activity or function of a protein and/or the expression of a gene identified in Tables 1-5 of Tables 1-5, e.g., encapsulation in liposomes, microparticles, and microcapsules (see, e.g., Wu and Wu, J. Biol. Chem., 262:4429-4432 (1987)). The composition can be delivered in a vesicle, in particular a liposome (see, Langer, Science, 249:1527-1533 (1990); Treat et al., in Liposomes in the Therapy of Infectious Disease and Cancer, Lopez-Berestein and Fidler, eds. (Liss, New York 1989), pp. 353-365; Lopez-Berestein, ibid., pp. 317-327; see, generally, ibid.).

Pharmaceutical compositions can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and infrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

Administration can be systemic or local. In addition, it can be desirable to introduce the pharmaceutical compositions of the invention into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

In one embodiment, the pharmaceutical formulation to be used for therapeutic administration must be sterile. Sterility is readily accomplished by filtration through sterile filtration membranes (e.g., 0.2 micron membranes). The pH of the pharmaceutical formulation typically should be about from 6 to 8.

In one embodiment, the composition can be delivered in a controlled release system. In one embodiment, a pump can be used (see Langer, supra; Sefton, CRC Crit. Ref. Biomed. Eng., 14:201 (1987); Buchwald et al., Surgery, 88:507 (1980); Saudek et al., N. Engl. J. Med., 321:574 (1989)). In another embodiment, polymeric materials can be used (see, Medical Applications of Controlled Release, Langer and Wise, eds. (CRC Press, Boca Raton, Fla. 1974); Controlled Drug Bioavailability, Drug Product Design and Performance, Smolen and Ball, eds. (Wiley, New York 1984); Ranger and Peppas, Macromol. Sci. Rev. Macromol. Chem., 23:61 (1983); see also Levy et al., Science, 228:190 (1985); During et al., Ann. Neurol., 25:35 1 (1989); Howard et al., J. Neurosurg., 7 1:105 (1989)). Other controlled release systems are discussed in the review by Langer (Science, 249:1527-1533 (1990)). For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

The precise dose to be employed in the formulation will also depend on the route of administration, and the severity of hyperactivity or inappropriate immune response, and should be decided according to the judgment of the practitioner and each patient's circumstances. Effective doses can be extrapolated from dose-response curves derived from in vitro or animal model test systems.

The dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. For gene therapy, viral vector should be in the range of $1\times10^6$ to $10^{14}$ viral vector particles per application per patient.

In addition, in vitro or in vivo assays can optionally be employed to help identify optimal dosage ranges. The precise dose to be employed will also depend on the route of administration, and the seriousness of the condition being treated and should be decided according to the judgment of the practitioner and each subject's circumstances in view of, e.g., published clinical studies. Suitable effective dosage amounts, however, range from about 10 micrograms to about 5 grams about every 4 hour, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, or about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered. The compositions comprising agent that inhibits the activity or function of a protein encoded by a gene identified in Tables 1-5 and/or the expression of a gene identified in Tables 1-5, including expression vectors and/or viral vectors are suitably administered to the patient at one time or over a series of treatments. For purposes herein, a "therapeutically effective amount" of a composition comprising an agent that inhibits the activity or function of a protein encoded by a gene identified in Tables 1-5 and/or the expression of a gene identified in Tables 1-5 is an amount that is effective to reduce the amount of NFAT nuclear translocation, $Ca^{2+}$ influx and/or cytokine production by at least 20%, or reduce the symptom associated hyperactive or inappropriate immune response by at least 10%.

In an embodiment, the composition comprising an agent that inhibits the activity or function of a protein encoded by a gene identified in Tables 1-5 and/or the expression of a gene identified in Tables 1-5 is administered in combination with immunosuppressive therapies including, but not limited to, azathioprine, infliximab, omalizumab, daclizumab, adalimumab, eculizumab, efalizumab, natalizumab, and omalizumab. In another embodiment, the composition comprising agent that inhibits the activity or function of a protein encoded by a gene identified in Tables 1-5 and/or the expression of a gene identified in Tables 1-5 is administered in combination with immunosuppressive therapies and cyclophosphamide, chlorambucil, and/or rituximab.

Gene Therapy

In one embodiment, the agent that inhibits the activity or function of a protein encoded by a gene identified in Tables 1-5 and/or the expression of a gene identified in Tables 1-5 is administered to an individual by any one of several gene therapy techniques known to those of skill in the art. In general, gene therapy can be accomplished by either direct transformation of target cells within the mammalian subject (in vivo gene therapy) or transformation of cells in vitro and subsequent implantation of the transformed cells into the mammalian subject (ex vivo gene therapy). A viral vector carries anRNAi agent such as a shRNA or anti-sense oligonucleotide for a gene identified in Tables 1-5 under a tissue specific regulatory element is administered to an individual. The tissue specific regulatory element allows the expression of the RNAi agent in the target cells, for example, the lymph nodes.

The principles of gene therapy are disclosed by Oldham, R. K. (In: Principles of Biotherapy, Raven Press, N.Y., 1987), and similar texts. Disclosures of the methods and uses for gene therapy are provided by Boggs, S. S. (Int. J. Cell Clon. 8:80-96 (1990)); Karson, E. M. (Biol. Reprod. 42:39-49 (1990)); Ledley, F. D., In: Biotechnology, A Comprehensive Treatise, volume 7B, Gene Technology, VCH Publishers, Inc. NY, pp 399-458 (1989)), all of which references are incorporated herein by reference.

The nucleic acid encoding an RNAi agent such as shRNA can be introduced into the somatic cells of an animal (particularly mammals including humans) in gene therapy. Most preferably, viral or retroviral vectors are employed for as the transfer vehicle this purpose. The gene therapy virus can be in the form of an adenovirus, adeno-associated virus or lentivirus.

Retroviral vectors are a common mode of delivery and in this context are retroviruses from which all viral genes have been removed or altered so that no viral proteins are made in cells infected with the vector. Viral replication functions are provided by the use of retrovirus "packaging" cells that produce all of the viral proteins but that do not produce infectious virus.

Introduction of the retroviral vector DNA into packaging cells results in production of virions that carry vector RNA and can infect target cells, but such that no further virus spread occurs after infection. To distinguish this process from a natural virus infection where the virus continues to replicate and spread, the term transduction rather than infection is often used.

In one embodiment, the method of treating the diseases or disorders described herein provides a recombinant lentivirus for the delivery and expression of an RNAi agent in either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4N5-DEST™, pLenti6/V5-DEST™ or pLenti vectors together with ViraPower™ Lentiviral Expression systems from Invitrogen.

Examples of use of lentiviral vectors for gene therapy for inherited disorders and various types of cancer, and these references are hereby incorporated by reference (Klein, C. and Baum, C. (2004). Hematol. J., 5, 103-111; Zufferey, R et al. (1997). Nat. Biotechnol., 15, 871-875; Morizono, K. et al. (2005). Nat. Med., 11, 346-352; Di Domenico, C. et. al. (2005), Hum. Gene Ther., 16, 81-90; Kim, E. Y., et al., (2004). Biochem. Biophys. Res. Comm., 318, 381-390).

Non-retroviral vectors also have been used in genetic therapy. One such alternative is the adenovirus (Rosenfeld, M. A., et al., Cell 68:143155 (1992); Jaffe, H. A. et al., Nature Genetics 1:372-378 (1992); Lemarchand, P. et al., Proc. Natl. Acad. Sci. USA 89:6482-6486 (1992)). Major advantages of adenovirus vectors are their potential to carry large segments of DNA (36 Kb genome), a very high titre ($10^{11}$/ml), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell 63:143-155 (1992)). Similarly, herpes viruses may also prove valuable for human gene therapy (Wolfe, J. H. et al., Nature Genetics 1:379-384 (1992)). Of course, any other suitable viral vector may be used for genetic therapy with the present invention.

U.S. Pat. No. 6,531,456 provides methods for the successful transfer of a gene into a solid tumor cell using recombinant AAV virions. Generally, the method described in U.S. Pat. No. 6,531,456 allows for the direct, in vivo injection of recombinant AAV virions into tumor cell masses, e.g., by intra-tumoral injection. The invention also provides for the simultaneous delivery of a second gene using the recombinant AAV virions, wherein the second gene is capable of providing an ancillary therapeutic effect when expressed within the transduced cell. U.S. Pat. No. 6,531,456 is hereby incorporated by reference in its entirety.

The viron used for gene therapy can be any viron known in the art including but not limited to those derived from adenovirus, adeno-associated virus (AAV), retrovirus, and lentivirus. Recombinant viruses provide a versatile system for gene expression studies and therapeutic applications.

The recombinant AAV virions described above, including the DNA of interest, can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, $>10^8$ viral particle/ml, are easily obtained in the supernatant and $10^{11}$-$10^{12}$ viral particle/ml with further concentration. The transgene is integrated into the host genome so expression is long term and stable.

A simplified system for generating recombinant adenoviruses is presented by He T C., et al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

The use of alternative AAV serotypes other than AAV-2 (Davidson et al (2000), Proc. Natl. Acad. Sci. USA 97(7) 3428-32; Passini et al (2003), J. Virol. 77(12):7034-40) has demonstrated different cell tropisms and increased transduction capabilities. With respect to brain cancers, the development of novel injection techniques into the brain, specifically convection enhanced delivery (CED; Bobo et al (1994), Proc. Natl. Acad. Sci. USA 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying a DNA coding sequence for an antisense oligonucleotide to hnRNPLL or an siRNA hnRNPLL nucleic acid molecule, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12:71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Pharmaceutical compositions used in the methods described herein can be delivered systemically via in vivo gene therapy. A variety of methods have been developed to accomplish in vivo transformation including mechanical means (e.g., direct injection of nucleic acid into target cells or particle bombardment), recombinant viruses, liposomes, and receptor-mediated endocytosis (RME) (for reviews, see Chang et al. 1994 Gastroenterol. 106:1076-84; Morsy et al. 1993 JAMA 270:2338-45; and Ledley 1992 J. Pediatr. Gastroenterol. Nutr. 14:328-37).

Another gene transfer method for use in humans is the transfer of plasmid DNA in liposomes directly to human cells in situ (Nabel, E. G., et al., Science 249:1285-1288 (1990)). Plasmid DNA should be easy to certify for use in human gene therapy because, unlike retroviral vectors, it can be purified to homogeneity. In addition to liposome-mediated DNA transfer, several other physical DNA transfer methods, such as those targeting the DNA to receptors on cells by conjugating the plasmid DNA to proteins, have shown promise in human gene therapy (Wu, G. Y., et al., J. Biol. Chem. 266:14338-14342 (1991); Curiel, D. T., et al., Proc. Natl. Acad. Sci. USA, 88:8850-8854 (1991)).

For gene therapy viruses, the dosage ranges from $10^6$ to $10^{14}$ particles per application. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The proteins, expression vector, and/or gene therapy virus can be coated on minute gold particles, and these coated particles are "shot" into biological tissues such as hemangiomas and melanoma under high pressure. An example of the gene gun-based method is described for DNA based vaccination of cattle by Loehr B. I. et al. J. Virol. 2000, 74:6077-86.

Materials and methods for the construction of the expression vectors NFAT-GFP and Stim1-RFP, and the transfection of expression vectors into HeLa cells are well known to one skilled in the art and are also described in Okamura, et al., Mol. Cell, 2000, 6:539-50; Aramburu, et. al., Science, 1999, 285:2129-33; Gwack Y, et al., Nature, 2006, 441:646-50, Oh-hora et al, Nature immunology 2008, 9:432-43; US Patent Application Nos. US2007/0031814 entirety.

More specifically, the expression vector Stim1-RFP was constructed by the following method. Full length murine Stim1 cDNA (Oh-hora et al, Nature immunology 2008, 9:432-43) was PCR-amplified and cloned into pDSRed-Monomer-N1 (Clontech) using the Xho1 I and BamH1 sites.

The expression vector Orai-FLAG was constructed by the following method and by any molecular methods known to one skilled in the art. Full length human Orai1 cDNA (Feske et al, Nature 2006, 441:179-85) was PCR-amplified and cloned into pFLAG-CMV2 (Sigma) using the Not1 and Xho1 sites.

HeLa cell line expressing NFAT1, Stim1, and Orai1: HeLa 13.10. A monoclonal population of HeLa NFAT1 (1-460)-GFP cells stably expressing the amino terminal signal responsive domain of NFAT1 fused to GFP (Gwack et al, Nature 2006, 441:646-50) were engineered to stably express full length Stim1-RFP and transiently transfected with full length Orai1-FLAG 1; efficiency of Orai1-FLAG expression was quantitated by anti-FLAG immunocytochemistry at 48 h post transfection (75%±6.7) and 96 h post transfection (42%±8). Cells were maintained at 37° C./10% $CO_2$ in DMEM 10% bovine calf serum (BCS), penicillin/streptomycin, HEPES and β-mercaptoethanol/L-glutamine and 100 μg/mL hygromycin B. Hygromycin B was removed 16 h before Orai1-FLAG transfection. All experiments were performed with cells kept at a passage number under 6.

HeLa 13.10 cells stably expressing NFAT1-GFP and Stim1-RFP and transiently expressing Orai1-FLAG were reverse transfected with 20 nM siRNA using Hiperfect Transfection Reagent (QIAGEN®) by robotic transfer of cells to 384-well plates (5000-6000 cells/well) pre-arrayed with siRNA corresponding to the annotated human genome (DHARMACON). 72 h post transfection with siRNA, cells were stimulated with thapsigargin (250 nM for 90 minutes at room temperature) to induce NFAT1-GFP nuclear translocation; cells were fixed with 3% paraformaldehyde, permeablized with 0.2% Triton-X 100, stained with the DNA intercalating dye DAPI and assessed for NFAT1-GFP nuclear translocation by fluorescent microscopy. Images were acquired using the ImageXpress Micro automated imaging system (Molecular Devices) using a 10× objective and analyzed using the Translocation Application module of MetaXpress software version 6.1 (Molecular Devices). Cytoplasmic to nuclear translocation was assessed by calculating a correlation of intensity between NFAT1-GFP fluorescence and DAPI staining: cells were scored as positive for nuclear NFAT1 when >60% of NFAT1-GFP fluorescence coincided with DAPI fluorescence. Each data point represents an average of at least 1200 individual cells per well and averaged for duplicate wells.

In some embodiments, the gene therapy described herein are used to expressed the septin genes and/ol UEV3 gene in cells or in a subject in need thereof. Standard PCR cloning methods are use to place the protein coding mRNA sequences of septins and/or UEV3 into expression vectors. The protein coding mRNA sequences of septins and/or UEV3 are described it Table 10.

The present invention can be defined in any of the following alphabetized paragraphs:

[A] A pharmaceutical composition comprising an agent that inhibits the function of a septin 4 protein and/or the expression of a septin 4 gene, and a pharmaceutically acceptable carrier.

[B] The pharmaceutical composition of paragraph 1 further comprising an agent that inhibits the function of a septin 5 protein and/or the expression of a septin 5 gene.

[C] A pharmaceutical composition comprising an agent that inhibits the function of a septin 4 protein and/or the expression of a septin 4 gene, an agent that inhibits the function of a septin 5 protein and/or the expression of a septin 5 gene and a pharmaceutically acceptable carrier.

[D] The pharmaceutical composition of paragraph [A], [B] or [C], wherein the agent is a nucleic acid inhibitor which inhibits gene expression.

[E] The pharmaceutical composition of paragraph [D], wherein the nucleic acid inhibitor is an siRNA or shRNA.

[F] The pharmaceutical composition of paragraph [E], wherein the siRNA or shRNA comprises the sequence of GGGUCAACAUCGUGCCUAU (SEQ ID NO: 19).

[G] A composition for use of modulating NFAT activity in a subject in need thereof, the composition comprising an agent that inhibits the function of a septin 4 protein and/or the expression of a septin 4 gene.

[H] A composition for use of modulating store-operated $Ca^{2+}$ entry into a cell, the composition comprising an agent that inhibits the function of a septin 4 protein and/or the expression of a septin 4 gene.

[I] A composition for use treating and/or preventing hyperactivity or inappropriate immune response in a subject in need thereof, the composition comprising an agent that inhibits the function of a septin 4 protein and/or the expression of a septin 4 gene.

[J] The composition of any one of paragraphs [G]-[I] further comprising an agent that inhibits the function of a septin 5 protein and/or the expression of a septin 5 gene.

[K] The composition of paragraph [J], wherein the agent is a nucleic acid inhibitor which inhibits gene expression.

[L] The composition of paragraph [K], wherein the nucleic acid inhibitor is an siRNA or shRNA.

[M] The composition of paragraph [L], wherein the siRNA or shRNA comprises the sequence of GGGUCAACAUCGUGCCUAU (SEQ ID NO: 19).

[N] A method of modulating NFAT activity in a subject in need thereof, the method comprising administering a therapeutically effective amount of a pharmaceutical composition of any one of paragraphs [A]-[F].

[O] A method of modulating store-operated $Ca^{2+}$ entry into a cell, the method comprising administering a therapeutically effective amount of a pharmaceutical composition of any one of paragraphs [A]-[F].

[P] A method of treating and/or preventing hyperactivity or inappropriate immune response in a subject in need thereof, the method comprising administering a therapeutically effective amount of a pharmaceutical composition of any one of paragraphs [A]-[F].

[Q] A method of modulating NFAT activity in a subject in need thereof, the method comprising administering a therapeutically effective amount of a pharmaceutical composition comprising an agent that inhibits the function of a septin 4 protein and/or the expression of a septin 4 gene.

[R] A method of modulating store-operated $Ca^{2+}$ entry into a cell, the method comprising administering a therapeutically effective amount of a pharmaceutical composition comprising an agent that inhibits the function of a septin 4 protein and/or the expression of a septin 4 gene.

[S] A method of treating and/or preventing hyperactivity or inappropriate immune response in a subject in need thereof, the method comprising administering a therapeutically effective amount of a pharmaceutical composition comprising an agent that inhibits the function of a septin 4 protein and/or the expression of a septin 4 gene.

[T] The method of any one of paragraphs [Q]-[S] further comprising administering a therapeutically effective amount of a pharmaceutical composition comprising an agent that inhibits the function of a septin 5 protein and/or the expression of a septin 5 gene.

[U] The method of paragraph [N] or [Q], wherein the modulation of NFAT activity comprises inhibiting NFAT translocation into the nucleus and decreasing the immune response in a subject.

[V] The method of paragraph [O] or [R], wherein the modulation of store-operated $Ca^{2+}$ entry comprises inhibiting store-operated $Ca^{2+}$ entry into the cell.

[W] The method of any one of paragraphs [Q]-[V], wherein the agent is a nucleic acid inhibitor which inhibits gene expression.

[X] The method of paragraph [W], wherein the nucleic acid inhibitor is an siRNA or shRNA.

[Y] The method of paragraph [X], wherein the siRNA or shRNA comprises the sequence of GGGUCAACAUCGUGCCUAU (SEQ ID NO: 19).

[Z] The method of any one of paragraphs [P], [S], [T], [W]-[X], wherein the hyperactivity or inappropriate immune response in a subject is associated with acute and chronic immune diseases selected from a group consisting of asthma, allergic rhinitis, allergic conjunctivitis, atopic dermatitis, rheumatoid arthritis, insulin-dependent diabetes, inflammatory bowel disease, autoimmune thyroiditis, hemolytic anemia, multiple sclerosis, transplant graft rejections and graft-versus-host disease.

[AA] The method of any one of paragraphs [U], [W]-[X], wherein the immune response in a subject is associated with acute and chronic immune diseases selected from a group consisting of asthma, allergic rhinitis, allergic conjunctivitis, atopic dermatitis, rheumatoid arthritis, insulin-dependent diabetes, inflammatory bowel disease, autoimmune thyroiditis, hemolytic anemia, multiple sclerosis, transplant graft rejections and graft-versus-host disease.

[BB] A method of modulating NFAT activity in a subject in need thereof, the method comprising administering a therapeutically effective amount of a pharmaceutical composition comprising an agent that inhibits the function of a UEV3 protein and/or the expression of UEV3 gene.

[CC] The method of paragraph [BB], wherein the subject is suffering from a cell proliferation disease or disorder.

[DD] The method of paragraph [CC], wherein the cell proliferation disease or disorder is a neoplastic cell proliferation disorder.

[EE] The method of paragraph [CC], wherein the neoplastic cell proliferation disorder is a therapy resistant cancer, a metastasis or malignant cancer.

[FF] The method of paragraph [BB], wherein the subject is suffering from a cardiovascular disorder.

[GG] The method of paragraph [FF], wherein the cardiovascular disorder is cardiac hypertrophy, restenosis, atherosclerosis, or angiogenesis.

[HH] The method of paragraph [BB], wherein the subject is suffering from a bone disease associated with excessive osteoclast formation and the excessive activity needs to be suppressed.

[II] The method of paragraph [BB], wherein the subject is suffering from an angiogenic disease or disorder.

[JJ] The method of paragraph [II], wherein the angiogenesic disorder is associated with VEGF-induced and IL-1 induced gene expression.

[KK] The method of paragraph [II], wherein the angiogenesis disorder is selected from a group consisting of cancer, age-related macular degeneration, diabetic retinopathy; rheumatoid arthritis; Alzheimer's disease; obesity and endometriosis.

[LL] The method of paragraph [BB], wherein the agent is nucleic acid inhibitor which inhibits gene expression.

[MM] The method of paragraph [LL], wherein the nucleic acid inhibitor is an siRNA or shRNA.

[NN] A method of modulating store-operated Calf entry into a cell, the method comprising administering a therapeutically effective amount of a pharmaceutical composition comprising an agent that inhibits the function of a UEV3 protein and/or the expression of UEV3.

[OO] The method of paragraph [NN], wherein the agent is a nucleic acid inhibitor which inhibits gene expression.

[PP] A method of treating and/or preventing hyperactivity or inappropriate immune response in a subject in need thereof, the method comprising administering a therapeutically effective amount of a pharmaceutical composition comprising an agent that inhibits the function of a UEV3 protein and/or the expression of UEV3 gene.

[QQ] The method of paragraph [PP], wherein the hyperactivity or inappropriate immune response in a subject is associated with acute and chronic immune diseases selected from a group consisting of asthma, allergic rhinitis, allergic conjunctivitis, atopic dermatitis, rheumatoid arthritis, insulin-dependent diabetes, inflammatory bowel disease, autoimmune thyroiditis, hemolytic anemia, multiple sclerosis, transplant graft rejections and graft-versus-host disease.

[RR] The method of paragraph [PP], wherein the agent is a nucleic acid inhibitor which inhibits gene expression.

[SS] The method of paragraph [RR], wherein the nucleic acid inhibitor is an siRNA or shRNA.

This invention is further illustrated by the following examples which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein, different culture medium and supplements can be used to culture expand the isolated cells. One skilled in the art would be able to perform tests to evaluate the choice of culture medium and supplements. Such equivalents are intended to be encompassed by the following claims.

The references cited herein and throughout the specification are incorporated herein by reference in their entirety.

EXAMPLES

Example 1

Experimental Procedures

The Genome-Wide siRNA Screen

The siRNA screen was performed at the Institute for Chemistry and Cell Biology (ICCB) at Harvard Medical School. HeLa cells stably expressing NFAT1-GFP and STIM1-mDsRed, and transiently expressing FLAG-ORAI1, were transfected with 21,757 pools of gene-specific siRNA oligonucleotide pools corresponding to the annotated human genome (4 gene-specific siRNA oligonucleotides/well, DHARMACON), which were arrayed in duplicate 384-well plates by robotic transfer. After 72 h in culture, cells were stimulated with 250 nM TG for 90 min at room temperature in full growth media, fixed, stained, imaged and analyzed for NFAT1-GFP nuclear translocation. For each 384-well plate, a preliminary Z score was calculated using the mean nuclear translocation score and standard deviation derived from experimental wells on each plate. Moderate and strong hits (Z score $<-3.0$ and $>3.0$) were then removed from the analysis, and a final Z score was calculated using the mean and SD of the remaining experimental wells. Genes were ranked using the averaged Z score from duplicate plates, and positive regulators of NFAT were selected provided that the Z score for both values was $<-2.0$. The final list of 887 positive gene regulators was established after removal of duplicate, discontinued and re-annotated EntrezGene identifiers.

Gene Expression Analysis of Mouse Tissues

Affymetrix M430 v2.0 microarray data for 79 mouse tissues in duplicate was generated as previously described (Lattin et al., 2008). GC-RMA normalized probe set-level data was obtained from the NCBI Gene Expression Omnibus (accession GSE10246). The 887 human EntrezGene identifiers selected by RNAi screening were mapped to 744 mouse EntrezGene identifiers using orthology tables from the Mouse Genome Database (World wide website of informatics, March 2011). Of these, 683 genes were measured by at least one probeset on the array. In cases of multiple probe sets per gene, the probe set with highest signal was chose, averaged across the 79 tissues. Expression data for these probe sets were re-scaled so that each probeset signal ranged from 0 to 1 across all tissues, and organized by hierarchical clustering (Eisen et al., 1998) using the Pearson correlation distance and average linkage.

Gene Ontology Analysis

Enrichment analysis for Gene Ontology (GO) terms was performed on the 887 RNAi screen hits (human EntrezGene identifiers) using Fisher's exact test, as implemented in the DAVID tool (Huang et al., 2007a; Huang et al., 2007b). GO terms with nominal p-values less than 0.1 were retained.

Reagents

Thapsigargin (TG), phorbol myristate acetate (PMA), ionomycin and cyclosporin A were purchased from CALBIOCHEM®; recombinant human TNF was purchased from CLONTECH®; and hygromycin B, puromycin and doxycycline were purchased from SIGMA ALDRICH®.

siRNA Sequences

All siRNA oligonucleotides are from the human DHARMACON siGenome collection (v2007 or 2010), with the exception of siControl, which was custom synthesized by DHARMACON (Gwack et al., 2006). The siRNA sequences are listed in Tables 6-8.

shRNA Sequences shRNA were designed using the Cold Spring Harbor Laboratory RNAi Codex (see World wide website of Cold Spring Harbor Laboratory). For each construct, a 97-nt strand containing the shRNA hairpin inserted within a miR30-based sequence context (Dickins et al., 2005; Silva et al., 2005; Zeng et al., 2002) was used as a template for PCR-amplification and sub-cloning within the MSCV-based retroviral vector pLMP (OPEN BIOSYSTEMS). The miR-30-based shRNA sequences and primers used are listed in Tables 6-7.

DNA Constructs

Full-length human STIM1 and human ORAI1 (Zhou et al., 2010) were PCR-amplified and sub-cloned into the mammalian expression vectors pmDsRed-N1, peGFP-N1, pFLAG-CMV2 or pmCherry-C1 (CLONTECH®). For peGFP-STIM1, the eGFP sequence was inserted immediately before the STIM1 signal sequence, and a full-length STIM1 fragment containing eGFP was re-cloned into the tetracycline-responsive vector pRevTRE (CLONTECH®). The STIM1-CT473 fragment was PCR-amplified from full length STIM1, sub-cloned into pmCherry-C1, and then re-cloned as a fusion protein into pcDNA3.1 (INVITROGEN™).

Cell Culture, Transfection and Transduction

HeLa cells stably expressing NFAT1-GFP have been previously described (Gwack et al., 2006; Sharma et al., 2011). HeLa cells were obtained from the American Type Tissue Collection (ATCC), and Phoenix ECO packaging cells were obtained from the Nolan lab at Stanford University. All cells were cultured at 37° C. under 10% $CO_2$ in Dulbecco's modified eagle medium (DMEM) containing 10% heat-inactivated fetal bovine serum, 100 U/mL penicillin, 100 U/mL streptomycin, 2 mM L-glutamine, non essential amino acids, sodium pyruvate, vitamins, 10 mM HEPES, and 50 μM 2-mercaptoethanol. For siRNA transfections, HeLa cells were reverse transfected with 20-60 nM of SmartPoolsiRNA or individual duplex siRNAusing HiPerfect transfection reagent (QIAGEN®), according to the manufacturer's instructions. For functional assays cells were incubated for 72 h with siRNA complexes while for qRT-PCR analysis they were incubated for 48 h. For DNA transfections, 80% confluent HeLa or Phoenix ECOcells were transfected using Lipofectamine 2000 (INVITROGEN™), according to the manufacturer's instructions. For generation of HeLa lines stably expressing NFAT1-GFP and STIM1-mDSRed (the genome-wide screen), or tetracycline-repressed GFP-STIM1 and mCherry-ORAI1 (confocal and TIRF microscopy), HeLa NFAT1-GFP or HeLa cells were transfected with the appropriate DNA constructs, placed under antibiotic selection 72 h post-transfection, and cultured for a minimum of 3 weeks with a media change every 72 h. Single colonies of antibiotic-resistant cells were isolated and re-cultured from single cell suspensions. Stable lines were maintained in the presence of selection antibiotics or selection antibiotics plus doxycycline (10 μg/mL) until transfection. CD4+ T lymphocytes were purified (>95% purity) from spleen and lymph nodes of C57BL/6 mice (6-12 weeks old) using positive magnetic separation (Dynal, INVITROGEN™), according to the manufacturer's instructions. Purified cells were plated at a concentration of $1\times10^6$ cells/mL in 12-well plates pre-coated with goat anti-hamster IgG (ICN Biomedical), and stimulated with 1 μg/mL anti-mouse CD3 (clone 2C11) and 1 μg/mL anti-mouse CD28 (clone 37.51). Retroviral supernatants were generated by DNA transfection of Phoenix ECO packaging cells and concentrated overnight by centrifugation at 6000×g. After 24 h of stimulation, CD4+ T cells were transduced with the viral supernatants by spin infection in the presence of 8 μg/mL polybrene (American Bioanalytical) for 2 h at 700×g, after which the viral supernatant was removed and replaced with stimulation media for an additional 24 h. After 48 h of stimulation, T cells were removed from the TCR signal and re-cultured at a concentration of 0.5×106 cells/mL in growth media supplemented with 20 U/mL recombinant human IL-2 and 2.5 μg/mL puromycin for 72 h. All mice were maintained in specific pathogen-free barrier facilities at Harvard Medical School, and were used in accordance with protocols approved by the Immune Disease Institute and Harvard Medical School animal care and use committees.

Quantification of Nuclear Translocation

Confluent cell monolayers seeded in black rim, clear bottom 384-well plates (Corning/Costar) were stimulated at room temperature in complete growth media with 250 nM-1 μM TG (for NFAT1) or 10 μg/mL TNF (for p65). After 30 min (1 μM TG and TNF) or 90 min (250 nM TG) of stimulation, cells were fixed in 4% paraformaldehyde (USB Corporation), permeabilized in phosphate buffered saline (PBS)/0.2% Triton-X 100 (Sigma), and stained with the DNA intercalating dye DAPI (INVITROGEN™). For visualization of endogenous p65, cells were immunostained with anti-p65 primary antibody (clone sc-109, Santa Cruz, 1:1000) and a Cy5-conjugated anti-rabbit IgG secondary antibody (clone 111-176-046, Jackson ImmunoResearch, 1:1000). Fluorescent images were acquired at 10× magnification on an ImageXpress Micro Automated Imaging System (Molecular Devices), and analyzed using the Translocation Application Module of MetaXpress software version 6.1 (Molecular Devices). Nuclear translocation was assessed by calculating the correlation of spatial fluorescence intensity between the GFP or Cy5 cellular compartment and the DAPI nuclear probe. Individual cells were scored as positive for nuclear translocation if >70% of GFP or Cy5 fluorescence correlated with DAPI fluorescence. Each data point represents the average of 3 separate wells on a plate (>1200 cells per well), with error bars reporting SD between wells.

Intracellular Cytokine Staining

On culture day 5 ex vivo, after 72 h of puromycin selection, murine CD4+ T cells transduced with gene-specific shRNA were stimulated for 6 h with 10 nM PMA and 500n Mionomycin in the presence of 2 μg/mL Brefeldin A (Sigma) for the last 4 h of stimulation. Cells were fixed with 2% PFA/PBS for 20 min at room temperature, washed twice with PBS, permeabilized in saponin buffer (PBS, 0.5% saponin [SIGMA ALDRICH®], 1% BSA [SIGMA ALDRICH®] and 0.1% sodium azide [SIGMA ALDRICH®]), and stained with APC-conjugated anti-mouse IL-2 (BD Bioscience, clone JES6-5H4, 1:100) for 40 min at room temperature. Cells were washed twice in PBS/1% FBS and analyzed with a FACS Calibur flow cytometer (BD Bioscience) and FloJo software (Treestar).

$Ca^{2+}$ Flux Assays

Intracellular $Ca^{2+}$ flux was monitored in live cells using fura-2 (Molecular Probes). For plate-reader assays, confluent monolayers of NFAT1-GFP, STIM1-mDsRed and FLAG-ORAI1-expressing HeLa cells were seeded in black rim, clear bottom 96-well plates (Corning/Costar) the day before analysis. Cells were loaded with 1-2 μM fura-2/AM in modified Ringer's solution (20 mM HEPES, 125 mM NaCl, 5 mM KCl, 1.5 mM $MgCl_2$, 1.5 mM $CaCl_2$, 10 mM Glucose pH 7.4) supplemented with 2.5 mM probenecid (SIGMAALDRICH®). After 20 min at room temperature in the dark, cells were washed twice in modified Ringer's/probenecid, and incubated for an additional 30' in the dark.

Time-lapse fluorescence was recorded at 5 s intervals on a FlexStation III (Molecular Devices), using dual 340 nm and 380 excitation and emission recorded at 510 nm. Data are represented as the log 340/380 emission over time. For single-cell Ca imaging, HeLa cells plated on 18 mm coverslips were loaded with 3 μM fura-2/AM for 30-45 mM at 37° C. in DMEM containing 2.5 mM Probenecid and 10 mM HEPES (Sigma), washed twice with fresh media, and analysed immediately. Coverslips were assembled into a chamber on the stage of an Olympus IX 71 microscope equipped with a 20× (Uplans/Apo), N.A 0.75) objective. Cells were alternatively illuminated at 340 and 380 nm with the Polychrome V (TILL Photonics) using ET Fura filter (Chroma Technology Corp, cat. 79001). The fluorescence emission at λ>400 nm (LP 400 nm, Emitter 510/80 nm) were captured with a CCD camera (SensiCam, TILL Imago), digitized and analyzed by TILL Vision software. Ratio pictures were recorded at intervals of 2 sec. $Ca^{2+}$ concentration was estimated from the relation [Ca2+]i=K*(R-Rmin)/(Rmax-R), where the values of K, Rmin, and Rmax were determined from an in situ calibration of fura-2 in HeLa cells as described (Grynkiewicz et al., 1985). $Ca^{2+}$ Ringer's solution contained (in mM): 155 NaCl, 4.5 KCl, 1 $CaCl_2$, 2 $MgCl_2$, 10 d-glucose, and 5 HEPES (pH 7.4 with NaOH). $CaCl_2$ were substituted by 1 mM EGTA in order to prepare 0-$Ca^{2+}$ Ringer's solution. 1 μM TG was used to stimulate the cells. Data were analyzed using TILL Vision (TILL Photonics), ImageJ (NIH) and Microsoft Excel (Microsoft). All values are given as mean±SEM (number of cells). Between three and five experiments were performed for each experimental condition. In case, data points were normally distributed, an unpaired two-sided student t-test was used. If normal distribution could not be confirmed, a non-parametric test (Mann-Whitney) was carried out. P-values are stated in the figure legends. The $[Ca^{2+}]$i peaks during $Ca^{2+}$ release and $Ca^{2+}$ influx, the initial $[Ca^{2+}]$i influx rate (average slope 10 s following the re-addition of $Ca^{2+}$), and the averaged $Ca^{2+}$ plateau were estimated from more than 80 single cells in each experiment.

TIRF Microscopy

Total Internal Reflection Microscopy (TIRFM) was performed using a 100×, 1.49 NA CFI Apo objective (Nikon) mounted on a Ti-Eclipse inverted microscope with Perfect Focus System (PFS; Nikon). Imaging was performed on HeLa cells stable transfected with GFP-STIM1 and mCherry-ORAI1. Cells were stimulated with 1 μM TG in the presence of 2 mM extracellular $Ca^{2+}$ solution for 20 min. Dual-channel time-lapse image sequences from 4-7 cells were acquired by sequential, nearly simultaneous acquisition of individual using a Coolsnap HQ2 monochrome CCD camera (Photometrics, Tuscon, Ariz.). Exposure times were 100 ms and 180 ms (for 488 nm and 561 nm channels, respectively) at a frame-rate of 20 sec. For co-localization, ImageJ macro JACoP was used. For particles counting, an initial threshold was applied by using the ImageJ function Analysis Particle. The threshold value was settled for every single cell at the time 0 where 98-99% of all fluorescence was subtracted after background subtraction. Following stimulation, only hot fluorescence spots (as a consequence of agglomeration of ORAI channels in the plasma membrane) were counted.

Confocal Microscopy and Quantification of STIM1-ORAI1 Co-Localization

To analyze STIM and ORAI distribution in cells, a method to quantify puncta formation and co-localization from confocal images of HeLa cells stably expressing low levels of tetracycline-regulated GFP-STIM 1 and mCherry-ORAI1 was developed. The day before analysis, cells were split, re-plated on glass coverslips and incubated overnight to adhere and recover cell morphology. Where indicated, cells were treated with 1 μM TG at RT in modified Ringer's Solution with or without 3 mM EGTA. After stimulation, cells were fixed with 4% PFA and stained with Phalloidin-647 (Molecular Probes). Images were acquired at 63× magnification on a Zeiss AxioObserver Spinning Disk microscope operated with Slidebook v4.12.2. Cells were selected for analysis on the basis of comparable fluorescent intensities, and were imaged at the basal layer ("footprint"). At least 15 different cell images were acquired for each condition. Images were imported to CellProfiler Cell Image Analysis Software (Broad Institute, Cambridge Mass.). After cell cropping, background correction and intensity thresholds were applied, two separate co-localization scores were calculated. First, GFP-STIM1 and mCherry-ORAI1 speckles were identified on each channel using an intensity threshold. Once a speckle mask was established for each image, the masks were overlaid and co-localized speckles were identified and normalized using the total cell area, as defined by the Phalloidin stain. Second, a correlation of spatial fluorescence intensity was calculated between the two channels using Pearson's co-efficient. Statistical significance was evaluated using a student's t-test.

qRT-PCR 48 h after siRNA transfection, total RNA was isolated from cells using the RNeasy extraction kit with on-column DNase I digestion (QIAGEN®), according to the manufacturer's protocol. cDNA was generated from 200-500 ng total RNA by oligo-dT priming and Superscript III (Invitrogen) reverse transcription, according to the manufacturer's protocol. qPCR was performed using FastStart Universal SYBR Green Master Mix reagents (Roche), and analyzed on a StepOnePlus Real-Time PCR Machine (Applied Biosystems). For each gene the relative expression was determined using a standard curve derived from siControl-treated RNA samples. All primer sets were designed to span exon junctions within conserved regions among transcript variants. Primer sequences are listed in Table 8.

STIM1-CT473 Rescue

For the rescue experiments, HeLa cells seeded in 12-well plates were transfected with control or septin 4/5-specific siRNA for 72H, and then plasmids encoding mCherry or mCherry STIM1-CT473 for 48H. Before analysis of NFAT1-GFP nuclear translocation, cells were incubated with media supplemented with 2 mM $CaCl_2$ or 1 uM TG and 2 mM $CaCl_2$, with or without pre-treatment with 1 uM CsA for 30 minutes.

Results

Figure 71A:
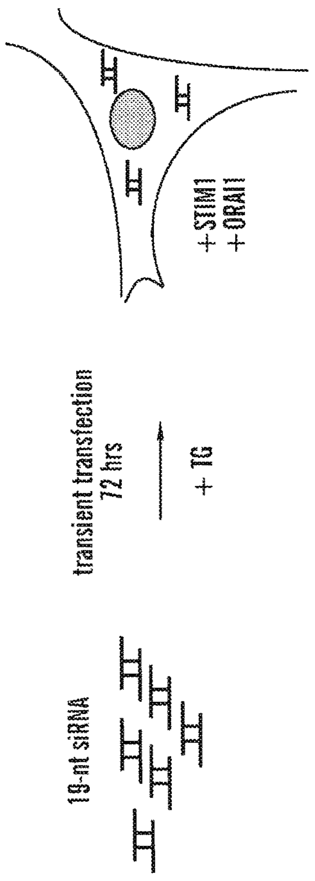
FIG. 71A shows the experimental design of the genome-wide siRNA screen in HeLa cells expressing NFAT1-GFP, STIM1-mDSRed and FLAG-ORAI1.

A Sensitive Assay to Quantify $Ca^{2+}$/calcineurin/NFAT Signaling in Mammalian Cells To facilitate the discovery of additional modulators in the $Ca^{2+}$/calcineurin/NFAT signaling pathway, the inventors developed a reliable and sensitive assay to quantify $Ca^{2+}$-induced NFAT activation in high-throughput format. A HeLa cell line stably expressing a $Ca^{2+}$-responsive NFAT1(1-460)-GFP reporter protein (NFAT1-GFP) was used in the assay, which shows greater than 80% target mRNA and protein depletion after transient transfection of duplex siRNA oligonucleotides (Gwack et al., 2006; Sharma et al., 2011) (FIG. 71). Since the inventors were particularly interested in identifying modulators of store-operated $Ca^{2+}$ entry, we increased the efficiency of this process (i.e., sensitized the biological assay) by over-expressing STIM1 and ORAI1 (Mercer et al., 2006; Prakriya et al., 2006; Soboloff et al., 2006).

Figure 3:
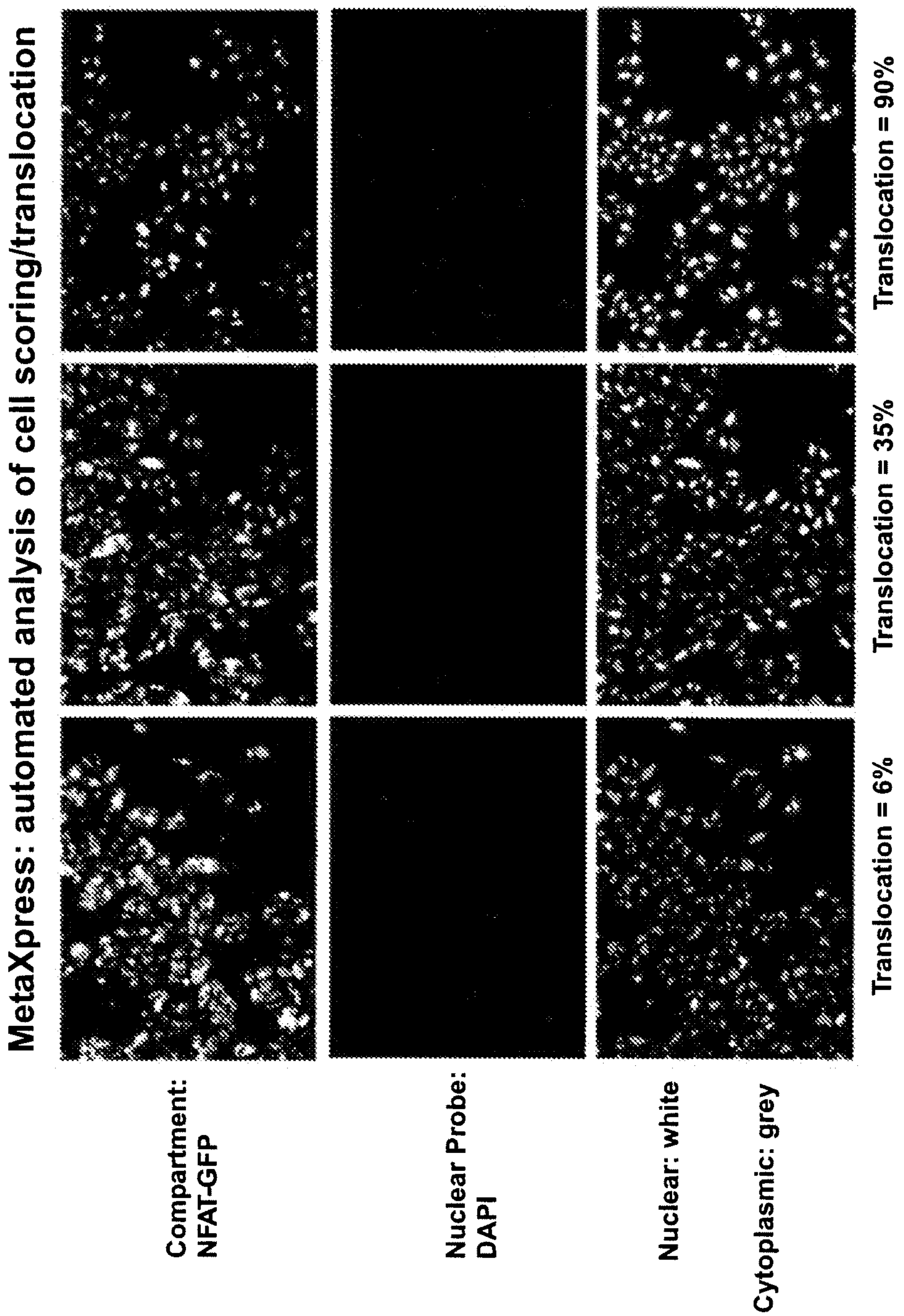
FIG. 3 shows the MetaXpress automated analysis of cell scoring and/or nuclear translocation of NFAT-GFP in thapsigargin (TG) treated cells.
Figure 4:
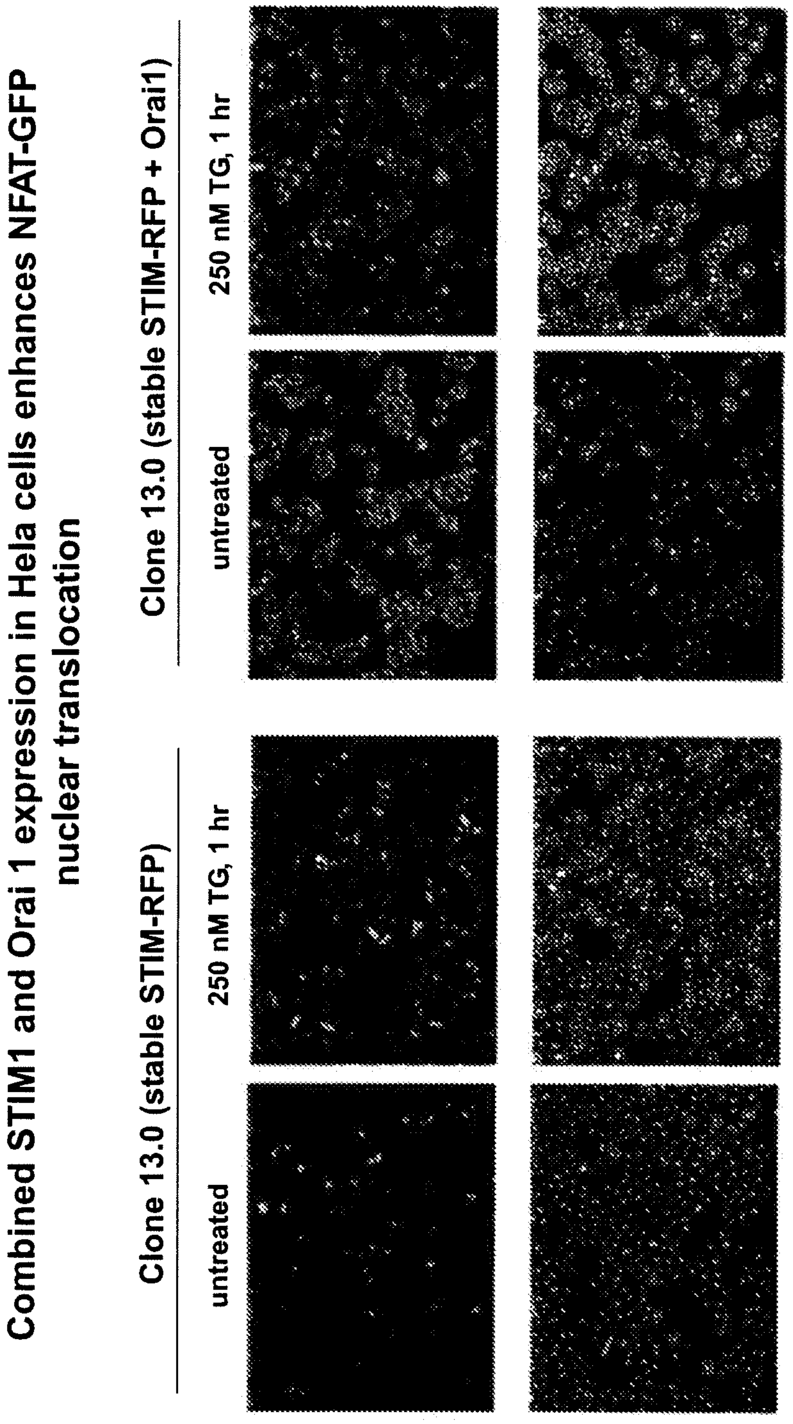
FIG. 4 shows that combined STIM1 and Orai1 expressions in HeLa cells enhances nuclear translocation of NFAT-GFP.
Figure 5:
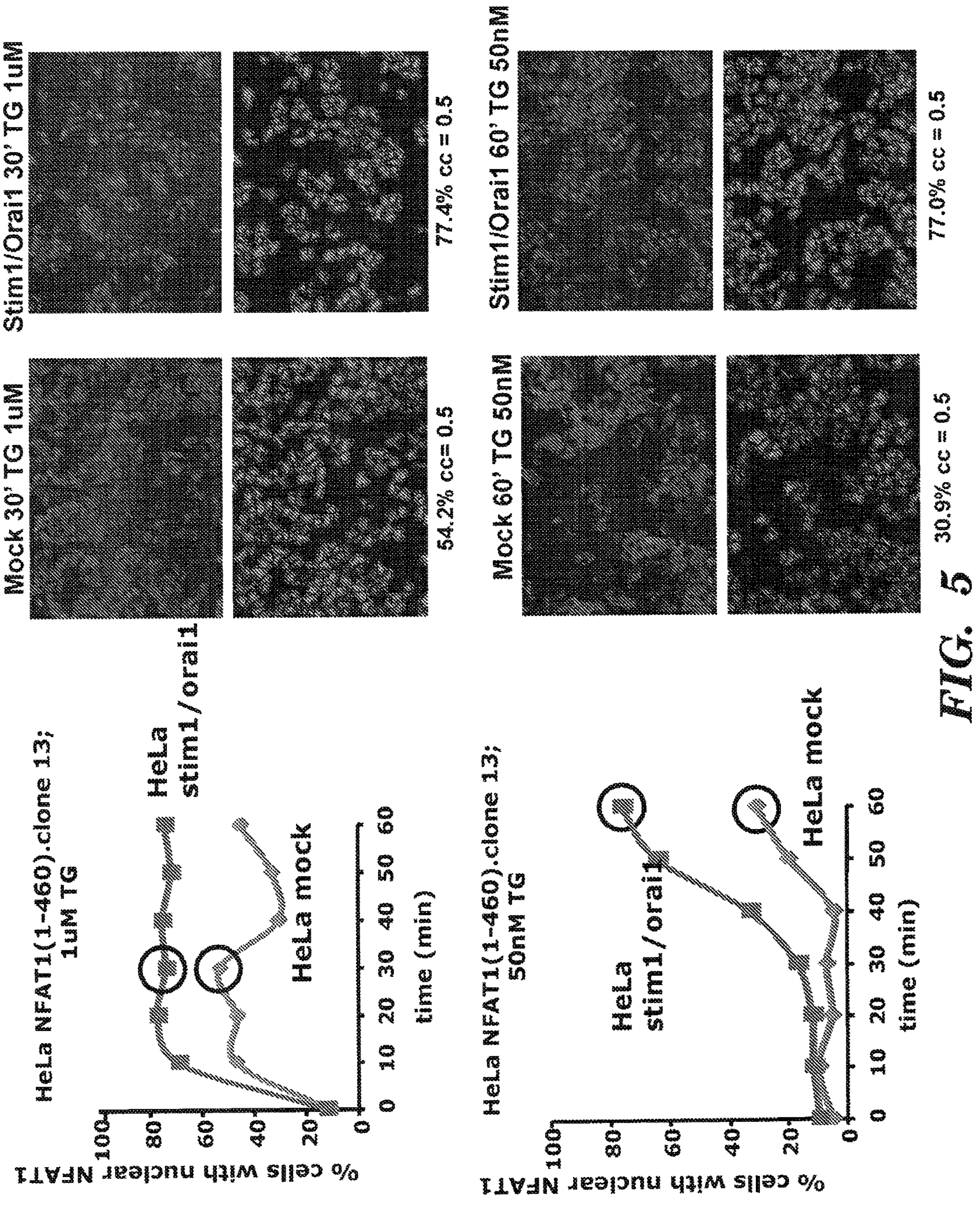
FIG. 5 shows that combined STIM1 and Orai1 expressions in HeLa cells enhances NFAT nuclear translocation.
Figure 6:
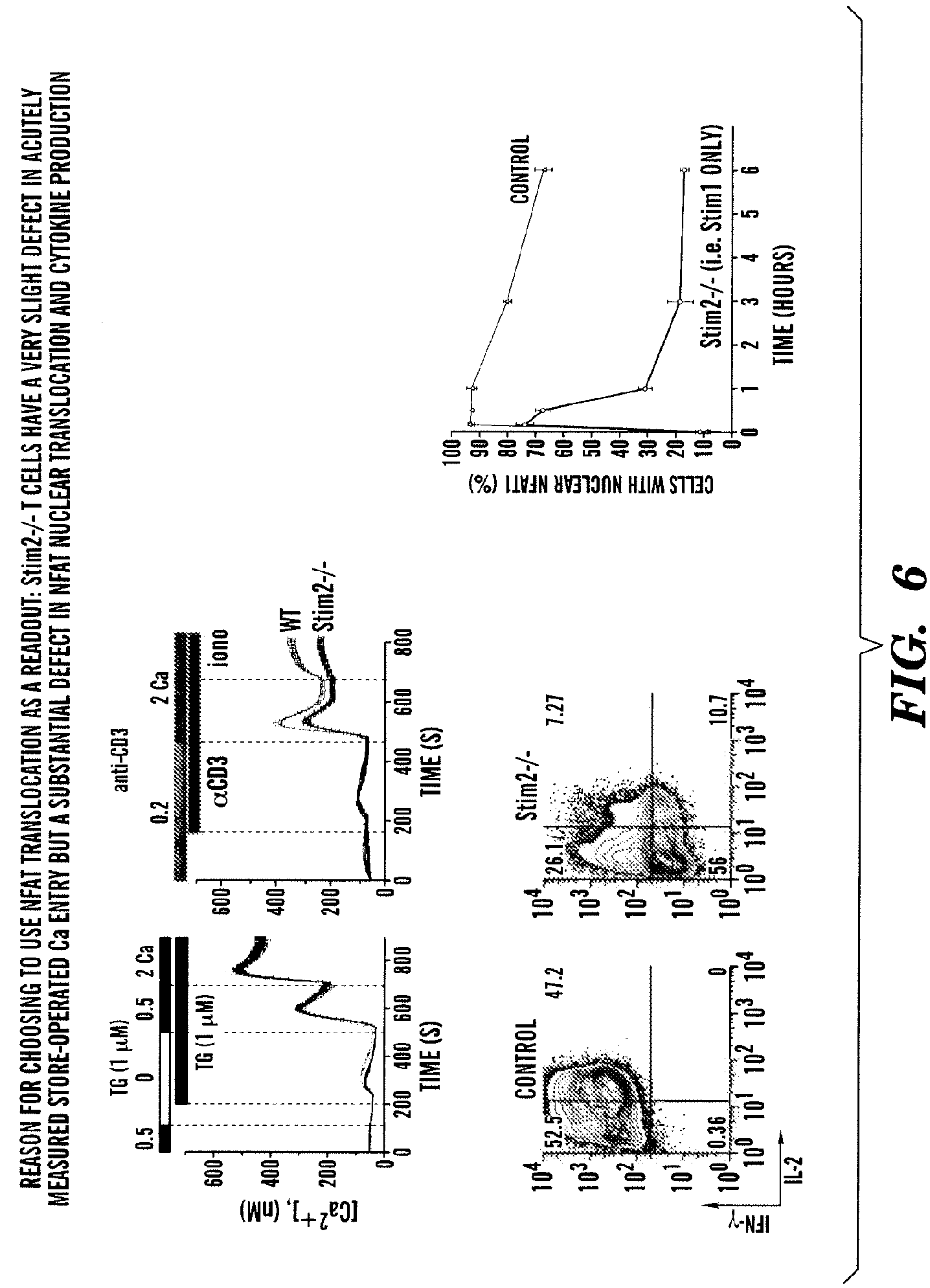
FIG. 6 shows the reason for choosing to use NFAT translocation as an screening assay: Stim2$^{-/-}$ T cells have a very slight defect in acutely measured store operated $Ca^{2+}$ entry (SOCE) but a substantial defect in NFAT nuclear translocation and cytokine production.
Figure 7:
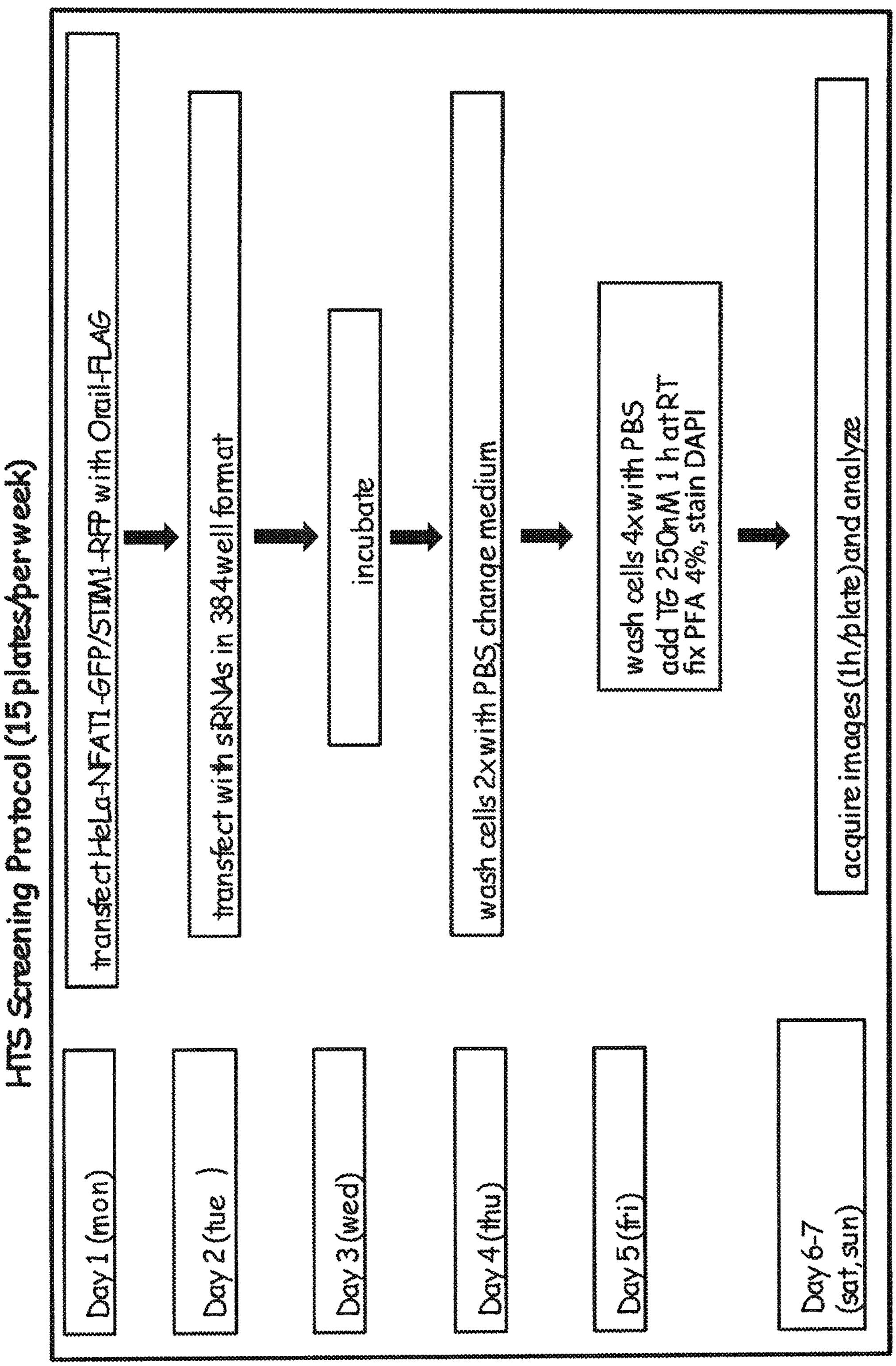
FIG. 7 shows an exemplary high-throughput screening (HTS) protocol in the form of a flow diagram.
Figure 9:
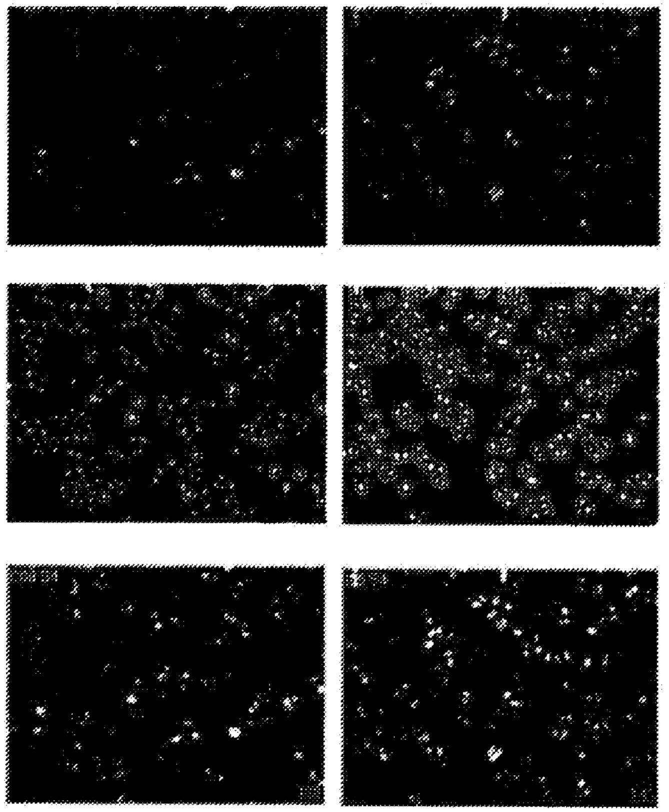
FIG. 9 shows the Z score calculation for HeLa cells transfected with STIM1 and Orai1.
Figure 11:
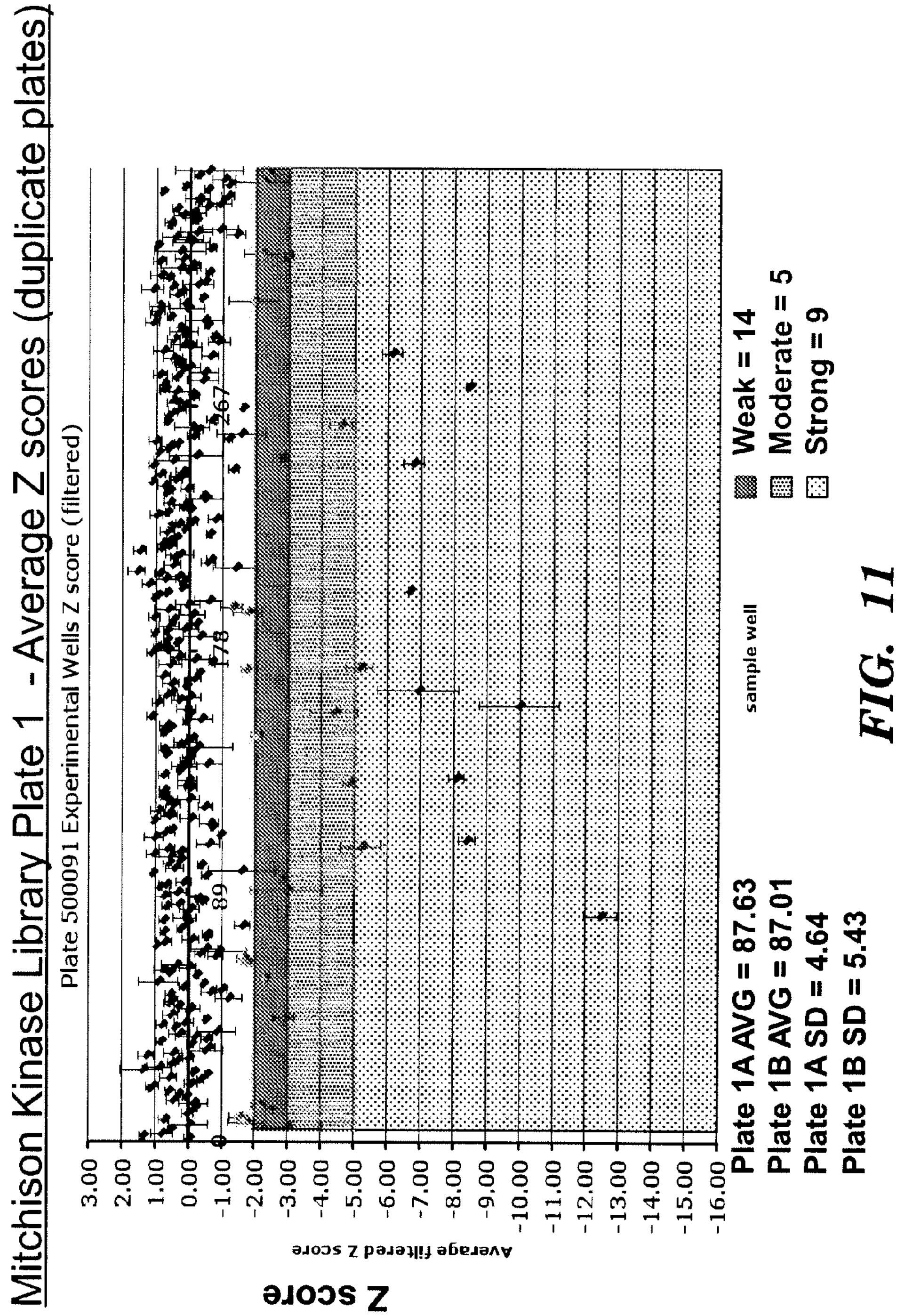
FIG. 11 shows the graph of average Z scores of kinases screened in sample wells of the HTS.
Figure 12:
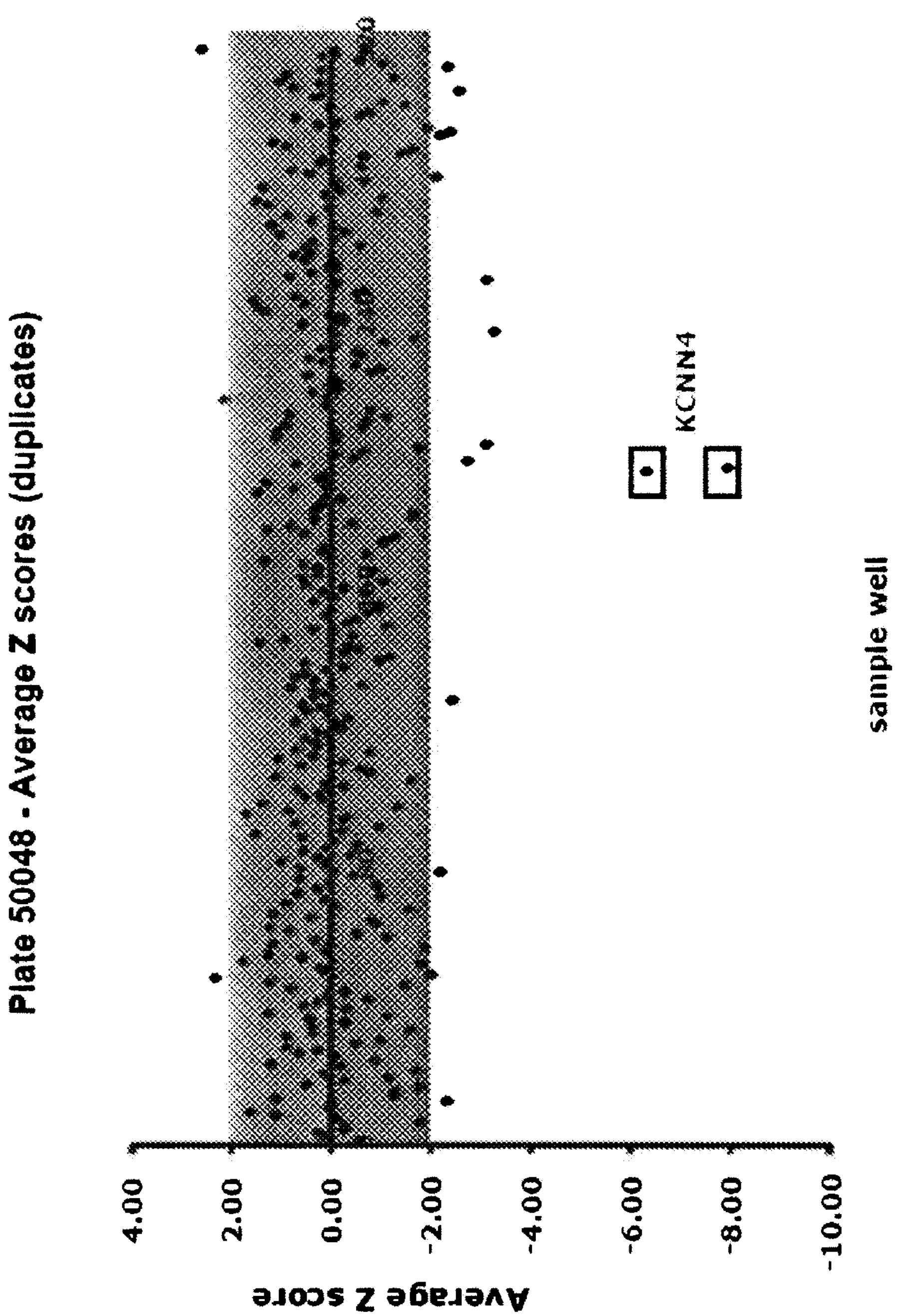
FIG. 12 shows the graph of the average Z scores of genes screened in the sample wells of the HTS plate #50048. Note that the duplicate Z-scores for KCNN4 (from duplicate wells) showing the knockdown of potassium channel KCNN4.
Figure 13:
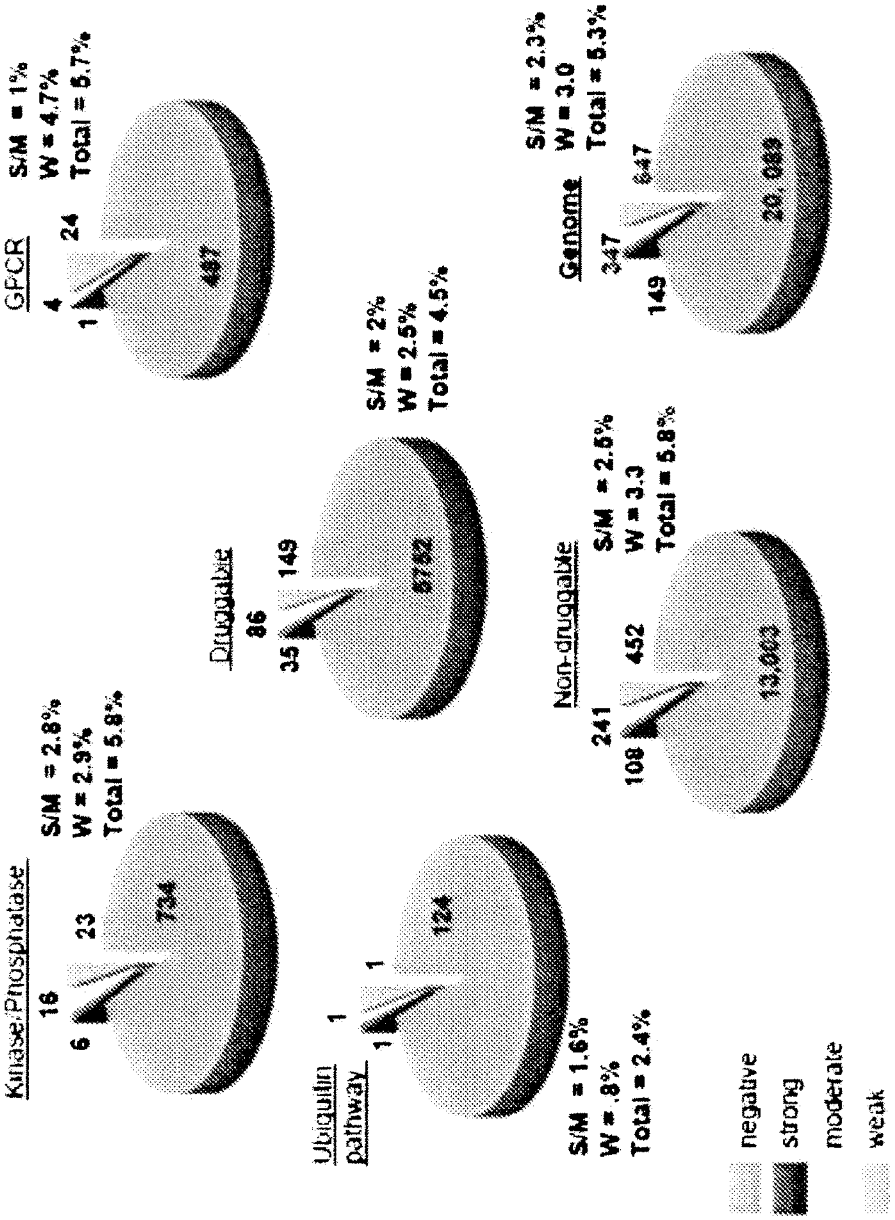
FIG. 13 shows the distribution and classification of the identified genes/proteins that modulate NFAT and/or store operated $Ca^{2+}$ entry (SOCE).
Figure 71B:
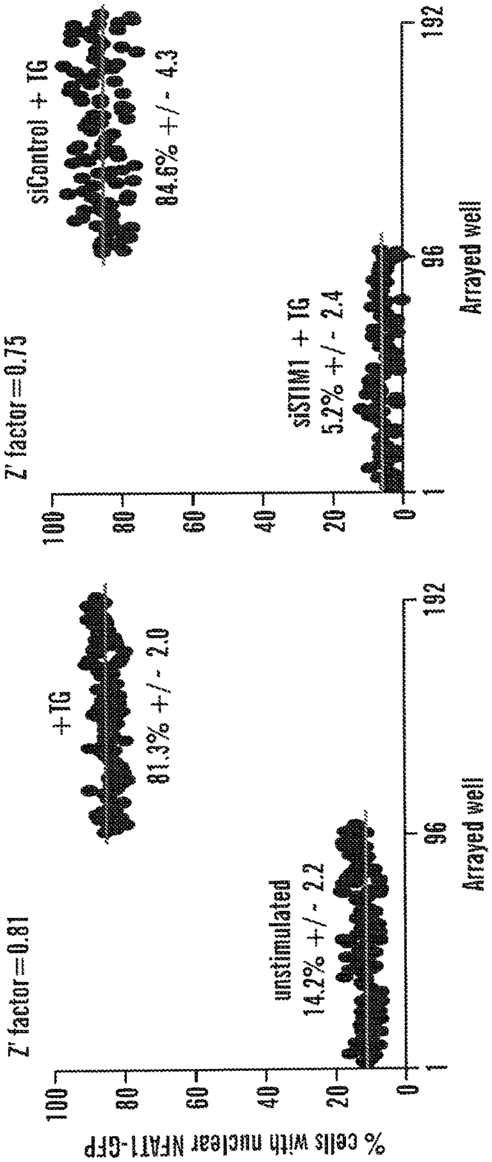
FIG. 71B shows that the assay robustness was evaluated using Z' factor calculated from a series of replicates (n=96 wells), corresponding to unstimulated or stimulated (+TG, 250 nM) cells (left), and siSTIM1- or siControl-treated cells after stimulation (right).
Figure 71C:
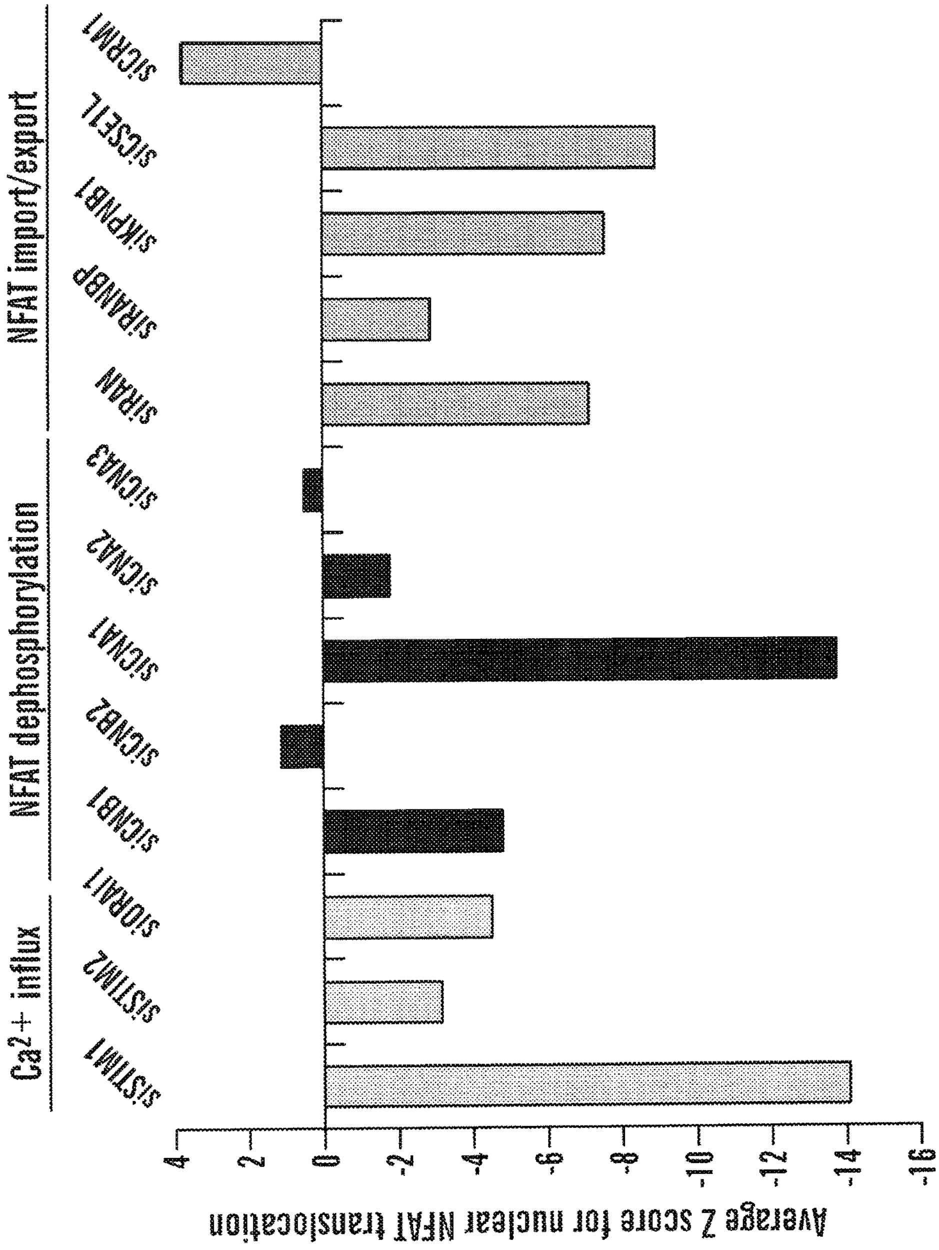
FIG. 71C shows the primary screen Z scores for known NFAT regulators obtained using the siRNA screen assay described.

NFAT1-GFP nuclear translocation was quantified in cells with and without stimulation (+TG, 50 nM) from fluorescent images (GFP and DAPI) analyzed using the Translocation Application Module of MetaXpress Software to score cells as cytoplasmic or nuclear for NFAT1-GFP (FIG. 3). $Ca^{2+}$-induced NFAT1-GFP nuclear translocation was scored at the single-cell level using an automated fluorescent microscope platform and MetaXpress Imaging Software, to analyze images of cells seeded in 384-well plates (Oh-hora and Rao, 2008; Sharma et al., 2011). Cells were scored as positive for nuclear translocation of 70% or more of NFAT1-GFP fluorescence co-localised with nuclear DAPI fluorescence. The majority of unstimulated cells were negative for NFAT1-GFP1 nuclear localisation (translocation score=6%) (FIG. 3, left panels); after treatment for 30 and 60 min with low concentrations (10 nM) of thapsigargin (TG), a compound that induces capacitive $Ca^{2+}$ entry in cells through passive depletion of the ER $Ca^{2+}$ stores (Takemura et al., 1989; Thastrup et al., 1990; Thastrup et al., 1989), 35% and 90% of cells scored positive for nuclear NFAT1 (FIG. 3, middle and right panels). The assay was robust and reproducible over a series of replicate wells, with a Z' factor of 0.81 for unstimulated versus TG-treated wells, and a lower but still satisfactory Z' factor of 0.75 for cells transfected with control and STIM1-specific siRNA and then stimulated with TG (FIG. 71B, left panel; n=96 wells each). The Z' factor is a calculation that reflects bio-assay robustness for high-throughput screening, by incorporating the dynamic range of the assay and its standard deviation (Zhang et al., 1999). The lower score for siRNA-treated cells reflects the higher variability in this population compared to untransfected cells (FIG. 71B, right panel).

Figure 14:
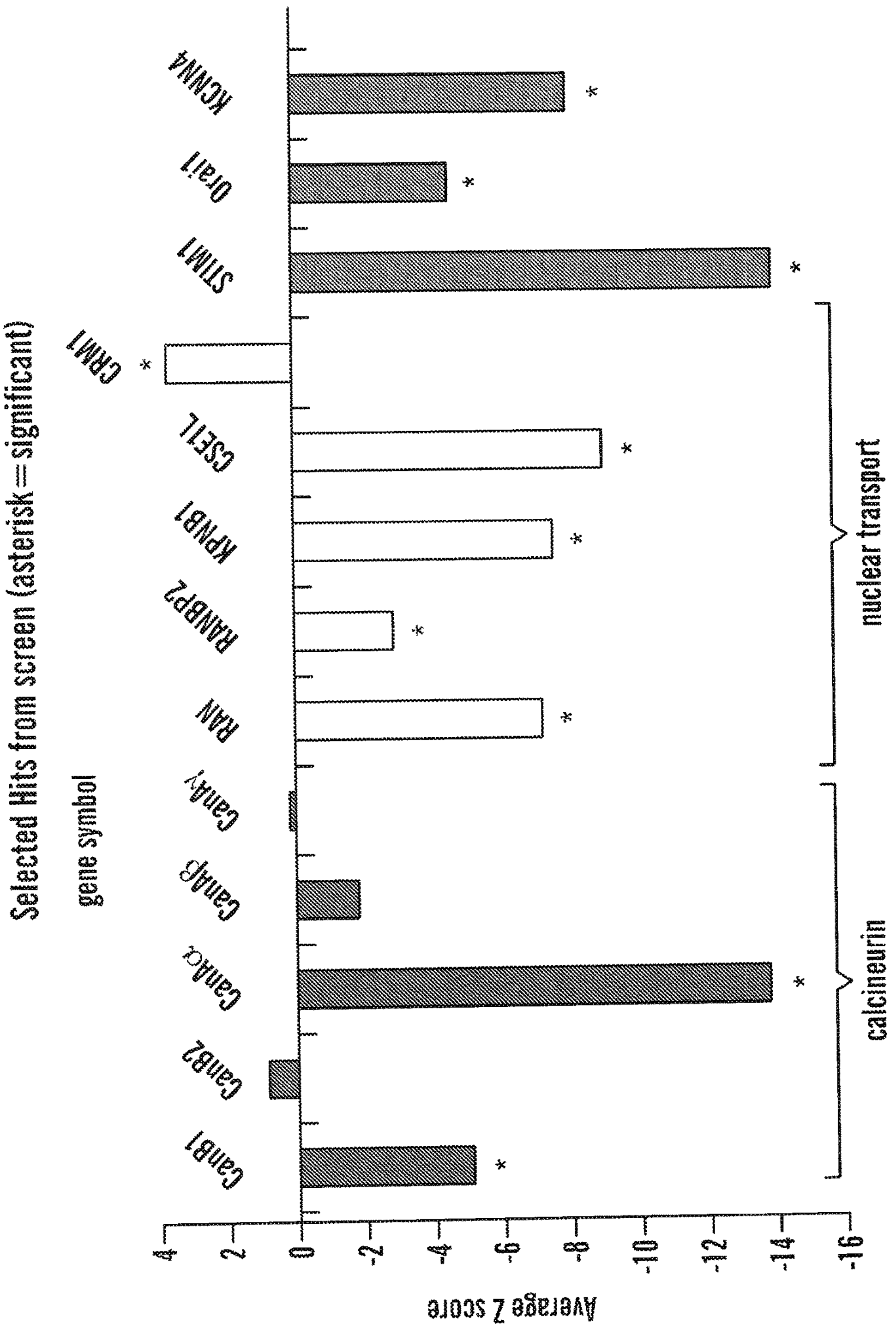
FIG. 14 shows the average Z score histogram of selected identified genes affecting NFAT.
Figure 15:
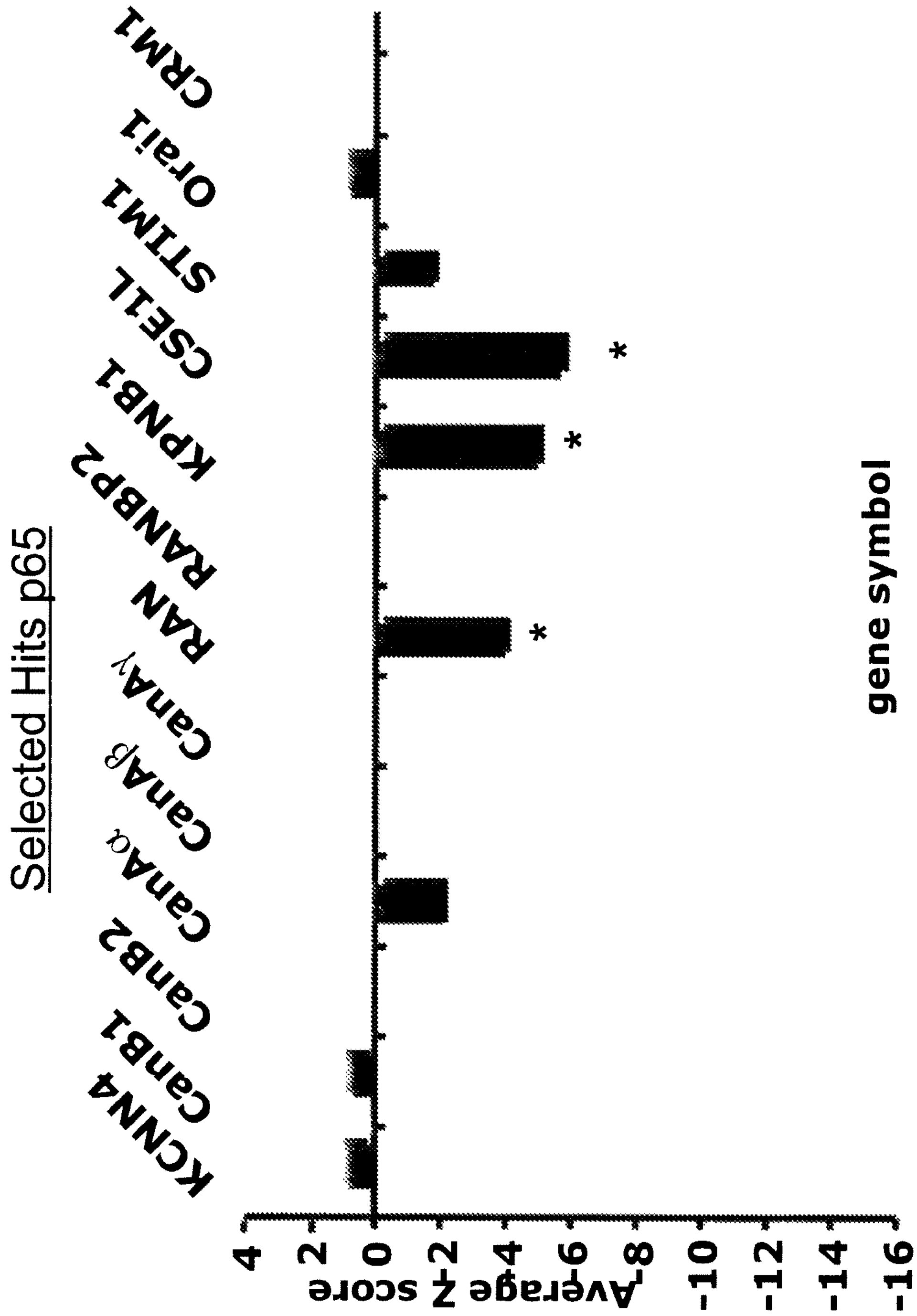
FIG. 15 shows the average Z score histogram of selected identified genes affecting p65.
Figure 18:
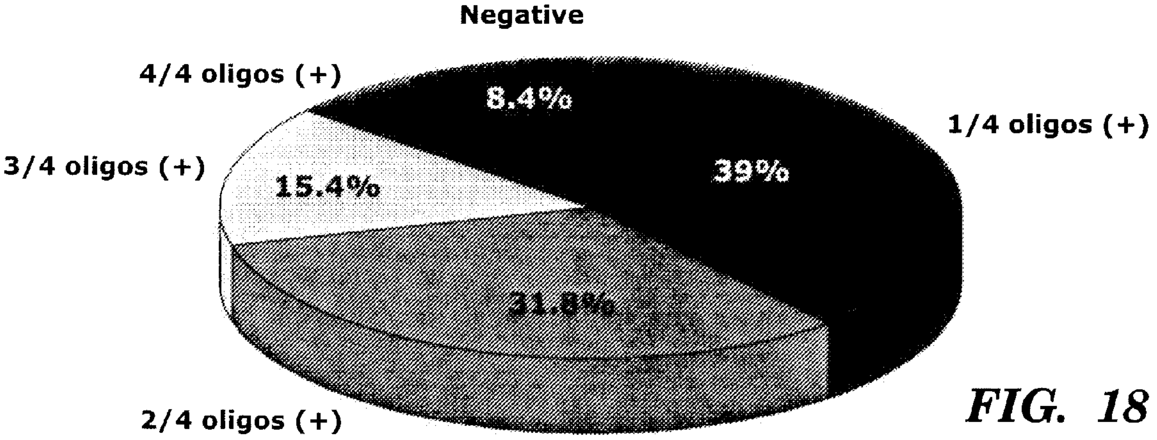
FIG. 18 shows the summary of the genes analyzed in the secondary HTS screen.
Figure 20:
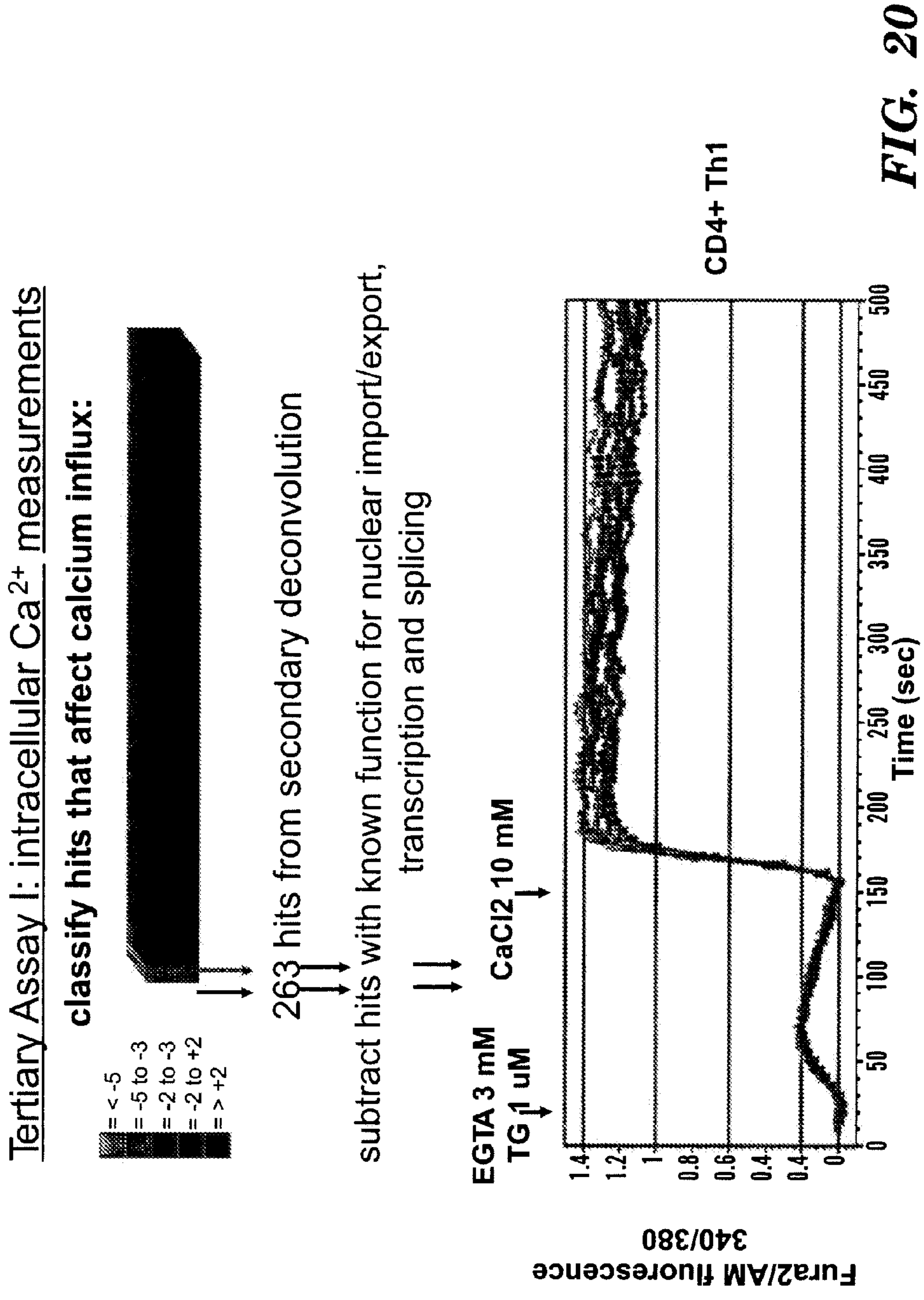
FIG. 20 shows the methodology of the tertiary screen.
Figure 21:
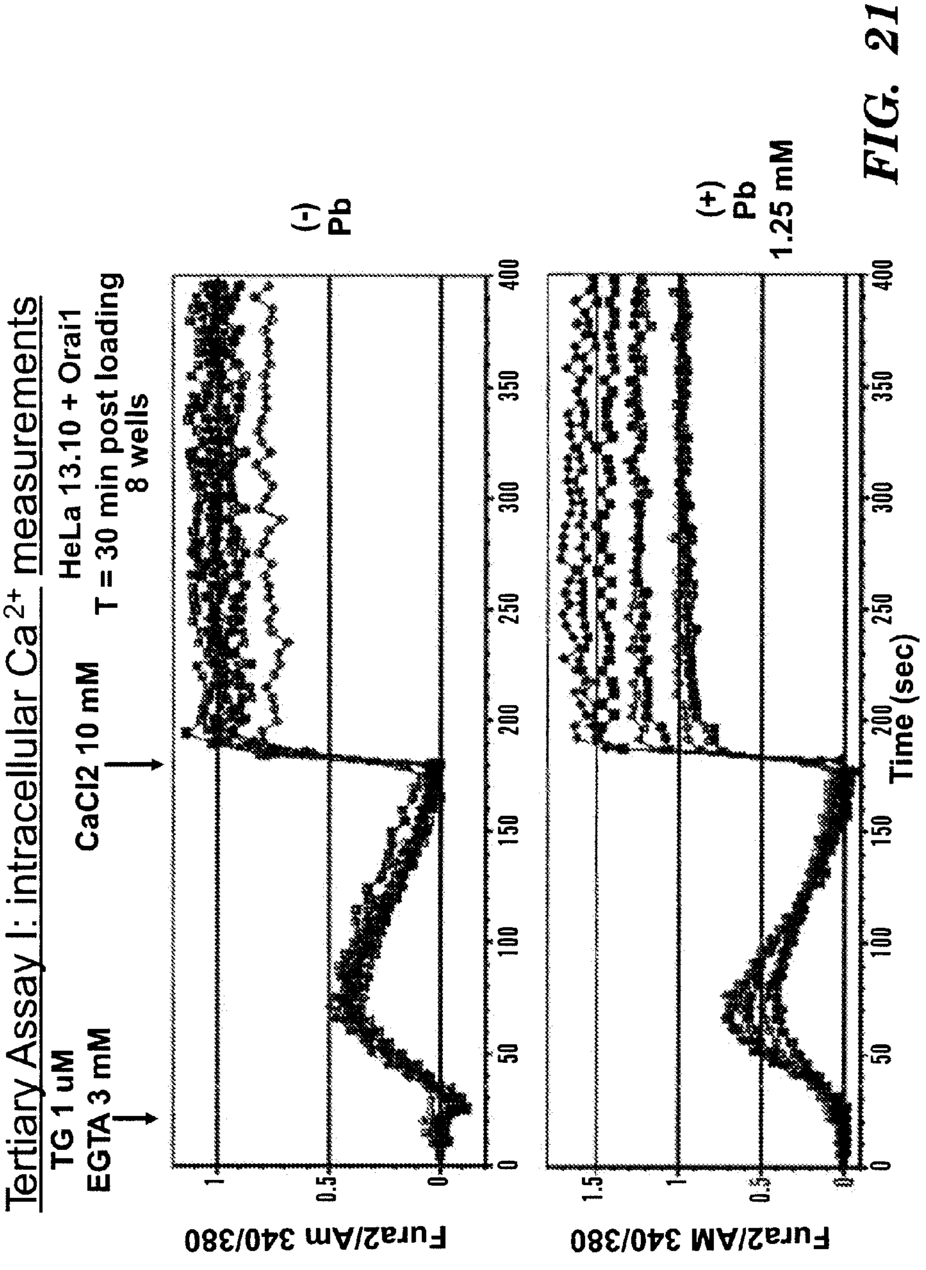
FIG. 21 shows eight reproducible traces of calcium fluxes in a tertiary screen in the presence (1.25 mM) or absence of lead (Pb).
Figure 22:
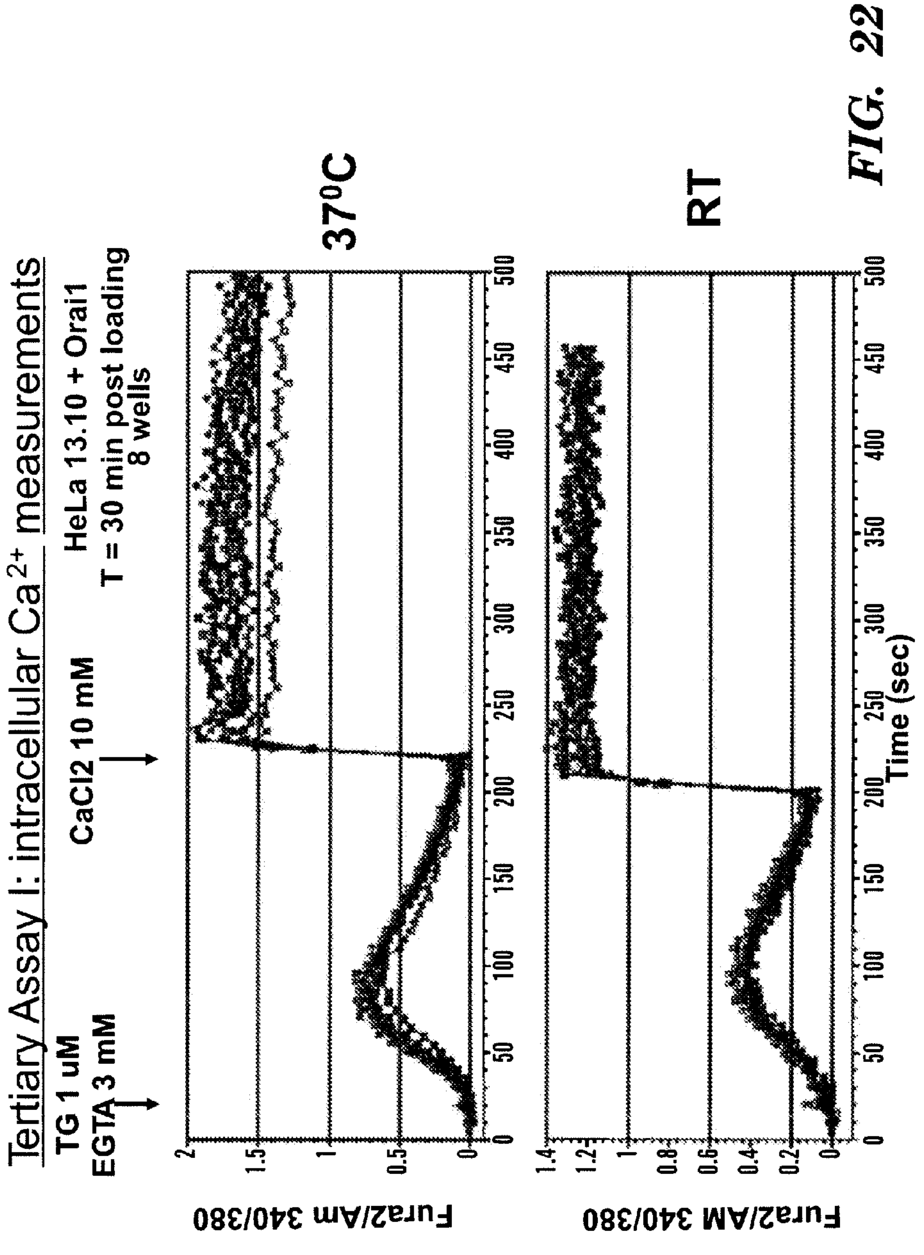
FIG. 22 shows eight reproducible traces of calcium fluxes in a tertiary screen at two different temperatures, at 37° C. and at room temperature (RT) (~25° C.).
Figure 23:
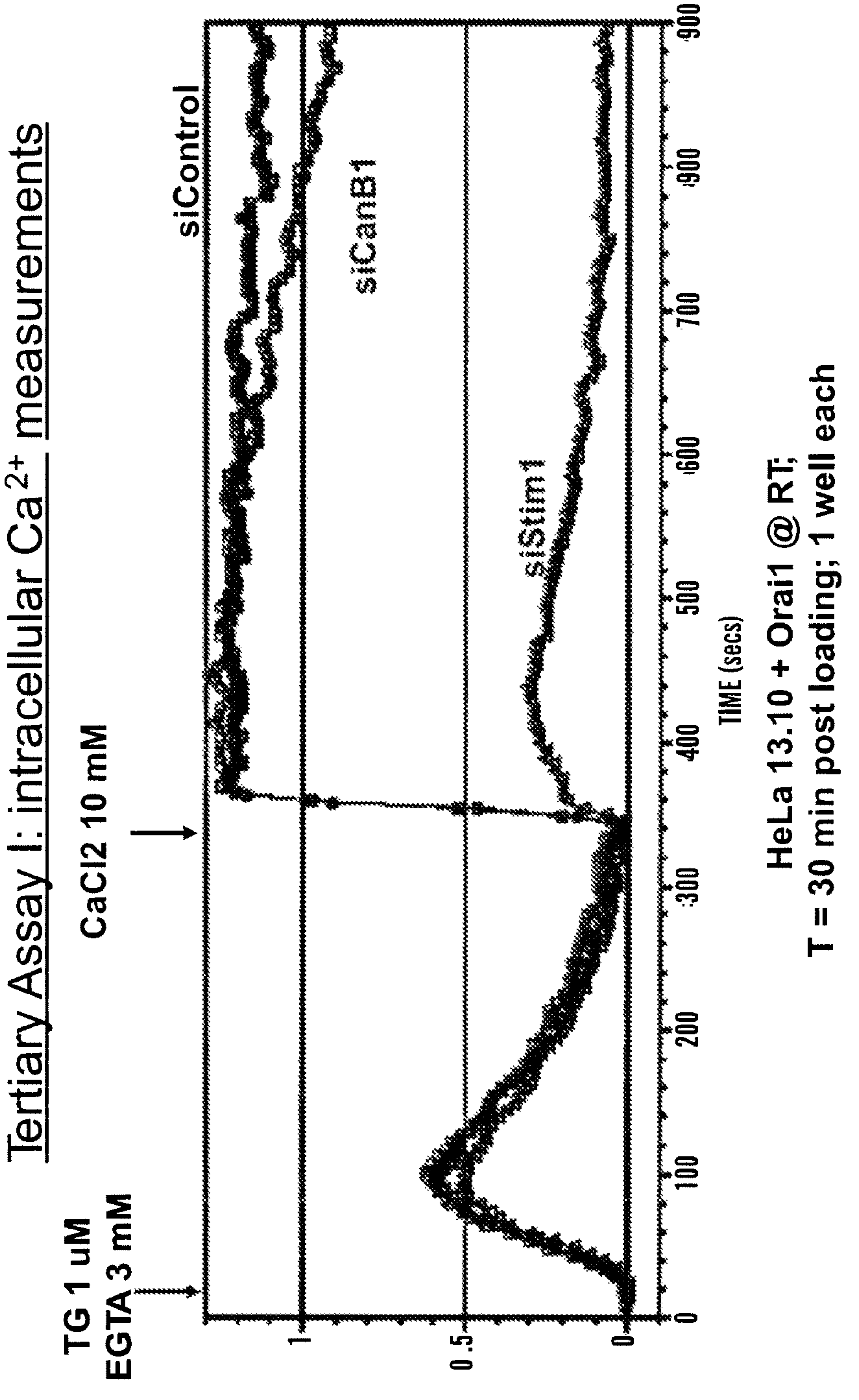
FIG. 23 shows additional traces of calcium fluxes in a tertiary screen at room temperature (RT) (~25° C.).
Figure 24:
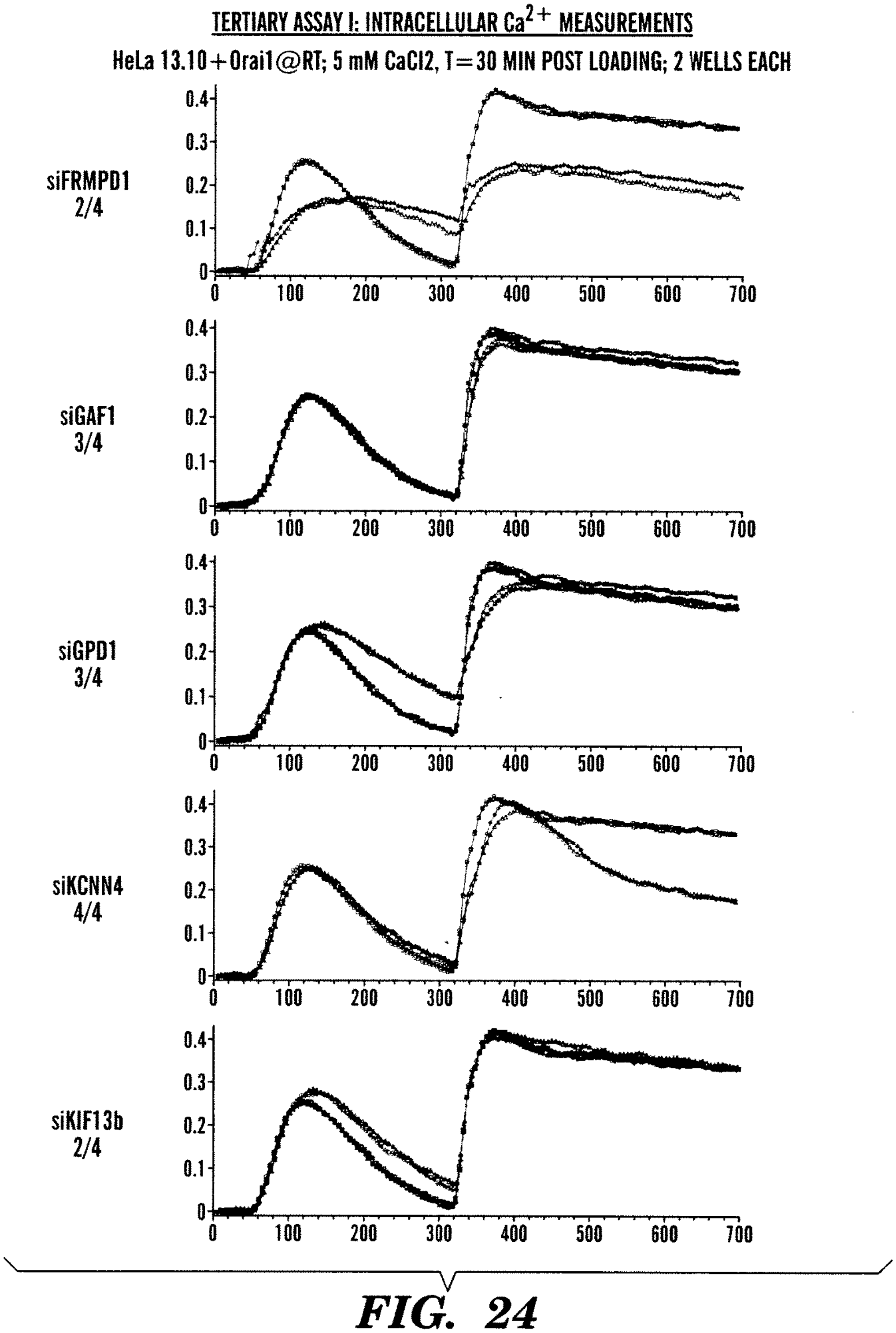
FIG. 24 shows additional traces of calcium fluxes in a tertiary screen of cells treated with siRNA to the respective genes: FRMPD1, GAF1, GPD1, KCNN4, KIF13B, SM14A, STIM1, SYT15, TROAP and UEV3.
Figure 24:
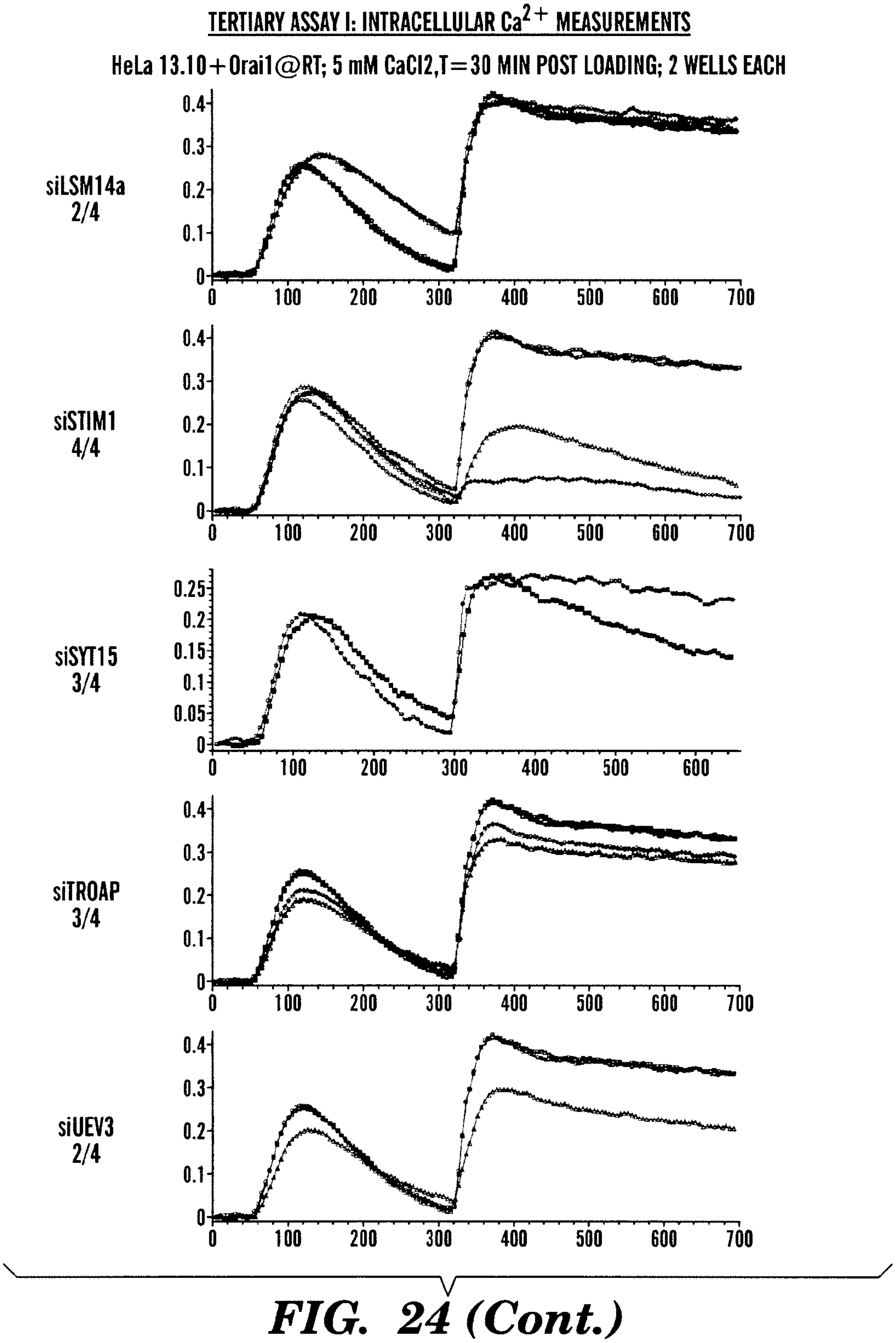
Figure 26:
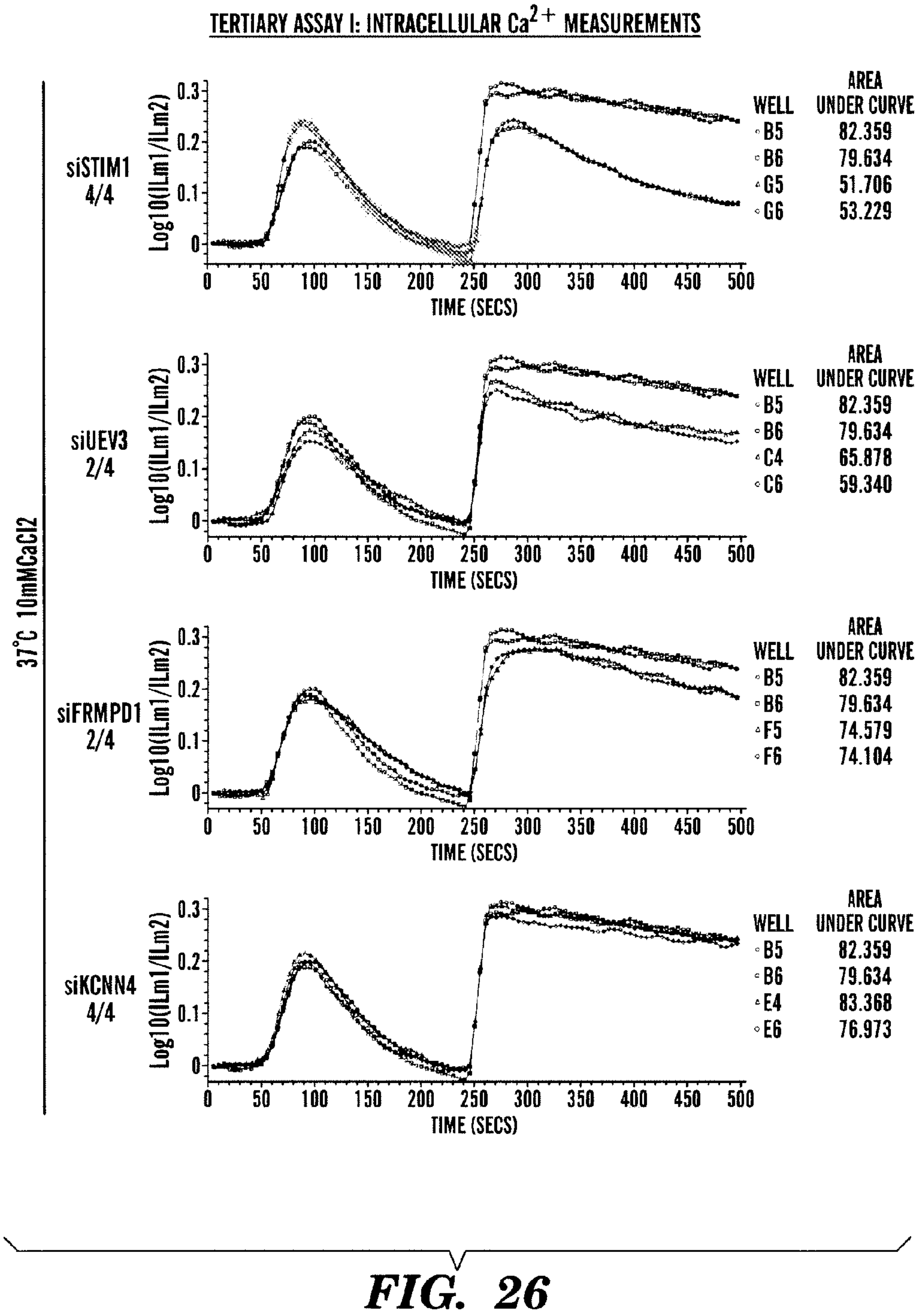
FIG. 26 shows additional traces of calcium fluxes in cells treated with siRNA to the respective genes: STIM1, UEV3, FRMPD1 and KCNN4, in a tertiary screen at two different temperatures, at 37° C. and at room temperature (RT) (~25° C.).
Figure 26:
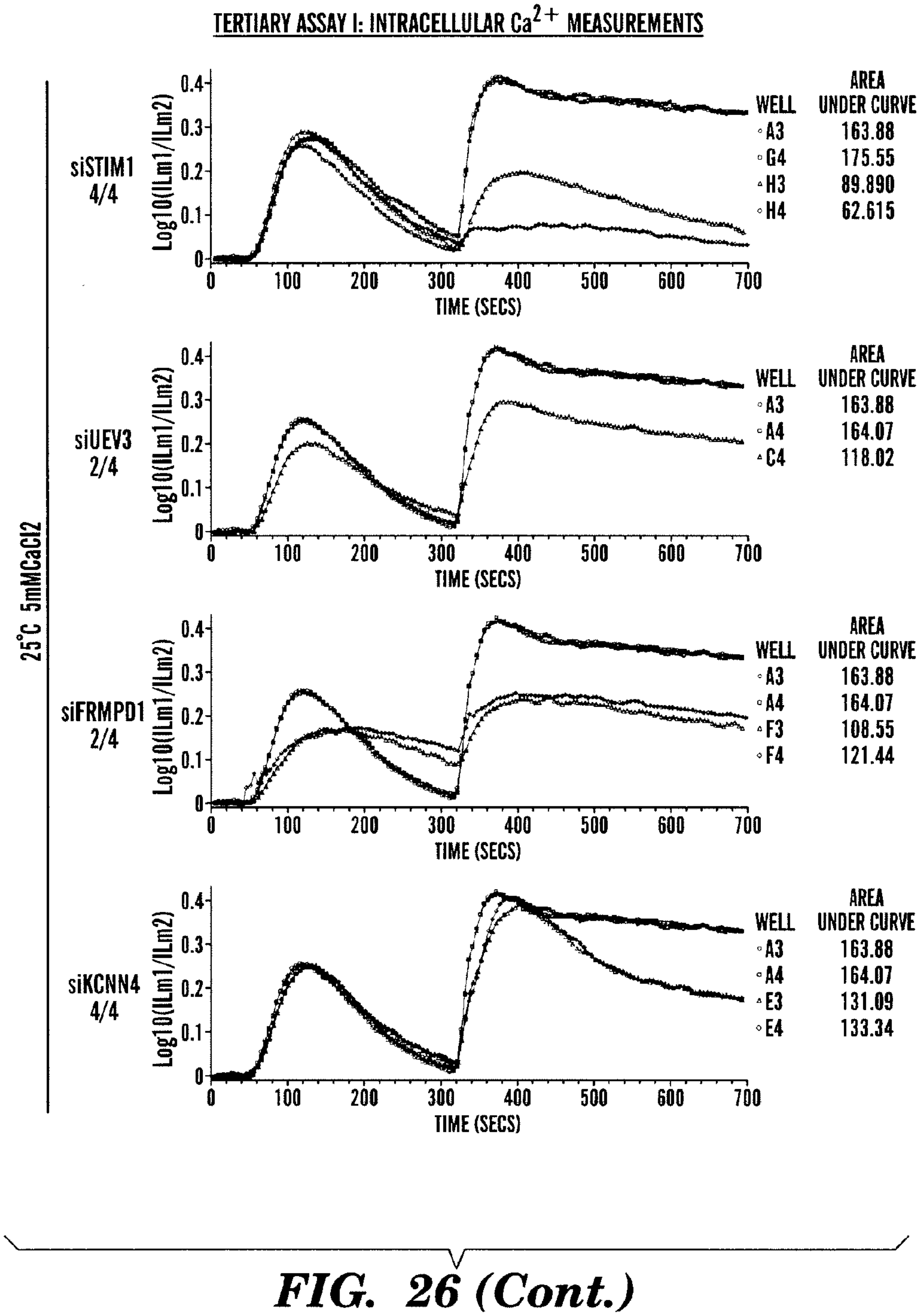
Figure 27:
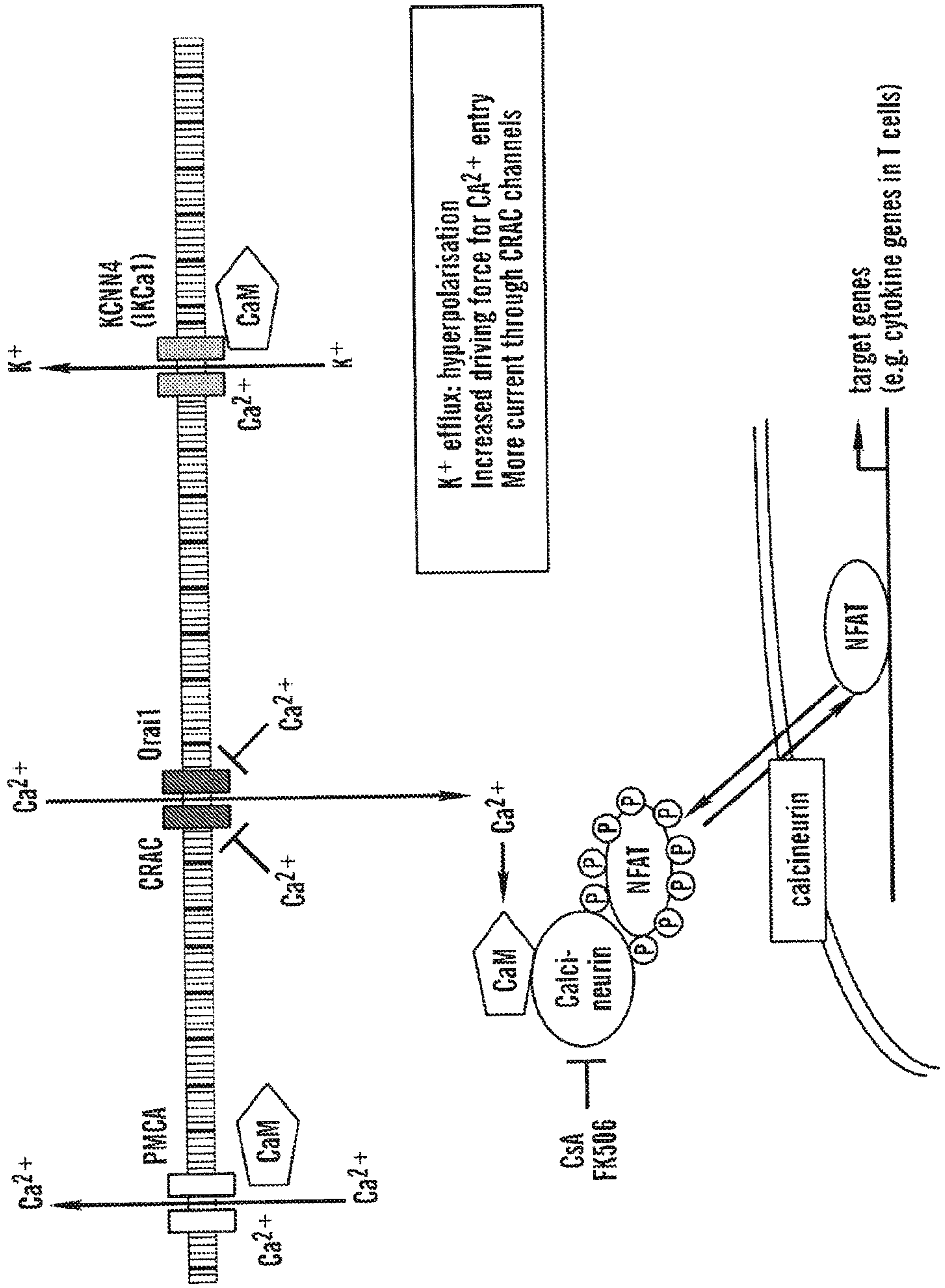
FIG. 27 shows the schematic diagram of the mechanism of action of the potassium channel KCNN4 in relation to the intracellular $Ca^{2+}$ concentration and the regulation of NFAT nuclear translocation, and the induction of increase in cytokine production by intracellular $Ca^{2+}$ concentration.
Figure 28:
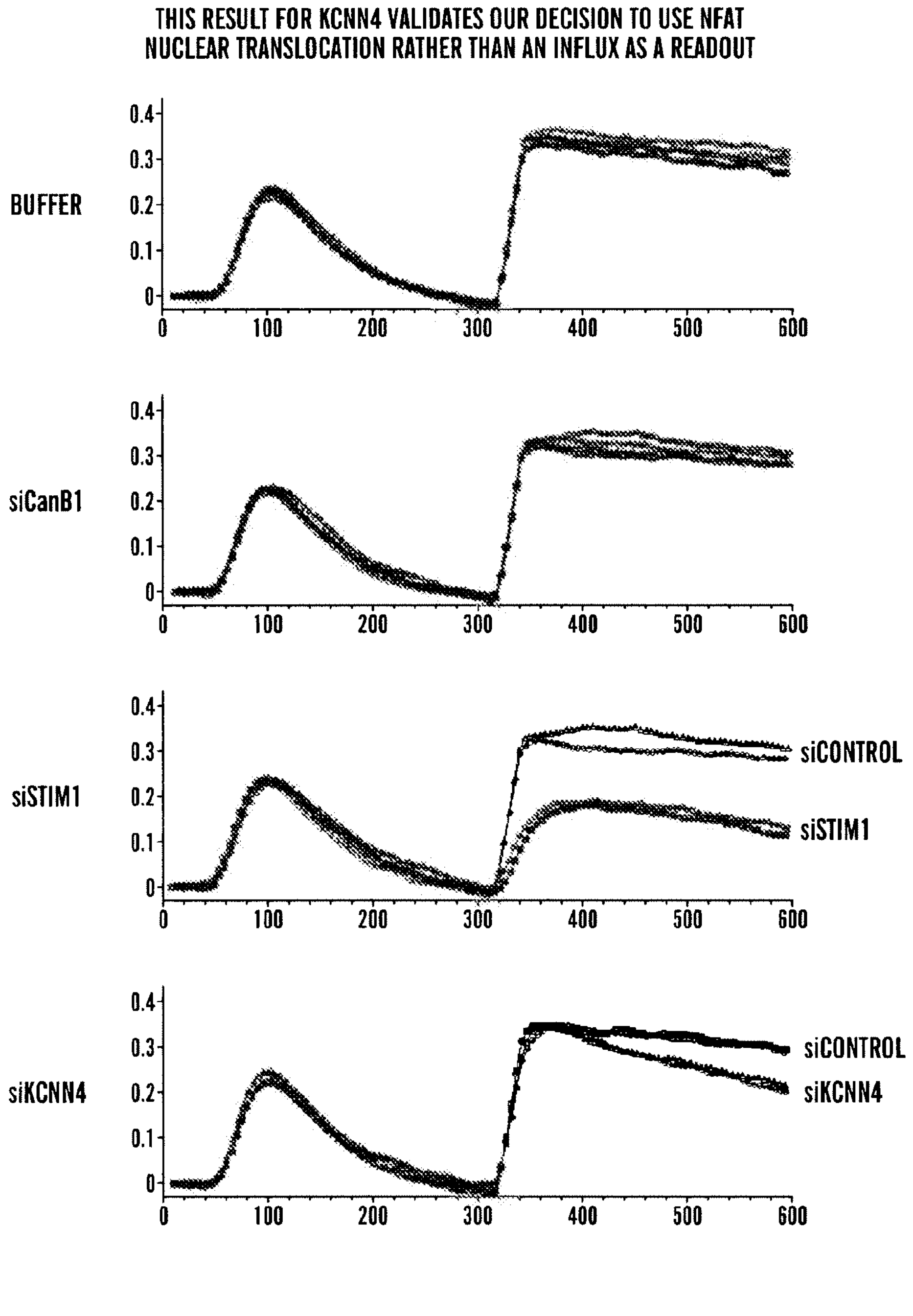
FIG. 28 shows the effects of siRNA of STIM1, CanB1, and KCNN4 on NFAT nuclear translocation. The figure also shows that siRNA CanB1 has no effect on $Ca^{2+}$ influx in contrast to the siRNA of STIM1 and KCNN4.
Figure 28:
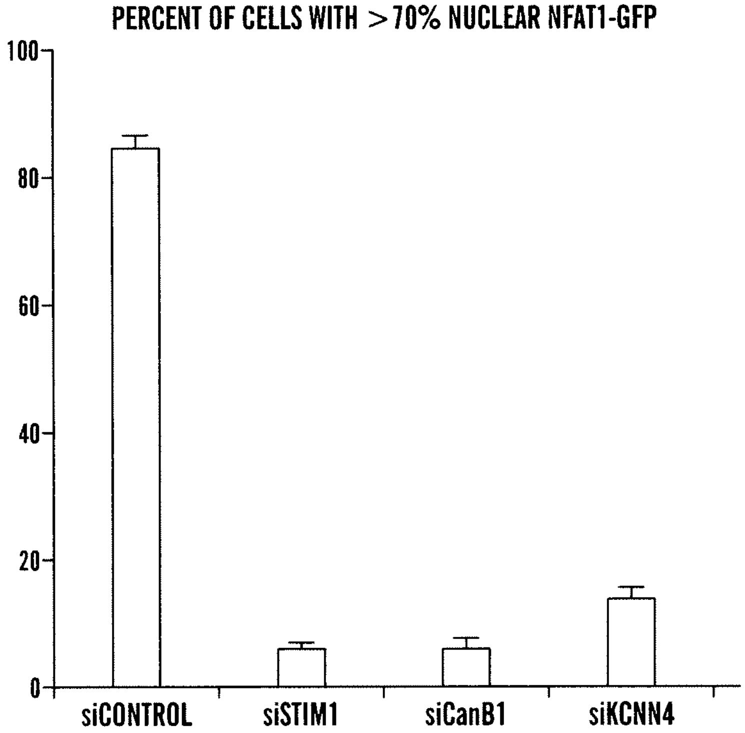
Figure 29:
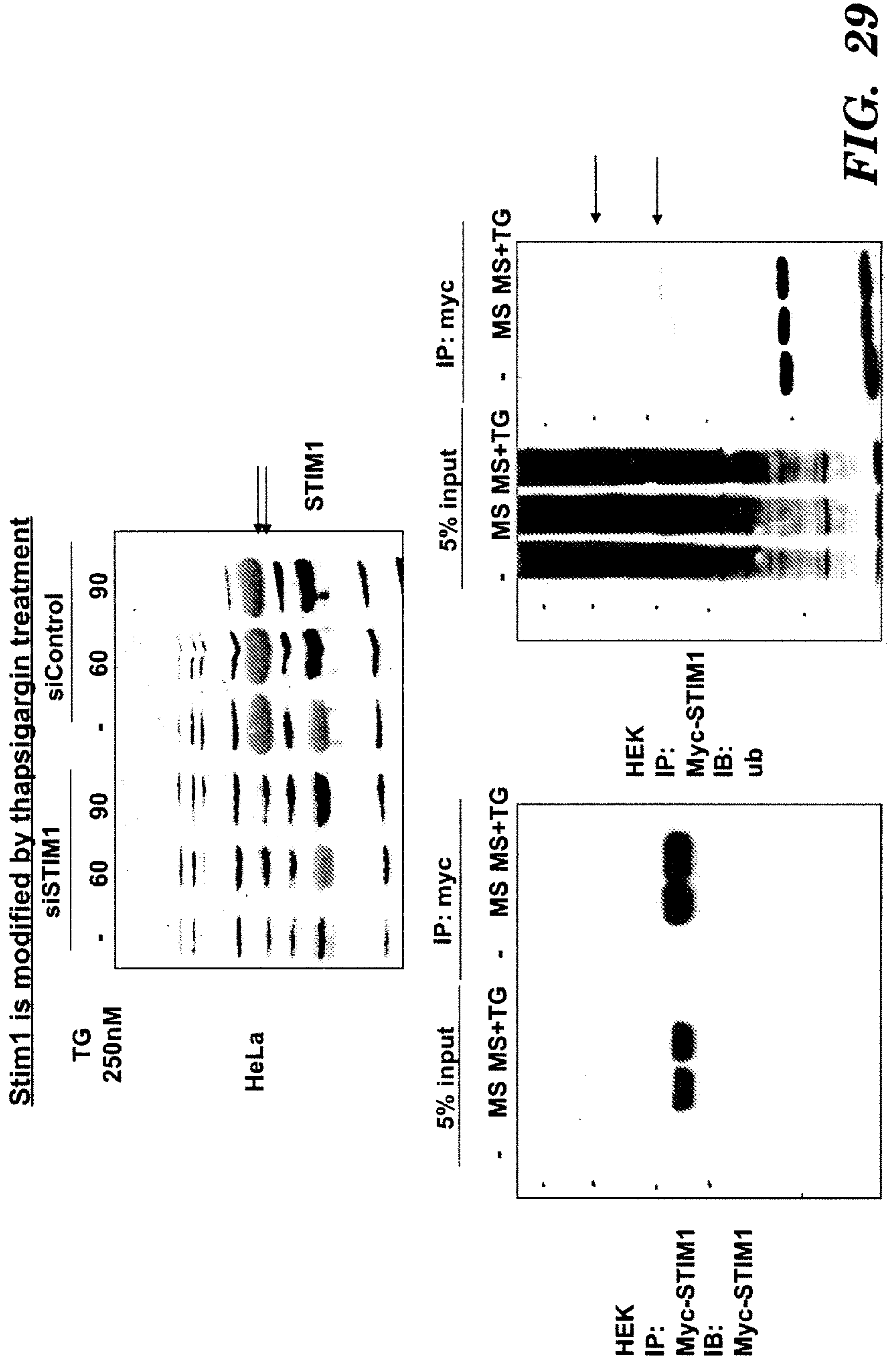
FIG. 29 shows that Stim1 is modified by thapsigargin treatment.
Figure 30:
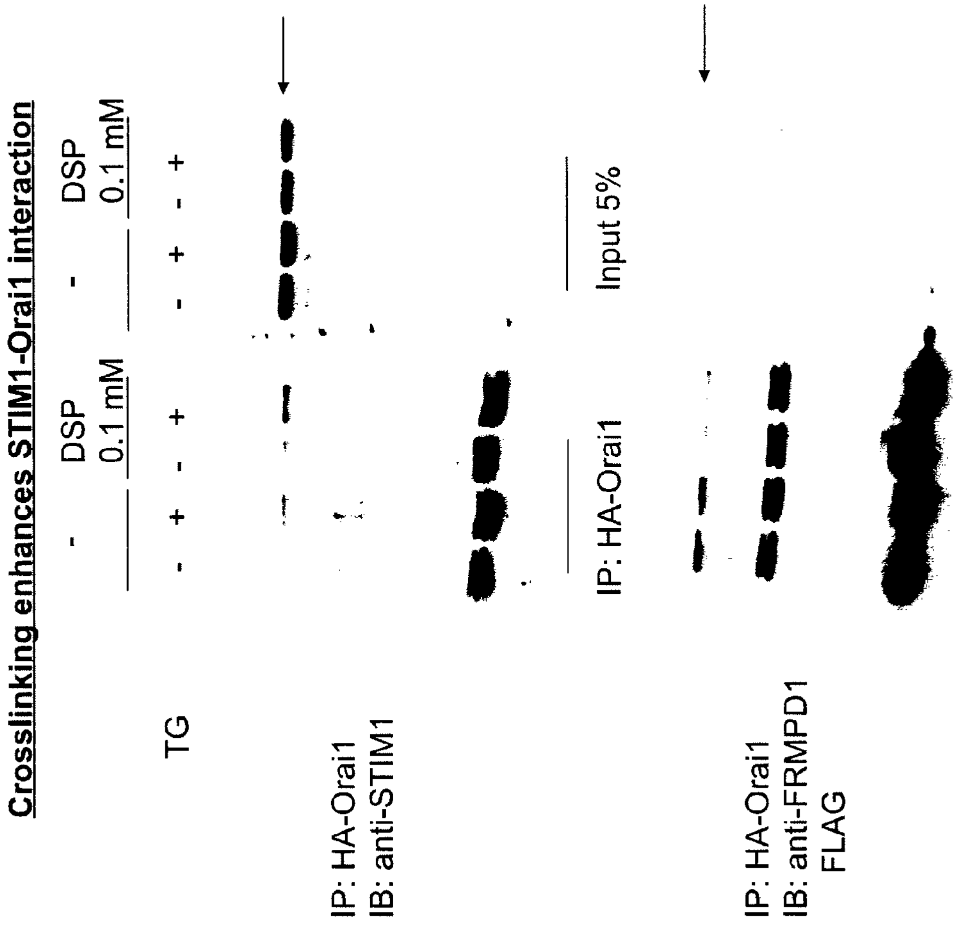
FIG. 30 shows that cross-linking enhances STIM1-Orai1 interaction.
Figure 31:
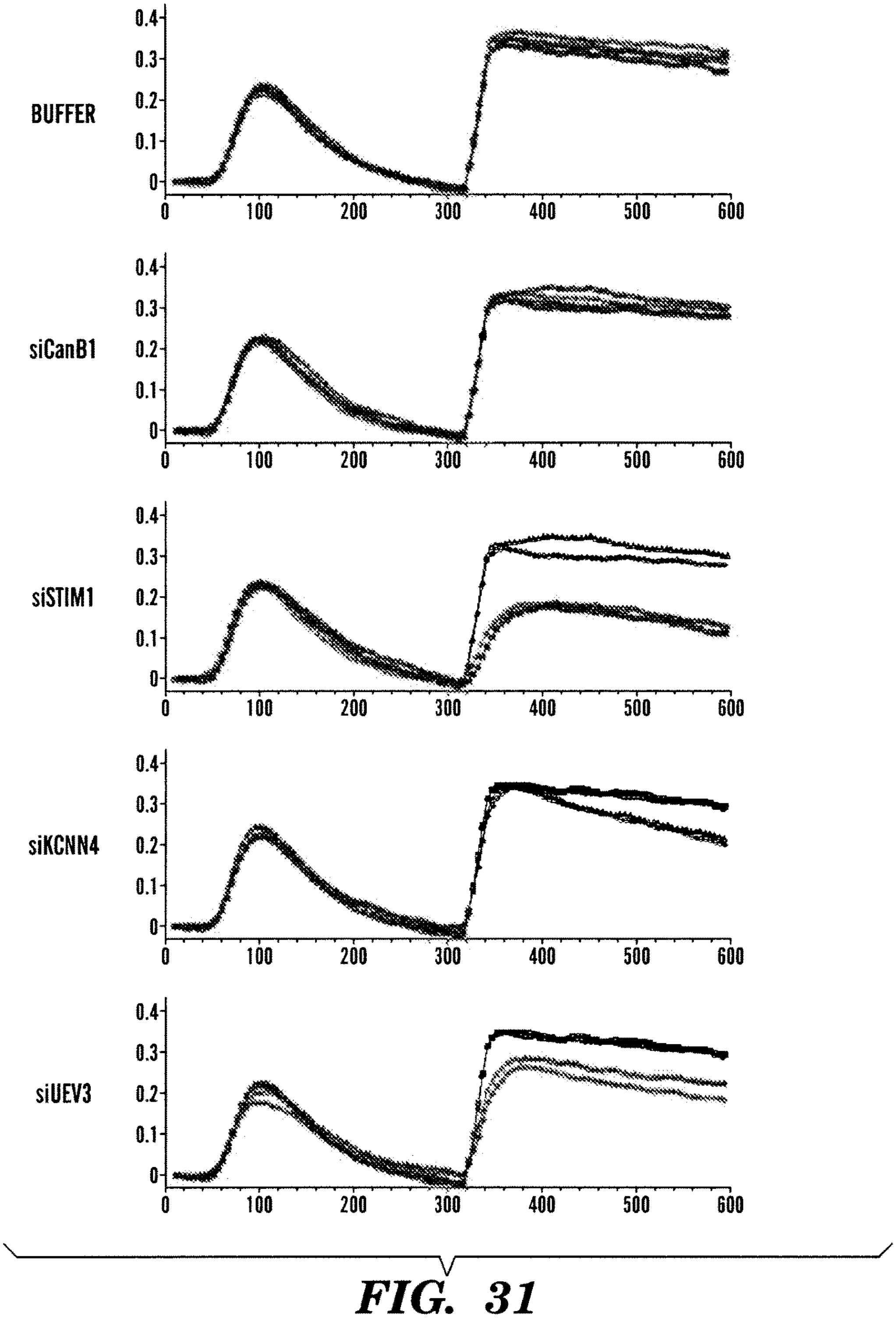
FIG. 31 shows some traces of calcium fluxes in cells treated with siRNA to the respective genes: CANb1, STIM1, KCNN4 and UEV3.
Figure 32:
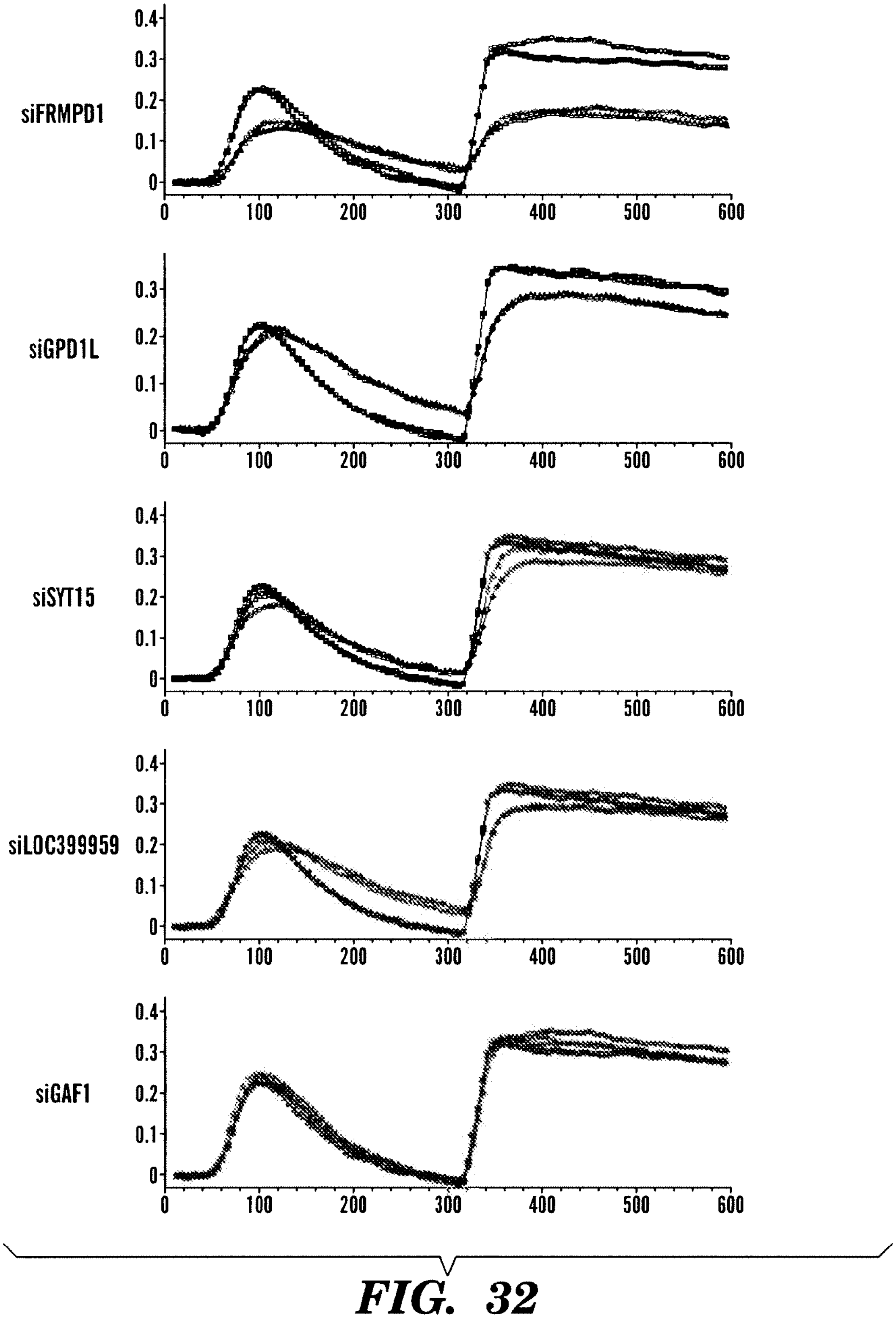
FIG. 32 shows some traces of calcium fluxes in cells treated with siRNA to the respective genes: FRMPD1, GPD1L, SYT15, LOC399959 and GAF1.
Figure 33:
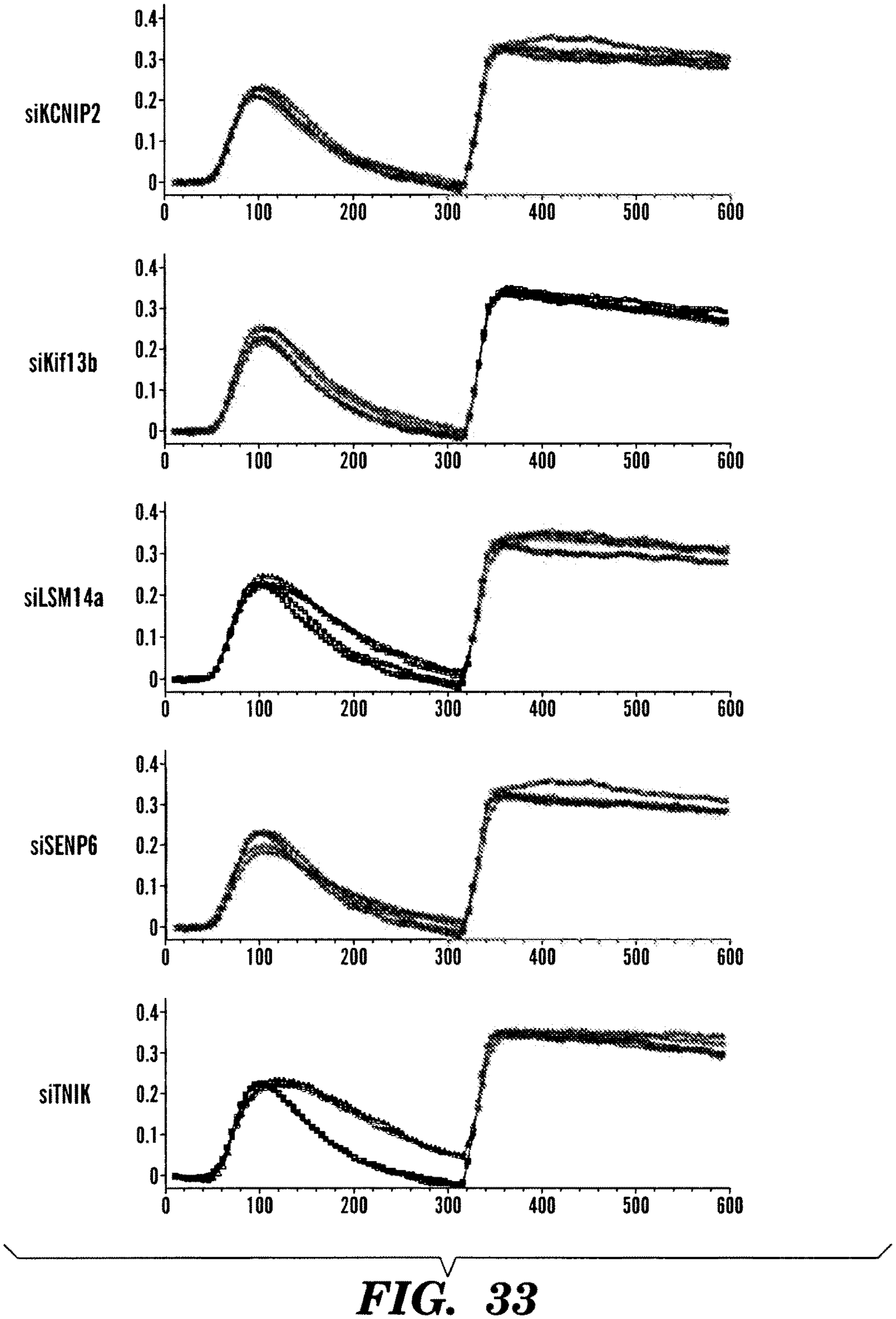
FIG. 33 shows some traces of calcium fluxes in cells treated with siRNA to the respective genes: KCNIP2, KIF13B, LSM14A, SENP6 and TNIK.
Figure 34:
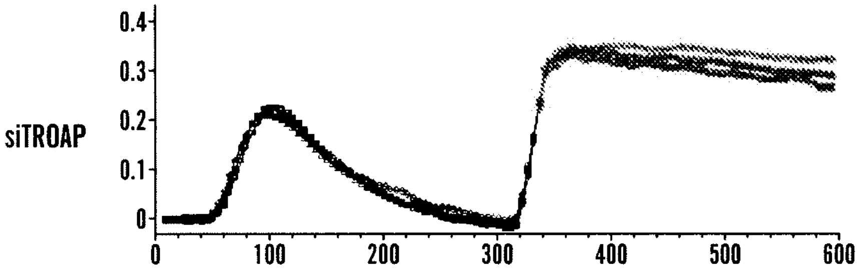
FIG. 34 shows some traces of calcium fluxes in cells treated with siRNA to TROAP.

For the genome-wide screen, 21,057 gene-specific siRNA pools were arrayed and screened on duplicate 384-well plates (FIG. 72A). 72 h after transfection, cells were stimulated with TG, fixed and stained with DAPI. Multiple images were collected from each well (>1200 cells/analysis), and a numerical Z-score corresponding to NFAT1-GFP translocation was assigned to each protein-coding gene. Validating the assay, several known regulators of the NFAT signaling pathway (FIG. 1) scored in the screen: proteins involved in store-operated $Ca^{2+}$ entry (STIM1, STIM2 and ORAI1); calcineurin subunits that are required to dephosphorylate NFAT (CNA1 and CNB1); and components of the nuclear import (RAN, RANBP, KPNB1, CSE1L) and export (CRM1) machinery (FIGS. 14, 15 and 71D). siRNAs against the closely-related calcineurin subunits CNA2, CNA3 and CNB2 were less effective, presumably because these subunits are not expressed in HeLa cells, or if expressed, are not effectively depleted by the siRNAs.

The Genome-Wide siRNA Screen Identifies 887 Positive Regulators of NFAT

Figure 72:
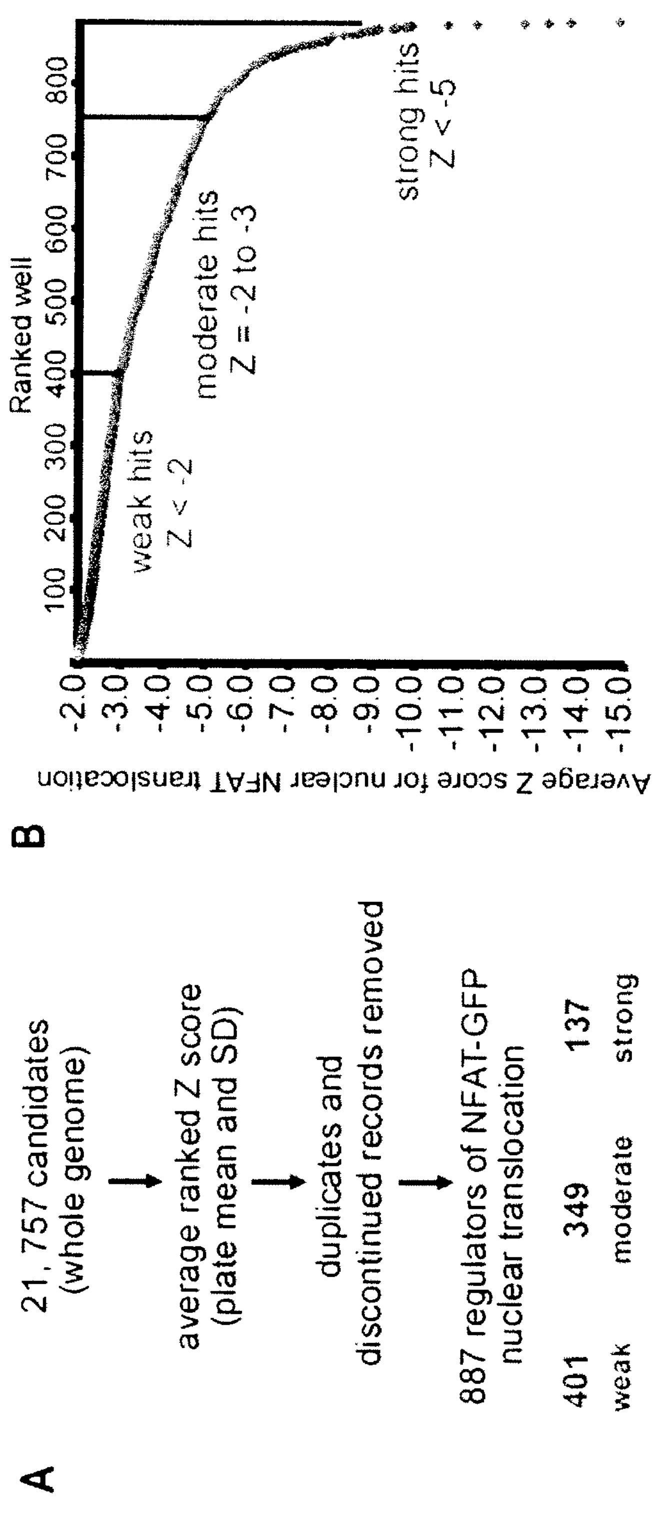
FIG. 72A summarizes the primary genome-wide screen for positive regulators of NFAT1-GFP nuclear translocation. Final numbers for weak, moderate and strong hits are indicated.
FIG. 72B shows the ranked average Z scores for each candidate gene. Inset graph represents ranked average Z scores for all 887 positive regulators of NFAT1-GFP nuclear translocation; color scheme corresponds to FIG. 72A.
FIG. 72C shows the gene expression profiles for the NFAT screen hits across 79 primary mouse tissues or cells. 683 mouse orthologues matched to one gene array probe-set were ranked and clustered using Pearson's correlation. Enriched blocks of hits corresponding to specific tissues are indicated.
FIG. 72D shows the validation of T cell-enriched hits in primary mouse CD4+ T cells. After target gene depletion by retroviral delivery of shRNA in vitro, IL-2 cytokine expression was analyzed by intracellular staining and flow cytometry after cell restimulation with PMA (10 nM) and ionomycin (500 nM) for 6 h. Shaded histograms represent unstimulated cells transduced with siControl, the unshaded histogram represents stimulated cells transduced with siControl, and bold histograms represent stimulated cells transduced with shSTIM1 or T cell enriched gene-specific shRNA, as indicated.
Figure 72:
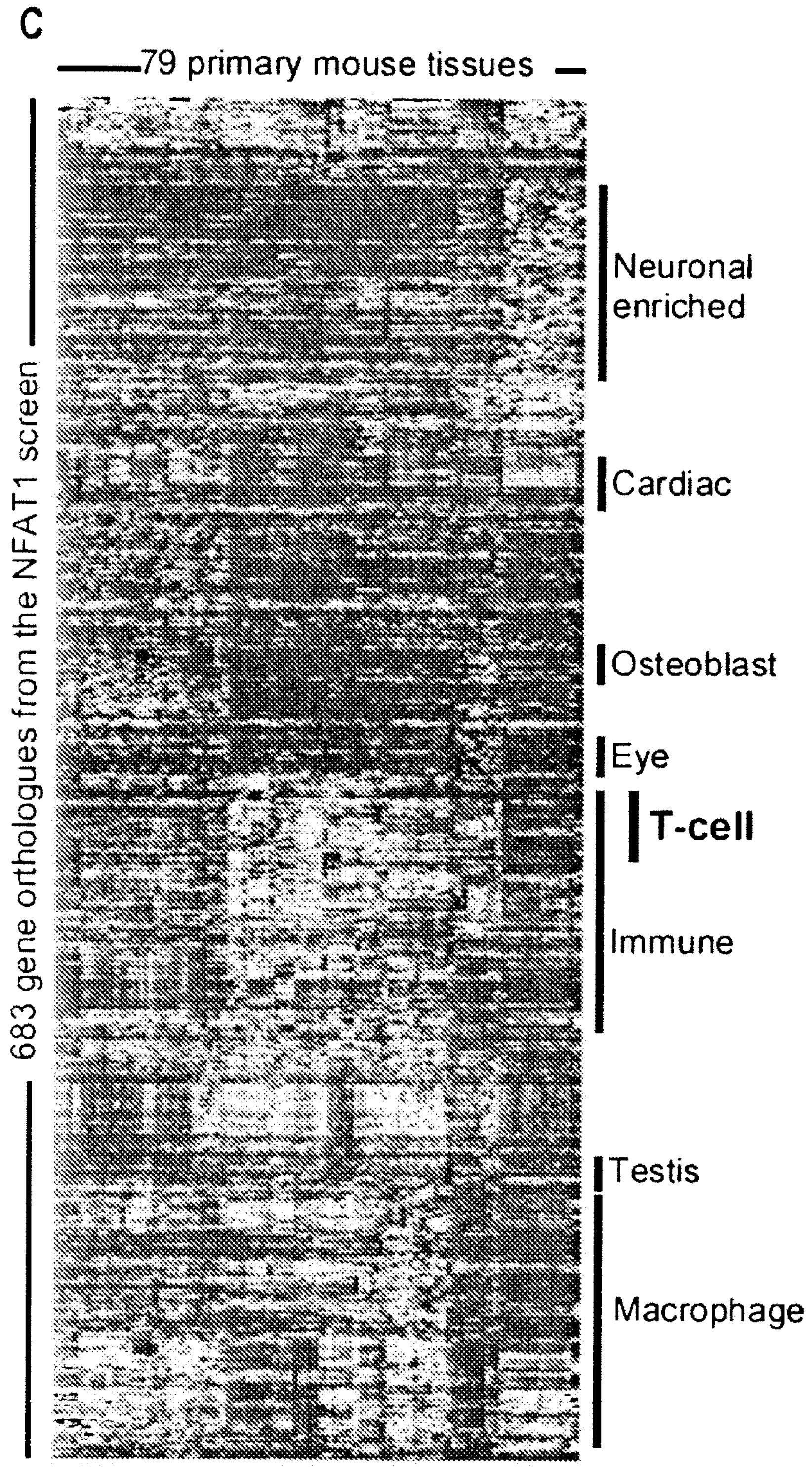

Each gene candidate was ranked by its Z-score for Ca2+-dependent NFAT translocation (FIGS. 72A and 72B). Because of the design of the screen, only a handful of negative regulators of NFAT whose depletion increased the amount of NFAT1-GFP in the nucleus were identified. These included the nuclear export factor CRM1 (Okamura et al., 2004) (FIGS. 14, 15 and 71C), and with a lesser Z-score the NFAT kinase GSK3 (Gwack et al., 2006) and the scaffold protein IQGAP1 ((Sharma et al., 2011) and data not shown). After removal of duplicate and discontinued gene records, we identified a total of 887 positive regulators of NFAT, with Z-scores ranging from −2.0 to −16.0 (FIG. 72B). These regulators, whose depletion impaired NFAT nuclear translocation, were classified as weak (Z score −2 to −3), moderate (Z score from −3 to −5) or strong (Z score <−5) (see Experimental Procedures).

Figure 76A:
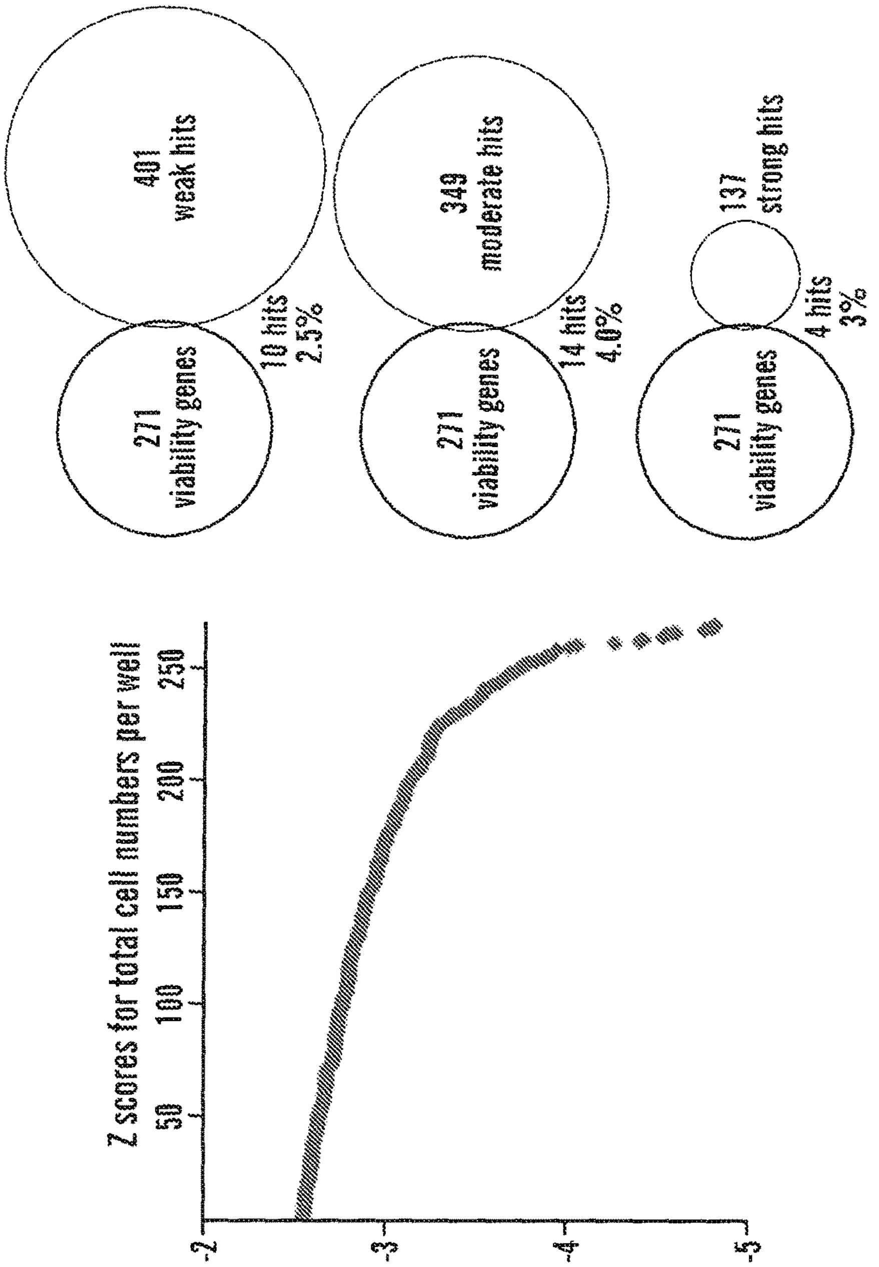
FIGS. 76A-76B show the genes required for cell survival and/or proliferation in the genome-wide screen show minimal overlap with NFAT regulators.
Figure 76B:
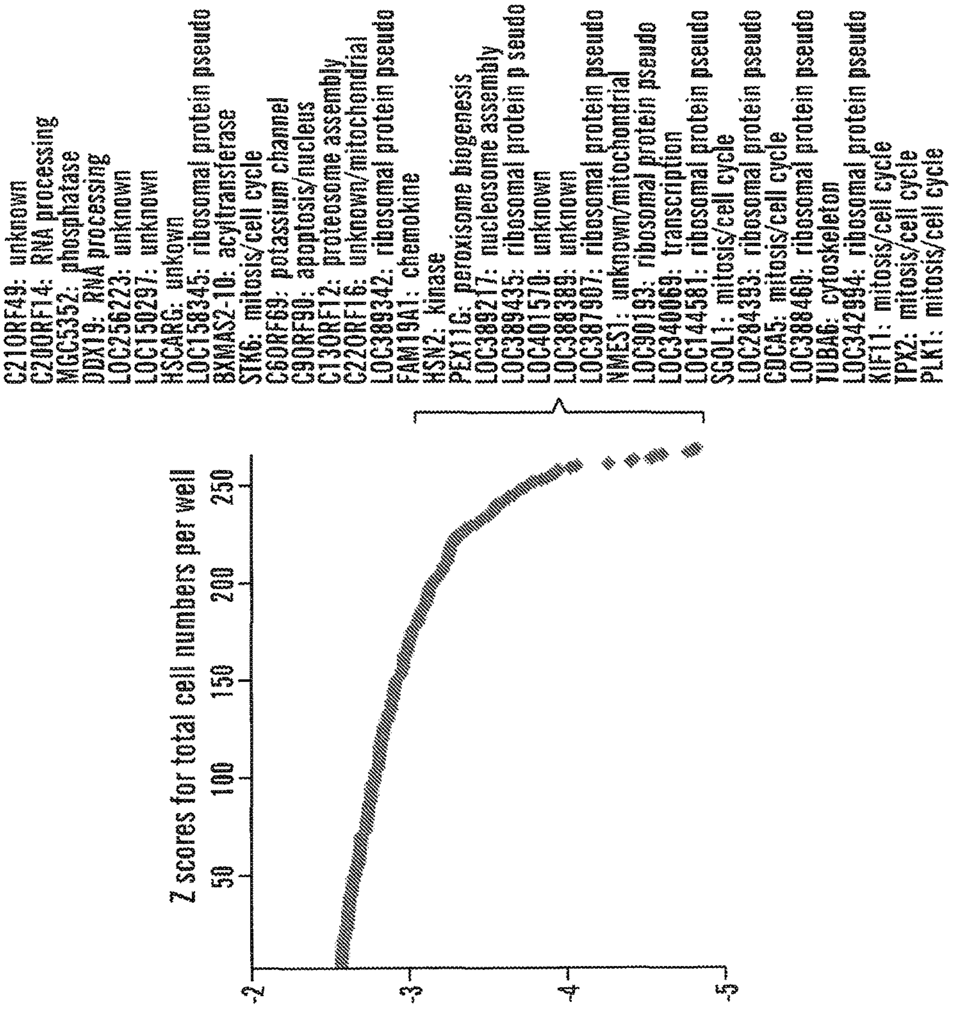

In was possible that some of these putative regulators scored as positive because they impaired cellular survival and/or proliferation. Indeed, depletion of 221 gene products (~1% of the total genome) decreased cell viability, but these showed minimal overlap with the positive NFAT regulators (FIG. 76A). The viability genes included known regulators of cell cycle/mitosis, RNA processing, and protein translation (FIG. 76B), and included PLK1, an essential regulator of G2/M transition that is required for cancer cell survival (Luo et al., 2009).

Figure 72D:
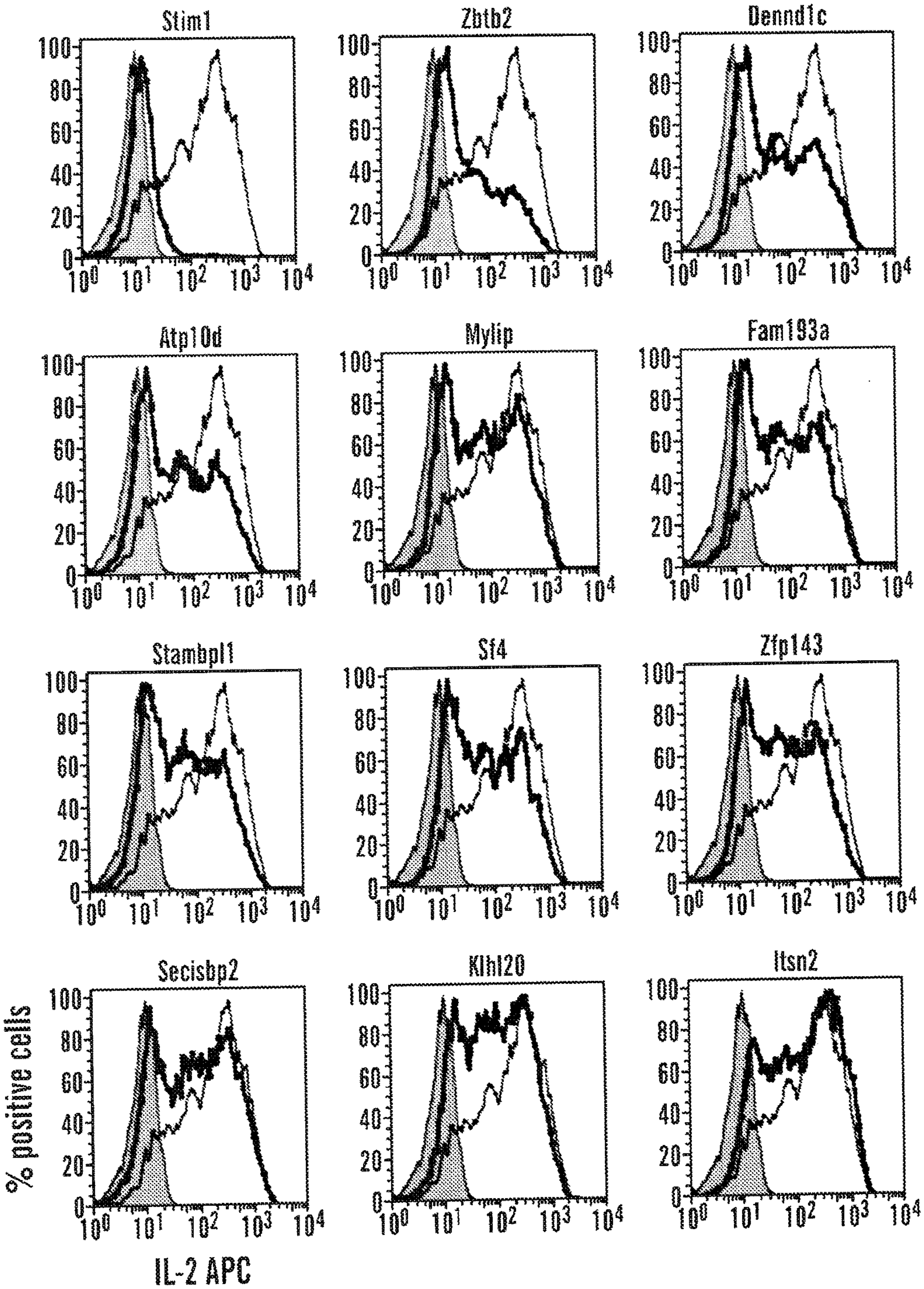

Expression Profiling can be Used to Identify Regulators Relevant in Other Cell Types mRNA expression profiling of the candidate NFAT regulators across 79 primary mouse tissues revealed visible clustering of groups of candidates within specific tissues including neuronal, cardiac, skeletal muscle, osteoblast and immune cells (FIG. 72C), consistent with the fact that $Ca^{2+}$/calcineurin/NFAT signaling is active in a variety of specialized cell types (Crabtree and Olson, 2002; Hogan et al., 2003; Horsley and Pavlath, 2002). Within the immune block, 11 NFAT regulators showing enriched expression in CD4+ T lymphocytes were further examined in that cellular context by depleting them in primary cultures of mouse CD4+ T cells over a period of 96 h, using miR30-embedded shRNA sequences delivered into activated cells by retroviral transduction. The transduced T cells were re-stimulated with PMA/ionomycin and assayed by intracellular staining for expression of interleukin-2 (IL-2), an NFAT-dependent cytokine whose expression is sensitive to the calcineurin inhibitor cyclosporin A (CsA) (FIG. 72D). This sub-screen demonstrated that 11 novel genes, including 3 uncharacterized transcription factors not previously associated with NFAT activation—Zbtb2, Zfp143 and Klh120—are positive regulators of IL-2 production in CD4+ T cells (FIG. 72D, bold lines).

Notably, the majority of these novel regulators scored weakly in the primary HeLa cell screen (9 out of 11, all except Denndlc and Zfp143), most likely because of their significantly lower expression in HeLa cells compared to primary T cells. This result underscores the utility of applying gene expression profiling to large-scale screening data, not only as a tool for prioritizing candidates from a large and complex data set, but also for identifying biologically relevant regulators that score weakly in the primary screen due to low expression levels in the cell type used for the screen. Particularly for ubiquitous cellular pathways such as $Ca^{2+}$/calcineurin/NFAT signaling, this approach makes it possible to identify candidates with physiologically relevant functions in primary cells and tissues, even though the original RNAi screens were performed in transformed cell lines chosen solely for ease of transfection.

Septin 4 is a Strong Regulator of NFAT and $Ca^{2+}$ Influx

Figure 73A:
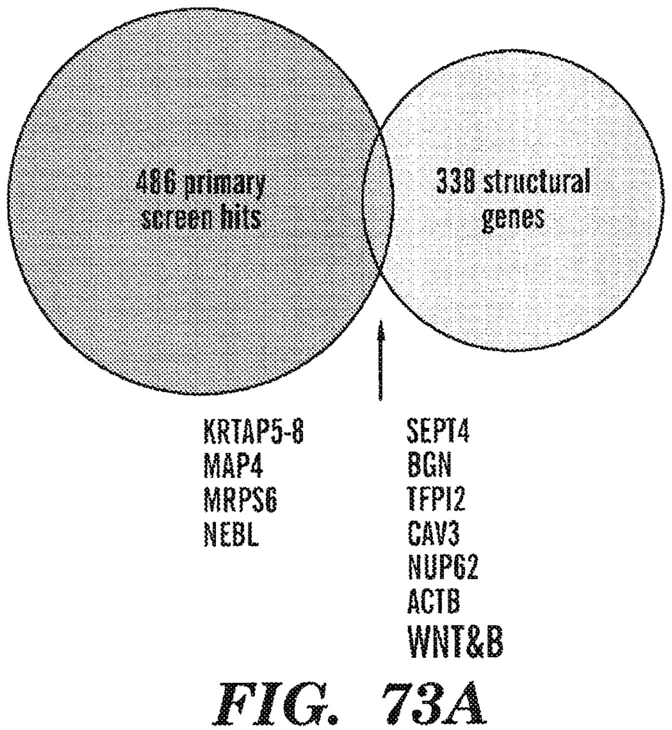
FIGS. 73A-73F demonstrate that septins 4 and 5 regulate NFAT activation and store-operated $Ca^{2+}$ Influx.
Figure 73B:
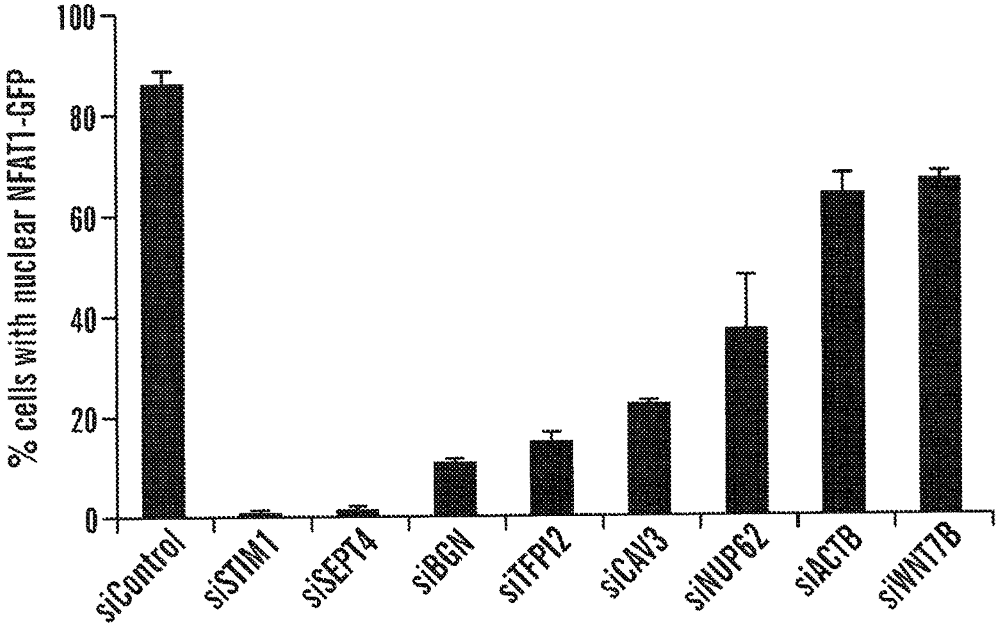

We have recently shown that NFAT nuclear translocation is governed by a cytoplasmic scaffold complex containing IQGAP1 and the noncoding RNA NRON (Sharma et al., 2011). To explore the potential role of other structural/scaffold proteins in the Ca2+/calcineurin/NFAT signaling pathway, we integrated our list of 486 strong and moderate positive regulators of NFAT with a list of genes encoding annotated as structural/scaffold proteins (GO:0005198). At the intersection of the two lists were 11 scaffold proteins whose depletion influenced NFAT nuclear translocation in mammalian cells (FIG. 73A). The inventors "de-convoluted" the data for these 11 potential regulators using each of the 4 individual siRNAs from the original SmartPools: HeLa cells were treated with the individual siRNAs, and NFAT1-GFP nuclear translocation was assayed. 4 candidates scored only with a single siRNA (FIG. 73A, grey font) and were excluded from further analyses due to a high potential for off-target effects (Echeverri et al., 2006; Perrimon and Mathey-Prevot, 2007; Sharma and Rao, 2009). The remaining 7 potential regulators (FIG. 73A, black font) were re-assayed using a single siRNA duplex (Table 6); SEPT4, BGN, TFPI2, CAV3 and NUP62 remained strong candidate NFAT regulators (>50% decrease compared to siControl), while ACTB and WNT7B were weaker upon re-assay (FIG. 73B).

Figure 77:
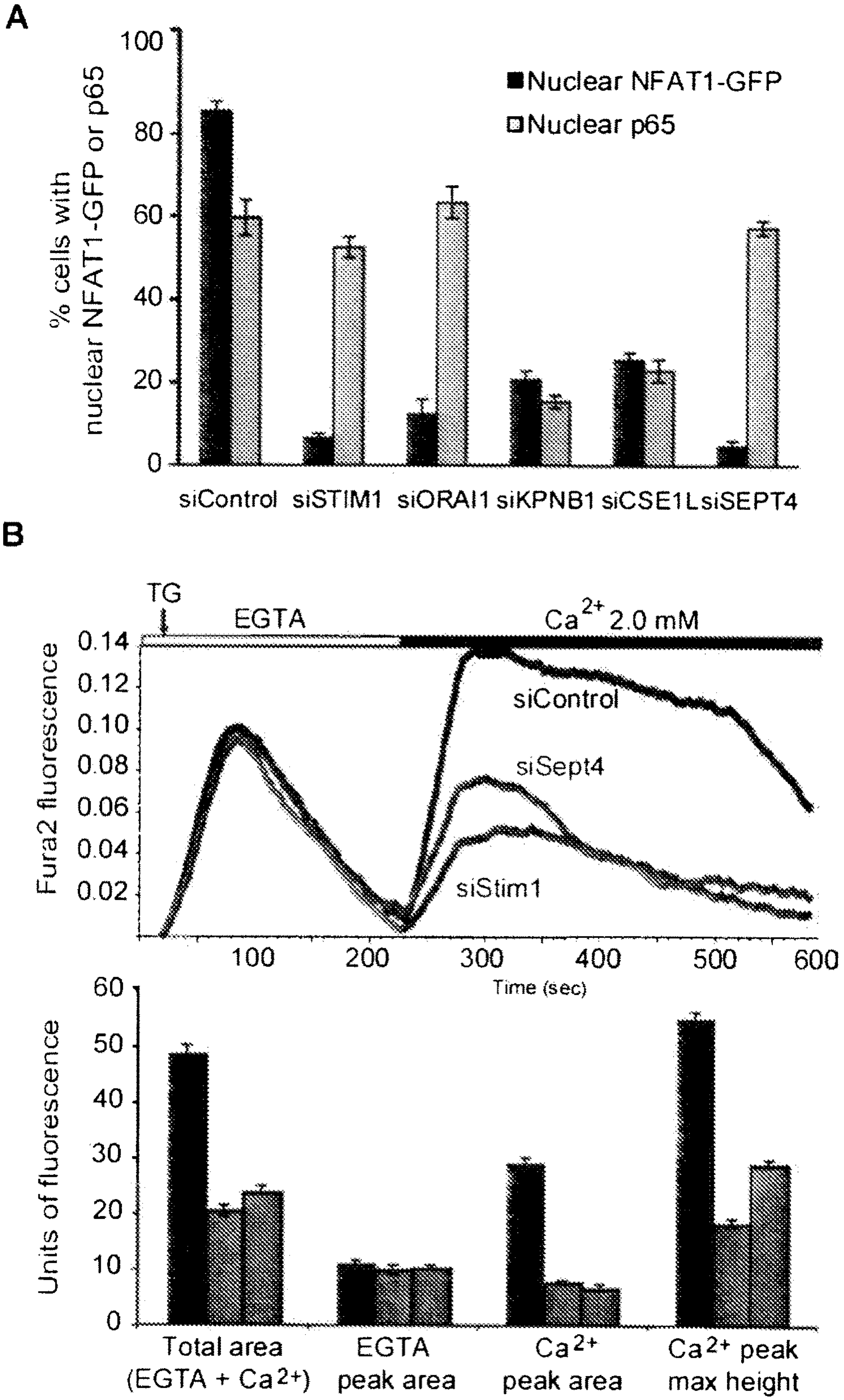
FIG. 77A-77B show that SEPT4 depletion impairs nuclear translocation of NFAT-GFP and store-operated $Ca^{2+}$ Entry.

To assess the specificity of these effects, we also examined the nuclear translocation of endogenous NFκB p651RelA in HeLa-NFAT1-GFP cells after TNF stimulation (FIG. 77A) Depletion of KPNB1, a nuclear importin beta, and CSE1L, a recycler of nuclear importin alpha, decreased the nuclear import of p65/RelA, as well as NFAT1-GFP as also found previously in *Drosophila* screens (Gwack et al., 2006; Gwack et al., 2007b) (FIG. 77A). In contrast, depletion of STIM1, ORAI1 and SEPT4 selectively diminished the $Ca^{2+}$-dependent nuclear translocation of NFAT1-GFP without affecting the TNF-dependent but $Ca^{2+}$-independent nuclear translocation of p65/RelA (FIG. 77A), suggesting that like STIM1 and ORAI1, septin 4 influences NFAT nuclear translocation through a selective effect on store-operated $Ca^{2+}$ entry, or calcineurin, or NFAT itself.

Figure 73C:
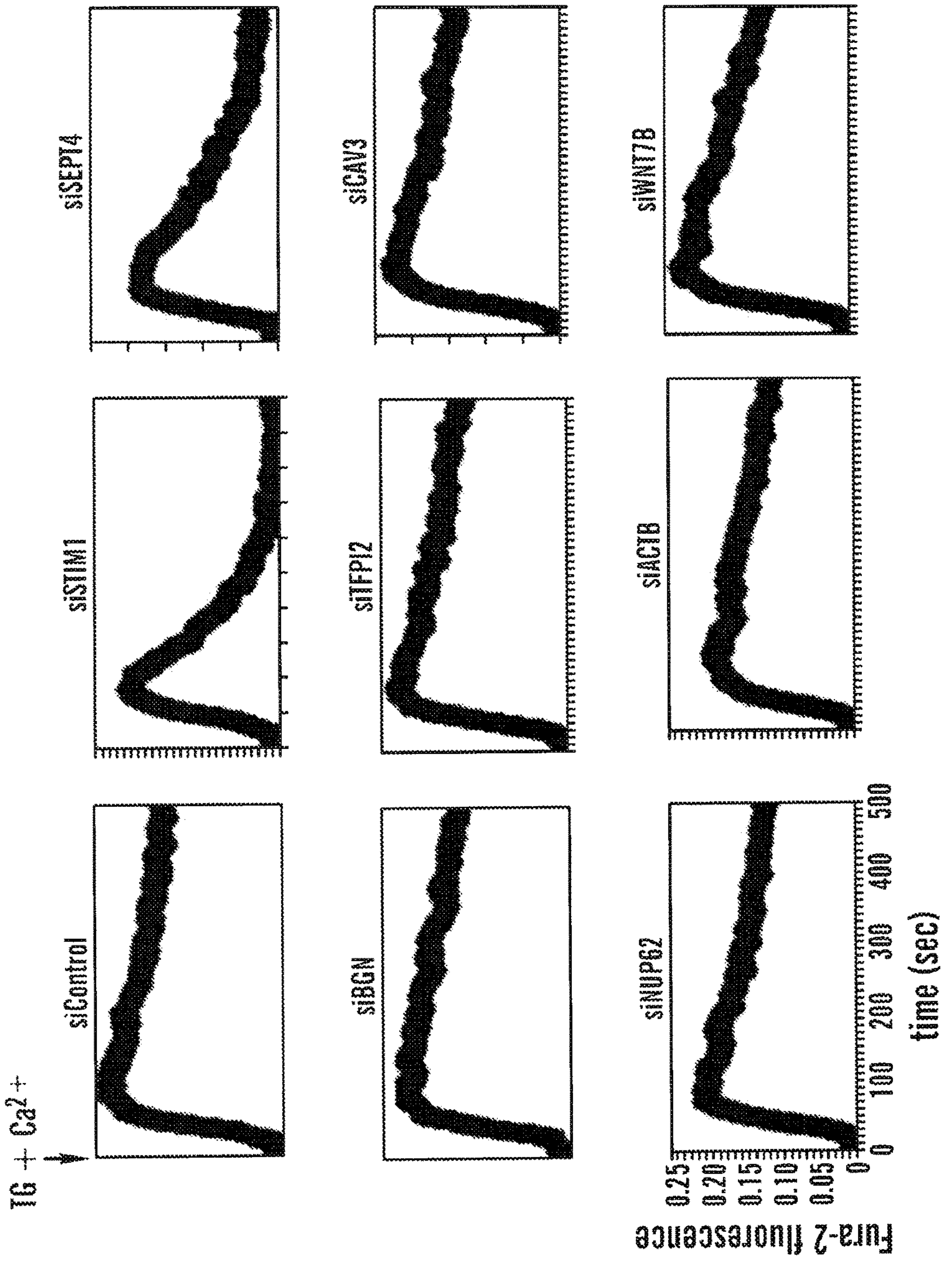
Figure 73D:
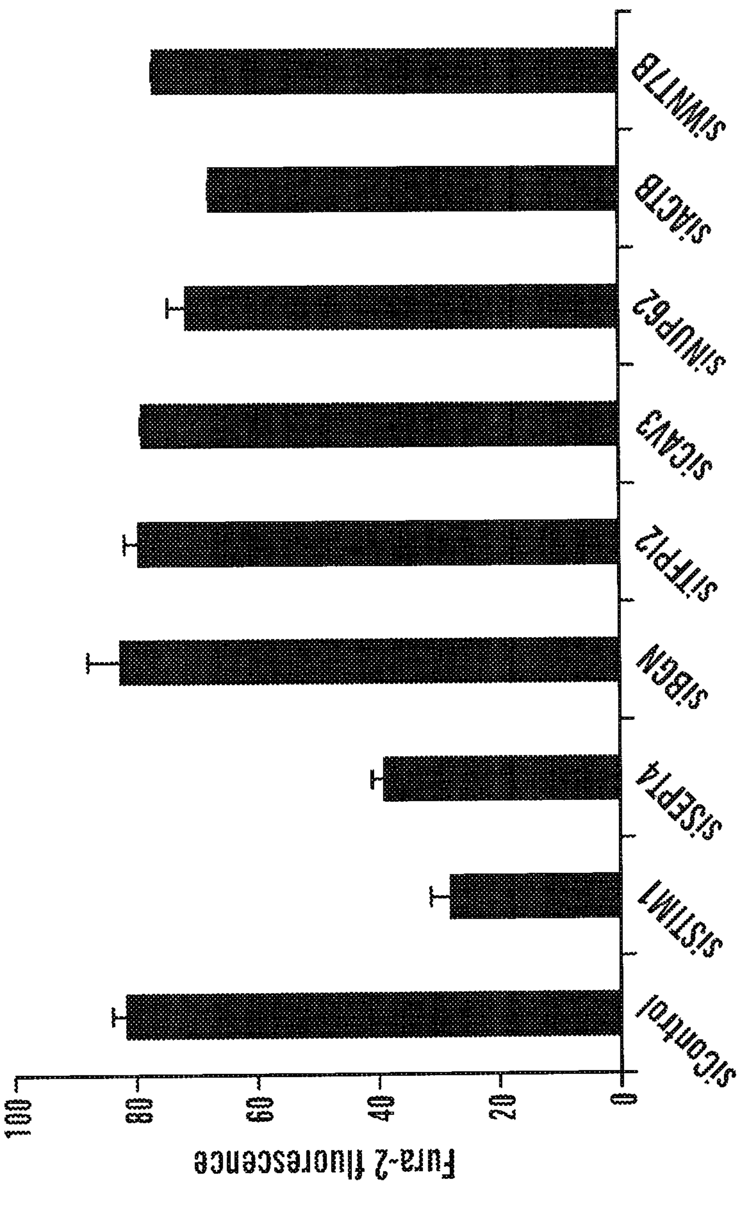
Figure 73E:
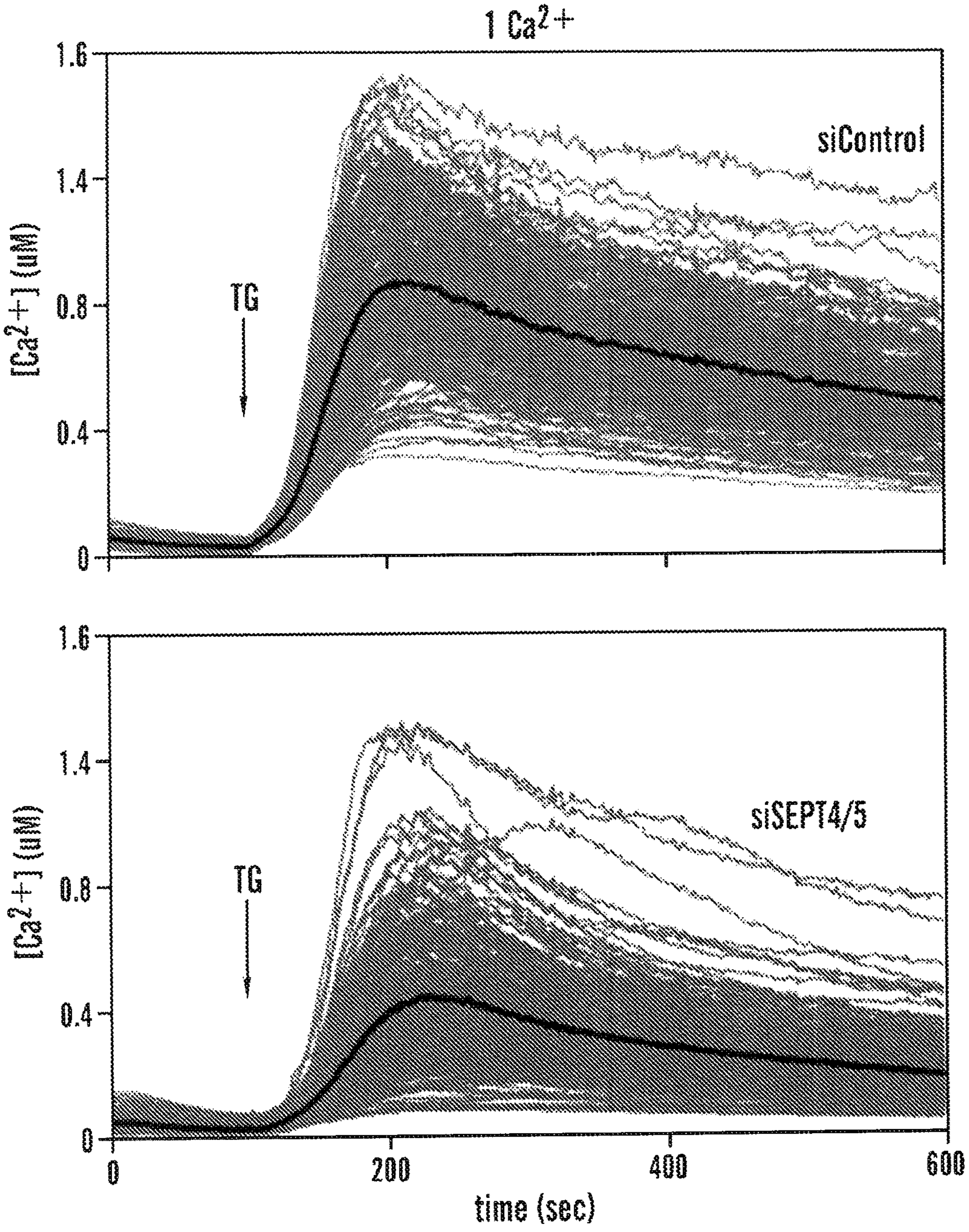
Figure 73F:
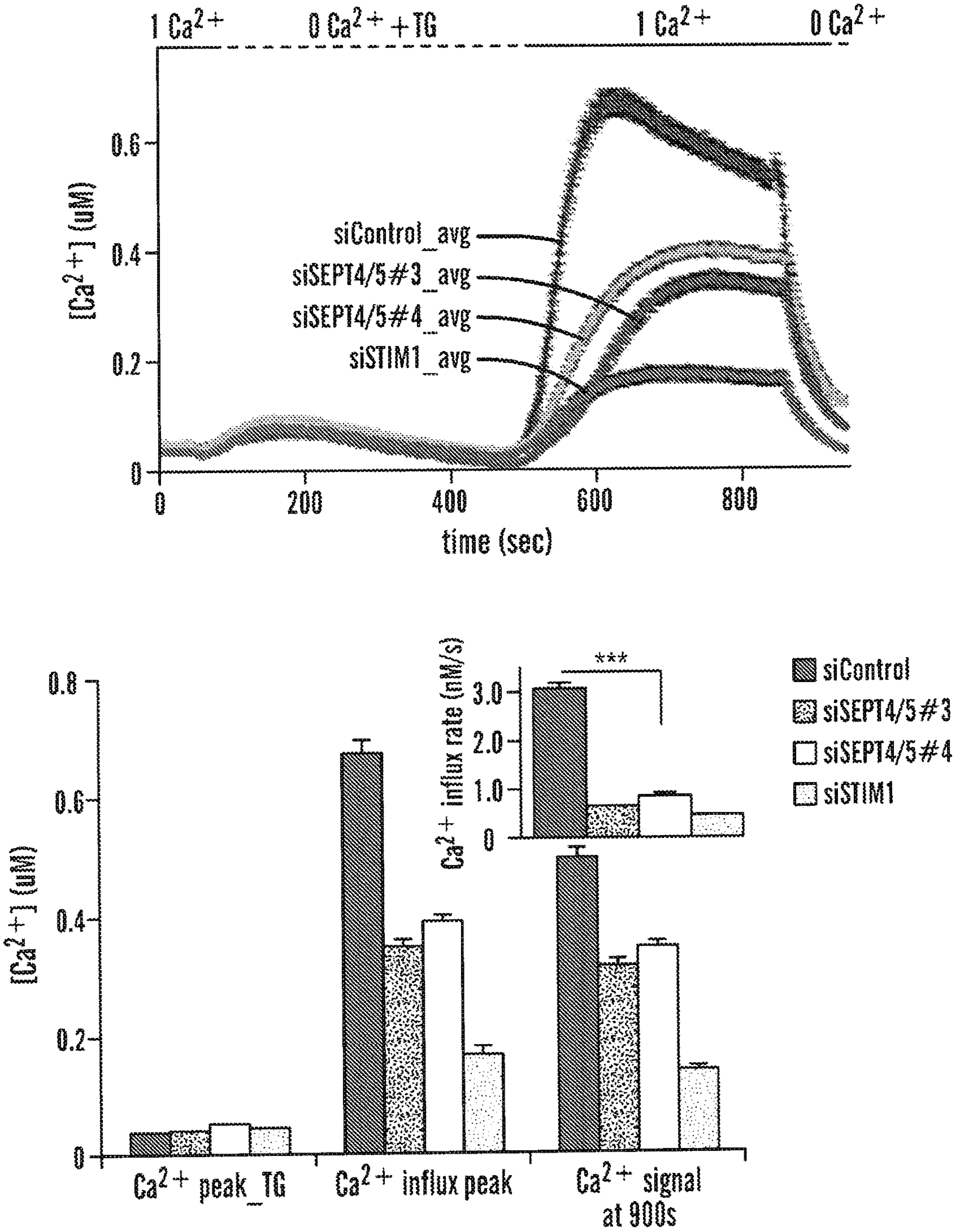

To establish the level at which the scaffold regulators affect NFAT nuclear translocation, we tested the effects of the siRNAs on store-operated $Ca^{2+}$ influx. HeLa cells expressing STIM1 and ORAI1 were cultured in 96-well plates, treated with siRNAs for several days, and then loaded with the ratiometric fluorescent $Ca^{2+}$ indicator dye fura-2 (FIGS. 73C and 73D). Fluorescence was recorded from the entire population of cells in each well as a function of time, before and after addition of a solution containing TG and $Ca^{2+}$ to induce ER $Ca^{2+}$ store depletion and $Ca^{2+}$ influx (Liou et al., 2005). Of the 7 scaffold regulators, only siSEPT4 strongly decreased $Ca^{2+}$ influx to a level comparable to that observed with our positive control, siSTIM1 (FIGS. 73C, 73D and 77B).

Septins 4 and 5 Act Together to Regulate $Ca^{2+}$ Influx

Analysis of septin function has been hampered by the fact that there are 14 septin genes encoded in the human genome (Cao et al., 2007). These have evolved through multiple gene duplications, and their functional annotation has been difficult due to their high homology and redundancy (Cao et al., 2007; Peng et al., 2002; Zieger et al., 2000). Bearing this in mind, we deconvoluted the siSEPT4 SmartPool by testing individual siRNAs for their effects on TG-induced NFAT1-GFP nuclear translocation. Compared to siControl, SEPT4 siRNA#1 had no significant effect, siRNA#2 had a weak but reproducible effect (20% reduction), and siRNA#3 had a strong effect comparable to siORAI1 (90% and 85% reduction, respectively) (FIG. 78A). The fourth SEPT4 siRNA in the SmartPool displayed some cell toxicity and was removed from the analysis.

The investigators asked if the strong effect of Sept4 siRNA#3 might be due to cross-reactive recognition of other septin mRNAs, leading to simultaneous depletion of multiple proteins in the septin family. As previously noted (Gwack et al., 2006; Sharma et al., 2011), this category of off-target effects has a marked advantage in RNAi screens: if a given siRNA depletes related members of a protein family, phenotypes that would otherwise be obscured by functional redundancies might be unmasked. Phylogenetic analysis clusters the human septin genes into 4 groups, based on nucleotide similarity within the central domain of the proteins, which contains the GTPase motif (Figure S3B); SEPT1, SEPT2, SEPT4 and SEPT5 comprise group III (Cao et al., 2007). We therefore analysed mRNA expression levels of the group III septins in HeLa cells treated with siControl or siSEPT4, using primers common to all transcript and splice variants of the SEPT1, SEPT2, SEPT4 and SEPT5 genes (FIG. 78B and Table 8). All 3 SEPT4 siRNAs reduced SEPT4 mRNA levels by >70% compared to siControl, but the most effective siRNA in the NFAT translocation screen, siSEPT4#3, also caused a significant depletion of SEPT5 mRNA levels by >50% (compare FIGS. 78A and 78C). These results suggested that the strong decrease in NFAT nuclear translocation observed with siSEPT4#3 correlated with diminished expression of both SEPT4 and SEPT5.

Figure 78:
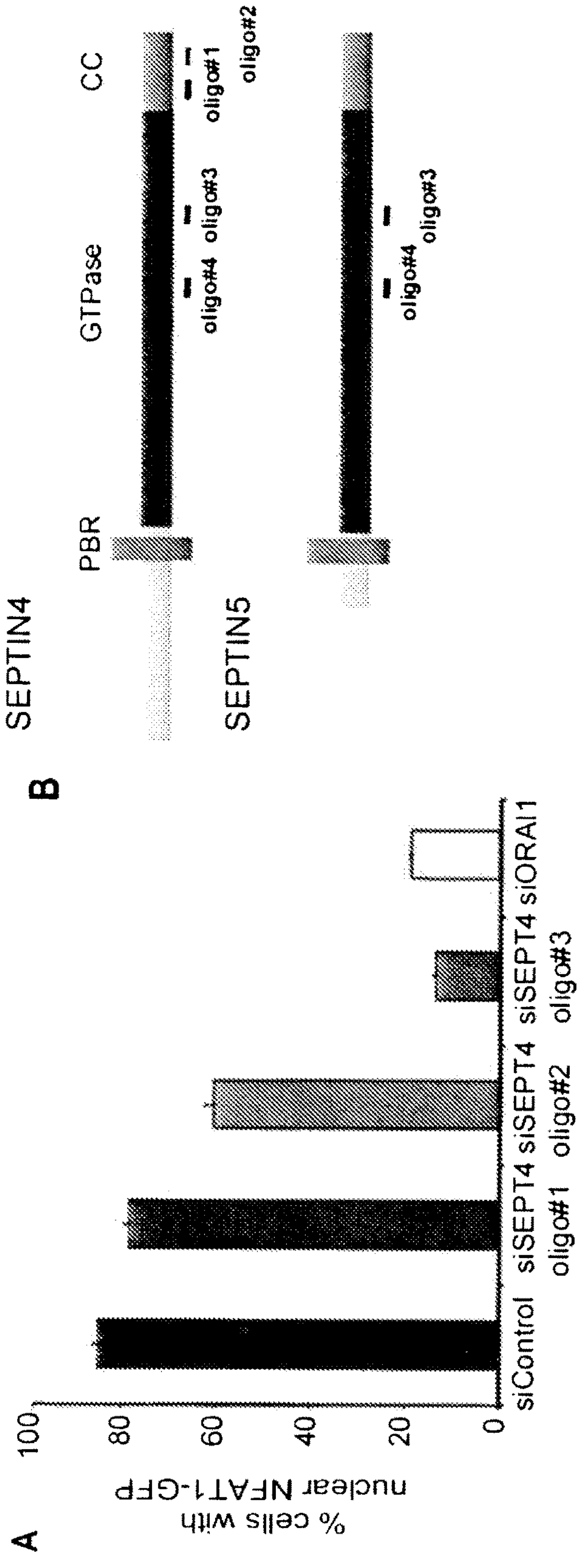
FIGS. 78A-78E demonstrate that Septin 4 and Septin 5 are required for store-operated $Ca^{2+}$ entry.
Figure 78:
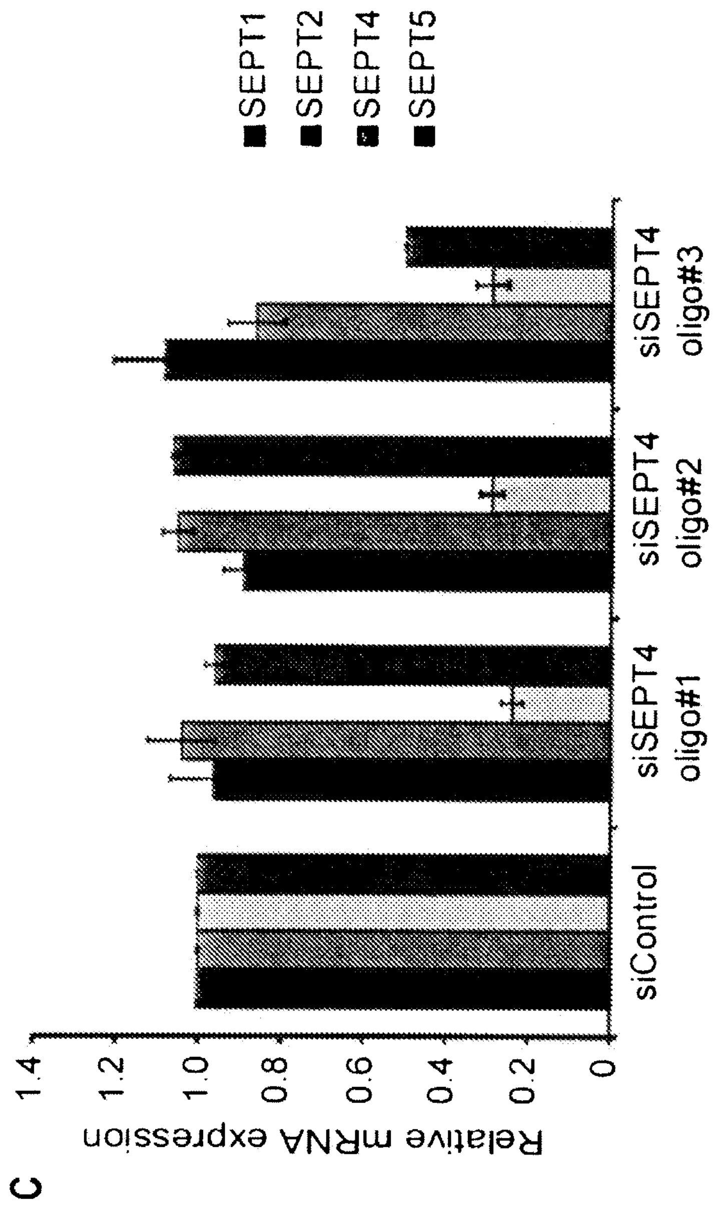
Figure 78:
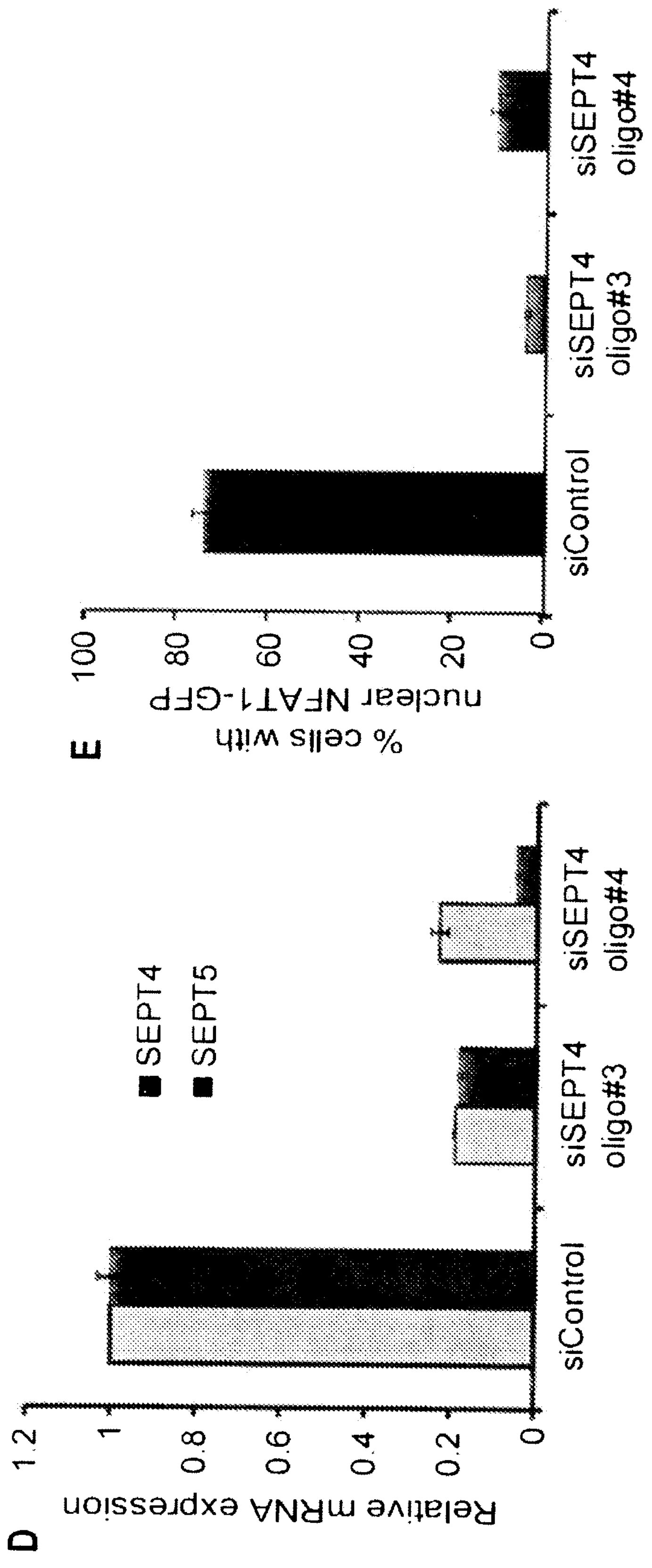

Among the group III septins, SEPT4 and SEPT5 display the highest nucleotide sequence similarity within the central domain (Cao et al., 2007), which notably encompasses the siSEPT4#3 targeting sequence (FIG. 78 S3B and Table 6). To confirm the requirement for double depletion of SEPT4 and SEPT5, we tested another siRNA (siSEPT4#4) that targets the conserved central motif of both SEPT4 and SEPT5 (FIG. 78D and Table 6). Treatment with siRNA#4 depleted both SEPT4 and SEPT5 mRNA (FIG. 78D), and also reduced TG-induced NFAT translocation to the nucleus (FIG. 78E). Depletion of septin 5 alone had no affect on NFAT translocation (S. Sharma, unpublished), which explains why septin 5 did not score as a hit in the primary screen. Thus, combined depletion of septins 4 and 5 is necessary to observe a striking defect in $Ca^{2+}$-dependent NFAT nuclear translocation. In all subsequent experiments, siSEPT4#3 or siSEPT4#4 were used individually, or both together (hereafter designated siSEPT4/5 or septin4/5-depleted).

Septin 4/5 Depletion Diminishes Store-Operated $Ca^{2+}$ Influx Without Affecting ER $Ca^{2+}$ Stores The effects of septin depletion on $Ca^{2+}$ influx were confirmed using time-lapse fura-2 imaging at the single-cell level. Wild-type (unengineered) HeLa cells were treated with siControl or siSEPT4/5 and perfused with solution containing 1 μM TG and 1.0 mM extracellular $CaCl_2$ ($[Ca^{2+}]_o$). Single-cell records demonstrated a uniform reduction in store-dependent $Ca^{2+}$ influx in siSEPT4/5-treated cells compared to siControl (FIG. 73E, each grey trace represents an individual cell), confirming the results obtained from integrated measurements of STIM1/ORAI1-expressing cell populations (FIG. 73C). To separate the phases of store depletion and store-operated $Ca^{2+}$ influx, fura-2-loaded HeLa cells were perfused with 1 μM TG in 0 mM $[Ca^{2+}]_o$ to elicit depletion of ER $Ca^{2+}$ stores, following which 1 mM $[Ca^{2+}]_o$ was added to elicit $Ca^{2+}$ influx through store-operated ORAI channels. Both in single-cell measurements (FIG. 73F) and in averaged population assays (FIG. 78), septin 4/5 depletion resembled STIM1 depletion in that there was no appreciable effect on the early peak of increased intracellular $Ca^{2+}$ that represents ER store depletion, but a substantial decrease in the late plateau phase that represents influx of extracellular $Ca^{2+}$ through store-operated $Ca^{2+}$ channels.

Septin 4/5 Depletion Delays STIM1 Translocation to the Plasma Membrane

Figure 74A:
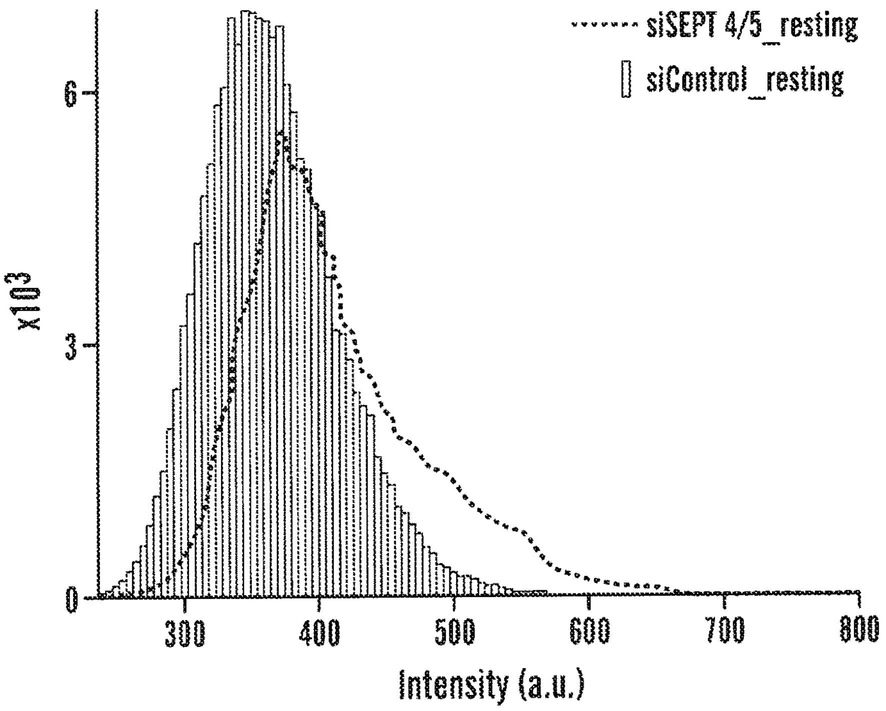
FIGS. 74A-74C show that the depletion of septins 4 and 5 causes disorganisation of ORAI1 in resting cells results in delays STIM1 Translocation to ER-plasma membrane junctions and diminishes STIM1-ORAI1 co-localisation.
Figure 74B:
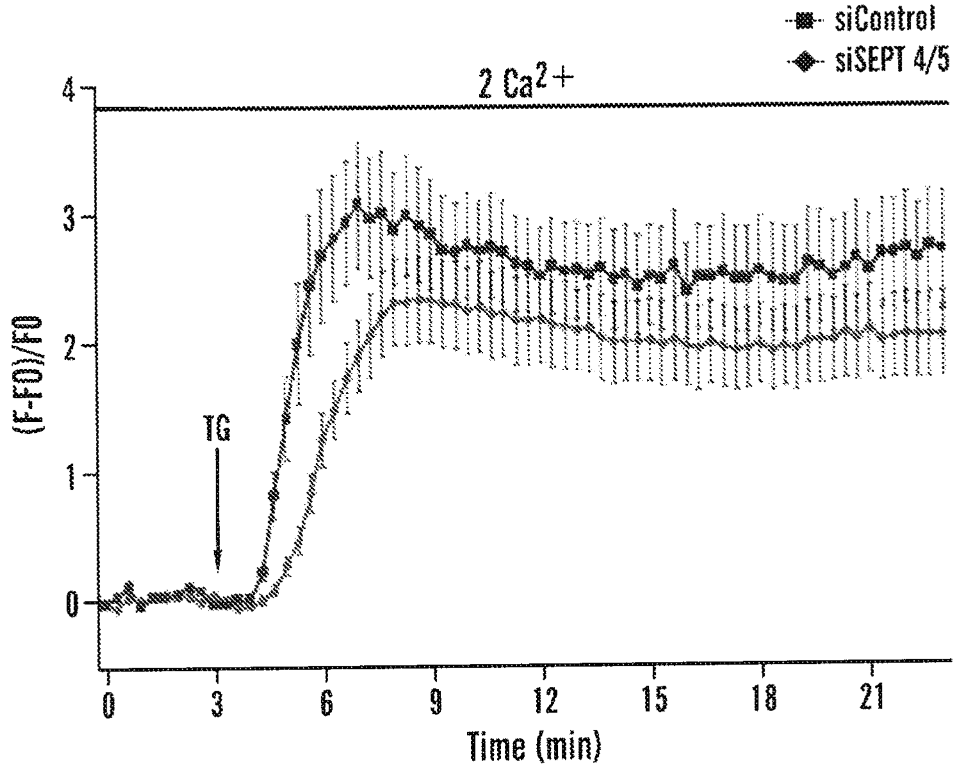
Figure 74:
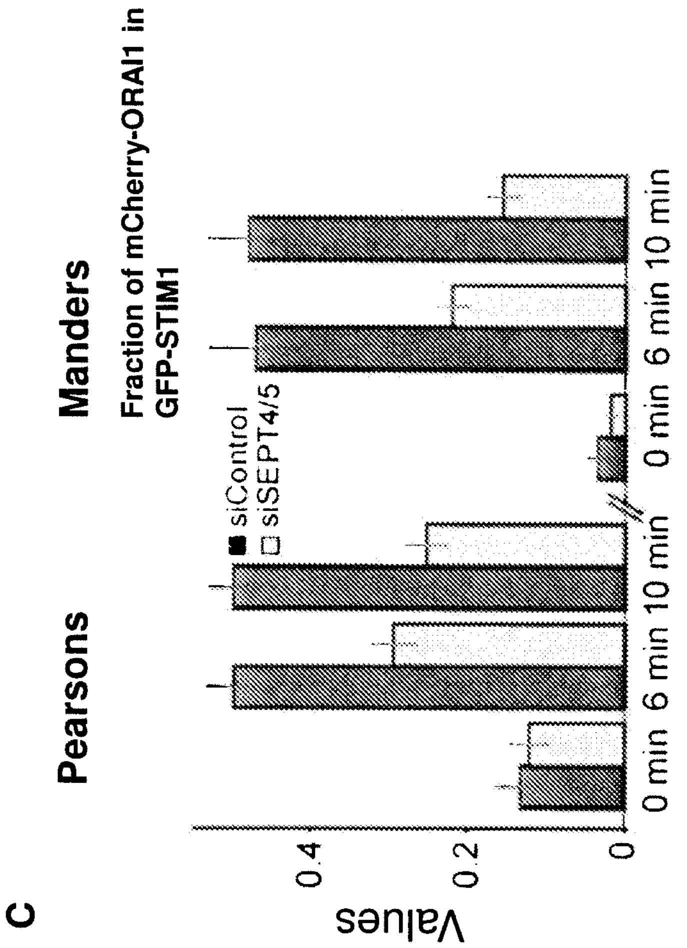

To investigate the mechanism by which septins regulate store-operated Ca2+ entry, we used total internal reflection fluorescence microscopy (TIRFM) to image live HeLa cells stably expressing low levels of tetracycline-regulated GFP-STIM1 and mCherry-ORAI1 (FIG. 74). Analysis of TIRFM images revealed a subtle but striking disorganization of ORAI1, even under resting conditions, in cells treated with siSEPT4/5 compared to siControl (FIG. 74A). This point was most easily demonstrated by comparing histograms of mCherry-ORAI1 intensity: resting siControl-treated cells displayed a uniform, almost Gaussian distribution of ORAI1 intensities, whereas resting siSEPT4/5-treated cells displayed a clear population of ° RAH with higher intensities, perhaps representing aggregated ORAI1 (FIG. 74A). The kinetics of GFP-STIM1 translocation to the plasma membrane, measured before and after TG treatment, was delayed in siSEPT4/5-treated cells compared to control (FIG. 74B). Moreover, after TG treatment, ORAI1 in septin 4/5-depleted cells formed larger aggregates than in control cells, and these aggregates did not co-localize as effectively with puncta formed by STIM1 (data not shown).

The areas and intensities of STIM1 puncta were unaffected (see Table 9). At two different times after TG addition (6 and 10 min), both the Pearson's correlation coefficient and the Manders overlap coefficient for the fraction of red mCherry-ORAI1 pixels overlapping with green GFP-STIM1 pixels were significantly decreased by 50-60% in siSEPT4/5-treated compared to siControl-treated cells (FIG. 74C).

Septin 4/5 Depletion Decreases Co-Localization Between STIM1 and ORAI1

Figure 79:
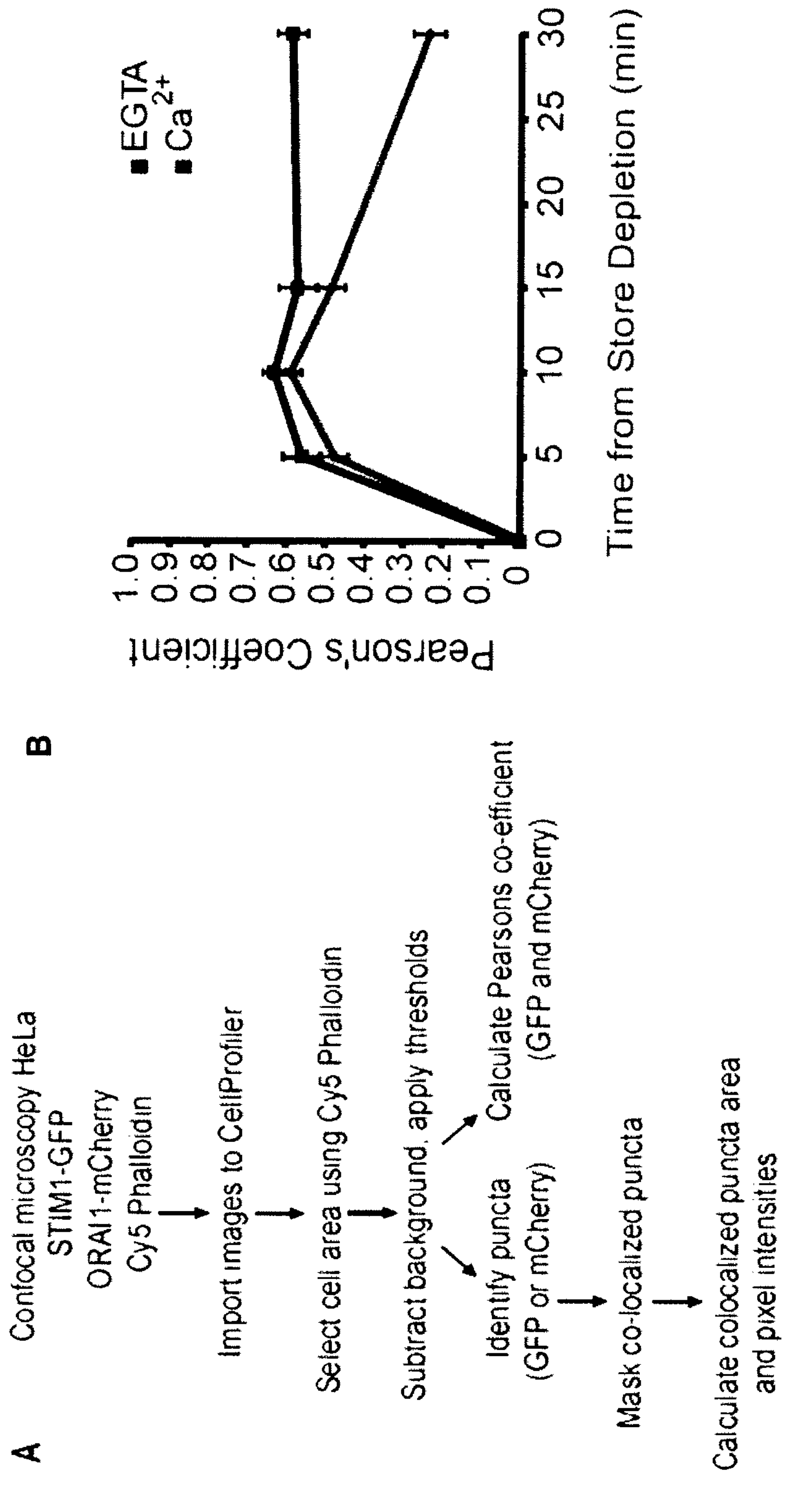
FIGS. 79A-79B show the quantitation of STIM1 and ORAI1 co-localization by cell profiler.

It was confirmed that the TIRFM observations by confocal microscopy. STIM1 and ORAI1 co-localization in HeLa cells stably expressing low levels of tetracycline-regulated GFP-STIM1 and mCherry-ORAI1 was quantified (FIG. 79A); the experiments were performed in 3.0 mM EGTA (0 mM $[Ca^{2+}]_o$) since puncta formation was stable for longer periods under these conditions than in 1.5 mM $[Ca^{2+}]_o$ (FIG. 79B). siControl and siSEPT4/5-treated HeLa cells were left unstimulated or treated with TG in the presence of 1.5 mM $[Ca^{2+}]_o$ for 10 min, and confocal images were taken at the "footprint" of the cell on the coverslip to analyze the effect of septin depletion on STIM1 or ORAI1 puncta formation and STIM1-ORAI1 co-localization (data not shown). In the absence of stimulation, both GFP-STIM1 and mCherry-ORAI1 were diffusely distributed (data not shown); after 10 min of TG stimulation, re-distribution of GFP-STIM1 to discrete puncta was detectable in both siControl and siSEPT4/5-treated cells (data not shown). However, in stimulated SEPT4/5 depleted cells, formation of mCherry-ORAI1 puncta was impaired compared to the control (data not shown), a phenomenon that was particularly obvious when examining STIM1-ORAI1 co-localization (data not shown). The decrease in STIM1-ORAI1 co-localization was reflected in a significantly lower Pearson's correlation coefficient as well as a reduction in the ratio of co-localized puncta to cell area when comparing siControl and siSEPT4/5-treated cells (Table 9). Notably, this decrease in co-localization did not reflect a change in total GFP-STIM1 and mCherry-ORAI1 intensity in the cells (Table 9). These STIM1-ORAI1 co-localization data are in agreement with those obtained by TIRFM (FIG. 74B).

Septin 4/5 Depletion Does Not Impair the Intrinsic Channel Function of ORAI1

Figure 75A:
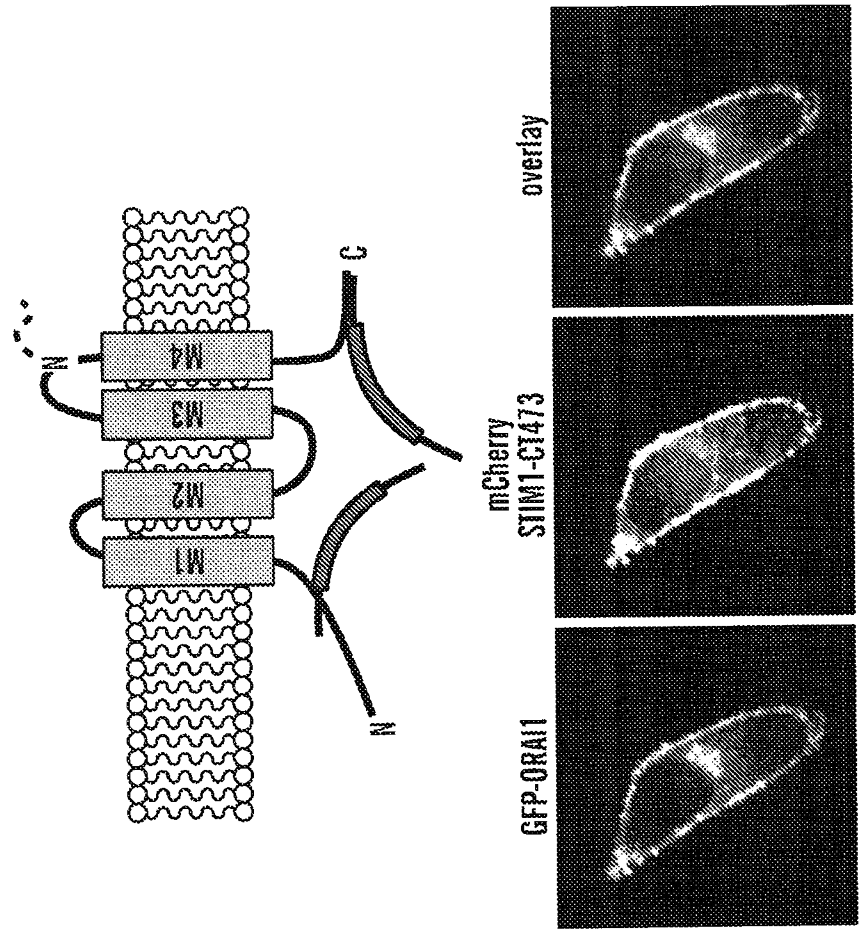
FIGS. 75A-75C show the expression of a soluble STIM1 C-terminal fragment rescues NFAT translocation and $Ca^{2+}$ entry in septin 4/5-depleted cells.
Figure 75B:
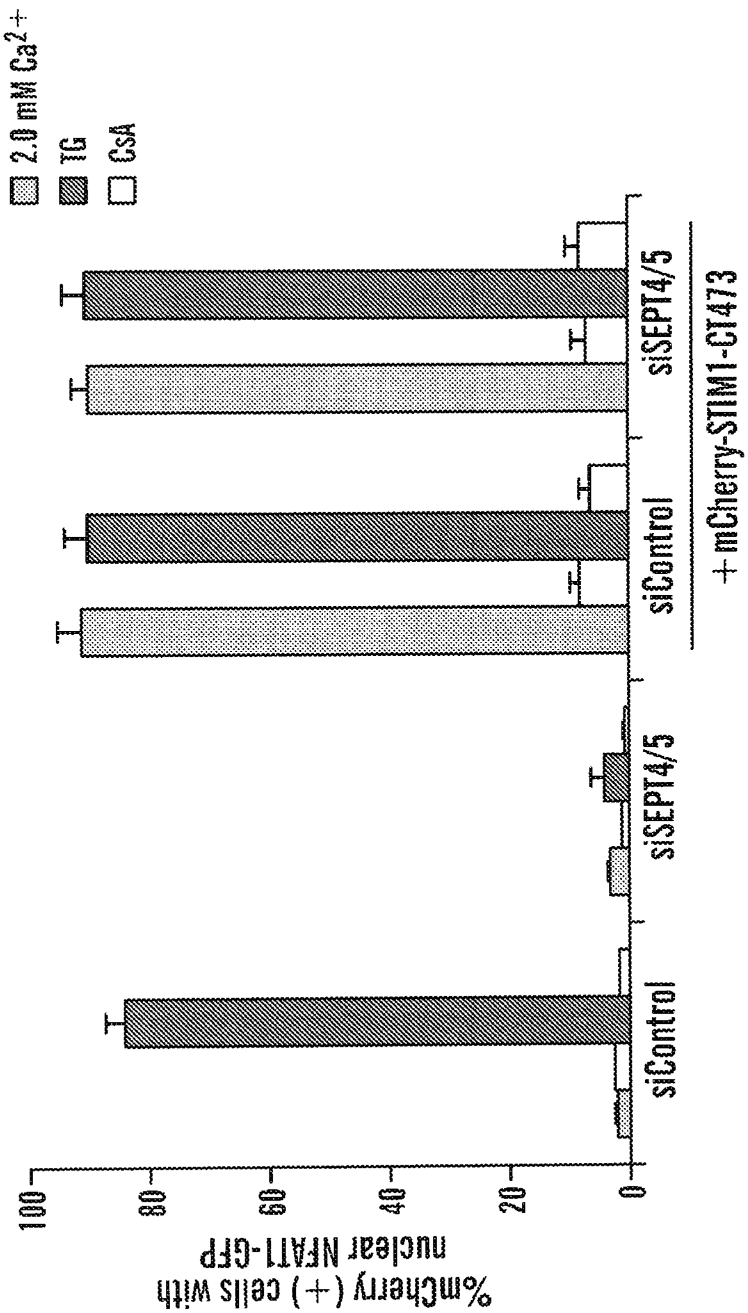

Several groups have shown that soluble fragments of the STIM1 C-terminus are capable of gating ORAI1 channels, both in vitro (Thou et al., 2010) and when the proteins are expressed in cells (Derler et al., 2009; Kawasaki et al., 2009; Muik et al., 2009; Park et al., 2009; Wang et al., 2009; Yuan et al., 2009). In HeLa cells over-expressing GFP-ORAI1, a soluble STIM1 fragment (mCherry-STIM1-CT473, amino acids 233-473), co-localized with ORAI at the plasma membrane in the absence of store depletion (FIG. 75A), reflecting its direct interaction with the channel (Thou et al., 2010). The inventors investigated whether STIM1-CT473 could induce $Ca^{2+}$ entry in septin 4 and 5-depleted cells. In HeLa-NFAT1-GFP cells, which do not over-express ORAI1, expression of STIM1-CT473 caused nuclear accumulation of NFAT1-GFP when the cells were incubated in the presence of 2 mM extracellular $Ca^{2+}$ (FIG. 75B, compare first and second bars of siControl and siControl+mCherry-STIM1-CT473 clusters). While septin 4/5 depletion eliminated TG-induced nuclear translocation of NFAT1-GFP (FIG. 75B, third bar of siSEPT4/5 cluster), expression of STIM1-CT473 in the presence of 2 mM extracellular $Ca^{2+}$ rescued NFAT1-GFP nuclear translocation to levels observed in control cells under the same conditions (FIG. 75B, first and second bars of siSEPT4/5 and siSEPT4/5+mCherry-STIM1-CT473 clusters). In the absence of CsA treatment, NFAT1-GFP is nuclear only in the cells that are expressing mCherry-STIM1-CT473, but becomes cytoplasmic when the cells are treated with CsA (data not shown).

Figure 75C:
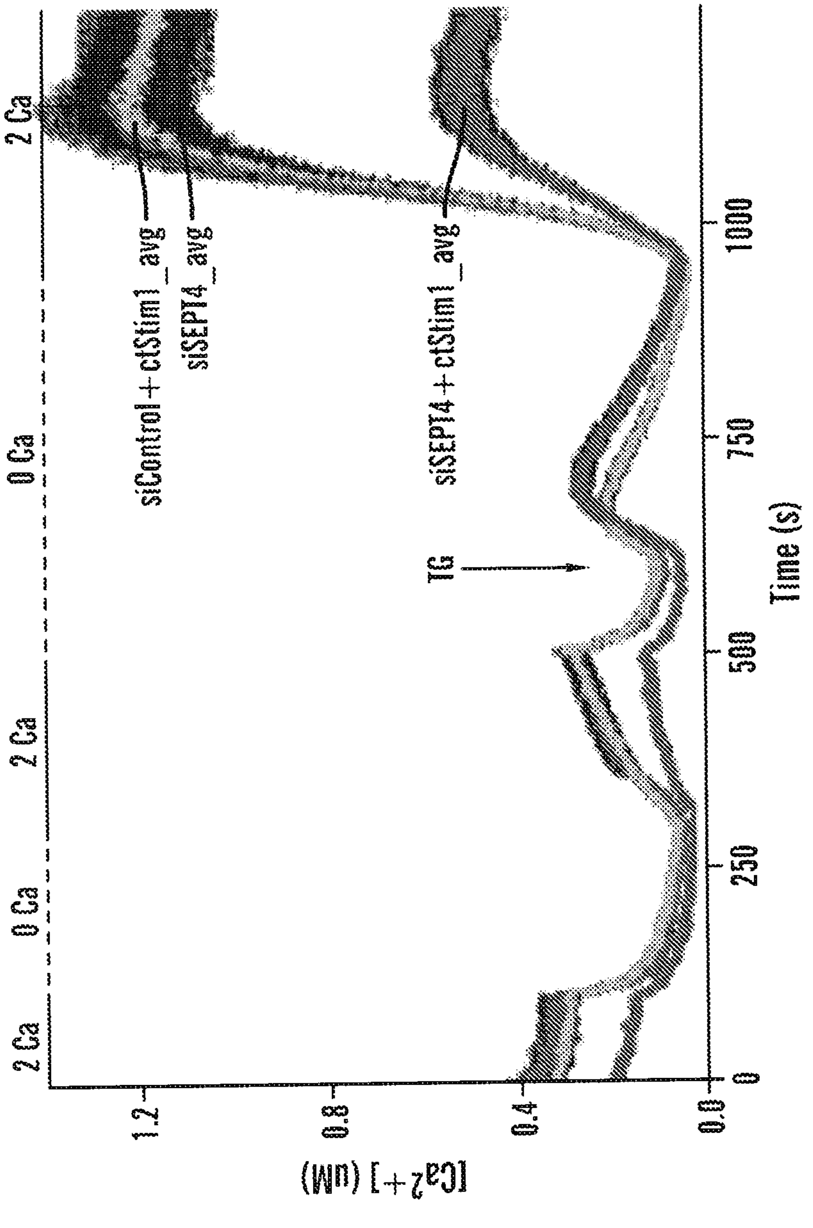

This experiment confirmed these results by single-cell $Ca^{2+}$ imaging (FIG. 75C). In the presence of 2 mM $[Ca^{2+}]_o$, expression of STIM1-CT473 increased $[Ca^{2+}]_i$ levels in both control and septin 4/5-depleted HeLa cells in the absence of ER store depletion (FIG. 75C). Together, these results indicate that septin 4/5 depletion does not irreversibly impair the channel function of ORAI1: expression of a soluble STIM1-CT473 fragment rescues the defect STIM1-ORAI-dependent $Ca^{2+}$ entry and NFAT nuclear translocation in septin 4/5-depleted cells under resting conditions.

Conclusion

To identify additional modulators of the $Ca^{2+}$-calcineurin-NFAT pathway, the inventors performed a genome-wide RNAi screen. To increase the sensitivity of the screen for $Ca^{2+}$ influx modulators, the inventors overexpressed STIM1 and ORAI1 in HeLa NFAT1-GFP cells. They chose NFAT nuclear translocation as a readout of the modulation that was technically more straight forward, as well as more reproducible, than measuring $Ca^{2+}$ influx directly (Feske et al., 2006; Gwack et al., 2007a). This format of the assay also held out the possibility of discovering novel calcineurin-NFAT regulators other than those involved in $Ca^{2+}$ entry (Gwack et al., 2007a). As with other genome-wide screens, several hundred (887) modulators of the pathway were identified, including known players at each step—i.e., involved in $Ca^{2+}$ influx, calcineurin, or nuclear import. The modulators divided relatively evenly into those with a strong or moderate and those with a weak effect (486 and 401 respectively). Remarkably, even the weak candidates made substantial contributions to NFAT activation in cell types in which they were highly expressed, as judged by analysis of 11 candidates expressed at high levels in T cells. These data showed the feasibility of extracting useful information from RNAi screens performed in transformed cell lines, by crossing the list of potential regulators to a list of candidates highly expressed in a cell type of interest.

Septin 4 emerged early as a strong candidate in the NFAT screen. Further analysis revealed that a strong effect on store-operated $Ca^{2+}$ entry was observed only with siRNAs that depleted both septins 4 and 5. The septin 5 siRNA SmartPool did not score in the screen, even though when individually tested, one of the siRNAs also moderately diminished the level of Septin 4 mRNA. The requirement for combined depletion of septins 4 and 5 is likely due to redundant function, consistent with the fact that septin 4-deficient (Kissel et al., 2005) mice have no obvious impairment of lymphocyte functions such as NFAT activation or cytokine production (data not shown). The effect of septin 4/5 depletion was not a general effect, since NFκB signaling, as judged by RelA nuclear translocation in response to TNF receptor signaling, was unaffected, and we did not observe toxic effects of septin 4/5 depletion on cytokinesis, cell proliferation or cell survival.

Septin 4/5 depletion resulted in a subtle disorganisation of ORAI1 in resting cells, visible as a tail in the ORAI pixel intensity distribution compared to control cells (FIG. 74A). TIRF microscopy does not resolve whether this reflects a clustering of ORAI channels themselves or a reorganization that increases the total amount of plasma membrane (or internalized vesicles) in these pixels. In either case, the phenomenon recalls the role of septins in establishing diffusion barriers that separate plasma membrane domains, for instance at the yeast bud neck (Barral et al., 2000; Takizawa et al., 2000), in the annulus separating anterior and posterior tail compartments of mammalian sperm (Ihara et al., 2005; Kissel et al., 2005; Kwitny et al., 2010), and at the boundary between the membrane of the primary cilium and the surrounding plasma membrane (Hu et al., 2010). Septins are thought to play a similar role in neuronal dendritic branching and in maintaining the structure of dendritic spines (Tada et al., 2007; Xie et al., 2007). In the cited examples, septins demarcate morphologically distinct regions of a cell, which at first seems to contrast with the subtler membrane domains related to STIM-ORAI function. However, the relevant common feature may be the characteristic small dimensions of septin rings and collars (Caudron and Barral, 2009), which are suited to the demarcation of both localized (submicron-scale) membrane domains and narrow boundaries between larger cellular regions.

The TIRFM experiments showed that septin 4/5 depletion resulted in slower movement of STIM1 to the vicinity of the plasma membrane (FIG. 74B). Septins contain C-terminal coiled-coil domains that could potentially interact with STIM1 or its associated proteins, thus recruiting STIM1 directly. Given that actin depolymerization with cytochalasin D causes STIM-ORAI puncta to aggregate and coalesce (Luik et al., 2006), it may be relevant that septins interact with the cortical actin cytoskeleton through anillin (Kinoshita et al., 2002; Versele and Thorner, 2005). Notably, anillin and at least two other proteins involved in cytokinesis (Feo, the orthologue of human PRC1, protein regulator of cytokinesis-1, and Fav, the orthologue of human kinesin family member KIF23) emerged as positive regulators of store-operated calcium entry in our genome-wide *Drosophila* screen (Gwack et al., 2007b). Septin itself (*Drosophila* Peanut) would have been discarded in this screen because cells with shape defects (such as the peanut shape assumed by cells arrested in cytokinesis) were automatically eliminated from consideration. In an intriguing precedent for septin-protein interactions that control a localized process at the plasma membrane, septins interact with syntaxin and act as a brake on vesicular release in platelets and neurons (Amin et al., 2008; Beites et al., 2005; Dent et al., 2002; Taniguchi et al., 2007).

Finally, septins could modulate the number or stability of ER-plasma membrane junctions at which STIM1 and ORAI1 interact, or the distance separating the two membranes at these contacts. This could provide an explanation for both the delay in STIM1 transit to ER-PM junctions (FIG. 74B) and the impaired colocalization with ORAI1.

Figure 80:
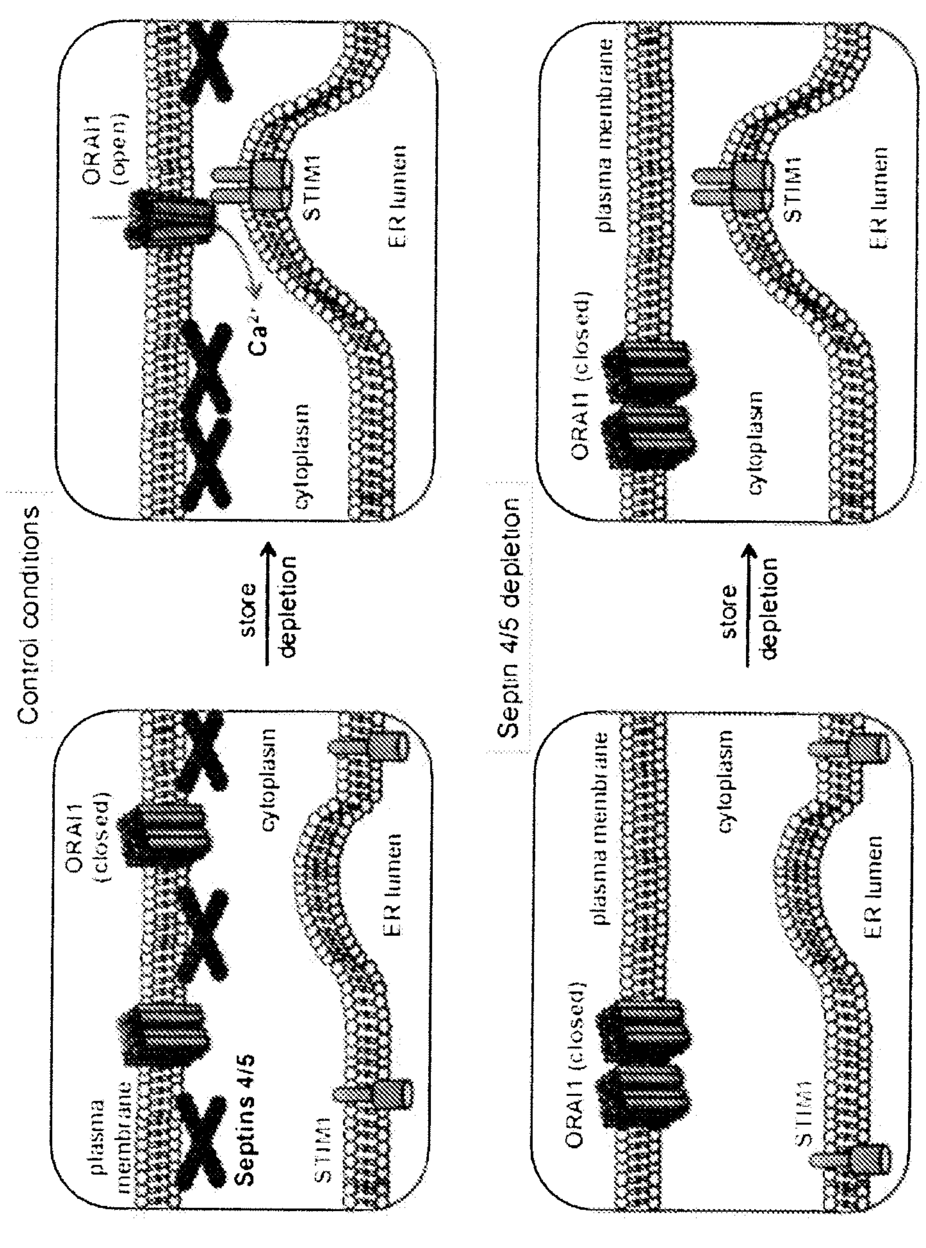
FIG. 80 shows a model for the regulation of store-operated $Ca^{2+}$ entry by Septins 4 and 5.

In summary, the sensitized genome-wide screen has identified septins 4 and 5, in addition to a large number of regulators that affect the nuclear import of NFAT in response to activation of $Ca^{2+}$ entry through the STIM1-ORAI1 pathway. Detailed analysis of septin 4, a strong early candidate emerging from the screen, has established a critical, previously unreported role for septins 4 and 5 in store-operated $Ca^{2+}$ entry. While wishing to be held in theory, the inventors speculate that in control cells, septins 4 and 5 maintain the membrane organization of ORAI1 (FIG. 80), and may also have a role in organising ER-plasma membrane junctions or in recruiting STIM1. The studies define a new physiological role for septins 4 and 5 in the regulation of store-operated $Ca^{2+}$ entry.

Example 2

Treatment of Rheumatoid Arthritis with a Septin Inhibitor

Purpose: The purpose of the study is to evaluate safety and efficacy of a septin 4 inhibitor for the treatment of subjects with rheumatoid arthritis.

Study Type: Interventional

Study Design: Allocation: Non-Randomized

Endpoint Classification: Safety/Efficacy Study

Intervention Model: Single Group Assignment

Masking: Open Label

Primary Purpose: Treatment

Primary Outcome Measures: Change in disease activity score at visit week 12 as compared to baseline Eligibility Ages Eligible for Study: 18 Years and older Genders Eligible for Study: Both Accepts Healthy Volunteers: No The following are criteria to be considered when selecting a test subject for the study:

Inclusion:

Subjects must meet ACR criteria for diagnosis of RA for at least 3 months, must meet ACR Functional Class I, II or III (1992 criteria) and must have a confirmed diagnosis of active moderate to severe rheumatoid arthritis as defined by 6 or more swollen joints and 9 or more tender joints.

Subjects must also have DAS of 3.2 or greater at study entry, normal laboratory parameters and ESR >20, satisfactory response or intolerance to one or more prior DMARDs and be willing and able to give informed consent.

Exclusion:

Subjects with a history of acute inflammatory joint disease other than RA, history of malignant lymphoma, history of uncontrolled diabetes, unstable ischemic heart disease, active inflammatory bowel disease, active peptic ulcer disease or stroke, positive HIV status, and positive serology for Hepatitis B or C should be excluded.

Subjects should have no previous history of tuberculosis or *listeria* infection, no previous history of cancer other than successfully treated skin cancer, and women cannot be pregnant or be breastfeeding.

Example 2

Use of an UEV3 Inhibitor for the Treatment of Rheumatoid Arthritis

Purpose: This study will assess the safety, tolerability and efficacy of an UEV3 inhibitor over a period of 2 yrs in patients with rheumatoid arthritis.

Study Type: Interventional

Study Design: Intervention Model: Single Group Assignment

Masking: Open Label

Primary Purpose: Treatment

Primary Outcome Measures: Long-term safety and tolerability by looking at the adverse events over time and the injection site reactions Secondary Outcome Measures: Efficacy, by looking at the number of swollen and tender joints over time, the high sensitivity C-reactive protein and the questionnaires for the pain, the disease activity and health assessment of the patient; Pharmacokinetics of agent; Immunogenicity of agent, by looking at the presence of antibodies.

Eligibility

Ages Eligible for Study: 18 Years and older

Genders Eligible for Study: Both

Accepts Healthy Volunteers: No

The following are criteria to be considered when selecting a test subject for the study.

Inclusion Criteria:

Patients who have rheumatoid arthritis should be included.

Exclusion Criteria:

Patients for whom continuation of treatment in the extension 2 is not considered appropriate by the physician should be excluded.

In addition, pregnant or nursing (lactating) women and women of childbearing potential should be excluded.

Other protocol-defined inclusion/exclusion criteria may apply.

Example 3

Method of Treating Psoriasis with a Septin Inhibitor

Purpose: To compare disease activity in psoriasis patent, as measured by PASI score, of three Septin-5 inhibitor dosing (injection) regimens vs. placebo.

Study Type: Interventional

Study Design: Allocation: Randomized

Endpoint Classification: Pharmacokinetics/Dynamics Study

Intervention Model: Single Group Assignment

Masking: Double-Blind

Primary Purpose: Treatment

Further Study Details:

Primary Outcome Measures: Biological activity will be assessed primarily by the Psoriasis Activity and Severity Index (PASI)

Secondary Outcome Measures: Observe adverse and serious adverse events

Detailed Description: The primary objective of this study is to compare disease activity, as measured by PASI score, of three Septin 5 Inhibitor dosing regimens (5 mg for 12 weeks, 5 mg for 6 weeks, 7 mg for 4 weeks) versus placebo administered weekly by SC injection.

Eligibility

Ages Eligible for Study: 18 Years to 65 Years

Genders Eligible for Study: Both

Accepts Healthy Volunteers: No

The following are criteria to be considered when selecting a test subject for the study.

Inclusion Criteria:

Psoriasis involving at least 10% of body surface area

Age 18 through 65 years at the time of the first dose of study drug

Both males and females are eligible. However, sexually active females, unless surgically sterile or at least 1 year post-menopausal, must have used an effective method of avoiding pregnancy (including oral or implanted contraceptives, IUD, female condom, diaphragm with spermicide, cervical cap, abstinence, use of a condom by the sexual partner or sterile sexual partner) for 30 days prior to the first dose of study drug and must agree to continue Currently receiving no therapy for psoriasis except emollients (certain other over-the-counter products may be allowed with prior approval of the sponsor)

Written informed consent obtained from the patient

Ability to complete follow-up period of 167 days as required by the protocol

Exclusion Criteria:

Pustular, guttate, or erythrodermic psoriasis as the predominant disease type

PASI score <8

At screening (must be within 21 days before study entry) any of the following: lymphocyte count under 1,200 cells/mm3, WBC under 4,000 cells/mm3, hematocrit below 32%, platelets below 110,000 cells/mm3, creatinine, AST, ALT over 1.5 times upper limit of normal At screening (must be within 21 days before study entry) any clinical evidence of HIV, hepatitis B, hepatitis C or active hepatitis A infection Pregnancy (must have a negative serum pregnancy test within 21 days prior to the first dose of study drug, and urine pregnancy test must be negative on Study Day 0 before study entry)

History of cancer (except excision of basal cell carcinoma)

Any documented immunodeficiency

A history of prior administration of monoclonal antibodies or related proteins

Receipt of systemic retinoids, corticosteroids, cyclosporin A, methotrexate, phototherapy or coal tar treatment in the past 4 weeks Use of topical therapy (except emollients) for psoriasis in the past 2 weeks (certain other over-the-counter products may be allowed with prior approval of the sponsor)

Receipt of any investigational drug therapy within 6 weeks before the first dose of study drug in this protocol (use of licensed agents for indications not listed in the package insert is permitted)

Current or planned participation in a research protocol in which an investigational agent or therapy may be administered Nursing mother Acute illness including infections Clinical manifestations of significant end organ dysfunction or failure that may compromise the safety of the volunteer in the study Example 4

Use of an UEV3 Inhibitor for the Treatment of Psoriasis

Purpose: An international, multi-centre, prospective, randomised, double-blind, 4-arm, placebo controlled, parallel group study with 12 weeks once daily oral treatment in subjects with psoriasis vulgaris.

Study Type: Interventional

Study Design: Allocation: Randomized

Endpoint Classification: Safety/Efficacy Study

Intervention Model: Parallel Assignment

Masking: Double Blind (Subject, Investigator)

Primary Purpose: Treatment

Further Study Details:

Primary Outcome Measures: Percentage change in Psoriasis Area and Severity Index (PASO from baseline to Week 12.

Secondary Outcome Measures: Subjects with PASI 75 (i.e., at least 75% reduction in PASI from baseline) at Week 12.

Subjects with "controlled disease" according to the Investigators' Global Assessment (IGA) at Week 12

Eligibility

Ages Eligible for Study: 18 Years and older

Genders Eligible for Study: Both

Accepts Healthy Volunteers: No

The following are criteria to be considered when selecting a test subject for the study.

Inclusion Criteria:

Following verbal and written information about the trial the subject must provide signed and dated informed consent before any study related activity is carried out, including activities relating to the washout period.

Clinical diagnosis of psoriasis vulgaris, for at least 6 months prior to randomisation, and currently covering at least 10% of the body surface area (BSA)

Candidates for systemic anti-psoriatic treatment

Psoriasis Area and Severity Index (PASI)≥10

Disease severity of moderate, severe or very severe according to the Investigators' Global Assessment of disease severity (IGA)

Aged 18 years or above

Any race or ethnicity

Males, surgically sterile females (bilateral tubal ligation, bilateral oophorectomy or hysterectomy) or post menopausal females (at least 1 year since last menses)

Attending hospital outpatient clinic or the private practice of a dermatologist

Exclusion Criteria:

Systemic treatment with all other therapies (other than biologics) with a possible effect on psoriasis vulgaris (e.g. corticosteroids, retinoids, immunosuppressants, methotrexate, cyclosporin or fumaric acid) within 4 weeks prior to randomisation PUVA therapy within 4 weeks prior to randomization UVB therapy within 2 weeks prior to randomisation Any topical treatment (except for emollients/medicated shampoo) within 2 weeks prior to randomisation Initiation of, or changes to concomitant medication that could affect psoriasis vulgaris (e.g. beta-blockers, anti-malaria drugs, lithium) 2 weeks prior to randomisation and during the study Current diagnosis with erythrodermic, exfoliative or pustular psoriasis Other current skin conditions that may confound the evaluation of psoriasis vulgaris as judged by the Investigator Generally in good health and does not have any clinically significant cardiac, endocrinologic, pulmonary, neurologic, psychiatric, hepatic, renal, haematologic, or gastrointestinal disease, immunologic insufficiency, or other major diseases or current condition which, in the opinion of the Investigator, would put the subject at risk by participating in the study Current active tuberculosis or latent tuberculosis Planned exposure to the sun during the study that may affect psoriasis vulgaris Known malignancy or history of malignancy (other than cervical carcinoma in situ, basal cell or squamous cell carcinoma) within the 5 year period prior to randomisation Live vaccination within the 4 weeks prior to randomisation Males who do not agree to use adequate contraception during the study (including follow-up) to ensure their partner does not become pregnant Known or suspected hypersensitivity to component(s) of the investigational product Current participation in any other interventional trial Treatment with any non-marketed drug substance (i.e. an agent which has not yet been made available for clinical use following registration) within 4 weeks or 5 half-lives (whichever is longer) prior to randomisation Previously randomised in this study Known or, in the opinion of the Investigator, is unlikely to comply with the Clinical Study Protocol (e.g., alcohol abuse, drug dependency or psychotic state).

Example 5

Use of a Septin Inhibitor for the Treatment of Irritable Bowel Syndrome

Purpose: The purpose of the study is to evaluate the benefit of treatment with oral dose of a Septin 4 inhibitor on IBS symptoms and the safety and tolerability of this therapy.

Study Type: Interventional

Study Design: Allocation: Randomized

Intervention Model: Parallel Assignment

Masking: Double Blind (Subject, Caregiver, Investigator)

Primary Purpose: Treatment

Further Study Details

Primary Outcome Measures: Response of Overall IBS Symptom Relief—50% Rule and Weekly binary question (yes/no): "Did you have satisfactory relief of your overall IBS symptoms since the last visit?"

Secondary Outcome Measures:

Response of Overall IBS Symptom Relief—75% Rule

Weekly binary question (yes/no): "Did you have satisfactory relief of your overall IBS symptoms since the last visit?"

Response of Overall IBs Symptom Relief in the Subgroup of Patients With IBS With Diarrhea (IBS-D)—75% Rule Weekly binary question (yes/no): "Did you have satisfactory relief of your overall IBS symptoms since the last visit?"

Detailed Description: Irritable Bowel Syndrome (IBS) is a functional disorder characterised by chronic or recurrent abdominal pain or discomfort associated with altered bowel habits. This trial aims to evaluate the efficacy of a Septin 4 inhibitor in improvement of IBS symptoms through a daily oral administration, testing three dosages or placebo in IBS patients for 4-weeks. In each patient, the experimental clinical phase encompasses a screening/2-week run-in period (no study medication), followed by a 4-weeks treatment period and a 2-weeks treatment withdrawal period, for total study duration of 8 weeks in each patient.

Eligibility

Ages Eligible for Study: 18 Years to 70 Years

Genders Eligible for Study: Both

Accepts Healthy Volunteers: No

The following are criteria to be considered when selecting a test subject for the study.

Inclusion Criteria:

Male or female patients aged 18-70 years.

Clinical diagnosis of IBS.

For patients older than 50 years or patients with positive family history of colorectal cancer: normal results from colonoscopy or flexible sigmoidoscopy.

Use of appropriate contraceptive methods.

Normal physical examination or without clinically relevant abnormalities.

Exclusion Criteria:

Patients with organic abnormalities of the gastro-intestinal tract including history of colonic or major abdominal surgery, current or previous diagnosis of neoplasia, inflammatory bowel diseases, symptomatic gallbladder stone disease, diverticulosis/diverticulitis, ectopic endometriosis.

History of gluten enteropathy.

Lactose intolerance as assessed by response to diet

Diagnosis of ova or parasites, or occult blood in the stool in the previous 6 months.

Previous diagnosis of Diabetes Mellitus (either type 1 or 2)

Unstable medical condition.

Concomitant medication within 7 days prior to screening with drugs known to interfere with gastro-intestinal motility and sensitivity.

Pregnancy or breastfeeding.

Patient not able to understand or collaborate throughout the study.

Participation in other clinical trials in the previous 4 weeks.

Example 6

A Method of Treating Irritable Bowel Disease with an UEV3 Inhibitor

Purpose: This study will compare the effects (both positive and negative) of an initial treatment with an UEV3 inhibitor to placebo over 8 weeks, in patients with moderately to severely active Irritable Bowel Disease.

Study Type: Interventional

Study Design: Allocation: Randomized

Endpoint Classification: Safety/Efficacy Study

Intervention Model: Parallel Assignment

Masking: Double Blind (Subject, Caregiver, Investigator, Outcomes Assessor)

Primary Purpose: Treatment

Further Study Details

Primary Outcome Measures: Clinical Response

Secondary Outcome Measures: Clinical remission and Clinical improvement/response Eligibility Ages Eligible for Study: 18 Years and older Genders Eligible for Study: Both Accepts Healthy Volunteers: No The following are criteria to be considered when selecting a test subject for the study.

Inclusion Criteria:

Have Inflammatory Bowel Disease

Have screening laboratory test results within protocol-specified parameters.

Exclusion Criteria:

Patients who have had any kind of bowel resection within 6 months

Are pregnant or planning pregnancy (both men and women) while enrolled in the study or for 20 weeks after receiving study agent Patients with certain complications of Inflammatory Bowel disease that would make it hard to assess response to study drug Patients with a history of or ongoing chronic or recurrent infectious disease

Example 7

Use of a Septin Inhibitor for the Treatment of Multiple Sclerosis

Purpose: This is an open-label, multicenter, study. Safety, efficacy, and pharmacodynamics (PD) will be assessed during the monotherapy period and the subsequent 6 month treatment period with a septin 5 inhibitor.

Study Type: Interventional

Study Design: Endpoint Classification: Safety Study

Intervention Model: Single Group Assignment

Masking: Open Label

Primary Purpose: Treatment

Official Title: An Open-Label, Multicenter Study in Subjects With Relapsing-Remitting Multiple Sclerosis to Evaluate the Safety of a Septin 5 inhibitor Further Study Details Primary Outcome Measures: The primary objective of the study is to evaluate the safety and tolerability of a septin 5 inhibitor administered in subjects with RRMS.

Secondary Outcome Measures: Explore the efficacy of a septin 5 inhibitor.

Detailed Description: A septin 5 inhibitor is being investigated to determine whether it is viable agent to consider for use in MS therapies.

Eligibility

Ages Eligible for Study: 18 Years to 55 Years

Genders Eligible for Study: Both

Accepts Healthy Volunteers: No

The following are criteria to be considered when selecting a test subject for the study.

Inclusion Criteria:

Aged 18 to 55 years old, inclusive, at the time of informed consent.

Must have a confirmed diagnosis of RRMS according to McDonald criteria #1-4 (Polman et al, 2005 [Appendix I]), and have a prior brain MRI demonstrating lesion (s) consistent with MS from any point in time.

Must have an EDSS between 0.0 and 5.0, inclusive.

Must be taking the same dose of a prescribed IFNβ (either Avonex, Betaseron, Rebif) or GA for at least 12 months consecutively at the time of enrollment and remain on this treatment for the duration of the study. Subjects receiving Rebif must be prescribed 44 μg by subcutaneous injection three times per week.

Exclusion Criteria:

Primary progressive, secondary progressive, or progressive relapsing MS (as defined by Polman et al. 2005

Other chronic disease of the immune system, malignancies, acute urologic, pulmonary, gastrointestinal disease.

Pregnant or nursing women.

Participation within 6 months prior to study enrollment in any other drug, biologic, or device study.

Example 8

Use of an UEV3 Inhibitor for the Treatment of Multiple Sclerosis

Purpose: The objective of this study is to evaluate the safety and efficacy of an UEV3 inhibitor in patients with relapsing-remitting multiple sclerosis over a 26-week treatment period.

Study Type: Interventional

Study Design: Allocation: Randomized

Endpoint Classification: Safety/Efficacy Study

Intervention Model: Parallel Assignment

Masking: Double Blind (Subject, Investigator)

Primary Purpose: Treatment

Further Study Details

Primary Outcome Measures: Total number of T-1-weighted Gd-enhanced lesions obtained with MRI at 4-week intervals for 26 weeks.

Secondary Outcome Measures: Total volume of Gd-enhanced lesions

Eligibility

Ages Eligible for Study: 18 Years to 55 Years

Genders Eligible for Study: Both

Accepts Healthy Volunteers: No

The following are criteria to be considered when selecting a test subject for the study.

Inclusion Criteria:

Adult male or female aged 18-55 years inclusive at screening

Patients who have a definite diagnosis of relapsing-remitting Multiple Sclerosis Exclusion Criteria:

Multiple Sclerosis course other than relapsing-remitting multiple sclerosis

History of malignancy

History of clinically significant chronic disease of the immune system (other than Multiple Sclerosis)

Inability to undergo Gd-enhanced MRI scans

Diagnosis of diabetes mellitus (type I or type H)

Example 9

Use of a Septin Protein for the Treatment of Severe Combined Immunodeficiency

Purpose: The purpose of this study is to evaluate the safety and efficacy of septin-4 in patients with severe combined immunodeficiency (SCID) currently being treated with Adagen.

Study Type: Interventional

Study Design: Allocation: Non-Randomized

Endpoint Classification: Safety/Efficacy Study

Intervention Model: Crossover Assignment

Masking: Open Label

Primary Purpose: Treatment

Further Study Details:

Primary Outcome Measures: total erythrocyte dAXP concentration from a trough blood sample.

Secondary Outcome Measures: (1) plasma ADA activity, (2) immune status, includes absolute lymphocyte counts, lymphocyte subset analysis, quantitative immunoglobulin concentration and (3) safety.

Eligibility

Genders Eligible for Study: Both

Accepts Healthy Volunteers: No

The following are criteria to be considered when selecting a test subject for the study.

Inclusion Criteria:

Diagnosis of severe combined immunodeficiency

Age greater than 36 months for the first three patients

Patients or parent/guardian must be capable of understanding the protocol requirements and risks and providing written informed assent/consent Exclusion Criteria:

Severe thrombocytopenia

Positive screening pregnancy test or is breast-feeding

Any condition that, in the opinion of the Investigator, makes the patient unsuitable for the study Current or prior (within the past 6 months) participation in another clinical study with an investigational agent and/or use of an investigational drug in the 30 days before the first administration of septin-4. Patients with documentation of failure of prior gene therapy may participate in the present clinical trial.

Inability to comply with the study protocol

Known planned participation in a gene-therapy study for the planned duration of this study Female subjects who are pregnant or lactating Female subjects of childbearing potential who are not using an FDA approved birth control method Example 10

Expression of Both Septin4 and Septin5 Rescues NFAT Nuclear Translocation

HeLa NFAT1-GFP cells were transfected with siControl or siSeptin4/5-specific oligonucleotides. After a period of 24 h, the cells were transfected with RNAi-resistant cDNAs encoding human septin 4 and septin 5. 48 h later after the cDNA transfection, the cells were stimulated with 1 uM TG for 30 minutes at 37° C., then fixed, DAPI stained, imaged and analyzed for NFAT1-GFP nuclear translocation.

Figure 81:
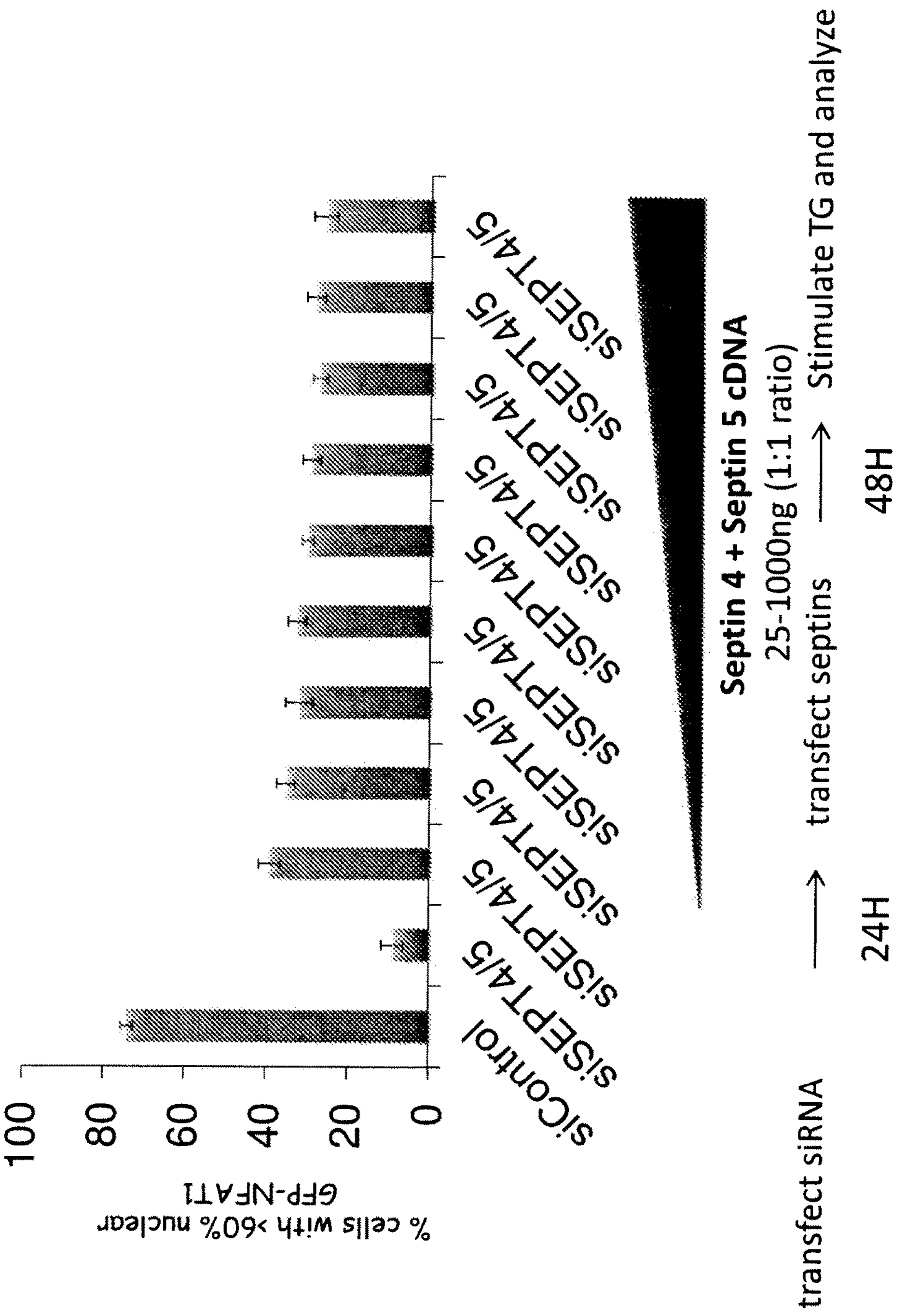
FIG. 81 shows that the expression of both septin 4 and septin 5 rescues NFAT nuclear translocation.

Expression of septin 4 and 5 from RNAi-resistant cDNAs after knockdown of endogenous septin 4 and 5 partially restores signaling (FIG. 81). In other words, at least in a cell where septin 4/5 levels are relatively low, calcium signalling can be increased by adding more septin.

REFERENCES

Amin, N. D., et al. (2008) J. Neurosci., 28, 3631-3643.

Anon, J. R., et al. (2006) Nature 441, 595-600.

Banal, Y., et al. (2000) Mol. Cell. 5, 841-851.

Beals, C. R., et al. (1997) Science 275, 1930-1934.

Beites, C. L., et al., (1999) Nat. Neurosci., 2:434-439

Beites, C. L., et al. (2005) Biochem. J., 385, 347-353.

Bertin, A., et al. (2010) J. Mol. Biol., 404, 711-731.

Calloway, N., et al. (2011) J. Cell Sci., 124, 2602-2610.

Cao, L., et al. (2007) FEBS Lett, 581, 5526-5532.

Carrasco, S., and Meyer, T. (2011) Annu. Rev. Biochem., 80, 973-1000.

Casamayor, A., and Snyder, M. (2003) Mol. Cell. Biol., 23, 2762-2777.

Caudron, F., and Banal, Y. (2009) Dev. Cell 16, 493-506.

Crabtree, G. R., and Olson, E. N. (2002) Cell 109 Suppl, S67-79.

Crist, S. A., et al. (2008) Blood 111, 3553-3561.

Dent, J., et al. (2002) Proc. Natl. Acad. Sci., U.S.A., 99, 3064-3069.
Derler, I., et al. (2009) J. Biol. Chem., 284, 24933-24938.
Dickins, R. A., et al. (2005) Nat. Genet., 37, 1289-1295.
Dolmetsch, R. E., et al. (1997) Nature 386, 855-858.
Echeverri, C. J., et al. (2006) Nat. Methods 3, 1-3.
Eisen, M. B., et al. (1998) Proc. Natl. Acad. Sci., U.S.A., 95, 14863-14868.
Ercan, E., et al. (2010) Traffic 10, 1802-1818.
Feske, S. (2007) Nat. Rev. Immunol., 7, 690-702.
Feske, S., et al. (2000) J. Immunol., 165, 297-305.
Feske, S., et al. (2006). Nature 441, 179-185.
Gambhir, A., et al. (2004) Biophys. J., 86, 2188-2207.
Graef, I. A., et al. (2001) Cell 105, 863-875.
Grigoriev, I., et al. (2008) Curr. Biol., 18, 177-182.
Grynkiewicz, G., et al. (1985) J. Biol. Chem., 260, 3440-3450.
Gwack, Y., et al. (2007a) Cell Calcium 42, 145-156.
Gwack, Y., et al. (2006) Nature 441, 646.
Gwack, Y., et al. (2007b) J. Biol. Chem., 282, 16232-16243.
Hall, P. A. and Russell S. E., (2004) J. Pathol., 204:489-505.
Hall, P. A., et al., (2008) The Septins. Wiley-Blackwell, West Sussex, England, UK. 370 PP.
Hartwell, L. H. (1971) Experimental Cell Research 69, 265-276.
Hilgemann, D. W. (2007) Pflugers Arch., 455, 55-67.
Hogan, P. G., et al. (2003) Genes Dev., 17, 2205-2232.
Hogan, P. G., et al. (2010) Annu. Rev. Immunol., 28, 491-533.
Honnappa, S., et al. (2009) Cell 138, 366-376.
Horsley, V., and Pavlath, G. K. (2002) J. Cell Biol., 156, 771-774.
Hoth, M., and Penner, R. (1992) Nature 355, 353-356.
Hu, Q., et al. (2010). Science 329, 1-5.
Huang, D. W., et al. (2007a). Genome Biol., 8, R183.
Huang, D. W., et al. (2007b). Nucleic Acids Res 35, W169-175.
Huang, G. N., et al. (2008). Science 319, 476-481.
Huang, Y. W., et al., (2008) Mol. Biol. Cell, 19:1717-1726.
Ihara, M., et al. (2005) Dev. Cell 8, 343-352.
Kawasaki, T., et al. (2009) Biochem. Biophys. Res. Commun., 385, 49-54.
Kinoshita, M., et al., (1997) Genes Dev., 11:1535-1547
Kinoshita, M., et al. (2002) Dev. Cell 3, 791-802.
Kissel, H., et al. (2005) Dev. Cell 8, 353-364.
Kremer, B. E., et al., (2005) Mol. Biol. Cell, 16:4648-4659.
Kwitny, S., et al. (2010) Biol. Reprod., 82, 669-678.
Latin, J. E., et al. (2008) Immunome Res., 4, 5.
Lavieu, G., et al. (2010) Proc. Natl. Acad. Sci., U.S.A., 107, 6876-6881.
Li, X., et al. (2011) Cell Stem Cell 8, 46-58.
Liou, J., et al. (2007) Proc. Natl. Acad. Sci., U.S.A., 104, 9301-9306.
Liou, J., et al. (2005) Curr. Biol., 15, 1235-1241.
Loewen, C., et al. (2007) J. Cell Biol., 179, 467.
Longtine, M. S., et al. (1996) Curr. Opin. Cell Biol., 8, 106-119.
Longtine M. S., et al., (1996) J Cell Biol, 3:719-36.
Luedeke, C., et al. (2005) J. Cell Biol., 169, 897-908.
Luik, R. M., et al. (2006) J. Cell Biol., 174, 815-825.
Luo, J., et al. (2009) Cell 137, 835-848.
Macian, F. (2005) Nat. Rev. Immunol., 5, 472-484.
Mathey-Prevot, B., and Perrimon, N. (2006) Cold Spring Harb. Symp. Quant. Biol., 71, 141-148.
Mbamala, E. C., et al. (2005) Biophys. J., 88, 1702-1714.
McLaughlin, S., and Murray, D. (2005) Nature 438, 605-611.
McLaughlin, S., et al. (2002) Annu. Rev. Biophys. Biomol. Struct., 31, 151-175.
Mercer, J. C., et al. (2006) J. Biol. Chem., 281, 24979-24990.
Muik, M., et al. (2009) J. Biol. Chem., 284, 8421-8426.
Muik, M., et al. (2008) J. Biol. Chem., 283, 8014-8022.
Müller, M. R., and Rao, A. (2010) Nat. Rev. Immunol., 10, 645-656.
Nagata, K., et al., (2003) J. Biol. Chem., 278:18538-18543.
Nakahira, M., et al. (2010). PLoS One 5, e13799.
Oh, Y., and Bi, E. (2011) Trends Cell Biol., 21, 141-148.
Oh-hora, M., et al., (2008) Nature Immunology, 9, 432-43.
Okamura, H., et al. (2004) Mol. Cell. Biol., 24, 4184-4195.
Orci, L., et al. (2009) Proc. Natl. Acad. Sci., U.S.A., 106, 19358-19362.
Parekh, A. B., and Putney, J. W. (2005) Physiol. Rev., 85, 757-810.
Park, C. Y., et al. (2009) Cell 136, 876-890.
Peng, S. L., et al. (2001) Immunity 14, 13-20.
Peng, X.-R., et al. (2002) Mol. Cell. Biol., 22, 378-387.
Perrimon, N., and Mathey-Prevot, B. (2007). Matter arising: off-targets and genome-scale RNAi screens in *Drosophila*. Fly (Austin) 1, 1-5.
Possemato, R., et al. (2011) Nature 476, 346-350.
Prakriya, M., et al. (2006) Nature 443, 230-233.
Putney, J. W., Jr. (1986) Cell Calcium 7, 1-12.
Rao, A., et al. (1997) Annu. Rev. Immunol., 15, 707-747.
Rauch, M. E., et al. (2002) J. Biol. Chem., 277, 14068-14076.
Roos, J., et al. (2005) J. Cell Biol., 169, 435-445.
Sampieri, A., et al. (2009) Cell Calcium 45, 439-446.
Shaffer, A. L., et al. (2008) Nature 454, 226-231.
Sharma, S., et al. (2011) PNAS, 1-6.
Sharma, S., and Rao, A. (2009) Nature Immunology 10, 799.
Silva, J. M., et al. (2005) Nat. Genet., 37, 1281-8.
Sirajuddin, M., et al., (2007) Nature, 449:311-315.
Soboloff, J., et al. (2006) J. Biol. Chem., 281, 20661-20665.
Spiliotis, E. T., et al., (2005) Science, 307:1781-1785.
Spiliotis, E. T., and Gladfelter, A. S. (2011). Spatial Guidance of Cell Asymmetry: Septin GTPases Show the Way. Traffic. In press.
Spiliotis, E. T., et al. (2008) J. Cell Biol., 180, 295-303.
Srikanth, S., et al. (2010) Nature Cell Biology 12, 436-446.
Stathopulos, P. B., et al. (2006) J. Biol. Chem., 281, 35855-35862.
Stathopulos, P. B., et al. (2008) Cell 135, 110-122.
Surka, M. C., et al., (2002) Mol. Biol. Cell, 13:3532-3545.
Tada, T., et al. (2007) Curr. Biol., 17, 1752-1758.
Takemura, H., et al. (1989) J. Biol. Chem., 264, 12266-12271.
Takizawa, P. A., et al. (2000) Science 290, 341-344.
Tanaka-Takiguchi, et al. (2009) Curr. Biol., 19, 140-145.
Taniguchi, M., et al. (2007) J. Biol. Chem., 282, 7869-7876.
Thastrup, O., et al. (1990) Proc. Natl. Acad. Sci., U.S.A., 87, 2466-2470.
Thastrup, O., et al. (1989) Agents Actions 27, 17-23.
Tooley, A. J., et al. (2009) Nature Cell Biology 11, 17-26.
Várnai, P., et al. (2007) J. Biol. Chem., 282, 29678-29690.
Versele, M., and Thorner, J. (2005) Trends Cell Biol., 15, 414-424.
Vig, M., et al. (2006a) Curr. Biol., 16, 2073-2079.
Vig, M., et al. (2006b) Science 312, 1220-1223.
Walsh, C. M., et al. (2010) Biochem. J., 425, 159-168.
Wang, Y., et al. (2009) Proc. Natl. Acad. Sci., U.S.A. 106, 7391-7396.
Waterman-Storer, C. M., and Salmon, E. D. (1998) Curr. Biol., 8, 798-806.

Weirich, C. S., et al. (2008) Nat. Rev. Mol. Cell. Biol., 9, 478-489.
Wu, M. M., et al. (2006) J. Cell Biol., 174, 803-813.
Xie, Y., et al. (2007) Curr. Biol., 17, 1746-1751.
Yang, Y. M., et al. (2010) Neuron 67, 100-115.
Yeromin, A. V., et al. (2006) Nature 443, 226-229.
Yuan, J. P., et al. (2009) Nature Cell Biology 11, 337-343.
Zanoni, I., et al. (2009) Nature 460, 264-268.
Zeng, Y., et al. (2002) Mol. Cell. 9, 1327-1333.
Zhang, J., et al. (1999) Current Biology 9, 1458-1467.
Zhang, S. L., et al. (2005) Nature 437, 902-905.
Zhou, Y., et al. (2010) Nat. Struct. Mol. Biol. 17, 112-116.
Zieger, B., et al. (2000) Gene 261, 197-203.
Zuber, J., et al. (2011) RNAi screen identifies Brd4 as a therapeutic target in acute myeloid leukaemia. Nature. In press.
Zweifach, A., and Lewis, R. S. (1993) Proc. Natl. Acad. Sci., U.S.A. 90, 6295-6299.

TABLE 1

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50049 | L11 | X | −3.09 | −1.83 | W | AB026190 | 27252 | NM_014458 | M-004893-00 |
| PL-50049 | J12 | X | −3.90 | −2.18 | W | ABLIM2 | 84448 | NM_032432 | M-014892-00 |
| PL-50047 | A21 | X | −3.03 | −1.80 | W | ACLY | 47 | NM_001096 | M-004915-00 |
| PL-50049 | F16 | X | −2.11 | −1.83 | W | ACY1L2 | 135293 | XM_072402 | M-024889-00 |
| PL-50049 | F02 | X | −3.49 | −2.11 | W | ADCY4 | 196883 | NM_139247 | M-006800-00 |
| PL-50001 | G15 | X | −3.55 | −2.27 | W | ADK | 132 | NM_001123 | M-004733-02 |
| PL-50004 | C05 | X | −2.16 | −2.22 | W | ADRA2B | 151 | NM_000682 | M-005423-01 |
| PL-50001 | I23 | X | −3.16 | −2.17 | W | AKAP11 | 11215 | NM_016248 | M-009277-01 |
| PL-50049 | D14 | X | −1.58 | −2.77 | W | AKR1CL1 | 340811 | XM_291723 | M-029709-00 |
| PL-50049 | F08 | X | −2.82 | −1.74 | W | ALS2CR13 | 150864 | NM_173511 | M-018538-00 |
| PL-50016 | D02 | X | −2.44 | −2.24 | W | AMH | 268.00 | NM_000479 | M-010991-00 |
| PL-50079 | J04 | X | −2.46 | −2.33 | W | AMIGO2 | 347902 | NM_181847 | M-018701-00 |
| PL-50058 | J08 | X | −2.91 | −1.32 | W | ANKFY1 | 51479 | NM_016376 | M-013161-00 |
| PL-50001 | M17 | X | −1.97 | −3.09 | W | ANKK1 | 255239 | NM_178510 | M-004930-01 |
| PL-50062 | A20 | X | −2.10 | −1.94 | W | ANKMY2 | 57037 | NM_020319 | M-013766-00 |
| PL-50072 | O18 | X | −2.66 | −2.06 | W | AP1S3 | 130340 | NM_178814 | M-018537-00 |
| PL-50051 | D07 | X | −0.16 | −2.82 | W | AP3B2 | 8120 | NM_004644 | M-021444-00 |
| PL-50060 | G04 | X | −1.92 | −2.66 | W | APG16L | 55054 | NM_017974 | M-021033-00 |
| PL-50020 | J11 | X | −2.32 | −3.58 | W | APOBEC1 | 339 | NM_001644 | M-011573-00 |
| PL-50047 | K17 | X | −2.04 | −2.52 | W | APXL | 357 | NM_001649 | M-011577-00 |
| PL-50052 | N16 | X | −2.02 | −2.39 | W | AQR | 9716 | NM_014691 | M-022214-00 |
| PL-50061 | P09 | X | −2.09 | −2.98 | W | ARHGAP15 | 55843 | NM_018460 | M-018019-00 |
| PL-50060 | D05 | X | −1.31 | −4.57 | W | ARHGAP17 | 55114 | NM_018054 | M-008335-00 |
| PL-50008 | M17 | X | −1.83 | −2.56 | W | ARHGDIA | 396 | NM_004309 | M-016253-00 |
| PL-50060 | P12 | X | −1.85 | −2.81 | W | ARL10C | 55207 | NM_018184 | M-020294-00 |
| PL-50067 | A12 | X | −2.08 | −2.58 | W | ARMC2 | 84071 | NM_032131 | M-018191-00 |
| PL-50054 | E09 | X | −1.82 | −2.26 | W | ARPP-21 | 10777 | NM_016300 | M-016091-00 |
| PL-50059 | A19 | X | −2.87 | −2.80 | W | ARS2 | 51593 | NM_015908 | M-019234-00 |
| PL-50072 | J21 | X | −2.98 | −2.50 | W | ASB10 | 136371 | NM_080871 | M-007725-00 |
| PL-50051 | L06 | X | −2.17 | −1.94 | W | ASMTL | 8623 | NM_004192 | M-012663-00 |
| PL-50089 | G02 | X | −3.39 | −1.60 | W | ASTL | 431705 | NM_001002036 | M-032349-00 |
| PL-50062 | L11 | X | −1.59 | −2.02 | W | ATP10D | 57205 | NM_020453 | M-018004-00 |
| PL-50047 | O19 | X | −3.42 | −1.02 | W | ATP2B4 | 493 | NM_001684 | M-006118-00 |
| PL-50057 | M21 | X | −0.60 | −3.79 | W | ATP5S | 27109 | NM_015684 | M-020544-00 |
| PL-50064 | G11 | X | −2.18 | −4.15 | W | AZ2 | 64343 | NM_022461 | M-014092-00 |
| PL-50062 | E06 | X | −1.54 | −3.01 | W | BBX | 56987 | NM_020235 | M-015289-00 |
| PL-50070 | I20 | X | −2.83 | −2.20 | W | BC002942 | 91289 | NM_033200 | M-015085-00 |
| PL-50057 | K14 | X | −2.54 | −2.67 | W | BC-2 | 27243 | NM_014453 | M-020247-00 |
| PL-50062 | G05 | X | −2.27 | −1.90 | W | BEXL1 | 56271 | XM_043653 | M-024780-00 |
| PL-50047 | K18 | X | −1.40 | −3.63 | W | BFSP1 | 631 | NM_001195 | M-011218-00 |
| PL-50017 | A09 | X | −2.42 | −2.70 | W | BMP15 | 9210 | NM_005448 | M-012018-01 |
| PL-50075 | G08 | X | −2.90 | −2.75 | W | BMPER | 168667 | NM_133468 | M-021489-00 |
| PL-50008 | A06 | X | −2.04 | −2.46 | W | BRD8 | 10902 | NM_006696 | M-006377-00 |
| PL-50063 | P09 | X | −3.57 | −2.70 | W | BRUNOL6 | 60677 | NM_052840 | M-015854-00 |
| PL-50020 | F10 | X | −2.48 | −1.85 | W | BSCL2 | 26580 | NM_032667 | M-016749-00 |
| PL-50053 | H23 | X | −2.62 | −2.25 | W | BTN3A3 | 10384 | NM_006994 | M-021359-00 |
| PL-50061 | A19 | X | −3.13 | −2.11 | W | C10ORF59 | 55328 | NM_018363 | M-021211-00 |
| PL-50070 | J06 | X | −2.62 | −2.52 | W | C10ORF94 | 93426 | NM_130784 | M-015298-00 |
| PL-50062 | K11 | X | −2.68 | −2.65 | W | C11ORF17 | 56672 | NM_020642 | M-015631-00 |
| PL-50063 | H04 | X | −1.74 | −2.73 | W | C13ORF10 | 64062 | NM_022118 | M-019088-00 |
| PL-50069 | D21 | X | −1.91 | −2.80 | W | C14ORF126 | 112487 | NM_080664 | M-021299-00 |
| PL-50075 | F13 | X | −2.34 | −3.25 | W | C14ORF147 | 171546 | NM_138288 | M-017156-00 |
| PL-50070 | A10 | X | −2.77 | −2.54 | W | C14ORF43 | 91748 | NM_194278 | M-031938-00 |
| PL-50070 | B11 | X | −2.37 | −2.86 | W | C14ORF73 | 91828 | XM_040910 | M-022006-00 |
| PL-50071 | G02 | X | −2.58 | −2.56 | W | C14ORF8 | 122664 | NM_173846 | M-017754-00 |
| PL-50053 | G11 | X | −3.12 | −2.14 | W | C14ORF92 | 9878 | XM_375045 | M-021236-00 |
| PL-50064 | P15 | X | −2.47 | −2.41 | W | C16ORF23 | 79006 | NM_024042 | M-014274-00 |
| PL-50004 | G11 | X | −2.61 | −2.46 | W | C17ORF35 | 8834 | NM_003876 | M-005440-01 |
| PL-50080 | M11 | X | −2.47 | −1.66 | W | C18ORF34 | 374864 | NM_198995 | M-032008-00 |
| PL-50060 | K20 | X | −2.53 | −1.97 | W | C19ORF24 | 55009 | NM_017914 | M-020936-00 |
| PL-50020 | B06 | X | −2.95 | −3.27 | W | C21ORF107 | 54014 | NM_018963 | M-010963-00 |
| PL-50059 | K06 | X | −2.50 | −1.66 | W | C21ORF45 | 54069 | NM_018944 | M-020789-00 |
| PL-50053 | K20 | X | −1.98 | −2.27 | W | C21ORF6 | 10069 | NM_016940 | M-013856-00 |
| PL-50069 | P16 | X | −2.84 | −2.91 | W | C21ORF84 | 114038 | NM_153752 | M-016161-00 |
| PL-50051 | L20 | X | −1.99 | −2.78 | W | C4ORF8 | 8603 | NM_003704 | M-019541-00 |
| PL-50075 | K06 | X | −2.03 | −2.45 | W | C5ORF11 | 167410 | NM_153234 | M-018373-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50061 | G11 | X | −2.72 | −3.09 | W | C6ORF110 | 55362 | XM_371822 | M-025105-00 |
| PL-50069 | D23 | X | −2.08 | −2.05 | W | C6ORF51 | 112495 | NM_138408 | M-015508-00 |
| PL-50072 | F23 | X | −2.27 | −2.07 | W | C6ORF57 | 135154 | NM_145267 | M-015985-00 |
| PL-50065 | B06 | X | −2.19 | −2.05 | W | C6ORF59 | 79992 | NM_024929 | |
| PL-50062 | O17 | X | −1.95 | −2.24 | W | C8ORF4 | 56892 | NM_020130 | M-015557-00 |
| PL-50072 | L10 | X | −2.48 | −2.75 | W | C9ORF115 | 138428 | XM_059972 | M-026208-00 |
| PL-50078 | D16 | X | −2.29 | −1.86 | W | C9ORF150 | 286343 | NM_203403 | M-031930-00 |
| PL-50074 | N18 | X | −2.11 | −3.35 | W | C9ORF84 | 158401 | NM_173521 | M-018530-00 |
| PL-50066 | B20 | X | −2.77 | −1.61 | W | CABLES2 | 81928 | NM_031215 | M-032282-00 |
| PL-50020 | A21 | X | −4.27 | −1.56 | W | CACNA1A | 773 | NM_000068 | M-006121-01 |
| PL-50057 | M05 | X | −2.50 | −1.67 | W | CACNG4 | 27092 | NM_014405 | M-012519-00 |
| PL-50051 | L10 | X | −2.82 | −1.93 | W | CADPS | 8618 | NM_003716 | M-019218-00 |
| PL-50006 | M11 | X | −2.76 | −2.97 | W | CARD12 | 58484 | NM_021209 | M-004396-00 |
| PL-50021 | J17 | X | −2.30 | −3.97 | W | CAV3 | 859 | NM_001234 | M-011229-00 |
| PL-50073 | H05 | X | −2.78 | −2.55 | W | CBLN2 | 147381 | NM_182511 | |
| PL-50006 | O05 | X | −3.04 | −1.72 | W | CBX6 | 23466 | NM_014292 | M-009555-00 |
| PL-50004 | K15 | X | −2.33 | −3.05 | W | CCR6 | 1235 | NM_004367 | M-005453-00 |
| PL-50006 | O19 | X | −2.27 | −2.03 | W | CD151 | 977 | NM_004357 | M-003637-02 |
| PL-50047 | A18 | X | −2.22 | −2.55 | W | CD1E | 913 | NM_030893 | M-014647-00 |
| PL-50017 | I09 | X | −2.00 | −2.04 | W | CD3G | 917 | NM_000073 | M-011005-00 |
| PL-50017 | I15 | X | −1.87 | −3.86 | W | CD5 | 921 | NM_014207 | M-007848-01 |
| PL-50014 | B06 | X | −3.64 | −2.09 | W | CD74 | 972.00 | NM_004355 | M-012667-00 |
| PL-50073 | B10 | X | −2.54 | −1.73 | W | CDC42EP5 | 148170 | NM_145057 | |
| PL-50006 | K08 | X | −2.95 | −2.84 | W | CDH9 | 1007 | NM_016279 | M-013169-00 |
| PL-50071 | E05 | X | −2.66 | −3.17 | W | CENTG1 | 116986 | NM_014770 | M-021010-00 |
| PL-50047 | B13 | X | −3.12 | −1.98 | W | CFL2 | 1073 | NM_021914 | M-019078-00 |
| PL-50067 | N08 | X | −2.59 | −2.83 | W | CHCHD5 | 84269 | NM_032309 | M-014849-00 |
| PL-50015 | G18 | X | −2.23 | −2.61 | W | CHD4 | 1108.00 | NM_001273 | M-009774-00 |
| PL-50053 | L12 | X | −2.50 | −2.99 | W | CHERP | 10523 | NM_006387 | M-016176-00 |
| PL-50015 | G16 | X | −2.93 | −2.08 | W | CHFR | 55743.00 | NM_018223 | M-007018-01 |
| PL-50004 | M21 | X | −2.16 | −1.86 | W | CHRM3 | 1131 | NM_000740 | M-005464-01 |
| PL-50018 | I11 | X | −2.72 | −2.11 | W | CHRNA4 | 1137 | NM_000744 | M-006138-01 |
| PL-50008 | D23 | X | −2.49 | −2.10 | W | CKN1 | 1161 | NM_000082 | M-011008-00 |
| PL-50047 | F05 | X | −0.87 | −3.50 | W | CLCN4 | 1183 | NM_001830 | M-006152-00 |
| PL-50057 | M11 | X | −0.66 | −4.26 | W | CLUL1 | 27098 | NM_014410 | M-017042-00 |
| PL-50054 | P09 | X | −2.07 | −2.02 | W | CMRF-35H | 11314 | NM_007261 | M-012778-00 |
| PL-50012 | P10 | X | −2.55 | −2.13 | W | COMT | 1312 | NM_000754 | M-009520-00 |
| PL-50047 | L05 | X | −2.66 | −1.83 | W | COX8A | 1351 | NM_004074 | M-011819-00 |
| PL-50058 | C06 | X | −1.80 | −2.20 | W | CRBN | 51185 | NM_016302 | M-021086-00 |
| PL-50004 | O11 | X | −3.31 | −1.98 | W | CRHR2 | 1395 | NM_001883 | M-005470-01 |
| PL-50018 | I12 | X | −2.54 | −2.67 | W | CRSP2 | 9282 | NM_004229 | M-011928-00 |
| PL-50021 | K20 | X | −2.15 | −2.49 | W | CRSP3 | 9439 | NM_004830 | M-013220-00 |
| PL-50018 | I10 | X | −2.43 | −2.89 | W | CRSP6 | 9440 | NM_004268 | M-006312-01 |
| PL-50018 | B18 | X | −6.60 | −1.80 | W | CRYBA2 | 1412 | NM_005209 | M-012024-00 |
| PL-50021 | K12 | X | −2.72 | −1.44 | W | CRYBB1 | 1414 | NM_001887 | M-011629-00 |
| PL-50018 | B16 | X | −2.65 | −2.48 | W | CRYBB3 | 1417 | NM_004076 | M-006480-01 |
| PL-50018 | B12 | X | −2.55 | −3.76 | W | CRYGC | 1420 | NM_020989 | M-013142-00 |
| PL-50010 | J07 | X | −2.43 | −2.25 | W | CSAD | 51380 | NM_015989 | M-008314-00 |
| PL-50021 | I10 | X | 2.08 | 2.02 | W | CST7 | 8530 | NM_003650 | M-017236-00 |
| PL-50051 | H11 | X | −2.42 | −2.76 | W | CXORF12 | 8269 | NM_003492 | M-011428-00 |
| PL-50047 | P10 | X | −3.46 | −2.51 | W | CYLC1 | 1538 | XM_088636 | M-024769-00 |
| PL-50012 | N08 | X | −3.15 | −2.69 | W | CYP1A1 | 1543 | NM_000499 | M-004790-01 |
| PL-50047 | N12 | X | −2.58 | −3.29 | W | CYP3A5 | 1577 | NM_000777 | M-009684-00 |
| PL-50014 | G17 | X | −2.77 | −2.17 | W | D2S448 | 7837.00 | XM_056455 | M-022772-00 |
| PL-50021 | E20 | X | −2.67 | −1.85 | W | DAAM1 | 23002 | NM_014992 | M-012925-00 |
| PL-50017 | O15 | X | −2.15 | −2.16 | W | DBI | 1622 | NM_020548 | M-006488-00 |
| PL-50063 | B23 | X | −2.01 | −1.97 | W | DC2 | 58505 | NM_021227 | M-027193-00 |
| PL-50053 | G13 | X | −3.37 | −2.98 | W | DDX46 | 9879 | NM_014829 | M-021234-00 |
| PL-50047 | H12 | X | −3.31 | −1.94 | W | DHPS | 1725 | NM_001930 | M-006670-00 |
| PL-50070 | K14 | X | −2.81 | −2.09 | W | DKFZP434B1231 | 91156 | NM_178275 | M-018250-00 |
| PL-50067 | M17 | X | −2.22 | −2.32 | W | DKFZP434I2117 | 83723 | NM_031478 | M-003996-00 |
| PL-50078 | A08 | X | −3.07 | −2.03 | W | DKFZP686P0288 | 285190 | NM_182588 | M-018854-00 |
| PL-50067 | P23 | X | −2.28 | −3.62 | W | DKFZP761B1514 | 84248 | NM_032288 | M-018604-00 |
| PL-50047 | H04 | X | −0.84 | −3.07 | W | DLAT | 1737 | NM_001931 | M-008490-00 |
| PL-50012 | J02 | X | −2.78 | −1.78 | W | DNM1L | 10059 | NM_005690 | M-012092-01 |
| PL-50015 | D06 | X | −2.37 | −2.28 | W | DUSP16 | 80824.00 | NM_030640 | M-007890-00 |
| PL-50015 | D04 | X | −3.96 | −2.15 | W | DUSP18 | 150290.00 | NM_152511 | M-007891-00 |
| PL-50008 | J19 | X | −2.31 | −2.93 | W | DUX1 | 26584 | NM_012146 | M-019955-00 |
| PL-50057 | C13 | X | −3.26 | −2.30 | W | DUX5 | 26581 | NM_012149 | M-019904-00 |
| PL-50014 | G08 | X | −2.02 | −2.27 | W | DVL3 | 1857.00 | NM_004423 | M-004070-00 |
| PL-50062 | K04 | X | −1.79 | −2.87 | W | E(Y)2 | 56943 | NM_020189 | M-018808-00 |
| PL-50058 | J09 | X | −2.00 | −2.33 | W | E2IG2 | 51287 | NM_016565 | M-021148-00 |
| PL-50068 | O21 | X | −2.47 | −3.28 | W | EBPL | 84650 | NM_032565 | M-014920-00 |
| PL-50063 | O20 | X | −2.25 | −1.71 | W | EPB41L5 | 57669 | NM_020909 | M-010729-00 |
| PL-50017 | H14 | X | −2.63 | −3.25 | W | EREG | 2069 | NM_001432 | M-011268-00 |
| PL-50001 | P14 | X | −0.93 | −3.04 | W | ERK8 | 225689 | NM_139021 | M-004807-01 |
| PL-50021 | F20 | X | −2.24 | −3.12 | W | ESRRBL1 | 55081 | NM_018010 | M-015367-00 |
| PL-50064 | D10 | X | −3.04 | −2.71 | W | ET | 79157 | NM_024311 | M-014329-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50089 | H08 | X | −2.63 | −2.63 | W | EVI5 | 7813 | NM_005665 | M-032510-00 |
| PL-50067 | E18 | X | −2.76 | −2.42 | W | FAM14A | 83982 | NM_032036 | M-014773-00 |
| PL-50052 | F08 | X | −3.64 | −2.59 | W | FAM38A | 9780 | NM_014745 | M-020870-00 |
| PL-50015 | K07 | X | −2.52 | −2.30 | W | FBXL20 | 84961.00 | NM_032875 | M-015029-00 |
| PL-50015 | G02 | X | −2.70 | −3.21 | W | FBXL3P | 26223.00 | NM_012159 | M-012423-00 |
| PL-50015 | E04 | X | −2.37 | −1.84 | W | FBXO22 | 26263.00 | NM_012170 | M-010812-01 |
| PL-50055 | L14 | X | −3.13 | −0.76 | W | FBXO46 | 23403 | XM_371179 | M-023753-00 |
| PL-50021 | B02 | X | −4.26 | −2.10 | W | FCGR3A | 2214 | NM_000569 | M-016308-00 |
| PL-50017 | D20 | X | −2.38 | −3.61 | W | FGF14 | 2259 | NM_004115 | M-011860-00 |
| PL-50017 | B16 | X | −3.45 | −2.97 | W | FGF7 | 2252 | NM_002009 | M-011659-00 |
| PL-50072 | H13 | X | −2.47 | −3.34 | W | FKBP1C | 135521 | XM_059776 | M-028635-00 |
| PL-50060 | C12 | X | −1.71 | −2.56 | W | FLJ10159 | 55084 | NM_018013 | M-021094-00 |
| PL-50060 | D19 | X | −3.09 | −1.32 | W | FLJ10352 | 55125 | NM_018069 | M-032250-00 |
| PL-50059 | J05 | X | −2.99 | −1.80 | W | FLJ10613 | 54552 | NM_019067 | M-015743-00 |
| PL-50001 | N08 | X | −2.62 | −2.33 | W | FLJ10842 | 55750 | NM_018238 | M-007256-00 |
| PL-50060 | B14 | X | −1.94 | −2.52 | W | FLJ11126 | 55308 | NM_018332 | M-015868-00 |
| PL-50061 | A09 | X | −3.15 | −1.98 | W | FLJ11193 | 55322 | NM_018356 | M-021223-00 |
| PL-50064 | F11 | X | −2.54 | −2.12 | W | FLJ12517 | 65094 | NM_023007 | M-014238-00 |
| PL-50059 | C04 | X | −2.27 | −2.61 | W | FLJ20152 | 54463 | NM_019000 | M-016936-00 |
| PL-50059 | P23 | X | −2.32 | −4.10 | W | FLJ20485 | 54517 | NM_019042 | M-015341-00 |
| PL-50060 | M09 | X | −2.74 | −2.48 | W | FLJ20509 | 54956 | NM_017851 | M-020837-01 |
| PL-50060 | M21 | X | −2.62 | −1.68 | W | FLJ20519 | 54964 | NM_017860 | M-016312-00 |
| PL-50066 | G23 | X | −2.48 | −2.37 | W | FLJ20972 | 80098 | NM_025030 | M-014556-00 |
| PL-50066 | O12 | X | −2.65 | −3.61 | W | FLJ22688 | 80199 | NM_025129 | M-016342-00 |
| PL-50065 | P09 | X | −1.79 | −2.78 | W | FLJ23554 | 79864 | NM_024806 | |
| PL-50074 | C18 | X | −2.54 | −2.85 | W | FLJ25286 | 153443 | NM_152546 | M-015445-00 |
| PL-50072 | P23 | X | −2.72 | −2.62 | W | FLJ32356 | 144717 | NM_144671 | M-015976-00 |
| PL-50073 | N18 | X | −1.95 | −2.38 | W | FLJ32421 | 148362 | NM_144695 | |
| PL-50073 | L02 | X | −2.70 | −2.68 | W | FLJ32569 | 148811 | NM_152491 | |
| PL-50076 | B12 | X | −2.68 | −2.73 | W | FLJ32682 | 220081 | NM_182542 | M-018973-00 |
| PL-50073 | B05 | X | −2.02 | −1.72 | W | FLJ32734 | 146849 | NM_144681 | |
| PL-50074 | C09 | X | −2.94 | −2.73 | W | FLJ33814 | 150275 | NM_173510 | M-018556-00 |
| PL-50078 | A05 | X | −2.34 | −2.88 | W | FLJ34690 | 284034 | NM_182567 | M-018978-00 |
| PL-50075 | A23 | X | −1.99 | −2.64 | W | FLJ35757 | 162333 | NM_152598 | M-007150-00 |
| PL-50075 | K07 | X | −2.32 | −2.31 | W | FLJ35838 | 163479 | NM_173532 | M-018510-00 |
| PL-50074 | F04 | X | −3.13 | −1.97 | W | FLJ35843 | 160762 | NM_152591 | M-016858-00 |
| PL-50071 | D02 | X | −2.23 | −3.04 | W | FLJ35961 | 127294 | NM_152372 | M-017014-00 |
| PL-50078 | C15 | X | −1.88 | −3.07 | W | FLJ36878 | 284114 | NM_178518 | M-018245-00 |
| PL-50078 | C14 | X | −1.82 | −4.10 | W | FLJ38379 | 285097 | NM_178530 | M-017660-00 |
| PL-50072 | A13 | X | −2.47 | −1.83 | W | FLJ38984 | 127703 | NM_152374 | M-016893-00 |
| PL-50071 | H12 | X | −2.59 | −2.77 | W | FLJ39117 | 126638 | XM_371312 | M-027449-00 |
| PL-50072 | A04 | X | −2.25 | −2.87 | W | FLJ39155 | 133584 | NM_152403 | M-019235-00 |
| PL-50072 | C21 | X | −2.26 | −2.24 | W | FLJ40160 | 128209 | NM_173484 | M-018431-00 |
| PL-50081 | A23 | X | −2.01 | −1.94 | W | FLJ42953 | 400892 | NM_207474 | M-032163-00 |
| PL-50080 | F18 | X | −3.91 | −2.00 | W | FLJ42957 | 400077 | NM_207436 | M-032113-00 |
| PL-50080 | P17 | X | −1.88 | −2.66 | W | FLJ43965 | 389206 | NM_207406 | M-032079-00 |
| PL-50080 | H12 | X | −2.85 | −2.57 | W | FLJ45803 | 399948 | NM_207429 | M-032104-00 |
| PL-50080 | O14 | X | −2.09 | −2.75 | W | FLJ46354 | 374977 | NM_198547 | M-027321-00 |
| PL-50080 | P11 | X | −1.43 | −2.78 | W | FLJ46481 | 389197 | NM_207405 | M-032082-00 |
| PL-50008 | P08 | X | −2.71 | −3.35 | W | FOXB1 | 27023 | NM_012182 | M-008906-00 |
| PL-50008 | L04 | X | −4.33 | −1.87 | W | FOXP2 | 93986 | NM_014491 | M-010359-01 |
| PL-50070 | I11 | X | −2.12 | −2.27 | W | FOXP4 | 116113 | NM_138457 | M-008255-00 |
| PL-50048 | G11 | X | −2.21 | −2.52 | W | FSHPRH1 | 2491 | NM_006733 | M-005268-00 |
| PL-50006 | J23 | X | −2.04 | −2.38 | W | FTH1 | 2495 | NM_002032 | M-019634-01 |
| PL-50057 | A13 | X | −2.11 | −2.61 | W | FXC1 | 26515 | NM_012192 | M-018242-00 |
| PL-50001 | H18 | X | −3.04 | −1.84 | W | FYN | 2534 | NM_002037 | M-003140-03 |
| PL-50018 | M05 | X | −2.18 | −1.95 | W | GABRB1 | 2560 | NM_000812 | M-006168-00 |
| PL-50011 | A05 | X | −2.25 | −3.32 | W | GART | 2618 | NM_000819 | M-008594-00 |
| PL-50013 | A23 | X | −2.25 | −2.53 | W | GBP1 | 2633 | NM_002053 | M-005153-01 |
| PL-50017 | M08 | X | −3.40 | −1.34 | W | GDNF | 2668 | NM_000514 | M-011040-00 |
| PL-50019 | J09 | X | −3.26 | −2.11 | W | GJB3 | 2707 | NM_024009 | M-019948-00 |
| PL-50062 | I16 | X | −1.91 | −2.17 | W | GL004 | 56947 | NM_020194 | M-018261-00 |
| PL-50001 | F18 | X | −2.66 | −1.52 | W | GMFG | 9535 | NM_004877 | M-019878-01 |
| PL-50004 | A18 | X | −2.43 | −2.90 | W | GNAQ | 2776 | NM_002072 | M-008562-00 |
| PL-50061 | N08 | X | −2.11 | −2.21 | W | GOLGA6 | 55889 | NM_018652 | M-013307-00 |
| PL-50064 | O08 | X | −3.58 | −2.42 | W | GORASP1 | 64689 | NM_031899 | M-013510-00 |
| PL-50048 | O17 | X | −2.13 | −2.49 | W | GOT1 | 2805 | NM_002079 | M-011673-00 |
| PL-50057 | K20 | X | −2.15 | −1.58 | W | GPKOW | 27238 | NM_015698 | M-015129-00 |
| PL-50048 | O16 | X | −2.42 | −1.85 | W | GPM6B | 2824 | NM_005278 | M-018825-00 |
| PL-50004 | D11 | X | −2.86 | −2.53 | W | GPR101 | 83550 | NM_054021 | M-005526-01 |
| PL-50015 | N19 | X | −3.90 | −2.32 | W | GPR114 | 221188.00 | NM_153837 | M-005535-01 |
| PL-50004 | P05 | X | −2.10 | −1.83 | W | GPR50 | 9248 | NM_004224 | M-005578-00 |
| PL-50004 | P15 | X | −3.01 | −2.29 | W | GPR56 | 9289 | NM_005682 | M-004552-00 |
| PL-50004 | P04 | X | −2.32 | −2.27 | W | GPR73L1 | 128674 | NM_144733 | M-005594-01 |
| PL-50016 | I16 | X | −2.60 | −1.70 | W | GRB7 | 2886.00 | NM_005310 | M-012701-00 |
| PL-50048 | O04 | X | −2.74 | −1.34 | W | GRID1 | 2894 | XM_043613 | M-007917-00 |
| PL-50016 | I06 | X | −2.41 | −2.33 | W | GRID2 | 2895.00 | NM_001510 | M-006188-00 |
| PL-50004 | J16 | X | −2.36 | −1.70 | W | GRK7 | 131890 | NM_139209 | M-004628-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50052 | F07 | X | −2.09 | −1.79 | W | GTPBP1 | 9567 | NM_004286 | M-017321-00 |
| PL-50006 | P09 | X | −2.87 | −2.40 | W | H2AFZ | 3015 | NM_002106 | M-011683-01 |
| PL-50052 | F05 | X | −2.54 | −2.09 | W | H6PD | 9563 | NM_004285 | M-004692-00 |
| PL-50022 | G10 | X | −2.20 | −2.29 | W | HBE1 | 3046 | NM_005330 | M-012069-00 |
| PL-50053 | J16 | X | −2.96 | −1.83 | W | HBXIP | 10542 | NM_006402 | M-012269-00 |
| PL-50008 | F14 | X | −2.40 | −2.43 | W | HCFC1 | 3054 | NM_005334 | M-019953-00 |
| PL-50020 | G12 | X | −2.47 | −2.33 | W | HD | 3064 | NM_002111 | M-003737-00 |
| PL-50013 | C17 | X | −2.51 | −2.37 | W | HDAC3 | 8841 | NM_003883 | M-003496-00 |
| PL-50061 | G13 | X | −2.86 | −3.19 | W | HEMGN | 55363 | NM_018437 | M-021355-00 |
| PL-50073 | B02 | X | −2.57 | −1.95 | W | HERV-FRD | 405754 | NM_207582 | |
| PL-50048 | K06 | X | −2.94 | −3.13 | W | HIST1H1B | 3009 | NM_005322 | M-012049-00 |
| PL-50081 | O18 | X | −3.97 | −1.63 | W | HIST1H2AL | 8332 | NM_003511 | M-011434-00 |
| PL-50051 | L09 | X | −4.54 | −1.37 | W | HIST1H3B | 8358 | NM_003537 | M-006475-00 |
| PL-50051 | L11 | X | −3.15 | −2.10 | W | HIST1H4A | 8359 | NM_003538 | M-011456-00 |
| PL-50008 | B12 | X | −2.39 | −2.71 | W | HOXA7 | 3204 | NM_006896 | M-017573-00 |
| PL-50048 | A18 | X | −0.65 | −2.78 | W | HOXB8 | 3218 | NM_024016 | M-017527-00 |
| PL-50048 | A14 | X | −1.59 | −2.94 | W | HOXC8 | 3224 | NM_022658 | M-012995-00 |
| PL-50060 | O23 | X | −3.65 | −1.92 | W | HRASLS2 | 54979 | NM_017878 | M-020862-00 |
| PL-50056 | O23 | X | −2.46 | −2.58 | W | HS747E2A | 25770 | NM_015370 | M-020284-00 |
| PL-50062 | P14 | X | −2.63 | −2.55 | W | HSCARG | 57407 | NM_020677 | M-020759-00 |
| PL-50070 | D04 | X | −1.86 | −2.59 | W | HSPB9 | 94086 | NM_033194 | M-009005-00 |
| PL-50004 | IF18 | X | −3.01 | −2.53 | W | HTR1A | 3350 | NM_000524 | M-005633-00 |
| PL-50001 | B04 | X | −5.47 | −2.28 | W | HUNK | 30811 | NM_014586 | M-004214-01 |
| PL-50051 | H06 | X | −0.80 | −3.81 | W | HYAL2 | 8692 | NM_003773 | M-013689-00 |
| PL-50048 | D21 | X | −1.83 | −2.41 | W | IDH3G | 3421 | NM_004135 | M-009361-00 |
| PL-50064 | A05 | X | −2.30 | −1.52 | W | IFRG15 | 64163 | NM_022347 | M-014044-00 |
| PL-50070 | L06 | X | −1.41 | −2.46 | W | IGSF8 | 93185 | NM_052868 | M-015148-00 |
| PL-50017 | C20 | X | −2.89 | −2.23 | W | IL10RB | 3588 | NM_000628 | M-007926-01 |
| PL-50017 | C06 | X | −2.44 | −2.31 | W | IL15RA | 3601 | NM_002189 | M-007935-00 |
| PL-50017 | C02 | X | −2.24 | −3.02 | W | IL17 | 3605 | NM_002190 | M-007937-00 |
| PL-50069 | F15 | X | −2.57 | −1.76 | W | IL17F | 112744 | NM_052872 | M-007942-00 |
| PL-50017 | B13 | X | −2.58 | −1.46 | W | IL1F9 | 56300 | NM_019618 | M-007959-00 |
| PL-50017 | B23 | X | −1.30 | −2.70 | W | IL1RL1 | 9173 | NM_003856 | M-007963-00 |
| PL-50017 | D11 | X | −3.96 | −2.20 | W | IL22 | 50616 | NM_020525 | M-007972-00 |
| PL-50004 | D08 | X | −2.78 | −1.96 | W | IL8RB | 3579 | NM_001557 | M-005647-00 |
| PL-50022 | F07 | X | −2.43 | −2.63 | W | INSIG1 | 3638 | NM_005542 | M-017880-01 |
| PL-50006 | H12 | X | −3.18 | −2.23 | W | INSM1 | 3642 | NM_002196 | M-006535-00 |
| PL-50061 | O18 | X | −1.70 | −2.66 | W | INTERSEX | 55588 | XM_290829 | M-023854-00 |
| PL-50009 | G21 | X | −2.37 | −3.10 | W | IRF7 | 3665 | NM_001572 | M-011810-01 |
| PL-50065 | A23 | X | −3.60 | −1.48 | W | IRX1 | 79192 | XM_380171 | |
| PL-50022 | H13 | X | −2.41 | −3.95 | W | ITSN2 | 50618 | NM_006277 | M-009841-00 |
| PL-50057 | B11 | X | −2.63 | −3.04 | W | JM1 | 28952 | NM_014008 | M-020554-00 |
| PL-50069 | M05 | X | −2.57 | −2.29 | W | JM11 | 90060 | NM_033626 | M-015130-00 |
| PL-50068 | P18 | X | −2.41 | −2.32 | W | JUB | 84962 | NM_198086 | M-021473-00 |
| PL-50014 | H15 | X | −2.07 | −1.96 | W | KALRN | 8997.00 | NM_003947 | M-010019-00 |
| PL-50061 | B06 | X | −2.43 | −2.45 | W | KBTBD7 | 84078 | NM_032138 | M-015708-00 |
| PL-50020 | I17 | X | −0.96 | −3.17 | W | KCNC4 | 3749 | NM_004978 | M-006223-01 |
| PL-50016 | A12 | X | −2.71 | −2.63 | W | KCNH4 | 23415.00 | NM_012285 | M-006234-01 |
| PL-50004 | B20 | X | −2.62 | −1.67 | W | KCNJ3 | 3760 | NM_002239 | M-006248-00 |
| PL-50064 | J17 | X | −2.90 | −2.72 | W | KCTD14 | 65987 | NM_023930 | M-014252-00 |
| PL-50002 | E19 | X | −2.70 | −2.08 | W | KDR | 3791 | NM_002253 | M-003148-01 |
| PL-50052 | B04 | X | −2.94 | −2.64 | W | KEAP1 | 9817 | NM_012289 | M-012453-00 |
| PL-50013 | E19 | X | −2.38 | −2.39 | W | KIAA0217 | 23185 | XM_040265 | M-026388-00 |
| PL-50052 | B08 | X | −2.95 | −1.93 | W | KIAA0542 | 9814 | XM_038520 | M-024567-00 |
| PL-50055 | A07 | X | −2.32 | −2.25 | W | KIAA0980 | 22981 | NM_025176 | M-018162-00 |
| PL-50055 | N10 | X | −2.87 | −1.91 | W | KIAA1068 | 23386 | NM_015332 | M-014018-00 |
| PL-50062 | L04 | X | −2.17 | −1.97 | W | KIAA1189 | 57471 | XM_371576 | M-027986-00 |
| PL-50062 | L02 | X | −3.14 | −2.74 | W | KIAA1194 | 57472 | NM_015455 | M-019101-00 |
| PL-50002 | G09 | X | −3.22 | −2.00 | W | KIAA1361 | 57551 | XM_290796 | M-004846-01 |
| PL-50063 | O18 | X | −2.09 | −2.19 | W | KIAA1549 | 57670 | XM_371956 | M-025462-00 |
| PL-50063 | O04 | X | −2.92 | −1.90 | W | KIAA1573 | 57685 | NM_020925 | M-014178-00 |
| PL-50075 | D05 | X | −1.73 | −2.14 | W | KIAA1987 | 170951 | XM_375298 | M-030681-00 |
| PL-50015 | P14 | X | −2.15 | −3.76 | W | KIF11 | 3832.00 | NM_004523 | M-003317-01 |
| PL-50048 | J21 | X | −3.22 | −2.12 | W | KIR2DL4 | 3805 | NM_002255 | M-018983-00 |
| PL-50069 | A02 | X | −2.13 | −2.22 | W | KRTAP9-4 | 85280 | NM_033191 | M-013676-00 |
| PL-50076 | L06 | X | −2.86 | −2.22 | W | LACE1 | 246269 | NM_145315 | M-008222-00 |
| PL-50013 | G09 | X | −3.29 | −2.26 | W | LAP3 | 51056 | NM_015907 | M-005923-03 |
| PL-50048 | P09 | X | −3.03 | −1.97 | W | LASP1 | 3927 | NM_006148 | M-010519-00 |
| PL-50089 | K04 | X | −1.63 | −2.44 | W | LCN10 | 414332 | NM_001001712 | M-032327-00 |
| PL-50064 | A17 | X | −2.69 | −1.83 | W | LEPRE1 | 64175 | NM_022356 | M-004271-00 |
| PL-50060 | P20 | X | −0.80 | −3.39 | W | LGI2 | 55203 | NM_018176 | M-017097-00 |
| PL-50002 | I23 | X | −2.41 | −2.59 | W | LIM | 10611 | NM_006457 | M-006930-00 |
| PL-50015 | O09 | X | −2.25 | −2.78 | W | LMO7 | 4008.00 | NM_005358 | M-019252-00 |
| PL-50002 | G21 | X | −1.85 | −2.25 | W | LMTK3 | 114783 | XM_055866 | M-005338-01 |
| PL-50076 | N21 | X | −2.84 | −1.85 | W | LNX2 | 222484 | NM_153371 | M-007164-00 |
| PL-50069 | P15 | X | −2.49 | −2.56 | W | LOC113828 | 113828 | NM_138435 | M-015492-00 |
| PL-50070 | I05 | X | −2.29 | −3.17 | W | LOC116068 | 116068 | XM_371760 | M-024521-00 |
| PL-50071 | O16 | X | −2.62 | −2.28 | W | LOC120376 | 120376 | XM_071712 | M-026516-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50071 | F07 | X | −1.59 | −3.04 | W | LOC124402 | 124402 | NM_145253 | M-015987-00 |
| PL-50071 | N23 | X | −2.21 | −2.15 | W | LOC125893 | 125893 | XM_064856 | M-023813-00 |
| PL-50071 | J04 | X | −2.12 | −2.12 | W | LOC126520 | 126520 | XM_059051 | M-023896-00 |
| PL-50072 | B11 | X | −2.71 | −2.54 | W | LOC134145 | 134145 | NM_199133 | M-024274-00 |
| PL-50073 | O11 | X | −2.34 | −2.31 | W | LOC144097 | 144097 | NM_138471 | |
| PL-50081 | J11 | X | −1.54 | −2.58 | W | LOC145414 | 0 | XM_085138 | M-021965-00 |
| PL-50073 | C20 | X | −1.77 | −2.26 | W | LOC146443 | 146443 | XM_378558 | |
| PL-50073 | A14 | X | −2.89 | −2.56 | W | LOC146713 | 146713 | XM_378712 | |
| PL-50081 | A20 | X | −2.17 | −2.43 | W | LOC149643 | 0 | XM_086616 | M-021537-00 |
| PL-50074 | O11 | X | −2.57 | −2.20 | W | LOC151484 | 151484 | XM_379159 | M-028022-00 |
| PL-50082 | F23 | X | −2.31 | −1.98 | W | LOC152877 | 0 | XM_094066 | M-024144-00 |
| PL-50074 | E06 | X | −2.75 | −2.53 | W | LOC153328 | 153328 | NM_145282 | M-007347-00 |
| PL-50074 | D11 | X | −2.07 | −1.79 | W | LOC154222 | 154222 | XM_379456 | M-028649-00 |
| PL-50083 | K09 | X | −2.24 | −2.33 | W | LOC154907 | 0 | XM_088072 | M-025440-00 |
| PL-50081 | C16 | X | −2.08 | −2.30 | W | LOC155036 | 155036 | XM_376722 | M-028875-00 |
| PL-50083 | A21 | X | −1.87 | −2.14 | W | LOC158796 | 0 | XM_088677 | M-025004-00 |
| PL-50074 | J08 | X | −2.30 | −2.90 | W | LOC159090 | 159090 | NM_145284 | M-016085-00 |
| PL-50075 | C11 | X | −2.52 | −2.87 | W | LOC162427 | 162427 | NM_178126 | M-018456-00 |
| PL-50075 | K13 | X | −1.93 | −4.79 | W | LOC163590 | 163590 | NM_145034 | M-016470-00 |
| PL-50082 | A17 | X | −2.23 | −1.70 | W | LOC200493 | 0 | XM_115715 | M-022826-00 |
| PL-50076 | E15 | X | −2.05 | −2.86 | W | LOC202051 | 202051 | XM_114430 | M-024410-00 |
| PL-50076 | M23 | X | −2.49 | −2.58 | W | LOC205251 | 205251 | NM_174925 | M-017831-00 |
| PL-50081 | N05 | X | −3.34 | −1.92 | W | LOC254897 | 0 | XM_170950 | M-022066-00 |
| PL-50077 | F13 | X | −2.72 | −1.86 | W | LOC283152 | 283152 | XM_378314 | |
| PL-50077 | D04 | X | −2.21 | −4.21 | W | LOC283989 | 283989 | NM_207346 | |
| PL-50078 | A11 | X | −2.08 | −3.17 | W | LOC284058 | 284058 | NM_015443 | M-031748-00 |
| PL-50078 | K13 | X | −2.09 | −2.15 | W | LOC284361 | 284361 | NM_175063 | M-018434-00 |
| PL-50078 | M13 | X | −1.80 | −2.88 | W | LOC284390 | 284390 | XM_371138 | M-031229-00 |
| PL-50078 | M04 | X | −2.89 | −1.65 | W | LOC284661 | 284661 | XM_378832 | M-027567-00 |
| PL-50078 | K08 | X | −2.34 | −1.86 | W | LOC284739 | 284739 | NM_207349 | M-031294-00 |
| PL-50078 | I02 | X | −2.15 | −2.35 | W | LOC284825 | 284825 | XM_375935 | M-031369-00 |
| PL-50078 | A12 | X | −1.94 | −3.54 | W | LOC285194 | 285194 | XM_379207 | M-028149-00 |
| PL-50082 | I14 | X | −3.00 | −2.75 | W | LOC285248 | 0 | XM_211816 | M-023664-00 |
| PL-50083 | G10 | X | −2.14 | −2.08 | W | LOC338734 | 0 | XM_290547 | M-026505-00 |
| PL-50083 | F05 | X | −2.20 | −2.58 | W | LOC338756 | 0 | XM_291989 | M-026922-00 |
| PL-50079 | B09 | X | −2.64 | −1.81 | W | LOC340109 | 340109 | XM_379322 | M-028502-00 |
| PL-50083 | I14 | X | −2.28 | −1.93 | W | LOC340843 | 0 | XM_291726 | M-026400-00 |
| PL-50083 | J05 | X | −2.17 | −2.03 | W | LOC341356 | 0 | XM_292023 | M-027076-00 |
| PL-50082 | P12 | X | −5.82 | −2.32 | W | LOC345651 | 0 | XM_293924 | M-024480-00 |
| PL-50080 | M14 | X | −4.93 | −2.81 | W | LOC375133 | 375133 | NM_199345 | M-032119-00 |
| PL-50080 | C02 | X | −3.73 | −1.73 | W | LOC386597 | 386597 | XM_379073 | M-027974-00 |
| PL-50086 | B14 | X | −3.37 | −2.68 | W | LOC387784 | 0 | XM_373506 | M-029865-00 |
| PL-50086 | H08 | X | −1.81 | −2.55 | W | LOC387810 | 0 | XM_373513 | M-029805-00 |
| PL-50087 | K18 | X | −1.48 | −3.48 | W | LOC387825 | 0 | XM_370668 | |
| PL-50087 | O04 | X | −2.59 | −2.12 | W | LOC387845 | 0 | XM_370684 | |
| PL-50087 | G02 | X | −4.14 | −2.44 | W | LOC387914 | 0 | XM_370718 | |
| PL-50088 | C11 | X | −2.83 | −2.18 | W | LOC388298 | 0 | XM_370992 | |
| PL-50088 | K21 | X | −2.71 | −2.99 | W | LOC388432 | 0 | XM_371086 | |
| PL-50081 | C12 | X | −4.87 | −2.48 | W | LOC388585 | 0 | XM_371215 | M-007769-00 |
| PL-50083 | P04 | X | −2.40 | −3.20 | W | LOC388697 | 0 | XM_373868 | M-027450-00 |
| PL-50084 | G20 | X | −3.63 | −2.37 | W | LOC389000 | 0 | XM_371534 | M-027916-00 |
| PL-50084 | A14 | X | −2.42 | −1.82 | W | LOC389067 | 0 | XM_374021 | M-028005-00 |
| PL-50084 | A10 | X | −2.39 | −2.59 | W | LOC389070 | 0 | XM_374022 | M-028009-00 |
| PL-50084 | H11 | X | −2.84 | −2.27 | W | LOC389102 | 0 | XM_371623 | M-028089-00 |
| PL-50084 | P13 | X | −2.00 | −2.17 | W | LOC389153 | 0 | XM_374053 | M-028171-00 |
| PL-50085 | A15 | X | −1.85 | −2.10 | W | LOC389273 | 0 | XM_374115 | M-028392-00 |
| PL-50085 | C02 | X | −2.12 | −3.30 | W | LOC389370 | 0 | XM_374162 | M-028681-00 |
| PL-50085 | B05 | X | −2.03 | −1.53 | W | LOC389386 | 0 | XM_371818 | M-028707-00 |
| PL-50085 | K08 | X | −3.31 | −2.67 | W | LOC389416 | 0 | XM_371837 | M-028580-00 |
| PL-50085 | P10 | X | −1.46 | −2.24 | W | LOC389541 | 0 | XM_371939 | M-028918-00 |
| PL-50086 | C08 | X | −2.54 | −2.06 | W | LOC389727 | 0 | XM_372092 | M-029462-00 |
| PL-50086 | B05 | X | −2.30 | −2.18 | W | LOC389753 | 0 | XM_372112 | M-029491-00 |
| PL-50086 | H18 | X | −3.76 | −1.94 | W | LOC389950 | 0 | XM_372307 | M-029790-00 |
| PL-50087 | C02 | X | −5.64 | −2.10 | W | LOC390377 | 0 | XM_372486 | |
| PL-50083 | P09 | X | −1.83 | −3.25 | W | LOC391059 | 0 | XM_372784 | M-027419-00 |
| PL-50084 | G23 | X | −2.56 | −1.54 | W | LOC391209 | 0 | XM_372840 | M-027739-00 |
| PL-50085 | B20 | X | −3.51 | −1.79 | W | LOC392702 | 0 | XM_374730 | M-029081-00 |
| PL-50085 | B08 | X | −3.38 | −1.62 | W | LOC392726 | 0 | XM_374734 | M-029100-00 |
| PL-50086 | C17 | X | −1.42 | −3.60 | W | LOC392791 | 0 | XM_374752 | M-029140-00 |
| PL-50086 | L06 | X | −2.71 | −2.95 | W | LOC399786 | 0 | XM_378236 | M-029755-00 |
| PL-50087 | A09 | X | −2.48 | −2.14 | W | LOC399920 | 0 | XM_378300 | |
| PL-50087 | O14 | X | −3.77 | −2.10 | W | LOC400092 | 0 | XM_378398 | |
| PL-50088 | G13 | X | −2.71 | −2.21 | W | LOC400479 | 0 | XM_375282 | |
| PL-50088 | I19 | X | −2.45 | −2.29 | W | LOC400619 | 0 | XM_378703 | |
| PL-50083 | P15 | X | −1.94 | −3.99 | W | LOC400740 | 0 | XM_378840 | M-027426-00 |
| PL-50084 | B06 | X | −1.60 | −2.62 | W | LOC401169 | 0 | XM_379306 | M-028377-00 |
| PL-50085 | A17 | X | −2.43 | −1.78 | W | LOC401175 | 0 | XM_379317 | M-028393-00 |
| PL-50085 | E18 | X | −2.43 | −1.56 | W | LOC401286 | 0 | XM_376555 | M-028648-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50085 | J11 | X | −3.03 | −2.86 | W | LOC401314 | 0 | XM_376586 | M-028821-00 |
| PL-50085 | J13 | X | −2.58 | −2.50 | W | LOC401316 | 0 | XM_376587 | M-028825-00 |
| PL-50085 | J15 | X | −1.74 | −2.76 | W | LOC401317 | 0 | XM_379479 | M-028826-00 |
| PL-50085 | J19 | X | −2.77 | −1.28 | W | LOC401321 | 0 | XM_379483 | M-028830-00 |
| PL-50086 | A16 | X | −2.87 | −1.88 | W | LOC401518 | 0 | XM_379638 | M-029475-00 |
| PL-50086 | J05 | X | −2.03 | −3.09 | W | LOC401548 | 0 | XM_376902 | M-029584-00 |
| PL-50086 | J15 | X | −2.49 | −2.92 | W | LOC401552 | 0 | XM_379668 | M-029594-00 |
| PL-50084 | L20 | X | −3.16 | −2.65 | W | LOC402148 | 0 | XM_377818 | M-028220-00 |
| PL-50085 | J04 | X | −2.32 | −2.36 | W | LOC402477 | 0 | XM_379803 | M-029005-00 |
| PL-50085 | D18 | X | −3.23 | −2.03 | W | LOC402515 | 0 | XM_380112 | M-029067-00 |
| PL-50085 | D12 | X | −1.79 | −4.81 | W | LOC402521 | 0 | XM_379848 | M-029073-00 |
| PL-50085 | B14 | X | −1.49 | −2.07 | W | LOC402537 | 0 | XM_380120 | M-029089-00 |
| PL-50089 | O21 | X | −3.27 | −2.66 | W | LOC402556 | 0 | XM_379877 | M-031795-00 |
| PL-50090 | A07 | X | −2.47 | −1.86 | W | LOC402560 | 0 | XM_380127 | M-031802-00 |
| PL-50086 | A19 | X | −2.56 | −3.08 | W | LOC402586 | 0 | XM_380138 | M-029126-00 |
| PL-50086 | A21 | X | −2.25 | −2.69 | W | LOC402587 | 0 | XM_380139 | M-029127-00 |
| PL-50086 | E21 | X | −1.65 | −3.01 | W | LOC402625 | 0 | XM_379975 | M-029163-00 |
| PL-50085 | F04 | X | −2.78 | −2.23 | W | LOC402641 | 0 | XM_379995 | M-029057-00 |
| PL-50081 | M17 | X | −3.94 | −1.80 | W | LOC404785 | 404785 | NM_207513 | M-032197-00 |
| PL-50058 | M23 | X | −3.15 | −0.63 | W | LOC51054 | 51054 | NM_015899 | M-020941-00 |
| PL-50057 | A16 | X | −2.13 | −1.90 | W | LOC51066 | 51066 | NM_015931 | M-020960-00 |
| PL-50058 | P07 | X | −2.64 | −3.28 | W | LOC51333 | 51333 | NM_016643 | M-006990-00 |
| PL-50059 | K05 | X | −2.62 | −2.50 | W | LOC51693 | 51693 | NM_016209 | M-021254-00 |
| PL-50070 | P05 | X | −2.95 | −2.76 | W | LOC92689 | 92689 | NM_138389 | M-015552-00 |
| PL-50069 | B23 | X | −2.30 | −2.80 | W | LOC96597 | 96597 | XM_378655 | M-023053-00 |
| PL-50019 | G07 | X | −3.09 | −2.93 | W | LOR | 4014 | NM_000427 | M-011077-00 |
| PL-50048 | P16 | X | −3.33 | −1.23 | W | LPO | 4025 | NM_006151 | M-023219-00 |
| PL-50022 | F18 | X | −2.00 | −2.26 | W | LTBP3 | 4054 | NM_021070 | M-014144-00 |
| PL-50016 | D07 | X | −2.46 | −3.34 | W | LU | 4059.00 | NM_005581 | M-010608-00 |
| PL-50017 | P04 | X | −1.87 | −2.52 | W | LY64 | 4064 | NM_005582 | M-020015-00 |
| PL-50007 | A15 | X | −2.28 | −2.10 | W | M96 | 22823 | NM_007358 | M-012796-00 |
| PL-50022 | D16 | X | −2.13 | −1.89 | W | MAD2L2 | 10459 | NM_006341 | M-003272-03 |
| PL-50059 | H23 | X | −2.81 | −2.75 | W | MAGEL2 | 54551 | NM_019066 | M-013374-00 |
| PL-50002 | M10 | X | −1.81 | −2.45 | W | MAPK13 | 5603 | NM_002754 | M-003591-02 |
| PL-50007 | C09 | X | −1.94 | −2.22 | W | MAPRE2 | 10982 | NM_014268 | M-012501-00 |
| PL-50049 | B16 | X | −2.58 | −2.31 | W | MASP1 | 5648 | NM_001879 | M-005937-00 |
| PL-50013 | I15 | X | −2.56 | −2.75 | W | MBTPS2 | 51360 | NM_015884 | M-005940-01 |
| PL-50005 | C07 | X | −2.90 | −2.51 | W | MC4R | 4160 | NM_005912 | M-005660-00 |
| PL-50016 | D17 | X | −2.17 | −2.39 | W | MCC | 4163.00 | NM_002387 | M-010523-01 |
| PL-50053 | N17 | X | −2.20 | −2.76 | W | MCRS1 | 10445 | NM_006337 | M-018557-00 |
| PL-50022 | B06 | X | −2.01 | −3.85 | W | MDGA1 | 266727 | NM_153487 | M-016082-00 |
| PL-50072 | M14 | X | −1.50 | −3.11 | W | MDH1B | 130752 | XM_059468 | M-023122-00 |
| PL-50009 | O11 | X | −2.86 | −2.47 | W | MEF2A | 4205 | NM_005587 | M-009362-00 |
| PL-50009 | O13 | X | −1.72 | −2.04 | W | MEF2B | 4207 | NM_005919 | M-009342-00 |
| PL-50068 | C08 | X | −2.94 | −2.77 | W | MGC13168 | 84821 | NM_032735 | M-014977-00 |
| PL-50068 | N14 | X | −3.07 | −2.59 | W | MGC14126 | 84984 | NM_032898 | M-015039-00 |
| PL-50070 | P23 | X | −2.16 | −1.23 | W | MGC16372 | 92749 | NM_145038 | M-016558-00 |
| PL-50079 | O04 | X | −4.23 | −2.82 | W | MGC16597 | 339230 | XM_375500 | M-030964-00 |
| PL-50070 | K02 | X | −2.66 | −1.94 | W | MGC17337 | 91283 | NM_080655 | M-015247-00 |
| PL-50081 | K21 | X | −2.40 | −2.20 | W | MGC21394 | 404203 | NM_205841 | M-031857-00 |
| PL-50074 | M16 | X | −2.23 | −2.69 | W | MGC23918 | 151903 | NM_144716 | M-015455-00 |
| PL-50072 | H08 | X | −2.51 | −3.29 | W | MGC23937 | 139596 | NM_145052 | M-016141-00 |
| PL-50005 | C13 | X | −2.91 | −2.23 | W | MGC26856 | 256710 | NM_152779 | M-016259-00 |
| PL-50074 | A12 | X | −1.93 | −2.28 | W | MGC39633 | 153733 | NM_152549 | M-015448-00 |
| PL-50072 | L02 | X | −2.46 | −2.58 | W | MGC41945 | 138724 | NM_203299 | M-031891-00 |
| PL-50067 | J04 | X | −3.26 | −2.46 | W | MGC4238 | 84292 | NM_032332 | M-014860-00 |
| PL-50073 | D11 | X | −2.10 | −2.65 | W | MGC45714 | 147007 | NM_152464 | |
| PL-50076 | D04 | X | −1.77 | −2.91 | W | MGC50559 | 254013 | NM_173802 | M-018388-00 |
| PL-50080 | M06 | X | −1.69 | −2.85 | W | MGC52000 | 375260 | NM_198943 | M-031853-00 |
| PL-50063 | A09 | X | −3.04 | −2.88 | W | MICAL3 | 57553 | XM_032997 | M-024432-00 |
| PL-50063 | D21 | X | −4.46 | −2.44 | W | MIG12 | 58526 | NM_021242 | M-015884-00 |
| PL-50068 | F16 | X | −3.31 | −2.68 | W | MIRAB13 | 85377 | NM_033386 | M-015102-00 |
| PL-50014 | I19 | X | −2.67 | −3.05 | W | MMP24 | 10893.00 | NM_006690 | M-005963-01 |
| PL-50059 | K17 | X | −1.71 | −2.84 | W | MO25 | 51719 | NM_016289 | M-015407-00 |
| PL-50054 | O16 | X | −2.84 | −2.14 | W | MORF4L1 | 10933 | NM_006791 | M-006379-00 |
| PL-50002 | E02 | X | −2.67 | −2.48 | W | MRC2 | 9902 | NM_006039 | M-020064-00 |
| PL-50059 | E21 | X | −1.55 | −2.18 | W | MRPL48 | 51642 | NM_016055 | M-017512-00 |
| PL-50059 | C10 | X | −1.16 | −3.52 | W | MRPS21 | 54460 | NM_018997 | M-013388-00 |
| PL-50007 | A04 | X | −3.23 | −1.63 | W | MT1A | 4489 | NM_005946 | M-012724-00 |
| PL-50071 | C02 | X | −2.23 | −1.74 | W | MTFMT | 123263 | NM_139242 | M-009633-00 |
| PL-50013 | O21 | X | −3.05 | −2.44 | W | MTMR9 | 66036 | NM_015458 | M-019244-01 |
| PL-50010 | O05 | X | −3.21 | −2.46 | W | MTRF1L | 54516 | NM_019041 | M-015386-00 |
| PL-50007 | K07 | X | −1.21 | −2.88 | W | MYH1 | 4619 | NM_005963 | M-013486-00 |
| PL-50057 | N09 | X | −2.73 | −1.89 | W | MYLIP | 29116 | NM_013262 | M-006976-00 |
| PL-50061 | J06 | X | −1.58 | −2.08 | W | MYO5C | 55930 | NM_018728 | M-031960-00 |
| PL-50051 | B13 | X | −3.48 | −1.64 | W | MYST3 | 7994 | NM_006766 | M-019849-00 |
| PL-50049 | E19 | X | −1.80 | −2.48 | W | NAP1L4 | 4676 | NM_005969 | M-012183-00 |
| PL-50051 | D06 | X | −0.40 | −2.39 | W | NAPG | 8774 | NM_003826 | M-011529-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50011 | C16 | X | −2.28 | −2.15 | W | NCB5OR | 51167 | NM_016230 | M-009347-00 |
| PL-50049 | G07 | X | −3.23 | −2.49 | W | NCF4 | 4689 | NM_000631 | M-011128-00 |
| PL-50023 | B18 | X | −2.59 | −1.76 | W | NCOA5 | 57727 | NM_020967 | M-013157-00 |
| PL-50023 | B10 | X | −2.36 | −4.21 | W | NDEL1 | 81565 | NM_030808 | M-018571-00 |
| PL-50049 | K07 | X | −2.82 | −2.10 | W | NDUFB9 | 4715 | NM_005005 | M-019899-00 |
| PL-50049 | K11 | X | −2.38 | −2.61 | W | NDUFC1 | 4717 | NM_002494 | M-019601-00 |
| PL-50013 | B04 | X | −2.95 | −2.65 | W | NDUFS1 | 4719 | NM_005006 | M-019069-00 |
| PL-50049 | K19 | X | −1.20 | −3.23 | W | NDUFS6 | 4726 | NM_004553 | M-019817-00 |
| PL-50054 | K17 | X | −2.42 | −1.80 | W | NET-5 | 10867 | NM_006675 | M-012293-00 |
| PL-50072 | O07 | X | −2.53 | −2.48 | W | NEU4 | 129807 | NM_080741 | M-013263-00 |
| PL-50009 | I06 | X | −3.19 | −2.49 | W | NFATC2 | 4773 | NM_012340 | M-003606-01 |
| PL-50009 | E20 | X | −2.89 | −1.53 | W | NFKB2 | 4791 | NM_002502 | M-003918-00 |
| PL-50052 | G09 | X | −2.89 | −2.46 | W | NFS1 | 9054 | NM_021100 | M-011564-00 |
| PL-50049 | M17 | X | −3.01 | −2.15 | W | NHLH2 | 4808 | NM_005599 | M-020020-00 |
| PL-50063 | I16 | X | −2.01 | −2.62 | W | NOPE | 57722 | NM_020962 | M-014170-00 |
| PL-50051 | L08 | X | −2.19 | −2.30 | W | NPFF | 8620 | NM_003717 | M-011502-00 |
| PL-50005 | G09 | X | −2.39 | −2.05 | W | NPY2R | 4887 | NM_000910 | M-005673-01 |
| PL-50005 | G11 | X | −1.74 | −2.32 | W | NPY5R | 4889 | NM_006174 | M-005674-00 |
| PL-50054 | N13 | X | −1.63 | −2.71 | W | NRM | 11270 | NM_007243 | M-012779-00 |
| PL-50007 | O12 | X | −2.70 | −3.03 | W | NUCB1 | 4924 | NM_006184 | M-015822-00 |
| PL-50062 | D13 | X | −1.82 | −2.48 | W | NUP107 | 57122 | NM_020401 | M-020440-00 |
| PL-50061 | D21 | X | −2.28 | −1.73 | W | NUP133 | 55746 | NM_018230 | M-013322-00 |
| PL-50061 | H02 | X | −2.48 | −3.27 | W | NXF2 | 56001 | NM_017809 | M-010445-00 |
| PL-50061 | H06 | X | −1.54 | −3.06 | W | NXF5 | 55998 | NM_032946 | M-013599-00 |
| PL-50019 | P20 | X | −4.00 | −2.02 | W | NXT1 | 29107 | NM_013248 | M-017194-00 |
| PL-50069 | A23 | X | −1.88 | −2.00 | W | NYD-SP28 | 85478 | NM_033124 | M-015072-00 |
| PL-50023 | G16 | X | −2.24 | −3.32 | W | OFD1 | 8481 | NM_003611 | M-009300-01 |
| PL-50005 | G23 | X | −1.96 | −2.04 | W | OPN3 | 23596 | NM_014322 | M-005681-01 |
| PL-50089 | P07 | X | −1.47 | −2.83 | W | OR3A4 | 390756 | NM_001005334 | M-032453-00 |
| PL-50089 | L07 | X | −1.44 | −2.78 | W | OR4A5 | 81318 | NM_001005272 | M-032433-00 |
| PL-50089 | J20 | X | −2.50 | −2.48 | W | OR5B2 | 390190 | NM_001005566 | M-032494-00 |
| PL-50089 | L05 | X | −1.83 | −3.72 | W | OR5M11 | 219487 | NM_001005245 | M-032432-00 |
| PL-50089 | P04 | X | −3.78 | −2.12 | W | OR6C74 | 254783 | NM_001005490 | M-032472-00 |
| PL-50056 | E19 | X | −2.02 | −1.91 | W | ORC3L | 23595 | NM_012381 | M-003285-01 |
| PL-50023 | E16 | X | −2.49 | −4.24 | W | OTOR | 56914 | NM_020157 | M-017390-00 |
| PL-50059 | K11 | X | −4.17 | −2.07 | W | PADI3 | 51702 | NM_016233 | M-021051-00 |
| PL-50069 | E06 | X | −1.66 | −2.78 | W | PAGE-5 | 90737 | NM_130467 | M-017468-00 |
| PL-50056 | L02 | X | −2.88 | −1.42 | W | PAI-RBP1 | 26135 | NM_015640 | M-020528-00 |
| PL-50060 | M10 | X | −3.27 | −1.51 | W | PAK1IP1 | 55003 | NM_017906 | M-020912-00 |
| PL-50076 | L05 | X | −2.26 | −1.72 | W | PAQR10 | 221938 | NM_198403 | M-008052-00 |
| PL-50009 | A18 | X | −3.07 | −2.42 | W | PAWR | 5074 | NM_002583 | M-004434-00 |
| PL-50049 | K02 | X | −3.58 | −2.13 | W | PCBP1 | 5093 | NM_006196 | M-012243-01 |
| PL-50062 | B07 | X | −3.19 | −2.38 | W | PCNP | 57092 | NM_320357 | M-020263-00 |
| PL-50007 | C20 | X | −2.34 | −1.95 | W | PCOLCE | 5118 | NM_002593 | M-011747-00 |
| PL-50023 | B07 | X | −2.40 | −2.28 | W | PDE6A | 5145 | NM_000440 | M-007651-00 |
| PL-50063 | B04 | X | −2.10 | −2.62 | W | PDF | 64146 | NM_022341 | M-003851-00 |
| PL-50011 | F21 | X | −2.31 | −1.75 | W | PDHA2 | 5161 | NM_005390 | M-023925-00 |
| PL-50016 | A19 | X | −2.67 | −2.94 | W | PDP2 | 57546.00 | NM_020786 | M-022572-00 |
| PL-50070 | L02 | X | −3.12 | −2.13 | W | PERLD1 | 93210 | NM_033419 | M-017912-00 |
| PL-50061 | E12 | X | −2.26 | −2.28 | W | PEX26 | 55670 | NM_017929 | M-019128-00 |
| PL-50002 | J23 | X | −2.09 | −2.44 | W | PFKFB3 | 5209 | NM_004566 | M-006763-00 |
| PL-50073 | N08 | X | −2.07 | −2.21 | W | PHF13 | 148479 | NM_153812 | |
| PL-50068 | C23 | X | −2.49 | −2.19 | W | PHYHIPL | 84457 | NM_032439 | M-014894-00 |
| PL-50078 | A23 | X | −2.16 | −2.00 | W | PIGW | 284098 | NM_178517 | M-021480-00 |
| PL-50002 | P07 | X | −1.58 | −3.31 | W | PIK3R3 | 8503 | NM_003629 | M-019546-00 |
| PL-50002 | P13 | X | −1.95 | −2.15 | W | PIK4CB | 5298 | NM_002651 | M-006777-02 |
| PL-50058 | H07 | X | −2.39 | −2.07 | W | PIPOX | 51268 | NM_016518 | M-010199-00 |
| PL-50075 | G16 | X | −2.79 | −2.75 | W | PKD1L1 | 168507 | NM_138295 | M-017434-00 |
| PL-50011 | L13 | X | −2.53 | −2.13 | W | PNLIP | 5406 | NM_000936 | M-008973-00 |
| PL-50011 | L15 | X | −2.42 | −2.27 | W | PNLIPRP1 | 5407 | NM_006229 | M-009145-00 |
| PL-50014 | G05 | X | −3.24 | −2.84 | W | PRDX3 | 10935.00 | NM_006793 | M-010355-00 |
| PL-50002 | L20 | X | −1.82 | −2.35 | W | PRKACA | 5566 | NM_002730 | M-004649-00 |
| PL-50018 | J11 | X | −2.05 | −1.97 | W | PROK1 | 84432 | NM_032414 | M-014883-00 |
| PL-50057 | A18 | X | −1.87 | −3.54 | W | PROL5 | 26952 | NM_012390 | M-020197-00 |
| PL-50002 | K13 | X | −2.45 | −1.79 | W | PRPS1L1 | 221823 | NM_175886 | M-006804-00 |
| PL-50050 | A09 | X | −2.02 | −3.81 | W | PSG3 | 5671 | NM_021016 | M-014137-00 |
| PL-50057 | P15 | X | −0.93 | −2.95 | W | PTD004 | 29789 | NM_013341 | M-015680-00 |
| PL-50058 | J11 | X | −2.32 | −2.24 | W | PTX1 | 51290 | NM_016570 | M-021151-00 |
| PL-50056 | G19 | X | −2.66 | −3.04 | W | RABGAP1 | 23637 | NM_012197 | M-012803-00 |
| PL-50013 | D11 | X | −2.20 | −1.93 | W | RABL2A | 11159 | NM_007082 | M-013620-00 |
| PL-50013 | F11 | X | −2.65 | −3.09 | W | RANBP2 | 5903 | NM_006267 | M-004746-01 |
| PL-50056 | A09 | X | −2.52 | −1.67 | W | RASD2 | 23551 | NM_014310 | M-009560-00 |
| PL-50070 | E02 | X | −1.96 | −2.22 | W | RASL10B | 91608 | NM_033315 | M-008344-00 |
| PL-50059 | E06 | X | −2.00 | −2.83 | W | RBM27 | 54439 | XM_291128 | M-024337-00 |
| PL-50007 | J19 | X | −2.21 | −2.60 | W | RBM5 | 10181 | NM_005778 | M-009220-01 |
| PL-50011 | P10 | X | −2.94 | −2.47 | W | RCE1 | 9986 | NM_005133 | M-006025-00 |
| PL-50073 | O02 | X | −2.85 | −1.93 | W | RDH12 | 145226 | NM_152443 | |
| PL-50011 | P08 | X | −2.92 | −1.42 | W | RDH5 | 5959 | NM_002905 | M-008220-01 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50057 | P18 | X | −1.73 | −2.54 | W | REPIN1 | 29803 | NM_013400 | M-006978-00 |
| PL-50054 | C09 | X | −2.31 | −2.46 | W | RFPL3 | 10738 | NM_006604 | M-006934-00 |
| PL-50054 | P10 | X | −1.95 | −2.06 | W | RNF13 | 11342 | NM_007282 | M-006944-00 |
| PL-50018 | D17 | X | −2.24 | −2.52 | W | RORB | 6096 | NM_006914 | M-003441-01 |
| PL-50080 | K20 | X | −1.57 | −2.35 | W | RP26 | 375298 | NM_201548 | M-027336-00 |
| PL-50074 | D21 | X | −2.03 | −2.89 | W | RPIB9 | 154661 | NM_138290 | M-015403-00 |
| PL-50050 | O09 | X | −3.26 | −1.86 | W | RPL3L | 6123 | NM_005061 | M-012009-00 |
| PL-50003 | C19 | X | −2.44 | −1.89 | W | RPS6KA2 | 6196 | NM_021135 | M-004663-01 |
| PL-50005 | C20 | X | −2.04 | −3.11 | W | RRH | 10692 | NM_006583 | M-005723-01 |
| PL-50050 | E08 | X | −1.85 | −4.78 | W | SAA2 | 6289 | NM_030754 | M-016279-00 |
| PL-50005 | C18 | X | −2.99 | −2.50 | W | SALPR | 51289 | NM_016568 | M-004774-00 |
| PL-50050 | C18 | X | −2.18 | −2.16 | W | SATB1 | 6304 | NM_002971 | M-011771-00 |
| PL-50007 | P16 | X | −2.75 | −1.65 | W | SCA7 | 6314 | NM_000333 | M-011106-00 |
| PL-50016 | N15 | X | −2.88 | −1.93 | W | SCG3 | 29106.00 | NM_013243 | M-013710-00 |
| PL-50007 | N20 | X | −2.05 | −2.03 | W | SEC22L1 | 9554 | NM_004892 | M-011963-00 |
| PL-50064 | N02 | X | −2.81 | −2.48 | W | SECISBP2 | 79048 | NM_024077 | M-015634-00 |
| PL-50011 | L20 | X | −2.73 | −2.88 | W | SENP1 | 29843 | NM_014554 | M-006357-00 |
| PL-50062 | P17 | X | −1.38 | −2.19 | W | SENP7 | 57337 | NM_020654 | M-006035-00 |
| PL-50071 | C04 | X | −2.84 | −1.66 | W | SENP8 | 123228 | NM_145204 | M-004071-00 |
| PL-50055 | B08 | X | −1.54 | −2.91 | W | SEZ6L | 23544 | NM_021115 | M-008081-00 |
| PL-50063 | G20 | X | −3.18 | −2.00 | W | SF4 | 57794 | NM_172231 | M-017511-00 |
| PL-50007 | L12 | X | −2.30 | −2.29 | W | SFRS7 | 6432 | NM_006276 | M-015909-00 |
| PL-50062 | G16 | X | −1.99 | −3.46 | W | SHD | 56961 | NM_020209 | M-023905-00 |
| PL-50016 | P12 | X | −2.04 | −2.07 | W | SLAMF6 | 114836.00 | NM_052931 | M-013423-01 |
| PL-50062 | C18 | X | −2.38 | −1.44 | W | SLC12A9 | 56996 | NM_020246 | M-007390-00 |
| PL-50049 | M08 | X | −3.20 | −1.97 | W | SLC22A1LS | 5003 | NM_007105 | M-019642-00 |
| PL-50064 | J04 | X | −2.51 | −2.24 | W | SLC25A23 | 79085 | NM_024103 | M-007360-00 |
| PL-50076 | O17 | X | −2.62 | −2.27 | W | SLC36A1 | 206358 | NM_078483 | M-007550-00 |
| PL-50054 | L23 | X | −2.77 | −2.46 | W | SLC6A14 | 11254 | NM_007231 | M-007601-00 |
| PL-50019 | H08 | X | −2.11 | −1.95 | W | SLC6A2 | 6530 | NM_001043 | M-007602-00 |
| PL-50019 | H06 | X | −2.68 | −2.10 | W | SLC6A4 | 6532 | NM_001045 | M-007604-00 |
| PL-50003 | G19 | X | −1.94 | −2.19 | W | SMG1 | 23049 | NM_014006 | M-005033-00 |
| PL-50063 | D20 | X | −2.37 | −2.17 | W | SMOC2 | 64094 | NM_022138 | M-013886-00 |
| PL-50051 | D08 | X | −0.53 | −2.93 | W | SNAP23 | 8773 | NM_003825 | M-017545-00 |
| PL-50066 | N08 | X | −2.00 | −3.51 | W | SNX27 | 81609 | NM_030918 | M-017346-00 |
| PL-50009 | P21 | X | −2.18 | −2.36 | W | SP4 | 6671 | NM_003112 | M-006562-00 |
| PL-50057 | I08 | X | −2.55 | −1.44 | W | SPINK4 | 27290 | NM_014471 | M-020235-00 |
| PL-50050 | N12 | X | −2.03 | −2.92 | W | SPINT1 | 6692 | NM_003710 | M-004578-00 |
| PL-50055 | P09 | X | −2.01 | −2.06 | W | SR140 | 23350 | XM_031553 | M-023607-00 |
| PL-50050 | J16 | X | −1.80 | −3.15 | W | SSA2 | 6738 | NM_004600 | M-017733-00 |
| PL-50005 | C04 | X | −2.07 | −3.32 | W | SSTR2 | 6752 | NM_001050 | M-005728-01 |
| PL-50005 | A20 | X | −2.44 | −2.38 | W | SSTR4 | 6754 | NM_001052 | M-005730-02 |
| PL-50009 | P10 | X | −2.02 | −2.97 | W | SSX1 | 6756 | NM_005635 | M-019194-00 |
| PL-50439 | E21 | X | −2.83 | −2.58 | W | STAMBPL1 | 57559 | NM_020799 | M-005783-01 |
| PL-50057 | E15 | X | −2.76 | −2.12 | W | STEAP | 26872 | NM_012449 | M-003713-00 |
| PL-50052 | G04 | X | −3.23 | −2.14 | W | STOML1 | 9399 | NM_004809 | M-009360-00 |
| PL-50058 | A05 | X | −1.40 | −2.62 | W | STOML2 | 30968 | NM_013442 | M-020518-00 |
| PL-50057 | M06 | X | −3.18 | −1.68 | W | SULT1C2 | 27233 | NM_006588 | M-010391-00 |
| PL-50050 | P19 | X | −2.48 | −1.21 | W | SUMO2 | 6613 | NM_006937 | M-016450-00 |
| PL-50050 | F02 | X | −2.15 | −2.47 | W | SYCP1 | 6847 | NM_003176 | M-019171-00 |
| PL-50007 | F02 | X | −1.95 | −2.02 | W | SYNCRIP | 10492 | NM_006372 | M-016218-00 |
| PL-50055 | A16 | X | −1.90 | −2.68 | W | SYNE2 | 23224 | NM_015180 | M-019259-00 |
| PL-50069 | B05 | X | −1.91 | −2.45 | W | SYTL4 | 94121 | NM_080737 | M-007111-00 |
| PL-50077 | G16 | X | −2.35 | −4.18 | W | TAB3 | 257397 | NM_152787 | |
| PL-50077 | E08 | X | −1.65 | −2.60 | W | TAS2R45 | 259291 | NM_176886 | |
| PL-50012 | G18 | X | −3.34 | −2.54 | W | TBCC | 6903 | NM_003192 | M-011401-00 |
| PL-50003 | O04 | X | −2.57 | −2.29 | W | TESK2 | 10420 | NM_007170 | M-005044-00 |
| PL-50062 | A07 | X | −3.15 | −2.06 | W | TEX13B | 56156 | NM_031273 | M-013485-00 |
| PL-50009 | B20 | X | −2.23 | −2.23 | W | TGIF2LY | 90655 | NM_139214 | M-017279-00 |
| PL-50050 | B02 | X | −1.78 | −2.85 | W | TGM3 | 7053 | NM_003245 | M-010088-00 |
| PL-50007 | B06 | X | −2.51 | −2.28 | W | TIMELESS | 8914 | NM_003920 | M-019488-00 |
| PL-50058 | F14 | X | −2.28 | −2.99 | W | TMEM14C | 51522 | NM_016462 | M-020269-00 |
| PL-50070 | C21 | X | −2.29 | −2.46 | W | TNFRSF13C | 115650 | NM_052945 | M-013424-00 |
| PL-50018 | A19 | X | −2.73 | −1.44 | W | TNFSF13B | 10673 | NM_006573 | M-017586-00 |
| PL-50068 | B04 | X | −2.26 | −2.71 | W | TNKS1BP1 | 85456 | NM_033396 | M-015106-00 |
| PL-50008 | A15 | X | −3.66 | −2.06 | W | TNXB | 7148 | NM_019105 | M-008106-00 |
| PL-50018 | C19 | X | −2.25 | −2.22 | W | TOLLIP | 54472 | NM_019009 | M-016930-00 |
| PL-50064 | I10 | X | −2.96 | −2.82 | W | TORC3 | 64784 | NM_022769 | M-014210-00 |
| PL-50015 | O08 | X | −2.51 | −1.97 | W | TRIM22 | 10346.00 | NM_006074 | M-006927-01 |
| PL-50015 | F23 | X | −2.38 | −2.30 | W | TRIM33 | 51592.00 | NM_015906 | M-005392-02 |
| PL-50053 | I20 | X | −2.24 | −3.53 | W | TSPAN-1 | 10103 | NM_005727 | M-003719-00 |
| PL-50012 | J09 | X | −2.74 | −1.51 | W | TULP1 | 7287 | NM_003322 | M-011413-00 |
| PL-50062 | C20 | X | −2.31 | −2.28 | W | TULP4 | 56995 | NM_020245 | M-013785-00 |
| PL-50066 | N17 | X | −2.02 | −2.71 | W | TXNDC | 81542 | NM_030755 | M-010675-00 |
| PL-50012 | J17 | X | −2.09 | −2.45 | W | TYMS | 7298 | NM_001071 | M-004717-01 |
| PL-50050 | N20 | X | −4.03 | −1.70 | W | UAP1 | 6675 | NM_003115 | M-017160-00 |
| PL-50012 | L13 | X | −2.86 | −2.62 | W | UBE2L6 | 9246 | NM_004223 | M-008569-00 |
| PL-50058 | B08 | X | −1.72 | −2.24 | W | UFM1 | 51569 | NM_016617 | M-021005-00 |

TABLE 1-continued

| Stock_ID | Row | Type | Z score_A | Z score_B | Screen+ | Gene Symbol | Entrez Gene ID | Accession # | Catalog # |
|---|---|---|---|---|---|---|---|---|---|
| PL-50071 | B19 | X | −1.54 | −2.68 | W | UNQ2446 | 123904 | NM_198443 | M-027207-00 |
| PL-50080 | C20 | X | −4.44 | −2.16 | W | UNQ2492 | 377841 | NM_198585 | M-027275-00 |
| PL-50078 | M23 | X | −2.63 | −1.54 | W | UNQ3033 | 284415 | NM_198481 | M-027236-00 |
| PL-50080 | D14 | X | −2.57 | −2.61 | W | UNQ9370 | 400454 | NM_207447 | M-032131-00 |
| PL-50064 | F15 | X | −2.44 | −2.66 | W | UPF3B | 65109 | NM_023010 | M-012871-00 |
| PL-50070 | M13 | X | −2.79 | −1.27 | W | VEST1 | 116328 | NM_052958 | M-015175-00 |
| PL-50076 | N14 | X | −2.58 | −2.97 | W | VGLL2 | 245806 | NM_153453 | M-015963-00 |
| PL-50005 | H07 | X | −2.62 | −3.09 | W | VN1R4 | 317703 | NM_173857 | M-017651-00 |
| PL-50019 | F05 | X | −2.18 | −2.02 | W | VPS13A | 23230 | NM_015186 | M-012878-00 |
| PL-50061 | B02 | X | −2.23 | −1.62 | W | VPS35 | 55737 | NM_018206 | M-010894-00 |
| PL-50064 | C18 | X | −2.66 | −2.10 | W | WARP | 64856 | NM_022834 | M-016331-00 |
| PL-50072 | B08 | X | −2.36 | −2.10 | W | WFDC3 | 140686 | NM_181522 | M-013334-00 |
| PL-50016 | F06 | X | −3.36 | −4.06 | W | WNT7B | 7477.00 | NM_058238 | M-003722-02 |
| PL-50063 | B10 | X | −3.24 | −2.28 | W | XYLT2 | 64132 | NM_022167 | M-013040-00 |
| PL-50003 | E06 | X | −3.18 | −2.63 | W | ZAK | 51776 | NM_133646 | M-005068-00 |
| PL-50063 | K05 | X | −1.49 | −2.73 | W | ZBTB2 | 57621 | NM_020861 | M-014129-00 |
| PL-50021 | B08 | X | −2.06 | −2.17 | W | ZBTB7 | 51341 | NM_015898 | M-020818-00 |
| PL-50061 | O10 | X | −1.65 | −2.48 | W | ZCCHC8 | 55596 | NM_017612 | M-021026-00 |
| PL-50072 | B18 | X | −1.71 | −2.12 | W | ZFP28 | 140612 | NM_020828 | M-014089-00 |
| PL-50010 | C23 | X | −2.43 | −2.86 | W | ZFP67 | 51043 | NM_015872 | M-020934-00 |
| PL-50059 | G23 | X | −2.13 | −1.92 | W | ZFR | 51663 | NM_016107 | M-019266-00 |
| PL-50051 | I10 | X | −1.86 | −4.52 | W | ZNF192 | 7745 | NM_006298 | M-020154-00 |
| PL-50058 | A11 | X | −2.88 | −2.74 | W | ZNF295 | 49854 | NM_020727 | M-013945-00 |
| PL-50055 | M17 | X | −2.52 | −1.51 | W | ZNF297B | 23099 | NM_014007 | M-020320-00 |
| PL-50062 | P19 | X | −3.24 | −2.42 | W | ZNF304 | 57343 | NM_020657 | M-020719-00 |
| PL-50056 | M18 | X | −2.34 | −2.31 | W | ZNF324 | 25799 | NM_014347 | M-006964-00 |
| PL-50061 | B09 | X | −1.88 | −2.35 | W | ZNF334 | 55713 | NM_018102 | M-017955-00 |
| PL-50057 | D02 | X | −2.35 | −2.62 | W | ZNF354C | 30832 | NM_014594 | M-014199-00 |
| PL-50068 | A18 | X | −2.28 | −2.49 | W | ZNF496 | 84838 | NM_032752 | M-014983-00 |
| PL-50070 | C15 | X | −2.56 | −3.03 | W | ZNF501 | 115560 | NM_145044 | M-007118-00 |
| PL-50068 | B07 | X | −3.37 | −2.84 | W | ZNF503 | 84858 | NM_032772 | M-015846-00 |
| PL-50057 | G12 | X | −1.43 | −2.54 | W | ZNF544 | 27300 | NM_014480 | M-020223-00 |
| PL-50073 | P08 | X | −2.79 | −2.65 | W | ZNF570 | 148268 | NM_144694 | |
| PL-50078 | K23 | X | −2.22 | −1.70 | W | ZNF615 | 284370 | NM_198480 | M-032239-00 |
| PL-50057 | B18 | X | −1.29 | −5.41 | W | ZNRD1 | 30834 | NM_014596 | M-017359-00 |

TABLE 2

| GeneSymbol | EntrezGeneID | Genbank Acc. No. | NFAT Score |
|---|---|---|---|
| AB026190 | 27252 | NM_014458 | W |
| ABCC13 | 150000 | NM__138726 | M |
| ABLIM2 | 84448 | NM_032432 | W |
| ACLY | 47 | NM_001096 | W |
| ACTB | 60 | NM__001101 | M |
| ACY1L2 | 135293 | XM__072402 | W |
| ADAM10 | 102 | NM_001110 | M |
| ADAMTS5 | 11096 | NM_007038 | S |
| ADCY4 | 196883 | NM_139247 | W |
| ADK | 132 | NM__001123 | W |
| ADRA2B | 151 | NM__000682 | W |
| AFG3L1 | 172 | NM__001132 | M |
| AGK | 55750 | NM__018238 | W |
| AKAP11 | 11215 | NM_016248 | W |
| AKR1CL1 | 340811 | XM__291723 | W |
| AKR1CL2 | 83592 | NM__031436 | M |
| ALCAM | 214 | NM__001627 | M |
| ALS2CR13 | 150864 | NM__173511 | W |
| ALS2CR15 | 130026 | NM__138468 | M |
| AMH | 268 | NM__000479 | W |
| AMIGO2 | 347902 | NM__181847 | W |
| ANC__2H01 | 51193 | NM__016331 | M |
| ANKFX1 | 51479 | NM__016376 | W |
| ANKK1 | 255239 | NM__178510 | W |
| ANKMX2 | 57037 | NM__020319 | W |
| ANKRD9 | 122416 | NM__152326 | M |
| AP1S3 | 130340 | NM__178814 | W |
| AP3B2 | 8120 | NM__004644 | W |
| APG16L | 55054 | NM__017974 | W |
| APH-1A | 51107 | NM__016022 | M |
| APOBEC1 | 339 | NM__001644 | W |
| APOL4 | 80832 | NM__030643 | M |
| APXL | 357 | NM__001649 | W |
| AQR | 9716 | NM__014691 | W |
| ARCN1 | 372 | NM__001655 | S |

TABLE 2-continued

| GeneSymbol | EntrezGeneID | Genbank Acc. No. | NFAT Score |
|---|---|---|---|
| ARHGAP15 | 55843 | NM__018460 | W |
| ARHGAP17 | 55114 | NM__018054 | W |
| ARHGDIA | 396 | NM__004309 | W |
| ARL10C | 55207 | NM__018184 | W |
| ARL11 | 115761 | NM__138450 | M |
| ARL5C | 390790 | XM__372668 | M |
| ARMC2 | 84071 | NM__032131 | W |
| ARPP-21 | 10777 | NM__016300 | W |
| ARS2 | 51593 | NM__015908 | W |
| ASB10 | 136371 | NM__080871 | W |
| ASB4 | 51666 | NM__016116 | S |
| ASMTL | 8623 | NM__004192 | W |
| ASTL | 431705 | NM__001002036 | W |
| ATP10D | 57205 | NM__020453 | W |
| ATP5L2 | 267020 | NM__198822 | M |
| ATP5S | 27109 | NM__015684 | W |
| ATP6V0D1 | 9114 | NM__004691 | M |
| ATP6V1D | 51382 | NM__015994 | M |
| AZ2 | 64343 | NM__022461 | W |
| BACE1 | 23621 | NM__012104 | M |
| BATF | 10538 | NM__006399 | M |
| BBX | 56987 | NM__020235 | W |
| BC-2 | 27243 | NM__014453 | W |
| BCL2L12 | 83596 | NM__052842 | M |
| BEST3 | 84821 | NM__032735 | W |
| BEXL1 | 56271 | XM__043653 | W |
| BFSP1 | 631 | NM__001195 | W |
| BG1 | 23205 | NM__015162 | S |
| BGN | 633 | NM__001711 | M |
| BIG1 | 10565 | NM__006421 | S |
| BIN3 | 55909 | NM__018688 | M |
| BMP15 | 9210 | NM__005448 | W |
| BMP4 | 652 | NM__001202 | S |
| BMPER | 168667 | NM__133468 | W |
| BMSC-UBP | 84993 | NM__032907 | S |

TABLE 2-continued

| GeneSymbol | EntrezGeneID | Genbank Acc. No. | NFAT Score |
|---|---|---|---|
| BRD8 | 10902 | NM_006696 | W |
| BRP44L | 51660 | NM_016098 | M |
| BRUNOL6 | 60677 | NM_052840 | W |
| BSCL2 | 26580 | NM_032667 | W |
| BTBD11 | 121551 | NM_152322 | M |
| BTN3A3 | 10384 | NM_006994 | W |
| C10ORF53 | 282966 | NM_182554 | M |
| C10ORF56 | 219654 | NM_153367 | M |
| C10ORF59 | 55328 | NM_018363 | W |
| C10ORF81 | 79949 | NM_024889 | M |
| C10ORF94 | 93426 | NM_130784 | W |
| C11ORF17 | 56672 | NM_020642 | W |
| C13ORF10 | 64062 | NM_022118 | W |
| C13ORF12 | 51371 | NM_015932 | M |
| C14ORF11 | 55837 | NM_018453 | M |
| C14ORF126 | 112487 | NM_080664 | W |
| C14ORF147 | 171546 | NM_138288 | W |
| C14ORF43 | 91748 | NM_194278 | W |
| C14ORF73 | 91828 | XM_040910 | W |
| C14ORF8 | 122664 | NM_173846 | W |
| C14ORF92 | 9878 | XM_375045 | W |
| C15ORF24 | 56851 | NM_020154 | S |
| C16ORF23 | 79006 | NM_024042 | W |
| C18ORF34 | 374864 | NM_198995 | W |
| C19ORF13 | 26065 | NM_015578 | S |
| C19ORF24 | 55009 | NM_017914 | W |
| C1ORF123 | 54987 | NM_017887 | M |
| C20ORF104 | 51230 | NM_016436 | S |
| C20ORF96 | 140680 | NM_153269 | M |
| C21ORF107 | 54014 | NM_018963 | W |
| C21ORF45 | 54069 | NM_018944 | W |
| C21ORF49 | 54067 | NM_001006116 | S |
| C21ORF6 | 10069 | NM_016940 | W |
| C21ORF84 | 114038 | NM_153752 | W |
| C3ORF6 | 152137 | NM_174908 | M |
| C4ORF8 | 8603 | NM_003704 | W |
| C5ORF11 | 167410 | NM_153234 | W |
| C6ORF115 | 58527 | XM_371848 | M |
| C6ORF191 | 253582 | XM_173166 | S |
| C6ORF51 | 112495 | NM_138408 | W |
| C6ORF57 | 135154 | NM_145267 | W |
| C6ORF59 | 79992 | NM_024929 | W |
| C6ORF84 | 22832 | XM_376518 | S |
| C8ORF4 | 56892 | NM_020130 | W |
| C9ORF11 | 54586 | XM_035953 | M |
| C9ORF138 | 158297 | NM_153707 | M |
| C9ORF150 | 286343 | NM_203403 | W |
| C9ORF71 | 169693 | XM_376874 | M |
| C9ORF72 | 203228 | NM_018325 | S |
| C9ORF79 | 286234 | NM_178828 | M |
| C9ORF84 | 158401 | NM_173521 | W |
| CABLES2 | 81928 | NM_031215 | W |
| CACNA1A | 773 | NM_000068 | W |
| CACNG4 | 27092 | NM_014405 | W |
| CADPS | 8618 | NM_003716 | W |
| CARD12 | 58484 | NM_021209 | W |
| CASC1 | 55259 | NM_018272 | S |
| CAV3 | 859 | NM_001234 | W |
| CBLL1 | 79872 | NM_024814 | S |
| CBLN2 | 147381 | NM_182511 | W |
| CBX6 | 23466 | NM_014292 | W |
| CCDC125 | 202243 | NM_176816 | M |
| CCK | 885 | NM_000729 | M |
| CCL11 | 6356 | NM_002986 | M |
| CCNB2 | 9133 | NM_004701 | S |
| CCNK | 8812 | NM_003858 | M |
| CCR6 | 1235 | NM_004367 | W |
| CCRN4L | 25819 | NM_012118 | M |
| CD151 | 977 | NM_004357 | W |
| CD1E | 913 | NM_030893 | W |
| CD209L | 10332 | NM_014257 | M |
| CD3G | 917 | NM_000073 | W |
| CD5 | 921 | NM_014207 | W |
| CD74 | 972 | NM_004355 | W |
| CDC27 | 996 | NM_001256 | S |
| CDC2L5 | 8621 | NM_003718 | M |
| CDC42EP5 | 148170 | NM_145057 | W |
| CDH9 | 1007 | NM_016279 | W |
| CENTG1 | 116986 | NM_014770 | W |
| CFL2 | 1073 | NM_021914 | W |
| CGI-04 | 51067 | NM_015936 | S |
| CHCHD5 | 84269 | NM_032309 | W |
| CHD4 | 1108 | NM_001273 | W |
| CHERP | 10523 | NM_006387 | W |
| CHFR | 55743 | NM_018223 | W |
| CHRM3 | 1131 | NM_000740 | W |
| CHRNA4 | 1137 | NM_000744 | W |
| CIRBP | 1153 | NM_001280 | M |
| CKN1 | 1161 | NM_000082 | W |
| CLCN4 | 1183 | NM_001830 | W |
| CLDN22 | 53842 | XM_210581 | S |
| CLPS | 1208 | NM_001832 | M |
| CLUL1 | 27098 | NM_014410 | W |
| CMAS | 55907 | NM_018686 | M |
| CMRF-35H | 11314 | NM_007261 | W |
| CNTN3 | 5067 | XM_039627 | M |
| COMT | 1312 | NM_000754 | W |
| COPA | 1314 | NM_004371 | S |
| COPB1 | 1315 | NM_016451 | S |
| COPB2 | 9276 | NM_004766 | S |
| COPE | 11316 | NM_007263 | S |
| COPG | 22820 | NM_016128 | S |
| COPZ1 | 22818 | NM_016057 | S |
| COX8A | 1351 | NM_004074 | W |
| CPEB4 | 80315 | NM_030627 | S |
| CPT2 | 1376 | NM_000098 | M |
| CRBN | 51185 | NM_016302 | W |
| CRHR2 | 1395 | NM_001883 | W |
| CRLF3 | 51379 | NM_015986 | M |
| CRSP2 | 9282 | NM_004229 | W |
| CRSP3 | 9439 | NM_004830 | W |
| CRSP6 | 9440 | NM_004268 | W |
| CRSP9 | 9443 | NM_004270 | M |
| CRXBA2 | 1412 | NM_005209 | W |
| CRXBB1 | 1414 | NM_001887 | W |
| CRXBB3 | 1417 | NM_004076 | W |
| CRXGC | 1420 | NM_020989 | W |
| CSAD | 51380 | NM_015989 | W |
| CSE1L | 1434 | NM_001316 | S |
| CST7 | 8530 | NM_003650 | W |
| CYLC1 | 1538 | XM_088636 | W |
| CYP1A1 | 1543 | NM_000499 | W |
| CYP2S1 | 29785 | NM_030622 | S |
| CYP3A5 | 1577 | NM_000777 | W |
| CYT19 | 57412 | NM_020682 | S |
| D2S448 | 7837 | XM_056455 | W |
| D4ST1 | 113189 | NM_130468 | S |
| DAAM1 | 23002 | NM_014992 | W |
| DACH1 | 1602 | NM_004392 | M |
| DBI | 1622 | NM_020548 | W |
| DC2 | 58505 | NM_021227 | W |
| DDX46 | 9879 | NM_014829 | W |
| DDX53 | 168400 | NM_182699 | M |
| DGCR6L | 85359 | NM_033257 | M |
| DHPS | 1725 | NM_001930 | W |
| DHRS4 | 10901 | NM_021004 | M |
| DHRS4L2 | 317749 | NM_198083 | M |
| DHRS9 | 10170 | NM_005771 | M |
| DIABLO | 56616 | NM_019887 | S |
| DIPA | 11007 | NM_006848 | S |
| DISP2 | 85455 | NM_033510 | M |
| DJ383J4.3 | 91687 | XM_371328 | M |
| DKFZP434B1231 | 91156 | NM_178275 | W |
| DKFZP547E1010 | 26097 | NM_015607 | M |
| DKFZP564D1378 | 84064 | NM_032124 | M |
| DKFZP566D1346 | 81573 | NM_030816 | M |
| DKFZP686P0288 | 285190 | NM_182588 | W |
| DKFZP761B1514 | 84248 | NM_032288 | W |
| DLAT | 1737 | NM_001931 | W |
| DNAJC5G | 285126 | NM_173650 | M |
| DNM1L | 10059 | NM_005690 | W |
| DONSON | 29980 | NM_145794 | M |
| DRPLA | 1822 | NM_001940 | M |
| DSEL | 92126 | NM_032160 | M |
| DSG4 | 147409 | NM_177986 | M |
| DUSP12 | 11266 | NM_007240 | M |

TABLE 2-continued

| GeneSymbol | EntrezGeneID | Genbank Acc. No. | NFAT Score |
|---|---|---|---|
| DUSP16 | 80824 | NM_030640 | W |
| DUSP18 | 150290 | NM_152511 | W |
| DUX1 | 26584 | NM_012146 | W |
| DUX5 | 26581 | NM_012149 | W |
| DVL3 | 1857 | NM_004423 | W |
| E(X)2 | 56943 | NM_020189 | W |
| E2IG2 | 51287 | NM_016565 | W |
| EBPL | 84650 | NM_032565 | W |
| EG1 | 80306 | NM_025205 | S |
| EGLN3 | 112399 | NM_022073 | M |
| EHD2 | 30846 | NM_014601 | M |
| ELMOD1 | 55531 | NM_018712 | S |
| ELXS | 25909 | NM_015446 | S |
| EML4 | 27436 | NM_019063 | M |
| EPB41L5 | 57669 | NM_020909 | W |
| EPO | 2056 | NM_000799 | M |
| EPSTI1 | 94240 | NM_033255 | M |
| ERBB4 | 2066 | NM_005235 | M |
| EREG | 2069 | NM_001432 | W |
| ERK8 | 225689 | NM_139021 | W |
| ESRRBL1 | 55081 | NM_018010 | W |
| EVI5 | 7813 | NM_005665 | W |
| F11R | 50848 | NM_016946 | M |
| FAM108C1 | 58489 | XM_051862 | S |
| FAM14A | 83982 | NM_032036 | W |
| FAM171A2 | 284069 | XM_208993 | S |
| FAM23B | 0 | XM_291726 | W |
| FAM31C | 79958 | NM_024898 | M |
| FAM38A | 9780 | NM_014745 | W |
| FAM57B | 83723 | NM_031478 | W |
| FAS | 355 | NM_000043 | S |
| FASTKD5 | 60493 | NM_021826 | M |
| FBXL20 | 84961 | NM_032875 | W |
| FBXL3P | 26223 | NM_012159 | W |
| FBXO11 | 80204 | NM_012167 | M |
| FBXO22 | 26263 | NM_012170 | W |
| FBXO46 | 23403 | XM_371179 | W |
| FBXO5 | 26271 | NM_012177 | S |
| FCGR3A | 2214 | NM_000569 | W |
| FCHSD2 | 9873 | NM_014824 | M |
| FGF14 | 2259 | NM_004115 | W |
| FGF7 | 2252 | NM_002009 | W |
| FGFR2 | 2263 | NM_000141 | M |
| FGFR4 | 2264 | NM_002011 | M |
| FKBP1C | 135521 | XM_059776 | W |
| FLJ10159 | 55084 | NM_018013 | W |
| FLJ10352 | 55125 | NM_018069 | W |
| FLJ10613 | 54552 | NM_019067 | W |
| FLJ10759 | 55223 | NM_018207 | M |
| FLJ10826 | 55239 | NM_018233 | M |
| FLJ11126 | 55308 | NM_018332 | W |
| FLJ11127 | 54491 | NM_019018 | M |
| FLJ11193 | 55322 | NM_018356 | W |
| FLJ12517 | 65094 | NM_023007 | W |
| FLJ14299 | 80139 | NM_025069 | S |
| FLJ20152 | 54463 | NM_019000 | W |
| FLJ20257 | 56257 | NM_019606 | M |
| FLJ20280 | 54876 | NM_017741 | M |
| FLJ20291 | 54883 | NM_017748 | M |
| FLJ20321 | 54897 | NM_017766 | M |
| FLJ20485 | 54517 | NM_019042 | W |
| FLJ20509 | 54956 | NM_017851 | W |
| FLJ20519 | 54964 | NM_017860 | W |
| FLJ20534 | 54969 | NM_017867 | S |
| FLJ20618 | 55000 | NM_017903 | M |
| FLJ20793/TMX3 | 54495 | NM_019022 | S |
| FLJ20972 | 80098 | NM_025030 | W |
| FLJ21415 | 79794 | NM_024738 | S |
| FLJ21687 | 79917 | NM_024859 | M |
| FLJ21986 | 79974 | NM_024913 | M |
| FLJ22531 | 79703 | NM_024650 | M |
| FLJ22688 | 80199 | NM_025129 | W |
| FLJ23554 | 79864 | NM_024806 | W |
| FLJ25286 | 153443 | NM_152546 | W |
| FLJ25555 | 124930 | NM_152345 | M |
| FLJ30656 | 124801 | NM_152344 | S |
| FLJ32356 | 144717 | NM_144671 | W |
| FLJ32421 | 148362 | NM_144695 | W |

TABLE 2-continued

| GeneSymbol | EntrezGeneID | Genbank Acc. No. | NFAT Score |
|---|---|---|---|
| FLJ32569 | 148811 | NM_152491 | W |
| FLJ32682 | 220081 | NM_182542 | W |
| FLJ32734 | 146849 | NM_144681 | W |
| FLJ32743 | 220136 | NM_145020 | M |
| FLJ33516 | 139221 | NM_152423 | M |
| FLJ33814 | 150275 | NM_173510 | W |
| FLJ33817 | 124997 | NM_152348 | M |
| FLJ34690 | 284034 | NM_182567 | W |
| FLJ35757 | 162333 | NM_152598 | W |
| FLJ35838 | 163479 | NM_173532 | W |
| FLJ35843 | 160762 | NM_152591 | W |
| FLJ35961 | 127294 | NM_152372 | W |
| FLJ36070 | 284358 | NM_182574 | S |
| FLJ36754/P18SRP | 285672 | NM_173829 | S |
| FLJ36878 | 284114 | NM_178518 | W |
| FLJ38379 | 285097 | NM_178530 | W |
| FLJ38984 | 127703 | NM_152374 | W |
| FLJ39117 | 126638 | XM_371312 | W |
| FLJ39155 | 133584 | NM_152403 | W |
| FLJ40160 | 128209 | NM_173484 | W |
| FLJ40172 | 285051 | NM_173649 | M |
| FLJ40311 | 124535 | XM_064190 | S |
| FLJ42953 | 400892 | NM_207474 | W |
| FLJ42957 | 400077 | NM_207436 | W |
| FLJ43965 | 389206 | NM_207406 | W |
| FLJ44290 | 375347 | NM_198564 | M |
| FLJ44313 | 400658 | NM_207460 | M |
| FLJ45121 | 400556 | NM_207451 | M |
| FLJ45803 | 399948 | NM_207429 | W |
| FLJ46354 | 374977 | NM_198547 | W |
| FLJ46365 | 401459 | NM_207504 | S |
| FLJ46481 | 389197 | NM_207405 | W |
| FOXB1 | 27023 | NM_012182 | W |
| FOXK2 | 3607 | NM_004514 | S |
| FOXP2 | 93986 | NM_014491 | W |
| FOXP4 | 116113 | NM_138457 | W |
| FRMPD1 | 22844 | NM_014907 | M |
| FRRS1 | 0 | XM_372784 | W |
| FSHPRH1 | 2491 | NM_006733 | W |
| FSIP1 | 161835 | NM_152597 | S |
| FTH1 | 2495 | NM_002032 | W |
| FXC1 | 26515 | NM_012192 | W |
| FXYD2 | 486 | NM_001680 | M |
| FYN | 2534 | NM_002037 | W |
| GABRB1 | 2560 | NM_000812 | W |
| GAF1 | 26056 | NM_015470 | S |
| GART | 2618 | NM_000819 | W |
| GBP1 | 2633 | NM_002053 | W |
| GBP5 | 115362 | NM_052942 | M |
| GCAT | 23464 | NM_014291 | M |
| GDNF | 2668 | NM_000514 | W |
| GGA1 | 26088 | NM_001001560 | M |
| GGA3 | 23163 | NM_014001 | M |
| GJB3 | 2707 | NM_024009 | W |
| GL004 | 56947 | NM_020194 | W |
| GLMN | 11146 | NM_053274 | M |
| GLT1D1 | 144423 | NM_144669 | M |
| GMFG | 9535 | NM_004877 | W |
| GNAQ | 2776 | NM_002072 | W |
| GOLGA6 | 55889 | NM_018652 | W |
| GORASP1 | 64689 | NM_031899 | W |
| GOSR2 | 9570 | NM_004287 | S |
| GOT1 | 2805 | NM_002079 | W |
| GPD1 | 2819 | NM_005276 | M |
| GPD1L | 23171 | NM_015141 | S |
| GPHA2 | 170589 | NM_130769 | M |
| GPKOW | 27238 | NM_015698 | W |
| GPM6B | 2824 | NM_005278 | W |
| GPR101 | 83550 | NM_054021 | W |
| GPR114 | 221188 | NM_153837 | W |
| GPR14 | 2837 | NM_018949 | M |
| GPR23 | 2846 | NM_005296 | M |
| GPR50 | 9248 | NM_004224 | W |
| GPR56 | 9289 | NM_005682 | W |
| GPR73L1 | 128674 | NM_144733 | W |
| GRB7 | 2886 | NM_005310 | W |
| GRID1 | 2894 | XM_043613 | W |
| GRID2 | 2895 | NM_001510 | W |

TABLE 2-continued

| GeneSymbol | EntrezGeneID | Genbank Acc. No. | NFAT Score |
|---|---|---|---|
| GRK4 | 2868 | NM_005307 | M |
| GRK7 | 131890 | NM_139209 | W |
| GRSP1 | 23150 | XM_114303 | S |
| GSR | 2936 | NM_000637 | M |
| GSTM2 | 2946 | NM_000848 | M |
| GTPBP1 | 9567 | NM_004286 | W |
| GUCA1B | 2979 | NM_002098 | S |
| H2AFZ | 3015 | NM_002106 | W |
| H6PD | 9563 | NM_004285 | W |
| HBB | 3043 | NM_000518 | S |
| HBE1 | 3046 | NM_005330 | W |
| HBXIP | 10542 | NM_006402 | W |
| HCFC1 | 3054 | NM_005334 | W |
| HD | 3064 | NM_002111 | W |
| HDAC3 | 8841 | NM_003883 | W |
| HEMGN | 55363 | NM_018437 | W |
| HERV-FRD | 405754 | NM_207582 | W |
| HES2 | 54626 | XM_375684 | S |
| HIST1H1B | 3009 | NM_005322 | W |
| HIST1H2AL | 8332 | NM_003511 | W |
| HIST1H3B | 8358 | NM_003537 | W |
| HIST1H4A | 8359 | NM_003538 | W |
| HMG4L | 128872 | NM_178467 | M |
| HMP19 | 51617 | NM_015980 | M |
| HOXA7 | 3204 | NM_006896 | W |
| HOXB8 | 3218 | NM_024016 | W |
| HOXC8 | 3224 | NM_022658 | W |
| HOXD4 | 3233 | NM_014621 | M |
| HRASLS2 | 54979 | NM_017878 | W |
| HS747E2A | 25770 | NM_015370 | W |
| HSCARG | 57407 | NM_020677 | W |
| HSD11B2 | 3291 | NM_000196 | M |
| HSPB9 | 94086 | NM_033194 | W |
| HTR1A | 3350 | NM_000524 | W |
| HUNK | 30811 | NM_014586 | W |
| HXAL2 | 8692 | NM_003773 | W |
| HXAL4 | 23553 | NM_012269 | M |
| IDH3G | 3421 | NM_004135 | W |
| IFRG15 | 64163 | NM_022347 | W |
| IGF1R | 3480 | NM_000875 | S |
| IGSF8 | 93185 | NM_052868 | W |
| IL10RB | 3588 | NM_000628 | W |
| IL15RA | 3601 | NM_002189 | W |
| IL17 | 3605 | NM_002190 | W |
| IL17F | 112744 | NM_052872 | W |
| IL1F9 | 56300 | NM_019618 | W |
| IL1RAPL1 | 11141 | NM_014271 | M |
| IL1RL1 | 9173 | NM_003856 | W |
| IL20RA | 53832 | NM_014432 | M |
| IL22 | 50616 | NM_020525 | W |
| IL8RB | 3579 | NM_001557 | W |
| IL9 | 3578 | NM_000590 | M |
| INM01 | 157695 | NM_175075 | S |
| INSIG1 | 3638 | NM_005542 | W |
| INSM1 | 3642 | NM_002196 | W |
| INTERSEX | 55588 | XM_290829 | W |
| IRF7 | 3665 | NM_001572 | W |
| IRX1 | 79192 | XM_380171 | W |
| ITIH5 | 80760 | NM_030569 | M |
| ITSN2 | 50618 | NM_006277 | W |
| JARID1D | 8284 | NM_004653 | M |
| JIK | 51347 | NM_016281 | M |
| JM1 | 28952 | NM_014008 | W |
| JM11 | 90060 | NM_033626 | W |
| JMJD2B | 23030 | NM_015015 | M |
| JPH2 | 57158 | NM_020433 | M |
| JUB | 84962 | NM_198086 | W |
| KALRN | 8997 | NM_003947 | W |
| KBTBD7 | 84078 | NM_032138 | W |
| KCNC4 | 3749 | NM_004978 | W |
| KCNH4 | 23415 | NM_012285 | W |
| KCNIP2 | 30819 | NM_014591 | M |
| KCNJ3 | 3760 | NM_002239 | W |
| KCNK9 | 51305 | NM_016601 | M |
| KCNN4 | 3783 | NM_002250 | S |
| KCTD14 | 65987 | NM_023930 | W |
| KDR | 3791 | NM_002253 | W |
| KEAP1 | 9817 | NM_012289 | W |

TABLE 2-continued

| GeneSymbol | EntrezGeneID | Genbank Acc. No. | NFAT Score |
|---|---|---|---|
| KIAA0217 | 23185 | XM_040265 | W |
| KIAA0284 | 283638 | XM_208766 | S |
| KIAA0303 | 23227 | XM_291141 | M |
| KIAA0527 | 26032 | XM_171054 | M |
| KIAA0540 | 23218 | XM_291064 | M |
| KIAA0542 | 9814 | XM_038520 | W |
| KIAA0701 | 23074 | XM_045423 | S |
| KIAA0841 | 23354 | XM_049237 | M |
| KIAA0980 | 22981 | NM_025176 | W |
| KIAA1012 | 22878 | NM_014939 | M |
| KIAA1068 | 23386 | NM_015332 | W |
| KIAA1189 | 57471 | XM_371576 | W |
| KIAA1194 | 57472 | NM_015455 | W |
| KIAA1280 | 55841 | NM_015691 | M |
| KIAA1361 | 57551 | XM_290796 | W |
| KIAA1510 | 57642 | NM_020882 | M |
| KIAA1549 | 57670 | XM_371956 | W |
| KIAA1573 | 57685 | NM_020925 | W |
| KIAA1726 | 85463 | XM_370654 | S |
| KIAA1862 | 84626 | XM_044212 | M |
| KIAA1971 | 123720 | XM_058720 | S |
| KIAA1987 | 170951 | XM_375298 | W |
| KIF11 | 3832 | NM_004523 | W |
| KIF13B | 23303 | NM_015254 | M |
| KIR2DL4 | 3805 | NM_002255 | W |
| KLHL11 | 55175 | NM_018143 | M |
| KLRC3 | 3823 | NM_002261 | M |
| KPNB1 | 3837 | NM_002265 | S |
| KRTAP21-2 | 337978 | NM_181617 | M |
| KRTAP4-5 | 85289 | NM_033188 | M |
| KRTAP9-4 | 85280 | NM_033191 | W |
| KRTHA5 | 3886 | NM_002280 | M |
| L1TD1 | 54596 | NM_019079 | M |
| LACE1 | 246269 | NM_145315 | W |
| LAP1B | 26092 | NM_015602 | M |
| LAP3 | 51056 | NM_015907 | W |
| LASP1 | 3927 | NM_006148 | W |
| LCN10 | 414332 | NM_001001712 | W |
| LEPRE1 | 64175 | NM_022356 | W |
| LGI2 | 55203 | NM_018176 | W |
| LIM | 10611 | NM_006457 | W |
| LIMCH1 | 22998 | XM_044461 | M |
| LMAN1L | 79748 | NM_021819 | S |
| LMF2 | 91289 | NM_033200 | W |
| LMNB1 | 4001 | NM_005573 | S |
| LMO7 | 4008 | NM_005358 | W |
| LMTK3 | 114783 | XM_055866 | W |
| LNX2 | 222484 | NM_153371 | W |
| LOC113828 | 113828 | NM_138435 | W |
| LOC116064 | 116064 | XM_057296 | M |
| LOC116068 | 116068 | XM_371760 | W |
| LOC120376 | 120376 | XM_071712 | W |
| LOC124402 | 124402 | NM_145253 | W |
| LOC125893 | 125893 | XM_064856 | W |
| LOC126520 | 126520 | XM_059051 | W |
| LOC131873 | 131873 | XM_067585 | M |
| LOC134145 | 134145 | NM_199133 | W |
| LOC144097 | 144097 | NM_138471 | W |
| LOC145414 | 0 | XM_085138 | W |
| LOC146443 | 146443 | XM_378558 | W |
| LOC146713 | 146713 | XM_378712 | W |
| LOC146795 | 146795 | XM_378701 | S |
| LOC146909 | 146909 | XM_085634 | M |
| LOC149643 | 0 | XM_086616 | W |
| LOC151484 | 151484 | XM_379159 | W |
| LOC152877 | 0 | XM_094066 | W |
| LOC153328 | 153328 | NM_145282 | W |
| LOC153441 | 153441 | XM_087671 | M |
| LOC154222 | 154222 | XM_379456 | W |
| LOC154907 | 0 | XM_088072 | W |
| LOC155036 | 155036 | XM_376722 | W |
| LOC158796 | 0 | XM_088677 | W |
| LOC159090 | 159090 | NM_145284 | W |
| LOC162427 | 162427 | NM_178126 | W |
| LOC163223 | 163223 | NM_001001411 | M |
| LOC164153 | 164153 | NM_203412 | M |
| LOC195977 | 195977 | XM_113625 | S |
| LOC196394 | 196394 | NM_207337 | M |

TABLE 2-continued

| GeneSymbol | EntrezGeneID | Genbank Acc. No. | NFAT Score |
|---|---|---|---|
| LOC200493 | 0 | XM_115715 | W |
| LOC200933 | 200933 | XM_117294 | M |
| LOC201475 | 201475 | XM_113967 | S |
| LOC202051 | 202051 | XM_114430 | W |
| LOC205251 | 205251 | NM_174925 | W |
| LOC254808 | 254808 | XM_374069 | M |
| LOC254897 | 0 | XM_170950 | W |
| LOC254938 | 254938 | XM_173120 | M |
| LOC256085 | 256085 | XM_172389 | M |
| LOC283152 | 283152 | XM_378314 | W |
| LOC283677 | 283677 | XM_208778 | M |
| LOC283914 | 283914 | XM_378589 | M |
| LOC283989 | 283989 | NM_207346 | W |
| LOC284058 | 284058 | NM_015443 | W |
| LOC284361 | 284361 | NM_175063 | W |
| LOC284371 | 284371 | XM_209155 | M |
| LOC284390 | 284390 | XM_371138 | W |
| LOC284661 | 284661 | XM_378832 | W |
| LOC284739 | 284739 | NM_207349 | W |
| LOC284825 | 284825 | XM_375935 | W |
| LOC285194 | 285194 | XM_379207 | W |
| LOC285248 | 0 | XM_211816 | W |
| LOC285636 | 285636 | NM_175921 | M |
| LOC285671 | 285671 | NM_178532 | M |
| LOC286076 | 286076 | XM_209889 | S |
| LOC338734 | 0 | XM_290547 | W |
| LOC338750 | 338750 | XM_291974 | M |
| LOC338756 | 0 | XM_291989 | W |
| LOC338829 | 338829 | XM_292122 | M |
| LOC339951 | 339951 | XM_293656 | M |
| LOC340109 | 340109 | XM_379322 | W |
| LOC340318 | 340318 | XM_290401 | M |
| LOC340591 | 340591 | XM_291346 | M |
| LOC340765 | 340765 | XM_291704 | M |
| LOC341356 | 0 | XM_292023 | W |
| LOC343578 | 343578 | XM_293123 | S |
| LOC345643 | 345643 | XM_293918 | S |
| LOC345651 | 0 | XM_293924 | W |
| LOC345711 | 345711 | XM_293937 | M |
| LOC347454 | 347454 | XM_293380 | S |
| LOC375133 | 375133 | NM_199345 | W |
| LOC375295 | 375295 | XM_374020 | M |
| LOC386597 | 386597 | XM_379073 | W |
| LOC387761 | 387761 | XM_373495 | S |
| LOC387784 | 0 | XM_373506 | W |
| LOC387810 | 0 | XM_373513 | W |
| LOC387825 | 0 | XM_370668 | W |
| LOC387845 | 0 | XM_370684 | W |
| LOC387914 | 0 | XM_370718 | W |
| LOC388298 | 0 | XM_370992 | W |
| LOC388381 | 388381 | XM_371053 | M |
| LOC388418 | 388418 | XM_373748 | M |
| LOC388432 | 0 | XM_371086 | W |
| LOC388469 | 388469 | XM_371111 | M |
| LOC388585 | 0 | XM_371215 | W |
| LOC388697 | 0 | XM_373868 | W |
| LOC388807 | 388807 | XM_373922 | M |
| LOC388847 | 388847 | XM_371424 | M |
| LOC389000 | 0 | XM_371534 | W |
| LOC389067 | 0 | XM_374021 | W |
| LOC389070 | 0 | XM_374022 | W |
| LOC389102 | 0 | XM_371623 | W |
| LOC389107 | 389107 | XM_371626 | M |
| LOC389153 | 0 | XM_374053 | W |
| LOC389224 | 389224 | XM_374086 | S |
| LOC389273 | 0 | XM_374115 | W |
| LOC389319 | 389319 | XM_374134 | M |
| LOC389370 | 0 | XM_374162 | W |
| LOC389386 | 0 | XM_371818 | W |
| LOC389416 | 0 | XM_371837 | W |
| LOC389541 | 0 | XM_371939 | W |
| LOC389705 | 389705 | XM_372076 | M |
| LOC389727 | 0 | XM_372092 | W |
| LOC389753 | 0 | XM_372112 | W |
| LOC389950 | 0 | XM_372307 | W |
| LOC390377 | 0 | XM_372486 | W |
| LOC390530 | 390530 | XM_372543 | M |
| LOC390734 | 390734 | XM_372640 | M |

TABLE 2-continued

| GeneSymbol | EntrezGeneID | Genbank Acc. No. | NFAT Score |
|---|---|---|---|
| LOC391209 | 0 | XM_372840 | W |
| LOC391426 | 391426 | XM_372950 | M |
| LOC392549 | 392549 | XM_373373 | M |
| LOC392702 | 0 | XM_374730 | W |
| LOC392726 | 0 | XM_374734 | W |
| LOC392791 | 0 | XM_374752 | W |
| LOC399786 | 0 | XM_378236 | W |
| LOC399920 | 0 | XM_378300 | W |
| LOC399959 | 399959 | XM_378316 | M |
| LOC399968 | 399968 | XM_374945 | M |
| LOC400047 | 400047 | XM_378363 | S |
| LOC400092 | 0 | XM_378398 | W |
| LOC400479 | 0 | XM_375282 | W |
| LOC400619 | 0 | XM_378703 | W |
| LOC400622 | 400622 | XM_375491 | M |
| LOC400687 | 400687 | XM_375602 | S |
| LOC400688 | 400688 | XM_375603 | M |
| LOC400740 | 0 | XM_378840 | W |
| LOC400877 | 400877 | XM_379025 | M |
| LOC400939 | 400939 | XM_379072 | S |
| LOC401155 | 401155 | XM_379276 | S |
| LOC401169 | 0 | XM_379306 | W |
| LOC401175 | 0 | XM_379317 | W |
| LOC401286 | 0 | XM_376555 | W |
| LOC401293 | 401293 | XM_376558 | M |
| LOC401314 | 0 | XM_376586 | W |
| LOC401316 | 0 | XM_376587 | W |
| LOC401317 | 0 | XM_379479 | W |
| LOC401321 | 0 | XM_379483 | W |
| LOC401322 | 401322 | XM_376591 | M |
| LOC401518 | 0 | XM_379638 | W |
| LOC401548 | 0 | XM_376902 | W |
| LOC401552 | 0 | XM_379668 | W |
| LOC401624 | 401624 | XM_377073 | M |
| LOC401720 | 401720 | XM_377265 | M |
| LOC401778 | 401778 | XM_377343 | M |
| LOC402148 | 0 | XM_377818 | W |
| LOC402251 | 402251 | XM_377933 | M |
| LOC402382 | 402382 | XM_378090 | S |
| LOC402477 | 0 | XM_379803 | W |
| LOC402515 | 0 | XM_380112 | W |
| LOC402521 | 0 | XM_379848 | W |
| LOC402537 | 0 | XM_380120 | W |
| LOC402556 | 0 | XM_379877 | W |
| LOC402560 | 0 | XM_380127 | W |
| LOC402586 | 0 | XM_380138 | W |
| LOC402587 | 0 | XM_380139 | W |
| LOC402625 | 0 | XM_379975 | W |
| LOC402641 | 0 | XM_379995 | W |
| LOC404785 | 404785 | NM_207513 | W |
| LOC51054 | 51054 | NM_015899 | W |
| LOC51066 | 51066 | NM_015931 | W |
| LOC51333 | 51333 | NM_016643 | W |
| LOC51693 | 51693 | NM_016209 | W |
| LOC57168 | 57168 | NM_020437 | M |
| LOC88523 | 88523 | NM_033111 | S |
| LOC90120 | 90120 | XM_379680 | M |
| LOC92689 | 92689 | NM_138389 | W |
| LOC96597 | 96597 | XM_378655 | W |
| LOR | 4014 | NM_000427 | W |
| LPO | 4025 | NM_006151 | W |
| LTBP3 | 4054 | NM_021070 | W |
| LU | 4059 | NM_005581 | W |
| LXNX1 | 66004 | NM_177477 | M |
| LXZL1 | 84569 | NM_032517 | M |
| LY64 | 4064 | NM_005582 | W |
| M96 | 22823 | NM_007358 | W |
| MAD2L2 | 10459 | NM_006341 | W |
| MAGEL2 | 54551 | NM_019066 | W |
| MAP4 | 4134 | NM_002375 | M |
| MAPBPIP | 28956 | NM_014017 | S |
| MAPK13 | 5603 | NM_002754 | W |
| MAPRE2 | 10982 | NM_014268 | W |
| MASP1 | 5648 | NM_001879 | W |
| MBP | 4155 | NM_002385 | M |
| MBTPS2 | 51360 | NM_015884 | W |
| MC4R | 4160 | NM_005912 | W |
| MCC | 4163 | NM_002387 | W |

TABLE 2-continued

| GeneSymbol | EntrezGeneID | Genbank Acc. No. | NFAT Score |
|---|---|---|---|
| MCRS1 | 10445 | NM_006337 | W |
| MDGA1 | 266727 | NM_153487 | W |
| MDH1B | 130752 | XM_059468 | W |
| MDS1 | 4197 | NM_004991 | S |
| MED19 | 219541 | NM_153450 | M |
| MEF2A | 4205 | NM_005587 | W |
| MEF2B | 4207 | NM_005919 | W |
| MET | 4233 | NM_000245 | M |
| MFSD11 | 79157 | NM_024311 | W |
| MFSD3 | 113655 | NM_138431 | S |
| MGAT4B | 11282 | NM_014275 | M |
| MGC11266 | 79172 | NM_024322 | M |
| MGC14126 | 84984 | NM_032898 | W |
| MGC15882 | 84970 | NM_032884 | M |
| MGC16279 | 85002 | NM_032916 | M |
| MGC16372 | 92749 | NM_145038 | W |
| MGC16491 | 115572 | NM_052943 | M |
| MGC16597 | 339230 | XM_375500 | W |
| MGC17337 | 91283 | NM_080655 | W |
| MGC21394 | 404203 | NM_205841 | W |
| MGC23918 | 151903 | NM_144716 | W |
| MGC23937 | 139596 | NM_145052 | W |
| MGC26856 | 256710 | NM_152779 | W |
| MGC2941 | 79142 | NM_024297 | M |
| MGC33584 | 285971 | NM_173680 | M |
| MGC33887 | 201134 | NM_145036 | M |
| MGC39633 | 153733 | NM_152549 | W |
| MGC39696 | 255193 | NM_152771 | M |
| MGC41945 | 138724 | NM_203299 | W |
| MGC4238 | 84292 | NM_032332 | W |
| MGC4734 | 138065 | NM_145051 | M |
| MGC50559 | 254013 | NM_173802 | W |
| MGC52000 | 375260 | NM_198943 | W |
| MGC87042 | 256227 | NM_207342 | M |
| MICAL3 | 57553 | XM_032997 | W |
| MIG12 | 58526 | NM_021242 | W |
| MIRAB13 | 85377 | NM_033386 | W |
| MLL | 4297 | NM_005933 | M |
| MLL4 | 9757 | NM_014727 | M |
| MLR2 | 84458 | XM_050988 | M |
| MLSTD1 | 55711 | NM_018099 | M |
| MMP24 | 10893 | NM_006690 | W |
| MO25 | 51719 | NM_016289 | W |
| MORF4L1 | 10933 | NM_006791 | W |
| MRC2 | 9902 | NM_006039 | W |
| MRPL48 | 51642 | NM_016055 | W |
| MRPS21 | 54460 | NM_018997 | W |
| MRPS6 | 64968 | NM_032476 | M |
| MRS2L | 57380 | NM_020662 | M |
| MSL3L1 | 10943 | NM_078628 | S |
| MT1A | 4489 | NM_005946 | W |
| MTFMT | 123263 | NM_139242 | W |
| MTMR6 | 9107 | NM_004685 | S |
| MTMR9 | 66036 | NM_015458 | W |
| MTRF1L | 54516 | NM_019041 | W |
| MYADM | 91663 | NM_138373 | M |
| MYBL2 | 4605 | NM_002466 | M |
| MYC | 4609 | NM_002467 | M |
| MYH1 | 4619 | NM_005963 | W |
| MYLIP | 29116 | NM_013262 | W |
| MYO5C | 55930 | NM_018728 | W |
| MYO9A | 4649 | NM_006901 | M |
| MYST3 | 7994 | NM_006766 | W |
| NAP1L4 | 4676 | NM_005969 | W |
| NAPA | 8775 | NM_003827 | M |
| NAPG | 8774 | NM_003826 | W |
| NBPF10 | 388776 | XM_371384 | M |
| NCB5OR | 51167 | NM_016230 | W |
| NCBP2 | 22916 | NM_007362 | M |
| NCF4 | 4689 | NM_000631 | W |
| NCOA5 | 57727 | NM_020967 | W |
| NDEL1 | 81565 | NM_030808 | W |
| NDRG1 | 10397 | NM_006096 | M |
| NDUFA5 | 4698 | NM_005000 | M |
| NDUFB9 | 4715 | NM_005005 | W |
| NDUFC1 | 4717 | NM_002494 | W |
| NDUFS1 | 4719 | NM_005006 | W |
| NDUFS6 | 4726 | NM_004553 | W |
| NEBL | 10529 | NM_006393 | M |
| NET-5 | 10867 | NM_006675 | W |
| NEU4 | 129807 | NM_080741 | W |
| NEURL | 9148 | NM_004210 | S |
| NFATC2 | 4773 | NM_012340 | W |
| NFKB2 | 4791 | NM_002502 | W |
| NFS1 | 9054 | NM_021100 | W |
| NHLH2 | 4808 | NM_005599 | W |
| NIPA | 51530 | NM_016478 | S |
| NIPA2 | 81614 | NM_030922 | S |
| NOLC1 | 9221 | NM_004741 | M |
| NOPE | 57722 | NM_020962 | W |
| NPEPPS | 9520 | NM_006310 | M |
| NPFF | 8620 | NM_003717 | W |
| NPY2R | 4887 | NM_000910 | W |
| NPY5R | 4889 | NM_006174 | W |
| NRAS | 4893 | NM_002524 | M |
| NRM | 11270 | NM_007243 | W |
| NUCB1 | 4924 | NM_006184 | W |
| NUP107 | 57122 | NM_020401 | W |
| NUP133 | 55746 | NM_018230 | W |
| NUP160 | 23279 | XM_113678 | S |
| NUP205 | 23165 | XM_058073 | M |
| NUP54 | 53371 | NM_017426 | M |
| NUP62 | 23636 | NM_012346 | S |
| NUP93 | 9688 | NM_014669 | M |
| NUPL1 | 9818 | NM_014089 | M |
| NXD-TSP1 | 84654 | NM_032567 | M |
| NXF2 | 56001 | NM_017809 | W |
| NXF5 | 55998 | NM_032946 | W |
| NXT1 | 29107 | NM_013248 | W |
| NYD-SP28 | 85478 | NM_033124 | W |
| OFD1 | 8481 | NM_003611 | W |
| OKL38 | 29948 | NM_013370 | M |
| OPN3 | 23596 | NM_014322 | W |
| OR2A2 | 442361 | NM_001005480 | M |
| OR2B3 | 442184 | NM_001005226 | S |
| OR3A4 | 390756 | NM_001005334 | W |
| OR4A5 | 81318 | NM_001005272 | W |
| OR4K15 | 81127 | NM_001005486 | M |
| OR5B2 | 390190 | NM_001005566 | W |
| OR5K4 | 403278 | NM_001005517 | S |
| OR5M11 | 219487 | NM_001005245 | W |
| OR6C74 | 254783 | NM_001005490 | W |
| Orai1 | 84876 | NM_032790 | M |
| ORC3L | 23595 | NM_012381 | W |
| OSM | 5008 | NM_020530 | M |
| OSTM1 | 28962 | NM_014028 | S |
| OTOR | 56914 | NM_020157 | W |
| P4HA2 | 8974 | NM_004199 | S |
| PADI3 | 51702 | NM_016233 | W |
| PAGE-5 | 90737 | NM_130467 | W |
| PAI-RBP1 | 26135 | NM_015640 | W |
| PAK1IP1 | 55003 | NM_017906 | W |
| PAQR10 | 221938 | NM_198403 | W |
| PASD1 | 139135 | NM_173493 | M |
| PAWR | 5074 | NM_002583 | W |
| PAX2 | 5076 | NM_000278 | M |
| PCBP1 | 5093 | NM_006196 | W |
| PCDH11X | 83259 | NM_032971 | M |
| PCDH11X | 27328 | NM_014522 | S |
| PCDHB13 | 56123 | NM_018933 | M |
| PCDHGB7 | 56099 | NM_018927 | S |
| PCNP | 57092 | NM_020357 | W |
| PCOLCE | 5118 | NM_002593 | W |
| PCOLN3 | 5119 | NM_002768 | S |
| PDCD1LG2 | 80380 | NM_025239 | S |
| PDE6A | 5145 | NM_000440 | W |
| PDF | 64146 | NM_022341 | W |
| PDHA2 | 5161 | NM_005390 | W |
| PDP2 | 57546 | NM_020786 | W |
| PELO | 53918 | NM_015946 | S |
| PEPP3 | 22874 | NM_014935 | M |
| PERLD1 | 93210 | NM_033419 | W |
| PEX11A | 8800 | NM_003847 | S |
| PEX11G | 92960 | NM_080662 | M |
| PEX26 | 55670 | NM_017929 | W |
| PEX3 | 8504 | NM_003630 | M |

TABLE 2-continued

| GeneSymbol | EntrezGeneID | Genbank Acc. No. | NFAT Score |
|---|---|---|---|
| PFKFB3 | 5209 | NM_004566 | W |
| PHF13 | 148479 | NM_153812 | W |
| PHF17 | 79960 | NM_024900 | M |
| PHF2 | 5253 | NM_005392 | M |
| PHYHIPL | 84457 | NM_032439 | W |
| PIGW | 284098 | NM_178517 | W |
| PIK3CB | 5291 | NM_006219 | S |
| PIK3R2 | 5296 | NM_005027 | S |
| PIK3R3 | 8503 | NM_003629 | W |
| PIK4CA | 5297 | NM_002650 | M |
| PIK4CB | 5298 | NM_002651 | W |
| PILRA | 29992 | NM_013439 | S |
| PIPOX | 51268 | NM_016518 | W |
| PIPPIN | 27254 | NM_014460 | S |
| PJA1 | 64219 | NM_022368 | M |
| PKD1L1 | 168507 | NM_138295 | W |
| PLA2G4D | 283748 | NM_178034 | M |
| PLAC8 | 51316 | NM_016619 | M |
| PMCA4 | 493 | NM_001684 | W |
| PMCH | 5367 | NM_002674 | M |
| PNLIP | 5406 | NM_000936 | W |
| PNLIPRP1 | 5407 | NM_006229 | W |
| PNUTL2 | 5414 | NM_004574 | S |
| POLG | 5428 | NM_002693 | M |
| POLH | 5429 | NM_006502 | M |
| PON3 | 5446 | NM_000940 | M |
| PPP1R13B | 23368 | NM_015316 | M |
| PPP1R9B | 84687 | NM_032595 | M |
| PPP3CA | 5530 | NM_000944 | S |
| PPP3R1 | 5534 | NM_000945 | M |
| PRDX3 | 10935 | NM_006793 | W |
| PRKACA | 5566 | NM_002730 | W |
| PRKWNK2 | 65268 | NM_006648 | M |
| PROK1 | 84432 | NM_032414 | W |
| PROL5 | 26952 | NM_012390 | W |
| PRPS1L1 | 221823 | NM_175886 | W |
| PRPSAP2 | 5636 | NM_002767 | S |
| PRRT1 | 80863 | NM_030651 | M |
| PRSS1 | 5644 | NM_002769 | M |
| PSG3 | 5671 | NM_021016 | W |
| PTD004 | 29789 | NM_013341 | W |
| PTD008 | 51398 | NM_016145 | M |
| PTPN13 | 5783 | NM_006264 | M |
| PTRH1 | 138428 | XM_059972 | W |
| PTX1 | 51290 | NM_016570 | W |
| PXGO1 | 26108 | NM_015617 | M |
| PXK | 54899 | NM_017771 | M |
| QP-C | 27089 | NM_014402 | S |
| RABGAP1 | 23637 | NM_012197 | W |
| RABGGTB | 5876 | NM_004582 | S |
| RABL2A | 11159 | NM_007082 | W |
| RAD9B | 144715 | NM_152442 | S |
| RAI14 | 26064 | NM_015577 | S |
| RAN | 5901 | NM_006325 | S |
| RANBP2 | 5903 | NM_006267 | W |
| RANBP2L1 | 84220 | NM_005054 | M |
| RAP1GA1 | 5909 | NM_002885 | M |
| RASD2 | 23551 | NM_014310 | W |
| RASL10B | 91608 | NM_033315 | W |
| RBM27 | 54439 | XM_291128 | W |
| RBM5 | 10181 | NM_005778 | W |
| RCE1 | 9986 | NM_005133 | W |
| RCOR1 | 23186 | NM_015156 | M |
| RDH12 | 145226 | NM_152443 | W |
| RDH5 | 5959 | NM_002905 | W |
| REPIN1 | 29803 | NM_013400 | W |
| REV3L | 5980 | NM_002912 | M |
| RFPL3 | 10738 | NM_006604 | W |
| RGS7 | 6000 | NM_002924 | M |
| RIOK3 | 8780 | NM_003831 | M |
| RKHD2 | 51320 | NM_016626 | M |
| RLN3 | 117579 | NM_080864 | M |
| RNF13 | 11342 | NM_007282 | W |
| RNF159 | 84333 | NM_032373 | M |
| RNF185 | 91445 | NM_152267 | M |
| RNF32 | 140545 | NM_030936 | M |
| RNPEPL1 | 57140 | NM_018226 | M |
| RORB | 6096 | NM_006914 | W |

TABLE 2-continued

| GeneSymbol | EntrezGeneID | Genbank Acc. No. | NFAT Score |
|---|---|---|---|
| RP26 | 375298 | NM_201548 | W |
| RPGR | 6103 | NM_000328 | S |
| RPIB9 | 154661 | NM_138290 | W |
| RPL3L | 6123 | NM_005061 | W |
| RPS6KA2 | 6196 | NM_021135 | W |
| RRAS2 | 22800 | NM_012250 | M |
| RRH | 10692 | NM_006583 | W |
| RRM2 | 6241 | NM_001034 | M |
| RX1 | 11017 | NM_006857 | S |
| SAA2 | 6289 | NM_030754 | W |
| SALPR | 51289 | NM_016568 | W |
| SAST | 22983 | NM_014975 | M |
| SATB1 | 6304 | NM_002971 | W |
| SCA7 | 6314 | NM_000333 | W |
| SCFD1 | 23256 | NM_016106 | M |
| SCG3 | 29106 | NM_013243 | W |
| SCML1 | 6322 | NM_006746 | M |
| SEC13L1 | 6396 | NM_030673 | S |
| SEC22L1 | 9554 | NM_004892 | W |
| SECISBP2 | 79048 | NM_024077 | W |
| SELENBP1 | 8991 | NM_003944 | S |
| SENP1 | 29843 | NM_014554 | W |
| SENP6 | 26054 | NM_015571 | S |
| SENP7 | 57337 | NM_020654 | W |
| SENP8 | 123228 | NM_145204 | W |
| SERPINA12 | 145264 | NM_173850 | M |
| SERPINA9 | 327657 | NM_175739 | M |
| SERPINB1 | 1992 | NM_030666 | M |
| SERPINE1 | 5054 | NM_000602 | M |
| SEZ6L | 23544 | NM_021115 | W |
| SF4 | 57794 | NM_172231 | W |
| SFPQ | 6421 | NM_005066 | M |
| SFRS2 | 6427 | NM_003016 | M |
| SFRS3 | 6428 | NM_003017 | S |
| SFRS7 | 6432 | NM_006276 | W |
| SFT2D1 | 113402 | NM_145169 | S |
| SFXN5 | 94097 | NM_144579 | M |
| SHD | 56961 | NM_020209 | W |
| SIAHBP1 | 22827 | NM_014281 | M |
| SIGLEC8 | 27181 | NM_014442 | S |
| SIRT7 | 51547 | NM_016538 | S |
| SKIP | 51763 | NM_016532 | S |
| SLAMF6 | 114836 | NM_052931 | W |
| SLC12A9 | 56996 | NM_020246 | W |
| SLC22A1LS | 5003 | NM_007105 | W |
| SLC25A23 | 79085 | NM_024103 | W |
| SLC25A3 | 5250 | NM_002635 | M |
| SLC30A5 | 64924 | NM_022902 | S |
| SLC36A1 | 206358 | NM_078483 | W |
| SLC38A6 | 145389 | NM_153811 | M |
| SLC41A3 | 54946 | NM_017836 | M |
| SLC6A14 | 11254 | NM_007231 | W |
| SLC6A2 | 6530 | NM_001043 | W |
| SLC6A4 | 6532 | NM_001045 | W |
| SLCO2B1 | 11309 | NM_007256 | S |
| SMAD2 | 4087 | NM_005901 | M |
| SMARCD3 | 6604 | NM_003078 | M |
| SMC5L1 | 23137 | NM_015110 | M |
| SMG1 | 23049 | NM_014006 | W |
| SMOC2 | 64094 | NM_022138 | W |
| SNAP23 | 8773 | NM_003825 | W |
| SNRP70 | 6625 | NM_003089 | M |
| SNRPC | 6631 | NM_003093 | S |
| SNX27 | 81609 | NM_030918 | W |
| SOX8 | 30812 | NM_014587 | S |
| SP4 | 6671 | NM_003112 | W |
| SPINK4 | 27290 | NM_014471 | W |
| SPINT1 | 6692 | NM_003710 | W |
| SPTLC2 | 9517 | NM_004863 | S |
| SR140 | 23350 | XM_031553 | W |
| SREBF1 | 6720 | NM_004176 | M |
| SRP46 | 10929 | NM_032102 | M |
| SSA2 | 6738 | NM_004600 | W |
| SSTR2 | 6752 | NM_001050 | W |
| SSTR4 | 6754 | NM_001052 | W |
| SSX1 | 6756 | NM_005635 | W |
| STAM | 8027 | NM_003473 | M |
| STAMBPL1 | 57559 | NM_020799 | W |

TABLE 2-continued

| GeneSymbol | EntrezGeneID | Genbank Acc. No. | NFAT Score |
|---|---|---|---|
| STEAP | 26872 | NM_012449 | W |
| STIM1 | 6786 | NM_003156 | S |
| STIM2 | 57620 | NM_020860 | M |
| STOML1 | 9399 | NM_004809 | W |
| STOML2 | 30968 | NM_013442 | W |
| STX18 | 53407 | NM_016930 | M |
| STXBP2 | 6813 | NM_006949 | M |
| SULT1C2 | 27233 | NM_006588 | W |
| SUMO2 | 6613 | NM_006937 | W |
| SV2C | 22987 | XM_043493 | S |
| SYCP1 | 6847 | NM_003176 | W |
| SYNCRIP | 10492 | NM_006372 | W |
| SYNE2 | 23224 | NM_015180 | W |
| SYT15 | 83849 | NM_181519 | S |
| SYTL4 | 94121 | NM_080737 | W |
| T2BP | 92610 | NM_052864 | M |
| TAB3 | 257397 | NM_152787 | W |
| TAS2R45 | 259291 | NM_176886 | W |
| TBCC | 6903 | NM_003192 | W |
| TBK1 | 29110 | NM_013254 | M |
| TCEB2 | 6923 | NM_007108 | S |
| TDRKH | 11022 | NM_006862 | M |
| TESK2 | 10420 | NM_007170 | W |
| TEX13B | 56156 | NM_031273 | W |
| TEX14 | 56155 | NM_031272 | M |
| TFCP2L3 | 79977 | NM_024915 | M |
| TFPI2 | 7980 | NM_006528 | S |
| TGIF2LX | 90655 | NM_139214 | W |
| TGM3 | 7053 | NM_003245 | W |
| THG-1 | 81628 | NM_030935 | M |
| TIMELESS | 8914 | NM_003920 | W |
| TIPARP | 25976 | NM_015508 | M |
| TLR6 | 10333 | NM_006068 | M |
| TMEM11 | 8834 | NM_003876 | W |
| TMEM110 | 375346 | NM_198563 | S |
| TMEM14C | 51522 | NM_016462 | W |
| TMEM187 | 8269 | NM_003492 | W |
| TMEM199 | 147007 | NM_152464 | W |
| TMEM43 | 79188 | NM_024334 | S |
| TMEM63B | 55362 | XM_371822 | W |
| TMP21 | 10972 | NM_006827 | M |
| TNFRSF13C | 115650 | NM_052945 | W |
| TNFRSF18 | 8784 | NM_004195 | M |
| TNFSF13B | 10673 | NM_006573 | W |
| TNIK | 23043 | XM_039796 | S |
| TNKS1BP1 | 85456 | NM_033396 | W |
| TNXB | 7148 | NM_019105 | W |
| TOE1 | 114034 | NM_025077 | M |
| TOLLIP | 54472 | NM_019009 | W |
| TOR1AIP2 | 163590 | NM_145034 | W |
| TORC3 | 64784 | NM_022769 | W |
| TPTE | 7179 | NM_013315 | M |
| TRAPPC1 | 58485 | NM_021210 | M |
| TRIM22 | 10346 | NM_006074 | W |
| TRIM3 | 10612 | NM_006458 | M |
| TRIM33 | 51592 | NM_015906 | W |
| TRIM59 | 286827 | NM_173084 | M |
| TRNT1 | 51095 | NM_016000 | M |
| TROAP | 10024 | NM_005480 | S |
| TSPAN-1 | 10103 | NM_005727 | W |
| TULP1 | 7287 | NM_003322 | W |
| TULP4 | 56995 | NM_020245 | W |
| TXK | 7294 | NM_003328 | M |
| TXMS | 7298 | NM_001071 | W |
| TXNDC | 81542 | NM_030755 | W |
| TXNDC15 | 79770 | NM_024715 | S |
| TXNRD2 | 10587 | NM_006440 | W |
| UAP1 | 6675 | NM_003115 | W |
| UBAP1 | 51271 | NM_016525 | M |
| UBC | 7316 | NM_021009 | M |
| UBE2L6 | 9246 | NM_004223 | W |
| UEV3 | 55293 | NM_018314 | S |
| UFM1 | 51569 | NM_016617 | W |
| UHSKERB | 57830 | NM_021046 | S |
| UMPS | 7372 | NM_000373 | M |
| UNQ2446 | 123904 | NM_198443 | W |
| UNQ2492 | 377841 | NM_198585 | W |
| UNQ3033 | 284415 | NM_198481 | W |
| UNQ9370 | 400454 | NM_207447 | W |
| UPF3B | 65109 | NM_023010 | W |
| USP13 | 8975 | NM_003940 | M |
| VAX2 | 25806 | NM_012476 | M |
| VCX2 | 51480 | NM_016378 | M |
| VEST1 | 116328 | NM_052958 | W |
| VGF | 7425 | NM_003378 | M |
| VGLL2 | 245806 | NM_153453 | W |
| VMP | 140767 | NM_080723 | S |
| VN1R4 | 317703 | NM_173857 | W |
| VPS13A | 23230 | NM_015186 | W |
| VPS28 | 51160 | NM_016208 | M |
| VPS35 | 55737 | NM_018206 | W |
| WARP | 64856 | NM_022834 | W |
| WFDC3 | 140686 | NM_181522 | W |
| WNT7B | 7477 | NM_058238 | W |
| WRNIP1 | 56897 | NM_020135 | S |
| XKR5 | 389610 | NM_207411 | M |
| XKRX2 | 353515 | NM_001002906 | M |
| XKRY | 9082 | NM_004677 | S |
| XPO7 | 23039 | NM_015024 | M |
| XYLT2 | 64132 | NM_022167 | W |
| YIPF3 | 25844 | NM_015388 | M |
| ZADH1 | 145482 | NM_152444 | M |
| ZAK | 51776 | NM_133646 | W |
| ZBTB2 | 57621 | NM_020861 | W |
| ZBTB7 | 51341 | NM_015898 | W |
| ZCCHC8 | 55596 | NM_017612 | W |
| ZDHHC2 | 51201 | NM_016353 | M |
| ZFP28 | 140612 | NM_020828 | W |
| ZFP67 | 51043 | NM_015872 | W |
| ZFR | 51663 | NM_016107 | W |
| ZNF143 | 7702 | NM_003442 | M |
| ZNF148 | 7707 | NM_021964 | S |
| ZNF157 | 7712 | NM_003446 | M |
| ZNF192 | 7745 | NM_006298 | W |
| ZNF267 | 10308 | NM_003414 | M |
| ZNF289 | 84364 | NM_032389 | S |
| ZNF295 | 49854 | NM_020727 | W |
| ZNF297B | 23099 | NM_014007 | W |
| ZNF304 | 57343 | NM_020657 | W |
| ZNF324 | 25799 | NM_014347 | W |
| ZNF334 | 55713 | NM_018102 | W |
| ZNF342 | 162979 | NM_145288 | S |
| ZNF354C | 30832 | NM_014594 | W |
| ZNF496 | 84838 | NM_032752 | W |
| ZNF501 | 115560 | NM_145044 | W |
| ZNF503 | 84858 | NM_032772 | W |
| ZNF512 | 84450 | NM_032434 | M |
| ZNF544 | 27300 | NM_014480 | W |
| ZNF568 | 374900 | NM_198539 | M |
| ZNF570 | 148268 | NM_144694 | W |
| ZNF615 | 284370 | NM_198480 | W |
| ZNF706 | 51123 | NM_016096 | M |
| ZNFN1A4 | 64375 | NM_022465 | M |
| ZNRD1 | 30834 | NM_014596 | W |
| ZSWIM1 | 90204 | NM_080603 | M |
| ZYX | 7791 | NM_003461 | M |
| ZZEF1 | 23140 | NM_015113 | S |
| ZZZ3 | 26009 | NM_015534 | M |

TABLE 3

| GeneSymbol | EntrezGeneID | Genbank Acc. No. | NFAT Score | Calcium Hit |
|---|---|---|---|---|
| ABCC13 | 150000 | NM_138726 | M | |
| ACSBG1 | 23205 | NM_015162 | S | X |
| ACTB | 60 | NM_001101 | M | X |
| ADAMTS5 | 11096 | NM_007038 | M | |
| AFG3L1 | 172 | NM_001132 | M | X |
| AKR1CL2 | 83592 | NM_031436 | M | |
| ALCAM | 214 | NM_001627 | M | X |
| ANKRD58 | 347454 | XM_293380 | S | |

TABLE 3-continued

| GeneSymbol | EntrezGeneID | Genbank Acc. No. | NFAT Score | Cal-cium Hit |
|---|---|---|---|---|
| ANKRD9 | 122416 | NM_152326 | M | |
| ANTXRL | 195977 | XM_113625 | S | |
| APH1A | 51107 | NM_016022 | M | |
| APOL4 | 80832 | NM_030643 | M | |
| ARCN1 | 372 | NM_001655 | S | |
| ARL5C | 390790 | XM_372668 | M | X |
| AS3MT | 57412 | NM_020682 | S | |
| ASB4 | 51666 | NM_016116 | S | |
| ASPHD2 | 57168 | NM_020437 | M | |
| ATN1 | 1822 | NM_001940 | M | X |
| ATP5L2 | 267020 | NM_198822 | M | X |
| ATP6V0D1 | 9114 | NM_004691 | M | X |
| ATP6V1D | 51382 | NM_015994 | M | |
| BCDIN3 | 56257 | NM_019606 | M | |
| BGN | 633 | NM_001711 | M | |
| BMP4 | 652 | NM_001202 | S | |
| BREA2 | 286076 | XM_209889 | S | |
| BRP44L | 51660 | NM_016098 | M | |
| C10orf53 | 282966 | NM_182554 | M | |
| C10orf56 | 219654 | NM_153367 | M | |
| C12orf49 | 79794 | NM_024738 | S | |
| C19orf34 | 255193 | NM_152771 | M | |
| C19orf56 | 51398 | NM_016145 | M | |
| C1orf123 | 54987 | NM_017887 | M | X |
| C1orf77 | 26097 | NM_015607 | M | |
| C20orf95 | 343578 | XM_293123 | S | |
| C20orf96 | 140680 | NM_153269 | M | X |
| C21orf49 | 54067 | NM_001006116 | S | |
| C4orf27 | 54969 | NM_017867 | S | |
| C4orf30 | 54876 | NM_017741 | M | |
| C5orf14 | 79770 | NM_024715 | S | |
| C6orf115 | 58527 | XM_371848 | M | |
| C6orf191 | 253582 | XM_173166 | S | X |
| C8orf42 | 157695 | NM_175075 | S | X |
| C9orf11 | 54586 | XM_035953 | M | |
| C9orf138 | 158297 | NM_153707 | M | |
| C9orf71 | 169693 | XM_376874 | M | |
| C9orf72 | 203228 | NM_018325 | S | |
| CA5BL | 340591 | XM_291346 | M | |
| CASC1 | 55259 | NM_018272 | S | |
| CBLL1 | 79872 | NM_024814 | S | |
| CCDC11 | 220136 | NM_145020 | M | |
| CCDC125 | 202243 | NM_176816 | M | X |
| CCDC46 | 201134 | NM_145036 | M | |
| CCDC49 | 54883 | NM_017748 | M | |
| CCDC50 | 152137 | NM_174908 | M | |
| CCDC85B | 11007 | NM_006848 | S | |
| CCK | 885 | NM_000729 | M | |
| CCL11 | 6356 | NM_002986 | M | |
| CCNB2 | 9133 | NM_004701 | S | X |
| CCNK | 8812 | NM_003858 | M | |
| CDC27 | 996 | NM_001256 | S | |
| CDC2L5 | 8621 | NM_003718 | M | |
| CENPO | 79172 | NM_024322 | M | |
| CHMP1A | 5119 | NM_002768 | S | |
| CHST14 | 113189 | NM_130468 | S | |
| CIRBP | 1153 | NM_001280 | M | |
| CLDN22 | 53842 | XM_210581 | S | |
| CLEC4M | 10332 | NM_014257 | M | |
| CLPS | 1208 | NM_001832 | M | |
| CMAS | 55907 | NM_018686 | M | |
| CNTN3 | 5067 | XM_039627 | M | X |
| COL20A1 | 57642 | NM_020882 | M | |
| COPA | 1314 | NM_004371 | S | X |
| COPB1 | 1315 | NM_016451 | S | X |
| COPB2 | 9276 | NM_004766 | S | X |
| COPE | 11316 | NM_007263 | S | X |
| COPG | 22820 | NM_016128 | S | X |
| COPZ1 | 22818 | NM_016057 | S | X |
| CPEB4 | 80315 | NM_030627 | S | X |
| CPT2 | 1376 | NM_000098 | M | X |
| CRLF3 | 51379 | NM_015986 | M | |
| CYP2S1 | 29785 | NM_030622 | S | |
| DDX53 | 168400 | NM_182699 | M | |
| DENND1C | 79958 | NM_024898 | M | |
| DGCR6L | 85359 | NM_033257 | M | |

TABLE 3-continued

| GeneSymbol | EntrezGeneID | Genbank Acc. No. | NFAT Score | Cal-cium Hit |
|---|---|---|---|---|
| DHRS4 | 10901 | NM_021004 | M | |
| DHRS4L2 | 317749 | NM_198083 | M | |
| DHRS9 | 10170 | NM_005771 | M | |
| DIABLO | 56616 | NM_019887 | S | |
| DISP2 | 85455 | NM_033510 | M | |
| DKFZP686A01247 | 22998 | XM_044461 | M | X |
| DNAJC5G | 285126 | NM_173650 | M | X |
| DONSON | 29980 | NM_145794 | M | |
| DSEL | 92126 | NM_032160 | M | |
| DSG4 | 147409 | NM_177986 | M | |
| DUSP12 | 11266 | NM_007240 | M | |
| EHD2 | 30846 | NM_014601 | M | |
| ELMOD1 | 55531 | NM_018712 | S | X |
| EPO | 2056 | NM_000799 | M | |
| ERBB4 | 2066 | NM_005235 | M | |
| F11R | 50848 | NM_016946 | M | |
| FAM105A | 54491 | NM_019018 | M | |
| FAM108C1 | 58489 | XM_051862 | S | X |
| FAM46B | 115572 | NM_052943 | M | |
| FAS | 355 | NM_000043 | S | X |
| FASTKD5 | 60493 | NM_021826 | M | X |
| FBXO11 | 80204 | NM_012167 | M | |
| FBXO45 | 200933 | XM_117294 | M | |
| FBXO5 | 26271 | NM_012177 | S | X |
| FLJ21986 | 79974 | NM_024913 | M | X |
| FLJ30698 | 400687 | XM_375602 | S | X |
| FLJ36070 | 284358 | NM_182574 | S | |
| FLJ40172 | 285051 | NM_173649 | M | |
| FLJ41047 | 399968 | XM_374945 | M | |
| FLJ44290 | 375347 | NM_198564 | M | |
| FLJ44313 | 400658 | NM_207460 | M | |
| FLJ45121 | 400556 | NM_207451 | M | |
| FLJ46365 | 401459 | NM_207504 | S | |
| FRMD4B | 23150 | XM_114303 | S | |
| FRMPD1 | 22844 | NM_014907 | M | X |
| FSIP1 | 161835 | NM_152597 | S | |
| FXYD2 | 486 | NM_001680 | M | |
| GBP5 | 115362 | NM_052942 | M | |
| GGA1 | 26088 | NM_001001560 | M | |
| GGA3 | 23163 | NM_014001 | M | X |
| GLMN | 11146 | NM_053274 | M | |
| GLT1D1 | 144423 | NM_144669 | M | X |
| GOSR2 | 9570 | NM_004287 | S | X |
| GPD1 | 2819 | NM_005276 | M | X |
| GPD1L | 23171 | NM_015141 | S | X |
| GPR23 | 2846 | NM_005296 | M | X |
| GRK4 | 2868 | NM_005307 | W | |
| GSR | 2936 | NM_000637 | M | |
| GSTM2 | 2946 | NM_000848 | M | X |
| GUCA1B | 2979 | NM_002098 | S | |
| HBB | 3043 | NM_000518 | S | |
| HDHD2 | 84064 | NM_032124 | M | |
| HSD11B2 | 3291 | NM_000196 | M | |
| HYAL4 | 23553 | NM_012269 | M | |
| ICA1L | 130026 | NM_138468 | M | |
| IGF1R | 3480 | NM_145574, NM_000875 | S | |
| IL20RA | 53832 | NM_014432 | M | |
| IL9 | 3578 | NM_000590 | M | X |
| ITIH5 | 80760 | NM_030569 | M | |
| JPH2 | 57158 | NM_020433 | M | X |
| KCNIP2 | 30819 | NM_014591 | M | X |
| KCNK9 | 51305 | NM_016601 | M | |
| KCNN4 | 3783 | NM_002250 | S | X |
| KIAA0284 | 283638 | XM_208766 | S | X |
| KIF13B | 23303 | NM_015254 | M | |
| KLHL11 | 55175 | NM_018143 | M | |
| KLRC3 | 3823 | NM_002261 | M | |
| KRBA1 | 84626 | XM_044212 | M | |
| KRT35 | 3886 | NM_002280 | M | X |
| KRTAP21-2 | 337978 | NM_181617 | M | X |
| KRTAP5-8 | 57830 | NM_021046 | S | X |
| L1TD1 | 54596 | NM_019079 | M | X |
| LASP1 | 3927 | NM_006148 | W | |
| LMAN1L | 79748 | NM_021819 | S | X |
| LMNB1 | 4001 | NM_005573 | S | X |

TABLE 3-continued

| GeneSymbol | EntrezGeneID | Genbank Acc. No. | NFAT Score | Cal-cium Hit |
|---|---|---|---|---|
| LOC131873 | 131873 | XM_067585 | M | |
| LOC146795 | 146795 | XM_378701 | S | |
| LOC153441 | 153441 | XM_087671 | M | |
| LOC254938 | 254938 | XM_173120 | M | |
| LOC283914 | 283914 | XM_378589 | M | X |
| LOC284371 | 284371 | XM_209155 | M | |
| LOC285636 | 285636 | NM_175921 | M | |
| LOC338750 | 338750 | XM_291974 | M | |
| LOC338829 | 338829 | XM_292122 | M | X |
| LOC340318 | 340318 | XM_290401 | M | |
| LOC340765 | 340765 | XM_291704 | M | |
| LOC345643 | 345643 | XM_293918 | S | |
| LOC345711 | 345711 | XM_293937 | M | X |
| LOC375295 | 375295 | XM_374020 | M | |
| LOC387761 | 387761 | XM_373495 | S | |
| LOC388381 | 388381 | XM_371053 | M | X |
| LOC388418 | 388418 | XM_373748 | M | |
| LOC388469 | 388469 | XM_371111 | M | X |
| LOC388776 | 388776 | XM_371384 | M | |
| LOC388807 | 388807 | XM_373922 | M | X |
| LOC389107 | 389107 | XM_371626 | M | X |
| LOC389224 | 389224 | XM_374086 | S | |
| LOC389319 | 389319 | XM_374134 | M | X |
| LOC390734 | 390734 | XM_372640 | M | |
| LOC391426 | 391426 | XM_372950 | M | X |
| LOC392549 | 392549 | XM_373373 | M | X |
| LOC399959 | 399959 | XM_378316 | M | |
| LOC400622 | 400622 | XM_375491 | M | |
| LOC400688 | 400688 | XM_375603 | M | |
| LOC400877 | 400877 | XM_379025 | M | X |
| LOC400939 | 400939 | XM_379072 | S | X |
| LOC401155 | 401155 | XM_379276 | S | X |
| LOC401293 | 401293 | XM_376558 | M | |
| LOC401322 | 401322 | XM_376591 | M | X |
| LOC401624 | 401624 | XM_377073 | M | X |
| LOC401720 | 401720 | XM_377265 | M | |
| LOC401778 | 401778 | XM_377343 | M | X |
| LOC402251 | 402251 | XM_377933 | M | |
| LOC402382 | 402382 | XM_378090 | S | |
| LOC90120 | 90120 | XM_379680 | M | |
| LRRC58 | 116064 | XM_057296 | M | |
| LSM12 | 124801 | NM_152344 | S | |
| LSM14A | 26065 | NM_015578 | S | |
| LYNX1 | 66004 | NM_177477 | M | X |
| LYZL1 | 84569 | NM_032517 | M | X |
| MAP4 | 4134 | NM_002375 | M | |
| MAPBPIP | 28956 | NM_014017 | S | |
| MAST4 | 23227 | XM_291141 | M | |
| MBP | 4155 | NM_002385 | M | |
| MED19 | 219541 | NM_153450 | M | X |
| MED28 | 80306 | NM_025205 | S | |
| MGAT4B | 11282 | NM_014275 | M | |
| MGC34829 | 284069 | XM_208993 | S | X |
| MGC87042 | 256227 | NM_207342 | M | |
| MICAL3 | 57553 | XM_332997 | W | |
| MLSTD1 | 55711 | NM_018099 | M | |
| MRPS6 | 64968 | NM_032476 | M | |
| MRS2L | 57380 | NM_020662 | M | X |
| MTMR6 | 9107 | NM_004685 | S | |
| MYADM | 91663 | NM_138373 | M | |
| MYO9A | 4649 | NM_006901 | M | X |
| NAPA | 8775 | NM_003827 | M | X |
| NAPG | 8774 | NM_003826 | | |
| NDRG1 | 10397 | NM_006096 | M | |
| NDUFA5 | 4698 | NM_005000 | M | X |
| NEBL | 10529 | NM_006393 | W | |
| NEURL | 9148 | NM_004210 | S | |
| NIPA2 | 81614 | NM_030922 | S | X |
| NRAS | 4893 | NM_002524 | M | |
| NRSN1 | 140767 | NM_080723 | S | |
| OR2A2 | 442361 | NM_001005480 | M | |
| OR2B3 | 442184 | NM_001005226 | S | |
| OR4K15 | 81127 | NM_001005486 | M | |
| OR5K4 | 403278 | NM_001005517 | S | |
| OSM | 5008 | NM_020530 | M | |
| OSTM1 | 28962 | NM_014028 | S | X |

TABLE 3-continued

| GeneSymbol | EntrezGeneID | Genbank Acc. No. | NFAT Score | Cal-cium Hit |
|---|---|---|---|---|
| P4HA2 | 8974 | NM_004199 | S | |
| PASD1 | 139135 | NM_173493 | M | X |
| PCDH11X | 27328 | NM_014522 | S | |
| PCDH11Y | 83259 | NM_032971 | M | |
| PCDHB13 | 56123 | NM_018933 | M | |
| PCDHGB7 | 56099 | NM_018927 | S | |
| PDCD1LG2 | 80380 | NM_025239 | S | |
| PELO | 53918 | NM_015946 | S | |
| PEX11A | 8800 | NM_003847 | S | |
| PEX3 | 8504 | NM_003630 | M | |
| PHF23 | 79142 | NM_024297 | M | |
| PIK3R2 | 5296 | NM_005027 | S | |
| PIK4CA | 5297 | NM_002650 | M | X |
| PILRA | 29992 | NM_013439 | S | X |
| PJA1 | 64219 | NM_022368 | M | X |
| PLA2G4D | 283748 | NM_178034 | M | |
| PLEKHA6 | 22874 | NM_014935 | M | |
| PMCH | 5367 | NM_002674 | M | |
| POLG | 5428 | NM_002693 | M | |
| POMP | 51371 | NM_015932 | M | |
| PPP1R9B | 84687 | NM_032595 | M | |
| PPP3CA | 5530 | NM_000944 | S | |
| PPP3R1 | 5534 | NM_000945 | M | |
| PRRT1 | 80863 | NM_030651 | M | X |
| PRSS1 | 5644 | NM_002769 | M | X |
| PTPN13 | 5783 | NM_006264 | M | |
| RAB11FIP5 | 26056 | NM_015470 | S | |
| RAB12 | 201475 | XM_113967 | S | |
| RABGGTB | 5876 | NM_004582 | S | |
| RAD9B | 144715 | NM_152442 | S | X |
| RAI14 | 26064 | NM_015577 | S | |
| RAP1GAP | 5909 | NM_002885 | M | |
| REV3L | 5980 | NM_002912 | M | |
| RGS7 | 6000 | NM_002924 | M | |
| RIOK3 | 8780 | NM_003831 | M | |
| RLN3 | 117579 | NM_080864 | M | |
| RNF180 | 285671 | NM_178532 | M | |
| RNF185 | 91445 | NM_152267 | M | X |
| RNF32 | 140545 | NM_030936 | M | |
| RNPEPL1 | 57140 | NM_018226 | M | X |
| RP11-298P3.3 | 88523 | NM_033111 | S | |
| RPGR | 6103 | NM_000328 | S | X |
| RY1 | 11017 | NM_006857 | S | |
| SEC13 | 6396 | NM_030673 | S | |
| SELENBP1 | 8991 | NM_003944 | S | |
| SENP6 | 26054 | NM_015571 | S | |
| SEPT4 | 5414 | NM_004574 | S | X |
| SERPINA12 | 145264 | NM_173850 | M | |
| SERPINA9 | 327657 | NM_175739 | M | |
| SERPINB1 | 1992 | NM_030666 | M | |
| SERPINE1 | 5054 | NM_000602 | M | |
| SFXN5 | 94097 | NM_144579 | M | X |
| SIGLEC8 | 27181 | NM_014442 | S | |
| SLC25A3 | 5250 | NM_002635 | M | |
| SLC30A5 | 64924 | NM_022902 | S | |
| SLC38A6 | 145389 | NM_153811 | M | |
| SLC41A3 | 54946 | NM_017836 | M | X |
| SPTLC2 | 9517 | NM_004863 | S | X |
| STAM | 8027 | NM_003473 | M | X |
| STIM1 | 6786 | NM_003156 | S | X |
| STIM2 | 57620 | NM_020860 | M | X |
| STX18 | 53407 | NM_016930 | M | |
| STXBP2 | 6813 | NM_006949 | M | X |
| SUSD5 | 26032 | XM_171054 | M | |
| SV2C | 22987 | XM_043493 | S | |
| SYT15 | 83849 | NM_181519 | S | |
| TBK1 | 29110 | NM_013254 | M | |
| TDRKH | 11022 | NM_006862 | M | |
| TEX14 | 56155 | NM_031272 | M | |
| TFPI2 | 7980 | NM_006528 | S | |
| TIFA | 92610 | NM_052864 | M | |
| TLR6 | 10333 | NM_006068 | M | |
| TMED10 | 10972 | NM_006827 | M | X |
| TMEM110 | 375346 | NM_198563 | S | X |
| TMEM142A | 84876 | NM_032790 | M | X |
| TMEM43 | 79188 | NM_024334 | S | |

TABLE 3-continued

| GeneSymbol | EntrezGeneID | Genbank Acc. No. | NFAT Score | Cal-cium Hit |
|---|---|---|---|---|
| TNFRSF18 | 8784 | NM_004195 | M | X |
| TNIK | 23043 | XM_039796 | S | |
| TOLLIP | 54472 | NM_019009 | W | |
| TOR1AIP1 | 26092 | NM_015602 | M | |
| TPTE | 7179 | NM_013315 | M | |
| TRIM59 | 286827 | NM_173084 | M | X |
| TRNT1 | 51095 | NM_016000 | M | |
| TROAP | 10024 | NM_005480 | S | |
| TUG1 | 55000 | NM_017903 | M | |
| TXNDC10 | 54495 | NM_019022 | S | |
| UBAP1 | 51271 | NM_016525 | M | |
| UBC | 7316 | NM_021009 | M | X |
| UBL4B | 164153 | NM_203412 | M | |
| UBL7 | 84993 | NM_032907 | S | |
| UEVLD | 55293 | NM_018314 | S | X |
| UQCRQ | 27089 | NM_014402 | S | |
| USP13 | 8975 | NM_003940 | M | |
| VGF | 7425 | NM_003378 | M | |
| VPS28 | 51160 | NM_016208 | M | |
| WDR81 | 124997 | NM_152348 | M | |
| WHDC1 | 123720 | XM_058720 | S | |
| WNK2 | 65268 | NM_006648 | M | |
| XKR5 | 389610 | NM_207411 | M | X |
| XKRY | 9082 | NM_004677 | S | |
| XKRY2 | 353515 | NM_001002906 | M | |
| YARS2 | 51067 | NM_015936 | S | |
| ZC3H12C | 85463 | XM_370654 | S | |
| ZDHHC2 | 51201 | NM_016353 | M | |
| ZNF289 | 84364 | NM_032389 | S | X |
| ZNF706 | 51123 | NM_016096 | M | X |
| ZYX | 7791 | NM_003461 | M | |
| ZZEF1 | 23140 | NM_015113 | S | X |
| ZZZ3 | 26009 | NM_015534 | M | |

TABLE 4

List of selected genes that are positive in the calcium screen assay

| | | | | | |
|---|---|---|---|---|---|
| ACSBG1 | DNAJC5G | IL9 | MRS2L | RPGR | UEVLD |
| ACTB | ELMOD1 | JPH2 | MYO9A | SEPT4/PNUTL2 | XKR5 |
| ALCAM | FAM108C1 | KCNIP2 | NAPA | SFXN5 | ZNF289 |
| ATN1 | FAS | KCNN4 | NDUFA5 | SLC41A3 | ZNF706 |
| ATPVOD1 | FASTKD5 | KIAA0284 | NIPA2 | SPTLC2 | ZZEF1 |
| C1ORF123 | FBXO5 | KRT35 | OSTM1 | STAM | SEPT1 |
| C20ORF96 | FLJ21986 | KRTAP21-2 | PASD1 | STIM1 | SEPT2 |
| C6ORF191 | FRMPD1 | KRTAP5-8 | PIK4CA | STIM2 | SEPT3 |
| C8ORF42 | GGA3 | L1TD1 | PILRA | STXBP2 | SEPT5 |
| CCDC125 | GLT1D1 | LMAN1L | PJA1 | TMED10 | SEPT6 |
| CCNB2 | GOSR2 | LMNB1 | PRRT1 | TMEM110 | SEPT7 |
| CNTN3 | GPD1 | LOC338829 | PRSS1 | TMEM142A | SEPT8 |
| CPEB4 | GPD1L | LOC388381 | RAD9B | TNFRSF18 | SEPT9 |
| CPT2 | GPR23 | LYZL1 | RNF185 | TRIM59 | SEPT10 |
| DKFZP686A01247 | GSTM2 | MGC34829 | RNPEPL1 | UBC | SEPT11 |

TABLE 5

| Gene Name/Gene Symbol | Description | GeneID |
|---|---|---|
| TRIM59 | tripartite motif-containing 59 | 286827 |
| SPTLC2 | serine palmitoyltransferase, long chain base subunit 2 | 9517 |
| PRRT1 = C6ORF31 | proline-rich transmembrane protein 1 | 80863 |
| TMEM110 = MGC52022 | transmembrane protein 110 | 375346 |
| FASTKD5 = FLJ13149 | FAST kinase domains 5 | 60493 |
| GPR23 = LPAR4 | lysophosphatidic acid receptor 4 | 2846 |
| SLC41A3 | solute carrier family 41, member 3 | 54946 |
| ATP6V0D1 | ATPase, H+ transporting | 9114 |
| KIAA0284 | hypothetical protein LOC2836382 | 283638 |
| PILRA | paired immunoglobin-like type 2 receptor alpha | 29992 |
| RAD9B | RAD9 homolog B (*S. pombe*) | 144715 |
| UHSKERB = KRTAP5-8 | keratin associated protein 5-8 | 57830 |
| GSTM2 | glutathione S-transferase mu 2 | 2946 |
| KRTHA5 = KRT35 | keratin 35 | 3886 |
| KRTAP21-2 | keratin associated protein 21-2 | 337978 |
| PCOLN3 = CHMP1A | involved in multivesicular body sorting of proteins to lysosomes | 5119 |
| PRSS1 | protease, serine, 1 (trypsin 1) = can this be correct? | 5644 |
| CPT2 | original designation CPT2B09 | 1376 |
| GOSR2 | carnitine palmitoyltransferase 2 | 9570 |
| C6ORF191 | chromosome 6 open reading frame 191 | 253582 |
| USP13 | ubiquitin specific peptidase 13 (isopeptidase T-3) | 8975 |
| UEV3 = UEVLD | UEV and lactate/malate dehyrogenase domains | 55293 |
| FBXO5 | F-box protein 5 | 26271 |
| PNUTL2 = Sept 4 & 5 | Septin 4 and Septin 5 | 5414 |
| TRIM3 | tripartite motif-containing 3 | 10612 |
| MYO9A | myosin IXA | 4649 |
| PJA1 | praja ring finger 1 | 64219 |
| RNPEPL1 | arginyl aminopeptidase (aminopeptidase B)-like 1 | 57140 |
| FASTKD5 = FLJ13149 | FAST kinase domains 5 | 60493 |
| C1ORF123 = FLJ20580 | FLJ20580 | 54987 |

TABLE 5-continued

| Gene Name/Gene Symbol | Description | GeneID |
|---|---|---|
| MICAL3 | microtubule associated monoxygenase | 57553 |
| ALCAM | activated leukocyte cell adhesion molecule | 214 |
| FRMPD1 | FERM and PDZ domain containing 1 | 22844 |
| CCNB2 | cyclin B2 | 9133 |
| DNAJC5G | DnaJ (Hsp40) homolog, subfamily C, member 5 gamma | 285126 |
| IL9 | interleukin 9 | 3578 |
| LOC338829 | RefSeq status: withdrawn (discontinued June 2009) | |
| PIK4CA | phosphatidylinositol 4-kinase, catalytic, alpha | 5297 |
| RPGR | retinitis pigmentosa GTPase regulator | 6103 |
| FLJ21986 = C7ORF58 | C7ORF58 | 79974 |
| FAS = TNFRSF6 | TNF receptor superfamily, member 6 | 355 |
| XKR5 = UNQ2754 | XK, Kell blood group complex subunit-related family, member 5 | 389610 |
| ZNF289 | ARFGAP2 ADP-ribosylation factor GTPase activating protein 2 | 84364 |
| NDUFA5 | NADH dehydrogenase (ubiquinone) 1 alpha subcomplex, 5, 13kD | 4698 |
| CBLL1 | Cas-Br-M (murine) ecotropic retroviral transforming sequence-like | 79872 |
| KCNIP2 | Kv channel interacting protein 2 | 30819 |
| TMED10 = TMP21 | transmembrane emp24-like trafficking protein 10 (yeast) | 10972 |
| UBC | ubiquitin C | 7316 |
| ACSBG1 = BG1 | acyl-CoA synthetase bubblegum family member 1 | 23205 |
| SFXN5 | sideroflexin 5 | 94097 |
| LOC388381 | C17orf98 | 388381 |
| L1TD1 = FLJ10884 | LINE-1 type transposase domain containing 1 | 54596 |
| STXBP2 | syntaxin binding protein 2 | 6813 |
| LYZL1 | lysozyme-like 1 | 84569 |
| ZNF706 = LOC51123 | zinc finger protein 706 | 51123 |

TABLE 6 siRNA sequences of selected hits

| Gene Symbol | EntrezGene ID | siRNA_sense | (SEQ. ID. NO:) |
|---|---|---|---|
| siControl | n/a | GCUAUUGCAUGUCGAAAUA | 15 |
| siSTIM1 | 6786 | GGUGGUGUCUAUCGUUAUU | 16 |
| siSEPT4#1 | 5414 | GGACAAUGCUGGUACGUAC | 17 |
| siSEPT4#2 | 5414 | GGAGACACAUUAUGAGAAC | 18 |
| siSEPT4#3 | 5414 | GGGUCAACAUCGUGCCUAU | 19 |
| siSEPT4#4 | 5414 | GAACAUCCAAGACAACCGA | 20 |
| siBGN | 633 | GGAGAACAGUGGCUUUGAA | 21 |
| siTFPI2 | 7980 | GUGGAGGGAAUGACAAUAA | 22 |

TABLE 6-continued siRNA sequences of selected hits

| Gene Symbol | EntrezGene ID | siRNA_sense | (SEQ. ID. NO:) |
|---|---|---|---|
| siCAV3 | 859 | UGCCAUGCAUUAAGAGCUA | 23 |
| siNUP62 | 23636 | GGACACAGGGCUUCAGCUU | 24 |
| siACTB | 60 | GGGCAUGGGUCAGAAGGAU | 25 |
| siWNT7B | 7477 | CAACAAGAUUCCUGGCCUA | 26 |
| siORAI1 | 84876 | GGCCUGAUCUUUAUCGUCU | 27 |
| siKPNB1 | 3837 | UCACACAGAUGGAGUAGUA | 28 |
| siCSE1L | 1434 | AUAGUGCACUUGAUGCUUA | 29 |

TABLE 7 shRNA Sequences

| Gene Symbol | EntrezGene ID | shRNA_sense; shRNA_asense |
|---|---|---|
| Scramble | n/a | AGCGTAGAATATGTACCTGGTA (SEQ. ID. NO: 30);<br>TACCAGGTACATATTCTACGCG (SEQ. ID. NO: 31) |
| Stim1 | 20866 | AGGCAAGGATGTTATATTTGAA (SEQ. ID. NO: 32);<br>TTCAAATATAACATCCTTGCCC (SEQ. ID. NO: 33) |
| Zbtb2 | 381990 | AACGGTTGCAATCGGCGATGTA (SEQ. ID. NO: 34);<br>TACATCGCCGATTGCAACCGTG (SEQ. ID. NO: 35) |
| Dennd1c | 70785 | AGGTGACTCCCTCCAGGAATAT (SEQ. ID. NO: 36);<br>ATATTCCTGGAGGGAGTCACCC (SEQ. ID. NO: 37) |
| Atp10d | 231287 | ACCCTTTGACTCTGTAAGGAAA (SEQ. ID. NO: 38);<br>TTTCCTTACAGAGTCAAAGGGC (SEQ. ID. NO: 39) |
| Mylip | 218203 | ACCCTATTAACAGGATAGCTTA (SEQ. ID. NO: 40);<br>TAAGCTATCCTGTTAATAGGGC (SEQ. ID. NO: 41) |

TABLE 7-continued

| shRNA Sequences | | |
|---|---|---|
| Gene Symbol | EntrezGene ID | shRNA_sense; shRNA_asense |
| Fam193a: | 231128 | CGCTAAGTTTGCTGACATTTAT (SEQ. ID. NO: 42);<br>ATAAATGTCAGCAAACTTAGCT (SEQ. ID. NO: 43) |
| Stambpl1 | 76630 | ACCTAAGCAAACTTGGTTGTAA (SEQ. ID. NO: 44);<br>TTACAACCAAGTTTGCTTAGGG (SEQ. ID. NO: 45) |
| Sf4 | 70616 | CGCCGAGACTCGGAGAGTGATA (SEQ. ID. NO: 46);<br>TATCACTCTCCGAGTCTCGGCT (SEQ. ID. NO: 47) |
| Zfp143 | 20841 | CGGGACTCAACATGTCAACATA (SEQ. ID. NO: 48);<br>TAGTTGACATGTTGAGTCCCAT (SEQ. ID. NO: 49) |
| Secisbp2 | 75420 | AGCACCTTTCCTTAAGAGCCTA (SEQ. ID. NO: 50);<br>TAGGCTCTTAAGGAAAGGTGCC (SEQ. ID. NO: 51) |
| Klhl20 | 226541 | CGGTGTCTCTTGCCTCAATATA (SEQ. ID. NO: 52);<br>TATATTGAGGCAAGAGACACCA (SEQ. ID. NO: 53) |
| Itsn2 | 20403 | ACGCCAGGACAGTTAATATTAA (SEQ. ID. NO: 54);<br>TTAATATTAACTGTCCTGGCGC (SEQ. ID. NO: 55) |

TABLE 8

| qRT-PCR primer sequences | | | |
|---|---|---|---|
| Gene Symbol | EntrezGene ID | Forward Primer | Reverse Primer |
| GAPDH | 2597 | TCTCCTCTGACTTCAACAGC (SEQ. ID. NO: 56) | CTGTTGCTGTAGCCAAATTCG (SEQ. ID. NO: 57) |
| SEPT1 | 1731 | AAAGTGAAGCTGACCCTTGTGGAC (SEQ. ID. NO: 58) | AGTCCTGGATGTTCTTCCGGTTCA (SEQ. ID. NO: 59) |
| SEPT2 | 4735 | TTGAGAGGTACCTGCATGACGAGA (SEQ. ID. NO: 60) | CCTTCATAAACGCCACATCTAAGGGC (SEQ. ID. NO: 61) |
| SEPT4 | 5414 | ATTTCTCAGGAAATGCGAGCTGCC (SEQ. ID. NO: 62) | AAGTACTGCTGGTTGTCAGAGGAC (SEQ. ID. NO: 63) |
| SEPT5 | 5413 | TGTCAACAACACCGAGTGCTGGAA (SEQ. ID. NO: 64) | GCCTTCATGAAACCCACATCCACT (SEQ. ID. NO: 65) |

TABLE 9

| Areas and intensities of STIM1 puncta in siSEPT4/5-treated Hela cells | | | |
|---|---|---|---|
| | siControl | siSept4/5 | P Value |
| Pearson's coefficient | 0.62 | 0.50 | 0.007 |
| Colocalized area | 0.050 | 0.040 | 0.007 |
| Fraction of Stim1 puncta colocalized with Orai1 puncta | 0.73 | 0.63 | 0.005 |

TABLE 9-continued

| Areas and intensities of STIM1 puncta in siSEPT4/5-treated Hela cells | | | |
|---|---|---|---|
| | siControl | siSept4/5 | P Value |
| Colocalized puncta area | 17.1 | 15.9 | 0.06 |
| Orai1 intensity | 1.05 | 1.02 | 0.42 |
| Stim1 intensity | 1.04 | 0.99 | 0.30 |

TABLE 10

| The mRNA variant transcripts of Septins and UEV3 genes. | | |
|---|---|---|
| Septin | mRNA Accession number | mRNAsequence |
| Septin1 | NM_052838 (SEQ. ID. NO: 66) | ccctgctaacaaagggagccacttccttcctctctgcacataccccatgtctcaccacgatg<br>atggagctacagtgggacttggaatccagatgtgtgaaggatggagggttgaagccgca<br>ctcagcttcctgccccaccagaggaagtggggagagacggcaggtgcagtgatggctg<br>gcggagtcatggacaaggagtacgtgggttttgctgccctccccaaccagctgcaccgc |

TABLE 10-continued

The mRNA variant transcripts of Septins and UEV3 genes.

| Septin | mRNA Accession number | mRNAsequence |
|---|---|---|
| | | aagtctgtcaagaaggggtttgacttcacgctaatggtggcaggggagtcaggcctaggg<br>aaatccaccctcatcaacagcctcttcctcaccaacctctatgaggatcgccaggtgccag<br>aggccagtgctcgcttgacacagaccctggccattgagcgccggggcgtagagattgag<br>gaaggggtgtgaaagtgaagctgacccttgtggacacacctggctttggggactcagtg<br>gactgctctgactgctggcttccggtggtgaaattcatcgaggagcaatttgagcagtacct<br>tagggatgagagtggcctgaaccggaagaacatccaggactcccgagtccactgctgcc<br>tctacttcatctcacccttcggccgggggctccggcccctagatjgtggccttcctccgggc<br>agtacacgagaaagtcaacatcatcccagtcattggcaaagcggatgctctgatgcccca<br>ggaaacccaggccctcaagcagaagatccgggatcagttgaaggaagaggagatccac<br>atctaccagttccccgaatgtgactctgatgaagatgaagacttcaagaggcaggatgca<br>gagatgaaggaaagcatcccttttgcagtcgtgggatcatgcgaggtggtgagggatgg<br>cgggaaccggccggtgaggggacgccgctactcctgggggaccgtggaggtggaga<br>acccacatcactgcgatttcctgaacctgcgacggatgctggtgcagacacacctgcagg<br>acctgaaagaggtgacgcacgatctgctctacgagggctaccgggcccgctgcctacag<br>agcctggcccggcctggggctcgcgatcgagccagccgcagtaagctttcccgccaga<br>gcgccacagagatcccgctgcccatgctgcctctggcggacaccgagaagctgatccg<br>cgagaaagacgaagagctgcgccgcatgcaagagatgctggagaagatgcaggccca<br>aatgcagcagagccaggcccagggcgagcagtcagacgccctctgaggccacgcccc<br>gcccggccttacctcggctccgccttcagtcggcctcttgtccaatccccgcgccccacac<br>tgcccagcgcccccccgggacctccgcgggtgccgccctcgcgcgggctagggggag<br>gttctcccagcctgagtccgtagccccgccccggcgctggtcccgcccacccagacacc<br>gcccacttcccggcccggggcctgcacaatctccgaccgcatcactgtcttccggagtcc<br>cccttcttctcccagactctgtcttcaataaaaactgagcttcccgcggccacgaaaaaaaa<br>aaaaaaaaa |
| Septin2 | NM_001008491,<br>(SEQ. ID.<br>NO: 67)<br>NM_001008492<br>(SEQ. ID.<br>NO: 68)<br>NM_004404<br>(SEQ. ID.<br>NO: 69)<br>NM_006155<br>(SEQ. ID.<br>NO: 70) | NM_001008491<br>gtggtgggctagaccagtttcgcgcggccgctcgccgtcccccgcccagtcgtactcgg<br>cgccccagctcggtgctgccgccatcttcttggaggacaggaggagaggcgaaggctc<br>cccctccccgtgatcgctccgcactcccgccaccacctgccctcccgcgaccgcctctct<br>cctcctcagtgggcacttgtctccttctaacaaacggccttccccccactccagttacccac<br>cgcaaggcgaagattctcattacctgttccactcttataagcataagaaaaccgagctcata<br>agcatacagaaactgctgtaaaagaagaagttgtgggtattttmtttttttttttgtctggagga<br>atggggacaccaaaactcatttggcagcagaggtgagacgaagcttcacaaaagatgtct<br>aagcaacagccaactcagtttataaatccagaaacacctggctatgttggatttgcaaacct<br>ccccaatcaagttcaccgaaaatcagtgaaaaaaggttttgagttcacactgatggtggtc<br>ggtgaatcaggtctaggaaaatcgactctcataaacagcctattcctaactgatctgtaccc<br>agaaagagtcatacctggagcagcagaaaaaattgaaagaactgtccagattgaggcttc<br>aactgttgaaattgaagagcgaggggtcaagctacgcctgacagtggtagataccccctgg<br>ctatggtgacgctatcaactgcagagattgttttaagacaattatctcctatattgatgagcaa<br>tttgagaggtacctgcatgacgagagcggcttgaacaggcggpacatcattgataatagg<br>gtgcattgttgcttttactttatttcaccttttggacatggacttaagcccttagatgtggcgttta<br>tgaaggcaatacacaacaaggtgaatattgtgcctgtcattgcaaaagctgacactctcac<br>cctgaaggaacgggagcggctgaagaaaaggattctggatgaaattgaagaacataaca<br>tcaaaatctatcacttacctgatgcagaatcagatgaagatgaagattttaaagagcagact<br>agacttctcaaggctagcatcccattctctgtggttggatccaatcagttgattgaagccaaa<br>ggaaagaaggtcagaggccgcctctaccccctggggtgttgtggaagtggagaacccag<br>agcacaatgactttctgaagctgagaaccatgctcatcacccacatgcaggatctccagga<br>ggtgacccaggaccttcattatgaaaacttccgttctgagagactcaagagaggcggcag<br>gaaagtggagaatgaggacatgaataaagaccagatcttgctggaaaaagaagctgagc<br>tccgccgcatgcaagagatgattgcaaggatgcaggcgcagatgcagatgcagatgca<br>gggcggggatggcgatggcggggctctcgggcaccacgtgtaaggtgatgtgcacata<br>tcaagaagtcagagaaaacactttcctggataaaaaagaaaacattccagatgcatgatcc<br>agctgtgtgttttcaatccttgggagggtgccatccacattttaacagtacctgtgcctgaga<br>atttaatttttaaaagactttgatgtgtttttgtatgaagtacttttaacgtatgtatttcattgctgt<br>gtcacactctgtgttttgtgaggtgaatgtcttcctttttctttctccctaaccactaatgttagaat<br>tgatttccaagaatcggcatgtatacttaatactgaatttctttgatttaactgacttaacaactg<br>actaaccattgatgagcactcctgatttttatctagaacattcagatttaccataatgttccttag<br>tggtagaggtgtgtgcctagtgatgtagaaagatacactgacttggtgcaaggccatctgc<br>ttaccacatcacaccacttggagatctttgcttccttgcttttatgtttgtacacaacacctaaa<br>accagttttgctgctataattctatactgttgattcgtctgcgattttatctgttaaccaaataaaa<br>cataatagaatttcctaatgagatatatctttatacttaaacagctttttttagaggtgagttttaaa<br>gaagtctcttaattctgatgctaggttgtttttaaaaccactatgcaaagaactcaccacaag<br>ccaccttttgtagtgttctccactaatactggttatcctgtgctacagagaaaatcaaagcagt<br>cataagctccagttttcgtattgcaaataagactcttacctacaaaatgagattcagtgaacta<br>atttggtttttactcaaccaaattaaaaatttttttaaggaaaattagcagttggtctattcagaat<br>caaacctttttatattttatactgcactttagtgtattttctgtcactgtaggtatagaagatctgc<br>ctcccctgtggaaattggggtctgttggtgggcgtgcccctgaagcctggcttgggttgaa<br>aagtgttcccgccctaaggccttggtgccctgaacctctgatgcctaccgggttctcctgat<br>ttgagtttcctttaaatactcccttttgagtaattttctgatgggaggaaagtagcagtcatcat<br>ctttttgtgtgcaggctgtctcatttatttttagccattgtcgtttcattcattttgtgtaatataaac<br>cgtgtgtcatgtcaaagtgaaagacatttcaaatctgtagcataggctagtgggcaggtcc<br>gcacagtcgaagccacacctggtctgttttctgtgcactgtagccttagtgtcacctttcttctt<br>gtgtctccttatggtacactccagcggttgcctttttttatcatttctactgaagttgggaaattca<br>accccagaaattgacagatgaaaggagacaatggttgtgtagggagatggagaaaatgc |

TABLE 10-continued

The mRNA variant transcripts of Septins and UEV3 genes.

| Septin | mRNA Accession number | mRNAsequence |
|---|---|---|
| | | ttaatctgaggatgagacagggtttttttcatttttgtgggggctagaaaaaacataaaatgag |
| | | gcagttaaataataatagttaatgaaggtgtgctacagaaaataatctggtgttcttgctaact |
| | | ttgcccttcactgttgcttaattgtgaacagccaaaagctatatgttatggcttattgtgtgaag |
| | | gtaactaagaagtggtgttccatgacttcagagtacatccatgcggagtccattatttgagttt |
| | | gacatttaataactttgctggaaaatctgtaaaaaagaaaaacaagtttgctagtgactaagc |
| | | cccgcatatgtgagtgaaagtacttcaggcacgctgcctcctggtaacagctatgcaggg |
| | | agggaggacccacactgctacacttctgatcccctttggttttactacccaaatctaaataga |
| | | tacttttgataatagataactgctcttttactaagacatagtctctacctatagaaatgtattttga |
| | | aaacacttattttacacagcaattttgtatccatttaaactaaccttttatcaataaagcactatt |
| | | gtttagatattaaaa |
| | | NM_001008492 |
| | | aatccgcctgcgcgctgggcggggcggggcgggctggggcgggctgtgagcggacc |
| | | gcgagcgctgggcgggtccgcggcgcggtcggtcggcgcctgttctcgggctgtttggc |
| | | ggaggcttggaatagttaaatgactttggtcttgtccaaggttagatggagttcaactctaac |
| | | gtcaagtcttggtccttttcattgacgaagcttcacaaaagatgtctaagcaacagccaactc |
| | | agtttataaatccagaaacacctggctatgttggatttgcaaacctccccaatcaagttcacc |
| | | gaaaatcagtgaaaaaaggttttgagttcacactgatggtggtcggtgaatcaggtctagg |
| | | aaaatcgactctcataaacagcctattcctaactgatctgtacccagaaagagtcatacctg |
| | | gagcagcagaaaaaattgaaagaactgtccagattgaggcttcaactgttgaaattgaaga |
| | | gcgaggggtcaagctacgcctgacagtggtagataccccctggctatggtgacgctatcaa |
| | | ctgcagagattgttttaagacaattatctcctatattgatgagcaatttgagaggtacctgcat |
| | | gacgagagcggcttgaacaggcggcacatcattgataatagggtgcattgttgcttttactt |
| | | tatttcaccttttggacatggacttaagcccttagatgtggcgtttatgaaggcaatacacaa |
| | | caaggtgaatattgtgcctgtcattgcaaaagctgacactctcaccctgaaggaacggga |
| | | gcggctgaagaaaaggattctggatgaaattgaagaacataacatcaaaatctatcactta |
| | | cctgatgcagaatcagatgaagatgaagattttaaagagcagactagacttctcaaggcta |
| | | gcatcccattctctgtggttggatccaatcagttgattgaagccaaaggaaagaaggtcag |
| | | aggccgcctctacccctggggtgttgtggaagtggagaacccagagcacaatgactttct |
| | | gaagctgagaaccatgctcatcacccacatgcaggatctccaggaggtgacccaggacc |
| | | ttcattatgaaaacttccgttctgagagactcaagagaggcggcaggaaagtggagaatg |
| | | aggacatgaataaagaccagatcttgctggaaaaagaagctgagctccgccgcatgcaa |
| | | gagatgattgcaaggatgcaggcgcagatgcagatgcagatgcagggcggggatggc |
| | | gatggcggggctctcgggcaccacgtgtaaggtgatgtgcacatatcaagaagtcagag |
| | | aaaacactttcctggataaaaaagaaaacattccagatgcatgatccagctgtgtgttttcaa |
| | | tccttgggagggtgccatccacatttaacagtacctgtgcctgagaatttaattttaaaaga |
| | | ctttgatgtgtttttgtatgaagtacttttaacgtatgtatttcattgctgtgtcacactctgtgtttt |
| | | gtgaggtgaatgtcttcctttttctttctccctaaccactaatgttagaattgatttccaagaatcg |
| | | gcatgtatacttaatactgaatttctttgatttaactgacttaacaactgactaaccattgatga |
| | | gcactcctgatttttatctagaacattcagatttaccataatgttccttagtggtagaggtgtgt |
| | | gcctagtgatgtagaaagatacactgacttggtgcaaggccatctgcttaccacatcacac |
| | | cacttggagatctttgcttccttgcttttatgtttgtacacaacacctaaaaccagttttgctgct |
| | | ataattctatactgttgattcgtctgcgattttatctgttaaccaaataaaacataatagaatttc |
| | | ctaatgagatatatctttatacttaaacagctttttttagaggtgagttttaaagaagtctcttaatt |
| | | ctgatgctaggttgtttttaaaaccactatgcaaagaactcaccacaagccaccttttgtagt |
| | | gttctccactaatactggttatcctgtgctacagagaaaatcaaagcagtcataagctccagt |
| | | tttcgtattgcaaataagactcttacctacaaaatgagattcagtgaactaatttggttttttactc |
| | | aaccaaattaaaaatttttttaaggaaaattagcagttggtctattcagaatcaaaccttttttata |
| | | ttttatactgcactttagtgtattttctgtcactgtaggtatagaagatctgcctcccctgtggaa |
| | | attggggtctgttggtgggcgtgcccctgaagcctggcttgggttgaaaagtgttcccgcc |
| | | ctaaggccttggtgccctgaacctctgatgcctaccgggttctcctgatttgagtttcctttaa |
| | | atactccctttttgagtaattttctgatgggaggaaagtagcagtcatcatctttttgtgtgcag |
| | | gctgtctcatttattttttagccattgtcgtttcattcattttgtgtaatataaaccgtgtgtcatgtc |
| | | aaagtgaaagacatttcaaatctgtagcataggctagtgggcaggtccgcacagtcgaag |
| | | ccacacctggtctgttttctgtgcactgtagccttagtgtcacctttcttcttgtgtctccttatg |
| | | gtacactccagcggttgcctttttttatcatttctactgaagttgggaaattcaaccccagaaat |
| | | tgacagatgaaaggagacaatggttgtgtagggagatggagaaaatgcttaatctgagga |
| | | tgagacagggtttttttcatttttgtgggggctagaaaaaacataaaatgaggcagttaaataa |
| | | taatagttaatgaaggtgtgctacagaaaataatctggtgttcttgctaactttgcccttcactg |
| | | ttgcttaattgtgaacagccaaaagctatatgttatggcttattgtgtgaaggtaactaagaag |
| | | tggtgttccatgacttcagagtacatccatgcggagtccattatttgagtttgacatttaataac |
| | | tttgctggaaaatctgtaaaaaagaaaaacaagtttgctagtgactaagccccgcatatgtg |
| | | agtgaaagtacttcaggcacgctgcctcctggtaacagctatgcagggagggaggaccc |
| | | acactgctacacttctgatcccctttggttttactacccaaatctaaatagatacttttgataata |
| | | gataactgctcttttactaagacatagtctctacctatagaaatgtattttgaaaacacttatttt |
| | | acacagcaattttgtatccatttaaactaaccttttatcaataaagcactattgtttagatattaa |
| | | aa |
| | | NM_004404 |
| | | aatccgcctgcgcgctgggcggggcggggcgggctggggcgggctgtgagcggacc |
| | | gcgagcgctgggcgggtccgcggcgcggtcggtcggcgcctgttctcgggctgtttggc |
| | | ggacgaagcttcacaaaagatgtctaagcaacagccaactcagtttataaatccagaaac |
| | | acctggctatgttggatttgcaaacctccccaatcaagttcaccgaaaatcagtgaaaaaa |
| | | ggttttgagttcacactgatggtggtcggtgaatcaggtctaggaaaatcgactctcataaa |
| | | cagcctattcctaactgatctgtacccagaaagagtcatacctggagcagcagaaaaaatt |
| | | gaaagaactgtccagattgaggcttcaactgttgaaattgaagagcgaggggtcaagcta |

TABLE 10-continued

The mRNA variant transcripts of Septins and UEV3 genes.

| Septin | mRNA Accession number | mRNAsequence |
|---|---|---|

cgcctgacagtggtagataccccctggctatggtgacgctatcaactgcagagattgttttaa
gacaattatctcctatattgatgagcaatttgagaggtacctgcatgacgagagcggcttga
acaggcggcacatcattgataatagggtgcattgttgcttttactttatttcaccttttggacat
ggacttaagcccttagatgtggcgtttatgaaggcaatacacaacaaggtgaatattgtgcc
tgtcattgcaaaagctgacactctcaccctgaaggaacgggagcggctgaagaaaagga
ttctggatgaaattgaagaacataacatcaaaatctatcacttacctgatgcagaatcagatg
aagatgaagattttaaagagcagactagacttctcaaggctagcatcccattctctgtggttg
gatccaatcagttgattgaagccaaaggaaagaaggtcagaggccgcctctacccctgg
ggtgttgtggaagtggagaacccagagcacaatgactttctgaagctgagaaccatgctc
atcacccacatgcaggatctccaggaggtgacccaggaccttcattatgaaaacttccgtt
ctgagagactcaagagaggcggcaggaaagtggagaatgaggacatgaataaagacc
agatcttgctggaaaaagaagctgagctccgccgcatgcaagagatgattgcaaggatg
caggcgcagatgcagatgcagatgcagggcggggatggcgatggcggggctctcggg
caccacgtgtaaggtgatgtgcacatatcaagaagtcagagaaaacactttcctggataaa
aaagaaaacattccagatgcatgatccagctgtgtgttttcaatccttgggagggtgccatc
cacattttaacagtacctgtgcctgagaatttaattttaaaagactttgatgtgtttttgtatgaa
gtacttttaacgtatgtatttcattgctgtgtcacactctgtgttttgtgaggtgaatgtcttccttt
tctttctccctaaccactaatgttagaattgatttccaagaatcggcatgtatacttaatactga
atttctttgatttaactgacttaacaactgactaaccattgatgagcactcctgatttttatctag
aacattcagatttaccataatgttccttagtggtagaggtgtgtgcctagtgatgtagaaaga
tacactgacttggtgcaaggccatctgcttaccacatcacaccacttggagatctttgcttcc
ttgcttttatgtttgtacacaacacctaaaaccagttttgctgctataattctatactgttgattcg
tctgcgattttatctgttaaccaaataaaacataatagaatttcctaatgagatatatctttatact
taaacagctttttagaggtgagttttaaagaagtctcttaattctgatgctaggttgtttttaaa
accactatgcaaagaactcaccacaagccacctttgtagtgttctccactaatactggttat
cctgtgctacagagaaaatcaaagcagtcataagctccagttttcgtattgcaaataagact
cttacctacaaaatgagattcagtgaactaatttggtttttactcaaccaaattaaaaattttttta
aggaaaattagcagttggtctattcagaatcaaaccttttatatttatactgcactttagtgta
ttttctgtcactgtaggtatagaagatctgcctcccctgtggaaattggggtctgttggtggg
cgtgcccctgaagcctggcttgggttgaaaagtgttcccgccctaaggccttggtgccctg
aacctctgatgcctaccgggttctcctgatttgagtttcctttaaatactccctttttgagtaattt
tctgatgggaggaaagtagcagtcatcatctttttgtgtgcaggctgtctcatttatttttagcc
attgtcgtttcattcatttgtgtaatataaaccgtgtgtcatgtcaaagtgaaagacatttcaaa
tctgtagcataggctagtgggcaggtccgcacagtcgaagccacacctggtctgttttctgt
gcactgtagccttagtgtcacctttcttcttgtgtctccttatggtacactccagcggttgccttt
tttatcatttctactgaagttgggaaattcaaccccagaaattgacagatgaaaggagacaa
tggttgtgtagggagatggagaaaatgcttaatctgaggatgagacagggtttttttcatttttg
tgggggctagaaaaaacataaaatgaggcagttaaataataatagttaatgaaggtgtgct
acagaaaataatctggtgttcttgctaactttgcccttcactgttgcttaattgtgaacagcca
aaagctatatgttatggcttattgtgtgaaggtaactaagaagtggtgttccatgacttcaga
gtacatccatgcggagtccattatttgagtttgacatttaataactttgctggaaaatctgtaaa
aaagaaaaacaagtttgctagtgactaagccccgcatatgtgagtgaaagtacttcaggca
cgctgcctcctggtaacagctatgcagggagggaggacccacactgctacacttctgatc
ccctttggttttactacccaaatctaaatagatacttttgataatagataactgctcttttactaa
gacatagtctctacctatagaaatgtattttgaaaacacttattttacacagcaattttgtatcca
tttaaactaaccttttatcaataaagcactattgtttagatattaaaa
NM_006155
gtggtgggctagaccagtttcgcgcggccgctcgccgtcccccgcccagtcgtactcgg
cgccccagctcggtgctgccgccatcttcttggaggacaggaggagaggcgaaggctc
cccctccccgtgatcgctccgcactcccgccaccacctgccctcccgcgaccgcctctct
cctcctcagtgggcacttgtctccttctaacaaacggccttcccccactccagttacccac
cgcaaggcgaagattctcattacctgttccactcttataagcataagaaaaccgagctcata
agacgaagcttcacaaaagatgtctaagcaacagccaactcagtttataaatccagaaaca
cctggctatgttggatttgcaaacctccccaatcaagttcaccgaaaatcagtgaaaaaag
gttttgagttcacactgatggtggtcggtgaatcaggtctaggaaaatcgactctcataaac
agcctattcctaactgatctgtacccagaaagagtcatacctggagcagcagaaaaaattg
aaagaactgtccagattgaggcttcaactgttgaaattgaagagcgaggggtcaagctac
gcctgacagtggtagataccccctggctatggtgacgctatcaactgcagagattgttttaag
acaattatctcctatattgatgagcaatttgagaggtacctgcatgacgagagcggcttgaa
caggcggcacatcattgataatagggtgcattgttgcttttactttatttcaccttttggacatg
gacttaagcccttagatgtggcgtttatgaaggcaatacacaacaaggtgaatattgtgcct
gtcattgcaaaagctgacactctcaccctgaaggaacgggagcggctgaagaaaaggat
tctggatgaaattgaagaacataacatcaaaatctatcacttacctgatgcagaatcagatg
aagatgaagattttaaagagcagactagacttctcaaggctagcatcccattctctgtggttg
gatccaatcagttgattgaagccaaaggaaagaaggtcagaggccgcctctacccctgg
ggtgttgtggaagtggagaacccagagcacaatgactttctgaagctgagaaccatgctc
atcacccacatgcaggatctccaggaggtgacccaggaccttcattatgaaaacttccgtt
ctgagagactcaagagaggcggcaggaaagtggagaatgaggacatgaataaagacc
agatcttgctggaaaaagaagctgagctccgccgcatgcaagagatgattgcaaggatg
caggcgcagatgcagatgcagatgcagggcggggatggcgatggcggggctctcggg
caccacgtgtaaggtgatgtgcacatatcaagaagtcagagaaaacactttcctggataaa
aaagaaaacattccagatgcatgatccagctgtgtgttttcaatccttgggagggtgccatc
cacattttaacagtacctgtgcctgagaatttaattttaaaagactttgatgtgtttttgtatgaa
gtacttttaacgtatgtatttcattgctgtgtcacactctgtgttttgtgaggtgaatgtcttccttt TABLE 10-continued The mRNA variant transcripts of Septins and UEV3 genes.

| Septin | mRNA Accession number | mRNAsequence |
|---|---|---|
| | | tctttctccctaaccactaatgttagaattgatttccaagaatcggcatgtatacttaatactga<br>atttctttgatttaactgacttaacaactgactaaccattgatgagcactcctgattttatctag<br>aacattcagatttaccataatgttccttagtggtagaggtgtgtgcctagtgatgtagaaaga<br>tacactgacttggtgcaaggccatctgcttaccacatcacaccacttggagatctttgcttcc<br>ttgcttttatgtttgtacacaacacctaaaaccagttttgctgctataattctatactgttgattcg<br>tctgcgattttatctgttaaccaaataaaacataatagaatttcctaatgagatatatctttatact<br>taaacagctttttttagaggtgagttttaaagaagtctcttaattctgatgctaggttgtttttaaa<br>accactatgcaaagaactcaccacaagccacctttttgtagtgttctccactaatactggttat<br>cctgtgctacagagaaaatcaaagcagtcataagctccagttttcgtattgcaaataagact<br>cttacctacaaaatgagattcagtgaactaatttggtttttactcaaccaaattaaaaattttttta<br>aggaaaattagcagttggtctattcagaatcaaaccttttttatattttatactgcactttagtgta<br>ttttctgtcactgtaggtatagaagatctgcctcccctgtggaaattggggtctgttggtggg<br>cgtgcccctgaagcctggcttgggttgaaaagtgttcccgccctaaggccttggtgccctg<br>aacctctgatgcctaccgggttctcctgatttgagtttcctttaaatactcccttttttgagtaattt<br>tctgatgggaggaaagtagcagtcatcatctttttgtgtgcaggctgtctcatttatttttagcc<br>attgtcgtttcattcattttgtgtaatataaaccgtgtgtcatgtcaaagtgaaagacatttcaaa<br>tctgtagcataggctagtgggcaggtccgcacagtcgaagccacacctggtctgttttctgt<br>gcactgtagccttagtgtcacctttcttcttgtgtctccttatggtacactccagcggttgccttt<br>tttatcatttctactgaagttgggaaattcaaccccagaaattgacagatgaaaggagacaa<br>tggttgtgtagggagatggagaaaatgcttaatctgaggatgagacagggtttttttcatttttg<br>tgggggctagaaaaaaacataaaatgaggcagttaaataataatagttaatgaaggtgtgct<br>acagaaaataatctggtgttcttgctaactttgcccttcactgttgcttaattgtgaacagcca<br>aaagctatatgttatggcttattgtgtgaaggtaactaagaagtggtgttccatgacttcaga<br>gtacatccatgcggagtccattatttgagtttgacatttaataactttgctggaaaatctgtaaa<br>aaagaaaaacaagtttgctagtgactaagccccgcatatgtgagtgaaagtacttcaggca<br>cgctgcctcctggtaacagctatgcagggagggaggacccacactgctacacttctgatc<br>ccctttggttttactacccaaatctaaatagatacttttgataatagataactgctcttttactaa<br>gacatagtctctacctatagaaatgtattttgaaaacacttattttacacagcaattttgtatcca<br>tttaaactaaccttttatcaataaagcactattgtttagatattaaaa |
| Septin3 | NM_019106<br>(SEQ. ID.<br>NO: 71)<br>NM_145733<br>(SEQ. ID.<br>NO: 72) | NM_019106<br>gggcgggtgggaggagagcgcgaaggggcgaggcccgtttgcaggggccgctcggc<br>ccggggaagcccgcgccccgctcagccttgcagccccgcgcccggagcatctccctgg<br>aggaacggagacaaaggaggattcatgtccaaagggctcccagagaccaggacggac<br>gcagccatgtcagagctggtgcctgagcccaggcctaagccagcggtgcccatgaagc<br>ccatgagcatcaactccaacctgctgggctacatcggcatcgacaccatcatcgagcaga<br>tgcgcaagaagaccatgaagaccggtttcgacttcaacatcatggtcgttggccagagtg<br>gactgggcaaatcaacgctggtcaacacgctcttcaaatcccaagtgagccgcaaggcct<br>ccagctggaaccgggaggagaagatccccaagacagtggagatcaaagctatcgggc<br>atgtgatagaggaaggcggtgtcaaaatgaagctgaccgtcatcgacaccccaggctttg<br>gagaccaaatcaacaatgaaaactgctgggagcccattgagaagtacatcaatgagcagt<br>acgagaagttcctgaaggaggaggtcaacatcgccaggaagaaacgcatccctgacact<br>cgtgtccactgctgcctttacttcatctctcccacaggacactccttgcgacctctggatcttg<br>agttcatgaaacacctcagcaaggttgtgaacatcatccctgtcattgctaaggctgacacc<br>atgaccctggaggagaagtctgaattcaagcaaagggttcgcaaggagcttgaagtaaat<br>ggcattgaattctaccccagaaggaatttgatgaggatttggaggataagacggagaat<br>gacaaaatcaggcaggagagcatgccttttgctgtggtgggaagtgacaaggagtacca<br>agtgaatggcaagagggtcctcggccgaaaaactccatggggatcatcgaagtggaa<br>aacctcaaccactgtgagtttgccctgcttcgagactttgtcatcaggacccacctccagga<br>cctcaaggaagtgacacacaacatccactatgagacttacagggccaagcggctcaatg<br>acaatggaggcctccctccggtgagcgtggacacagaggaaagccacgacagtaaccc<br>atgacgaccacttctctgtgtcatcacacatacccacttcacacacacacatcccaaatacc<br>accaccaaccaccttcttcctctcaactctgtcccacaggcctgtctggtatttgtggagcat<br>cttgtctgtgtgtgtgtgtgtgtgtgtgtgtgtgtgtgtgtgtgtgacagagagagagcgaga<br>gagcctgtgtgtgtgcatgcaggggtgaggtattttcactgccctccctggagagtcccttg<br>taagtttggctcctccatgcctgtccattatctgtctcctttccttgtgtcccaaaacaaagctg<br>tttgcctcactcaggagatctgggggaggtttcatttaaaagtgctgggagcaggtgagcc<br>acaggcaactcttctctcggaacctgcacacaaactggggctatagagattctccaagga<br>cagatggcagtggagctagacctgagtagggggcagggagttcaggacaaccctcctgt<br>aagttgggggtggtctgggggtaaggctggggcttcctgggaaaaggaaggccatgag<br>aaggcagagaagtaggccagagctgggttcttgcagaaagcatcagtgcctacaaatgg<br>agctccacccttcagtctgtgtcgtgttcagtgtcacaaagctaccacctgtcaccagagcc<br>tactgctgctctccactcaactggcctctgctgccaggccactgcctgtctctgcttccgact<br>ttgtcttctttctccctttccctccttccctcatacattgctttctctccctctcctgcgtgtctctg<br>acatctctcacttccttttagatgaatctactttaggttcattcctatatttagcatttatgcccagt<br>ctacttccagaaatgactttagactgcctttcacataaaatcacaaaactacaggacagtac<br>aaacagattgccagagaaatctgggtcaaagaaaggaataggaaagaaagtttctgtagt<br>caagcacctgaacaggccctgagctcacaggcagccaatgtaaagagggaaacacagt<br>gagttatgcagttcccagtgtccagttaaaggaagcacacatgctagtcatgtgagacaac<br>cttttattgggacatcaggttctagaactaattctaaag<br>aagtatcagaaacaatatacataatttgtctttcttagtaatttggcttcaaagacaaatttttga<br>ccacacctccgttttctccgtcagacttctctcccttctaagcaggcttctctgttgctccattt<br>gcttcatacatacttgacctctcttttctattccccatcacttttgtgctgaagctaatcatatttat<br>gtctgtctttctctacttttccctaattccctctcctcctgactcctgtagacattcccaatgatac |

TABLE 10-continued

The mRNA variant transcripts of Septins and UEV3 genes.

| Septin | mRNA Accession number | mRNAsequence |
|---|---|---|
| | | ccaccgtcatacatttaggcttttcttgcctttccctgaagccctgtatttattaatgcatatattt |
| | | cccctgcttgttgtacaagtaagttactcttttccttttaatctgtaagattcatgaaattcgggg |
| | | ccagggaaacagtttagccttagggaagggaaaacactaagtgaaactgtttacaataac |
| | | ctcatacaaccttctgtcccatctcctggttcagcctaggtgtttcactggtcctctatgaatcc |
| | | cagcacttataatcccagtcttttatcactcaggtgctaggaaaaaaaacatagactcaaga |
| | | cccaagattcaatggaccaggagaaaggggggcggtgatcaggtcaccagtgacccca |
| | | acctatgctctcggtctttcctggaggctgccaacccagccctcatcctcccttgctcacaa |
| | | agttacagggtaggcacctgtcaggacagaacagcagcagcgctacagcccagaggtt |
| | | atacatttcaacagaacagggatccttggctactgtagaagcagtcctgtatggagaccttg |
| | | gaccagcaggggaagatctatgggcatgggaggtgggcgttggaaaggctgagtagga |
| | | atggtgcctggcacccctgaaccatgatctgagcctccctggagaaggtattttatatgtct |
| | | gctgccagctgctggtctccacaccctcaaccgttctcaacccccctgcagggagaaggc |
| | | ctcctgggcactgtccttccacctgtgccagccaccccctgccccactgctgaatgaagg |
| | | ccatttcaagcgctgcttctcactccattcctctcagctgttattgctgcagggccaagccctt |
| | | tttagtgctgtgctcgtccagctcaccaccacagcccctctcagccctcagtaggtgggag |
| | | gggccagctgcctctttaggccagttgcatcctccatttatccaaaccactcctctcctccca |
| | | gtggagtggggttctgccagtacagccctactgcatcatctgcgtcagccggtcctagccc |
| | | atctgcagggtgaaagaactcatcaagagctccttctgcccttgtaagcccatcccagcta |
| | | cttgtaaccatctctaagggcaatggcattgctccctacccattcatctgcatgagctactctt |
| | | ggcttccttaaagggtcaagaaagcaattttctgcttactagattcattgagatcagctgtgt |
| | | gagccccaaagtgggacaagggtgtctccttcattacttaaagatattcatgagggt |
| | | gggtcactacagatgttggggagcaagggctaggatcacttttttaaaaaatcaccacttgt |
| | | ggctgtcccagagtgcggttgtacatcctccccacctcataacgcagccactgaggaaga |
| | | gtggttttcctaagaagacattgctggagttgactttcttctgtccaaacaaacaaacaaaaa |
| | | ctaaacacacacacaaaccccccagaaacccacaatatgtacacgctaaggaaaaactag |
| | | caccccttctgtccactcagcaataagagggatctcttcccacctaccctacctactcctacc |
| | | cccaaccccccttccccattaatgtgagtaatgaattagcctgaccacaggtggtcactgtag |
| | | gctaatggaaaatacccaagggagggcaaagccccccatcagatgcatgaatgtttgcg |
| | | aatgttgactgccactgccccacacactgtgtctttatagaattccccttttgcccaccctcttc |
| | | ctgtctccacctggacacaacttgctcaaaggctggtgacttgtgggccattcatctacaac |
| | | caagtcctgatggagcaagaggcccacgcctaggggatgcaagaacaacccgtttctta |
| | | aatgttaccagtcccagccaatcttacggtgacattacagttaaatttcccaattgaaaacaa |
| | | gcaaacagacactcaaactggtcctgtaattgttgctagactttatgtgttgtacaactaaac |
| | | attgctgtttgaacagtaa |
| | | NM_145733 |
| | | gggcgggtgggaggagagcgcgaaggggcgaggcccgtttgcaggggccgctcggc |
| | | ccggggaagcccgcgccccgctcagccttgcagccccgcgcccggagcatctccctgg |
| | | aggaacggagacaaaggaggattcatgtccaaagggctcccagagaccaggacggac |
| | | gcagccatgtcagagctggtgcctgagcccaggcctaagccagcggtgcccatgaagc |
| | | ccatgagcatcaactccaacctgctgggctacatcggcatcgacaccatcatcgagcaga |
| | | tgcgcaagaagaccatgaagaccggtttcgacttcaacatcatggtcgttggccagagtg |
| | | gactgggcaaatcaacgctggtcaacacgctcttcaaatcccaagtgagccgcaaggcct |
| | | ccagctggaaccgggaggagaagatccccaagacagtggagatcaaagctatcgggc |
| | | atgtgatagaggaaggcggtgtcaaaatgaagctgaccgtcatcgacaccccaggctttg |
| | | gagaccaaatcaacaatgaaaactgctgggagcccattgagaagtacatcaatgagcagt |
| | | acgagaagttcctgaaggaggaggtcaacatcgccaggaagaaacgcatccctgacact |
| | | cgtgtccactgctgcctttacttcatctctcccacaggacactccttgcgacctctggatcttg |
| | | agttcatgaaacacctcagcaaggttgtgaacatcatccctgtcattgctaaggctgacacc |
| | | atgaccctggaggagaagtctgaattcaagcaaagggttcgcaaggagcttgaagtaaat |
| | | ggcattgaattctacccccagaaggaatttgatgaggatttggaggataagacggagaat |
| | | gacaaaatcaggcaggagagcatgccttttgctgtggtgggaagtgacaaggagtacca |
| | | agtgaatggc |
| | | aagagggtcctcggccgaaaaactccatggggggatcatcgaagtggaaaacctcaacca |
| | | ctgtgagtttgccctgcttcgagactttgtcatcaggacccacctccaggacctcaaggaa |
| | | gtgacacacaacatccactatgagacttacagggccaagcggctcaatgacaatggagg |
| | | cctccctccgggagaaggcctcctgggcactgtccttccacctgtgccagccaccccctg |
| | | ccccactgctgaatgaaggccatttcaagcgctgcttctcactccattcctctcagctgtt |
| | | attgctgcagggccaagcccttttttagtgctgtgctcgtccagctcaccaccacagcccctc |
| | | tcagccctcagtaggtgggagggggccagctgcctctttaggccagttgcatcctccatttat |
| | | ccaaaccactcctctcctcccagtggagtggggttctgccagtacagccctactgcatcat |
| | | ctgcgtcagccggtcctagcccatctgcagggtgaaagaactcatcaagagctccttctgc |
| | | ccttgtaagcccatcccagctacttgtaaccatctctaagggcaatggcattgctccctacc |
| | | cattcatctgcatgagctactcttggcttccttaaagggtcaagaaagcaattttctgcttact |
| | | agattcattgagatcagctgtgtgagccccaaagtgggacaagggtgtctccttcattactt |
| | | aaagatattcatgagggtgggtcactacagatgttggggagcaagggctaggatcactttt |
| | | taaaaaatcaccacttgtggctgtcccagagtgcggttgtacat |
| | | cctccccacctcataacgcagccactgaggaagagtggttttcctaagaagacattgctgg |
| | | agttgactttcttctgtccaaacaaacaaacaaaaactaaacacacacacaaaccccccaga |
| | | aacccacaatatgtacacgctaaggaaaaactagcaccccttctgtccactcagcaataaga |
| | | gggatctcttcccacctaccctacctactcctacccccaacccccccttccccattaatgtgagt |
| | | aatgaattagcctgaccacaggtggtcactgtaggctaatggaaaatacccaagggagg |
| | | gcaaagccccccatcagatgcatgaatgtttgcgaatgttgactgccactgccccacacac |
| | | tgtgtctttatagaattccccttttgcccaccctcttcctgtctccacctggacacaacttgctca |
| | | aaggctggtgacttgtgggccattcatctacaaccaagtcctgatggagcaagaggccca |

TABLE 10-continued

The mRNA variant transcripts of Septins and UEV3 genes.

| Septin | mRNA Accession number | mRNAsequence |
|---|---|---|
| | | cgcctaggggatgcaagaacaacccgtttcttaaatgttaccagtcccagccaatcttacg |
| | | gtgacattacagttaaatttcccaattgaaaacaagcaaacagacactcaaactggtcctgt |
| | | aattgttgctagactttatgtgttgtacaactaaacattgctgtttgaacagtaa |
| Septin4 | NM_001198713 | NM_001198713 |
| | (SEQ. ID. NO: | acttgcactaggaagggattgggccaggtttgcccaagtccactgggcatctttagtaaatt |
| | 13) | tctctttttctcctcctattggcactctctgaattccatttgctgcccctgggaatgcctggctt |
| | NM_004574 | ctactctgttatgacagatgaggagatcaagcgtttcctggaggacaccacggatgatgga |
| | (SEQ. ID. | gaactgagcaagttcgtgaaggatttctcaggaaatgcgagctgccacccaccagaggct |
| | NO: 73) | aagacctgggcatccaggccccaagtcccggagccaaggccccaggccccggacctc |
| | NM_080415 | tatgatgatgacctggagttcagacccccctcgcggccccagtcctctgacaaccagcag |
| | (SEQ. ID. | tacttctgtgccccagcccctctcagcccatctgccaggccccgcagcccatggggcaag |
| | NO: 74) | cttgatccctatgattcctctgaggatgacaaggagtatgtgggctttgcaaccctccccaa |
| | NM_080416 | ccaagtccaccgaaagtccgtgaagaaaggctttgactttaccctcatggtggcaggaga |
| | (SEQ. ID. | gtctggcctgggcaaatccacacttgtcaatagcctcttcctcactgatctgtaccgggacc |
| | NO: 75) | ggaaacttcttggtgctgaagagaggatcatgcaaactgtggagatcactaagcatgcagt |
| | | ggacatagaagagaagggtgtgaggctgcggctcaccattgtggacacaccaggttttg |
| | | gggatgcagtcaacaacacagagtgctggaagcctgtggcagaatacattgatcagcag |
| | | tttgagcagtatttccgagacgagagtggcctgaaccgaaagaacatccaagacaacag |
| | | ggtgcactgctgcctgtacttcatctcacccttcggccatgggctccggccattggatgttg |
| | | aattcatgaaggccctgcatcagcgggtcaacatcgtgcctatcctggctaaggcagaca |
| | | cactgacacctcccgaagtggaccacaagaaacgcaaaatccgggaggagattgagca |
| | | ttttggaatcaagatctatcaattcccagactgtgactctgatgaggatgaggacttcaaatt |
| | | gcaggaccaagccctaaaggaaagcatcccatttgcagtaattggcagcaacactgtagt |
| | | agaggccagagggcggcgagttcggggtcgactctaccccctggggcatcgtggaagtg |
| | | gaaaacccagggcactgcgactttgtgaagctgaggacaatgctggtacgtacccacatg |
| | | caggacctgaaggatgtgacacgggagacacattatgagaactaccgggcacagtgcat |
| | | ccagagcatgacccgcctggtggtgaaggaacggaatcgcaacaaactgactcgggaa |
| | | agtggtaccgacttccccatccctgctgtcccaccagggacagatccagaaactgagaag |
| | | cttatccgagagaaagatgaggagctgcggcggatgcaggagatgctacacaaaataca |
| | | aaaacagatgaaggagaactattaactggctttcagccctggatatttaaatctcctcctctt |
| | | cttcctgtccatgccggcccctcccagcaccagctctgctcaggccccttcagctactgcc |
| | | acttcgccttacatccctgctgactgcccagagactcagaggaaataaagtttaataaatct |
| | | gtaggtggcttctggaa |
| | | NM_004574 |
| | | gagctgtccttggagggtgggagccaagggaaggggaggagaagaggggtggggaa |
| | | ggacattccacaggctttttggcccctgccagagacagaaggggggtcaaagagaaagg |
| | | gaaaggagcaagccaggaagccagacaacaacagcatcaaaacaaggctgtttctgtgt |
| | | gtgaggaactttgcctgggagataaaattagacctagagctttctgacagggagtctgaag |
| | | cgtgggacatggaccgttcactgggatggcaagggaattctgtccctgaggacaggact |
| | | gaagctgggatcaagcgtttcctggaggacaccacggatgatggagaactgagcaagtt |
| | | cgtgaaggatttctcaggaaatgcgagctgccacccaccagaggctaagacctgggcat |
| | | ccaggccccaagtcccggagccaaggccccaggccccggacctctatgatgatgacct |
| | | ggagttcagacccccctcgcggccccagtcctctgacaaccagcagtacttctgtgcccc |
| | | agcccctctcagcccatctgccaggccccgcagcccatggggcaagcttgatccctatga |
| | | ttcctctgaggatgacaaggagtatgtgggctttgcaaccctccccaaccaagtccaccga |
| | | aagtccgtgaagaaaggctttgactttaccctcatggtggcaggagagtctggcctgggc |
| | | aaatccacacttgtcaatagcctcttcctcactgatctgtaccgggaccggaaacttcttggt |
| | | gctgaagagaggatcatgcaaactgtggagatcactaagcatgcagtggacatagaaga |
| | | gaagggtgtgaggctgcggctcaccattgtggacacaccaggttttggggatgcagtcaa |
| | | caacacagagtgctggaagcctgtggcagaatacattgatcagcagtttgagcagtatttc |
| | | cgagacgagagtggcctgaaccgaaagaacatccaagacaacagggtgcactgctgcc |
| | | tgtacttcatctcacccttcggccatgggctccggccattggatgttgaattcatgaaggcc |
| | | ctgcatcagcgggtcaacatcgtgcctatcctggctaaggcagacacactgacacctccc |
| | | gaagtggaccacaagaaacgcaaaatccgggaggagattgagcattttggaatcaagat |
| | | ctatcaattcccagactgtgactctgatgaggatgaggacttcaaattgcaggaccaagcc |
| | | ctaaaggaaagcatcccatttgcagtaattggcagcaacactgtagtagaggccagaggg |
| | | cggcgagttcggggtcgactctaccccctggggcatcgtggaagtggaaaacccagggc |
| | | actgcgactttgtgaagctgaggacaatgctggtacgtacccacatgcaggacctgaagg |
| | | atgtgacacgggagacacattatgagaactaccgggcacagtgcatccagagcatgacc |
| | | cgcctggtggtgaaggaacggaatcgcaacaaactgactcgggaaagtggtaccgactt |
| | | ccccatccctgctgtcccaccagggacagatccagaaactgagaagcttatccgagaga |
| | | aagatgaggagctgcggcggatgcaggagatgctacacaaaatacaaaaacagatgaa |
| | | ggagaactattaactggctttcagccctggatatttaaatctcctcctcttcttcctgtccatgc |
| | | cggcccctcccagcaccagctctgctcaggccccttcagctactgccacttcgccttacat |
| | | ccctgctgactgcccagagactcagaggaaataaagtttaataaatctgtaggtggcttctg |
| | | gaa |
| | | NM_080415 |
| | | agcggtccgcactcggggaggcgggagggtgacggcggtgctgcgaggtcggcgcg |
| | | cagctccgccgcgggtcgctcgggcgctgtccaggcggagccggccccgcccgggct |
| | | gcagccatgatcaagcgtttcctggaggacaccacggatgatggagaactgagcaagtt |
| | | cgtgaaggatttctcaggaaatgcgagctgccacccaccagaggctaagacctgggcat |
| | | ccaggccccaagtcccggagccaaggccccaggccccggacctctatgatgatgacct |
| | | ggagttcagacccccctcgcggccccagtcctctgacaaccagcagtacttctgtgcccc |

TABLE 10-continued

The mRNA variant transcripts of Septins and UEV3 genes.

| Septin | mRNA Accession number | mRNAsequence |
|---|---|---|
| | | agcccctctcagcccatctgccaggccccgcagcccatggggcaagcttgatccctatga<br>ttcctctgaggatgacaaggagtatgtgggctttgcaaccctccccaaccaagtccaccga<br>aagtccgtgaagaaaggctttgactttaccctcatggtggcaggagagtctggcctgggc<br>aaatccacacttgtcaatagcctcttcctcactgatctgtaccgggaccggaaacttcttggt<br>gctgaagagaggatcatgcaaactgtggagatcactaagcatgcagtggacatagaaga<br>gaagggtgtgaggctgcggctcaccattgtggacacaccaggttttggggatgcagtcaa<br>caacacagagtgctggaagcctgtggcagaatacattgatcagcagtttgagcagtatttc<br>cgagacgagagtggcctgaaccgaaagaacatccaagacaacagggtgcactgctgcc<br>tgtacttcatctcacccttcggccatgggtatggtccaagcctgaggctcctggcaccacc<br>gggtgctgtcaagggaacaggccaagagcaccaggggcagggctgccactagcaggt<br>ggtcacaggttcctgttccccaggctccggccattggatgttgaattcatgaaggccctgc<br>atcagcgggtcaacatcgtgcctatcctggctaaggcagacacactgacacctcccgaag<br>tggaccacaagaaacgcaaaatccgggaggagattgagcattttggaatcaagatctatc<br>aattcccagactgtgactctgatgaggatgaggacttcaaattgcaggaccaagccctaaa<br>ggaaagcatcccatttgcagtaattggcagcaacactgtagtagaggccagagggcggc<br>gagttcggggtcgactctaccccttggggcatcgtggaagtggaaaacccagggcactgc<br>gactttgtgaagctgaggacaatgctggtacgtacccacatgcaggacctgaaggatgtg<br>acacgggagacacattatgagaactaccgggcacagtgcatccagagcatgacccgcct<br>ggtggtgaaggaacggaatcgcaagtatgaccagaagccaggacaaagctggcaggg<br>ggagatcccaagcctagccttgggtgagaccaagccctacttttgttcttctataggccctg<br>ggctcaatctaagcgggtgctggggtcctcctcgccttatcaacccttttctccctttagcaa<br>actgactcgggaaagtggtaccgacttccccatccctgctgtcccaccagggacagatcc<br>agaaactgagaagcttatccgagagaaagatgaggagctgcggcggatgcaggagatg<br>ctacacaaaatacaaaaacagatgaaggagaactattaactggctttcagccctggatattt<br>aaatctcctcctcttcttcctgtccatgccggcccctcccagcaccagctctgctcaggccc<br>cttcagctactgccacttcgccttacatccctgctgactgcccagagactcagaggaaata<br>aagtttaataaatctgtaggtggcttctggaa<br>NM_080416<br>agcggtccgcactcggggaggcgggagggtgacggcggtgctgcgaggtcggcgcg<br>cagctccgccgcgggtcgctcgggcgctgtccaggcggagccggccccgcccgggct<br>gcagccatgatcaagcgtttcctggaggacaccacggatgatggagaactgagcaagtt<br>cgtgaaggatttctcaggaaatgcgagctgccacccaccagaggctaagacctgggcat<br>ccaggccccaagtcccggagccaaggccccaggccccggacctctatgatgatgacct<br>ggagttcagacccccctcgcggccccagtcctctgacaaccagcagtacttctgtgcccc<br>agcccctctcagcccatctgccaggccccgcagcccatggggcaagcttgatccctatga<br>ttcctctgaggatgacaaggagtatgtgggctttgcaaccctccccaaccaagtccaccga<br>aagtccgtgaagaaaggctttgactttaccctcatggtggcaggagagtctggcctgggc<br>aaatccacacttgtcaatagcctcttcctcactgatctgtaccgggaccggaaacttcttggt<br>gctgaagagaggatcatgcaaactgtggagatcactaagcatgcagtggacatagaaga<br>gaagggtgtgaggctgcggctcaccattgtggacacaccaggttttggggatgcagtcaa<br>caacacagagtgctggaagcctgtggcagaatacattgatcagcagtttgagcagtatttc<br>cgagacgagagtggcctgaaccgaaagaacatccaagacaacagggtgcactgctgcc<br>tgtacttcatctcacccttcggccatgggctccggccattggatgttgaattcatgaaggcc<br>ctgcatcagcgggtcaacatcgtgcctatcctggctaaggcagacacactgacacctccc<br>gaagtggaccacaagaaacgcaaaatccgggaggagattgagcattttggaatcaagat<br>ctatcaattcccagactgtgactctgatgaggatgaggacttcaaattgcaggaccaagcc<br>ctaaaggaaagcatcccatttgcagtaattggcagcaacactgtagtagaggccagaggg<br>cggcgagttcggggtcgactctaccccttggggcatcgtggaagtggaaaacccagggc<br>actgcgactttgtgaagctgaggacaatgctggtacgtacccacatgcaggacctgaagg<br>atgtgacacgggagacacattatgagaactaccgggcacagtgcatccagagcatgacc<br>cgcctggtggtgaaggaacggaatcgcaacaaactgactcgggaaagtggtaccgactt<br>ccccatccctgctgtcccaccagggacagatccagaaactgagaagcttatccgagaga<br>aagatgaggagctgcggcggatgcaggagatgctacacaaaatacaaaaacagatgaa<br>ggagaactattaactggctttcagccctggatatttaaatctcctcctcttcttcctgtccatgc<br>cggcccctcccagcaccagctctgctcaggccccttcagctactgccacttcgccttacat<br>ccctgctgactgcccagagactcagaggaaataaagtttaataaatctgtaggtggcttctg<br>gaa |
| Septin5 | NM_001009939 (SEQ. ID. NO: 14)<br>NM_002688 (SEQ. ID. NO: 76) | NM_001009939<br>gggcgcctgcgacgccccgcctctggctcgggtgcgggagcggggcctgcccggact<br>gcgacgccgccacagcttggggccagttcgcccagtcaggggatggctcggtcggcc<br>tcgggggtcgacgatcccccgggtaggcgacgtgccctgtccaggcctcacttcccgcg<br>tccgcaaaacggggtggacaacgcagcctaaggcagagccgcgccaaggtccctcgct<br>gtcgccgggctctggcggcctgaccgggcctggggtccgagcgtgcccccgggcctg<br>ggggggtcgccgcgatggactcgctggcagcgccccaggaccgcctggtggagcagc<br>tgctgtcgccgcggacccaggcccagaggcggctcaaggacattgacaagcagtacgt<br>gggcttcgccacactgcccaaccaggtgcaccgcaagtcggtgaagaaaggctttgactt<br>cacactcatggtggctggtgagtcaggcctggggaagtccacactggtccacagcctctt<br>cctgacagacttgtacaaggaccggaagctgctcagtgctgaggagcgcatcagccaga<br>cggtagagattctaaaacacacggtggacattgaggagaagggagtcaagctgaagctc<br>accatcgtggacacgccgggattcggggacgctgtcaacaacaccgagtgctggaagc<br>ccatcaccgactatgtggaccagcagtttgagcagtacttccgtgatgagagcggcctca<br>accgaaagaacatccaagacaaccgagtgcactgctgcctatacttcatctccccttcgg<br>gcatgggctgcggccagtggatgtgggtttcatgaaggcattgcatgagaaggtcaacat |

TABLE 10-continued

The mRNA variant transcripts of Septins and UEV3 genes.

| Septin | mRNA Accession number | mRNAsequence |
|---|---|---|
| | | cgtgcctctcatcgccaaagctgactgtcttgtccccagtgagatccggaagctgaagga |
| | | gcggatccgggaggagattgacaagtttgggatccatgtataccagttccctgagtgtgac |
| | | tcggacgaggatgaggacttcaagcagcaggaccgggaactgaaggagagcgcgccc |
| | | ttcgccgttataggcagcaacacggtggtggaggccaaggggcagcgggtccggggc |
| | | cgactgtaccctggggatcgtggagggcgcattgcgacttcgtgaagctgcgcaaca |
| | | tgctcatccgcacgcatatgcacgacctcaaggacgtgacgtgcgacgtgcactacgag |
| | | aactaccgcgcgcactgcatccagcagatgaccagcaaactgacccaggacagccgca |
| | | tggagagccccatcccgatcctgccgctgcccaccccggacgccgagactgagaagctt |
| | | atcaggatgaaggatgaggaactgaggcgcatgcaggagatgctgcagaggatgaagc |
| | | agcagatgcaggaccagtgacgctcgccgcggacacaccgtccgtctccgggacgccc |
| | | tcgcaccccctggacaccagaccggactgttcccgacccggagacgcggggccacagc |
| | | ccccagctgaccctaatttattctcagcaccacccccctcccaggtcattgtgtctgtttccga |
| | | ggggcctggaccgtagcccccgcccagctggccctctctgaccttgggggatcaggag |
| | | cgaagttgggcgggacttcagagatccgcctcccttgcccttcccccgcccccggacggt |
| | | cacagcacccaaaccgcaggccctgctctggcaggcaggcaaagctaggcagaagag |
| | | gattcccaggatcctgggtctgttccctgccccagtgctgcagaacggacttgggagccct |
| | | cctttgcctgctcccgcgggtcacccagcgagtgctgagaccccatttctgtcgaggcgg |
| | | gccgagtcttcccttatccccagacgcctagcgggcagggttgggctgaatcaaatggga |
| | | gccctccagacataaggaggccagaggctgcaaggagcggggtcgtgaccgcttacac |
| | | cccttctccacagcccggcccgacctggagggcccccggggcactgggcggtgagcc |
| | | acctcctggcaactctcggtgccgtcccctgccctcgctcgaggcctcttctccccagcac |
| | | cgctgtggtgtgccgggatcctgagcctaggcctcccgatgttcccacccgcatgatccct |
| | | tcccgccacacgatgctccgttttcttccgttgtgaatgccgcgtcctgtcctggtgacagg |
| | | agaacaatgttggtgaacgtcgcaaaaaaaaaaaaaaaaaa |
| | | NM_002688 |
| | | ggagcgggcggcggcggcggcggcgcggagggggccgctcaccccgcagcccggc |
| | | ctcggcctccgccgcttgtcgtcgcgccccgcccgcgagcccgccccgcacgtccccc |
| | | gccggcggccaccatgagcacaggcctgcggtacaagagcaagctggcgaccccaga |
| | | ggacaagcaggacattgacaagcagtacgtgggcttcgccacactgcccaaccaggtg |
| | | caccgcaagtcggtgaagaaaggctttgacttcacactcatggtggctggtgagtcaggc |
| | | ctggggaagtccacactggtccacagcctcttcctgacagacttgtacaaggaccggaag |
| | | ctgctcagtgctgaggagcgcatcagccagacggtagagattctaaaacacacggtgga |
| | | cattgaggagaagggagtcaagctgaagctcaccatcgtggacacgccgggattcggg |
| | | gacgctgtcaacaacaccgagtgctggaagcccatcaccgactatgtggaccagcagttt |
| | | gagcagtacttccgtgatgagagcggcctcaaccgaaagaacatccaagacaaccgagt |
| | | gcactgctgcctatacttcatctccccccttcgggcatgggctgcggccagtggatgtgggtt |
| | | tcatgaaggcattgcatgagaaggtcaacatcgtgcctctcatcgccaaagctgactgtctt |
| | | gtccccagtgagatccggaagctgaaggagcggatccgggaggagattgacaagtttg |
| | | ggatccatgtataccagttccctgagtgtgactcggacgaggatgaggacttcaagcagc |
| | | aggaccgggaactgaaggagagcgcgcccttcgccgttataggcagcaacacggtggt |
| | | ggaggccaaggggcagcgggtccggggccgactgtaccctggggatcgtggaggt |
| | | ggagaaccaggcgcattgcgacttcgtgaagctgcgcaacatgctcatccgcacgcatat |
| | | gcacgacctcaaggacgtgacgtgcgacgtgcactacgagaactaccgcgcgcactgc |
| | | atccagcagatgaccagcaaactgacccaggacagccgcatggagagccccatcccga |
| | | tcctgccgctgcccaccccggacgccgagactgagaagcttatcaggatgaaggatgag |
| | | gaactgaggcgcatgcaggagatgctgcagaggatgaagcagcagatgcaggaccag |
| | | tgacgctcgccgcggacacaccgtccgtctccgggacgccctcgcaccccctggacacc |
| | | agaccggactgttcccgacccggagacgcggggccacagcccccagctgaccctaattt |
| | | attctcagcaccacccccctcccaggtcattgtgtctgtttccgaggggcctggaccgtagc |
| | | ccccgcccagctggccctctctgaccttgggggatcaggagcgaagttgggcgggactt |
| | | cagagatccgcctcccttgcccttcccccgcccccggacggtcacagcacccaaaccgc |
| | | aggccctgctctggcaggcaggcaaagctaggcagaagaggattcccaggatcctggg |
| | | tctgttccctgccccagtgctgcagaacggacttgggagccctcctttgcctgctcccgcg |
| | | ggtcacccagcgagtgctgagaccccatttctgtcgaggcgggccgagtcttcccttatc |
| | | cccagacgcctagcgggcagggttgggctgaatcaaatgggagccctccagacataag |
| | | gaggccagaggctgcaaggagcggggtcgtgaccgcttacaccccttctccacagccc |
| | | ggcccgacctggagggcccccggggcactgggcggtgagccacctcctggcaactctc |
| | | ggtgccgtcccctgccctcgctcgaggcctcttctccccagcaccgctgtggtgtgccgg |
| | | gatcctgagcctaggcctcccgatgttcccacccgcatgatcccttcccgccacacgatgc |
| | | tccgttttcttccgttgtgaatgccgcgtcctgtcctggtgacaggagaacaatgttggtgaa |
| | | cgtcgcaaaaaaaaaaaaaaaaaa |
| Septin6 | NM_015129 | NM_015129 |
| | (SEQ. ID. | gaagaactggaactggtctggccataggggggaagcggcgcgttaaatccgccccctctc |
| | NO: 77) | catacccctactttcaaggggtgggcggtagaggggaggttggggttggagcagcggcg |
| | NM_145799 | agggggcccctcccttgcacctccccccaccggacttggtcgcgcccgaagtgtaacac |
| | (SEQ. ID. | tttctctttgtcggaggagctcctctgtttcctgtgcagtagctcccgttgcggcggcacccg |
| | NO: 78) | tggcagccctggcggacgcaggagcgatggcagcgaccgatatagctcgccaggtgg |
| | NM_145800 | gtgaaggttgccgaactgtccccctggctggacatgtggggtttgacagcttgcctgacca |
| | (SEQ. ID. | gctggtgaataagtccgtcagccagggcttctgcttcaacatcctgtgcgtgggagagac |
| | NO: 79) | aggtttgggcaagtccaccctcatggacaccctgttcaacaccaaattcgaaggggagcc |
| | NM_145802 | agccacccacacacagccgggtgtccagctccagtctaatacctatgacctccaagaga |
| | (SEQ. ID. | gcaacgtgaggctaaagctcacgatcgttagcacagttggctttggggaccagatcaaca |
| | NO: 80) | aagaggacagctacaagcctatcgtggaattcatcgatgcacaattcgaggcctacctgc |

TABLE 10-continued

The mRNA variant transcripts of Septins and UEV3 genes.

| Septin | mRNA Accession number | mRNAsequence |
|---|---|---|
| | | aggaagagctaaagatccgaagagtgctacacacctaccatgactcccgaatccatgtct<br>gcttgtatttcattgcccccacgggtcattccctgaagtctctggacctagtgactatgaaga<br>agctggacagtaaggtgaacatcatccccatcattgccaaagcagatgccatttcgaaga<br>gtgagctaacaaagttcaaaatcaaaatcaccagcgagcttgtcagcaacggagtccaga<br>tctatcagtttcctacagatgatgagtcggtggcagagatcaatggaaccatgaacgccca<br>cctgccgtttgctgtcattggcagcacagaagaactgaagataggcaacaagatgatgag<br>ggcgcggcagtatccttggggcactgtgcaggttgaaaacgaggcccactgcgactttgt<br>gaagctgcgggagatgctgattcgggtcaacatggaggatctgcgggagcagacccac<br>acccggcactatgagctgtatcgccgctgtaagctggaggagatgggcttcaaggacac<br>cgaccctgacagcaaacccttcagtttacaggagacatatgaggccaaaaggaacgagtt<br>cctaggggaactccagaaaaaagaagaggagatgagacagatgttcgtccagcgagtc<br>aaagagaaagaagcggagctcaaagaggcagagaaagagctgcacgagaagtttgac<br>cgtctgaagaaactgcaccaggacgagaagaagaaactggaggataagaagaaatccc<br>tggatgatgaagtgaatgctttcaagcaaagaaagacggcggctgagctgctccagtccc<br>agggctcccaggctggaggctcacagactctgaagagagacaaagagaagaaaaataa<br>tccatggctgtg<br>tactgaatagtattccccgctacagctggactggactccatttagccttttaagccgaggttc<br>ctattttaactgacagctttcctttggggtgccaggcagcgaggccccccacccctatcctg<br>ccatgtacttcaagctcacttcttctttttgagttccgcaacttgctcctgcctcccagcccca<br>ctggcactgaccatgaccacctacttctatttttttttttagagtttctttt<br>tttgatcacttactttcaaagcacacagtcaaacaaggttatgccaaatttccaggcctttttg<br>aagtattgagaaggggaaggggatttctcacttcaattatagatcataataggaagcaaaa<br>agaaaaaaatgaaaagcaaacatatgcacgcacttttcttgttgacaaagcaagaatatag<br>gtttgctgtgtaggtttggtgctctattgattggtgagtgaccagagcaagtatgaaggtgat<br>gctgccaaagcacaagccagtttcttgggaaaattcaagttacagtggagtatttttttgaag<br>accatatgcttggaggtagaaacaaaccaacgaccaaaaaaaaaaaaaaaaaaatctgct<br>cagatactcagccagtagctcagagagatgctgagttaggcctgtcaggtctccttgggaa<br>aggcttcatatttgcaactttgatgattctatgtccagcttcagagctgctttcccagaaattca<br>cgcttaaacaaccaaccggtaaccaccacttccccacaccgccgcccggtaattatttgca<br>ttacaaaccggaggcgccctcatttgcatttgtgtacagattaactagttaaggcttgagaa<br>gctctgaataattcaaaagtattagacccacacagccttggagagaccttcagaaactaag<br>gaggagttttatattaagggagacattttagtcagtaagacgatataacctacttactccgta<br>aggggaaatgaaggcccagagaagggaagggacttgaccgaggtcccacttctgtttcg<br>aggcagaagccagactaattttcatgcctcctgactcccaatcagtttcacaaagggattca<br>atctgtttatatacgttacattcctggatacgaggtcttttgatgttcagagtaactgactagtta<br>gtattagaagaccctcgaggtttttttccacagaaaaacatctgaagatggattgggtgagg<br>gctggcaaaacgaaggcatgccgggccagctccttaacccaatgacccagtgatgctgc<br>aaggctggaacggggtccaggagactgtgtgtaacaggtgccctaggtgacccttataat<br>cagggaagtttggtgaacaaaaatcgaacccatgagtgaacataaattaaaaagttgatca<br>acctattaaaatgtgtatttcattgggtagcttttctcactgtagacagatttttttccttcttcaatg<br>aaaaggcttttaaattagtacaactgttactatttaaaaaaaaaataccctaagtactctgttta<br>cttctggtgaaac<br>aaaaccagtcattagaaatggtctgtgcttttattttcccagactggagtggcttttctgaaac<br>acacacacacacacacacacacacacacacacacacacacacacacgtacacacat<br>ccctcacttctcttaagccaagaagtttgctttccctagctgcagtgtagatggctcttgttttt<br>gttttttgttttaatcatttggcattcacatgtggctgttaatatgtgcttgtttttaattaaaacaa<br>gaagctttaaa<br>NM_145799<br>gaagaactggaactggtctggccataggggaagcggcgcgttaaatccgccccctctc<br>cataccctactttcaaggggtgggcggtagaggggaggttggggttggagcagcggcg<br>agggggcccctcccttgcacctccccccaccggacttggtcgcgcccgaagtgtaacac<br>tttctctttgtcggaggagctcctctgtttcctgtgcagtagctcccgttgcggcggcacccg<br>tggcagccctggcggacgcaggagcgatggcagcgaccgatatagctcgccaggtgg<br>gtgaaggttgccgaactgtccccctggctggacatgtggggtttgacagcttgcctgacca<br>gctggtgaataagtccgtcagccagggcttctgcttcaacatcctgtgcgtgggagagac<br>aggtttgggcaagtccaccctcatggacaccctgttcaacaccaaattcgaaggggagcc<br>agccacccacacacagccgggtgtccagctccagtctaatacctatgacctccaagaga<br>gcaacgtgaggctaaagctcacgatcgttagcacagttggctttggggaccagatcaaca<br>aagaggacagctacaagcctatcgtggaattcatcgatgcacaattcgaggcctacctgc<br>aggaagagctaaagatccgaagagtgctacacacctaccatgactcccgaatccatgtct<br>gcttgtatttcattgcccccacgggtcattccctgaagtctctggacctagtgactatgaaga<br>agctggacagtaaggtgaacatcatccccatcattgccaaagcagatgccatttcgaaga<br>gtgagctaacaaagttcaaaatcaaaatcaccagcgagcttgtcagcaacggagtccaga<br>tctatcagtttcctacagatgatgagtcggtggcagagatcaatggaaccatgaacgccca<br>cctgccgtttgctgtcattggcagcacagaagaactgaagataggcaacaagatgatgag<br>ggcgcggcagtatccttggggcactgtgcaggttgaaaacgaggcccactgcgactttgt<br>gaagctgcgggagatgctgattcgggtcaacatggaggatctgcgggagcagacccac<br>acccggcactatgagctgtatcgccgctgtaagctggaggagatgggcttcaaggacac<br>cgaccctgacagcaaacccttcagtttacaggagacatatgaggccaaaaggaacgagtt<br>cctaggggaactccagaaaaaagaagaggagatgagacagatgttcgtccagcgagtc<br>aaagagaaagaagcggagctcaaagaggcagagaaagagctgcacgagaagtttgac<br>cgtctgaagaaactgcaccaggacgagaagaagaaactggaggataagaagaaatccc<br>tggatgatgaagtgaatgctttcaagcaaagaaagacggcggctgagctgctccagtccc<br>agggctcccaggctggaggctcacagactctgaagagagacaaagagaagaaaaatta |

TABLE 10-continued

The mRNA variant transcripts of Septins and UEV3 genes.

| Septin | mRNA Accession number | mRNAsequence |
|---|---|---|
| | | actctgctgttt |
| | | gctgcatgctgcatgagacccagggtcctgtttgggcttcctgtagacacccttttcctgcg |
| | | caacagagctgggcctccctttctctaatttccccttaacatgcctgggggcatacaatc |
| | | caacccgcgccctctcctctcttcctgccaaggtttatagaaacctgagaatctgagggtga |
| | | tgtctggccgctggtcaagaagccaacagtcatgtggctcgcagatgcatcctgcatccc |
| | | agtccccctcccagcacccccagccatccccccctgtcttcccccacatctttgccagaggt |
| | | gtgacatggtcaggggggcccatctgctactctttcccaccagctcccctgttccagttctgg |
| | | ttgctgttagtttccctgaggtatttgcaaccaccatggctgggtaaccaccgatcagcaca |
| | | gctgtccccttggtctcctgtatcccagtcactagtcctccctggtccaccccaccctcatcc |
| | | tcaggagccacagccatttcttagagggtttcaaaaggacagcctttggcgccttttccttct |
| | | aacctttgagtccagccctttccagttttcattcactcgaagtaactgcactcaagctgtgctc |
| | | aaaatcggcaacgcatttatttacaccaagcccttcccataaaacacaactgctgaagaaa |
| | | atagcagacgtttcccctctctctaactctgggtatcccacagatgcaaaagggagaataa |
| | | acctgaatattattaccagcctagagtcttgaatgatagccttaccgaattcttcttgtgaggt |
| | | atttcagcatctcggggggtaatttccggaagggctccatactgtcccaataaggtgaggc |
| | | cagtagcaggaataataaatcccactttgtaggctggaaaactgagctgtcaaaagaatca |
| | | agtgtttgggggtttgctctgatgagtcttctagttcatttggtgaatgtcatgatgatttttaac |
| | | atgcattttgcatgcatcccccaataagaagagatgagactcggccggagagaagaaaa |
| | | ggcccttaactttctttccaatttaaggagttgagagtttaaaaatattccagccctaagtttta |
| | | tcatgggtcccatctgatagtggctttgggaacctctgtgaagtagagagccctcccttgtc |
| | | agggttatgaggcacagtggcctttggtgtttggccagtgacagtgtgagagatggagttg |
| | | acctggcaatgatctgtggctaacatgccgtctctctgcccttcctttgcagtaatccatggc |
| | | tgtgtactgaatagtattccccgctacagctggactggactccatttagccttttaagccgag |
| | | gttcctattttaactgacagctttcctttggggtgccaggcagcgaggccccccacccctat |
| | | cctgccatgtacttcaagctcacttcttcttttttgagttccgcaacttgctcctgcctcccagcc |
| | | ccactggcactgaccatgaccacctacttctatttttttttttagagtttcttttttttgatcacttactt |
| | | tcaaagcacacagtcaaacaaggttatgccaaatttccaggccttttttgaagtattgagaag |
| | | gggaaggggatttctcacttcaattatagatcataataggaagcaaaaagaaaaaaatgaa |
| | | aagcaaacatatgcacgcacttttcttgttgacaaagcaagaatataggtttgctgtgtaggt |
| | | ttggtgctctattgattggtgagtgaccagagcaagtatgaaggtgatgctgccaaagcac |
| | | aagccagtttcttgggaaaattcaagttacagtggagtattttttttgaagaccatatgcttgga |
| | | ggtagaaacaaaccaacgaccaaaaaaaaaaaaaaaaaaaaatctgctcagatactcagcc |
| | | agtagctcagagagatgctgagttaggcctgtcaggtctccttgggaaaggcttcatatttg |
| | | caactttgatgattctatgtccagcttcagagctgctttcccagaaattcacgcttaaacaacc |
| | | aaccggtaaccaccacttccccacaccgccgcccggtaattatttgcattacaaaccgga |
| | | ggcgccctcatttgcatttgtgtacagattaactagttaaggcttgagaagctctgaataattc |
| | | aaaagtattagacccacacagccttggagagaccttcagaaactaaggaggagttttatatt |
| | | aagggagacattttagtcagtaagacgatataacctacttactccgtaaggggaaatgaag |
| | | gcccagagaagggaagggacttgaccgaggtcccacttctgtttcgaggcagaagcca |
| | | gactaattttcatgcctcctgactcccaatcagtttcacaaagggattcaatctgtttatatacg |
| | | ttacattcctggatacgaggtcttttgatgttcagagtaactgactagttagtattagaagacc |
| | | ctcgaggtttttttccacagaaaaacatctgaagatggattgggtgagggctggcaaaacg |
| | | aaggcatgccgggccagctccttaacccaatgacccagtgatgctgcaaggctggaacg |
| | | gggtccaggagactgtgtgtaacaggtgccctaggtgacccttataatcagggaagtttgg |
| | | tgaacaaaaatcgaacccatgagtgaacataaattaaaaagttgatcaacctattaaaatgt |
| | | gtatttcattgggtagcttttctcactgtagacagatttttttccttcttcaatgaaaaggcttttaa |
| | | attagtacaactgttactatttaaaaaaaaaataccctaagtactctgtttacttctggtgaaac |
| | | aaaaccagtcattagaaatggtctgtgcttttattttcccagactggagtggcttttctgaaac |
| | | acacacacacacacacacacacacacacacacacacacacacacacacgtacacacat |
| | | ccctcacttctcttaagccaagaagtttgctttccctagctgcagtgtagatggctcttgttttt |
| | | gtttttttgttttaatcatttggcattcacatgtggctgttaatatgtgcttgtttttaattaaaacaa |
| | | gaagctttaaaaaaaaaaaaaaaaaaaaaa |
| | | NM_145800 |
| | | gaagaactggaactggtctggccataggggggaagcggcgcgttaaatccgccccctctc |
| | | cataccctactttcaaggggtgggcggtagaggggaggttggggttggagcagcggcg |
| | | agggggcccctcccttgcacctccccccaccggacttggtcgcgcccgaagtgtaacac |
| | | tttctctttgtcggaggagctcctctgtttcctgtgcagtagctcccgttgcggcggcacccg |
| | | tggcagccctggcggacgcaggagcgatggcagcgaccgatatagctcgccaggtgg |
| | | gtgaaggttgccgaactgtccccctggctggacatgtggggtttgacagcttgcctgacca |
| | | gctggtgaataagtccgtcagccagggcttctgcttcaacatcctgtgcgtgggagagac |
| | | aggtttgggcaagtccaccctcatggacaccctgttcaacaccaaattcgaaggggagcc |
| | | agccacccacacacacagccgggtgtccagctccagtctaatacctatgacctccaagaga |
| | | gcaacgtgaggctaaagctcacgatcgttagcacagttggctttggggaccagatcaaca |
| | | aagaggacagctacaagcctatcgtggaattcatcgatgcacaattcgaggcctacctgc |
| | | aggaagagctaaagatccgaagagtgctacacacctaccatgactcccgaatccatgtct |
| | | gcttgtatttcattgcccccacgggtcattccctgaagtctctggacctagtgactatgaaga |
| | | agctggacagtaaggtgaacatcatccccatcattgccaaagcagatgccatttcgaaga |
| | | gtgagctaacaaagttcaaaatcaaaatcaccagcgagcttgtcagcaacggagtccaga |
| | | tctatcagtttcctacagatgatgagtcggtggcagagatcaatggaaccatgaacgccca |
| | | cctgccgtttgctgtcattggcagcacagaagaactgaagataggcaacaagatgatgag |
| | | ggcgcggcagtatccttggggcactgtgcaggttgaaaacgaggcccactgcgactttgt |
| | | gaagctgcgggagatgctgattcgggtcaacatggaggatctgcgggagcagacccac |
| | | acccggcactatgagctgtatcgccgctgtaagctggaggagatgggcttcaaggacac |
| | | cgaccctgacagcaaacccttcagtttacaggagacatatgaggccaaaaggaacgagtt |

TABLE 10-continued

The mRNA variant transcripts of Septins and UEV3 genes.

| Septin | mRNA Accession number | mRNAsequence |
|---|---|---|
| | | cctaggggaactccagaaaaaagaagaggagatgagacagatgttcgtccagcgagtc<br>aaagagaaagaagcggagctcaaagaggcagagaaagagctgcacgagaagtttgac<br>cgtctgaagaaactgcaccaggacgagaagaagaaactggaggataagaagaaatccc<br>tggatgatgaagtgaatgctttcaagcaaagaaagacggcggctgagctgctccagtccc<br>agggctcccaggctggaggctcacagactctgaagagagacaaagagaagaaaaatta<br>actctgctgtttgctgcatgctgcatgagacccagggtcctgcttttttttaatcttgtcttcagc<br>agctgcactaagtctaaaggagaagactgccattatagaagagttagggttccatattgtct<br>caaatcagaaatcaaccaatttcctctcccctcaaactgcaagcacacacacatacaccac<br>accactcaacaagtgttcatgtgtccctgtgtccaggcaagaagctctcttcctgactcacat<br>ggtattttaaatggaagtgtcttgtcctaactaacaaggcaggaaaagaaccatcagagct<br>ggaaaatggacgaaatgtaacctcagagaaacaactacaggaccactcacccaagtgta<br>agtgactggggcaggacacctcagctgtgggtatgaaagtactgttctgttcacaaggtttt<br>gtttgagttttatgtttttcttttaaacatttctctggttcgatgggttgactgtctacagccactgt<br>taaacatttctgaatatgcaagagaaagtcaagtgacatttgtatcttcttcagcattcgcaga<br>ccttctatagattccagcaaaggggaaaatgtatccactatctaacacttaggtagagaag<br>ggagggggtttaagcttagtgagggcaaaattactccattccaccttccgagaccagttag<br>ggttttgagagaggtttctgctcaacctgggatctggagggagagctttgatgttggtaaat<br>ctgccttgaattcattggtttaacttgcatcaaaataccatgtgagtgtgctcattctcatatatc<br>ccctaccaccatcaccaccattctgctgttcagtgtctcttgagagagcctctttgcatgttttc<br>cagaatctgtgtgtgtttttcctttcttctcctttgttctttttgctcaaaggtgtgaccagtcattg<br>cccctctggggctttcattctccaggagaaacatcccagaaccagcactgtttagcctgata<br>cctttctaatgtccatgtcaattttcaataaaattcaaagaaatgctaaa<br>NM_145802<br>gaagaactggaactggtctggccatagggggaagcggcgcgttaaatccgccccctctc<br>cataccctactttcaaggggtgggcggtagaggggaggttggggttggagcagcggcg<br>agggggcccctcccttgcacctcccccaccggacttggtcgcgcccgaagtgtaacac<br>tttctctttgtcggaggagctcctctgtttcctgtgcagtagctcccgttgcggcggcacccg<br>tggcagccctggcggacgcaggagcgatggcagcgaccgatatagctcgccaggtgg<br>gtgaaggttgccgaactgtcccccctggctggacatgtggggtttgacagcttgcctgacca<br>gctggtgaataagtccgtcagccagggcttctgcttcaacatcctgtgcgtgggagagac<br>aggtttgggcaagtccaccctcatggacaccctgttcaacaccaaattcgaaggggagcc<br>agccacccacacacagccgggtgtccagctccagtctaatacctatgacctccaagaga<br>gcaacgtgaggctaaagctcacgatcgttagcacagttggctttggggaccagatcaaca<br>aagaggacagctacaagcctatcgtggaattcatcgatgcacaattcgaggcctacctgc<br>aggaagagctaaagatccgaagagtgctacacacctaccatgactcccgaatccatgtct<br>gcttgtatttcattgcccccacgggtcattccctgaagtctctggacctagtgactatgaaga<br>agctggacagtaaggtgaacatcatccccatcattgccaaagcagatgccatttcgaaga<br>gtgagctaacaaagttcaaaatcaaaatcaccagcgagcttgtcagcaacggagtccaga<br>tctatcagtttcctacagatgatgagtcggtggcagagatcaatggaaccatgaacgccca<br>cctgccgtttgctgtcattggcagcacagaagaactgaagataggcaacaagatgatgag<br>ggcgcggcagtatccttggggcactgtgcaggttgaaaacgaggcccactgcgactttgt<br>gaagctgcgggagatgctgattcgggtcaacatggaggatctgcgggagcagacccac<br>acccggcactatgagctgtatcgccgctgtaagctggaggagatgggcttcaaggacac<br>cgaccctgacagcaaacccttcagtttacaggagacatatgaggccaaaaggaacgagtt<br>cctaggggaactccagaaaaaagaagaggagatgagacagatgttcgtccagcgagtc<br>aaagagaaagaagcggagctcaaagaggcagagaaagagctgcacgagaagtttgac<br>cgtctgaagaaactgcaccaggacgagaagaagaaactggaggataagaagaaatccc<br>tggatgatgaagtgaatgctttcaagcaaagaaagacggcggctgagctgctccagtccc<br>agggctcccaggctggaggctcacagactctgaagagagacaaagagaagaaaaactt<br>tttttaatcttgtcttcagcagctgcactaagtctaaaggagaagactgccattatagaagag<br>ttagggttccatattgtctcaaatcagaaatcaaccaatttcctctcccctcaaactgcaagc<br>acacacacatacaccacaccactcaacaagtgttcatgtgtccctgtgtccaggcaagaa<br>gctctcttcctgactcacatggtattttaaatggaagtgtcttgtcctaactaacaaggcagg<br>aaaagaaccatcagagctggaaaatggacgaaatgtaacctcagagaaacaactacagg<br>accactcacccaagtgtaagtgactggggcaggacacctcagctgtgggtatgaaagtac<br>tgttctgttcacaaggttttgtttgagttttatgtttttcttttaaacatttctctggttcgatgggttg<br>actgtctacagccactgttaaacatttctgaatatgcaagagaaagtcaagtgacatttgtat<br>cttcttcagcattcgcagaccttctatagattccagcaaaggggaaaatgtatccactatct<br>aacacttaggtagagaagggagggggtttaagcttagtgagggcaaaattactccattcca<br>ccttccgagaccagttagggttttgagagaggtttctgctcaacctgggatctggagggag<br>agctttgatgttggtaaatctgccttgaattcattggtttaacttgcatcaaaataccatgtgag<br>tgtgctcattctcatatatcccctaccaccatcaccaccattctgctgttcagtgtctcttgaga<br>gagcctctttgcatgttttccagaatctgtgtgtgtttttcctttcttctcctttgttctttttgctcaa<br>aggtgtgaccagtcattgcccctctggggctttcattctccaggagaaacatcccagaacc<br>agcactgtttagcctgatacctttctaatgtccatgtcaattttcaataaaattcaaagaaatgc<br>taaa |
| Septin7 | NM_001011553<br>(SEQ. ID.<br>NO: 81)<br>NM_001788<br>(SEQ. ID.<br>NO: 82) | NM_001011553<br>agcctcgtctgagggggcgggggacggaggagggagcgggagtcgagcgagagcct<br>gtgg<br>aggagtccgcctgctgtagcgtgcgtaagcaaggcagctacgccgggcggctacgctg<br>cggaatcggcgtaggcgcctttggagaatcggcgggctgcgctccgctggggctggtc<br>gcggagggggggaggggatgtcggtcagtgcgagatccgctgctgctgaggagagga<br>gcgtcaacagcagcaccatggctcaacagaagaaccttgaaggctatgtgggatttgcca |

TABLE 10-continued

The mRNA variant transcripts of Septins and UEV3 genes.

| Septin | mRNA Accession number | mRNAsequence |
|---|---|---|
| | | atctcccaaatcaagtatacagaaaatcggtgaagagaggttttgaattcacgcttatggta |
| | | gtgggtgaatctggattgggaaagtcgacattaatcaactcattattcctcacagatttgtatt |
| | | ctccagagtatccaggtccttctcatagaattaaaaagactgtacaggtggaacaatccaa |
| | | agttttaatcaaagaaggtggtgttcagttgctgctcacaatagttgataccccaggatttgg |
| | | agatgcagtggataatagtaattgctggcagcctgttatcgactacattgatagtaaatttga |
| | | ggactacctaaatgcagaatcacgagtgaacagacgtcagatgcctgataacagggtgc |
| | | agtgttgtttatacttcattgctccttcaggacatggacttaaaccattggatattgagtttatga |
| | | agcgtttgcatgaaaaagtgaatatcatcccacttattgccaaagcagacacactcacacc |
| | | agaggaatgccaacagtttaaaaaacagataatgaaagaaatccaagaacataaaattaa |
| | | aatatacgaatttccagaaacagatgatgaagaagaaaataaacttgttaaaaagataaag |
| | | gaccgtttacctcttgctgtggtaggtagtaatactatcattgaagttaatggcaaaagggtc |
| | | agaggaaggcagtatccttggggtgttgctgaagttgaaaatggtgaacattgtgattttac |
| | | aatcctaagaaatatgttgataagaacacacatgcaggacttgaaagatgttactaataatgt |
| | | ccactatgagaactacagaagcagaaaacttgcagctgtgacttataatggagttgataac |
| | | aacaagaataaagggcagctgactaagagccctctggcacaaatggaagaagaaagaa |
| | | gggagcatgtagctaaaatgaagaagatggagatggagatggagcaggtgtttgagatg |
| | | aaggtcaaagaaaaagttcaaaaactgaaggactctgaagctgagctccagcggcgcca |
| | | tgagcaaatgaaaaagaatttggaagcacagcacaaagaattggaggaaaaacgtcgtc |
| | | agttcgaggatgagaaagcaaactgggaagctcaacaacgtattttagaacaacagaact |
| | | cttcaagaaccttggaaaagaacaagaagaaagggaagatcttttaaactctctattgacc |
| | | accagttaacgtattagttgccaatatgccagcttggacatcagtgtttgttggatccgtttga |
| | | ccaatttgcaccagttttatccataatgatggatttaacagcatgacaaaaattatttttttttttg |
| | | ttcttgatggagattaagatgccttgaattgtctagggtgttctgtacttagaaagtaagagct |
| | | ctaagtacctttcctacattttctttttttattaaacagatatcttcagtttaatgcaagagaacatt |
| | | ttactgttgtacaatcatgttctggtggtttgattgtttacaggatattccaaaataaaaggact |
| | | ctggaagattttcattgaggataaattgccataatatgatgcaaactgtgcttctctatgataat |
| | | tacaatacaaaggttccattcagtgcagcatatacaataatgtaatttagtctaacacagttga |
| | | ccctatttttttgacacttccattgtttaaaaatacacatggaaaaaaaaaaaaccctatatgctt |
| | | actgtgcacctagagctttttttataacaacgtctttttgtttgtttgttttggattctttaaatatata |
| | | ttattctcatttagtgccctctttagccagaatctcattactgcttcatttttgtaataacatttaatt |
| | | tagatattttccatatattggcactgctaaaatagaatatagcatctttcatatggtaggaacca |
| | | acaaggaaactttcctttaactccctttttacactttatggtaagtagcaggggggggaaatgc |
| | | atttatagatcatttctaggcaaaattgtgaagctaatgaccaacctgtttctacctatatgcag |
| | | tctctttattttactagaaatgggaatcatggcctcttgaagagaaaaaagtcaccattctgca |
| | | tttagctgtattcatatattgcatttctgtatttttttgtttgtattgtaaaaaattcacataataaacg |
| | | atgttgtgatgtaaaaaaaaaaaaaaa |
| | | NM_001788 |
| | | gagatggaagccagcctccgctaggcccggaagcctcgtctgagggggcgggggacg |
| | | gag |
| | | gagggagcgggagtcgagcgagagcctgtggaggagtccgcctgctgtagcgtgcgta |
| | | agcaaggcagctacgccgggcggctacgctgcggaatcggcgtaggcgcctttggaga |
| | | atcggcgggctgcgctccgctggggctggtcgcggagggggggaggggatgtcggtc |
| | | agtgcgagatccgctgctgctgaggagaggagcgtcaacagcagcaccatggtagctc |
| | | aacagaagaaccttgaaggctatgtgggatttgccaatctcccaaatcaagtatacagaaa |
| | | atcggtgaagagaggttttgaattcacgcttatggtagtgggtgaatctggattgggaaagt |
| | | cgacattaatcaactcattattcctcacagatttgtattctccagagtatccaggtccttctcat |
| | | agaattaaaaagactgtacaggtggaacaatccaaagttttaatcaaagaaggtggtgttc |
| | | agttgctgctcacaatagttgataccccaggatttggagatgcagtggataatagtaattgct |
| | | ggcagcctgttatcgactacattgatagtaaatttgaggactacctaaatgcagaatcacga |
| | | gtgaacagacgtcagatgcctgataacagggtgcagtgttgtttatacttcattgctccttca |
| | | ggacatggacttaaaccattggatattgagtttatgaagcgtttgcatgaaaaagtgaatatc |
| | | atcccacttattgccaaagcagacacactcacaccagaggaatgccaacagtttaaaaaa |
| | | cagataatgaaagaaatccaagaacataaaattaaaatatacgaatttccagaaacagatg |
| | | atgaagaagaaaataaacttgttaaaaagataaaggaccgtttacctcttgctgtggtaggt |
| | | agtaatactatcattgaagttaatggcaaaagggtcagaggaaggcagtatccttggggtg |
| | | ttgctgaagttgaaaatggtgaacattgtgattttacaatcctaagaaatatgttgataagaac |
| | | acacatgcaggacttgaaagatgttactaataatgtccactatgagaactacagaagcaga |
| | | aaacttgcagctgtgacttataatggagttgataacaacaagaataaagggcagctgacta |
| | | agagccctctggcacaaatggaagaagaaagaagggagcatgtagctaaaatgaagaa |
| | | gatggagatggagatggagcaggtgtttgagatgaaggtcaaagaaaaagttcaaaaact |
| | | gaaggactctgaagctgagctccagcggcgccatgagcaaatgaaaaagaatttggaag |
| | | cacagcacaaagaattggaggaaaaacgtcgtcagttcgaggatgagaaagcaaactg |
| | | ggaagctcaacaacgtattttagaacaacagaactcttcaagaaccttggaaaagaacaa |
| | | gaagaaagggaagatcttttaaactctctattgaccaccagttaacgtattagttgccaatat |
| | | gccagcttggacatcagtgtttgttggatccgtttgaccaatttgcaccagttttatccataat |
| | | gatggatttaacagcatgacaaaaattatttttttttttgttcttgatggagattaagatgccttg |
| | | aattgtctagggtgttctgtacttagaaagtaagagctctaagtacctttcctacattttcttttttt |
| | | tattaaacagatatcttcagtttaatgcaagagaacattttactgttgtacaatcatgttctggtg |
| | | gtttgattgtttacaggatattccaaaataaaaggactctggaagattttcattgaggataaatt |
| | | gccataatatgatgcaaactgtgcttctctatgataattacaatacaaaggttccattcagtgc |
| | | agcatatacaataatgtaatttagtctaacacagttgaccctatttttttgacacttccattgttta |
| | | aaaatacacatggaaaaaaaaaaaaccctatatgcttactgtgcacctagagctttttttataa |
| | | caacgtctttttgtttgtttgttttggattctttaaatatatattattctcatttagtgccctctttagc |
| | | cagaatctcattactgcttcatttttgtaataacatttaatttagatattttccatatattggcactg |

TABLE 10-continued

The mRNA variant transcripts of Septins and UEV3 genes.

| Septin | mRNA Accession number | mRNAsequence |
| --- | --- | --- |
| | | ctaaaatagaatatagcatctttcatatggtaggaaccaacaaggaaactttcctttaactcc<br>ctttttacactttatggtaagtagcagggggggaaatgcatttatagatcatttctaggcaaaa<br>ttgtgaagctaatgaccaacctgtttctacctatatgcagtctctttattttactagaaatggga<br>atcatggcctcttgaagagaaaaaagtcaccattctgcatttagctgtattcatatattgcattt<br>ctgtatttttttgtttgtattgtaaaaaattcacataataaacgatgttgtgatgtaatattgtgtga<br>ggtcttaaatatcctacagtcgatgtacaagagtagagtatgtttgggaagaaacttttcagc<br>ttaagtttgcctcctctacaatgacatcttttatatgcttgtctcatttagaatgcatatgtgctga<br>ttttctaatttaagagataccatatctctctattcatttctatctctcatttgtatgcttatttttctga<br>gaacatttttttttccccccagacagggtcttgcttcattgcccaggctggagtgcggtggca<br>caaacacgacttgactgcagcctcaaccctctgggctcaagcagtcctcctgcctcagcc<br>ccctgagtatctgggattgcaggcgtgcaccaccacgcctggctaattttttgtatttttttgca<br>gcctcccaaagttctgggattacaggcatgagccgtcatgcctggcctctgagaacagttt<br>ctgactcattcagattaggtatactctcaagtccctggaaactgaaatttttttttaactgtaaag<br>agggtagtgtcatttcttttcttaaggtcaagtgacatagattttaatgtaatgcataatttaggt<br>aagaaattaattaatgtagcctagtttattatcttgaaatgttttaccctatttacttttttaaaatta<br>atgacctaagcggagggaataattataagtcaatagcagagagattgttgtttgggtgtttat<br>tttttcagtttttgttttgagagattgggttaacacctctagccaaaattgtttggttttagggag<br>gctaacaataacctactgaatttggaaaatgcaaaggtaaaaaatgtatatagactgcctgc<br>tgaactggttaagtactactgcttctgggaaatactatttcaaaattctatgtattataataataa<br>atttgtaagacattcattattctaccatcctaatgaaaactttcagaagtctttctttatccatgg<br>catgcccagggttttacctgaatctgatacaggatctatataactttactaggacttttgattgt<br>tgactccaggcttaggtatatcagaaggttctttttgccatttggcctgtggatgtctgagaag<br>atcattcacaatacatgtaaaattcaggtaggcctaaggaaaggccagcctgtagaaagc<br>aaaatggcagtgtctgttctccactgttggaggcattatgtaatttaagtatcctgttagccac<br>tgtctttctgctaattaagtggggctgaacaagtaagcactaataataccagtgaaccacttg<br>ggcaccttgtgggtagagttttgctgccacctagtggaatgggatatcattgcttccatatca<br>ggttcacaagcaagttaagtgggcacagtttatttctgtgtagctcaggctgtaatcttgaaa<br>gctgaggagatacccatgcctctcagactcattagctgggtgtcacattaccacctgcacat<br>tctgacccaccgcatcttaatatgttttgtcctcttggagaaactaggagtagaagtcaggat<br>atggtaggtaaggggggaaaaaggaaagacggcttgatagctatgaatgcatgaggagc<br>gaaatgttgactcagttatctagatcatggtctccaaacctgatgctatttccttacaaaaatat<br>ttgttgagcatgtgtccataattatatgtattgaacaatgaaaatatgtgtcaacaaatgtactg<br>ctacactaatgtgaacattatggaacaaaatttgaaagagtgaaataaaaggtttacactttc<br>aaaaaaaaaaaaaaaaaaaaaaaaaaaaaa |
| Septin8 | NM_001098811<br>(SEQ. ID.<br>NO: 83)<br>NM_001098812<br>(SEQ. ID.<br>NO: 84)<br>NM_001098813<br>(SEQ. ID.<br>NO: 85)<br>NM_015146<br>(SEQ. ID.<br>NO: 86) | NM_001098811<br>gcggcggggctccggctgcgctcgtggccgggccgggcggggaggccggtcccgcg<br>ggcg<br>ggggcaggggcggctccgcggcttctcccgccgccgccgccaaggggagtttccagg<br>aagtggccatattggatccattcagccgcagccgcccgggcggagcgcgtcccgcagc<br>cggctggtccctgtcgctgcccctgcgctcgtcccagcccacccgcccggtgcggagct<br>cgccatggcggccaccgacctggagcgcttctcgaatgcagagccagagccccggag<br>cctctccctgggcggccatgtgggtttcgacagcctccccgaccagctggtcagcaagtc<br>ggtcactcagggcttcagcttcaacatcctctgtgtgggggagaccggcattggcaaatcc<br>acactgatgaacacactcttcaacacgaccttcgagactgaggaagccagtcaccatgag<br>gcatgcgtgcgcctgcggccccagacctatgacctccaggagagcaacgtgcagctca<br>agctgaccattgtggatgccgtgggctttggggatcagatcaataaggatgagagttacag<br>gcccatagttgactacatcgatgcgcagtttgaaaattatctgcaggaggagctgaagatc<br>cgccgctcgctcttcgactaccatgacacaaggatccacgtttgcctctacttcatcacgcc<br>cacagggcactccctgaagtctctagatctagtgaccatgaagaaactagacagcaaggt<br>gaacattattcccatcatcgccaaggctgacaccatctccaagagcgagctccacaagttc<br>aagatcaagatcatgggcgagttggtcagcaacggggtccagatctaccagttccccacg<br>gatgatgaggctgttgcagagattaacgcagtcatgaatgcacatctgccctttgccgtggt<br>gggcagcaccgaggaggtgaaggtggggaacaagctggtccgagcacggcagtacc<br>cctggggagtggtgcaggtggagaatgagaatcactgcgacttcgtgaagctgcgggag<br>atgttgatccgggtgaacatggaagacctccgcgagcagacccacagccggcactacg<br>agctctaccggcgctgcaagttggaggagatgggctttcaggacagcgatggtgacagc<br>cagcccttcagcctacaagagacatacgaggccaagaggaaggagttcctaagtgagct<br>gcagaggaaggaggaagagatgaggcagatgtttgtcaacaaagtgaaggagacaga<br>gctggagctgaaggagaaggaaagggagctccatgagaagtttgagcacctgaagcgg<br>gtccaccaggaggagaagcgcaaggtggaggaaaagcgccgggaactggaggagga<br>gaccaacgccttcaatcgccggaaggctgcggtggaggccctgcagtcgcaggccttg<br>cacgccacctcgcagcagcccctgaggaaggacaaggacaagaagaacagatcagat<br>ataggagcacaccagccgggcatgagcctctccagctctaaggtgatgatgaccaaggc<br>cagtgtggagcccttgaactgcagcagctggtggcccgccatacagtgctgcagctgcct<br>ggtcagggatgcgacgtggagggaaggattcctctgaggcagcagctccaacacatgg<br>ggccagctcaggaccaccagggcatggaactggagaccatggtttttaatgttagaacag<br>aaaacgccatacttttcctatatcaatgatcaaaagtgcaaacaatttaaatttccatcaggg<br>aacatcaaatgttgcccaacccttttcattcctatccatggctccgtaaggggcttgaggctt<br>aatgcccatcctgtggccaagctgagcttccactccgggaccaaaaaaaaaaaaaaagtct<br>gctttgtgacatcatcgttatga<br>gcggaaagtacctagatgacaatgtttccattctgaaaaatagaaacatactattcaagacc<br>aaggtagcagaaaagttacttgtatctgcttatcataagacgaaactctgcaacttggcaac<br>ggtggccagttttcgtaatgaaacagtctttagtaatttaatcttcatgcttcataacaaaccaa |

TABLE 10-continued

The mRNA variant transcripts of Septins and UEV3 genes.

| Septin | mRNA Accession number | mRNAsequence |
|---|---|---|
| | | aaccccatgagatttccacattgcataattttgccttactaacagaatcatatccttaaggatg |
| | | accatcattcccccaactaaaacaaatacaaactaatgtatgatattttttaagtgccagatc |
| | | aatatggtctaaagcttcaataaggattgtgtgtaggtgaataaagacagctaagtgaatgt |
| | | gtgtaaagtgtagcaaaagcagacagatatttatgtacagtattcatagaatggaaagttaa |
| | | atatttttgcagtgtgtatttaaaagagaaactcaccataatagtgccgtctaaaaatctttgta |
| | | aagttaatttaatgtcctttagaagtgggagtctggtggaactgtgttggatttaagataccttt |
| | | tcactcttccgtatgtcatgagccttgtgcgtcacctcactgtggtgcatgtgcaagggcgt |
| | | gtgcacgcctgtgctttgccatcccatgttgtaaacagctgttccaaaggcacaaacgagtt |
| | | tagggtagactctgtaaacacctccttactcactatagtcaagaagtccagcggcgtccca |
| | | atatagaggtcccagtgcagtctgtccagaatagccagctccatcctcagcagctcattcg |
| | | gggaatagtcagagccatagtgctttgtgaagtcttttacttgtggaataaactgtaaaaaga |
| | | aaataaagaggccaaagccctacatcatg |
| | | NM_001098812 |
| | | gcggcggggctccggctgcgctcgtggccgggccgggcggggaggccggtcccgcg |
| | | ggcg |
| | | ggggcaggggcggctccgcggcttctcccgccgccgccgccaaggggagtttccagg |
| | | aagtggccatattggatccattcagccgcagccgcccgggcggagcgcgtcccgcagc |
| | | cggctggtccctgtcgctgcccctgcgctcgtcccagcccacccgcccggtgcggagct |
| | | cgccatggcggccaccgacctggagcgcttctcgaatgcagagccagagccccggag |
| | | cctctccctgggcggccatgtgggtttcgacagcctccccgaccagctggtcagcaagtc |
| | | ggtcactcagggcttcagcttcaacatcctctgtgtgggggagaccggcattggcaaatcc |
| | | acactgatgaacacactcttcaacacgaccttcgagactgaggaagccagtcaccatgag |
| | | gcatgcgtgcgcctgcggccccagacctatgacctccaggagagcaacgtgcagctca |
| | | agctgaccattgtggatgccgtgggctttggggatcagatcaataaggatgagagttacag |
| | | gcccatagttgactacatcgatgcgcagtttgaaaattatctgcaggaggagctgaagatc |
| | | cgccgctcgctcttcgactaccatgacacaaggatccacgtttgcctctacttcatcacgcc |
| | | cacagggcactccctgaagtctctagatctagtgaccatgaagaaactagacagcaaggt |
| | | gaacattattcccatcatcgccaaggctgacaccatctccaagagcgagctccacaagttc |
| | | aagatcaagatcatgggcgagttggtcagcaacggggtccagatctaccagttccccacg |
| | | gatgatgaggctgttgcagagattaacgcagtcatgaatgcacatctgccctttgccgtggt |
| | | gggcagcaccgaggaggtgaaggtggggaacaagctggtccgagcacggcagtacc |
| | | cctggggagtggtgcaggtggagaatgagaatcactgcgacttcgtgaagctgcgggag |
| | | atgttgatccgggtgaacatggaagacctccgcgagcagacccacagccggcactacg |
| | | agctctaccggcgctgcaagttggaggagatgggctttcaggacagcgatggtgacagc |
| | | cagcccttcagcctacaagagacatacgaggccaagaggaaggagttcctaagtgagct |
| | | gcagaggaaggaggaagagatgaggcagatgtttgtcaacaaagtgaaggagacaga |
| | | gctggagctgaaggagaaggaaagggagctccatgagaagtttgagcacctgaagcgg |
| | | gtccaccaggaggagaagcgcaaggtggaggaaaagcgccgggaactggaggagga |
| | | gaccaacgccttcaatcgccggaaggctgcggtggaggccctgcagtcgcaggccttg |
| | | cacgccacctcgcagcagcccctgaggaaggacaaggacaagaagaaagccagtggc |
| | | tggtcttccatttacagtgtcactattccctgacggagctgttatgtgccgctctagcgaagg |
| | | ccccagccgggatgctaggcctaattgttcagcgtggagatggcaactcacgtggtgccc |
| | | taggtgcagctgcgtggtctggtatacatgctgcaaaattcacccagttcccctcattttaatt |
| | | tttctaacctacagcttaattttaataactttaaaacacttctaaatatttattttggcaccagcgt |
| | | caagacaaataatatcctctcccattattttcataagtaacacagattccctgatttttaaaaac |
| | | taaaaatacagctaaacctttcttatgtataaagtatgcctatcatatacagggagaggtggg |
| | | taataaacttcctgtaatgacagtgtttggcatttctttatggatggaattggaacatgaacaa |
| | | gaccatgtccagcgtttttactgtgaatgtaaatggaacagcagcccaaagctgttgtctgt |
| | | gccccagaggtgctacctgtagacagggaccaactccatgtgtgtgtgttaagtgtttgact |
| | | ccaattaagactcccaagcaaatcctgcatattccaaatgtaaagagtactcagtgggaaa |
| | | aaggttgttacctcaaagtcattgcttctttcctggctgggtcacagggtgaagagatgaag |
| | | gtgtctgatgtatatagacaattagggaaaaatgagcggcaaaggagctttccccttcagct |
| | | gcactctaaaggggaacattttaaggaagtactagcagctttgactcttctatgctcctgttg |
| | | gtttacaagccaccaagaatgtcagtgttgagaatacggcctggtaaaatgggagatgtaa |
| | | aatgactaaatgaaaggaagggtagttttaatgttgaagcaccgtgctgggcactggagct |
| | | acccagaggaatgcacaacgctcccctcaaggagctcacagtctagcctactccctggct |
| | | ggaagcctcaggaagacgtgctaatttattgtggaattggtagtttgcttttcatgcccctgtc |
| | | ttccttctcatgaccatttccccctttctgtctggcttgcattattgatttccaggaccaagtcct |
| | | ggcttcctcctgccttcctgagatgatgttctgctcagggagaagtggaggggtgagctgt |
| | | gtgtgtccaccgaggcacggccaggaagaggcagcctttacctgtgaggggctccatgc |
| | | tccagcagcagagcaggttctagtgacaattcaactttttatgctatgaccaggggtggatc |
| | | taaattttatggggctgaaagcttgaattatttagaaagacttctttaagaaaaacaatgttaat |
| | | ataaaattaggtacagggtcttggaaggggccctgaagattaagcttccttagcgtcacaat |
| | | aagtccgtatctggttgcaattgaaaactgatgcttcagtgagggtatctaaaaaggtaaac |
| | | tggcatatccagggcaaatgtgggctgccaatggctcatctctagggtaattttatgtctgaa |
| | | agtgtatgcagttgggtcagagcatgacctttaagatagcctctctcagctaacatatttatg |
| | | aagatgaggcctggtgacccagcaggttcattggatacataagaaatgagaattcctggtt |
| | | catgggccaacctaggactctggagtatgcagacttggccattcgtccattgtggcctgcg |
| | | ggtcgcaccccaggcatactgaaaggccatactcgtggctggctgcctgcgggcctaag |
| | | ccttcccaggatcttcaggacacttgacagacttgtgttttctggtctgagctgcctccacag |
| | | gtccctccagcaagcctcactgcacctctcccctgctgtttgtgtttggaattttgtcttcttta |
| | | gctgagaccaaattaaaccttggtgcataaagtgagcttaaaacttgccactgtttagtaagt |
| | | tagcccccatagaatgtgaccctgtctgcagagtctcatttacccctctttttctcattgtcattt |
| | | gttggctttattagggctgtcttacaggatcatgttggcatttactatcatgtctttatcataaac |

TABLE 10-continued

The mRNA variant transcripts of Septins and UEV3 genes.

| Septin | mRNA Accession number | mRNAsequence |
|---|---|---|
| | | catgtttgtttgaggtagaagaatcaccatataattcgttgcccaaattgggactattgagag |
| | | agaaaggggatgctattaattacaccagatcaaaaggcataaaccagacctgtcccaggc |
| | | cgatgtggaaatatgttctttctagttgtgggtaccctgatctaggtggtttgtaattgtgcatt |
| | | actgactgcatatgtttgtgtatgtgtaaatgtgggctccctgttaagtggggctcatggata |
| | | cgaggcctgaggaagtgtggcttgctagtctgttacgttaacatgcttttctaaaattgcttca |
| | | cgtgttaattcatttactcctgcattcattgactgtttttgttcttttccattcactttgtacttatttttt |
| | | tcattaaattttgcatttattttg |
| | | NM_001098813 |
| | | tgctcgttggttgcacaaggagccgaaggctggtcccttgcccgggaaggccgcctggcc |
| | | ggacgcgcgggtcccgccggggttcccgccttagctccggccggagcatcaggtggg |
| | | gcccaagacacccgcagactaggctgccgcggcctctcccggatccgacgggtctccc |
| | | gcagcttgtccacactctgaatgcagagccagagccccggagcctctccctgggcggcc |
| | | atgtgggtttcgacagcctccccgaccagctggtcagcaagtcggtcactcagggcttca |
| | | gcttcaacatcctctgtgtgggggagaccggcattggcaaatccacactgatgaacacact |
| | | cttcaacacgaccttcgagactgaggaagccagtcaccatgaggcatgcgtgcgcctgc |
| | | ggccccagacctatgacctccaggagagcaacgtgcagctcaagctgaccattgtggat |
| | | gccgtgggctttggggatcagatcaataaggatgagagttacaggcccatagttgactac |
| | | atcgatgcgcagtttgaaaattatctgcaggaggagctgaagatccgccgctcgctcttcg |
| | | actaccatgacacaaggatccacgtttgcctctacttcatcacgcccacagggcactccct |
| | | gaagtctctagatctagtgaccatgaagaaactagacagcaaggtgaacattattcccatc |
| | | atcgccaaggctgacaccatctccaagagcgagctccacaagttcaagatcaagatcatg |
| | | ggcgagttggtcagcaacggggtccagatctaccagttccccacggatgatgaggctgtt |
| | | gcagagattaacgcagtcatgaatgcacatctgccctttgccgtggtgggcagcaccgag |
| | | gaggtgaaggtggggaacaagctggtccgagcacggcagtaccctggggagtggtg |
| | | caggtggagaatgagaatcactgcgacttcgtgaagctgcgggagatgttgatccgggtg |
| | | aacatggaagacctccgcgagcagacccacagccggcactacgagctctaccggcgct |
| | | gcaagttggaggagatgggctttcaggacagcgatggtgacagccagcccttcagccta |
| | | caagagacatacgaggccaagaggaaggagttcctaagtgagctgcagaggaaggag |
| | | gaagagatgaggcagatgtttgtcaacaaagtgaaggagacagagctggagctgaagg |
| | | agaaggaaagggagctccatgagaagtttgagcacctgaagcgggtccaccaggagga |
| | | gaagcgcaaggtggaggaaaagcgccgggaactggaggaggagaccaacgccttca |
| | | atcgccggaaggctgcggtggaggccctgcagtcgcaggccttgcacgccacctcgca |
| | | gcagcccctgaggaaggacaaggacaagaagaattaacgcacgcacagacttacatgt |
| | | caagagtggactttagactttcatgtgttaagttgcttgagttacaccttgtgacccttctccca |
| | | taacatggtgtgaggacggactgggagccggtacagactccagtgtttacagccttgcttt |
| | | cctcccaccgaccctggccccaggctgccccgggcctggcgggccacccctctctatgc |
| | | aaacacgtaaaagccatgaatgctggaatccaaaactgacgaggtttattttttttcagagcc |
| | | agtggctggtcttccatttacagtgtcactattccctgacggagctgttatgtgccgctctag |
| | | cgaaggccccagccgggatgctaggcctaattgttcagcgtggagatggcaactcacgt |
| | | ggtgccctaggtgcagctgcgtggtctggtatacatgctgcaaaattcacccagttcccctc |
| | | attttaatttttctaacctacagcttaattttaataactttaaaacacttctaaatatttattttggca |
| | | ccagcgtcaagacaaataatatcctctcccattattttcataagtaacacagattccctgatttt |
| | | taaaaactaaaaatacagctaaacctttcttatgtataaagtatgcctatcatatacagggag |
| | | aggtgggtaataaacttcctgtaatgacagtgtttggcatttctttatggatggaattggaaca |
| | | tgaacaagaccatgtccagcgtttttactgtgaatgtaaatggaacagcagcccaaagctg |
| | | ttgtctgtgccccagaggtgctacctgtagacagggaccaactccatgtgtgtgtgttaagt |
| | | gtttgactccaattaagactcccaagcaaatcctgcatattccaaatgtaaagagtactcagt |
| | | gggaaaaaggttgttacctcaaagtcattgcttctttcctggctgggtcacagggtgaagag |
| | | atgaaggtgtctgatgtatatagacaattagggaaaaatgagcggcaaaggagctttcccc |
| | | ttcagctgcactctaaaggggaacattttaaggaagtactagcagctttgactcttctatgct |
| | | cctgttggtttacaagccaccaagaatgtcagtgttgagaatacggcctggtaaaatggga |
| | | gatgtaaaatgactaaatgaaaggaagggtagttttaatgttgaagcaccgtgctgggcac |
| | | tggagctacccagaggaatgcacaacgctcccctcaaggagctcacagtctagcctactc |
| | | cctggctggaagcctcaggaagacgtgctaatttattgtggaattggtagtttgcttttcatgc |
| | | ccctgtcttccttctcatgaccatttccccctttctgtctggcttgcattattgatttccaggacc |
| | | aagtcctggcttcctcctgccttcctgagatgatgttctgctcagggagaagtggaggggt |
| | | gagctgtgtgtgtccaccgaggcacggccaggaagaggcagcctttacctgtgagggg |
| | | ctccatgctccagcagcagagcaggttctagtgacaattcaactttttatgctatgaccagg |
| | | ggtggatctaaattttatggggctgaaagcttgaattatttagaaagacttctttaagaaaaac |
| | | aatgttaatataaaattaggtacagggtcttggaaggggccctgaagattaagcttccttag |
| | | cgtcacaataagtccgtatctggttgcaattgaaaactgatgcttcagtgagggtatctaaaa |
| | | aggtaaactggcatatccagggcaaatgtgggctgccaatggctcatctctagggtaatttt |
| | | atgtctgaaagtgtatgcagttgggtcagagcatgacctttaagatagcctctctcagctaa |
| | | catatttatgaagatgaggcctggtgacccagcaggttcattggatacataagaaatgaga |
| | | attcctggttcatgggccaacctaggactctggagtatgcagacttggccattcgtccattgt |
| | | ggcctgcgggtcgcaccccaggcatactgaaaggccatactcgtggctggctgcctgcg |
| | | ggcctaagccttcccaggatcttcaggacacttgacagacttgtgttttctggtctgagctgc |
| | | ctccacaggtccctccagcaagcctcactgcacctctcccctgctgtttgtgtttggaattttg |
| | | tcttctttagctgagaccaaattaaaccttggtgcataaagtgagcttaaaacttgccactgtt |
| | | tagtaagttagcccccatagaatgtgaccctgtctgcagagtctcatttacccctctttttctca |
| | | ttgtcatttgttggctttattagggctgtcttacaggatcatgttggcatttactatcatgtctttat |
| | | cataaaccatgtttgtttgaggtagaagaatcaccatataattcgttgcccaaattgggactat |
| | | tgagagagaaaggggatgctattaattacaccagatcaaaaggcataaaccagacctgtc |
| | | ccaggccgatgtggaaatatgttctttctagttgtgggtaccctgatctaggtggtttgtaatt |

TABLE 10-continued

The mRNA variant transcripts of Septins and UEV3 genes.

| Septin | mRNA Accession number | mRNAsequence |
|---|---|---|
| | | gtgcattactgactgcatatgtttgtgtatgtgtaaatgtgggctccctgttaagtggggctca<br>tggatacgaggcctgaggaagtgtggcttgctagtctgttacgttaacatgcttttctaaaatt<br>gcttcacgtgttaattcatttactcctgcattcattgactgtttttgttcttttccattcactttgtact<br>tatttttttcattaaattttgcatttattttg<br>NM_015146<br>gcggcggggctccggctgcgctcgtggccgggccgggcggggaggccggtcccgcg<br>ggcg<br>ggggcaggggcggctccgcggcttctcccgccgccgccgccaaggggagtttccagg<br>aagtggccatattggatccattcagccgcagccgcccgggcggagcgcgtcccgcagc<br>cggctggtccctgtcgctgcccctgcgctcgtcccagcccacccgcccggtgcggagct<br>cgccatggcggccaccgacctggagcgcttctcgaatgcagagccagagccccggag<br>cctctccctgggcggccatgtgggtttcgacagcctccccgaccagctggtcagcaagtc<br>ggtcactcagggcttcagcttcaacatcctctgtgtgggggagaccggcattggcaaatcc<br>acactgatgaacacactcttcaacacgaccttcgagactgaggaagccagtcaccatgag<br>gcatgcgtgcgcctgcggccccagacctatgacctccaggagagcaacgtgcagctca<br>agctgaccattgtggatgccgtgggctttggggatcagatcaataaggatgagagttacag<br>gcccatagttgactacatcgatgcgcagtttgaaaattatctgcaggaggagctgaagatc<br>cgccgctcgctcttcgactaccatgacacaaggatccacgtttgcctctacttcatcacgcc<br>cacagggcactccctgaagtctctagatctagtgaccatgaagaaactagacagcaaggt<br>gaacattattcccatcatcgccaaggctgacaccatctccaagagcgagctccacaagttc<br>aagatcaagatcatgggcgagttggtcagcaacggggtccagatctaccagttccccacg<br>gatgatgaggctgttgcagagattaacgcagtcatgaatgcacatctgccctttgccgtggt<br>gggcagcaccgaggaggtgaaggtggggaacaagctggtccgagcacggcagtacc<br>cctggggagtggtgcaggtggagaatgagaatcactgcgacttcgtgaagctgcgggag<br>atgttgatccgggtgaacatggaagacctccgcgagcagacccacagccggcactacg<br>agctctaccggcgctgcaagttggaggagatgggctttcaggacagcgatggtgacagc<br>cagcccttcagcctacaagagacatacgaggccaagaggaaggagttcctaagtgagct<br>gcagaggaaggaggaagagatgaggcagatgtttgtcaacaaagtgaaggagacaga<br>gctggagctgaaggagaaggaaagggagctccatgagaagtttgagcacctgaagcgg<br>gtccaccaggaggagaagcgcaaggtggaggaaaagcgccgggaactggaggagga<br>gaccaacgccttcaatcgccggaaggctgcggtggaggccctgcagtcgcaggccttg<br>cacgccacctcgcagcagcccctgaggaaggacaaggacaagaagaattaacgcacg<br>cacagacttacatgtcaagagtggactttagactttcatgtgttaagttgcttgagttacacctt<br>gtgacccttctcccataacatggtgtgaggacggactgggagccggtacagactccagtg<br>tttacagccttgctttcctcccaccgaccctggccccaggctgccccgggcctggcgggc<br>cacccctctctatgcaaacacgtaaaagccatgaatgctggaatccaaaactgacgaggtt<br>tatttttttcagagccagtggctggtcttccatttacagtgtcactattccctgacggagctgtt<br>atgtgccgctctagcgaaggccccagccgggatgctaggcctaattgttcagcgtggaga<br>tggcaactcacgtggtgccctaggtgcagctgcgtggtctggtatacatgctgcaaaattc<br>acccagttcccctcattttaatttttctaacctacagcttaattttaataactttaaaacacttcta<br>aatatttattttggcaccagcgtcaagacaaataatatcctctcccattattttcataagtaaca<br>cagattccctgatttttaaaaactaaaaatacagctaaacctttcttatgtataaagtatgccta<br>tcatatacagggagaggtgggtaataaacttcctgtaatgacagtgtttggcatttctttatgg<br>atggaattggaacatgaacaagaccatgtccagcgtttttactgtgaatgtaaatggaacag<br>cagcccaaagctgttgtctgtgccccagaggtgctacctgtagacagggaccaactccat<br>gtgtgtgtgttaagtgtttgactccaattaagactcccaagcaaatcctgcatattccaaatgt<br>aaagagtactcagtgggaaaaaggttgttacctcaaagtcattgcttctttcctggctgggtc<br>acagggtgaagagatgaaggtgtctgatgtatatagacaattagggaaaaatgagcggca<br>aaggagctttccccttcagctgcactctaaaggggaacattttaaggaagtactagcagctt<br>tgactcttctatgctcctgttggtttacaagccaccaagaatgtcagtgttgagaatacggcc<br>tggtaaaatgggagatgtaaaatgactaaatgaaaggaagggtagttttaatgttgaagca<br>ccgtgctgggcactggagctacccagaggaatgcacaacgctcccctcaaggagctcac<br>agtctagcctactccctggctggaagcctcaggaagacgtgctaatttattgtggaattggt<br>agtttgcttttcatgcccctgtcttccttctcatgaccatttccccctttctgtctggcttgcattat<br>tgatttccaggaccaagtcctggcttcctcctgccttcctgagatgatgttctgctcagggag<br>aagtggaggggtgagctgtgtgtgtccaccgaggcacggccaggaagaggcagcccttt<br>acctgtgaggggctccatgctccagcagcagagcaggttctagtgacaattcaactttttat<br>gctatgaccaggggtggatctaaattttatggggctgaaagcttgaattatttagaaagactt<br>ctttaagaaaaacaatgttaatataaaattaggtacagggtcttggaaggggccctgaagat<br>taagcttccttagcgtcacaataagtccgtatctggttgcaattgaaaactgatgcttcagtg<br>agggtatctaaaaaggtaaactggcatatccagggcaaatgtgggctgccaatggctcat<br>ctctagggtaattttatgtctgaaagtgtatgcagttgggtcagagcatgacctttaagatag<br>cctctctcagctaacatatttatgaagatgaggcctggtgacccagcaggttcattggatac<br>ataagaaatgagaattcctggttcatgggccaacctaggactctggagtatgcagacttgg<br>ccattcgtccattgtggcctgcgggtcgcaccccaggcatactgaaaggccatactcgtg<br>gctggctgcctgcgggcctaagccttcccaggatcttcaggacacttgacagacttgtgttt<br>tctggtctgagctgcctccacaggtccctccagcaagcctcactgcacctctcccctgctgt<br>ttgtgtttggaattttgtcttctttagctgagaccaaattaaaccttggtgcataaagtgagctta<br>aaacttgccactgtttagtaagttagcccccatagaatgtgaccctgtctgcagagtctcattt<br>acccctctttttctcattgtcatttgttggctttattagggctgtcttacaggatcatgttggcattt<br>actatcatgtctttatcataaaccatgtttgtttgaggtagaagaatcaccatataattcgttgc<br>ccaaattgggactattgagagagaaaggggatgctattaattacaccagatcaaaaggcat<br>aaaccagacctgtcccaggccgatgtggaaatatgttctttctagttgtgggtaccctgatct<br>aggtggtttgtaattgtgcattactgactgcatatgtttgtgtatgtgtaaatgtgggctccctg |

TABLE 10-continued

The mRNA variant transcripts of Septins and UEV3 genes.

| Septin | mRNA Accession number | mRNAsequence |
|---|---|---|
| | | ttaagtggggctcatggatacgaggcctgaggaagtgtggcttgctagtctgttacgttaac<br>atgcttttctaaaattgcttcacgtgttaattcatttactcctgcattcattgactgtttttgttctttt<br>ccattcactttgtacttatttttttcattaaattttgcatttattttg |
| Septin9 | NM_001113491<br>(SEQ. ID.<br>NO: 87)<br>NM_001113492<br>(SEQ. ID.<br>NO: 88)<br>NM_001113493<br>(SEQ. ID.<br>NO: 89)<br>NM_001113494<br>(SEQ. ID.<br>NO: 90)<br>NM_001113495<br>(SEQ. ID.<br>NO: 91)<br>NM_001113496<br>(SEQ. ID.<br>NO: 92)<br>NM_006640<br>(SEQ. ID.<br>NO: 93) | NM_001113491<br>actccagacggcgggccgccccctcttcccgccttcctactaccggcccaggattagcgc<br>cctgggagcgcgcgccccgctgcctcgccgccacactttcctgggagcggcggccacg<br>gaggcaccatgaagaagtcttactcaggaggcacgcggacctccagtggccggctccg<br>gaggcttggtgactccagtggcccagccttgaaaagatcttttgaggtcgaggaggtcga<br>gacacccaactccaccccaccccggagggtccagactcccctactccgagccactgtgg<br>ccagctccacccagaaattccaggacctgggcgtgaagaactcagaaccctcggcccg<br>ccatgtggactccctaagccaacgctcccccaaggcgtccctgcggagggtggagctct<br>cgggccccaaggcggccgagccggtgtcccggcgcactgagctgtccattgacatctc<br>gtccaagcaggtggagaacgccggggccatcggcccgtcccggttcgggctcaagag<br>ggccgaggtgttgggccacaagacgccagaaccggcccctcggaggacggagatcac<br>catcgtcaaaccccaggagtcagcccaccggaggatggagcccccctgcctccaaggtc<br>cccgaggtgcccactgcccctgccaccgacgcagcccccaagagggtggagatccag<br>atgcccaagcctgctgaggcgcccaccgcccccagcccagcccagaccttggagaatt<br>cagagcctgcccctgtgtctcagctgcagagcaggctggagcccaagccccagcccccct<br>gtggctgaggctacaccccggagccaggaggccactgaggcggctcccagctgcgttg<br>gcgacatggccgacacccccagagatgccgggctcaagcaggcgcctgcatcacgga<br>acgagaaggccccggtggacttcggctacgtggggattgactccatcctggagcagatg<br>cgccggaaggccatgaagcagggcttcgagttcaacatcatggtggtcgggcagagcg<br>gcttgggtaaatccaccttaatcaacaccctcttcaaatccaaaatcagccggaagtcggt<br>gcagcccacctcagaggagcgcatccccaagaccatcgagatcaagtccatcacgcac<br>gatattgaggagaaaggcgtccggatgaagctgacagtgattgacacaccagggttcgg<br>ggaccacatcaacaacgagaactgctggcagcccatcatgaagttcatcaatgaccagta<br>cgagaaatacctgcaggaggaggtcaacatcaaccgcaagaagcgcatcccggacacc<br>cgcgtccactgctgcctctacttcatccccgccaccggccactccctcaggcccctggac<br>atcgagtttatgaaacgcctgagcaaggtggtcaacatcgtccctgtcatcgccaaggcg<br>gacacactcaccctggaggagagggtccacttcaaacagcggatcaccgcagacctgct<br>gtccaacggcatcgacgtgtacccccagaaggaatttgatgaggactcggaggaccggc<br>tggtgaacgagaagttccgggagatgatcccatttgctgtggtgggcagtgaccacgagt<br>accaggtcaacggcaagaggatccttgggaggaagaccaagtggggtaccatcgaagt<br>tgaaaacaccacacactgtgagtttgcctacctgcgggaccttctcatcaggacgcacatg<br>cagaacatcaaggacatcaccagcagcatccacttcgaggcgtaccgtgtgaagcgcct<br>caacgagggcagcagcgccatggccaacggcatggaggagaaggagccagaagccc<br>cggagatgtagacgccaccctgcccacccccgggatcctgcccccaagtcatttccgtcc<br>ccccccaggccctcccaccaccccatttatttatatgattttctccatttgtcatcgttcccca<br>ccccttcgacatgctgccaggaaacaagggaaggggcc<br>tccctccgagtgagtcagtgatgaggccgcggcctccccgaggttgtggggaggctgca<br>ctggagccacaggcaggggtgagagcacccactgaattgacatgaccctctgtccccag<br>gcctggctccccgagggctcagaagagcagcttcggtgtgcagatcatccgtctgtgtgg<br>ggttctcagtgccggaggccttggggtgggggccaggcctcgcacttgcagaggagcc<br>cagtgggctgcacgctcccctccatccccatcggccctgtcccctggagtgtgtcagagc<br>ccaggggagaatgcagcccaccaggagcacctggacccccctgcccgccacatggtgtg<br>gccatcactcagcccctacccctgccctgctcctaagggtagaaaactccagggtcccct<br>gccaccgactgcccagccactccaagccccctggcagctgcccctcctggagcagaaa<br>gtgcctttatctcagccatccgcagactgcttggccagatgcggggacaggctggaatga<br>gggaggcgtcttcatctccctgccatccccctctcacgccacccccgcccccaccgggct<br>gcaggtgctgctgatgcgctgggatctgattgaggataaaaaggaaggagagatgaccc<br>ctacccccctcatcccccagttttgaaaaggtctaagcaagtgagtctggtggaggagctga<br>gggagggagccatggaaggtgccagaaggaaggttggcgggggcacgtgtgggccg<br>tggcttgggctggtcagagtggcgtgagctgcccggcgcctgccctgcccaagtgacca<br>gggaagtgtgtgtgtgtccatgtgtatgcgtgtccgtctgtctgtctagtgtctgggtttggcc<br>caagactgggctgtagttacattaatgcccagccagccacccctgccactcacccctcctg<br>gcccaggccttgctgactctctgagctggggaggtgggaggccaggcgagcctgactct<br>gttgatctacccgtgcctgggcccctcccctcagagcccatggtaacgaaccccctagaaa<br>ggagagaacgggcgtcaggggtgcacagtccacagctgaagagcaaggtttcgtggca<br>gcacggcccggcccctcaccctctgtccccacgaggggacccatgggggctgtctttgc<br>agggcacagatgaccaaagtcccttcctgcttcctgttacctgtcttgctcctggggagaaa<br>gaggggcctgatgagactccactcaggtgcacacatcaccaggtgcatctgcaggcacc<br>gggctggctgcttgcagccaggagaaggtcagcgagaaggagtgtatgagtgtgagtgt<br>gtgtgcatggaagttggggcactgggcgtctgactccctccccacccaagagaggaagg<br>acccctcaccacccccactggcgagacagtttactttgccgacttgccatgtttttgccaaa<br>accaagattttgaaggaaatgagtggccagcgccagggcccaggccatgtggcctgccc<br>agcctcaatgtcacttggtggcggggtggggtgggggtgggcagcagcatcccagcctt<br>gagatgcttcactttccttctctgtaaccagactttgaaaaattgttcgtttcatcaggctctgtt<br>cctcaatggccttttgctacgtgcctcccgagaaatttgtctttttgtataaatgacaaagtgtt<br>gaaaatgtatttcctgaaataaatgtttcaaatgcagaaacccagaaaaaaaaaaaaaa<br>NM_001113492<br>actgggcggcccttagacccaggctgcctgctgtctctggcaggaactcaagtcgctggt<br>catcctcagagcggtgttggcccggggccttcagtggcctttgtgtctgggtgagaggaa<br>ccctggatggccactctgccctgagtgtgtgggtccccagaagtgctgggttagggggca |

TABLE 10-continued

The mRNA variant transcripts of Septins and UEV3 genes.

| Septin | mRNA Accession number | mRNAsequence |
|---|---|---|
| | | cggagggccagaaagtccccttggagcgctggactctctcgctgactcctaccccaccc |
| | | cggcctggggtttcagagaaggggtccaggcaggagtgtcatcttttctcaatggggatgt |
| | | ggcttcagtctctgtccaggaggcacgcggacctccagtggccggctccggaggcttgg |
| | | tgactccagtggcccagccttgaaaagatcttttgaggtcgaggaggtcgagacacccaa |
| | | ctccaccccaccccggagggtccagactcccctactccgagccactgtggccagctcca |
| | | cccagaaattccaggacctgggcgtgaagaactcagaaccctcggcccgccatgtggac |
| | | tccctaagccaacgctcccccaaggcgtccctgcggagggtggagctctcgggcccca |
| | | aggcggccgagccggtgtcccggcgcactgagctgtccattgacatctcgtccaagcag |
| | | gtggagaacgccggggccatcggcccgtcccggttcgggctcaagagggccgaggtg |
| | | ttgggccacaagacgccagaaccggcccctcggaggacggagatcaccatcgtcaaac |
| | | cccaggagtcagcccaccggaggatggagcccccctgcctccaaggtccccgaggtgcc |
| | | cactgcccctgccaccgacgcagcccccaagagggtggagatccagatgcccaagcct |
| | | gctgaggcgcccaccgcccccagcccagcccagaccttggagaattcagagcctgccc |
| | | ctgtgtctcagctgcagagcaggctggagcccaagccccagccccctgtggctgaggct |
| | | acaccccggagccaggaggccactgaggcggctcccagctgcgttggcgacatggcc |
| | | gacacccccagagatgccgggctcaagcaggcgcctgcatcacggaacgagaaggcc |
| | | ccggtggacttcggctacgtggggattgactccatcctggagcagatgcgccggaaggc |
| | | catgaagcagggcttcgagttcaacatcatggtggtcgggcagagcggcttgggtaaatc |
| | | caccttaatcaacaccctcttcaaatccaaaatcagccggaagtcggtgcagcccacctca |
| | | gaggagcgcatccccaagaccatcgagatcaagtccatcacgcacgatattgaggagaa |
| | | aggcgtccggatgaagctgacagtgattgacacaccagggttcggggaccacatcaaca |
| | | acgagaactgctggcagcccatcatgaagttcatcaatgaccagtacgagaaatacctgc |
| | | aggaggaggtcaacatcaaccgcaagaagcgcatcccggacacccgcgtccactgctg |
| | | cctctacttcatccccgccaccggccactccctcaggcccctggacatcgagtttatgaaa |
| | | cgcctgagcaaggtggtcaacatcgtccctgtcatcgccaaggcggacacactcaccct |
| | | ggaggagagggtccacttcaaacagcggatcaccgcagacctgctgtccaacggcatc |
| | | gacgtgtacccccagaaggaatttgatgaggactcggaggaccggctggtgaacgaga |
| | | agttccgggagatgatcccatttgctgtggtgggcagtgaccacgagtaccaggtcaacg |
| | | gcaagaggatccttgggaggaagaccaagtggggtaccatcgaagttgaaaacaccac |
| | | acactgtgagtttgcctacctgcgggaccttctcatcaggacgcacatgcagaacatcaag |
| | | gacatcaccagcagcatccacttcgaggcgtaccgtgtgaagcgcctcaacgagggca |
| | | gcagcgccatggccaacggcatggaggagaaggagccagaagccccggagatgtag |
| | | acgccaccctgcccacccccgggatcctgcccccaagtcatttccgtcccccccccaggc |
| | | cctcccaccaccccatttatttatatgatttctccatttgtcatcgttccccacccccttcgac |
| | | atgctgccaggaaacaagggaaggggcctccctccgagtgagtcagtgatgaggccgc |
| | | ggcctccccgaggttgtggggaggctgcactggagccacaggcaggggtgagagcac |
| | | ccactgaattgacatgaccctctgtccccaggcctggctccccgagggctcagaagagc |
| | | agcttcggtgtgcagatcatccgtctgtgtggggttctcagtgccggaggccttggggtgg |
| | | gggccaggcctcgcacttgcagaggagcccagtgggctgcacgctcccctccatcccc |
| | | atcggccctgtcccctggagtgtgtcagagcccaggggagaatgcagcccaccaggag |
| | | cacctggacccccctgcccgccacatggtgtggccatcactcagcccctacccctgccctg |
| | | ctcctaagggtagaaaactccagggtcccctgccaccgactgcccagccactccaagcc |
| | | ccctggcagctgcccctcctggagcagaaagtgcctttatctcagccatccgcagactgct |
| | | tggccagatgcggggacaggctggaatgagggaggcgtcttcatctccctgccatcccc |
| | | ctctcacgccaccccccgcccccaccgggctgcaggtgctgctgatgcgctgggatctgat |
| | | tgaggataaaaaggaaggagagatgacccctacccccctcatcccccagttttgaaaaggt |
| | | ctaagcaagtgagtctggtggaggagctgagggagggagccatggaaggtgccagaa |
| | | ggaaggttggcgggggcacgtgtgggccgtggcttgggctggtcagagtggcgtgagc |
| | | tgcccggcgcctgccctgcccaagtgaccagggaagtgtgtgtgtgtccatgtgtatgcgt |
| | | gtccgtctgtctgtctagtgtctgggtttggcccaagactgggctgtagttacattaatgccc |
| | | agccagccacccctgccactcacccctcctggcccaggccttgctgactctctgagctgg |
| | | ggaggtgggaggccaggcgagcctgactctgttgatctacccgtgcctgggcccctccc |
| | | ctcagagcccatggtaacgaaccccctagaaaggagagaacgggcgtcaggggtgcac |
| | | agtccacagctgaagagcaaggtttcgtggcagcacggcccggcccctcaccctctgtc |
| | | cccacgaggggacccatgggggctgtctttgcagggcacagatgaccaaagtcccttcc |
| | | tgcttcctgttacctgtcttgctcctggggagaaagaggggcctgatgagactccactcag |
| | | gtgcacacatcaccaggtgcatctgcaggcaccgggctggctgcttgcagccaggagaa |
| | | ggtcagcgagaaggagtgtatgagtgtgagtgtgtgtgcatggaagttggggcactggg |
| | | cgtctgactccctccccacccaagagaggaaggacccctcaccacccccactggcgag |
| | | acagtttactttgccgacttgccatgtttttgccaaaaccaagattttgaaggaaatgagtgg |
| | | ccagcgccagggcccaggccatgtggcctgcccagcctcaatgtcacttggtggcggg |
| | | gtggggtgggggtgggcagcagcatcccagccttgagatgcttcactttccttctctgtaa |
| | | ccagactttgaaaaattgttcgtttcatcaggctctgttcctcaatggccttttgctacgtgcct |
| | | cccgagaaatttgtctttttgtataaatgacaaagtgttgaaaatgtatttcctgaaataaatgtt |
| | | tcaaatgcagaaacccagaaaaaaaaaaaaaa |
| | | NM_001113493 |
| | | ccccaggcctggccttgacaggcgggcggagcagccagtgcgagacagggaggccg |
| | | gtgc |
| | | gggtgcgggaacctgatccgcccgggaggcgggggcggggcgggggcgcagcgcg |
| | | cggggaggggccggcgcccgccttcctcccccattcattcagctgagccagggggcct |
| | | aggggctcctccggcggctagctctgcactgcaggagcgcgggcgcggcgccccagc |
| | | cagcgcgcagggcccgggccccgccgggggcgcttcctcgccgctgccctccgcgcg |
| | | acccgctgcccaccagccatcatgtcggaccccgcggtcaacgcgcagctggatggga |
| | | tcatttcggacttcgaagccttgaaaagatcttttgaggtcgaggaggtcgagacacccaa |

TABLE 10-continued

The mRNA variant transcripts of Septins and UEV3 genes.

| Septin | mRNA Accession number | mRNAsequence |
|---|---|---|
| | | ctccaccccaccccggagggtccagactcccctactccgagccactgtggccagctcca |
| | | cccagaaattccaggacctgggcgtgaagaactcagaaccctcggcccgccatgtggac |
| | | tccctaagccaacgctcccccaaggcgtccctgcggagggtggagctctcgggcccca |
| | | aggcggccgagccggtgtcccggcgcactgagctgtccattgacatctcgtccaagcag |
| | | gtggagaacgccggggccatcggcccgtcccggttcgggctcaagagggccgaggtg |
| | | ttgggccacaagacgccagaaccggcccctcggaggacggagatcaccatcgtcaaac |
| | | cccaggagtcagcccaccggaggatggagcccccctgcctccaaggtccccgaggtgcc |
| | | cactgcccctgccaccgacgcagcccccaagagggtggagatccagatgcccaagcct |
| | | gctgaggcgcccaccgcccccagcccagcccagaccttggagaattcagagcctgccc |
| | | ctgtgtctcagctgcagagcaggctggagcccaagccccagccccctgtggctgaggct |
| | | acaccccggagccaggaggccactgaggcggctcccagctgcgttggcgacatggcc |
| | | gacacccccagagatgccgggctcaagcaggcgcctgcatcacggaacgagaaggcc |
| | | ccggtggacttcggctacgtggggattgactccatcctggagcagatgcgccggaaggc |
| | | catgaagcagggcttcgagttcaacatcatggtggtcgggcagagcggcttgggtaaatc |
| | | caccttaatcaacaccctcttcaaatccaaaatcagccggaagtcggtgcagcccacctca |
| | | gaggagcgcatccccaagaccatcgagatcaagtccatcacgcacgatattgaggagaa |
| | | aggcgtccggatgaagctgacagtgattgacacaccagggttcggggaccacatcaaca |
| | | acgagaactgctggcagcccatcatgaagttcatcaatgaccagtacgagaaatacctgc |
| | | aggaggaggtcaacatcaaccgcaagaagcgcatcccggacacccgcgtccactgctg |
| | | cctctacttcatccccgccaccggccactccctcaggcccctggacatcgagtttatgaaa |
| | | cgcctgagcaaggtggtcaacatcgtccctgtcatcgccaaggcggacacactcaccct |
| | | ggaggagagggtccacttcaaacagcggatcaccgcagacctgctgtccaacggcatc |
| | | gacgtgtacccccagaaggaatttgatgaggactcggaggaccggctggtgaacgaga |
| | | agttccgggagatgatcccatttgctgtggtgggcagtgaccacgagtaccaggtcaacg |
| | | gcaagaggatccttgggaggaagaccaagtggggtaccatcgaagttgaaaacaccac |
| | | acactgtgagtttgcctacctgcgggaccttctcatcaggacgcacatgcagaacatcaag |
| | | gacatcaccagcagcatccacttcgaggcgtaccgtgtgaagcgcctcaacgagggca |
| | | gcagcgccatggccaacggcatggaggagaaggagccagaagccccggagatgtag |
| | | acgccaccctgcccaccccgggatcctgcccccaagtcatttccgtccccccccaggc |
| | | cctcccaccaccccattttattttatatgattttctccatttgtcatcgttccccacccccttcgac |
| | | atgctgccaggaaacaagggaagggcctccctccgagtgagtcagtgatgaggccgc |
| | | ggcctccccgaggttgtggggaggctgcactggagccacaggcaggggtgagagcac |
| | | ccactgaattgacatgaccctctgtccccaggcctggctccccgagggctcagaagagc |
| | | agcttcggtgtgcagatcatccgtctgtgtggggttctcagtgccggaggccttggggtgg |
| | | gggccaggcctcgcacttgcagaggagcccagtgggctgcacgctcccctccatcccc |
| | | atcggccctgtcccctggagtgtgtcagagcccaggggagaatgcagcccaccaggag |
| | | cacctggacccccctgcccgccacatggtgtggccatcactcagcccctacccctgccctg |
| | | ctcctaagggtagaaaactccagggtcccctgccaccgactgcccagccactccaagcc |
| | | ccctggcagctgcccctcctggagcagaaagtgcctttatctcagccatccgcagactgct |
| | | tggccagatgcggggacaggctggaatgagggaggcgtcttcatctccctgccatcccc |
| | | ctctcacgccaccccgcccccaccgggctgcaggtgctgctgatgcgctgggatctgat |
| | | tgaggataaaaaggaaggagagatgacccctacccctcatcccccagttttgaaaaggt |
| | | ctaagcaagtgagtctggtggaggagctgagggagggagccatggaaggtgccagaa |
| | | ggaaggttggcgggggcacgtgtgggccgtggcttgggctggtcagagtggcgtgagc |
| | | tgcccggcgcctgccctgcccaagtgaccagggaagtgtgtgtgtgtccatgtgtatgcgt |
| | | gtccgtctgtctgtctagtgtctgggtttggcccaagactgggctgtagttacattaatgccc |
| | | agccagccacccctgccactcacccctcctggcccaggccttgctgactctctgagctgg |
| | | ggaggtgggaggccaggcgagcctgactctgttgatctacccgtgcctgggcccctccc |
| | | ctcagagcccatggtaacgaacccctagaaaggagagaacgggcgtcaggggtgcac |
| | | agtccacagctgaagagcaaggtttcgtggcagcacggcccggcccctcaccctctgtc |
| | | cccacgaggggacccatgggggctgtctttgcagggcacagatgaccaaagtcccttcc |
| | | tgcttcctgttacctgtcttgctcctggggagaaagaggggcctgatgagactccactcag |
| | | gtgcacacatcaccaggtgcatctgcaggcaccgggctggctgcttgcagccaggagaa |
| | | ggtcagcgagaaggagtgtatgagtgtgagtgtgtgtgcatggaagttggggcactggg |
| | | cgtctgactccctccccacccaagagaggaaggacccctcaccacccccactggcgag |
| | | acagtttactttgccgacttgccatgtttttgccaaaaccaagattttgaaggaaatgagtgg |
| | | ccagcgccagggcccaggccatgtggcctgcccagcctcaatgtcacttggtggcggg |
| | | gtggggtgggggtgggcagcagcatcccagccttgagatgcttcactttccttctctgtaa |
| | | ccagactttgaaaaattgttcgtttcatcaggctctgttcctcaatggccttttgctacgtgcct |
| | | cccgagaaatttgtctttttgtataaatgacaaagtgttgaaaatgtatttcctgaaataaatgtt |
| | | tcaaatgcagaaacccagaaaaaaaaaaaaaa |
| | | NM_001113494 |
| | | gtcagtatggaggaggcggaccttgagggagagtaggaattggattgcaagaggaagg |
| | | ag |
| | | agccttctggccagcagcagccagcagcagtgggggaggctggaatgagctggctgga |
| | | gagggggctggggcataaggaggggcctgcctgtgaagatcatatgggccaggctgcg |
| | | gagggccaggcatgcccgccgggagtgcagctggtccacgggaagcatctggagtgg |
| | | ctgggaatgggcgcaggagcagcgccgtgggagcacaggtctctttcccggggcggct |
| | | cacctggtgtcttggttcctgcaagccttgaaaagatcttttgaggtcgaggaggtcgagac |
| | | acccaactccaccccaccccggagggtccagactcccctactccgagccactgtggcca |
| | | gctccacccagaaattccaggacctgggcgtgaagaactcagaaccctcggcccgccat |
| | | gtggactccctaagccaacgctcccccaaggcgtccctgcggagggtggagctctcgg |
| | | gccccaaggcggccgagccggtgtcccggcgcactgagctgtccattgacatctcgtcc |
| | | aagcaggtggagaacgccggggccatcggcccgtcccggttcgggctcaagagggcc |

TABLE 10-continued

The mRNA variant transcripts of Septins and UEV3 genes.

| Septin | mRNA Accession number | mRNAsequence |
|---|---|---|
| | | gaggtgttgggccacaagacgccagaaccggcccctcggaggacggagatcaccatc |
| | | gtcaaaccccaggagtcagcccaccggaggatggagccccctgcctccaaggtccccg |
| | | aggtgcccactgcccctgccaccgacgcagcccccaagagggtggagatccagatgcc |
| | | caagcctgctgaggcgcccaccgcccccagcccagcccagaccttggagaattcagag |
| | | cctgcccctgtgtctcagctgcagagcaggctggagcccaagccccagccccctgtggc |
| | | tgaggctacaccccggagccaggaggccactgaggcggctcccagctgcgttggcgac |
| | | atggccgacaccccccagagatgccgggctcaagcaggcgcctgcatcacggaacgag |
| | | aaggccccggtggacttcggctacgtggggattgactccatcctggagcagatgcgccg |
| | | gaaggccatgaagcagggcttcgagttcaacatcatggtggtcgggcagagcggcttgg |
| | | gtaaatccaccttaatcaacaccctcttcaaatccaaaatcagccggaagtcggtgcagcc |
| | | cacctcagaggagcgcatccccaagaccatcgagatcaagtccatcacgcacgatattg |
| | | aggagaaaggcgtccggatgaagctgacagtgattgacacaccagggttcggggacca |
| | | catcaacaacgagaactgctggcagcccatcatgaagttcatcaatgaccagtacgagaa |
| | | atacctgcaggaggaggtcaacatcaaccgcaagaagcgcatcccggacacccgcgtc |
| | | cactgctgcctctacttcatccccgccaccggccactccctcaggcccctggacatcgagt |
| | | ttatgaaacgcctgagcaaggtggtcaacatcgtccctgtcatcgccaaggcggacacac |
| | | tcaccctggaggagagggtccacttcaaacagcggatcaccgcagacctgctgtccaac |
| | | ggcatcgacgtgtaccccccagaaggaatttgatgaggactcggaggaccggctggtgaa |
| | | cgagaagttccgggagatgatcccatttgctgtggtgggcagtgaccacgagtaccaggt |
| | | caacggcaagaggatccttgggaggaagaccaagtggggtaccatcgaagttgaaaac |
| | | accacacactgtgagtttgcctacctgcgggaccttctcatcaggacgcacatgcagaac |
| | | atcaaggacatcaccagcagcatccacttcgaggcgtaccgtgtgaagcgcctcaacga |
| | | gggcagcagcgccatggccaacggcatggaggagaaggagccagaagccccggag |
| | | atgtagacgccaccctgcccacccccgggatcctgcccccaagtcatttccgtccccccc |
| | | caggccctcccaccaccccattttattttatatgattttctccatttgtcatcgttccccacccct |
| | | tcgacatgctgccaggaaacaagggaaggggcctccctccgagtgagtcagtgatgag |
| | | gccgcggcctccccgaggttgtggggaggctgcactggagccacaggcaggggtgag |
| | | agcacccactgaattgacatgaccctctgtccccaggcctggctccccgagggctcagaa |
| | | gagcagcttcggtgtgcagatcatccgtctgtgtggggttctcagtgccggaggccttggg |
| | | gtgggggccaggcctcgcacttgcagaggagcccagtgggctgcacgctcccctccat |
| | | ccccatcggccctgtcccctggagtgtgtcagagcccaggggagaatgcagcccacca |
| | | ggagcacctggacccccctgcccgccacatggtgtggccatcactcagcccctacccctg |
| | | ccctgctcctaagggtagaaaactccagggtcccctgccaccgactgcccagccactcc |
| | | aagccccctggcagctgcccctcctggagcagaaagtgcctttatctcagccatccgcag |
| | | actgcttggccagatgcggggacaggctggaatgagggaggcgtcttcatctccctgcc |
| | | atccccctctcacgccacccccgcccccaccgggctgcaggtgctgctgatgcgctggg |
| | | atctgattgaggataaaaaggaaggagagatgacccctacccccctcatcccccagttttga |
| | | aaaggtctaagcaagtgagtctggtggaggagctgagggagggagccatggaaggtgc |
| | | cagaaggaaggttggcgggggcacgtgtgggccgtggcttgggctggtcagagtggcg |
| | | tgagctgcccggcgcctgccctgcccaagtgaccagggaagtgtgtgtgtgtccatgtgt |
| | | atgcgtgtccgtctgtctgtctagtgtctgggtttggcccaagactgggctgtagttacatta |
| | | atgcccagccagccacccctgccactcacccctcctggcccaggccttgctgactctctg |
| | | agctggggaggtgggaggccaggcgagcctgactctgttgatctacccgtgcctgggcc |
| | | cctcccctcagagcccatggtaacgaacccctagaaaggagagaacgggcgtcagggg |
| | | tgcacagtccacagctgaagagcaaggtttcgtggcagcacggcccggcccctcaccct |
| | | ctgtccccacgaggggacccatgggggctgtctttgcagggcacagatgaccaaagtcc |
| | | cttcctgcttcctgttacctgtcttgctcctggggagaaagaggggcctgatgagactccac |
| | | tcaggtgcacacatcaccaggtgcatctgcaggcaccgggctggctgcttgcagccagg |
| | | agaaggtcagcgagaaggagtgtatgagtgtgagtgtgtgtgcatggaagttggggcact |
| | | gggcgtctgactccctccccacccaagagaggaaggacccctcaccacccccactggc |
| | | gagacagtttactttgccgacttgccatgtttttgccaaaaccaagattttgaaggaaatgag |
| | | tggccagcgccagggcccaggccatgtggcctgcccagcctcaatgtcacttggtggcg |
| | | gggtggggtgggggtgggcagcagcatcccagccttgagatgcttcactttccttctctgt |
| | | aaccagactttgaaaaattgttcgtttcatcaggctctgttcctcaatggccttttgctacgtgc |
| | | ctcccgagaaatttgtctttttgtataaatgacaaagtgttgaaaatgtatttcctgaaataaat |
| | | gtttcaaatgcagaaacccagaaaaaaaaaaaaaa |
| | | NM_001113495 |
| | | agttaccatcgtggggagactgtctggacgcagagagcaggctctgtgtgggagcggg |
| | | ga |
| | | gggcaagccctggttgcgaggcagggcttccccaggattcagcagggatctgaaggact |
| | | ttgcaggcacccagggagataggagaggaggagggagcagccctggccggacactgt |
| | | cctcctagcattgcctgcatcagggactcactcagctttaagaagcccctttgtgggggac |
| | | agggagcatctgttagtttataggacctgaagtgccccccatgggctcaagtttctgggaag |
| | | gcctgcaggtggccgtagggctgccgcaggggtgctggccccagggtctggattcagg |
| | | ggagcctgcagagggagggcagctggaggctgctccagtgtgcattgttacgaggcaa |
| | | agtaaggagactgctgggcccacgctgggccggggtggatggaggcaaggaagtcttc |
| | | gccggggcaagggcaccagctgtagatgccggcagctttctcctggacacgggcctgg |
| | | aaggctgacagggtgtggtgagtgccaccggctcccctgccgtggcctggtcagtggctt |
| | | cacaggcctccgtgggcaggaggaggatgaccttgcattctgcttggccaccattggcag |
| | | tgacagacaagccactgaggcggctcccagctgcgttggcgacatggccgacaccccc |
| | | agagatgccgggctcaagcaggcgcctgcatcacggaacgagaaggccccggtggac |
| | | ttcggctacgtggggattgactccatcctggagcagatgcgccggaaggccatgaagca |
| | | gggcttcgagttcaacatcatggtggtcgggcagagcggcttgggtaaatccaccttaatc |
| | | aacaccctcttcaaatccaaaatcagccggaagtcggtgcagcccacctcagaggagcg |

TABLE 10-continued

The mRNA variant transcripts of Septins and UEV3 genes.

| Septin | mRNA Accession number | mRNAsequence |
|---|---|---|
| | | catccccaagaccatcgagatcaagtccatcacgcacgatattgaggagaaaggcgtcc |
| | | ggatgaagctgacagtgattgacacaccagggttcggggaccacatcaacaacgagaa |
| | | ctgctggcagcccatcatgaagttcatcaatgaccagtacgagaaatacctgcaggagga |
| | | ggtcaacatcaaccgcaagaagcgcatcccggacacccgcgtccactgctgcctctactt |
| | | catccccgccaccggccactccctcaggcccctggacatcgagtttatgaaacgcctgag |
| | | caaggtggtcaacatcgtccctgtcatcgccaaggcggacacactcaccctggaggaga |
| | | gggtccacttcaaacagcggatcaccgcagacctgctgtccaacggcatcgacgtgtac |
| | | ccccagaaggaatttgatgaggactcggaggaccggctggtgaacgagaagttccggg |
| | | agatgatcccatttgctgtggtgggcagtgaccacgagtaccaggtcaacggcaagagg |
| | | atccttgggaggaagaccaagtggggtaccatcgaagttgaaaacaccacacactgtga |
| | | gtttgcctacctgcgggaccttctcatcaggacgcacatgcagaacatcaaggacatcac |
| | | cagcagcatccacttcgaggcgtaccgtgtgaagcgcctcaacgagggcagcagcgcc |
| | | atggccaacggcatggaggagaaggagccagaagccccggagatgtagacgccaccc |
| | | tgcccaccccccgggatcctgcccccaagtcatttccgtcccccccaggccctcccacca |
| | | ccccatttttattttatatgattttctccatttgtcatcgttccccacccccttcgacatgctgccag |
| | | gaaacaagggaaggggcctccctccgagtgagtcagtgatgaggccgcggcctccccg |
| | | aggttgtggggaggctgcactggagccacaggcaggggtgagagcacccactgaattg |
| | | acatgaccctctgtccccaggcctggctccccgagggctcagaagagcagcttcggtgt |
| | | gcagatcatccgtctgtgtggggttctcagtgccggaggccttggggtgggggccaggc |
| | | ctcgcacttgcagaggagcccagtgggctgcacgctcccctccatccccatcggccctgt |
| | | cccctggagtgtgtcagagcccaggggagaatgcagcccaccaggagcacctggacc |
| | | ccctgcccgcccacatggtgtggccatcactcagcccctaccctgccctgctcctaaggg |
| | | tagaaaactccagggtcccctgccaccgactgcccagccactccaagcccccctggcagc |
| | | tgcccctcctggagcagaaagtgcctttatctcagccatccgcagactgcttggccagatg |
| | | cggggacaggctggaatgagggaggcgtcttcatctccctgccatcccccctctcacgcca |
| | | cccccgcccccaccgggctgcaggtgctgctgatgcgctgggatctgattgaggataaa |
| | | aaggaaggagagatgaccccctacccccctcatccccccagttttgaaaaggtctaagcaagt |
| | | gagtctggtggaggagctgagggagggagccatggaaggtgccagaaggaaggttgg |
| | | cgggggcacgtgtgggccgtggcttgggctggtcagagtggcgtgagctgcccggcgc |
| | | ctgccctgcccaagtgaccagggaagtgtgtgtgtgtccatgtgtatgcgtgtccgtctgtc |
| | | tgtctagtgtctgggtttggcccaagactgggctgtagttacattaatgcccagccagccac |
| | | ccctgccactcacccctcctggcccaggccttgctgactctctgagctggggaggtggga |
| | | ggccaggcgagcctgactctgttgatctacccgtgcctgggcccctcccctcagagccca |
| | | tggtaacgaacccctagaaaggagagaacgggcgtcaggggtgcacagtccacagctg |
| | | aagagcaaggtttcgtggcagcacggcccggcccctcaccctctgtccccacgagggg |
| | | acccatgggggctgtctttgcagggcacagatgaccaaagtcccttcctgcttcctgttacc |
| | | tgtcttgctcctggggagaaagaggggcctgatgagactccactcaggtgcacacatcac |
| | | caggtgcatctgcaggcaccgggctggctgcttgcagccaggagaaggtcagcgagaa |
| | | ggagtgtatgagtgtgagtgtgtgtgcatggaagttggggcactgggcgtctgactccctc |
| | | cccacccaagagaggaaggacccctcaccacccccactggcgagacagtttactttgcc |
| | | gacttgccatgtttttgccaaaaccaagattttgaaggaaatgagtggccagcgccagggc |
| | | ccaggccatgtggcctgcccagcctcaatgtcacttggtggcggggtggggtgggggtg |
| | | ggcagcagcatcccagccttgagatgcttcactttccttctctgtaaccagactttgaaaaat |
| | | tgttcgtttcatcaggctctgttcctcaatggccttttgctacgtgcctcccgagaaatttgtctt |
| | | tttgtataaatgacaaagtgttgaaaatgtatttcctgaaataaatgtttcaaatgcagaaacc |
| | | cagaaaaaaaaaaaaaaa |
| | | NM_001113496 |
| | | acttgggttcagaggtcgtggcactgagatgggtctggcagatcccagcgtccaggccc |
| | | agcccctatagtgtcagctccctcctctggggacccccttgcttgtgcccctctgggtccca |
| | | gcacatcccaggcctgcagggaggggagaggaagagactgactcactggccaggtc |
| | | ccccaggggctggagaggctggagaggcaggagctggatcagatctgaatccagagg |
| | | ctctcggaggaagagctcaggccactgaggcggctcccagctgcgttggcgacatggc |
| | | cgacacccccagagatgccgggctcaagcaggcgcctgcatcacggaacgagaaggc |
| | | cccggtggacttcggctacgtggggattgactccatcctggagcagatgcgccggaagg |
| | | ccatgaagcagggcttcgagttcaacatcatggtggtcgggcagagcggcttgggtaaat |
| | | ccaccttaatcaacaccctcttcaaatccaaaatcagccggaagtcggtgcagcccacctc |
| | | agaggagcgcatccccaagaccatcgagatcaagtccatcacgcacgatattgaggaga |
| | | aaggcgtccggatgaagctgacagtgattgacacaccagggttcggggaccacatcaac |
| | | aacgagaactgctggcagcccatcatgaagttcatcaatgaccagtacgagaaatacctg |
| | | caggaggaggtcaacatcaaccgcaagaagcgcatcccggacacccgcgtccactgct |
| | | gcctctacttcatccccgccaccggccactccctcaggcccctggacatcgagtttatgaa |
| | | acgcctgagcaaggtggtcaacatcgtccctgtcatcgccaaggcggacacactcaccct |
| | | ggaggagagggtccacttcaaacagcggatcaccgcagacctgctgtccaacggcatc |
| | | gacgtgtaccccagaaggaatttgatgaggactcggaggaccggctggtgaacgaga |
| | | agttccgggagatgatcccatttgctgtggtgggcagtgaccacgagtaccaggtcaacg |
| | | gcaagaggatccttgggaggaagaccaagtggggtaccatcgaagttgaaaacaccac |
| | | acactgtgagtttgcctacctgcgggaccttctcatcaggacgcacatgcagaacatcaag |
| | | gacatcaccagcagcatccacttcgaggcgtaccgtgtgaagcgcctcaacgagggca |
| | | gcagcgccatggccaacggcatggaggagaaggagccagaagccccggagatgtag |
| | | acgccaccctgcccaccccccgggatcctgcccccaagtcatttccgtcccccccaggc |
| | | cctcccaccaccccatttttattttatatgattttctccatttgtcatcgttccccacccccttcgac |
| | | atgctgccaggaaacaagggaaggggcctccctccgagtgagtcagtgatgaggccgc |
| | | ggcctccccgaggttgtggggaggctgcactggagccacaggcaggggtgagagcac |
| | | ccactgaattgacatgaccctctgtccccaggcctggctccccgagggctcagaagagc |

TABLE 10-continued

The mRNA variant transcripts of Septins and UEV3 genes.

| Septin | mRNA Accession number | mRNAsequence |
|---|---|---|
| | | agcttcggtgtgcagatcatccgtctgtgtggggttctcagtgccggaggccttggggtgg |
| | | gggccaggcctcgcacttgcagaggagcccagtgggctgcacgctcccctccatcccc |
| | | atcggccctgtcccctggagtgtgtcagagcccaggggagaatgcagcccaccaggag |
| | | cacctggacccccctgcccgccacatggtgtggccatcactcagcccctacccctgccctg |
| | | ctcctaagggtagaaaactccagggtcccctgccaccgactgcccagccactccaagcc |
| | | ccctggcagctgcccctcctggagcagaaagtgcctttatctcagccatccgcagactgct |
| | | tggccagatgcggggacaggctggaatgagggaggcgtcttcatctccctgccatcccc |
| | | ctctcacgccaccccgcccccaccgggctgcaggtgctgctgatgcgctgggatctgat |
| | | tgaggataaaaaggaaggagagatgacccctacccctcatcccccagttttgaaaaggt |
| | | ctaagcaagtgagtctggtggaggagctgagggagggagccatggaaggtgccagaa |
| | | ggaaggttggcgggggcacgtgtgggccgtggcttgggctggtcagagtggcgtgagc |
| | | tgcccggcgcctgccctgcccaagtgaccagggaagtgtgtgtgtgtccatgtgtatgcgt |
| | | gtccgtctgtctgtctagtgtctgggtttggcccaagactgggctgtagttacattaatgccc |
| | | agccagccacccctgccactcacccctcctggcccaggccttgctgactctctgagctgg |
| | | ggaggtgggaggccaggcgagcctgactctgttgatctacccgtgcctgggcccctccc |
| | | ctcagagcccatggtaacgaacccctagaaaggagagaacgggcgtcaggggtgcac |
| | | agtccacagctgaagagcaaggtttcgtggcagcacggcccggcccctcaccctctgtc |
| | | cccacgaggggacccatgggggctgtctttgcagggcacagatgaccaaagtcccttcc |
| | | tgcttcctgttacctgtcttgctcctggggagaaagaggggcctgatgagactccactcag |
| | | gtgcacacatcaccaggtgcatctgcaggcaccgggctggctgcttgcagccaggagaa |
| | | ggtcagcgagaaggagtgtatgagtgtgagtgtgtgtgcatggaagttggggcactggg |
| | | cgtctgactccctccccacccaagagaggaaggacccctcaccacccccactggcgag |
| | | acagtttactttgccgacttgccatgtttttgccaaaaccaagattttgaaggaaatgagtgg |
| | | ccagcgccagggcccaggccatgtggcctgcccagcctcaatgtcacttggtggcggg |
| | | gtggggtgggggtgggcagcagcatcccagccttgagatgcttcactttccttctctgtaa |
| | | ccagactttgaaaaattgttcgtttcatcaggctctgttcctcaatggccttttgctacgtgcct |
| | | cccgagaaatttgtctttttgtataaatgacaaagtgttgaaaatgtatttcctgaaataaatgtt |
| | | tcaaatgcagaaacccagaaaaaaaaaaaaaa |
| | | NM_006640 |
| | | tgcctctgtcactgcagactaatgggacggagggggggtgacttctcagggttcctcctgg |
| | | gcaggtgctccggaaccttttctcagcacgctggcctggggcacggccgttcctcctgcc |
| | | cagccacgttggggtacagggtgaagaagggctggggccagcccaggacagaggaa |
| | | ggcgaggcaggcacgcaggaactgggctttttaaacccttaagcccaaggaaatcgtag |
| | | catcgcgggacagggaaaatgaaagactttggaagtcgtcaggaatttgactctgtgagtt |
| | | ggtttccaagagtctaagttaagcatctccaagtggatattaaaaaggagcagcaagcctc |
| | | ggggcggcgggggctggaggaggtggagagaggaggctgccggaagccgcactcg |
| | | ggacctctgcagccaccgaccagaccgggcggccgggactctgggactctcgcaggc |
| | | agacccggtggtctgccggactcctcggggcccacttcgggccctctctcctgcctcctat |
| | | ttttggatttctctcctttgctcccttttttcctcccgttttgaagagacaatgctacttcagtttgg |
| | | agcacaaacatatgatcagcacatggaaatgtggtaattcggatgcattcgtgattgcaac |
| | | agattgaagaaattagaccagacaaagagtgtttttagaggaggaggaggaggaggag |
| | | gaggctgagagagggagggcgacgggggtgagaaaggggaggccgcctctgagcg |
| | | ggacgccgggactcccgccgctgctaaatatatccgtaggaatggagagggaccggat |
| | | ctcagccttgaaaagatcttttgaggtcgaggaggtcgagacacccaactccaccccacc |
| | | ccggagggtccagactcccctactccgagccactgtggccagctccacccagaaattcc |
| | | aggacctgggcgtgaagaactcagaaccctcggcccgccatgtggactccctaagccaa |
| | | cgctcccccaaggcgtccctgcggagggtggagctctcgggccccaaggcggccgag |
| | | ccggtgtcccggcgcactgagctgtccattgacatctcgtccaagcaggtggagaacgc |
| | | cggggccatcggcccgtcccggttcgggctcaagagggccgaggtgttgggccacaag |
| | | acgccagaaccggcccctcggaggacggagatcaccatcgtcaaaccccaggagtca |
| | | gcccaccggaggatggagccccctgcctccaaggtccccgaggtgcccactgcccctg |
| | | ccaccgacgcagcccccaagagggtggagatccagatgcccaagcctgctgaggcgc |
| | | ccaccgcccccagcccagcccagaccttggagaattcagagcctgcccctgtgtctcag |
| | | ctgcagagcaggctggagcccaagccccagcccccctgtggctgaggctacaccccgga |
| | | gccaggaggccactgaggcggctcccagctgcgttggcgacatggccgacaccccca |
| | | gagatgccgggctcaagcaggcgcctgcatcacggaacgagaaggccccggtggactt |
| | | cggctacgtggggattgactccatcctggagcagatgcgccggaaggccatgaagcag |
| | | ggcttcgagttcaacatcatggtggtcgggcagagcggcttgggtaaatccaccttaatca |
| | | acaccctcttcaaatccaaaatcagccggaagtcggtgcagcccacctcagaggagcgc |
| | | atccccaagaccatcgagatcaagtccatcacgcacgatattgaggagaaaggcgtccg |
| | | gatgaagctgacagtgattgacacaccagggttcggggaccacatcaacaacgagaact |
| | | gctggcagcccatcatgaagttcatcaatgaccagtacgagaaatacctgcaggaggag |
| | | gtcaacatcaaccgcaagaagcgcatcccggacacccgcgtccactgctgcctctacttc |
| | | atccccgccaccggccactccctcaggcccctggacatcgagtttatgaaacgcctgagc |
| | | aaggtggtcaacatcgtccctgtcatcgccaaggcggacacactcaccctggaggagag |
| | | ggtccacttcaaacagcggatcaccgcagacctgctgtccaacggcatcgacgtgtaccc |
| | | ccagaaggaatttgatgaggactcggaggaccggctggtgaacgagaagttccgggag |
| | | atgatcccatttgctgtggtgggcagtgaccacgagtaccaggtcaacggcaagaggatc |
| | | cttgggaggaagaccaagtggggtaccatcgaagttgaaaacaccacacactgtgagttt |
| | | gcctacctgcgggaccttctcatcaggacgcacatgcagaacatcaaggacatcaccag |
| | | cagcatccacttcgaggcgtaccgtgtgaagcgcctcaacgagggcagcagcgccatg |
| | | gccaacggcatggaggagaaggagccagaagccccggagatgtagacgccaccctgc |
| | | ccacccccgggatcctgcccccaagtcatttccgtccccccccaggccctcccaccaccc |
| | | cattttattttatatgattttctccatttgtcatcgttccccaccccttcgacatgctgccaggaa |

TABLE 10-continued

The mRNA variant transcripts of Septins and UEV3 genes.

| Septin | mRNA Accession number | mRNAsequence |
|---|---|---|
| | | acaagggaaggggcctccctccgagtgagtcagtgatgaggccgcggcctccccgag<br>gttgtggggaggctgcactggagccacaggcaggggtgagagcacccactgaattgac<br>atgaccctctgtccccaggcctggctccccgagggctcagaagagcagcttcggtgtgc<br>agatcatccgtctgtgtggggttctcagtgccggaggccttggggtgggggccaggcctc<br>gcacttgcagaggagcccagtgggctgcacgctcccctccatccccatcggccctgtcc<br>cctggagtgtgtcagagcccaggggagaatgcagcccaccaggagcacctggacccc<br>ctgcccgccacatggtgtggccatcactcagcccctacccctgccctgctcctaagggta<br>gaaaactccagggtcccctgccaccgactgcccagccactccaagcccccctggcagctg<br>cccctcctggagcagaaagtgcctttatctcagccatccgcagactgcttggccagatgcg<br>gggacaggctggaatgagggaggcgtcttcatctccctgccatccccctctcacgccacc<br>cccgcccccaccgggctgcaggtgctgctgatgcgctgggatctgattgaggataaaaa<br>ggaaggagagatgacccctacccccctcatcccccagttttgaaaaggtctaagcaagtga<br>gtctggtggaggagctgagggagggagccatggaaggtgccagaaggaaggttggcg<br>ggggcacgtgtgggccgtggcttgggctggtcagagtggcgtgagctgcccggcgcct<br>gccctgcccaagtgaccagggaagtgtgtgtgtgtccatgtgtatgcgtgtccgtctgtctg<br>tctagtgtctgggtttggcccaagactgggctgtagttacattaatgcccagccagccaccc<br>ctgccactcacccctcctggcccaggccttgctgactctctgagctggggaggtgggagg<br>ccaggcgagcctgactctgttgatctacccgtgcctgggcccctcccctcagagcccatg<br>gtaacgaacccctagaaaggagagaacgggcgtcaggggtgcacagtccacagctga<br>agagcaaggtttcgtggcagcacggcccggcccctcaccctctgtccccacgaggga<br>cccatgggggctgtctttgcagggcacagatgaccaaagtcccttcctgcttcctgttacct<br>gtcttgctcctggggagaaagaggggcctgatgagactccactcaggtgcacacatcac<br>caggtgcatctgcaggcaccgggctggctgcttgcagccaggagaaggtcagcgagaa<br>ggagtgtatgagtgtgagtgtgtgtgcatggaagttggggcactgggcgtctgactccctc<br>cccacccaagagaggaaggacccctcaccaccccactggcgagacagtttactttgcc<br>gacttgccatgtttttgccaaaaccaagattttgaaggaaatgagtggccagcgccagggc<br>ccaggccatgtggcctgcccagcctcaatgtcacttggtggcggggtggggtgggggtg<br>ggcagcagcatcccagccttgagatgcttcactttccttctctgtaaccagactttgaaaaat<br>tgttcgtttcatcaggctctgttcctcaatggccttttgctacgtgcctcccgagaaatttgtctt<br>tttgtataaatgacaaagtgttgaaaatgtatttcctgaaataaatgtttcaaatgcagaaacc<br>cagaaaaaaaaaaaaaa |
| Septin10 | NM_144710<br>(SEQ. ID.<br>NO: 94)<br>NM_178584<br>(SEQ. ID.<br>NO: 95) | NM_144710<br>cacttccggcctcgcgagggccgcaatcactgctccgcagttcccgcctgcattcctcgc<br>gccgtcttcctggagtcccagctctccttcagcccgccccaacgctgacgctcagtcctca<br>ggcgtcgagggtagctcctgtgaggggctcgcttggcgcacgcaaaacgctcagcgcg<br>caccacagggcgtccgccccaaccccgcccccggaggcctccagctcggccccgccc<br>ctgtcccttccccgtcgcggaggcagcctagcctcgcgccccgcccgttgcttctgccctc<br>cggccttcccgccgccgtcgccgggaccagccgctcggggccgggctgatacagccg<br>cttcaccgtgcccctgcccgcgaccatggcctcctccgaggtggcgcggcacctgctctt<br>tcagtctcacatggcaacgaaaacaacttgtatgtcttcacaaggatcagatgatgaacag<br>ataaaaagagaaaacattcgttcgttgactatgtctggccatgttggttttgagagtttgcctg<br>atcagctggtgaacagatccattcagcaaggtttctgctttaatattctctgtgtgggggaaa<br>ctggaattggaaaatcaacactgattgacacattgtttaatactaattttgaagactatgaatc<br>ctcacatttttgcccaaatgttaaacttaaagctcagacatatgaactccaggaaagtaatgtt<br>caattgaaattgaccattgtgaatacagtgggatttggtgaccaaataaataaagaagaga<br>gctaccaaccaatagttgactacatagatgctcagtttgaggcctatctccaagaagaactg<br>aagattaagcgttctctctttacctaccatgattctcgcatccatgtgtgtctctacttcatttca<br>ccgacaggccactctctgaagacacttgatctcttaaccatgaagaaccttgacagcaagg<br>taaacattataccagtgattgccaaagcagatacggtttctaaaactgaattacagaagttta<br>agatcaagctcatgagtgaattggtcagcaatggcgtccagatataccagttcccaacgga<br>tgatgacactattgctaaggtcaacgctgcaatgaatggacagttgccgtttgctgttgtgg<br>gaagtatggatgaggtaaaagtcggaaacaagatggtcaaagctcgccagtacccttgg<br>ggtgttgtacaagtggaaaatgaaaaccactgtgactttgtaaagctgcgggaaatgctca<br>tttgtacaaatatggaggacctgcgagagcagacccataccaggcactatgagctttacag<br>gcgctgcaaactggaggaaatgggctttacagatgtgggcccagaaaacaagccagtca<br>gtgttcaagagacctatgaagccaaaagacatgagttccatggtgaacgtcagaggaag<br>gaagaagaaatgaaacagatgtttgtgcagcgagtaaaggagaaagaagccatattgaa<br>agaagctgagagagagctacaggccaaatttgagcaccttaagagacttcaccaagaag<br>agagaatgaagcttgaagaaaagagaagacttttggaagaagaaataattgctttctctaa<br>aaagaaagctacctccgagatatttcacagccagtcctttctggcaacaggcagcaacctg<br>aggaaggacaaggaccgtaagaactccaatttttttgtaaaacagaagttccagagcacag<br>aaggtcatcatcacaagcaaactttattaaaaaaaaactagaagtgtgctttgattttgctgtt<br>atttgttttatcacttctatatttggtgaacagccacagttactgatatttatggaaaagtactttc<br>aagtacaaggtcaatacataagccagagtgaatgatactacaagttgagcatctctaattca<br>aaaatctgaaatccagaagcttcaaaatctgaatctttttgagcactgacttgaccccacaa<br>gtggaaaattccccacccgacacctttgctttctgatggttcagtttaaacagattttgtttctt<br>gcacaaaatttttgtataaattactttcaggctatatgtataaggtggatgtgaaacatgaatta<br>tgtaattagagtcgggtcccgttgtgtatatgcagatattccaaacctgaaatccaaaacact<br>tctggtccctagcattttggataagggatactcagcttgtacctatatattcatatatattcactg<br>ttgttagaaatgtttaagttgctgttctgtgatgaatctaaatcttttctcttgctaccaagctatt<br>gtcactgcagtgcattataccaaagagcgaagtcagtgccactgaaaatacagaacccatt<br>aatatcgtggctatctgattacatttatattccaagatgaaccttttttatatatgctaaaatttt<br>ggggaatatgttttgggatgtattatggagctaaaactctaacctcttaatagttttatagaact |

TABLE 10-continued

The mRNA variant transcripts of Septins and UEV3 genes.

| Septin | mRNA Accession number | mRNAsequence |
|---|---|---|
| | | taaaaatttttatacaattacccaattggtgatatgatcttaagcttttgtgtcagattatttaata<br>tgatgacttcatgctttattatgccttattatggctgacgtattactgtggtgaaacaaaatatct<br>ttaaaagttaaaacatccagatatataagctatttttcctaaggataaagtacctttgagcatg<br>agtgtatcacagctttcattaggaaaacttttcattacatacttgtttaaactctgtcttccaggg<br>taaaaataataaggttgaatcattttattaaaaatacttttaagaaaataactatgaacatctg<br>aatattaaagatataaaaatgcacataattcatatttcaggtggtatttgcattcagtgccttac<br>tggtattctcagaacattttaatgatttctaacatttcttaacagtcatagatatatacattttcatt<br>ttttgtacttgaatattctaaataaaactgacatttactcttgacaaataaaacatatatttactaa<br>aatgtgtttaattttcctttctgaaaactctcattttaaaaacgttcatttaattatgtatttgaattat<br>tttggagatgaggtattttatgagtattttcagacaatgaaacttattagtctgtgtcagattctg<br>agcaatcatagagtcatctaagttgtaaataaaaccttgcatagcacaaaaaaaaaaaaaa<br>aaa<br>NM_178584<br>cacttccggcctcgcgagggccgcaatcactgctccgcagttcccgcctgcattcctcgc<br>gccgtcttcctggagtcccagctctccttcagcccgccccaacgctgacgctcagtcctca<br>ggcgtcgagggtagctcctgtgaggggctcgcttggcgcacgcaaaacgctcagcgcg<br>caccacagggcgtccgccccaaccccgcccccggaggcctccagctcggccccgccc<br>ctgtcccttccccgtcgcggaggcagcctagcctcgcgccccgcccgttgcttctgccctc<br>cggccttcccgccgccgtcgccgggaccagccgctcggggccgggctgatacagccg<br>cttcaccgtgcccctgcccgcgaccatggcctcctccgaggtggcgcggcacctgaaaa<br>gagaaaacattcgttcgttgactatgtctggccatgttggttttgagagtttgcctgatcagct<br>ggtgaacagatccattcagcaaggtttctgctttaatattctctgtgtgggggaaactggaat<br>tggaaaatcaacactgattgacacattgtttaatactaattttgaagactatgaatcctcacatt<br>tttgcccaaatgttaaacttaaagctcagacatatgaactccaggaaagtaatgttcaattga<br>aattgaccattgtgaatacagtgggatttggtgaccaaataaataaagaagagagctacca<br>accaatagttgactacatagatgctcagtttgaggcctatctccaagaagaactgaagatta<br>agcgttctctctttacctaccatgattctcgcatccatgtgtgtctctacttcatttcaccgaca<br>ggccactctctgaagacacttgatctcttaaccatgaagaaccttgacagcaaggtaaaca<br>ttataccagtgattgccaaagcagatacggtttctaaaactgaattacagaagtttaagatca<br>agctcatgagtgaattggtcagcaatggcgtccagatataccagttcccaacggatgatga<br>cactattgctaaggtcaacgctgcaatgaatggacagttgccgtttgctgttgtgggaagta<br>tggatgaggtaaaagtcggaaacaagatggtcaaagctcgccagtacccttggggtgttg<br>tacaagtggaaaatgaaaaccactgtgactttgtaaagctgcgggaaatgctcatttgtaca<br>aatatggaggacctgcgagagcagacccataccaggcactatgagctttacaggcgctg<br>caaactggaggaaatgggctttacagatgtgggcccagaaaacaagccagtcagtgttca<br>agagacctatgaagccaaaagacatgagttccatggtgaacgtcagaggaaggaagaa<br>gaaatgaaacagatgtttgtgcagcgagtaaaggagaaagaagccatattgaaagaagct<br>gagagagagctacaggccaaatttgagcaccttaagagacttcaccaagaagagagaat<br>gaagcttgaagaaaagagaagacttttggaagaagaaataattgctttctctaaaaagaaa<br>gctacctccgagatatttcacagccagtcctttctggcaacaggcagcaacctgaggaag<br>gacaaggaccgtaagaactccaatttttttgtaaaacagaagttccagagcacagaaggtc<br>atcatcacaagcaaactttattaaaaaaaaactagaagtgtgctttgattttgctgttatttgtttt<br>atcacttctatatttggtgaacagccacagttactgatatttatggaaaagtactttcaagtaca<br>aggtcaatacataagccagagtgaatgatactacaagttgagcatctctaattcaaaaatct<br>gaaatccagaagcttcaaaatctgaatctttttgagcactgacttgaccccacaagtggaaa<br>attccccacccgacacctttgctttctgatggttcagtttaaacagattttgtttcttgcacaaa<br>atttttgtataaattactttcaggctatatgtataaggtggatgtgaaacatgaattatgtaatta<br>gagtcgggtcccgttgtgtatatgcagatattccaaacctgaaatccaaaacacttctggtc<br>cctagcattttggataagggatactcagcttgtacctatatattcatatatattcactgttgttag<br>aaatgtttaagttgctgttctgtgatgaatctaaatcttttctcttgctaccaagctattgtcactg<br>cagtgcattataccaaagagcgaagtcagtgccactgaaaatacagaacccattaatatcg<br>tggctatctgattacatttatattccaagatgaaccttttttatatatgctaaaaattttggggaat<br>atgttttgggatgtattatggagctaaaactctaacctcttaatagttttatagaacttaaaaatt<br>ttttatacaattacccaattggtgatatgatcttaagcttttgtgtcagattatttaatatgatgact<br>tcatgctttattatgccttattatggctgacgtattactgtggtgaaacaaaatatctttaaaagt<br>taaaacatccagatatataagctatttttcctaaggataaagtacctttgagcatgagtgtatc<br>acagctttcattaggaaaacttttcattacatacttgtttaaactctgtcttccagggtaaaaata<br>ataaggttgaatcattttattaaaaatacttttaagaaaataactatgaacatctgaatattaaa<br>gatataaaaatgcacataattcatatttcaggtggtatttgcattcagtgccttactggtattctc<br>agaacattttaatgatttctaacatttcttaacagtcatagatatatacattttcatttttgtacttg<br>aatattctaaataaaactgacatttactcttgacaaataaaacatatatttactaaaatgtgttta<br>attttcctttctgaaaactctcattttaaaaacgttcatttaattatgtatttgaattattttggagat<br>gaggtattttatgagtattttcagacaatgaaacttattagtctgtgtcagattctgagcaatca<br>tagagtcatctaagttgtaaataaaaccttgcatagcacaaaaaaaaaaaaaaaaa |
| Septin11 | NM_018243<br>(SEQ. ID.<br>NO: 96) | NM_018243<br>ggcgtgggggagcagatgccgctggctgccagcgggacgccggcgagcagagcgc<br>agccgcgagggaggcgcgagggaggcgagccggagcccgagcactagcagcagcc<br>ggagtcggcgtaaagcacccgggcgcagccggagccggtgccgcagctgcgatggc<br>cgtggccgtggggagaccgtctaatgaagagcttcgaaacttgtctttgtctggccatgtg<br>ggatttgacagcctccctgaccagctggtcaacaagtctacttctcaaggattctgtttcaac<br>atcctttgtgttggtgagacaggcattggcaaatccacgttaatggacactttgttcaacacc<br>aaatttgaaagtgacccagctactcacaatgaaccaggtgttcggttaaaagccagaagtt<br>atgagcttcaggaaagcaatgtacggctgaagttaaccattgttgacaccgtgggatttgg |

TABLE 10-continued

The mRNA variant transcripts of Septins and UEV3 genes.

| Septin | mRNA Accession number | mRNAsequence |
| --- | --- | --- |
| | | agaccagataaataaagatgacagctataagccgatagtagaatatattgatgcccagttc<br>gaggcctacctgcaagaggaattgaagattaaacgttctctcttcaactaccatgacacga<br>ggatccatgcctgcctctactttattgcccctactggacattcactaaagtccctggatctggt<br>caccatgaaaaagctggacagtaaggtgaacatcattccaataattgcaaaagctgacac<br>cattgccaagaatgaactgcacaaattcaagagtaagatcatgagtgaactggtcagcaat<br>ggggtccagatatatcagtttcccactgatgaagaaacggtggcagagattaacgcaaca<br>atgagtgtccatctcccatttgcagtggttggcagcaccgaagaggtgaagattggcaaca<br>agatggcaaaggccaggcagtaccccctggggtgtggtgcaggttgagaatgaaaatcat<br>tgcgattttgtgaaacttcgagagatgctgatccgcgtgaacatggaggacttgcgagagc<br>agactcacacccgccactatgaattgtaccgacgctgtaagcttgaagagatggggttcaa<br>ggacactgaccctgacagcaaacccttcagtcttcaggagacatatgaagcaaaaagga<br>atgaattcctgggagaactgcagaagaaagaagaagaaatgagacaaatgtttgttatga<br>gagtgaaggagaaagaagctgaacttaaggaggcagagaaagagcttcacgagaagtt<br>tgaccttctaaagcggacacaccaagaagaaaagaagaaagtggaagacaagaagaag<br>gagcttgaggaggaggtgaacaacttccagaagaagaaagcagcggctcagttactaca<br>gtcccaggcccagcaatctggggcccagcaaaccaagaaagacaaggataagaaaaat<br>gcaagcttcacataaagcctggcaagccaaggatgttcccgcattcacctgcttttgcagta<br>atatcgtatctctgccatgtgtgttctttagttttattttattttattttatttttttacccttcctcaaac<br>accagtaactattattaactcgttttgctgaatgttgttgggtggtagaaaatgatagaacaag<br>ggaataaccgcgaatgctctgtgcagctggactctgtttccggaaagtaaatgatttgctttt<br>tatgcctgttctgaatggcagcacgaagcaggcctgttacttgtatgtcgctttggacagag<br>gaaagtggggtaaaatgctacctgtacgtctgacatgaaaacttctcaccgcctcagcagc<br>tgaactaaaaacctgaatagccatgacaagagtttgcattttcttgatgattcatctccatgag<br>tgcacaatccctgaactcactgtcttttctccacacttgtcctaagccaaggtagatttgtacg<br>tagacagactggtgagcaagcattatatttatttttacccttgcatgacattttcattttaatcaa<br>taacattatttggcctgagcttgtgggtctgttcagactgtctcctctcatggtttgaaactgca<br>tctgaatgcctgccttcaatcctggccaagttggagtagactggtatgagaaaactatgatt<br>agttcacatttactggtgcatccttgatcctctcacagatagaggtcttaaaggttggatcatg<br>taacattgcttagtagaagaatcttcttctaaggatgatgggctttctacagcctgcttaccac<br>taacagtaaggaatctttcataaacacacctcagtttgttcccagtgggcttagagggagga<br>cctgatgactgattccaggatacttgtacttctaataacatttttcatgaatcatgagaaaattt<br>ccacagatacttcccttagaaaatttgctataaactctgtatcattggtagcacaaatttgagc<br>gaggccttgtcaattttaaggtggaaataggaaggaccacaacatgacccgtaagtcaag<br>aaggtagacatttcatatccagcttccttgcttagtctcctttcagtatttggcaataaaagaaa<br>gaagaaatagaacagctgaagtctcaaatcattgtctggaattttcctcaccttggctagctc<br>cacctgctctttgtctaaggcccttgcctcatcagggattagaactggcccatatgccagaa<br>cctgtactaaatgcctaatttgtatggaagagtgcatatttaatctcttttctatactgctcctttc<br>tgatgcttatcctttcatctgtgtgattgtttttcccctctactaacaagatcctcccagctttct<br>ctctacatgtagaaaggataacatttctcatgaacccactgcccctctgcattttcctcactgg<br>ttagagattaagtaaataggatagaatatgctgcgtctcccctgacacacactttctttttttga<br>atgagcaagtctccattttgatttcagcaaagatttttctccttttctttgtcctcaaccatactta<br>gaggaaagaaggaatggtcttccatgaactgattatgcttaattaagcaaagtaaggaaatt<br>agtttcatggaagcctaaacaaagctggaatagaaactacacactagacacagcagtagt<br>catagtcttcacaggtttaggagctactggaccaacattcttgtttttgcttttgtttttttaaata<br>attctagtctggagctaactgtggagcagccaaatagtagctggcatgttgattcaaaccat<br>gggctgaatttgctcataggctgtgcatcagacaaaagcttgaatatttgtgttgtatgcttgt<br>tccaaccaccgcttgtgtgagcatttttgtggcttgtacagaaagtacacttttaaattgtctct<br>tgcatcactaaaatttttttaaaatgagcataacaacgaaaggcatccagctgacttttttgatt<br>ccaagattattgattggattgactttttttgcattaaatttttcccagcaaaataaatcatatggcg<br>agtcagggaataaaaagtcaaaagaaacaaatagaagctttttttttttaaaaaatgtattgctt<br>ctgaactttttttctgccactgctccctagccctgtttagtttgttattgctgcttttctttttttctttct<br>gtatctatgcctttttttcacagtagtccttggctctgcacggaataaatgataccctcaaatct<br>aattggatgtgctttcgcctttgcatgtaagtacggtagtaagaaacctttgagatctttctga<br>cttttcaaaattagagaaagcaaatgggatggatagatttttttttttcttttcaagggggggcag<br>gaaggtaatggtttgagtagcctttgtttaaaaaaaagactaaatatatttaaaaggccacatt<br>tatatttttttcacaagaaccacataataaattccacttcttgacctgaatttggaaatccgaaa<br>ttactaatccaggccaggtgtggtggctcatgcctgtaatcccagcactttgagaggccga<br>ggtgggcagatcacttgaggcctggagttcaagaccaccttggcgaacacggtgaaacc<br>ccgtctctacaaaaaatacaaaaattagccaggcgtggtggcacgtgcctgtagtcccag<br>ctacttgggaggctaagtcaggagaattgcttgaacttgggagatggaggttgcagtgag<br>ccaagattgcaccactgcattccaacctgggtgatgaagtgagactctccaaaaaaaaaa<br>aagaaattattaatccctgcctgtgctctacatagcctcatgggcatcattggatagctcaga<br>gggcccttgattctggcaaggcaaataaagccagaatgagaaattaccatcttctactaga<br>gaaaaccaagagaaaaatttttatgctaggatgcctttatgaccacttaatttttttaatcttagtt<br>taatggtctctccctggtgctaactgctgacagtggccacctctttttttggggattgaggggc<br>ctacataactagctggccttaccccatatcttttgttcaaacataataccatctttttgcttcttct<br>gaactttagatctccataacacatgtactgtagaatgtgatggaaaagcattgatgagaattt<br>attggcagttcagattgtgttttcccaacttaggctctttattaattggttaaggttttctccaaaa<br>agggcatttcaacaatgggaattatttaatgtaacagtgggcacagattacttatcttccttct<br>ctgctttgtgactcaccagcagtaacacacacaatccacatcttgtgcacctcaaatgaaca<br>gacttggtttccttgctttcttgacatttccatgactgtttcacatacaaactattgggtgaggtt<br>tttcagctgttaccgacccacgtcctgctgtctctgtgtggtcctacaaaaactgtccattccc<br>acccctttgctttgccatttgcaagagtctggaattgtcaggtctcagcttcgaaaagtcctg<br>gttccactgacaggacacattctttagtgggaattaagacctacaaagtctagtttgtatgta |

TABLE 10-continued

The mRNA variant transcripts of Septins and UEV3 genes.

| Septin | mRNA Accession number | mRNAsequence |
|---|---|---|
| | | ggtatgaagggaatttttaaataaattgaaaagctgtgaacagcattagaactttgtctatttc |
| | | ttaattttaaaatatgctgatatgccttaaactgtagttgtagatccttgtcattttgctgtttgaa |
| | | aataaccaatgtgttttctaaaactgtcgtgtaatctactttcattgttaatgcagaattgtcatat |
| | | atgtaagctgcatgttagacatttgtctttttttaaactaaagtaattgtattgatgtgaagcatat |
| | | catttttcaaatatgaaagtgatcacttagcaacatgcttggtaatttggcatctgttaaggta |
| | | ggagagtggtgaacagataatctatgcatatatcactagtgccaagacataaagcggggg |
| | | aaaatatatttttacccaaacattaaaaaaaaaaaaaaaaaaaaaaaaaaaaa |
| Septin12 | NM_001154458 | NM_001154458 |
| | (SEQ. ID. | gcagatggagctcagattcttcggttaactgtcaccctctcccctcccccatcacacacacc |
| | NO: 97) | aggccctgccaggacaaggcagctcctggaagctccaccaggacccacgtccaccag |
| | NM_144605 | gcatctcgaacccttggcccccatggacccccctgaggcgctccccctctccctgcctgtcc |
| | (SEQ. ID. | tcgcagccctccagccccagcaccccaccctgcgagatgcttggtcctgtgggcattgag |
| | NO: 98) | gctgtgctggaccagctgaagatcaaggctatgaagatggggtttgagttcaacatcatgg |
| | | tggtggggcaaagcgggctgggcaagtccacgatggtgaacacgctgttcaagtccaaa |
| | | gtgtggaagtcaaacccaccgggcttgggggtgcccacaccccagacgctgcagctgc |
| | | attcactgacccatgtcatagaggagaagggtgtgaagctgaagctgacggtgacggac |
| | | acgcccggcttcggggaccagatcaacaatgacaactgcctgcggcccctggacattga |
| | | gttcctgcagcggctgtgccggactgtgaatgtggtgcccgtgattgccagggccgacag |
| | | cctgaccatggaggagcgagaggccttcaggcgcaggatccagcagaacctgaggac |
| | | ccactgcatcgacgtctacccccagatgtgctttgacgaggacatcaatgacaaaatcctc |
| | | aacagcaagttacgggaccgaatcccttttgccgtggtaggggctgaccaagagcacct |
| | | ggtgaacgggaggtgtgtcctgggccggaagaccaagtggggcatcattgaagtggag |
| | | aacatggcgcactgtgaatttcctctcctgagagacctgcttatccgctcccacctccaaga |
| | | cctgaaggacataacccacaacatccactatgagaactaccgcgtcatcagactcaatga |
| | | aagccacctgctgccccgcgggcccggctgggtgaacctggccccggcctccccagg |
| | | acagctgaccacccccccggaccttcaaggtctgcaggggggcccatgacgattctgatg |
| | | atgagttctgaccaccggcggatcccggggctgctgggcttcctgagtccccagcggctc |
| | | tcaacacacacctatgtaccagagcatctattaaatgtgagccttgctttttatgaaaagctgt |
| | | gctttgaaaacaaaaaaaaaaaaaaaaaa |
| | | NM_144605 |
| | | cttgggcccctggttctacttggggattattgtattattaggctggggtcattgtgggga |
| | | ttagaagggtaacagctcctgctcctgctgcagagaagcctccaggtgggggtcacagc |
| | | aagtgcagatggagctcagattcttcggttaactgtcaccctctcccctcccccatcacaca |
| | | caccaggccctgccaggacaaggcagctcctggaagctccaccaggacccacgtccac |
| | | caggcatctcgaacccttggcccccatggacccccctgaggcgctccccctctccctgcct |
| | | gtcctcgcagccctccagccccagcaccccaccctgcgagatgcttggtcctgtgggcat |
| | | tgaggctgtgctggaccagctgaagatcaaggctatgaagatggggtttgagttcaacatc |
| | | atggtggtggggcaaagcgggctgggcaagtccacgatggtgaacacgctgttcaagtc |
| | | caaagtgtggaagtcaaacccaccgggcttgggggtgcccacaccccagacgctgcag |
| | | ctgcattcactgacccatgtcatagaggagaagggtgtgaagctgaagctgacggtgacg |
| | | gacacgcccggcttcggggaccagatcaacaatgacaactgctgggaccccatcctgg |
| | | gctacatcaacgagcaatacgagcagtacctgcaggaggagatcctcatcacccgccag |
| | | cgccacatcccagacacccgggtgcactgctgcgtgtactttgtaccacccactgggcac |
| | | tgcctgcggcccctggacattgagttcctgcagcggctgtgccggactgtgaatgtggtg |
| | | cccgtgattgccagggccgacagcctgaccatggaggagcgagaggccttcaggcgca |
| | | ggatccagcagaacctgaggacccactgcatcgacgtctacccccagatgtgctttgacg |
| | | aggacatcaatgacaaaatcctcaacagcaagttacgggaccgaatcccttttgccgtggt |
| | | aggggctgaccaagagcacctggtgaacgggaggtgtgtcctgggccggaagaccaa |
| | | gtggggcatcattgaagtggagaacatggcgcactgtgaatttcctctcctgagagacctg |
| | | cttatccgctcccacctccaagacctgaaggacataacccacaacatccactatgagaact |
| | | accgcgtcatcagactcaatgaaagccacctgctgccccgcgggcccggctgggtgaa |
| | | cctggccccggcctccccaggacagctgaccacccccccggaccttcaaggtctgcagg |
| | | ggggcccatgacgattctgatgatgagttctgaccaccggcggatcccggggctgctgg |
| | | gcttcctgagtccccagcggctctcaacacacacctatgtaccagagcatctattaaatgtg |
| | | agccttgctttttatgaaaagctgtgctttgaaaacaaaaggcattttgtaaatgacttctttga |
| | | gctatc |
| | | cacaaataaaaaggctgggtgtca |
| Septin13(a. | AK056032 | AK056032 |
| k.a.septin7 | (SEQ. ID. | ctagccagacccacccctttatttcaggccatcccttcatttcccataagggatacttttagtt |
| pseudogene2) | NO: 99) | aattgaatatctatagaaacaatgctaatgactggtttgctgttaataaataagtgggtaaatc |
| | AK128034 | tctgttcggggctctcagctctgaaggctgtgagacccctgatttcccactttacacctctat |
| | (SEQ. ID. | atttctgtgtgtgtgtctttaattcctctagcaccactgggttagggtctccccaactgagctg |
| | NO: 100) | gtctcggcacttctctttgccttaaaaacaggtacagcggaccttcctggcatcagaaaaag |
| | AL832059 | gcctccagaaaaagagacacaggtactagcaattccaaattatccagagcccttctaagtt |
| | (SEQ. ID. | gtaagatctgaaagaaatgtctgccatctatattctcagccacacttagtttcttaatctgcaa |
| | NO: 101) | gatggaattaataatagtacttactttatgatgctgttgcagaaattcactgagttgctacacg |
| | BC015774 | ccaaacactgagaacccagctgggcatataataagcattctattgcatggcattattgccat |
| | (SEQ. ID. | catttttacttctattactgctactgcttgtaactgcttgtaactgtttgtgctttttttgatatgaaag |
| | NO: 102) | tccaccatcagggagcactgtagtggaaaaggtattaggccaggcatagcctttagttctct |
| | BC092503 | ggccttgggtccttcatctgtgatattcagttaacaatacctagccagtaggggtgttaaaga |
| | (SEQ. ID. | ttaaataaatgtgagaatgtgcctgttgcttaatcttcctcaaagggttatggactctcagagc |
| | NO: 103) | cagaagaaggtcatctctcctttgctcctcgtatgctgggatctgccacatcaatggcaaca |

TABLE 10-continued

The mRNA variant transcripts of Septins and UEV3 genes.

| Septin | mRNA Accession number | mRNAsequence |
|---|---|---|
| | | gctgggcctccagaatttgctccagggtgtttggaagtcctgacaccctcctgatcttctctg |
| | | taacatgcacactttggcctgtgtcagtttgctggaaccacatcaggccggccctcttcctg |
| | | ggacaaaattctttctttttctttctttctttttctttctctttctttcttttttctttctctttctttctcttttc |
| | | ccttccttccttccttccttccttccttccttccttccttccctttttcttttcttttctttctactgtgaca |
| | | taatcttggctcactgcaatctctctctcctgggttcaagtgattctactgcctcagcctccaa |
| | | agtagctgggattacaggtttgcaccaccatgcccggctaatttttttgtatttttagtagagac |
| | | agtgtttcaccatgttggccaggctggtctccatcacctgatctcaggtgatccacccacct |
| | | cagcctcccaaagtgctgggactacaggcatgagccaccacgcctggccgagagacag |
| | | ttaagttatactttaaatgataataggcctcccccaaaactcagctgcttttgtaaagctaatg |
| | | ggaggccatcaggctgggggcaaggaggagagcccggatcctgctaaggtgcagaca |
| | | taaacgagtatcagccattattctggaggttataagatatgcaccttccccaattacccctgc |
| | | aatcacaccattattgtagattggcccttagagtatcttttcaggtttttttggcatgtctgacact |
| | | catggctctacttggacccaccaaccctgctcctatggctccacccagaagccattcagcc |
| | | tagaggacagctctgacccccccctgtgatttcatacaatcagcagcaagtaactgttacctc |
| | | accatccccacccccttctgccagactgcctttgaaaaacctctaacctgtgagcacgagat |
| | | gattccagaacaaactctgtctcccatgtggcatgaccagccttgggtctcttaaactttttct |
| | | ccactataatgccatggtctttatgcagcaggcaggaagaattcaggtggttataattccgt |
| | | atgtgctttttgaacatttttctactgggctattgctctcttcataatgatttttttaacttctctctat |
| | | aaggaactgatttcatctgaaattgaagagacaatcagagaaaaactatagaccactcatg |
| | | atggttgttatatgtgcttggctgggccatgggtcccagtgtttggtgaaacacagcagcag |
| | | atgtccctgtgagtagatgttgctttgaaggtatcttttagatgtgatgaacatttgtcatcagt |
| | | agactttgagtaaggcagatagcccgtcacaatgtggatgggccttatccaattagttgaa |
| | | ggcctttgaaaaaagactgagatcccaaacgaagaaggaattctgcctccag |
| | | acagccttccaactcaagtagcaacattacctcctccctgcggctctagcctgctggccttt |
| | | cctatagacttcagacttgccagccccacaatcatgtaagccaattccttaaaataaattctct |
| | | gtcctgtttttgccccctctctctttctgacagcacacacatgccctcttggttctgtttctttga |
| | | agaaccccaggaaaacacacaaaggaaaaacaactcgatagacagaagattcttcaatg |
| | | acaacaatggaagccatcttcaccattcaactaaacttgaatgggatattatcaaacttaaaa |
| | | aaaaattatcaactgatcgtgtaatcagtttcatcttttaagacaggaaatgaaataaagtattt |
| | | acagatgaatgt |
| | | AK128034 |
| | | gatatctgagaatagtaggaaaaaaattgggtaatcccaaaataaatcagtgatttcagt |
| | | atgaagttttctcaacataaatctgctataattaaaaattacaggccttcaggaagtgtcgagt |
| | | ctgggacgcccagcgcgggcccgagcaggggggaagggaagcgcagctcggtccgc |
| | | gtgggtggaggggacgtgaagccgccctgagatgatggttgaggaagggctctacggc |
| | | tcccaagccaggccaaatgcctccggcggccgcgcccgggcgccccttcccctgtggg |
| | | gcaaccctagcttgggacgcgtgaaccacctccgtagctgccccaccagcacccccagc |
| | | cgtgcgcccctgcaccatgcagctgccctgcgcatggagccgcgagggacagcaggc |
| | | ccagccctcagcaccacctgcctgccaggaggttcgggaaactggcgccgcagcgga |
| | | gagggcatctgtccaacgcctcccccggggctcagctgcgggcccccaggcataggca |
| | | cccatgacccttctgtgttgtttgtctttgtatagtctgcagatgtggatcctgactcctgagag |
| | | aagtagctcaccgtgacgaagctgcgtttgcttttatcgatttgcaaatcaaagaaggggg |
| | | acatattgggagaaggcccccaaaatctggccataaactggccacaaaactggccata |
| | | aaatctctgcagcactgtgacatgctcatgatggccataacgcccacgctggaaggttttg |
| | | ggtttaccggaatgaaagcaaggaacacctggcctgcccagggcagaaaaccacttaaa |
| | | ggcattcttaaaccacaaacagtagcatgagcgatctgtgccttaagggcatgttcctgctg |
| | | cagataactagccagacccacccctttatttcaggccatcccttcatttcccataagggatac |
| | | ttttagttaattgaatatctatagaaacaatgctaatgactggtttgctgttaataaataagtgg |
| | | gtaaatctctgttcggggctctcagctctgaaggctgtgagacccctgatttcccactttaca |
| | | cctctatatttctgtgtgtgtgtctttaattcctctagcaccactgggttagggtctccccaact |
| | | gagctggcctcggcacttctctttgccttaaaaacaggtacagcggaccttcctggcatca |
| | | gaaaaaggcctccagaaaaagagacacaggtactagcaattccaaattatccagagccct |
| | | tctaagttgtaagatctgaaagaaatgtctgccatctatattctcagccacacttagtttcttaa |
| | | tctgcaagatggaattaataatagtacttactttatgatgctgttgcagaaattcactgagttgc |
| | | tacacgccaaacactgagaacccagctgggcatataataagcattctattgcatggcattat |
| | | tgccatcatttttacttctattactgctactgcttgtaactgcttgtaactgtttgtgctttttttgata |
| | | tgaaagtccaccatcagggagcactgtagtggaaaaggtattaggccaggcatagccttt |
| | | agttctctggccttgggtccttcatctgtgatattcagttaacaatacctagccagtaggggt |
| | | gttaaagattaaataaatgtgagaatgtgcctgttgcttaatcttcctcaaagggttatggact |
| | | ctcagagccagaagaaggtcatctctcctttgctcctcgtatgctgggatctgccacatcaa |
| | | tggcaaccgctgggcctccagaatttgctccagggtgtttggaagtcctgacaccctcctg |
| | | atcttctctgtaacatgcacactttggcctgtgtcagtttgctggaaccacatcaggccggcc |
| | | ctcttcctgggacaaaattctttctttttctttctttctttttctttctctttctttctttttctttctctttctt |
| | | tctcttttcccttccttccttccttccttccttccttccttccttccttccttccttccctttttcttttcttt |
| | | tctttctactgtgacatgatcttggctcactgcaatctctctctcctgggttcaagtgattctact |
| | | gcctcagcctccaaagtagctgggattacaggtttgcaccaccatgcccggctaatttttttgt |
| | | atttttagtagagacagtgtttcaccatgttggccaggctggtctccatcacctgatctcaggt |
| | | gatccacccacctcagcctcccaaagtgctgggactacaggcatgagccaccacgcctg |
| | | gccgagagacagttaagttatactttaaatgataataggcctcccccaaaactcagctgcttt |
| | | tgtaaagctaatgggaggccatcaggctgggggcaaggaggagagcccggatcctgct |
| | | aaggtgcagacataaacgagtatcagccattattctggaggttataagatatgcaccttccc |
| | | caattacccctgcaatcacaccattattgtagattggcccttagagtatcttttcaggttttttttgg |
| | | catgtctgacactcatggctctacttggacccaccaaccctgctcctatggctccacccaga |
| | | agccattcagcctagaggacagctctgacccccccctgtgatttcatacaatcagcagcaag |

TABLE 10-continued

The mRNA variant transcripts of Septins and UEV3 genes.

| Septin | mRNA Accession number | mRNAsequence |
|---|---|---|
| | | taactgttacctcaccatccccaccccttctgccagactgcctttgaaaaacctctaacctgt |
| | | gagcacgagatgattccagaacaaactctgtctcccatgtggcatgaccagccttgggtct |
| | | cttaaactttttctccactataatgccatggtctttatgcagcaggcaggaagaattcaggtg |
| | | gttataattccgtatgtgcttttttgaacatttttctactgggctattgctctcttcataatgatttctt |
| | | taacttctctctataaggaactgatttcatctgaaattgaagagacaatcagagaaaaactat |
| | | agaccactcatgatggtcgttatatgtgcttggctgggccatgggtcccagtgtttggtgaa |
| | | acacagcagcagatgtccctgtgagtagatgttgctttgaaggtatcttttagatgtgatgaa |
| | | catttgtcatcagtagactttgagtaaggcagatagcccgtcacaatgtggatgggccttat |
| | | ccaattagttgaaggcctttgaaaaaagactgagatcccaaacgaagaaggaattctgcct |
| | | ccagacagccttccaactcaagtagcaacataacctcctccctgcggctctagcctgctgg |
| | | cctttcctatagacttcagacttgccagccccacaatcatgtaagccaattccttaaaataaat |
| | | tctctgtcctgtttttgccccctctctctttctgacagcacacacatgccctcttggttctgtttct |
| | | ttgaagaaccccaggaaaacacacaaaggaaaaacaactcgatagacagaagattcttc |
| | | aatgacaacaatggaagccatcttcaccattcaactaaacttgaatgggatattatcaaactt |
| | | aaaaaaaaattatcaactgatcgtgtaatcagtttcatcttttaagacaggaaatgaaataaa |
| | | gtatttacagatg |
| | | AL832059 |
| | | ggacgctggctacgggtggccgggcgggatgtaaccggctgctgagctggcagttctgt |
| | | gtccccaggcttcggcccggccgccgccgcacataaactgcgaggaggagctttacga |
| | | cttcccggtcttcggggccgggcgcagcaagggccagactctgcgctagcaggcgctg |
| | | cgcgccaaccggccggcccctgtcgcagaaggtgcaaccgatcgcactgtcgcgcaga |
| | | agctcctcaatggccagcgccagctgcagccccggctgcccactcgcctcacctgagcc |
| | | tgggtggaacaatccaaagttttaatcaaagaaggtggtattcagttgctgcttacaatagtt |
| | | gataccccaggatttggagatgcagtggataatagtaattgctggcagcctgttatcaatta |
| | | cattgatagtaaatttgaggactacctaaatgcagaatcgcaagtgaacagatgtcagatg |
| | | cctggtaacagggtgcactgttgtttatacttcattgctccttcaggacatggaccgttacata |
| | | actgaagactcccaccttcaggcaggattgggtagtacatgtttgtaactacctggcattgc |
| | | cttttgttgagacttaaaccattggatattgagtttacaaagcatttgcatgaaaaagtgaatat |
| | | catcccacttattgccaaagcagacacactcatgccagaggaatgccaacagtttaaaaaa |
| | | cagataaagaaatccaagaacataaagttaaaatatatgaatttccagaaacagatgatga |
| | | agaagaaaaaaaacttgttaaaaagataaaggaccatttacctcttgctgtggtgggtagta |
| | | atactatcattgaagttaatggcaaaagggtcataggaaggcagtatccttggagtgttgct |
| | | gaagatggagtctcgctctgccacccaggctggaatgcagtggcatgatcttggctcact |
| | | gcaacctccgcctcccgagttcaagagattcttctgcctcagcctcccaagtagctgggac |
| | | taaagttgaaaatggtgaacattgtgattttacagttttaagaaatatgttgataagaacacac |
| | | gcaggacttgaaagatgttactaataatgtccactacgagaactatggaatcagaaaactg |
| | | gcggctgtgacttatcatggagttgataacaagaagaataaagggcagctcactaagagc |
| | | cctctggcacaaatggaagaagaaagaagggagcaagtagctaaaattaagaagatgg |
| | | agatggagatggagcaggtgtttgagatgaaggtcaaagaaaaagttcaaaaactgaag |
| | | gactctgaagctgaggtacagcggaccttcctggcatcagaaaaaggcctccagaaaaa |
| | | gagacacagggttatggactctcagagccagaagaaggtcatctctcctttgctcctcgtat |
| | | gctgggatctgccacatcaatggcaaccgctgggcctccagaatttgctccagggtgtttg |
| | | gaagtcctgacaccctcctgatcttctctgtaacatgcacactttggcctgtgtcagtttgctg |
| | | gaaccacatcaggccggccctcttcctgggacaaaattctttctttttctttctttctttttctttct |
| | | ctttctttctttttctttctctttctttctcttttcccttccttccttccttccttccttccttccttcc |
| | | ttccctttttcttttcttttctttctactgtgacatgatcttggctcactgcaatctctctctcctgggt |
| | | tcaagtgattctactgcctcagcctccaaagtagctgggattacaggtttgcaccaccatgc |
| | | ccggctaatttttttgtatttttagtagagacagtgtttcaccatgttggccaggctggtctccat |
| | | cacctgatctcaggtgatccacccacctcagcctcccaaagtgctgggactacaggcatg |
| | | agccaccacgcctggccgagagacagttaagttatactttaaatgataataggcctccccc |
| | | aaaactcagctgcttttgtaaagctaatgggaggccatcaggctgggggcaaggaggag |
| | | agcccggatcctgctaaggtgcagacataaacgagtatcagccattattctggaggttata |
| | | agatatgcaccttccccaattacccctgcaatcacaccattattgtagattggcccttagagt |
| | | atcttttcaggtttttttggcatgtctgacactcatggctctacttggacccaccaaccctgctc |
| | | ctatggctccacccagaagccattcagcctagaggacagctctgaccccccctgtgatttc |
| | | atacaatcagcagcaagtaactgttacctcaccatccccaccccttctgccagactgccttt |
| | | gaaaaacctctaacctgtgagcacgagatgattccagaacaaactctgtctcccatgtggc |
| | | atgaccagccttgggtctcttaaactttttctccactataatgccatggtctttatgcagcagg |
| | | caggaagaattcaggtggttataattccgtatgtgcttttttgaacatttttctactgggctattg |
| | | ctctcttcataatgatttttttaacttctctctataaggaactgatttcatctgaaattgaagtgac |
| | | aatcagagaaaaactatagaccactcatgatggttgttatatgtgcttggctgggccatggg |
| | | tcccagtgtttggtgaaacacagcagcagatgtccctcacacacatgccctcttggttctgtt |
| | | tctttgaagaaccccaggaaaacacacaaaggaaaaacaactcgatagacagaagattct |
| | | tcaatgacaacaatggaagccatcttcaccattcaactaaacttgaatgggatattatcaaac |
| | | ttaaaaaaaaattatcaactgatcgtgtaatcagtttcatcttttaagacaggaaatgaaataa |
| | | agtatttacagatgaatgtaaaataaaaaaaaaaaaaaaaaaaaaaaaaaaa |
| | | BC015774 |
| | | gtgaagccgccctgagatgatggttgaggaagggctctacggctcccaagctaggccaaa |
| | | tgcctccggcggccgcgcccgggcgccccttcccctgtggggcaaccctagcttggga |
| | | cgcgtgaaccacctccgtagctgccccaccagcacccccagccgtgcgcccctgcacc |
| | | atgcagctgccctgcgcatggagccgcgagggacagcaggcccagccctcagcacca |
| | | cctgcctgccaggaggttcgggaaactggcgccgcagcggagagggcatctgtccaac |
| | | gcctcccccggggctcagctgcgggcccccaggcataggcacccatgacccttctgtgtt |
| | | gtttgtctttgtatagtctgcagatgtggatcctgactcctgagagaagtagctcaccgtgac |

TABLE 10-continued

The mRNA variant transcripts of Septins and UEV3 genes.

| Septin | mRNA Accession number | mRNAsequence |
| --- | --- | --- |
| | | gaagctgcgtttgcttttatcgatttgcaaatcaaagaaggggggacatattgggagaaggc<br>cccccaaaatctggccataaactggccacaaaactggccataaaatctctgcagcactgt<br>gacatgctcatgatggccataacgcccacgctggaaggttttgggtttaccggaatgaag<br>gcaaggaacacctggcctgcccagggcagaaaaccacttaaaggcattcttaaaccaca<br>aacagtagcatgagcgatctgtgccttaagggcatgttcctgctgcagataactagccaga<br>cccaccccctttatttcaggccatcccttcatttcccataagggatacttttagttaattgaatatc<br>tatagaaacaatgctaatgactggtttgctgttaataaataagtgggtaaatctctgttcggg<br>gctctcagctctgaaggctgtgagacccctgatttcccccctttacacctctaaaaaaaaaaa<br>aaaaaaaaaaaaaaaaaaaaaaaaaaa<br>BC092503<br>gcgcattagcggacgctggctacgggtggccgggcgggatgtaaccggctgctgagcg<br>gcagttctgtgtccccaggcttcggcccggccgccgccgcacataaactgcgaggagga<br>gctttacgacttcccggtcttcggggccgggcgcagcaagggccagactctgcgctagc<br>aggcgctgcgcgccaaccggccggcccctgtcgcagaaggtgcaaccgatcgcactgt<br>cgcgcagaagctcctcaatggccagcgccagctgcagccccggctgcccactcgcctc<br>acctgagcctgggtggaacaatccaaagttttaatcaaagaaggtggtattcagttgctgct<br>tacaatagttgataccccaggatttggagatgcagtggataatagtaattgctggcagcctg<br>ttatcaattacattgatagtaaatttgaggactacctaaatgcagaatcgcaagtgaacagat<br>gtcagatgcctggtaacagggtgcactgttgtttatacttcattgctccttcaggacatggac<br>cgttacataactgaggactcccaccttcaggcaggattgggtagtacatgtttgtaactacct<br>ggcattgccttttgttgagacttaaaccattggatattgagtttacaaagcatttgcatgaaaa<br>agtgaatatcatcccacttattgccaaagcagacacactcatgccagaggaatgccaaca<br>gtttaaaaaacagataaagaaatccaagaacataaagttaaaatatatgaatttccagaaac<br>agatgatgaagaagaaaaaaaacttgttaaaaagataaaggaccatttacctcttgctgtgg<br>tgggtagtaatactatcattgaagttaatggcaaaagggtcataggaaggcagtatccttgg<br>agtgttgctgaagttgaaaatggtgaacattgtgattttacagttttaagaaatatgttgataag<br>aacacacgcaggacttgaaagatgttactaataatatccactacgagaactatggaatcag<br>aaaactggcagctgtgacttatcatggagttgataacaagaagaataaagggcagctcact<br>aatagagacggtatttcaccatgttagccaggatggtcttgatctcctgacctcgtgatccac<br>ccgcctcggcctcccaaagtgctgggattacaggcatgagccaccacgcccggccaagt<br>ggaatgaattttcaagagcattgaagttaccataaggggcctagaaatactctgtatacctat<br>atagtgctctaggagccctctggcacaaatggaagaagaaagaagggagcaagtagcta<br>aaattaagaagatggagatggagatggagcaggtgtttgagatgaaggtcaaagaaaaa<br>gttcaaaaactgaaggactctgaagctgaggtacagcggaccttcctggcatcagaaaaa<br>ggcctccagaaaaagagacacaggaactgatttcatctgaaattgaagagacaatcagag<br>aaaaactatagaccactcatgatggttgttatatgtgcttggctgggccatgggtcccagtgt<br>ttggtgaaacacagcagcagatgtccctgtgagtagatgttgctttgaaggtatcttttagat<br>gcgatgaacatttgtcatcagtagactttgagtaaggcagacagcccgtcacaatgtggat<br>gggccttatccaattagttgaaggcctttgaaaaaagactgagatcccaaacgaagaagg<br>aattctgcctccagacagccttccaactcaagtagcaacataacctcctccctgcggctcta<br>gcctgctggcctttcctatagacttcagacttgccagccccacaatcatgtaagccaattcct<br>taaaataaattctctgtcctgtaaaaaaaaaaaaaaaa |
| Septin14 | NM_207366<br>(SEQ. ID.<br>NO: 104) | NM_207366<br>acagtgaatatttatttggtccacaactggggacagtagaaaggacaccagcttggaatca<br>gttcggacctgtgtctgctgcacagctgaatccctgggaaactcttttagtgtagcatggca<br>gaaagaacaatggctatgcccacacaaatacctgctgatggagatacacaaaaagaaaat<br>aatattcgttgtttaactacgattggacattttggttttgaatgtttgcccaatcagttggtgagc<br>agatctatccgacaaggattcacttttaatattctctgtgtgggggagactggaattggaaaa<br>tcgacactgatagacacattgtttaatactaacttgaaagataacaaatcctcacatttttactc<br>aaatgttggacttcaaattcagacatatgaacttcaggaaagcaatgttcagttgaaattgac<br>tgttgtggagacagtagggtatggtgatcaaatagacaaagaagccagctaccaaccaat<br>agttgactacatagatgcccaatttgaggcctatcttcaagaagaactgaagattaaacgtt<br>ccttgtttgagtaccatgattctcgcgtccacgtgtgtctttacttcatttcacctacaggacatt<br>ccctgaagtctcttgatctattaacaatgaagaaccttgacagtaaggtgaatattataccac<br>tgattgccaaagcagacactatttctaaaaatgatttacagacgtttaagaataagataatga<br>gtgaattgattagcaatggcatccagatatatcagctcccaacagatgaagaaactgctgct<br>caagcgaactcctcagttagtgggctgttacccttttgctgtggtagggagtacagatgaagt<br>gaaagttggaaaaaggatggtcagaggccgtcactacccttggggagttttgcaagtgga<br>aaatgaaaatcactgtgacttcgttaagctccgagatatgcttctttgtaccaatatggaaaat<br>ctaaaagaaaaaacccacactcagcactatgaatgttataggtaccaaaaactgcagaaa<br>atgggctttacagatgtgggtccaaacaaccagccagttagttttcaagaaatctttgaagc<br>caaaagacaagagttctatgatcaatgtcagagggaagaagaagagttgaaacagagatt<br>tatgcagcgagtcaaggagaaagaagcaacatttaaagaagctgaaaaagagctgcag<br>gacaagttcgagcatcttaaaatgattcaacaggaggagataaggaagctcgaggaaga<br>gaaaaaacaactggaaggagaaatcatagatttttataaaatgaaagctgcctccgaagca<br>ctgcagactcagctgagcaccgatacaaagaaagacaaacatcgtaagaaataatagttt<br>ctcttactattctgagagccctatcattctacatcgcaacttcctgtgagattgtctttgtagcat<br>ttaactctgaagttctcattttaaaaattggcttgcttattgtatattttccccaactaaagtgtga<br>actcctagcggggtgtggtggctcatgcctgtaatcccagcactttgggaggctgaggcg<br>ggtggaccacctgaggtcaggagttcaaaaccagcctgaccaaaatgatgaaaccctgc<br>ctctactaaaaatacaaaaattagctgggtttggtggccggtacctgtaatcccagccactt<br>gggaggctgaggcaggagaatcacttgaaccccggaggtggaggttgcagtgagccaa<br>gatctcaccattgtactccagcctgggtgacaagagcaaaactccgcctcaaaaaaaaaa |

TABLE 10-continued

The mRNA variant transcripts of Septins and UEV3 genes.

| Septin | mRNA Accession number | mRNAsequence |
|---|---|---|
| | | aaaaaaaaaaaaagtatgaactcccagaaggcagatcctgtgtccctcttttcagattctgtat<br>cttggcacttaggacgtacactaacacaaatatgactttcaatcaatatttgccaaaatgaaa<br>aaacaaaagaaacacgtagcatcatgtaaaaggagctggttaggtggagaaatttatttac<br>catagtcctgcttttggatccagtagtgacttttaacttttatatccaaatagaagctggaggct<br>ttgttggggactcataggcataaaatgttaagttatacaaatctaattaataggcctattttcctt<br>tttaagttctactactgataatttcttgacagtttttatgataaaaggttggaatttgataagaact<br>cccatgcttttgtgtcagacttaaaactgatattagaataaagaattcaaaagctagagaaag<br>agttgcatttgaatgataatattatgtgttacagatttggggtatatgccaaagttatcaaagtt<br>gtagaaaataaggccaggtgtggtggctcacacctgtaatcccagcactttgggaggccg<br>aggtgggcggatcacttgcggtcaggagcttgagaacagcccggccaacatgacgaaa<br>ccccatctctactaataatacaaaagttagccgggtgtggtgttgtgcacctgtagtccctgc<br>tactcggaaagctgaggcaggagaatcgcttgtagccaggaggcagaggttgtagtgag<br>cagagattgcgccactgcactccagcctgggtgacagagcgctgagtcaccacacctgg<br>tataagccactgtgcctgacccacaatgacttttatacatattgttaaatcatcttacagatttta<br>taatttggggaagaaaaatttactaaatgatcttttaatggaaactctacaagaaccagaa<br>tctttgctttgttcacttatgtatccattcctaggcctagaaaaatgtctgacgcatagcagca<br>attattcattgaataaatgga<br>cccagcaatagtacattagctatgccatatgcatacattaaaaatgtagattattgactttcaa<br>aagataattaatgtaacttcttactgcttctgaacatgtttgtgagttatattgctgagggacctt<br>tatcttctcattctttcatcttaatccaatgttattaaaactgaaactgaaatcaccaatattattc<br>catatttaaaaataacatctaccttataaaaattatcattgtgctgcatttgagaatagacttttta<br>ggtaataatggtataatccatagggtttttgagggcacagaaggattcatgctaacagaaca<br>ttttattttctattttccaagagctataaaacatgatattatatgatactataaggcatatttttatttt<br>ccataatttttctaaaaaaaattagtgttggtttccatataacttttaactttataagtaaatattt<br>gtctctttcagctccagtttcatgtgaaatagagtttccagatttatgtagcatggaaagtttta<br>atacgtcagttactgattttgccagtcattttctcaattatttacttcttttatctttagttgattttttt<br>tgtagtgacaagttttgtttctattctcatttccttttgtgtatattctatgtagatttcgtttttggtta<br>ctatgaaaattacatataacatcctggagttataacattctgatttgaatttatttcaacttaactt<br>caatcacataccaaaattctactgctatataggtctactctttttaggttattgatgtaacaaatt<br>gtatctttattcattgtacaccacctaacagatttataattacattttatgcatttgtcttttaaatcc<br>tgtagaaaataaaaagcggagttacaaacc |
| UEV3 | NM_001040697<br>(SEQ. ID.<br>NO: 105)<br>NM_018314<br>(SEQ. ID.<br>NO: 106) | NM_001040697<br>agcggcttccgtcctgcagcaagtccggaagaaggtccgggggctggagtcctgggac<br>ctagctcgggaccggcctggagatggagttcgactgcgagggcctgagacggctgcttg<br>gcaagtacaagttcagggacctaactgtggaagaactaaggaatgtaaatgtatttttccca<br>catttcaaatattccatggacacctatgtttttaaagatagttctcagaaagacctgctgaattt<br>tactggcacaattcctgtgatgtatcagggtaatacatataacataccaattcgtttctggattt<br>tggattctcaccctttcgctcccccctatttgcttcttgaagccaactgcaaatatgggaatctta<br>gtcggaaaacatgtggatgctcaaggcagaatatatttgccctatctccaaaactggagcc<br>atcctaaatctgtcattgttggattaattaaagaaatgattgccaagtttcaagaggaacttcc<br>catgtattctctatcatcatctgatgaggcacggcaggtagacttgctagcctatattgcaaa<br>aatcactgaaggtgtttcagatacaaattcaaagagctgggcaaatcatgagaataaaaca<br>gtcaataaaattactgtggttggaggtggagaactcggtattgcctgcacattagcaatttca<br>gcaaagggtattgcagacaggcttgtcctcttagacctctcagaagggactaaaggagcc<br>acgatggaccttgaaatcttcaaccttcctaatgtggagatcagcaaagatttgtctgcctct<br>gctcattccaaggtggtgatcttcacagtcaactctttgggtagttctcagtcgtaccttgatg<br>tggtacagagcaatgtggatatgttcagagcccttgtcccagctctgggacattatagtcaa<br>cacagtgtcctgctcgttgcatctcaaccagtggaaatcatgacctatgtaacatggaaact<br>gagtacatttcctgcaaatcgagtgatcggaattggatgtaatctggattcacagagattac<br>agtatattattacaaatgttttgaaggcacagacttcaggcaaagaagtatgggttattggcg<br>agcaaggagaagacaaagtgctcacatggagtggccaagaagaagtagtgagtcatac<br>ctctcaagtgcagctgtccaacagagccatggaactgctaagagtaaaaggtcaaagatc<br>ctggtctgttggactatcagtagctgacatggttgacagtattgtaaacaataagaagaaag<br>tgcattctgtatcagctttagcaaagggatattatgatataaatagtgaagtgtttttaagtttgc<br>cttgcatccttggaaccaatggagtatctgaagttatcaaaaccacactgaaagaagatac<br>agttactgagaaactccaaagcagtgcatcctcaatccacagtctccaacaacagttaaaa<br>ctttgattctcaaatgcaatttgagaggctggacttctacctaaagggaaaagtcatttaatttt<br>acctatatataggtttgaggatttctgtatcctgctacttacttttacaaactgcttggttaaagt<br>agagggtttcttgattagctttgtgatgtaaatccttaaggagttatacaaggaggggaaaa<br>attaattttatttggggttcttgagatatctatgctgttctttaaatctacagcaggggtaaacat<br>tcatctgcagtgtgcatcaatttaaatcatatatcctaaactaaaagcacaattcatacttcgg<br>gaatattttataagtaatatatctttaaaagaaaattaccctttgacttttataatcaacataagtt<br>ccaggcccagtatggatttacaaaatctgtgtcagttgtacattcacaggatccacagctta<br>agttactaatgtttcttgtgtaaaatcctgttggtagtaatagtaaagcattgtatttcccttcttc<br>aaattaattacctaccaaaaaatggaaaagaattttacatgcactttaaaatagtaaaatgga<br>aagtgaattttttaaaatatatgcattaaaagtttactttaatttccaaaaaaaaaaaaaaaaaa<br>NM_018314<br>agcggcttccgtcctgcagcaagtccggaagaaggtccgggggctggagtcctgggac<br>ctagctcgggaccggcctggagatggagttcgactgcgagggcctgagacggctgcttg<br>gcaagtacaagttcagggacctaactgtggaagaactaaggaatgtaaatgtatttttccca<br>catttcaaatattccatggacacctatgtttttaaagatagttctcagaaagacctgctgaattt<br>tactggcacaattcctgtgatgtatcagggtaatacatataacataccaattcgtttctggattt<br>tggattctcaccctttcgctcccccctatttgcttcttgaagccaactgcaaatatgggaatctta |

TABLE 10-continued

The mRNA variant transcripts of Septins and UEV3 genes.

| Septin | mRNA Accession number | mRNAsequence |
|---|---|---|
| | | gtcggaaaacatgtggatgctcaaggcagaatatatttgccctatctccaaaactggagcc<br>atcctaaatctgtcattgttggattaattaaagaaatgattgccaagtttcaagaggaacttcc<br>catgtattctctatcatcatctgatgaggcacggcaggtagacttgctagcctatattgcaaa<br>aatcactgaaggtgtttcagatacaaattcaaagagctgggcaaatcatgagaataaaaca<br>gtcaataaaattactgtggttggaggtggagaactcggtattgcctgcacattagcaatttca<br>gcaaagggtattgcagacaggcttgtcctcttagacctctcagaagggactaaaggagcc<br>acgatggaccttgaaatcttcaaccttcctaatgtggagatcagcaaagatttgtctgcctct<br>gctcattccaaggtggtgatcttcacagtcaactctttgggtagttctcagtcgtaccttgatg<br>tggtacagagcaatgtggatatgttcagagcccttgtcccagctctgggacattatagtcaa<br>cacagtgtcctgctcgttgcatctcaaccagtggaaatcatgacctatgtaacatggaaact<br>gagtacatttcctgcaaatcgagtgatcggaattggatgtaatctggattcacagagattac<br>agtatattattacaaatgttttgaaggcacagacttcaggcaaagaagtatgggttattggcg<br>agcaaggagaagacaaagtgctcacatggagtggccaagaagaagtagtgagtcatac<br>ctctcaagtgcagctgtccaacagggatattatgatataaatagtgaagtgtttttaagtttgc<br>cttgcatccttggaaccaatggagtatctgaagttatcaaaaccacactgaaagaagatac<br>agttactgagaaactccaaagcagtgcatcctcaatccacagtctccaacaacagttaaaa<br>ctttgattctcaaatgcaatttgagaggctggacttctacctaaagggaaaagtcatttaatttt<br>acctatatataggtttgaggatttctgtatcctgctacttacttttacaaactgcttggttaaagt<br>agagggtttcttgattagctttgtgatgtaaatccttaaggagttatacaaggaggggaaaa<br>attaattttatttggggttcttgagatatctatgctgttctttaaatctacagcaggggtaaacat<br>tcatctgcagtgtgcatcaatttaaatcatatatcctaaactaaaagcacaattcatacttcgg<br>gaatattttataagtaatatatctttaaaagaaaattaccctttgacttttataatcaacataagtt<br>ccaggcccagtatggatttacaaaatctgtgtcagttgtacattcacaggatccacagctta<br>agttactaatgtttcttgtgtaaaatcctgttggtagtaatagtaaagcattgtatttcccttcttc<br>aaattaattacctaccaaaaaatggaaaagaattttacatgcactttaaaatagtaaaatgga<br>aagtgaattttttaaaatatatgcattaaaagtttactttaatttccaaaaaaaaaaaaaaaaaa |

What is claimed:

1. A pharmaceutical composition comprising an agent that inhibits the expression of a septin gene, an agent that inhibits the expression of a UEV3 gene, and a pharmaceutically acceptable carrier.

2. The pharmaceutical composition of claim 1, wherein the septin is septin 4.

3. The pharmaceutical composition of claim 1, wherein the septin is both septin 4 and septin 5.

4. The pharmaceutical composition of claim 1 further comprising an agent that inhibits the expression of a septin 5 gene.

5. A pharmaceutical composition comprising an agent that inhibits the expression of a septin 4 gene, an agent that inhibits the expression of a septin 5 gene, an agent that inhibits the expression of a UEV3 gene, and a pharmaceutically acceptable carrier.

6. The pharmaceutical composition of claim 1, wherein the agent that inhibits the expression of the respective gene is a nucleic acid inhibitor.

7. The pharmaceutical composition of claim 6, wherein at least one of the nucleic acid inhibitors is an siRNA or shRNA.

8. The pharmaceutical composition of claim 7, wherein the siRNA or shRNA comprises the sequence of GGGUCAACAUCGUGCCUAU (SEQ ID NO: 19).

9. A method of modulating store-operated $Ca^{2+}$ entry into a cell, the method comprising administering a therapeutically effective amount of a pharmaceutical composition of claim 1.

10. A method of modulating store-operated $Ca^{2+}$ entry into a cell, the method comprising administering a therapeutically effective amount of a pharmaceutical composition of claim 5.

11. The method of claim 9, wherein the modulation of store-operated $Ca^{2+}$ entry comprises inhibiting store-operated $Ca^{2+}$ entry into the cell.

* * * * *